United States Patent
Anderson et al.

(10) Patent No.: US 8,163,737 B2
(45) Date of Patent: Apr. 24, 2012

(54) CGRP RECEPTOR ANTAGONISTS

(75) Inventors: Corey Anderson, San Diego, CA (US); Andreas Termin, Encinitas, CA (US); Sara Hadida-Ruah, La Jolla, CA (US); Pramod Joshi, San Diego, CA (US); Sanghee Yoo, San Diego, CA (US); Daniele Bergeron, La Mesa, CA (US); Hayley Binch, San Diego, CA (US); Jon Come, Cambridge, MA (US); Jingrong Cao, Newton, MA (US); Suganthi Nanthakumar, Newton, MA (US); Elaine Krueger, Milton, MA (US); John Maxwell, Hingham, MA (US); Arnaud Le Tiran, Lexington, MA (US); Yusheng Liao, Lexington, MA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 313 days.

(21) Appl. No.: 11/955,874

(22) Filed: Dec. 13, 2007

(65) Prior Publication Data
US 2009/0176769 A1  Jul. 9, 2009

Related U.S. Application Data

(63) Continuation-in-part of application No. 11/818,224, filed on Jun. 13, 2007, now Pat. No. 7,834,000.

(60) Provisional application No. 60/813,178, filed on Jun. 13, 2006.

(51) Int. Cl.
- A61K 31/551 (2006.01)
- A61K 31/496 (2006.01)
- A61K 31/437 (2006.01)
- C07D 417/14 (2006.01)
- C07D 471/04 (2006.01)
- A61P 25/06 (2006.01)
- A61P 19/02 (2006.01)

(52) U.S. Cl. ......... 514/221; 514/253.04; 514/303; 540/500; 544/362; 546/118

(58) Field of Classification Search .......... None
See application file for complete search history.

(56) References Cited

U.S. PATENT DOCUMENTS
2008/0004261 A1  1/2008  Gutierrez et al.

FOREIGN PATENT DOCUMENTS
| WO | 03104236 A1 | 12/2003 |
|----|-------------|---------|
| WO | 2004017965 A1 | 3/2004 |
| WO | 2004092166 A2 | 10/2004 |

OTHER PUBLICATIONS

Alzheimer's Disease Treatment Phases, http://www.alzheimerstreatment.org/treatment/disease-treatment.htm (2008).*
Alzheimer's Drugs, Consumer Reports Best Buy Drugs (p. 1-5).*
Migraine, http://www.drugdevelopment-technology.com/projects/olcegepant/ (2010).*
Scheuerman et al., caplus an 2002:107109 (2002).*
PCT/US2007/013896: International Search Report dated Jul. 23, 2008.
Office Action dated Jan. 7, 2010 in U.S. Appl. No. 11/818,224.
Office Action dated Jun. 22, 2009 in U.S. Appl. No. 11/818,224.
Office Action dated Nov. 19, 2008 in U.S. Appl. No. 11/818,224.
Office Action dated Aug. 14, 2008 in U.S. Appl. No. 11/818,224.
Recober, et al. Curr. Opin. Neurol. 22, pp. 241-246 (2009).
Hay, et al. Maturitas 64, pp. 104-108 (2009).
Yu, et al. Neurosci. and Biobehav. Rev. 33, pp. 1185-1191 (2009).
Schafer et al. Drug Discovery Today 2008, 13 (21/22), 913-916.
Horig et al. Journal of Transitional Medicine 2004, 2:44.

* cited by examiner

Primary Examiner — Sun Jae Loewe
(74) Attorney, Agent, or Firm — Michael C. Badia

(57) ABSTRACT

The present invention relates to CGRP receptor antagonists, pharmaceutical compositions thereof, and methods therewith for treating CGRP receptor-mediated diseases and conditions.

12 Claims, 74 Drawing Sheets

CGRP RECEPTOR ANTAGONISTS

CROSS REFERENCE TO RELATED APPLICATIONS

This application, as a continuation-in-part application, claims the benefit, under 35 U.S.C. §120, of U.S. patent application Ser. No. 11/818,224 filed Jun. 13, 2007 now U.S. Pat. No. 7,834,000, entitled "CGRP Receptor Antagonists" which claims the benefit, under 35 U.S.C. §119, of U.S. Provisional Patent Application No. 60/813,178, filed Jun. 13, 2006, entitled "CGRP Receptor Antagonists" and the entire contents of each of these two applications is hereby incorporated by reference.

TECHNICAL FIELD OF THE INVENTION

The present invention relates to CGRP receptor antagonists, pharmaceutical compositions thereof, and methods therewith for treating CGRP receptor-mediated diseases and conditions.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP (8-37), a peptide CGRP antagonist (Williamson et al., Cephalalgia, 1997, 17, 525-531). Trigeminal ganglion stimulation increased facial blood flow in the rat, which was inhibited by CGRP (8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist. In recently reported clinical trials, the CGRP receptor antagonist BIBN 4096 BS was reported to be effective in treating acute attacks of migraine (Olesen et al., N. Engl. J. Med. 2004, 350:1104-1110).

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr. Opin. Inves. Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists of CGRP receptors, pharmaceutical compositions thereof, and uses therewith.

SUMMARY OF THE INVENTION

The present invention provides compounds of formula I:

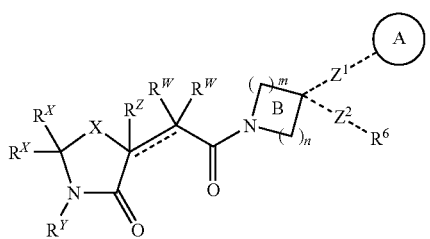

or a pharmaceutically acceptable salt thereof.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

2. Compounds and Definitions

Figure 1:
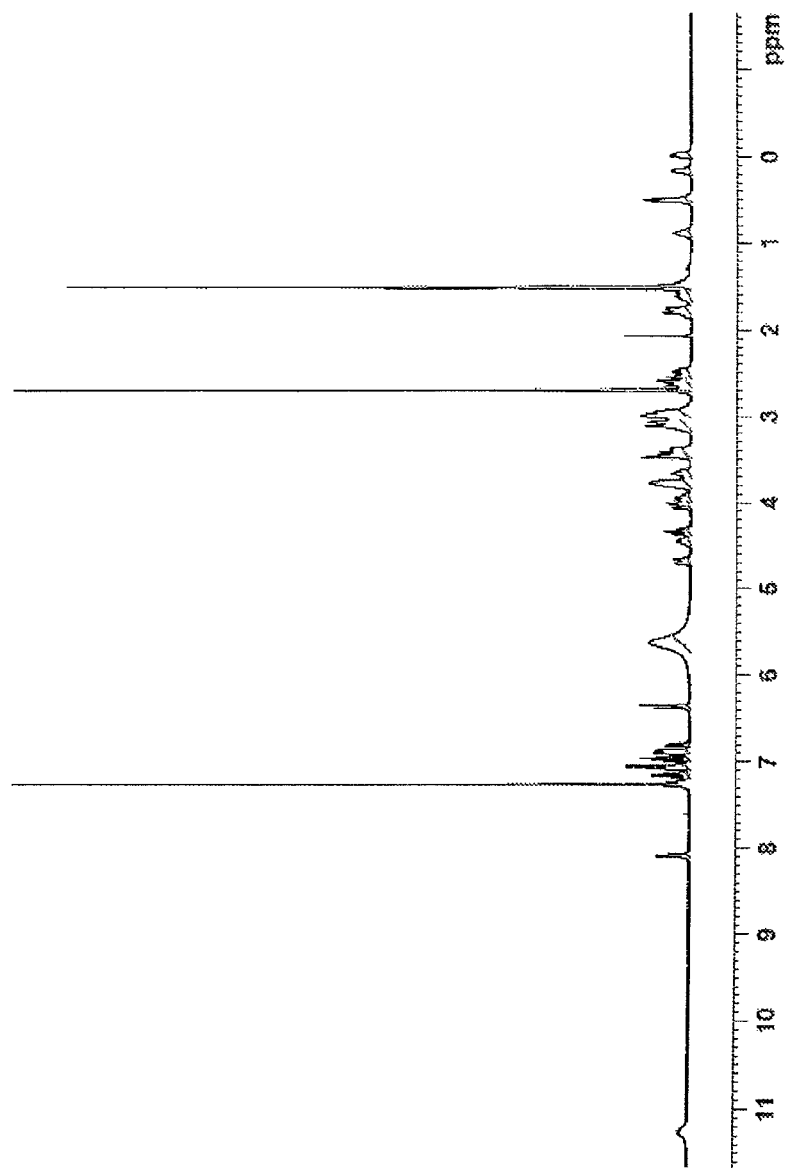
FIG. 1 depicts a $^1$H NMR trace (CDCl$_3$, 300 MHz) of compound I-488.
Figure 2:
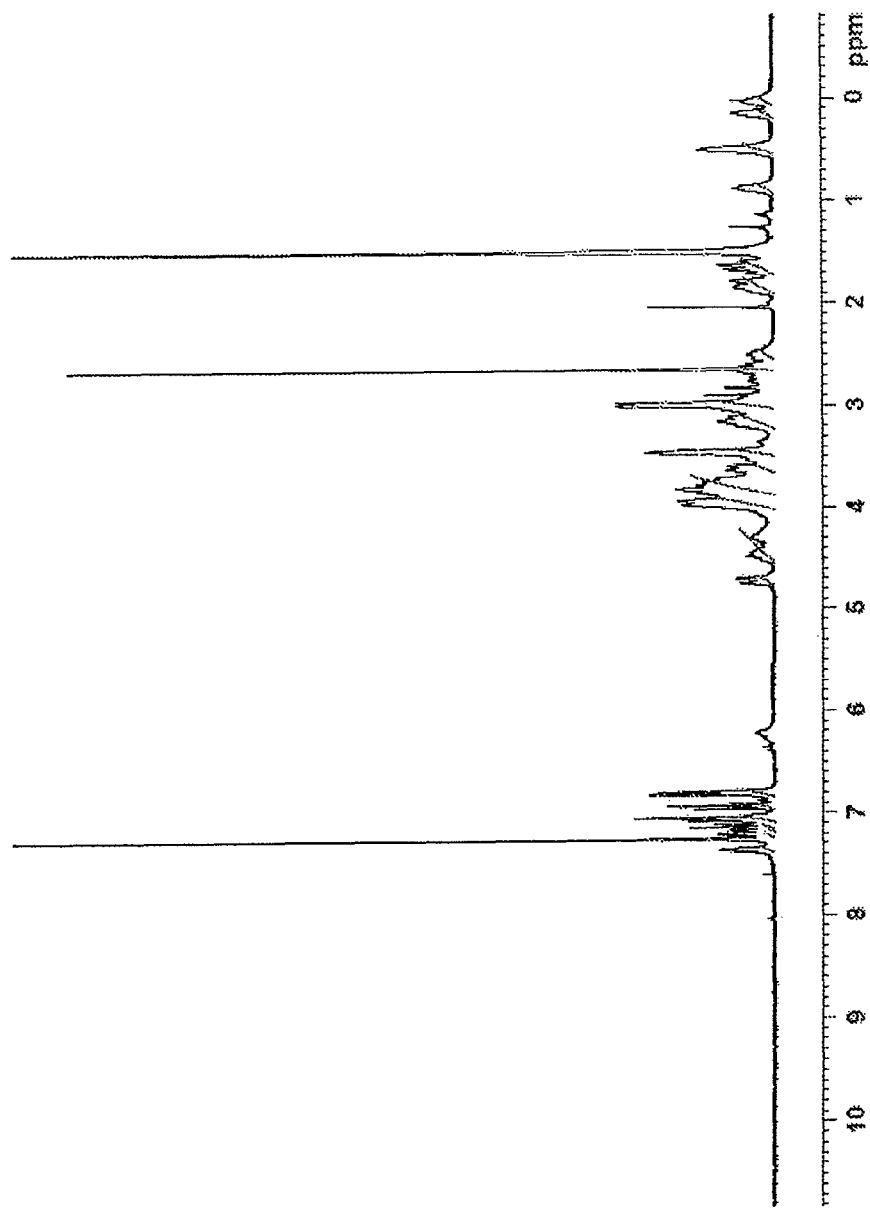
FIG. 2 depicts a $^1$H NMR trace (CDCl$_3$, 300 MHz) of compound I-489.
Figure 3:
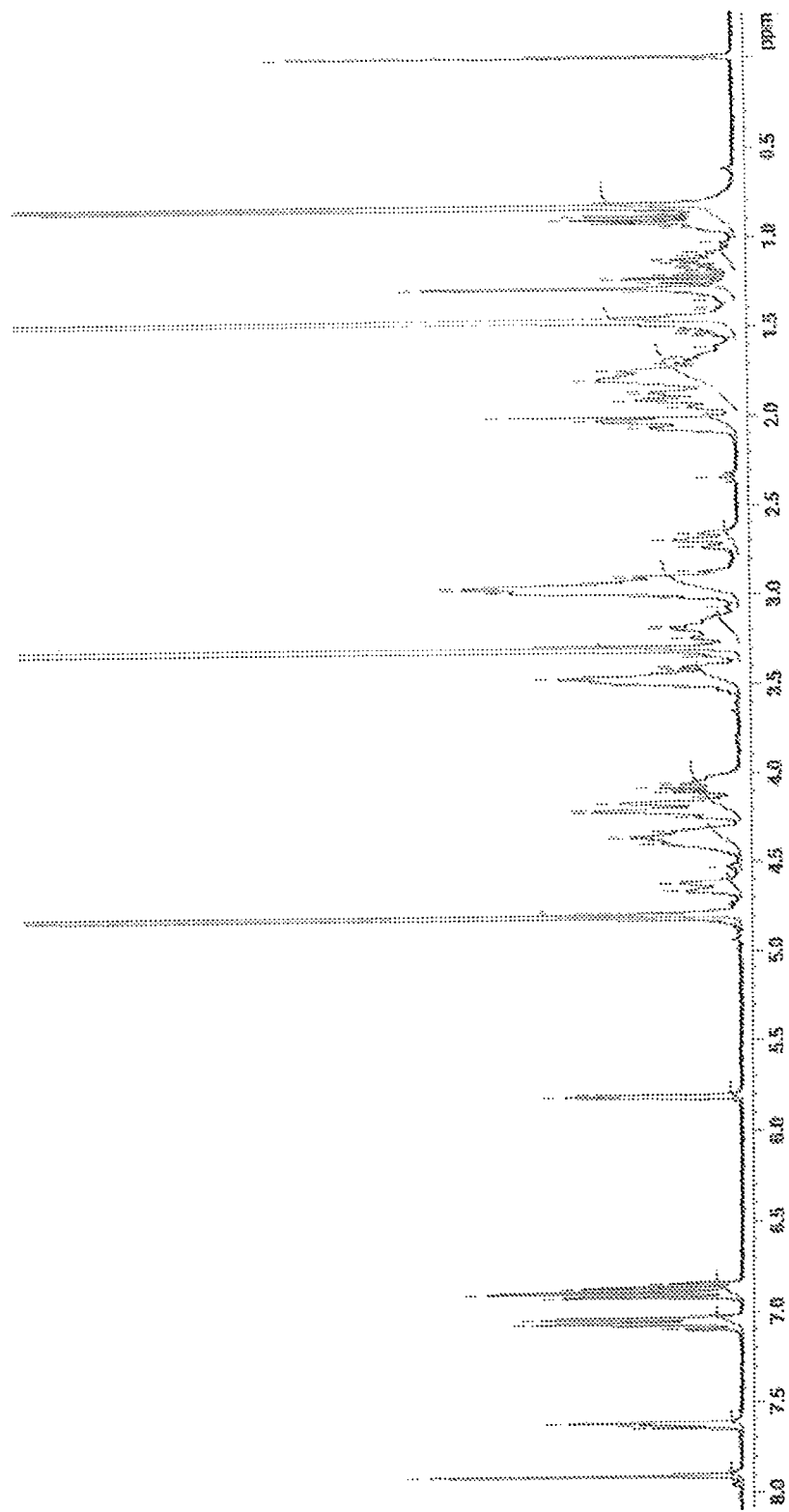
FIG. 3 depicts a $^1$H NMR trace (CD$_3$OD, 300 MHz) of compound I-490.
Figure 4:
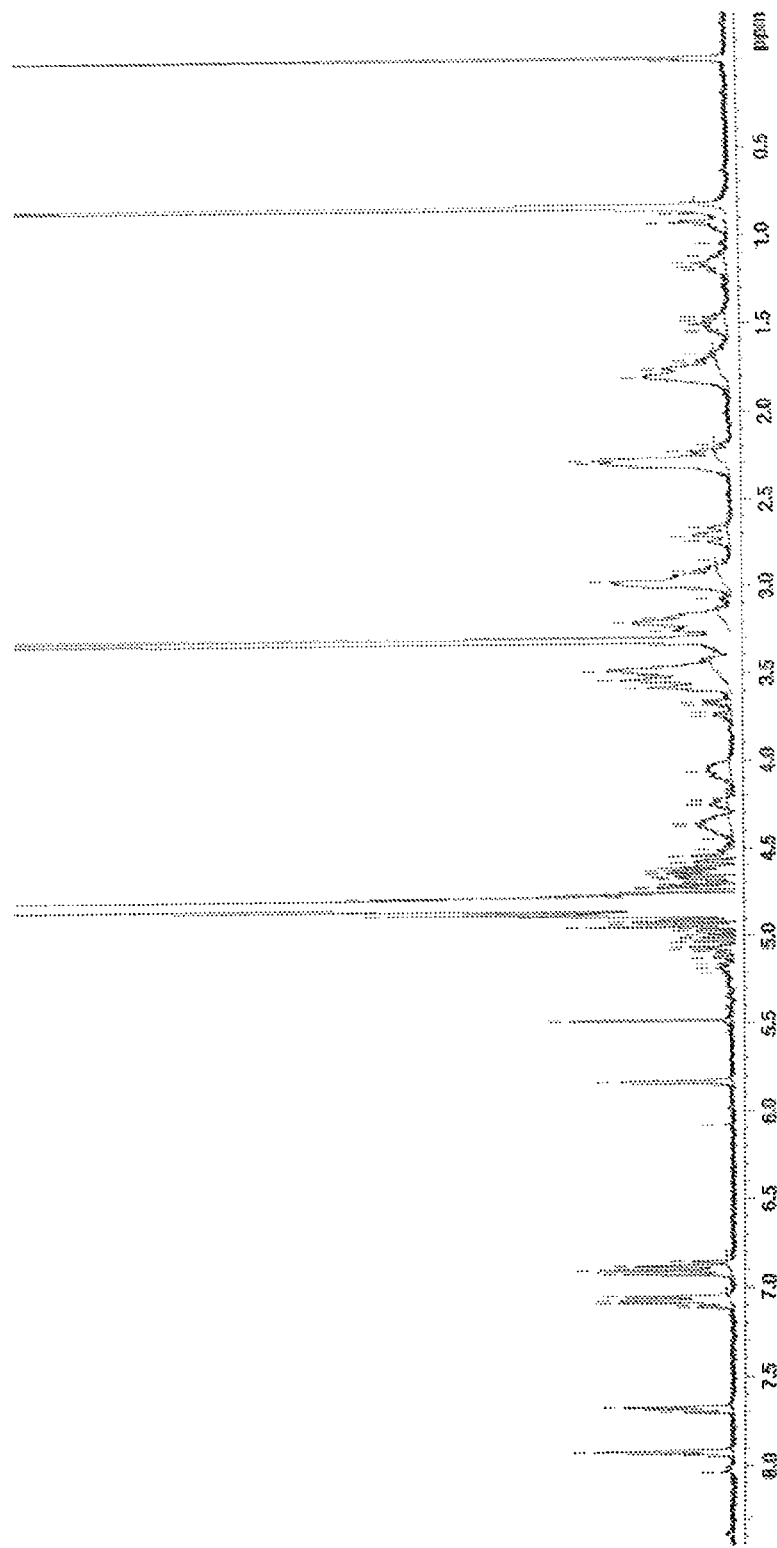
FIG. 4 depicts a $^1$H NMR trace (CD$_3$OD, 300 MHz) of compound I-491.
Figure 5:
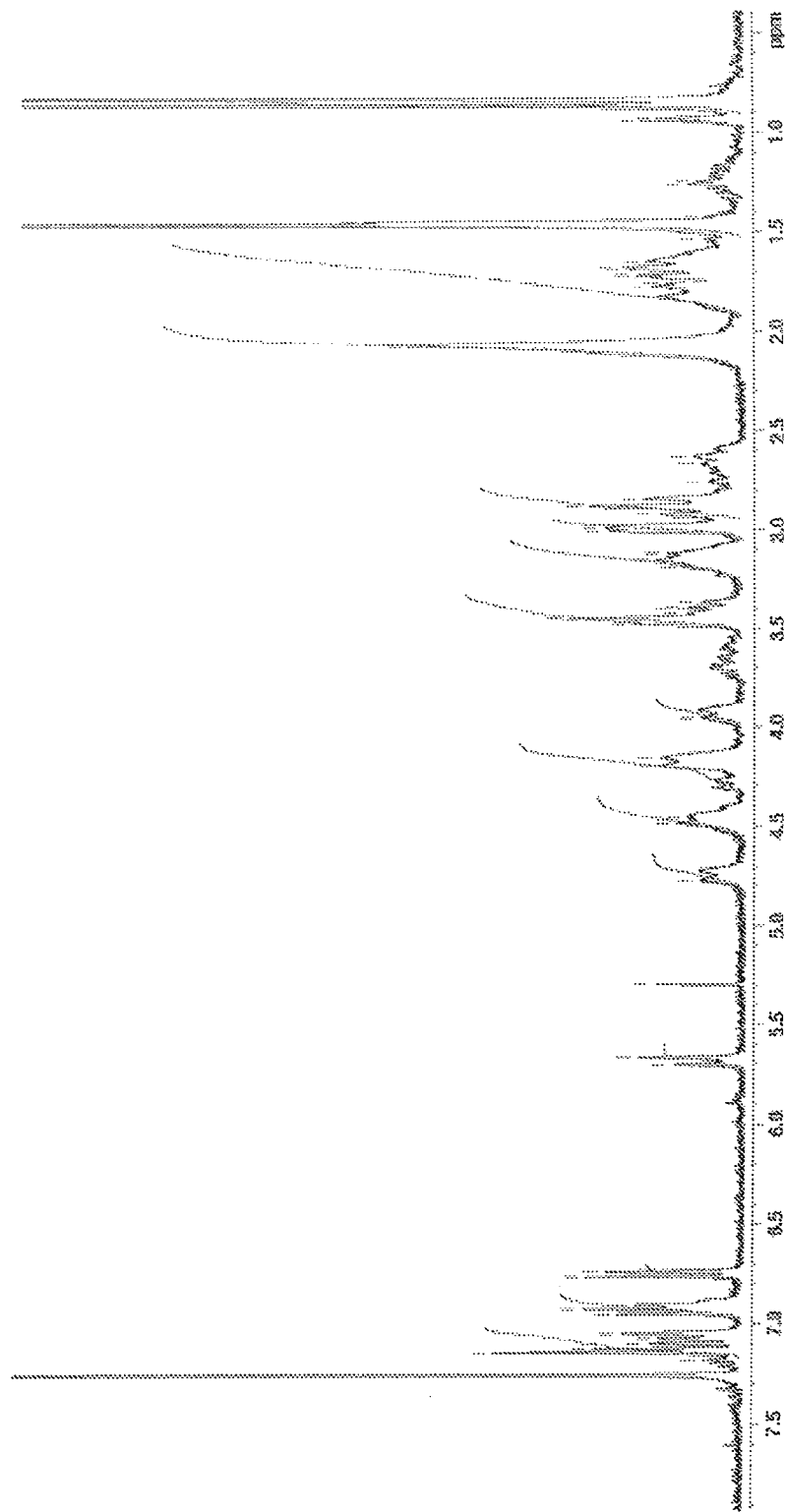
FIG. 5 depicts a $^1$H NMR trace (CDCl$_3$, 300 MHz) of compound I-492.
Figure 6:
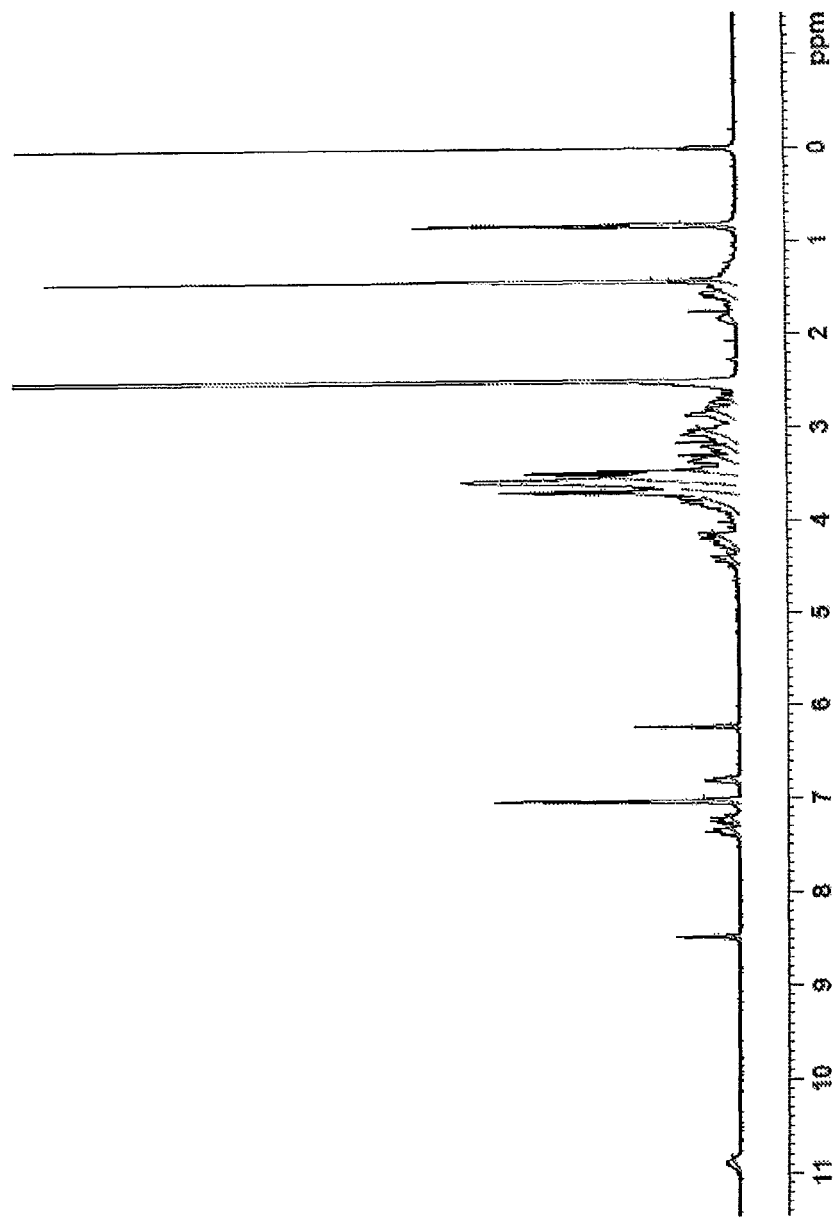
FIG. 6 depicts a $^1$H NMR trace (DMSO-d6, 300 MHz) of compound I-493.
Figure 7:
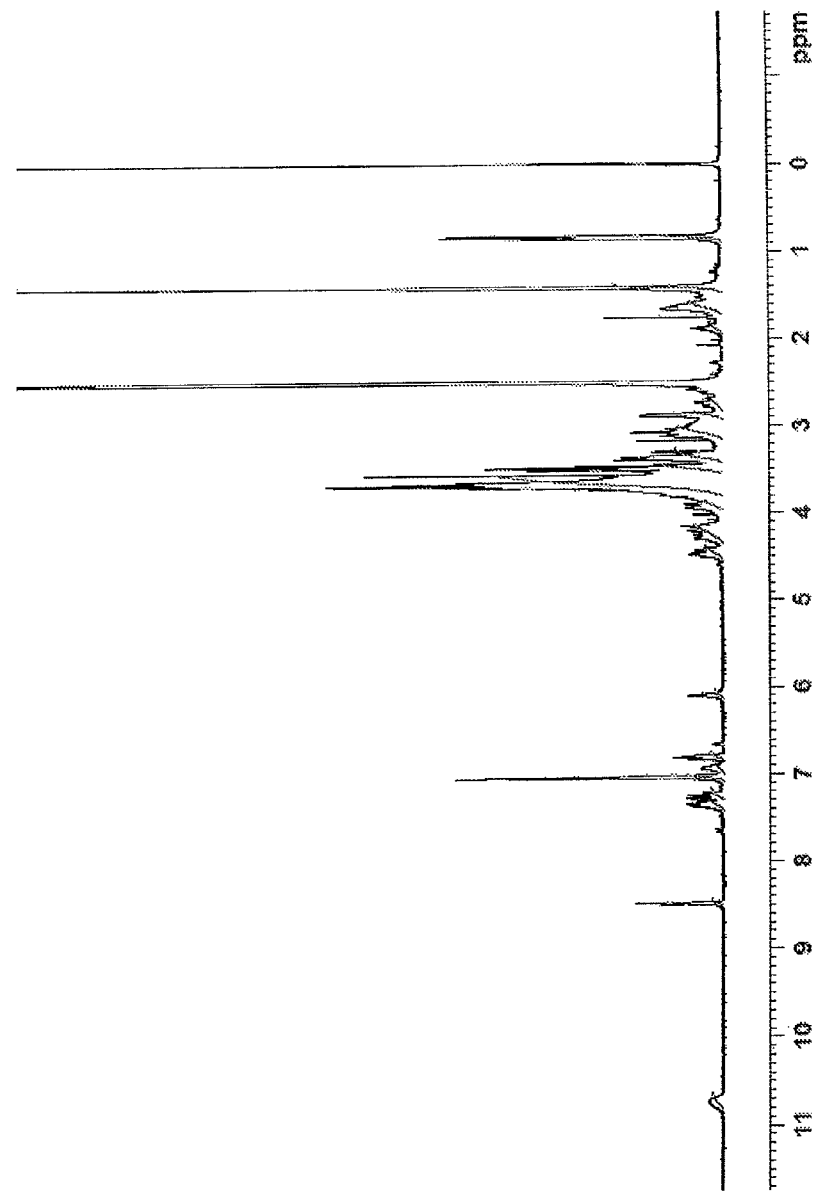
FIG. 7 depicts a $^1$H NMR trace (DMSO-d6, 300 MHz) of compound I-494.
Figure 8:
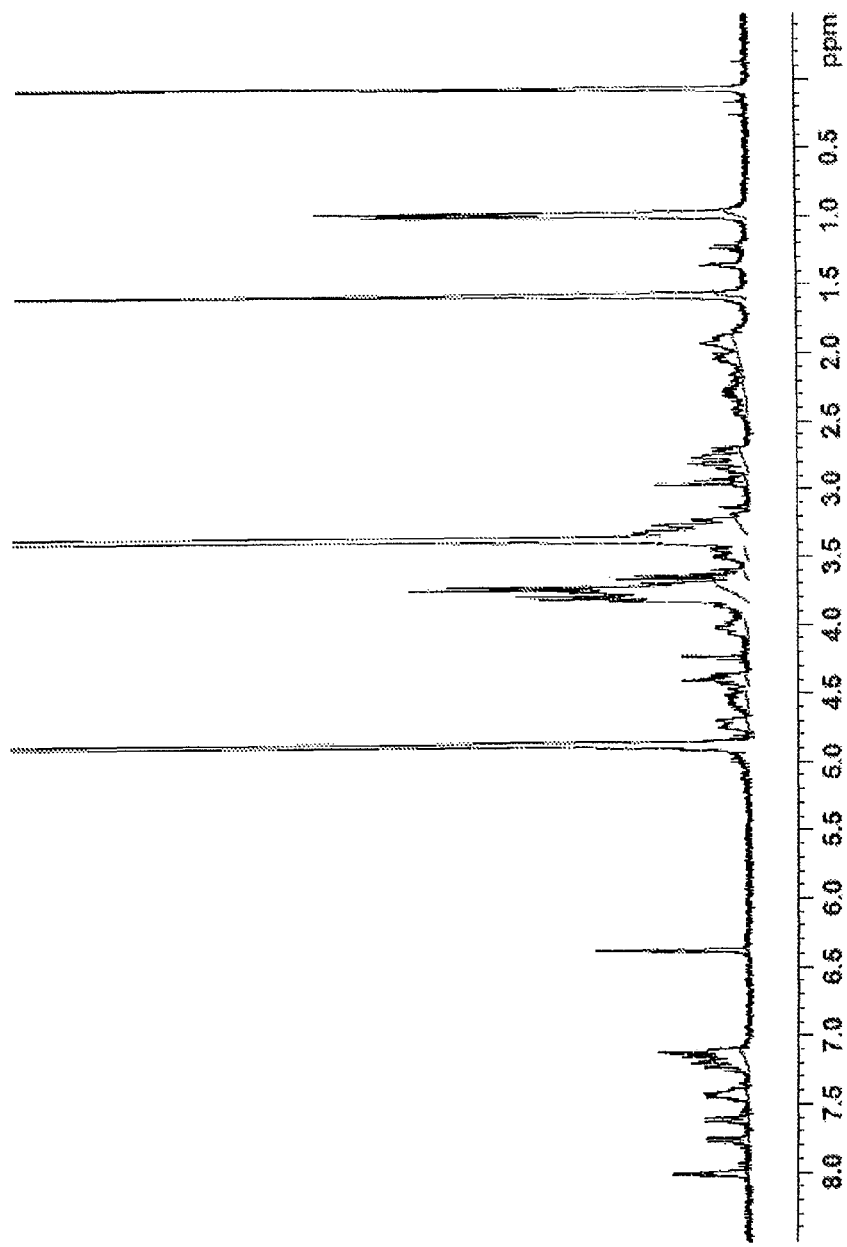
FIG. 8 depicts a $^1$H NMR trace (CD$_3$OD, 300 MHz) of compound I-495.
Figure 9:
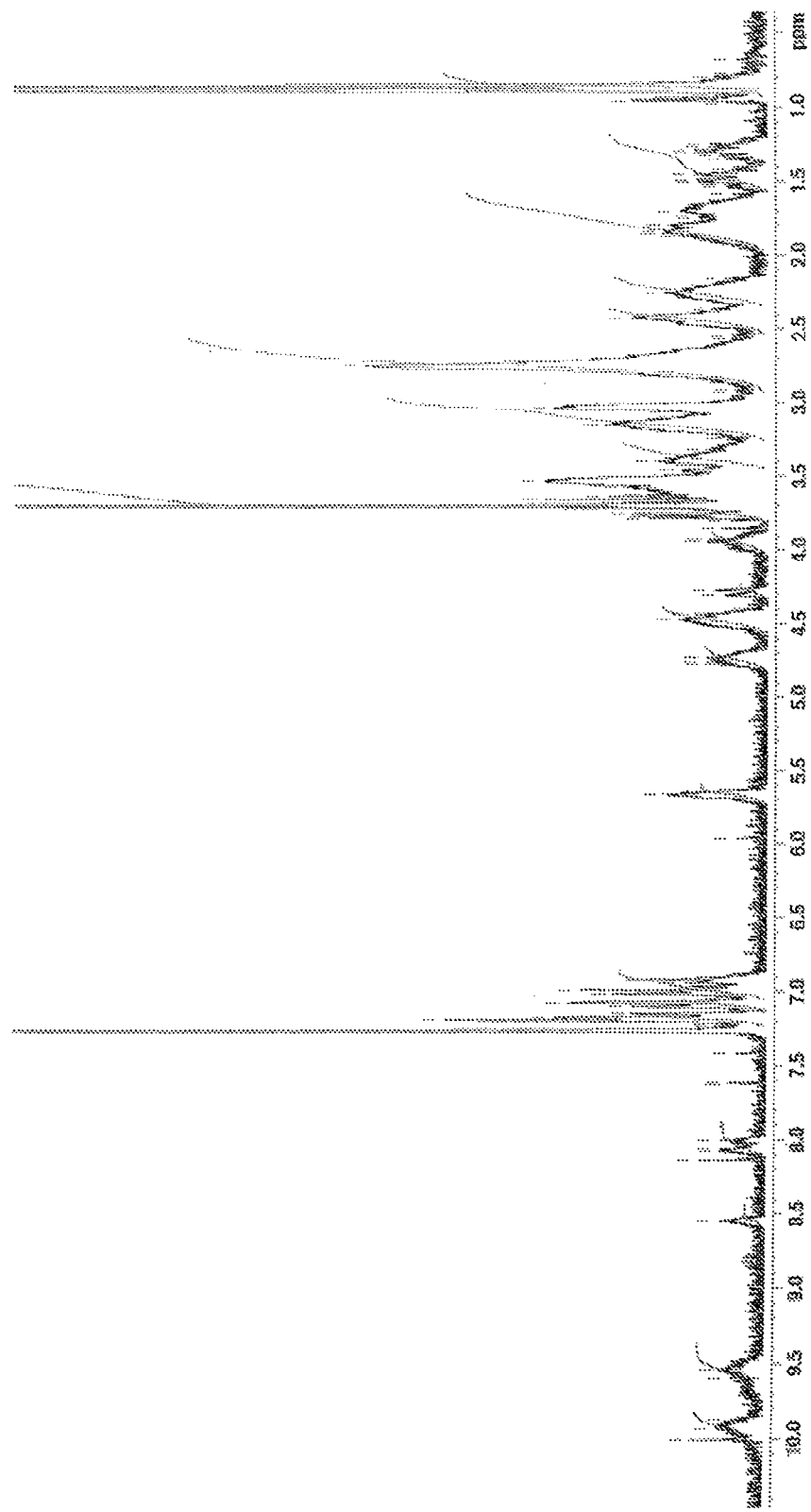
FIG. 9 depicts a $^1$H NMR trace (CDCl$_3$, 300 MHz) of compound I-497.
Figure 10:
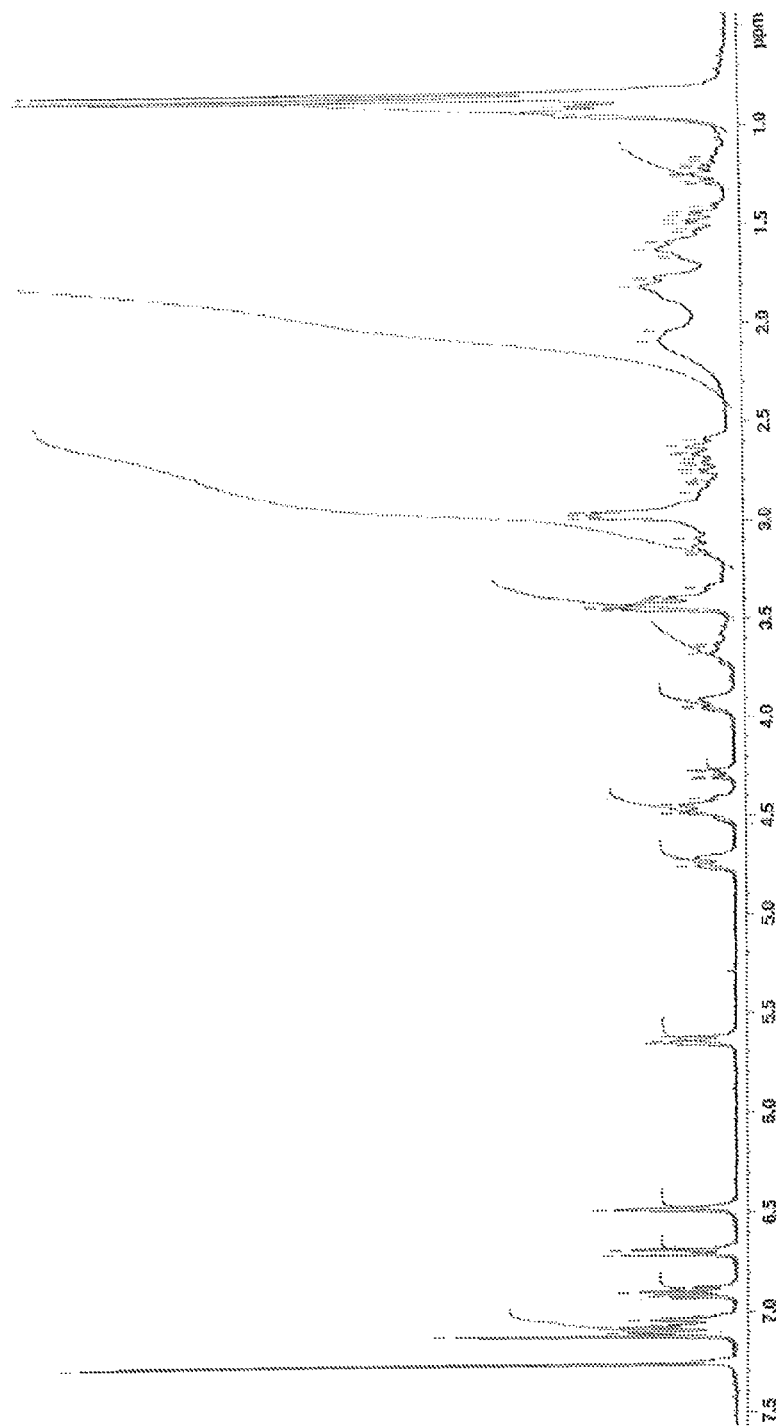
FIG. 10 depicts a $^1$H NMR trace (CDCl$_3$, 300 MHz) of compound I-498.
Figure 11:
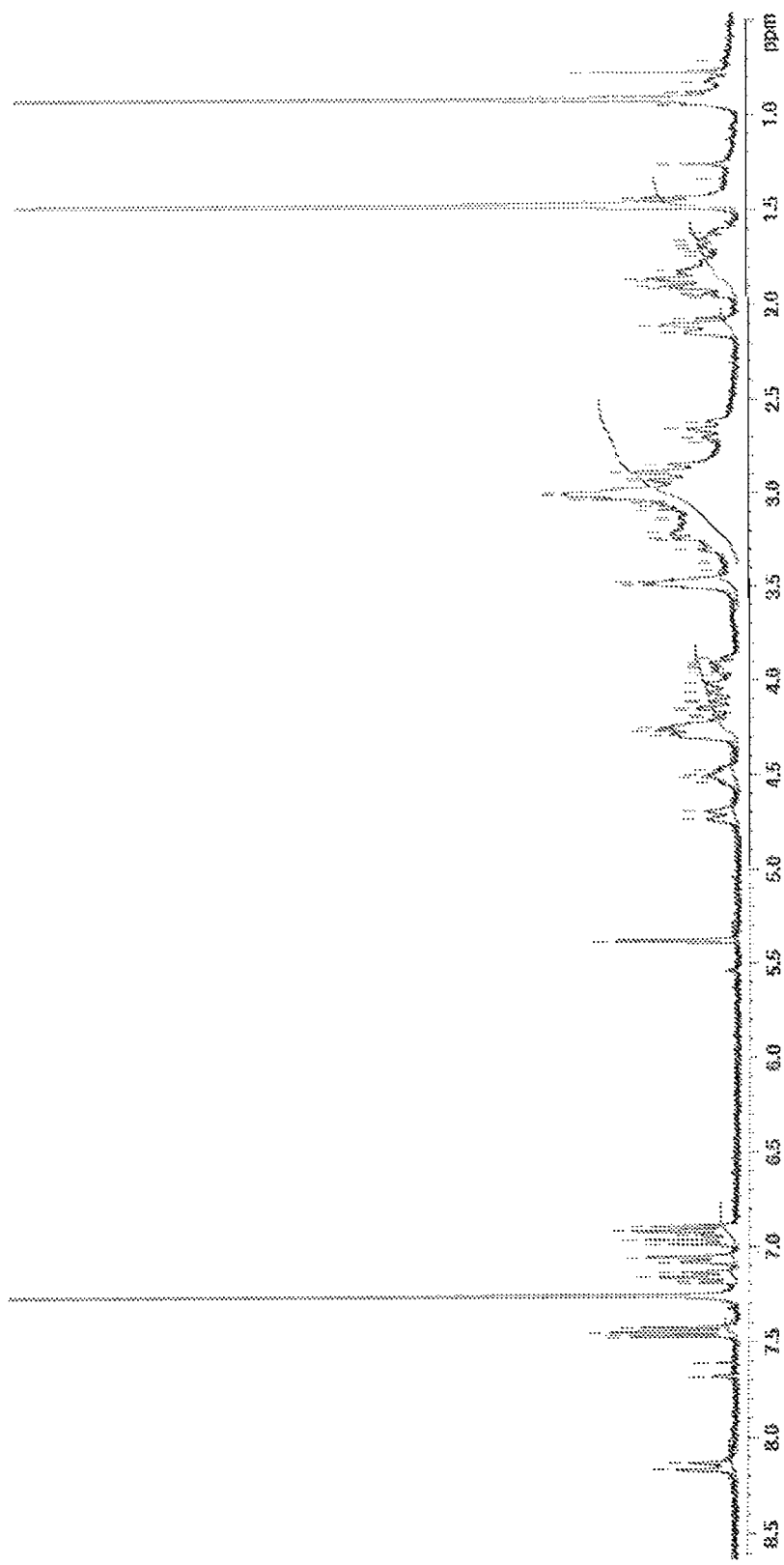
FIG. 11 depicts a $^1$H NMR trace (CDCl$_3$, 300 MHz) of compound I-499.
Figure 12:
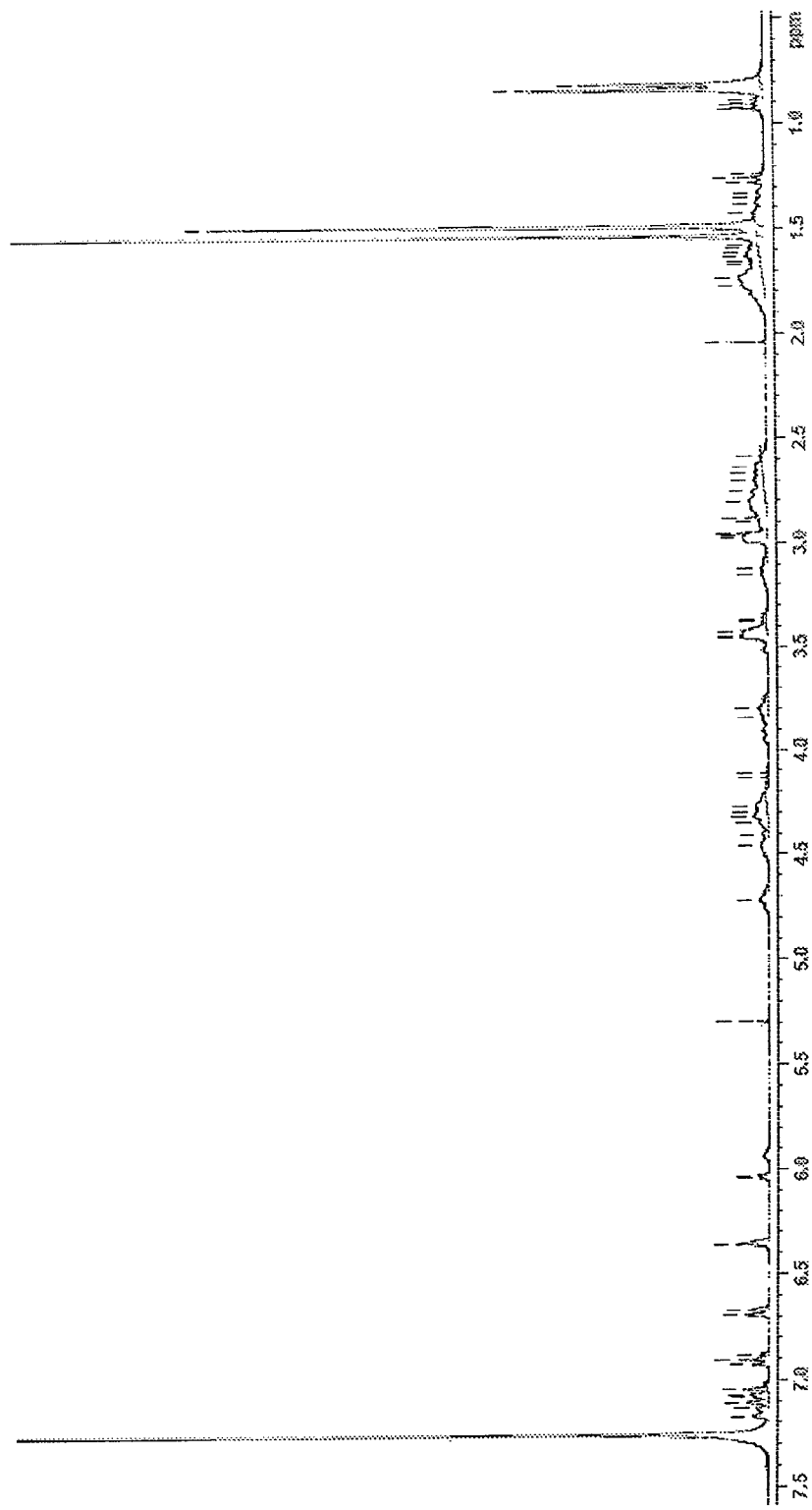
FIG. 12 depicts a $^1$H NMR trace (CDCl$_3$, 300 MHz) of compound I-500.
Figure 13:
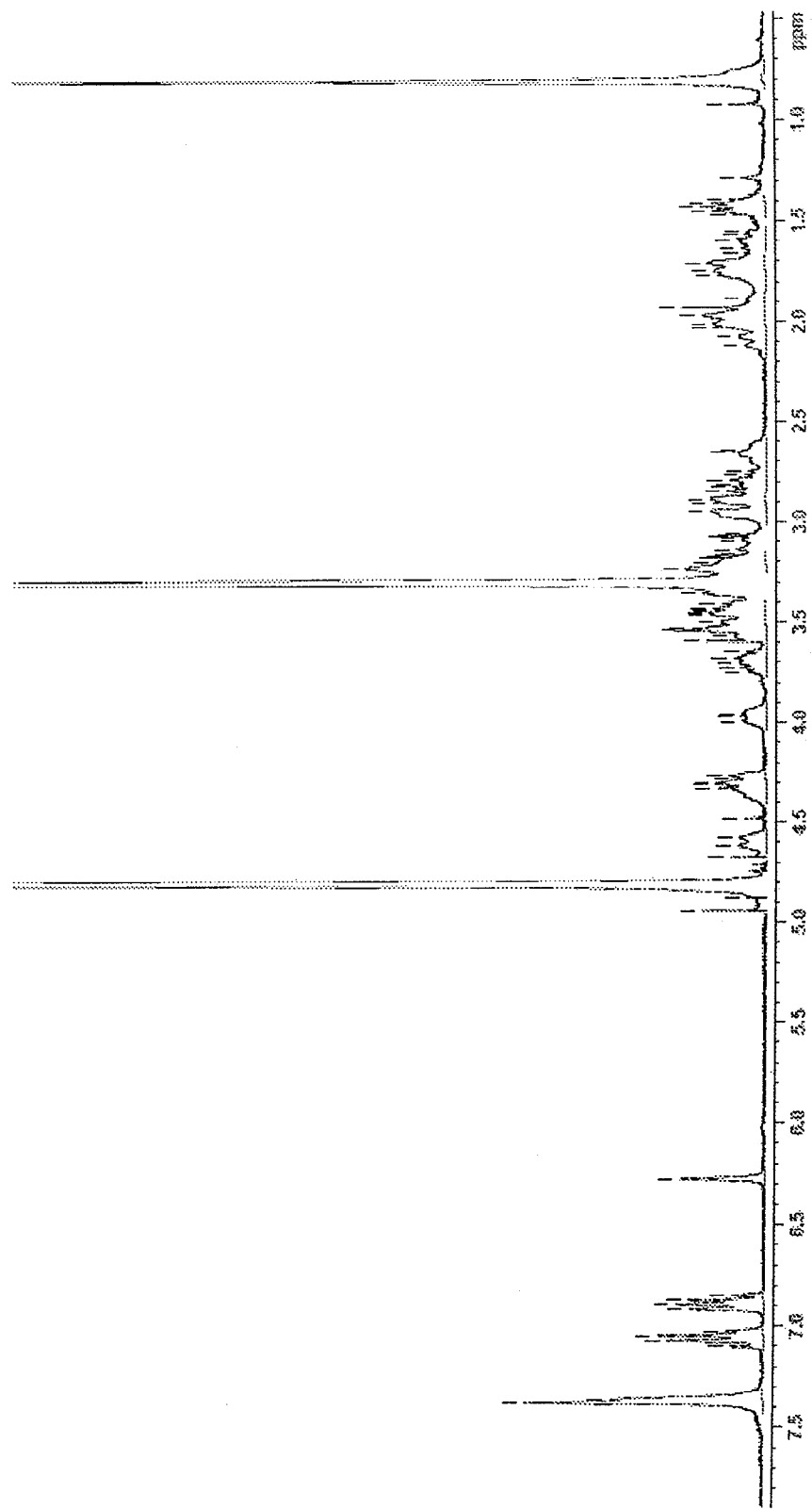
FIG. 13 depicts a $^1$H NMR trace (CD$_3$OD, 300 MHz) of compound I-501.
Figure 14:
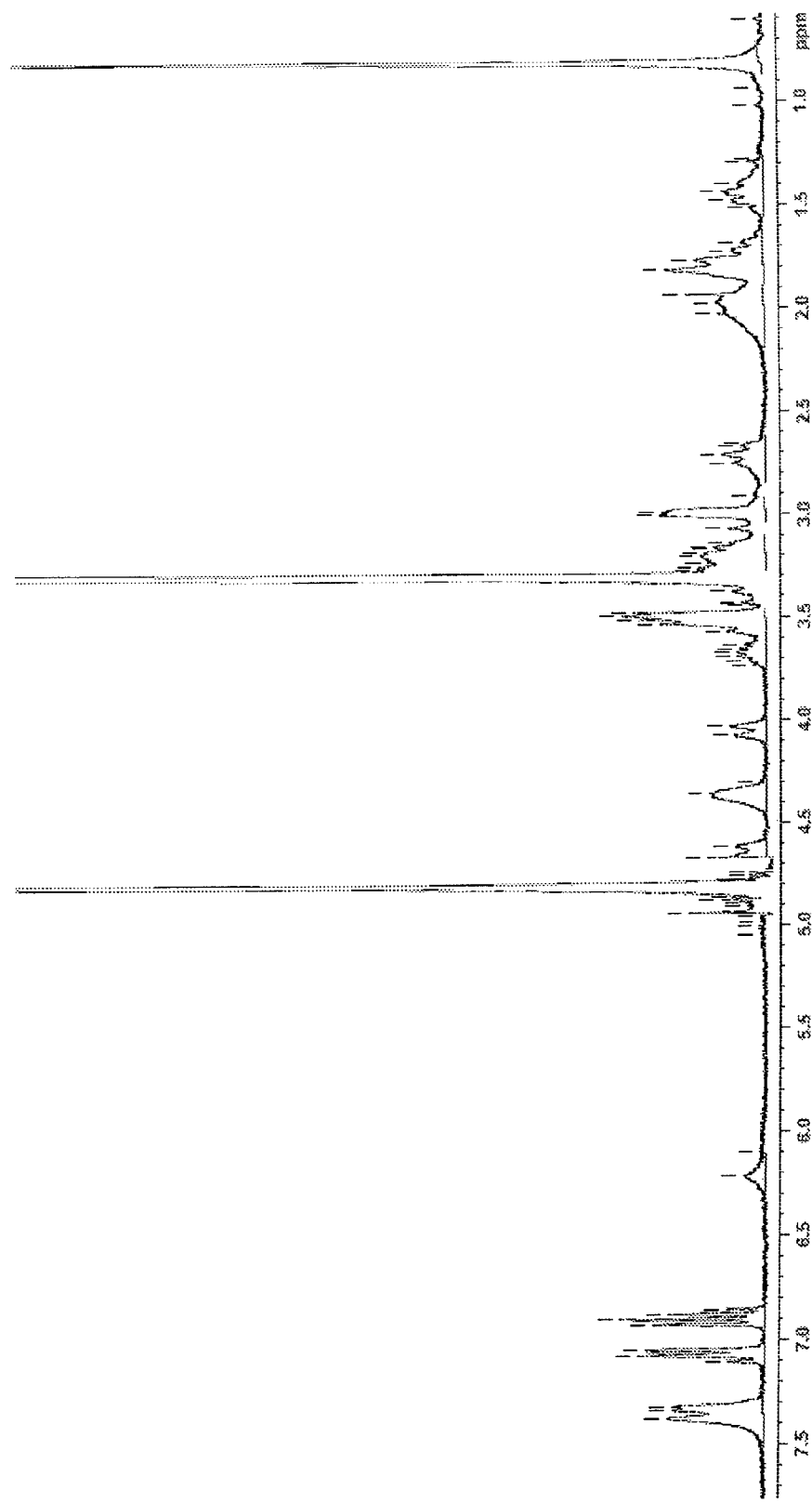
FIG. 14 depicts a $^1$H NMR trace (CD$_3$OD, 300 MHz) of compound I-502.
Figure 15:
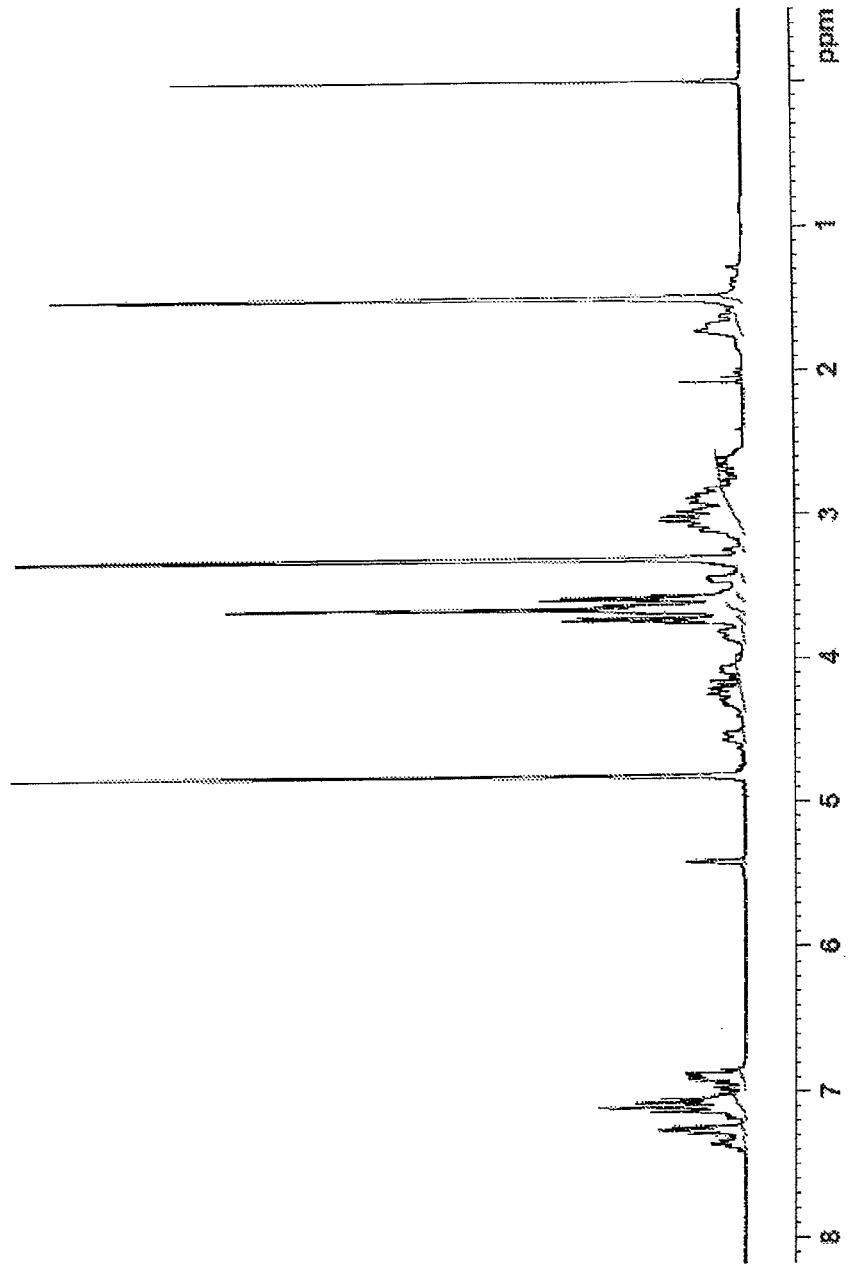
FIG. 15 depicts a $^1$H NMR trace (CD$_3$OD, 300 MHz) of compound I-503.
Figure 16:
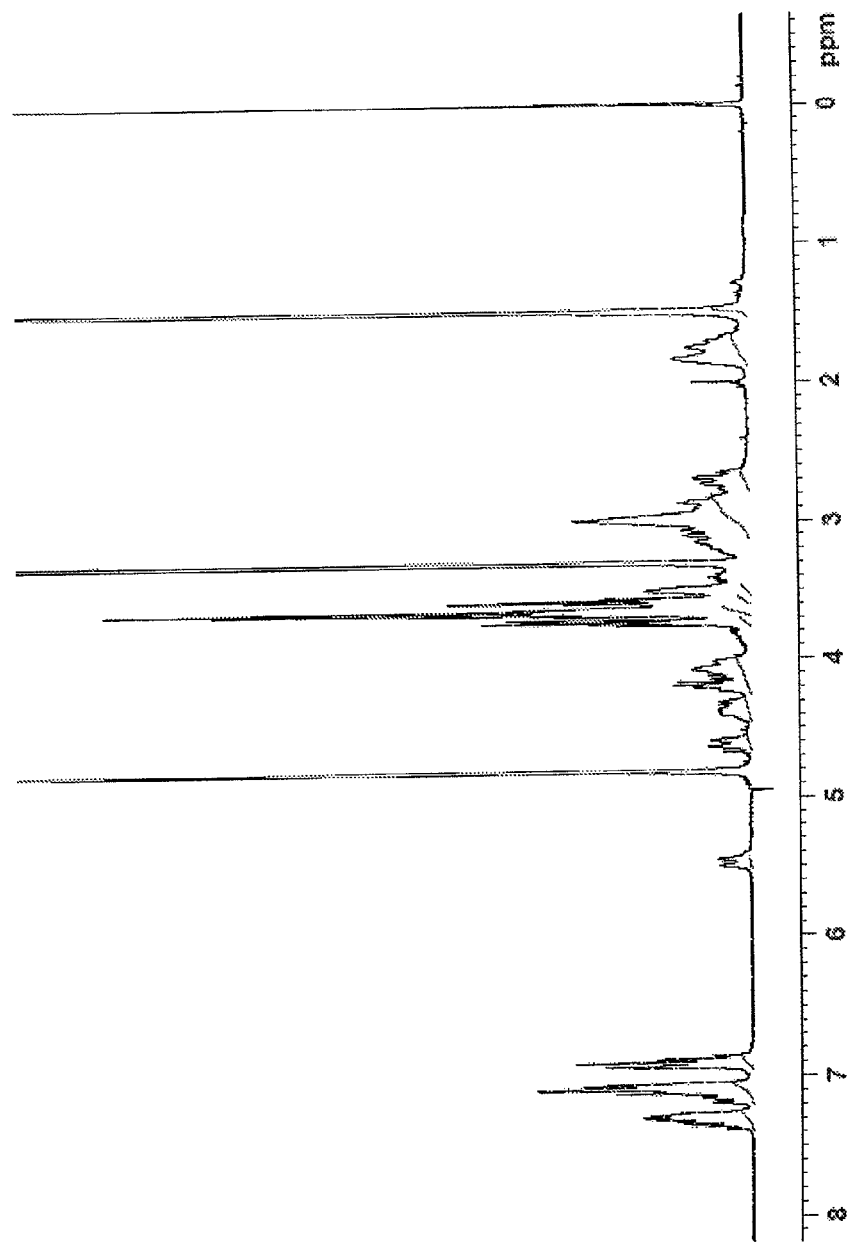
FIG. 16 depicts a $^1$H NMR trace (CD$_3$OD, 300 MHz) of compound I-504.
Figure 17:
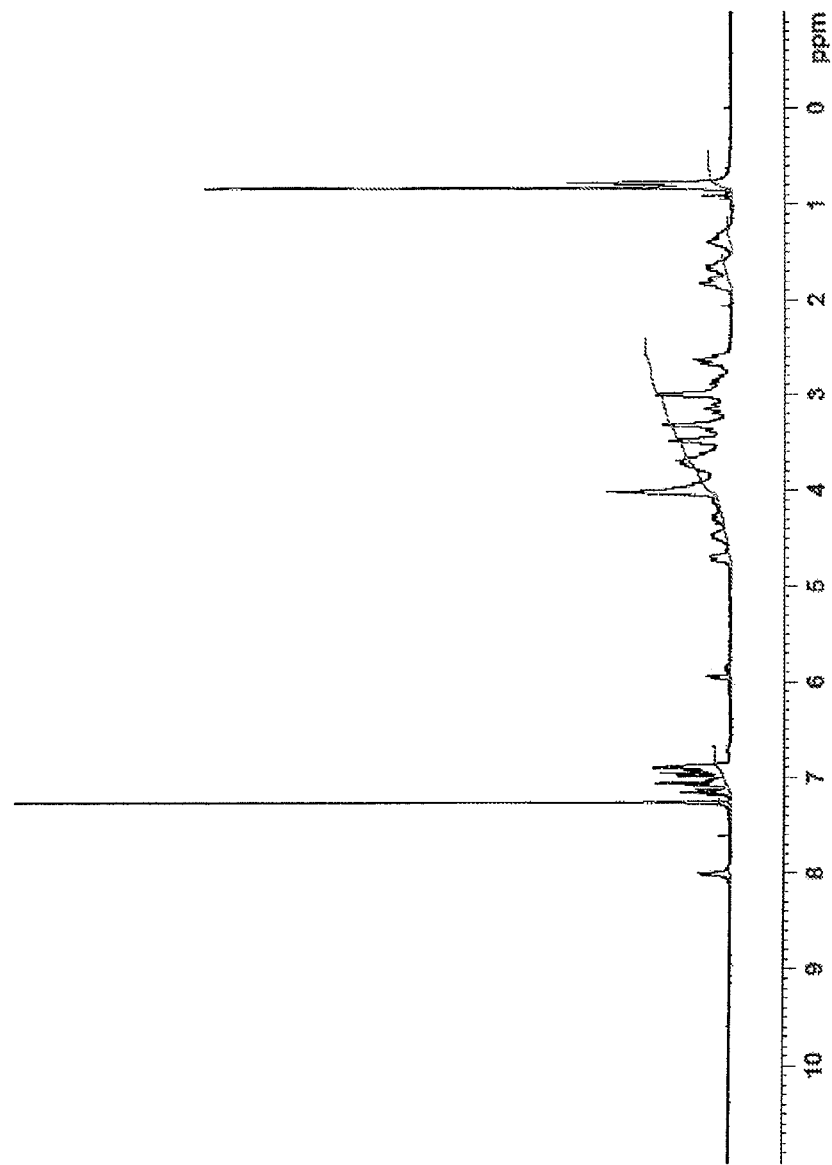
FIG. 17 depicts a $^1$H NMR trace (CDCl$_3$, 300 MHz) of compound I-506.
Figure 18:
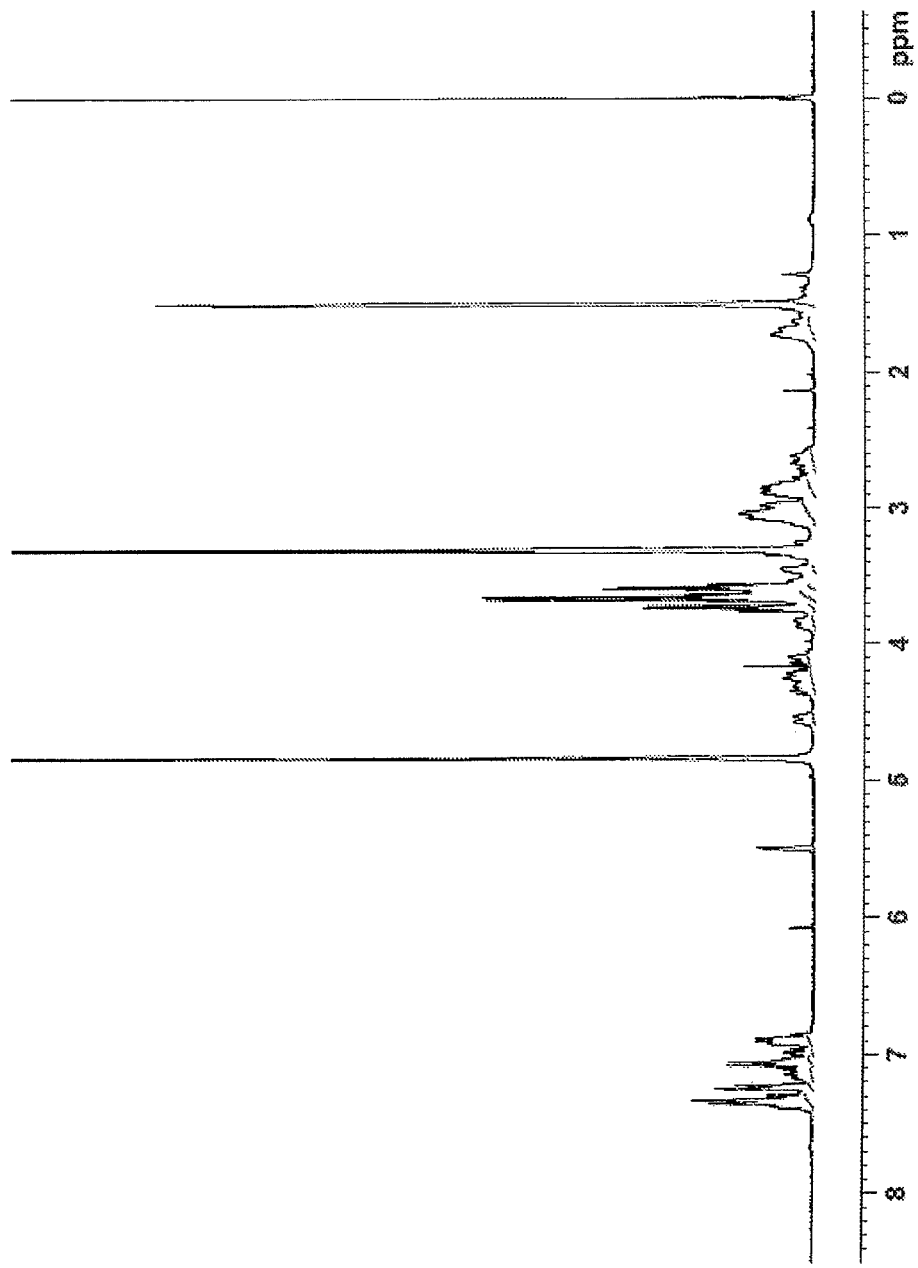
FIG. 18 depicts a $^1$H NMR trace (CD$_3$OD, 300 MHz) of compound I-507.
Figure 19:
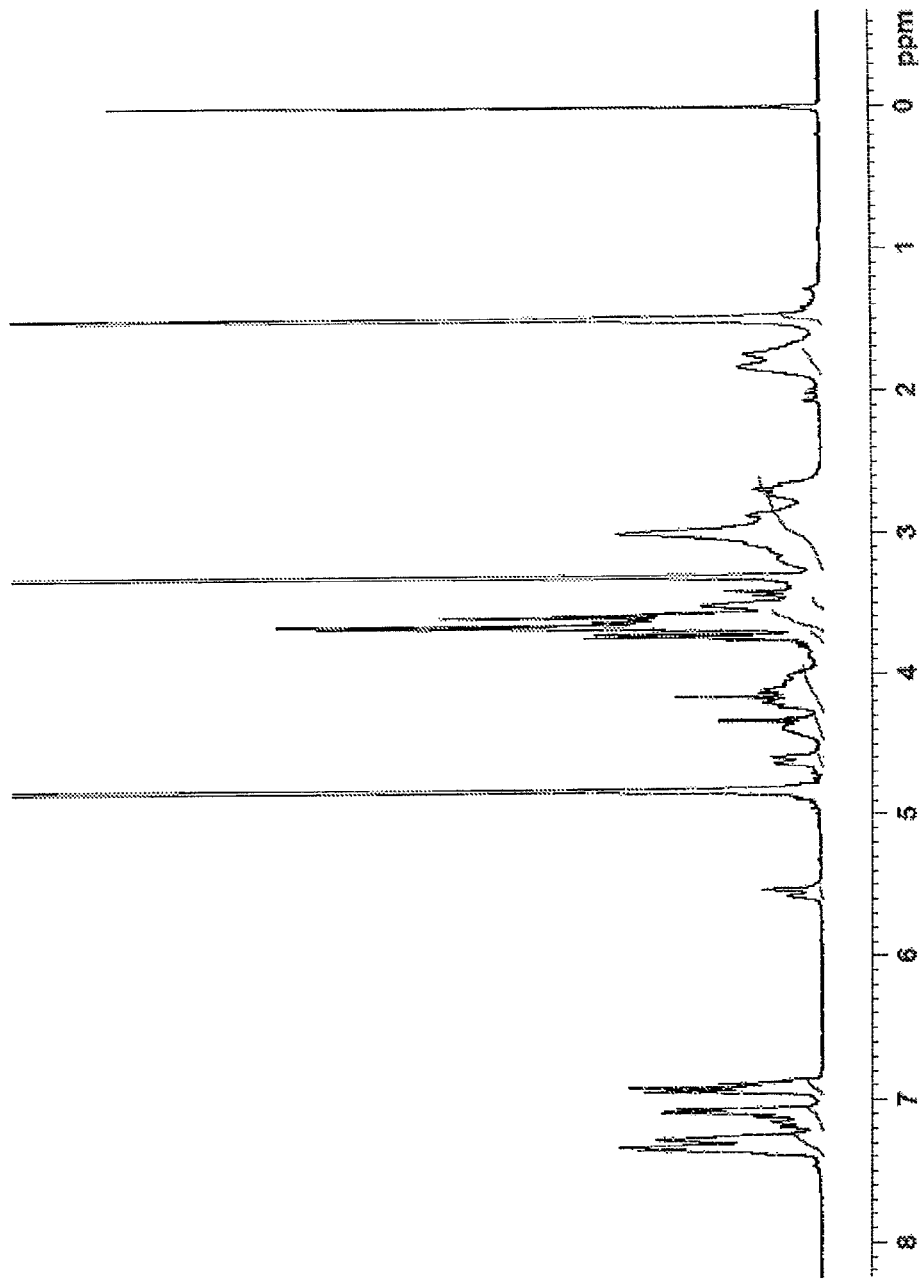
FIG. 19 depicts a $^1$H NMR trace (CD$_3$OD, 300 MHz) of compound I-508.
Figure 20:
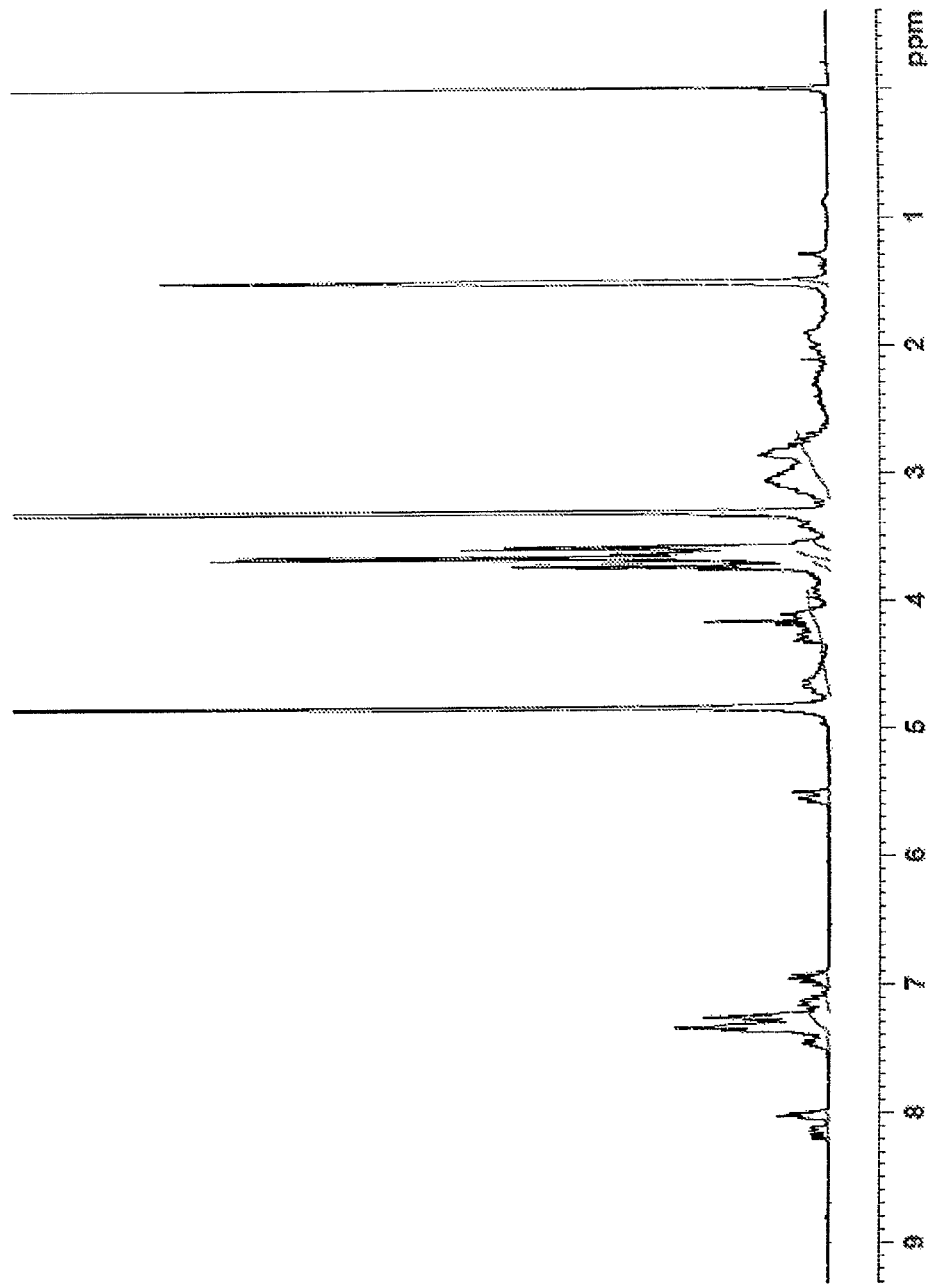
FIG. 20 depicts a $^1$H NMR trace (CD$_3$OD, 300 MHz) of compound I-509.
Figure 21:
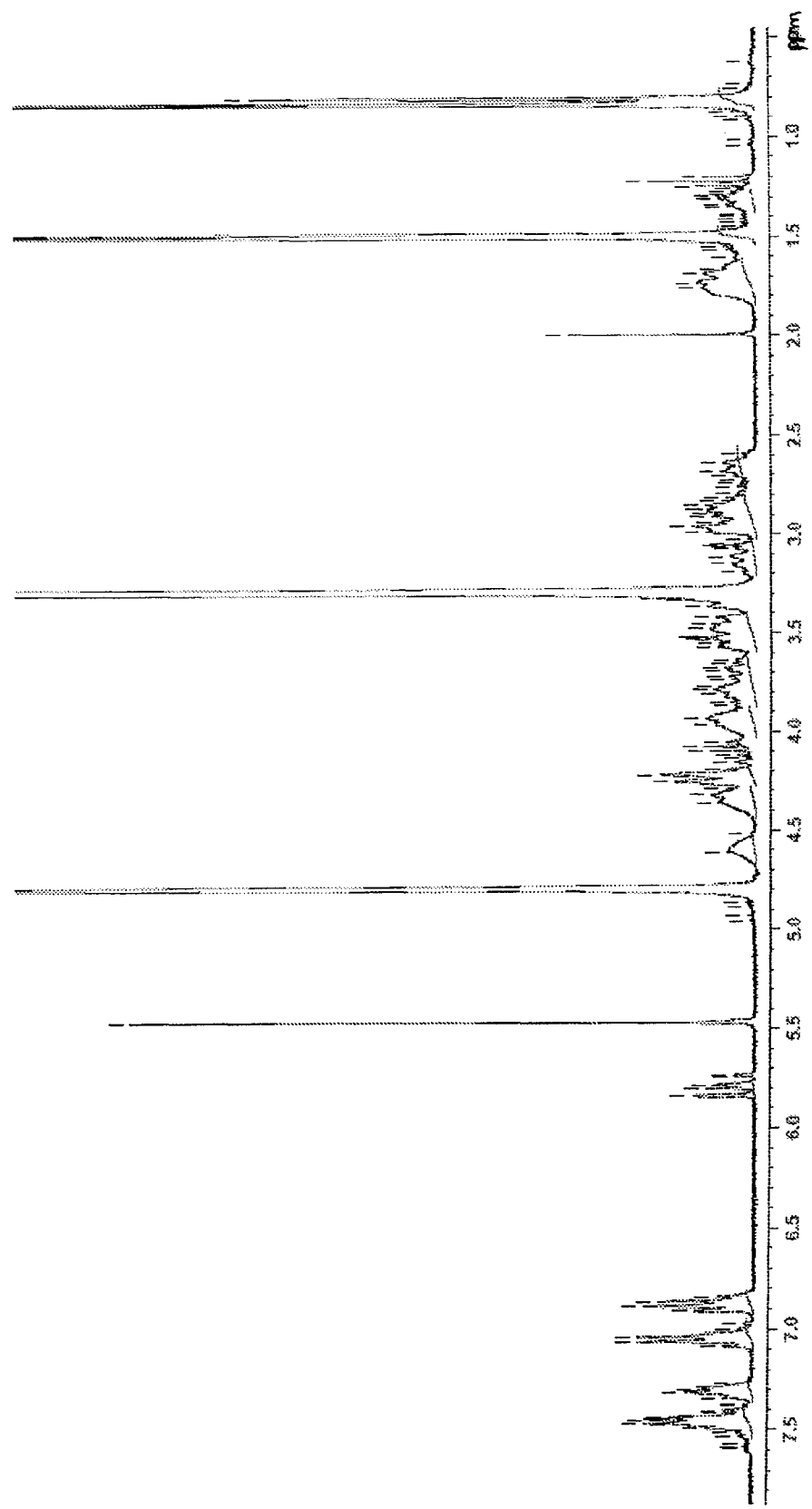
FIG. 21 depicts a $^1$H NMR trace (CD$_3$OD, 300 MHz) of compound I-510.
Figure 22:
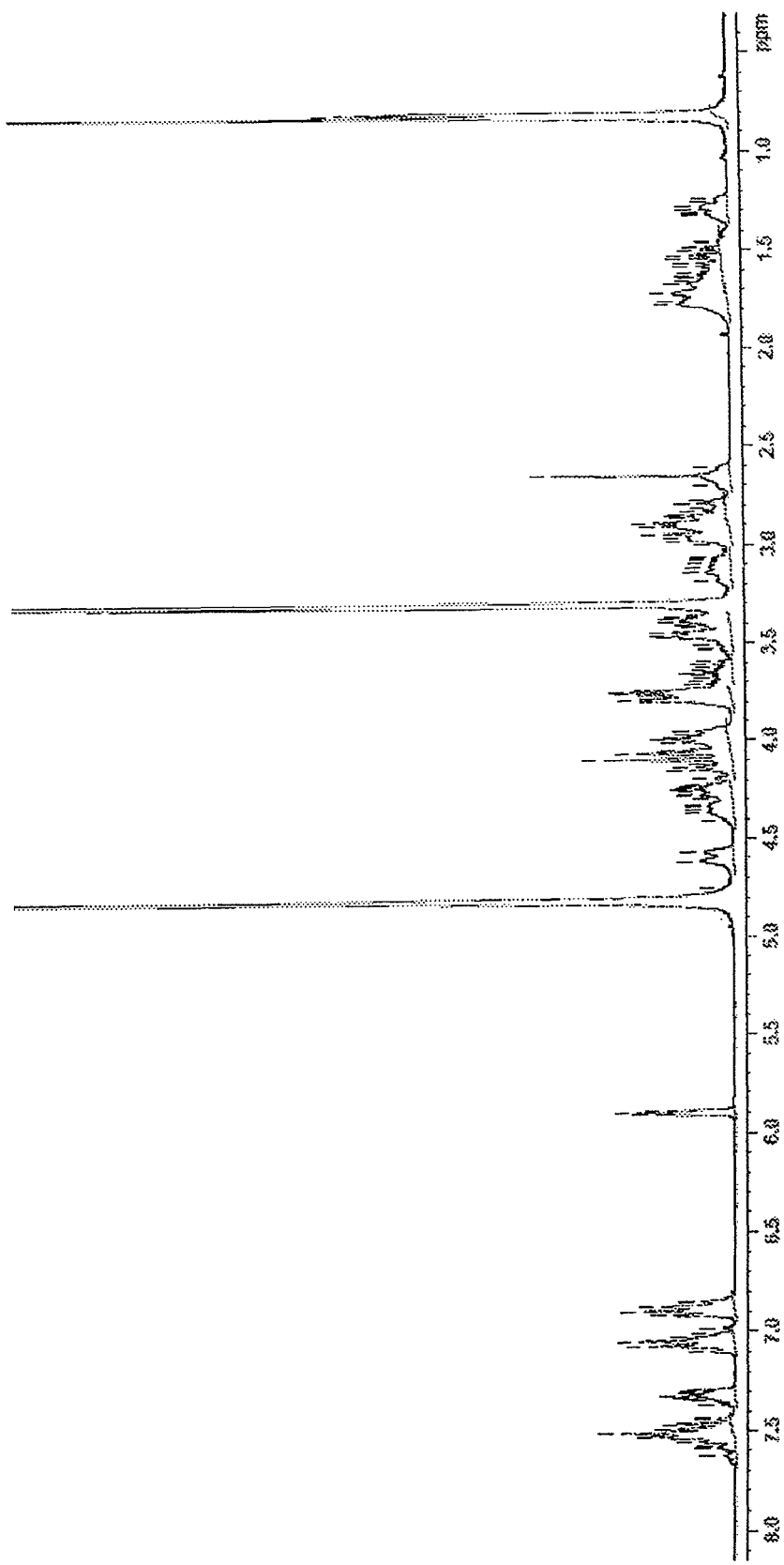
FIG. 22 depicts a $^1$H NMR trace (CD$_3$OD, 300 MHz) of compound I-511.
Figure 23:
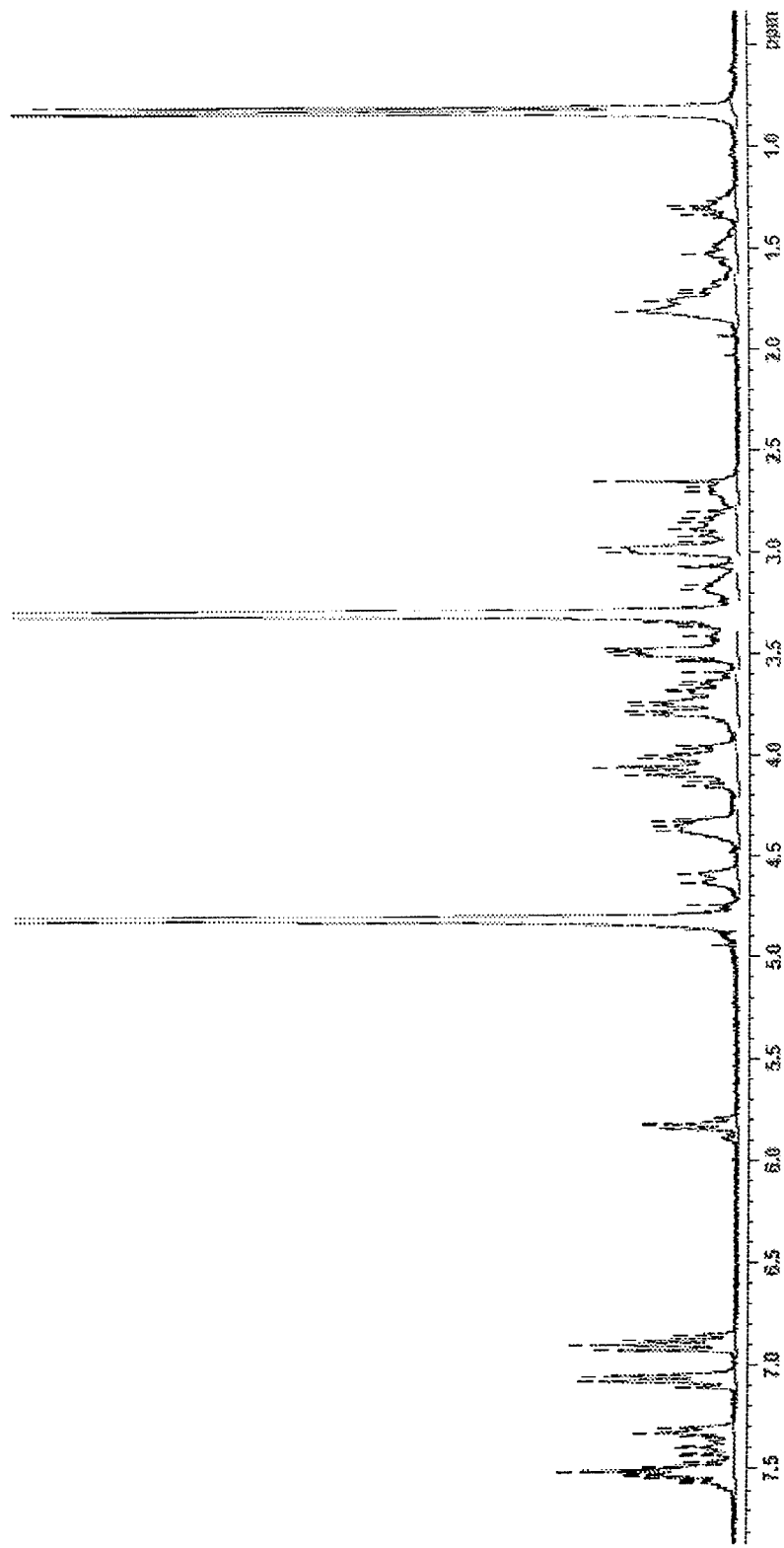
FIG. 23 depicts a $^1$H NMR trace (CD$_3$OD, 300 MHz) of compound I-512.
Figure 24:
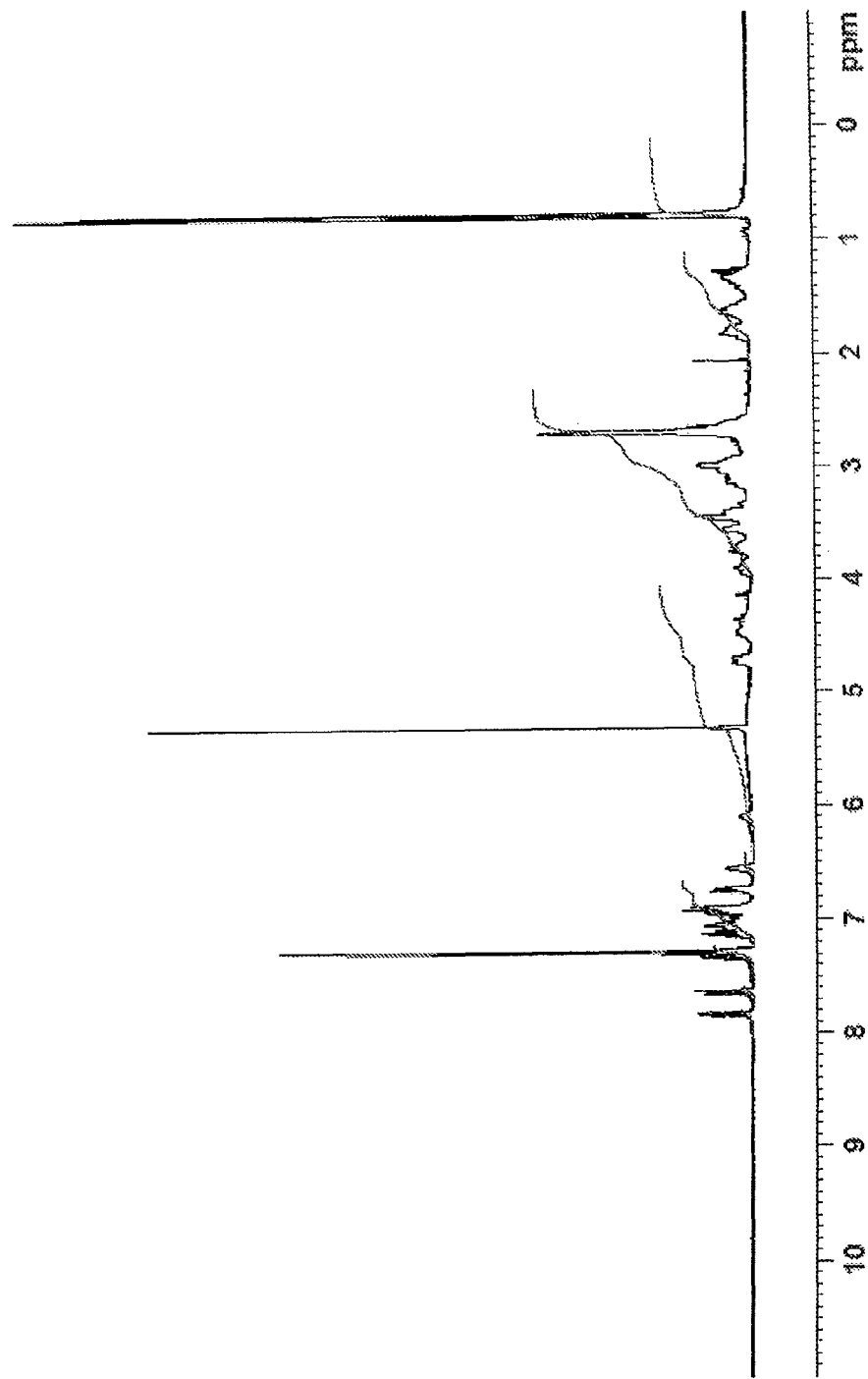
FIG. 24 depicts a $^1$H NMR trace (CDCl$_3$, 300 MHz) of compound I-513.
Figure 25:
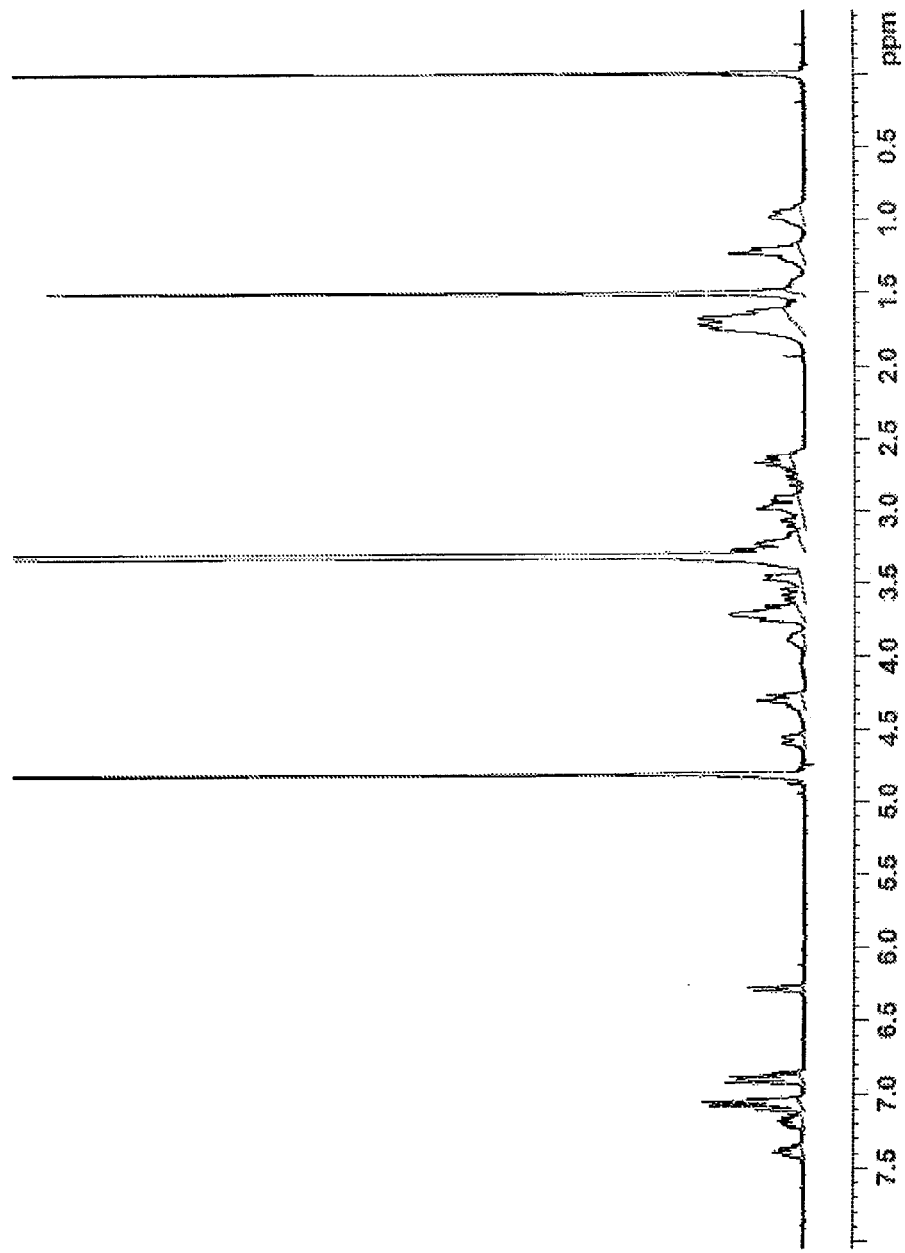
FIG. 25 depicts a $^1$H NMR trace (CD$_3$OD, 300 MHz) of compound I-514.
Figure 26:
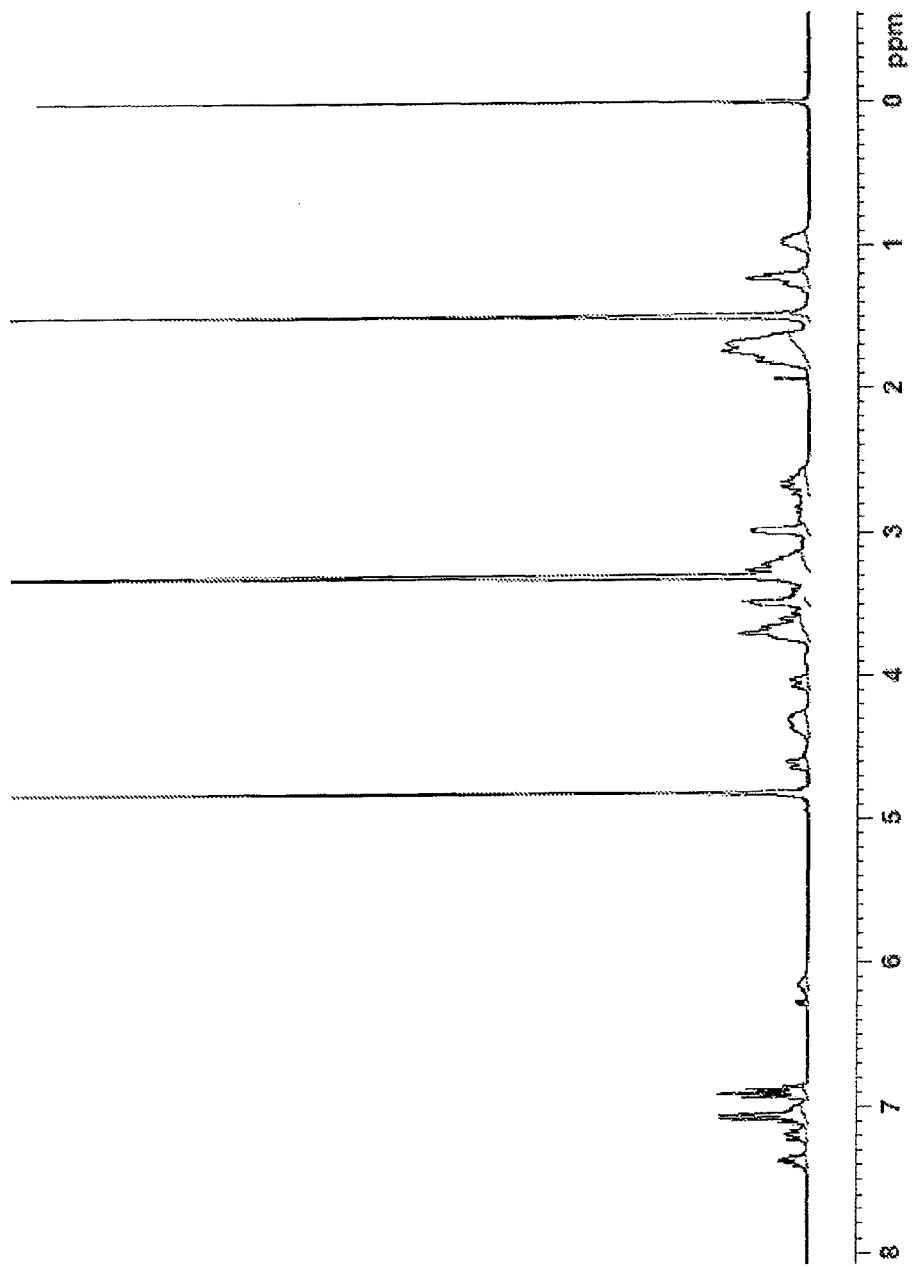
FIG. 26 depicts a $^1$H NMR trace (CD$_3$OD, 300 MHz) of compound I-515.
Figure 27:
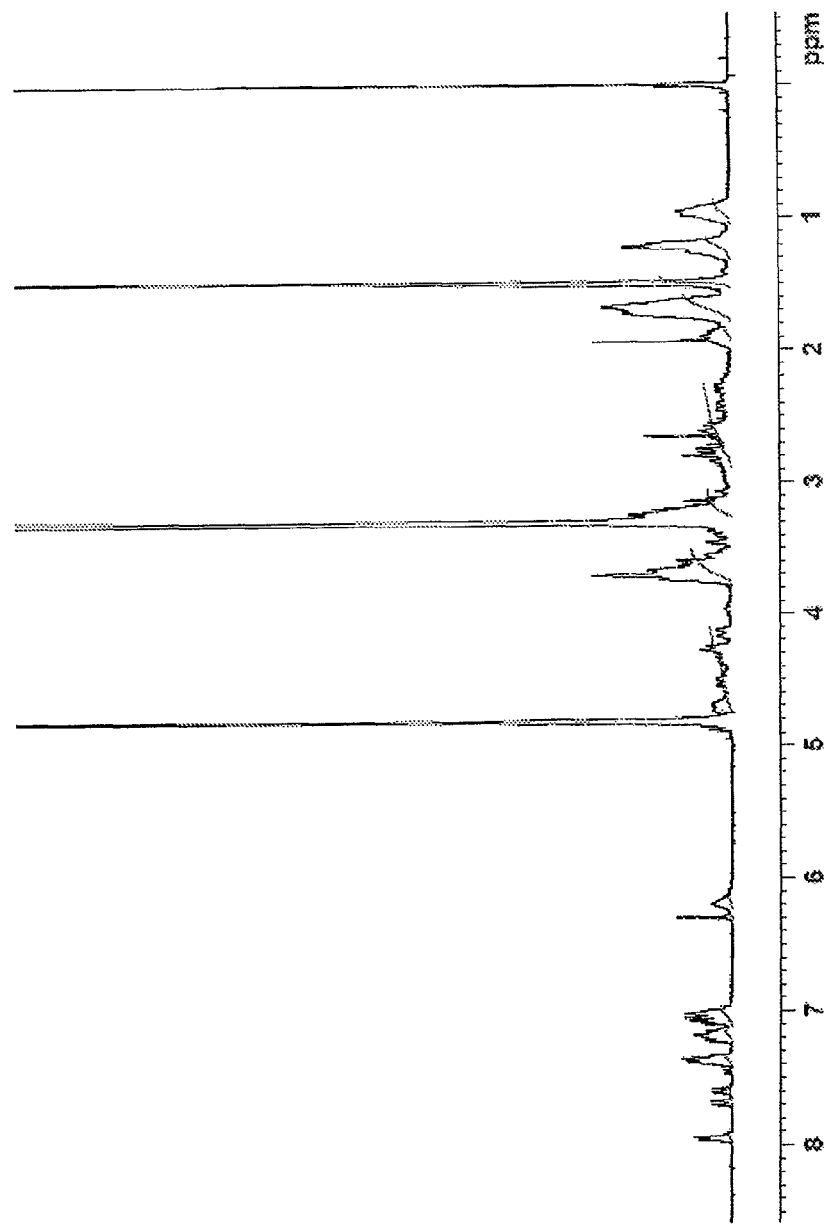
FIG. 27 depicts a $^1$H NMR trace (CD$_3$OD, 300 MHz) of compound I-516.
Figure 28:
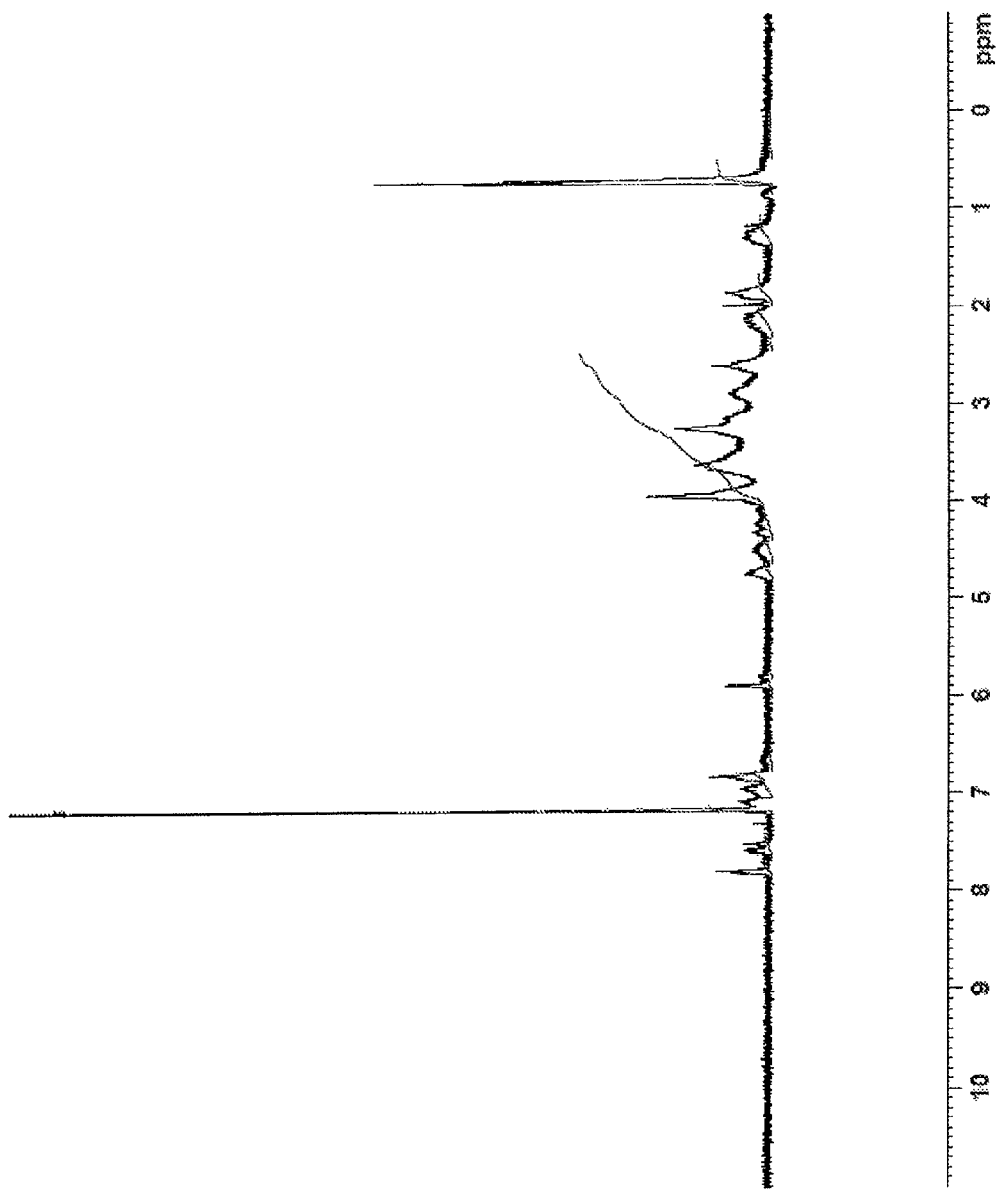
FIG. 28 depicts a $^1$H NMR trace (CDCl$_3$, 300 MHz) of compound I-517.
Figure 29:
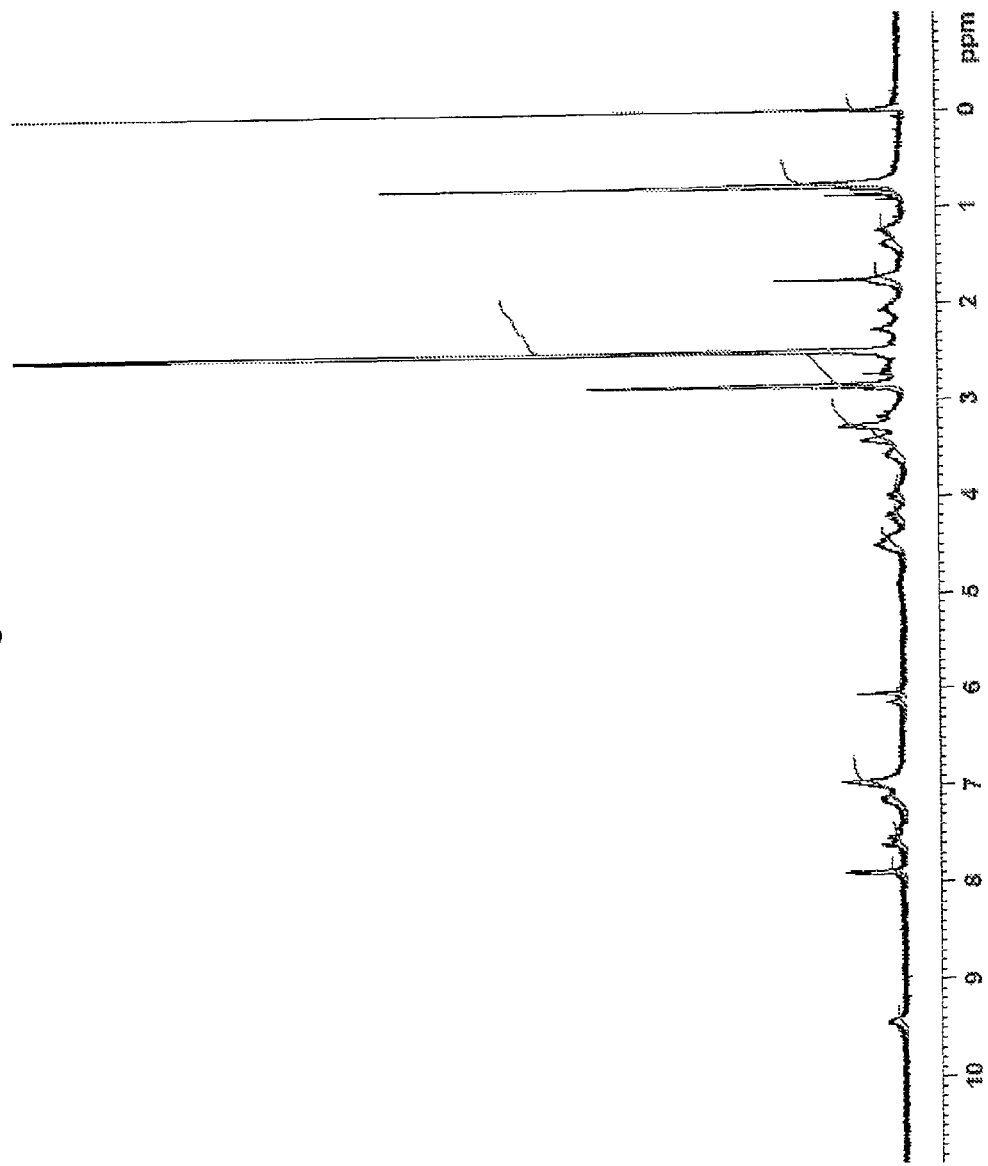
FIG. 29 depicts a $^1$H NMR trace (DMSO-d6, 300 MHz) of compound I-518.
Figure 30:
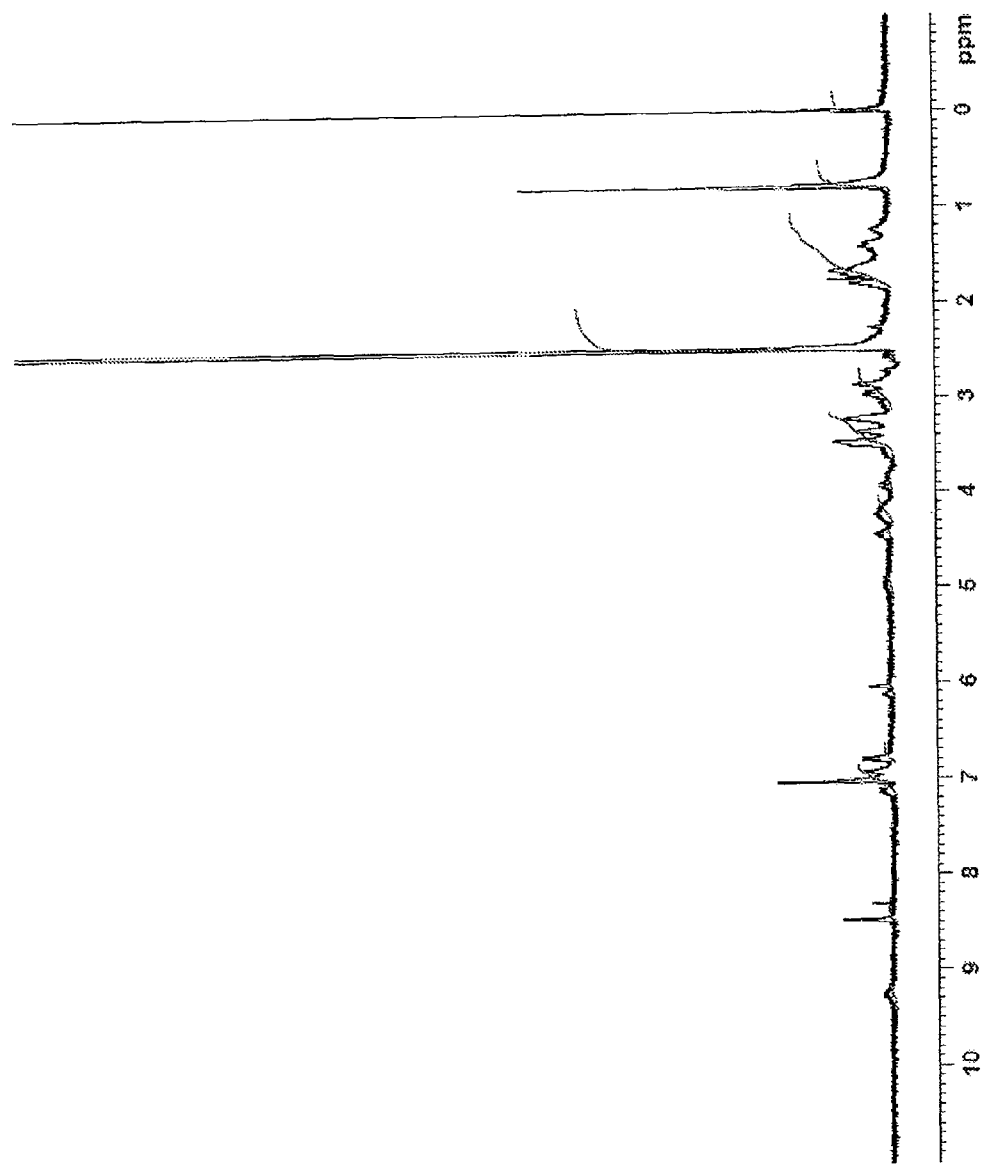
FIG. 30 depicts a $^1$H NMR trace (DMSO-d6, 300 MHz) of compound I-520.
Figure 31:
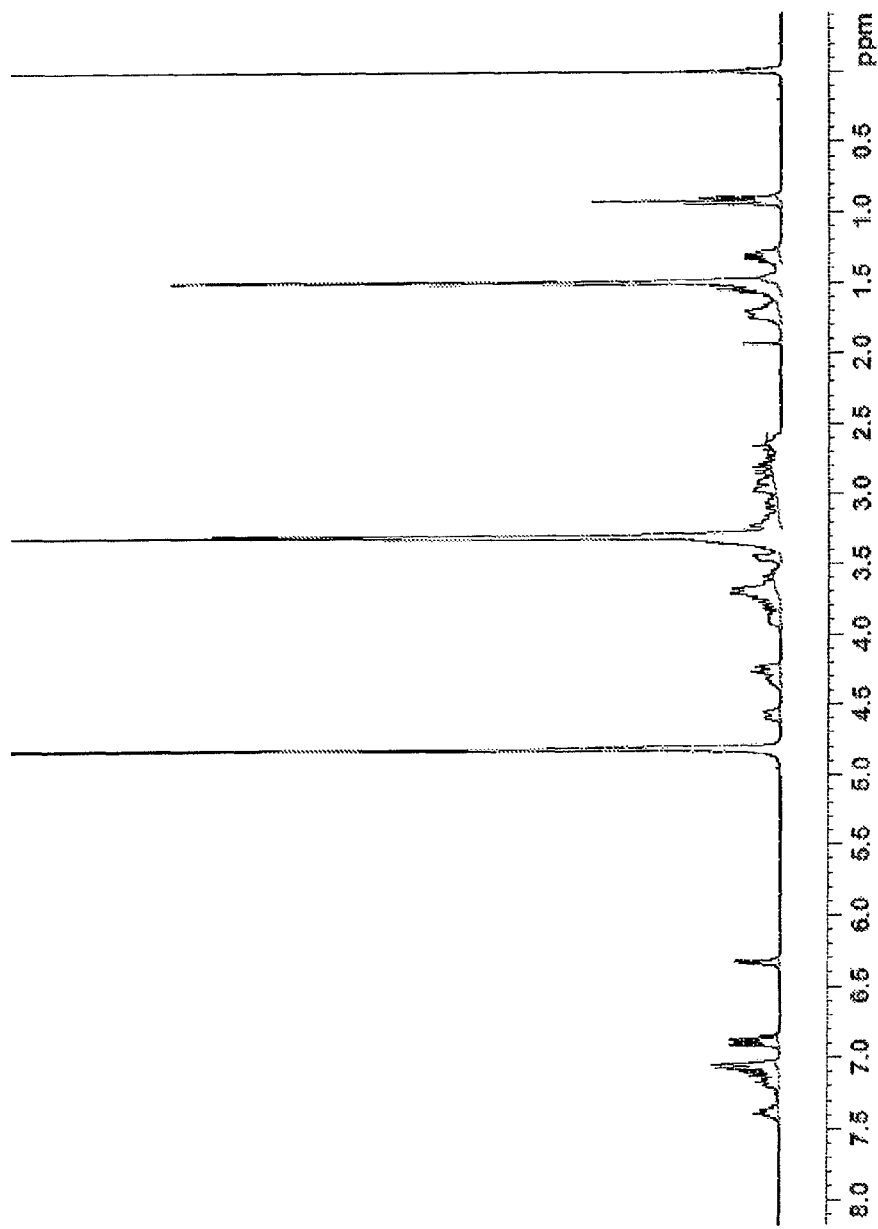
FIG. 31 depicts a $^1$H NMR trace (CD$_3$OD, 300 MHz) of compound I-521.
Figure 32:
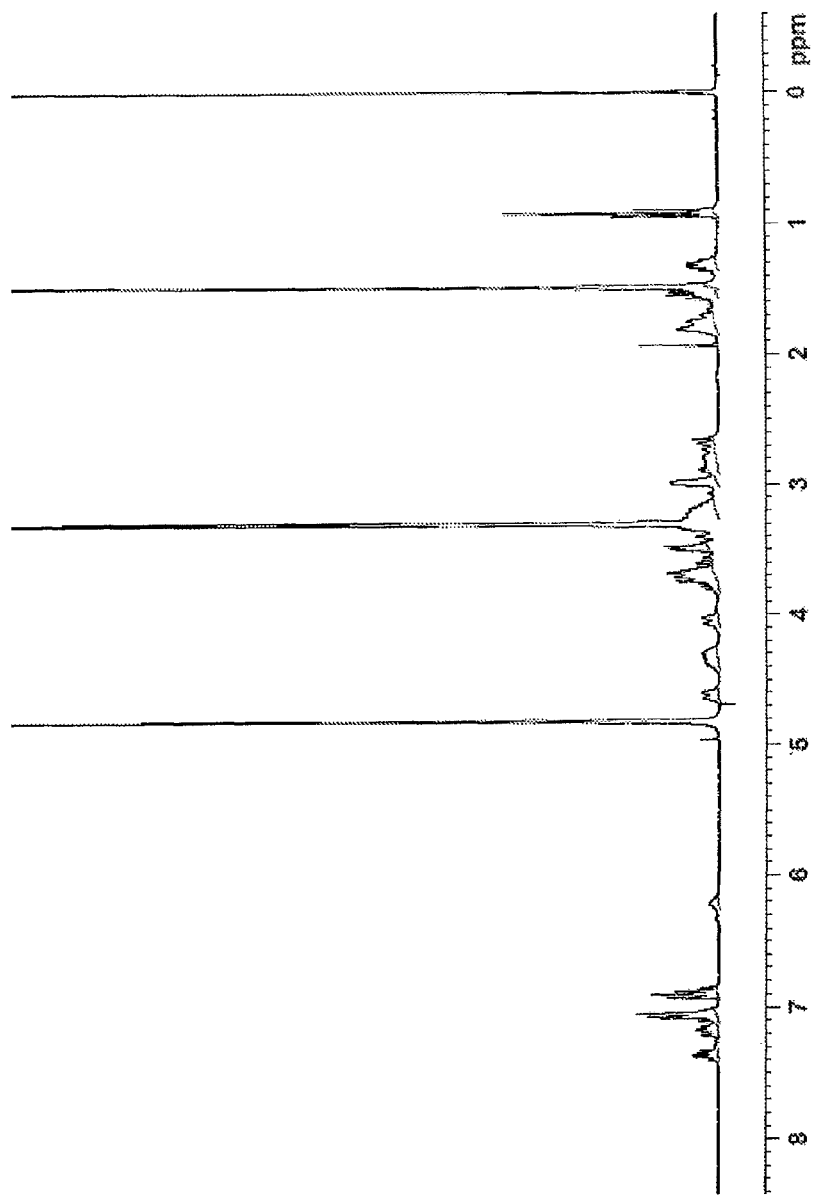
FIG. 32 depicts a $^1$H NMR trace (CD$_3$OD, 300 MHz) of compound I-522.
Figure 33:
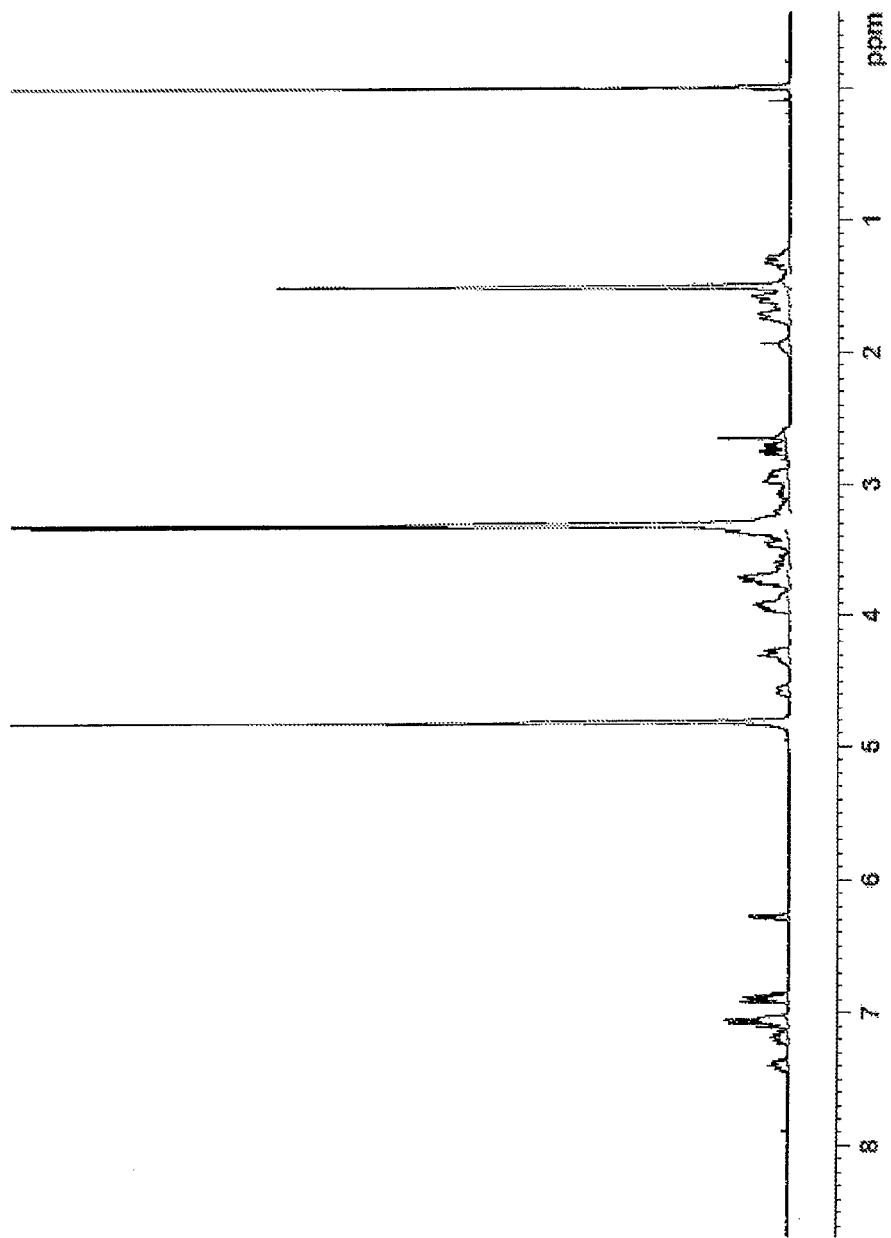
FIG. 33 depicts a $^1$H NMR trace (CD$_3$OD, 300 MHz) of compound I-523.
Figure 34:
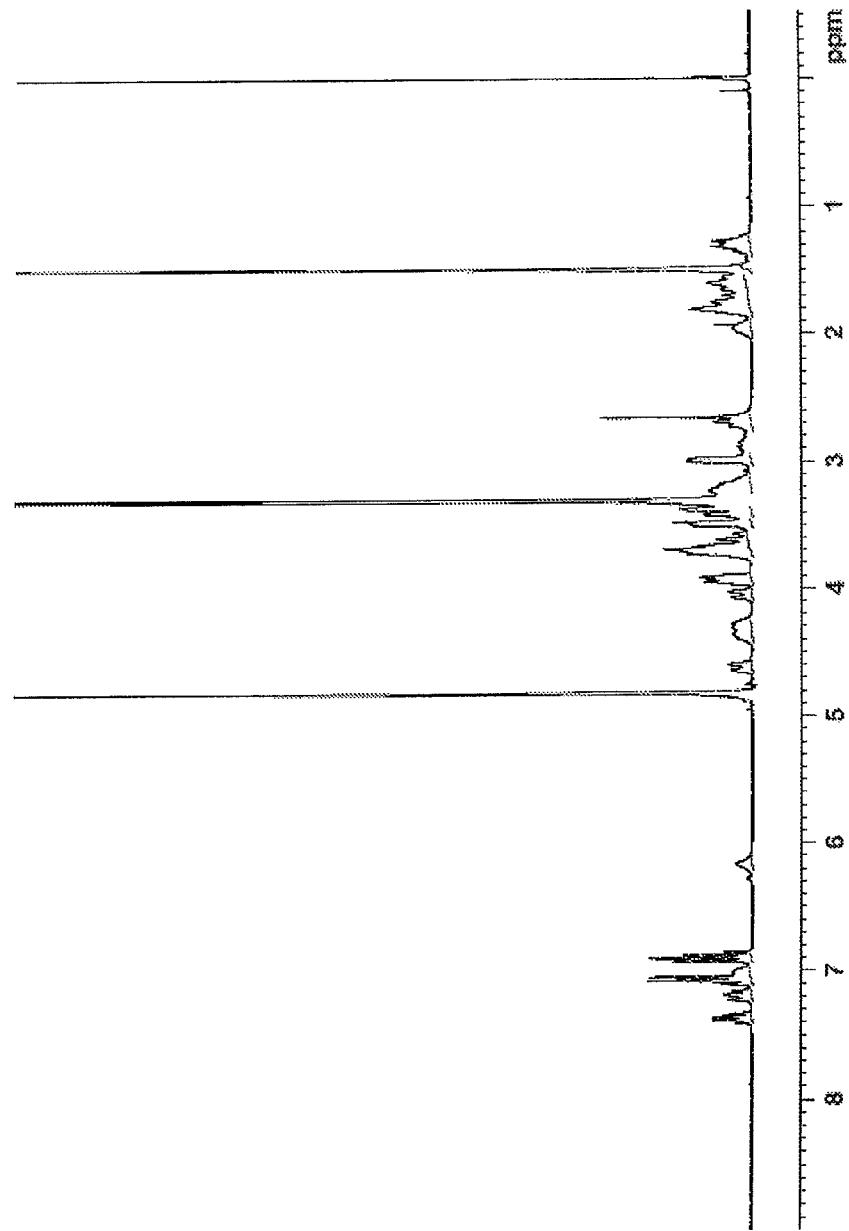
FIG. 34 depicts a $^1$H NMR trace (CD$_3$OD, 300 MHz) of compound I-524.
Figure 35:
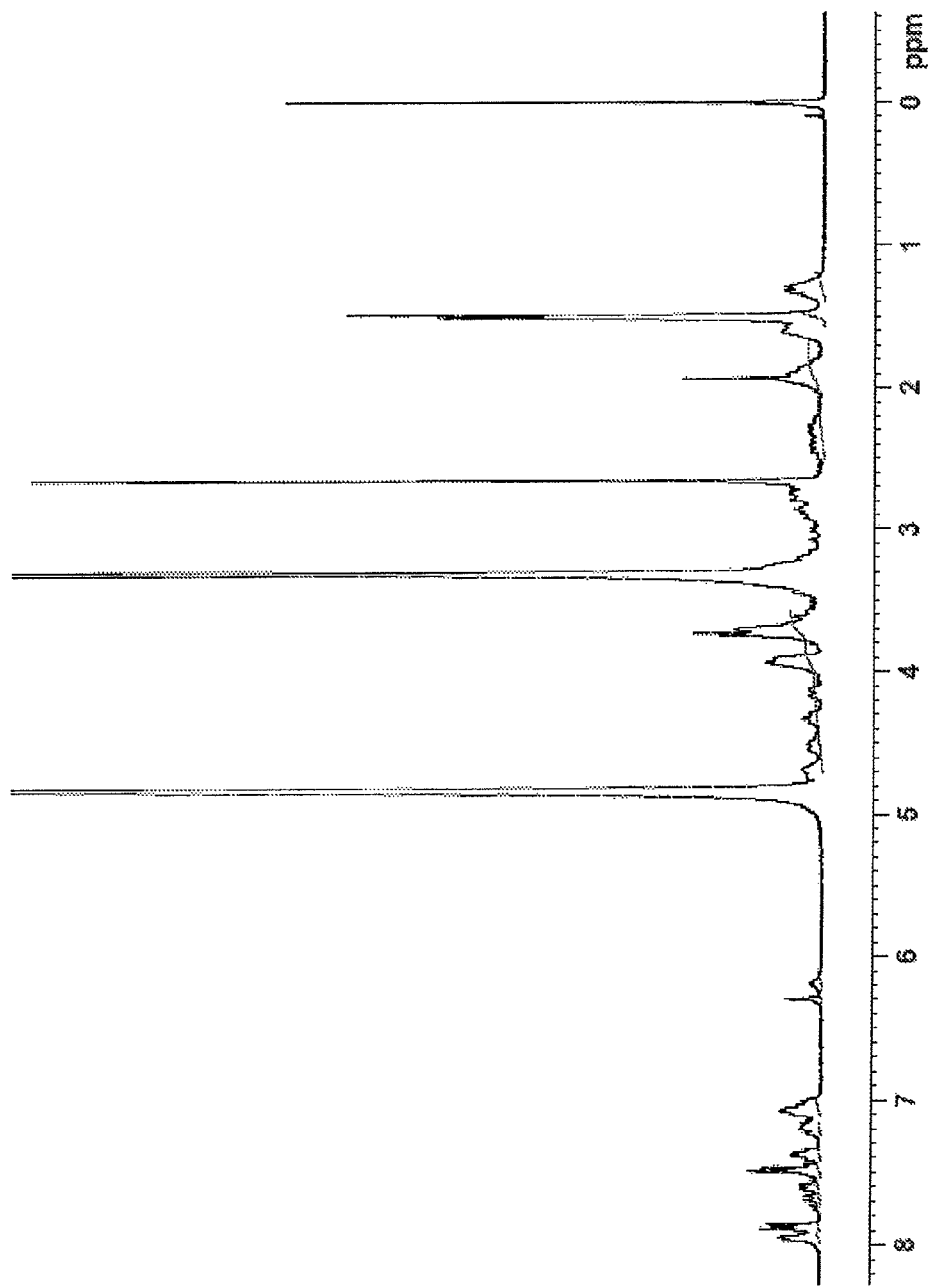
FIG. 35 depicts a $^1$H NMR trace (CD$_3$OD, 300 MHz) of compound I-525.
Figure 36:
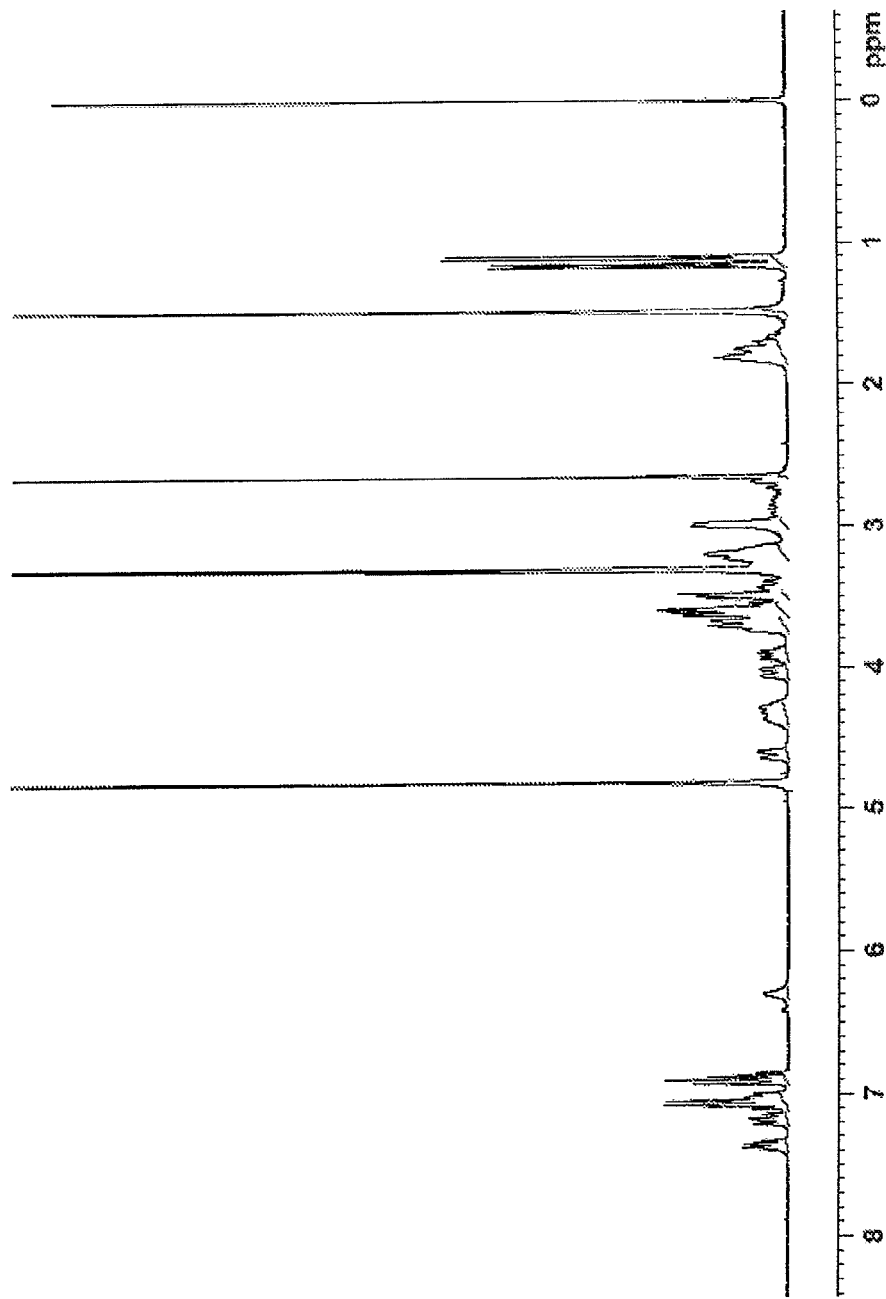
FIG. 36 depicts a $^1$H NMR trace (CD$_3$OD, 300 MHz) of compound I-526.
Figure 37:
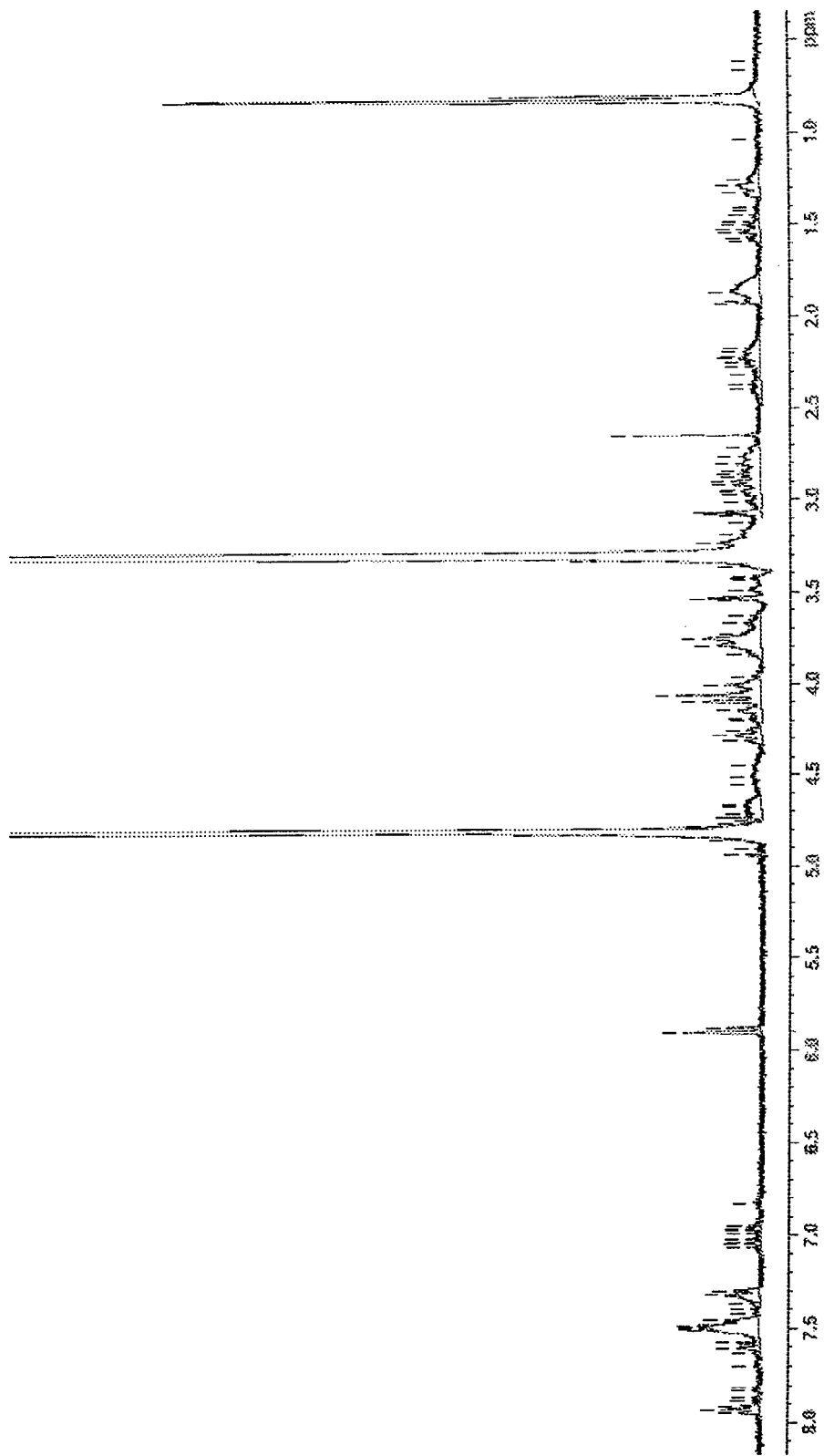
FIG. 37 depicts a $^1$H NMR trace (CD$_3$OD, 300 MHz) of compound I-527.
Figure 38:
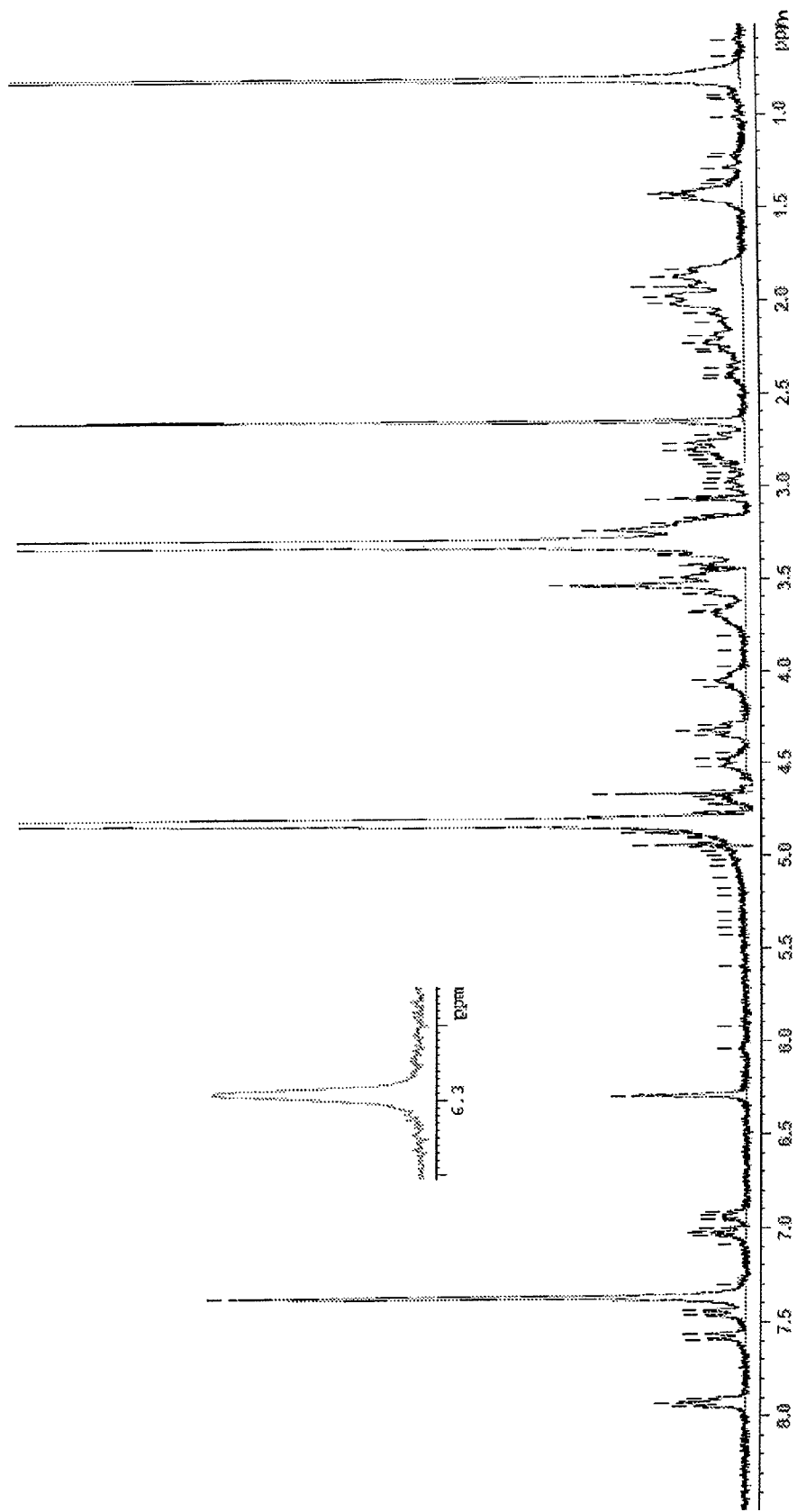
FIG. 38 depicts a $^1$H NMR trace (CD$_3$OD, 300 MHz) of compound I-528.
Figure 39:
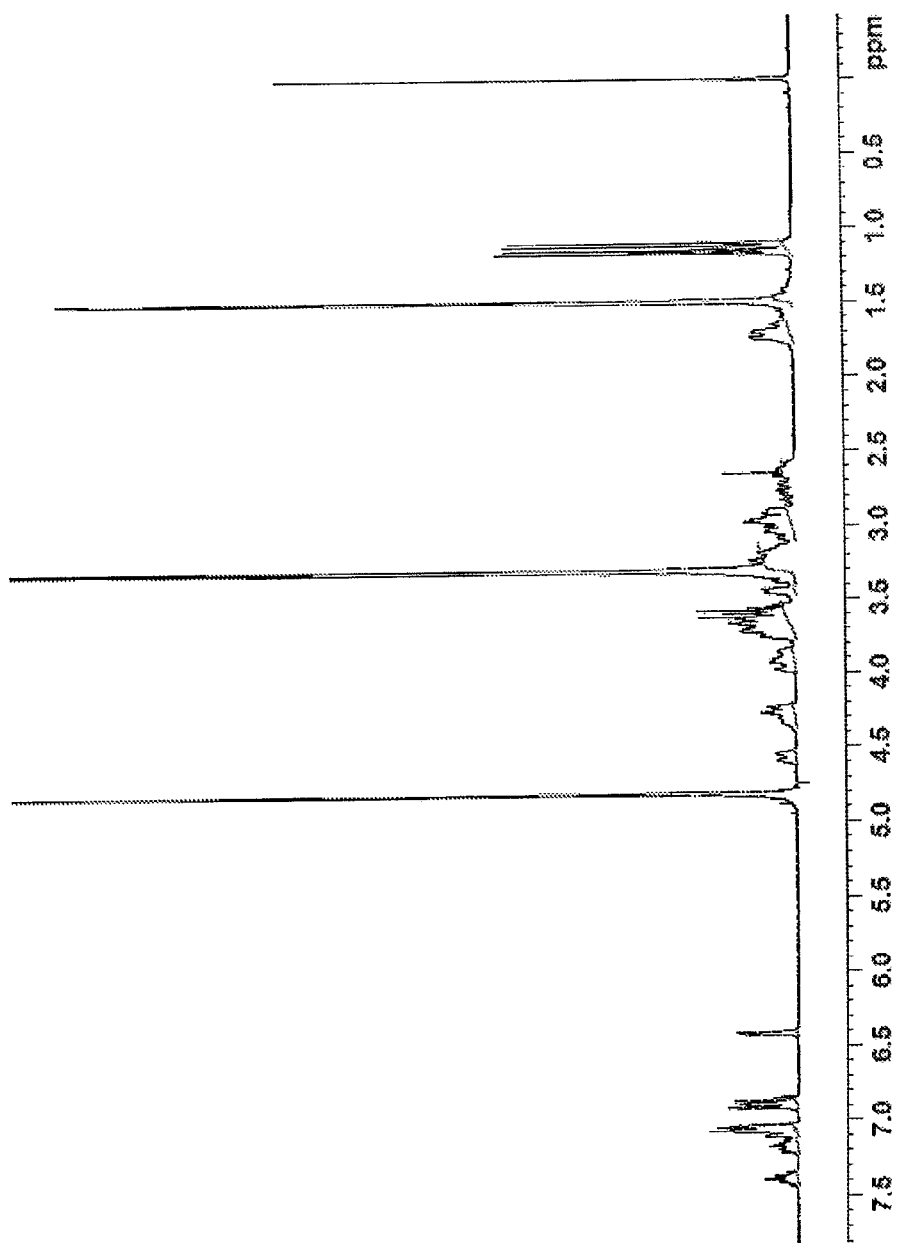
FIG. 39 depicts a $^1$H NMR trace (CD$_3$OD, 300 MHz) of compound I-529.
Figure 40:
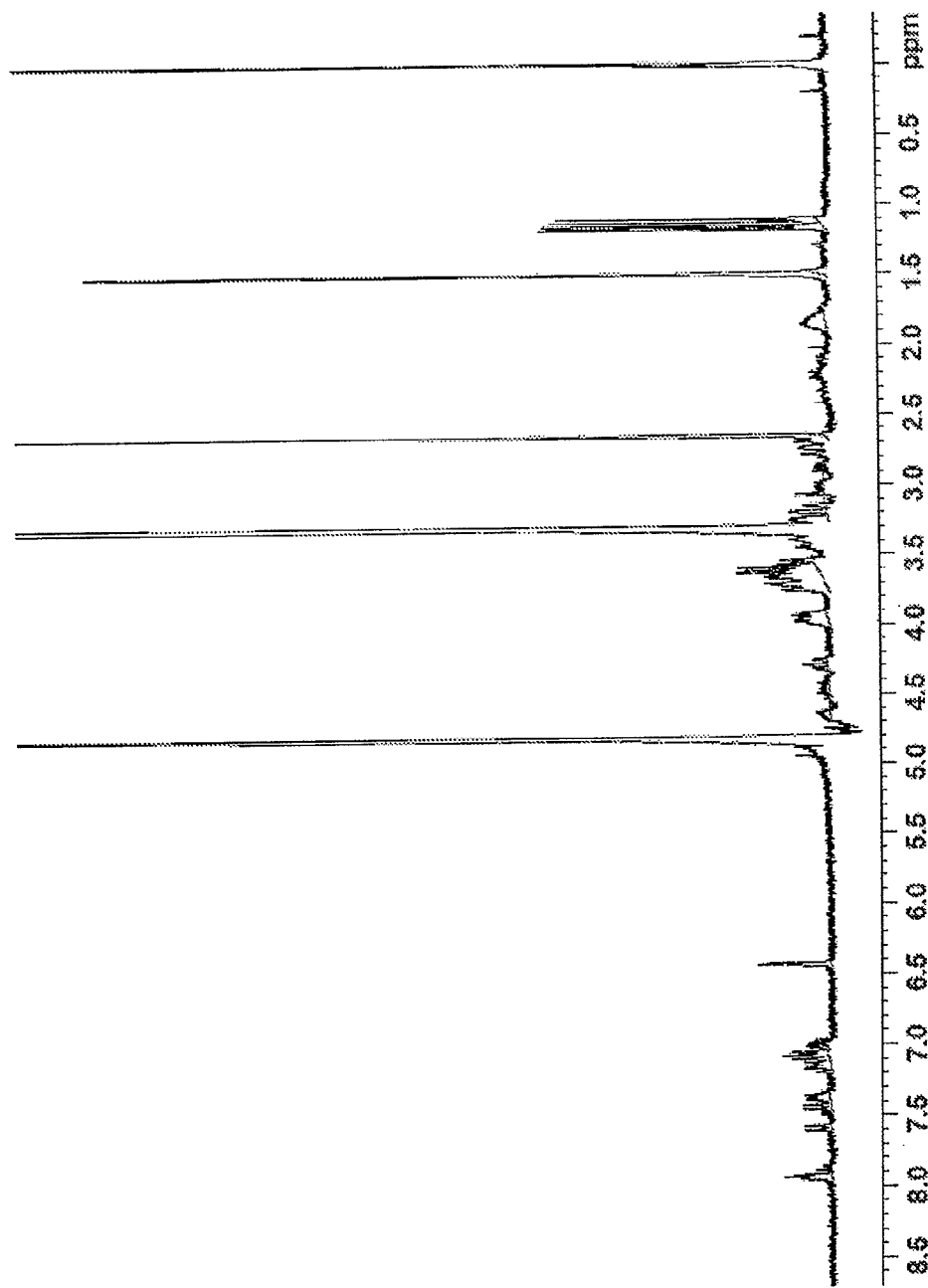
FIG. 40 depicts a $^1$H NMR trace (CD$_3$OD, 300 MHz) of compound I-530.
Figure 41:
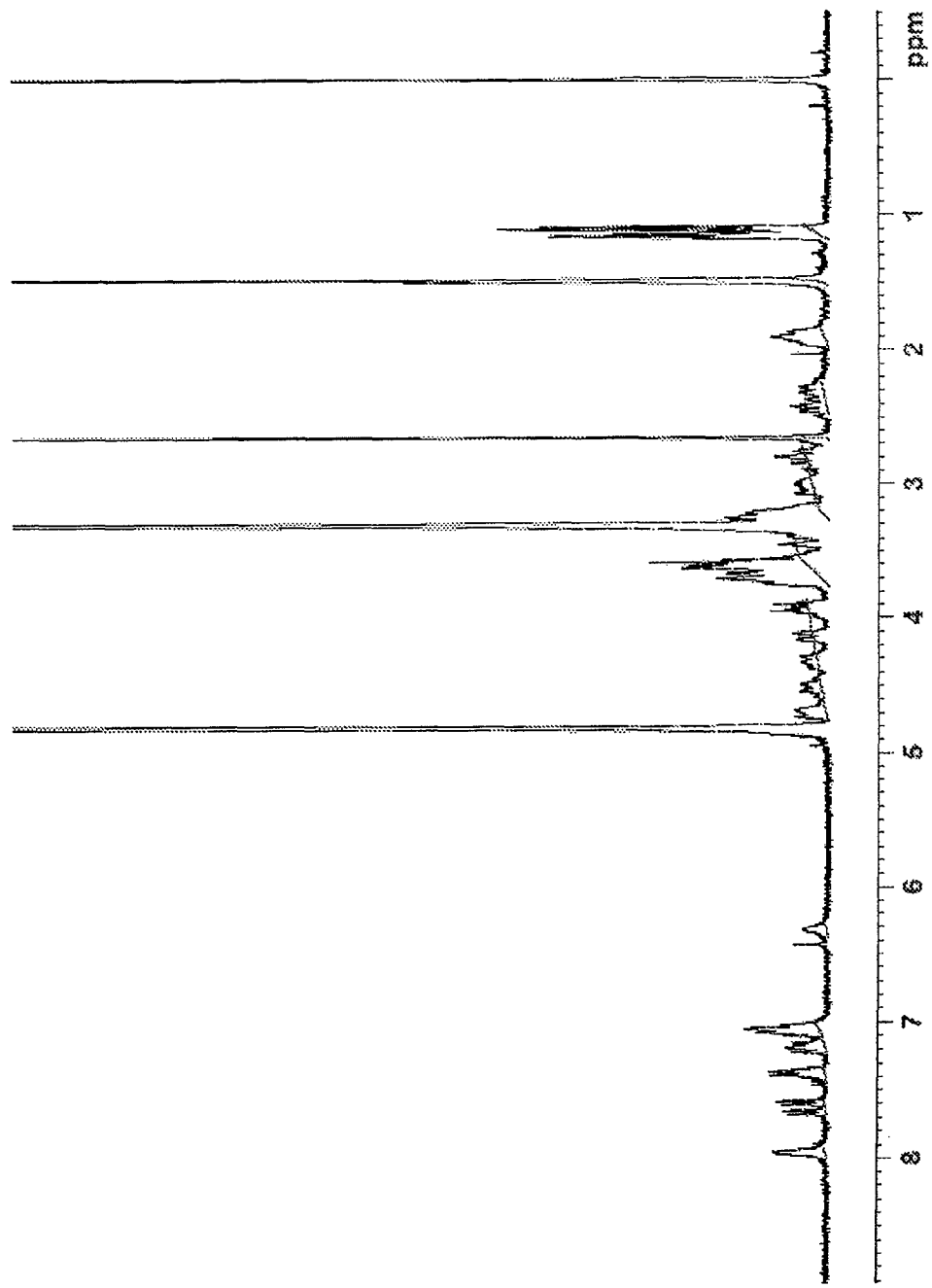
FIG. 41 depicts a $^1$H NMR trace (CD$_3$OD, 300 MHz) of compound I-531.
Figure 42:
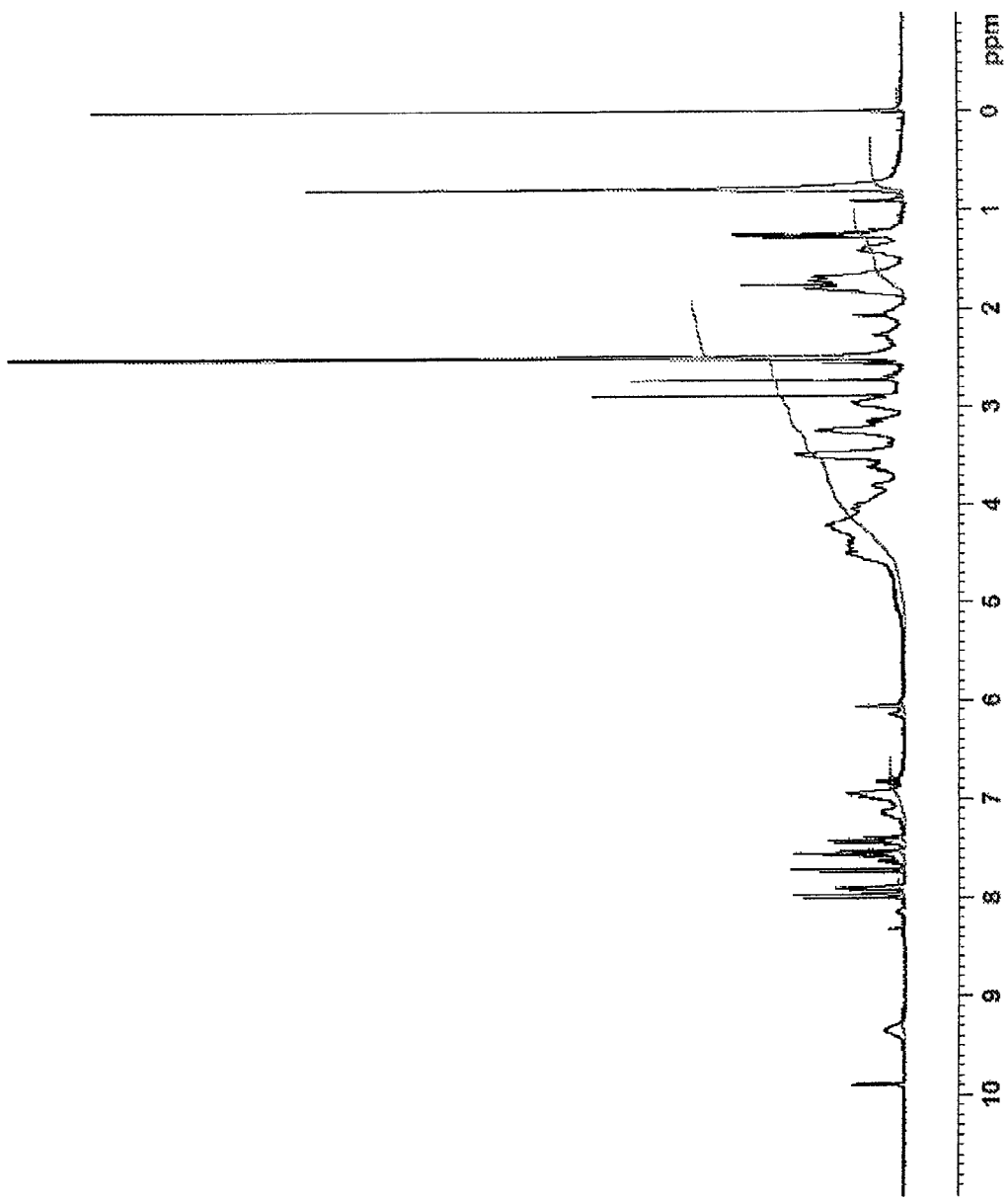
FIG. 42 depicts a $^1$H NMR trace (DMSO-d6, 300 MHz) of compound I-532.
Figure 43:
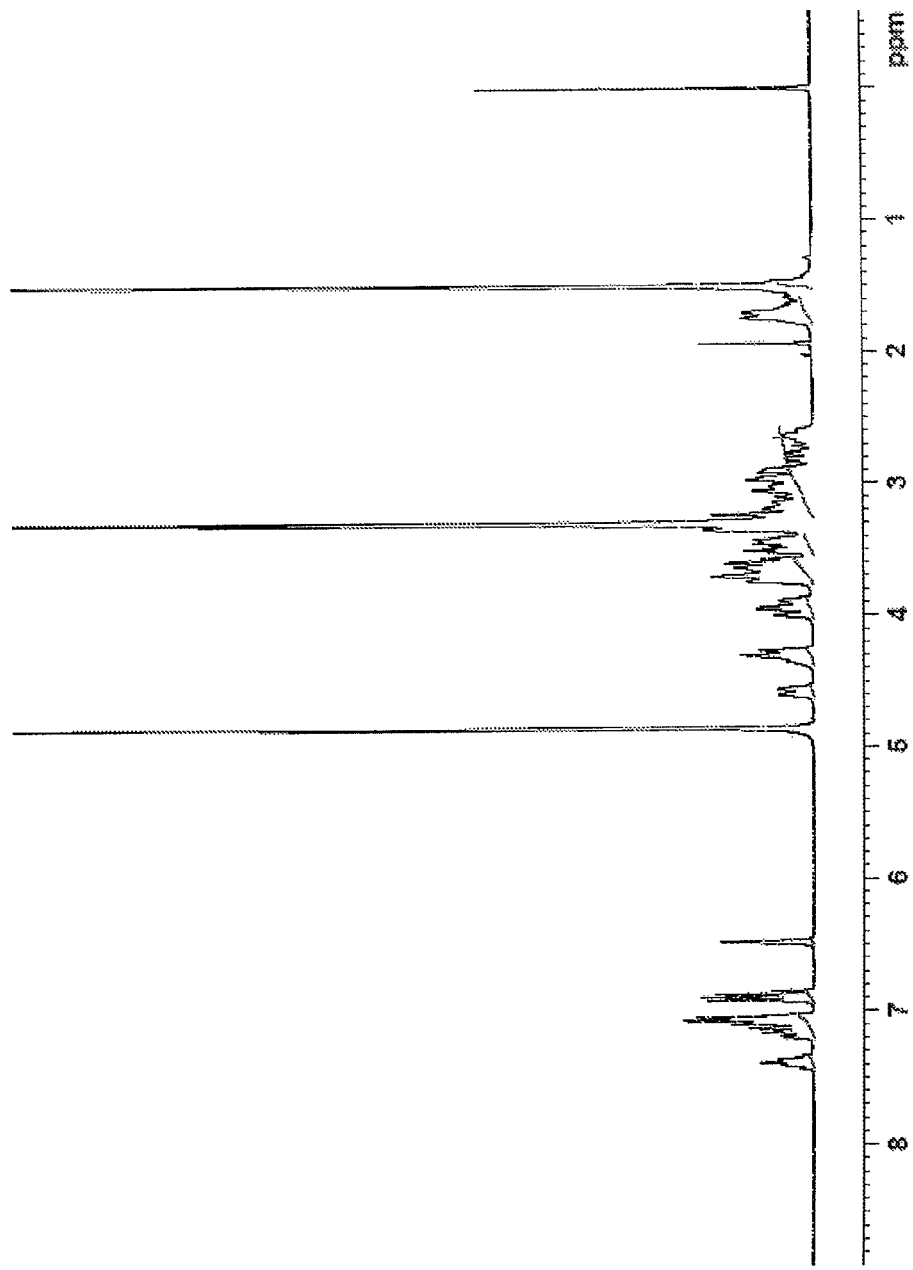
FIG. 43 depicts a $^1$H NMR trace (CD$_3$OD, 300 MHz) of compound I-533.
Figure 44:
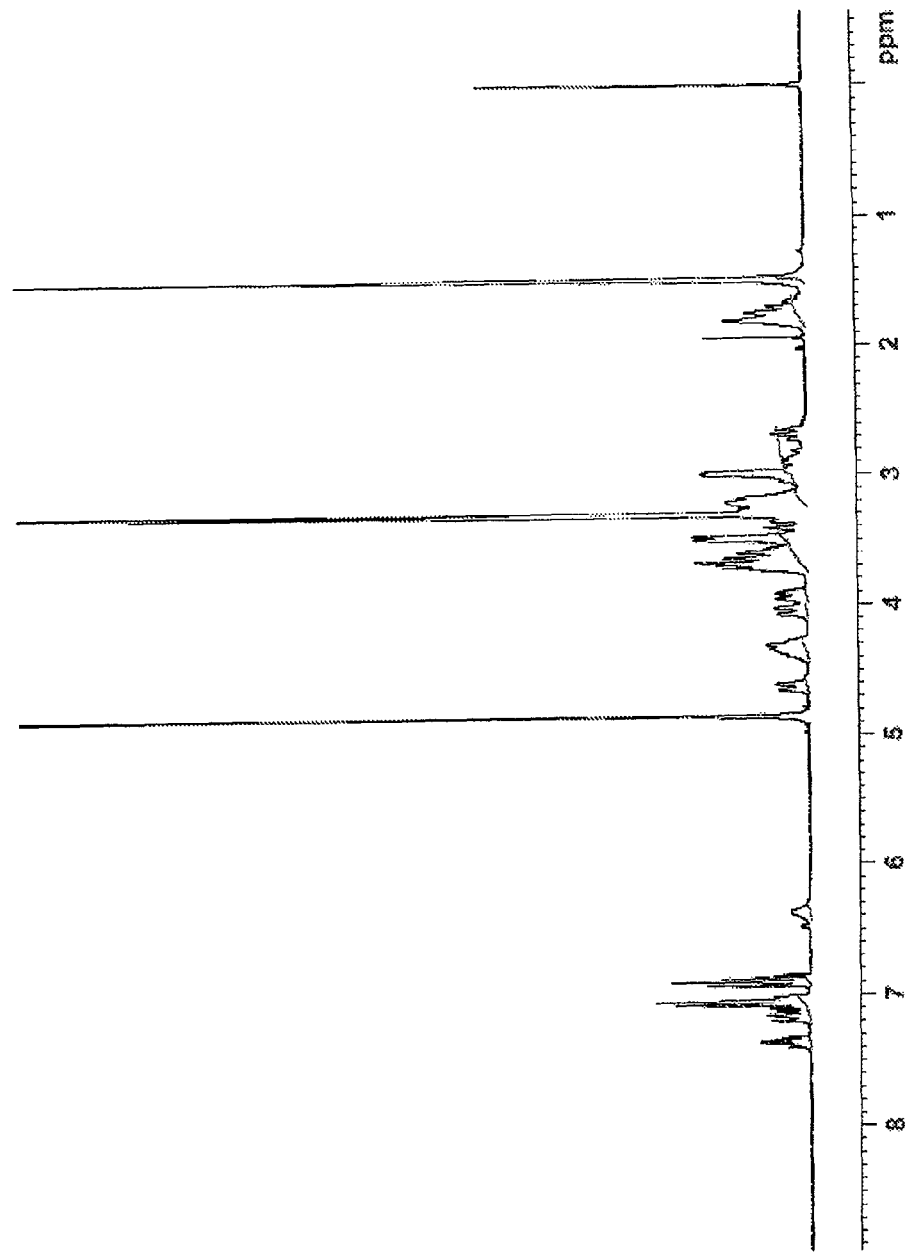
FIG. 44 depicts a $^1$H NMR trace (CD$_3$OD, 300 MHz) of compound I-534.
Figure 45:
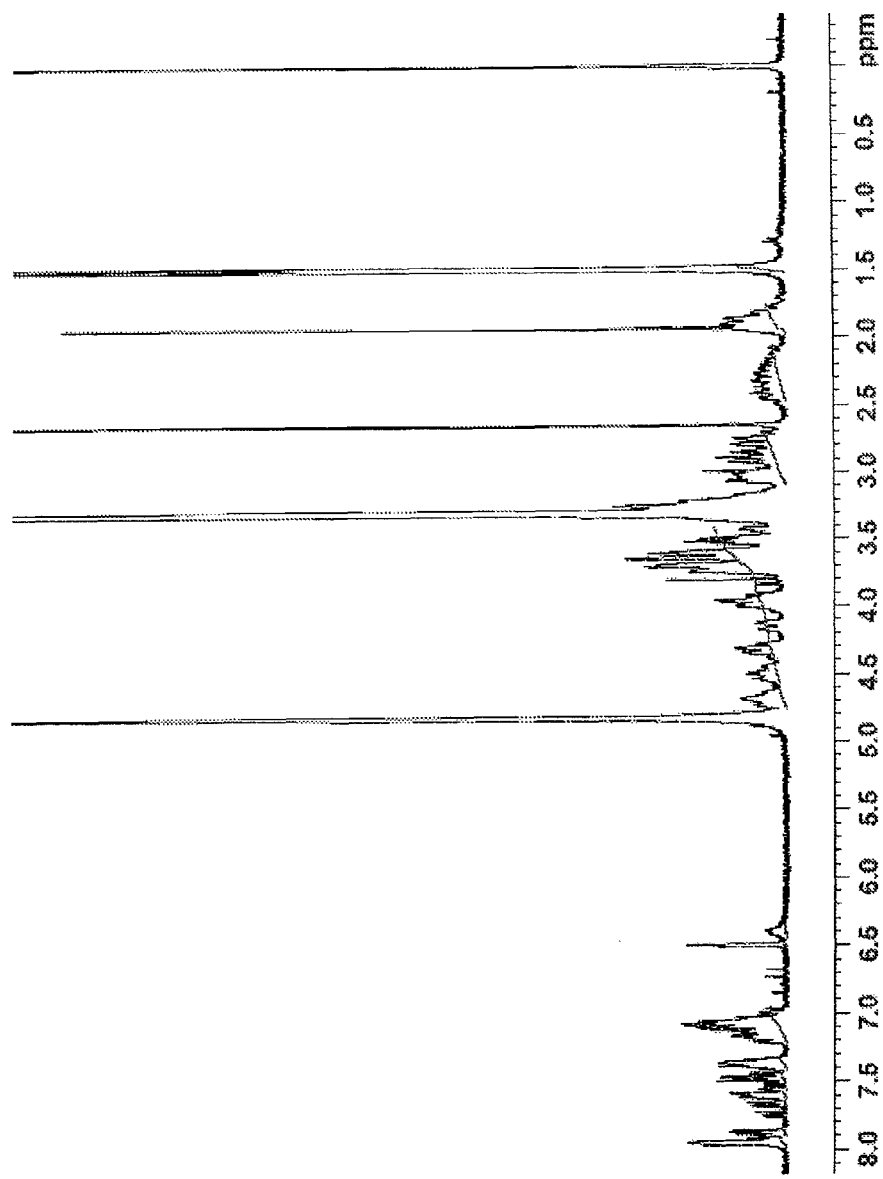
FIG. 45 depicts a $^1$H NMR trace (CD$_3$OD, 300 MHz) of compound I-535.
Figure 46:
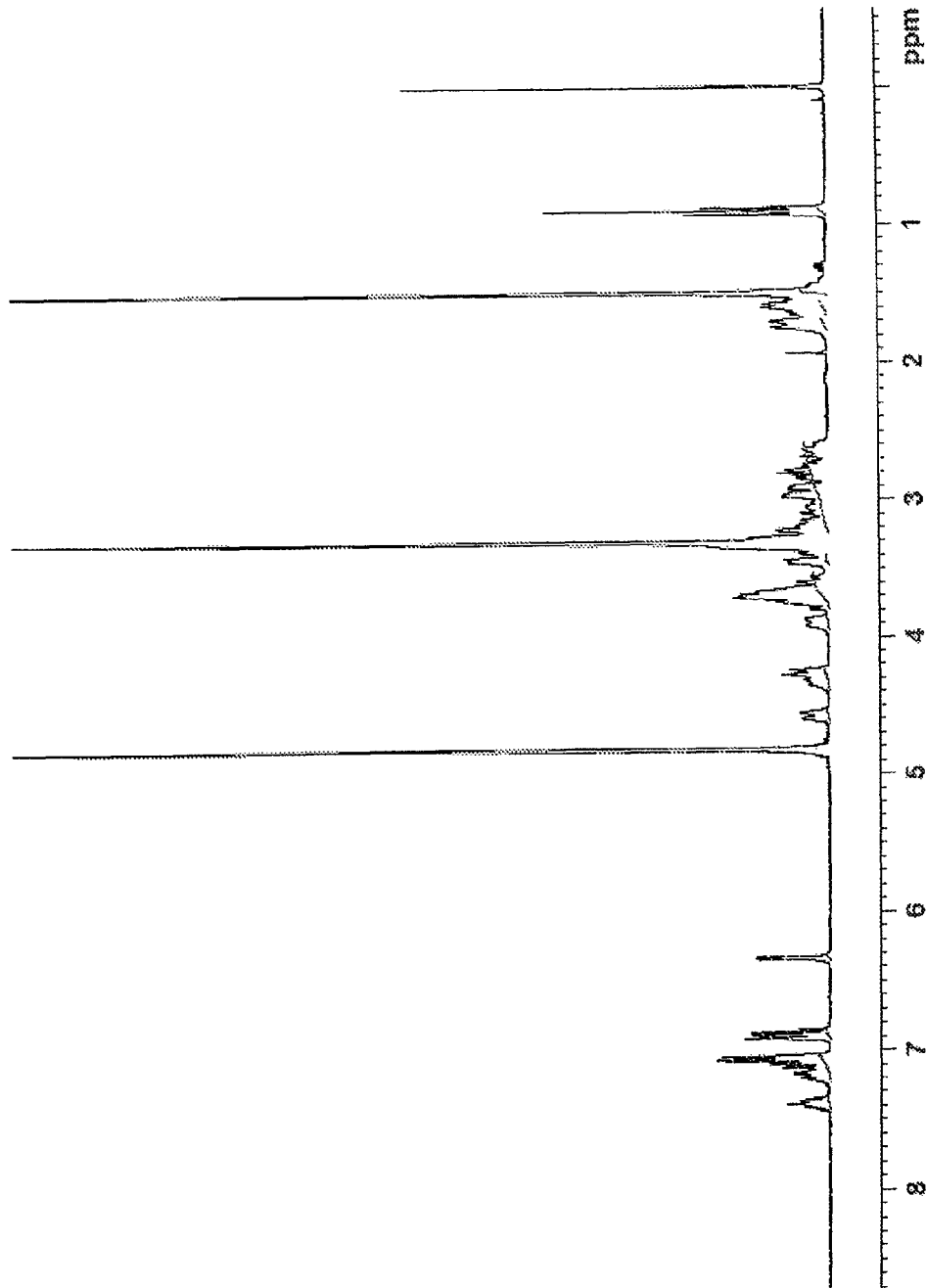
FIG. 46 depicts a $^1$H NMR trace (CD$_3$OD, 300 MHz) of compound I-536.
Figure 47:
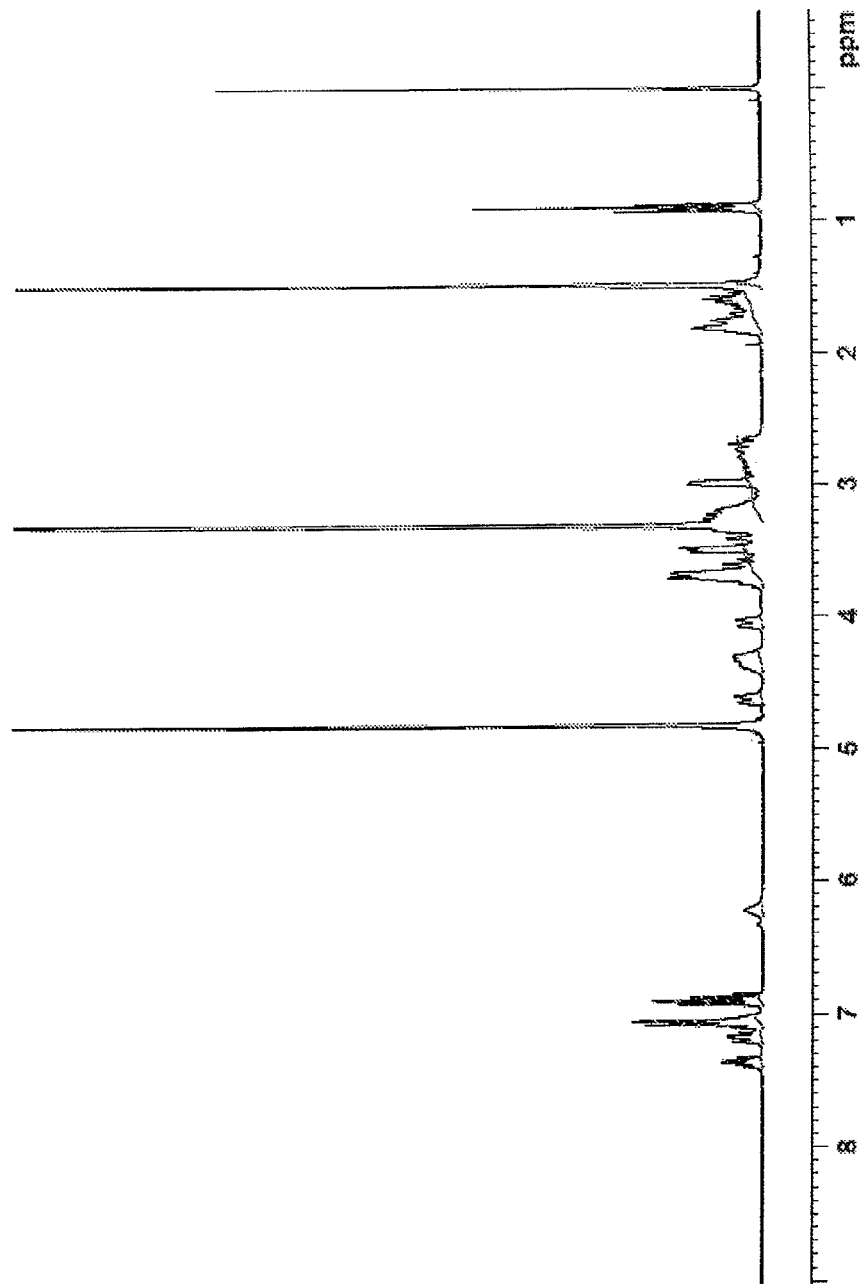
FIG. 47 depicts a $^1$H NMR trace (CD$_3$OD, 300 MHz) of compound I-537.
Figure 48:
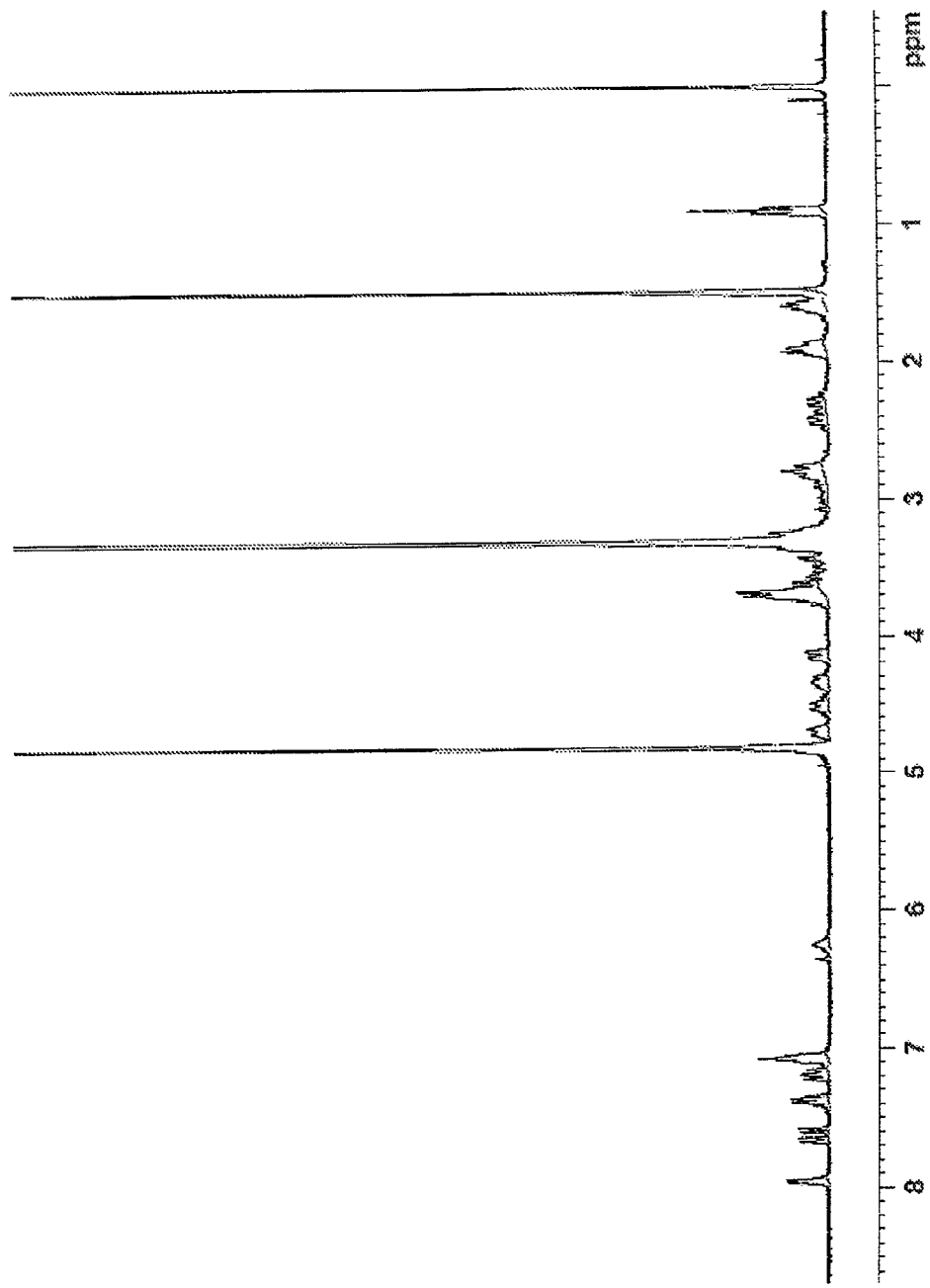
FIG. 48 depicts a $^1$H NMR trace (CD$_3$OD, 300 MHz) of compound I-538.
Figure 49:
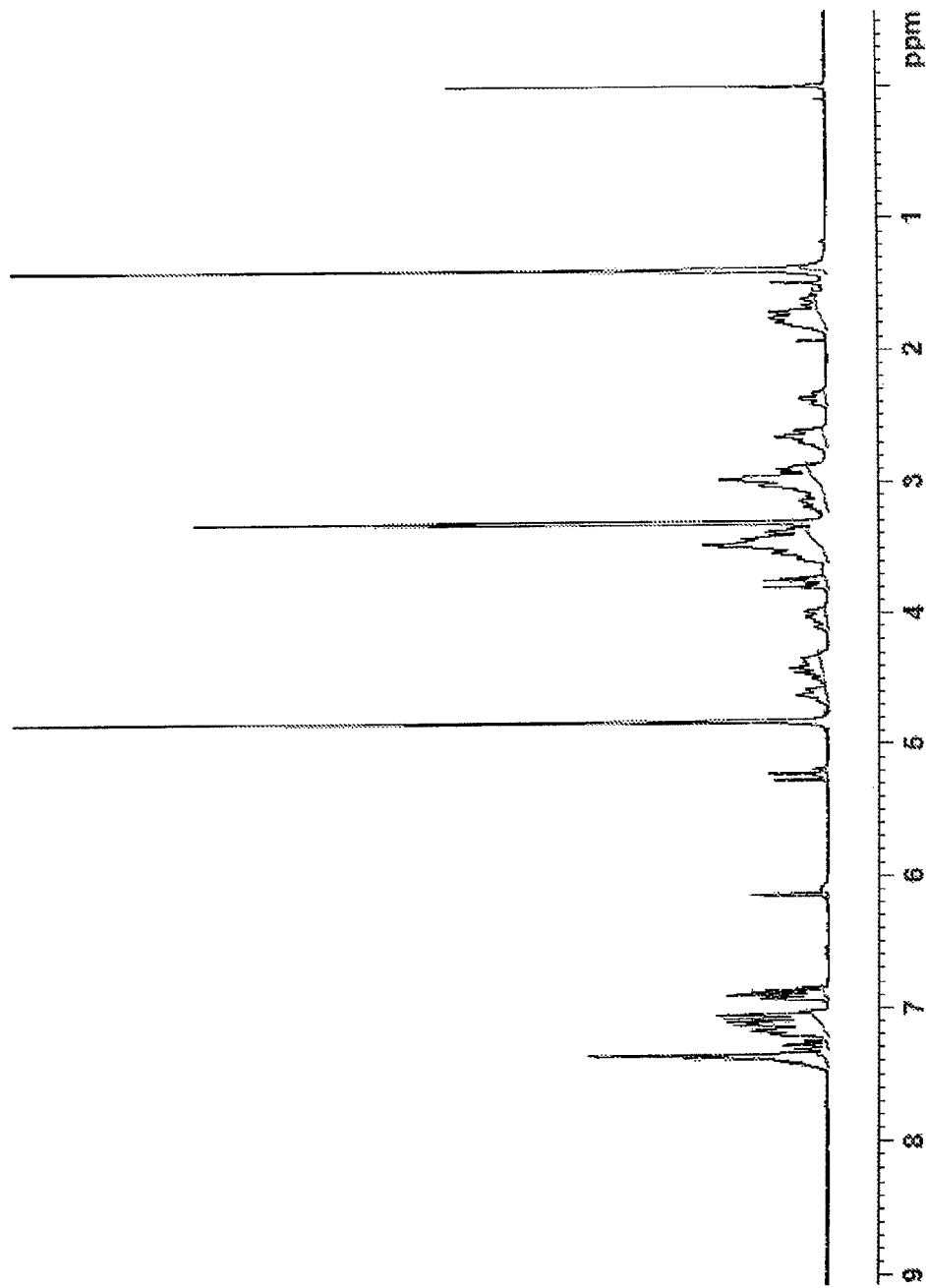
FIG. 49 depicts a $^1$H NMR trace (CD$_3$OD, 300 MHz) of compound I-539.
Figure 50:
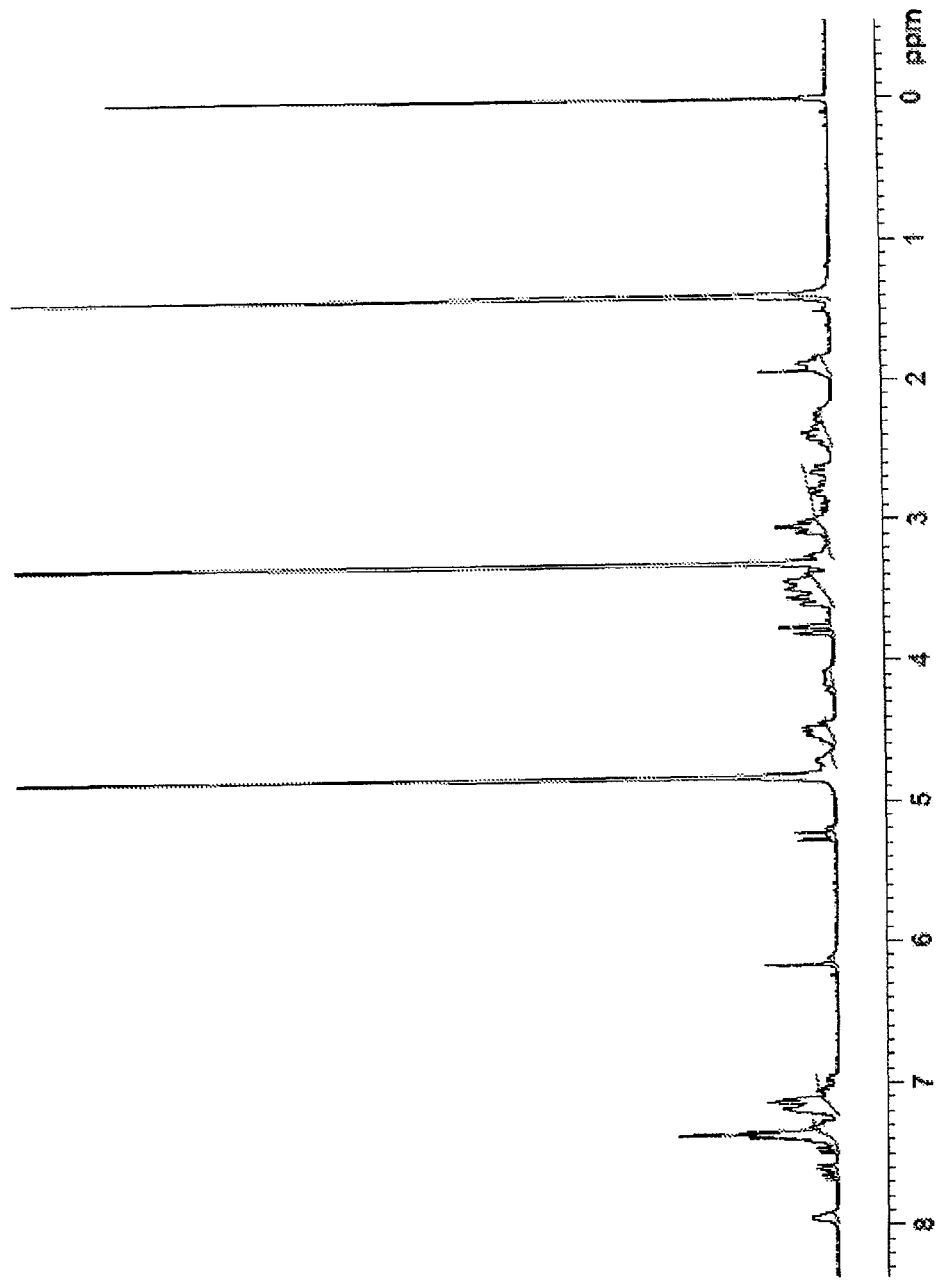
FIG. 50 depicts a $^1$H NMR trace (CD$_3$OD, 300 MHz) of compound I-540.
Figure 51:
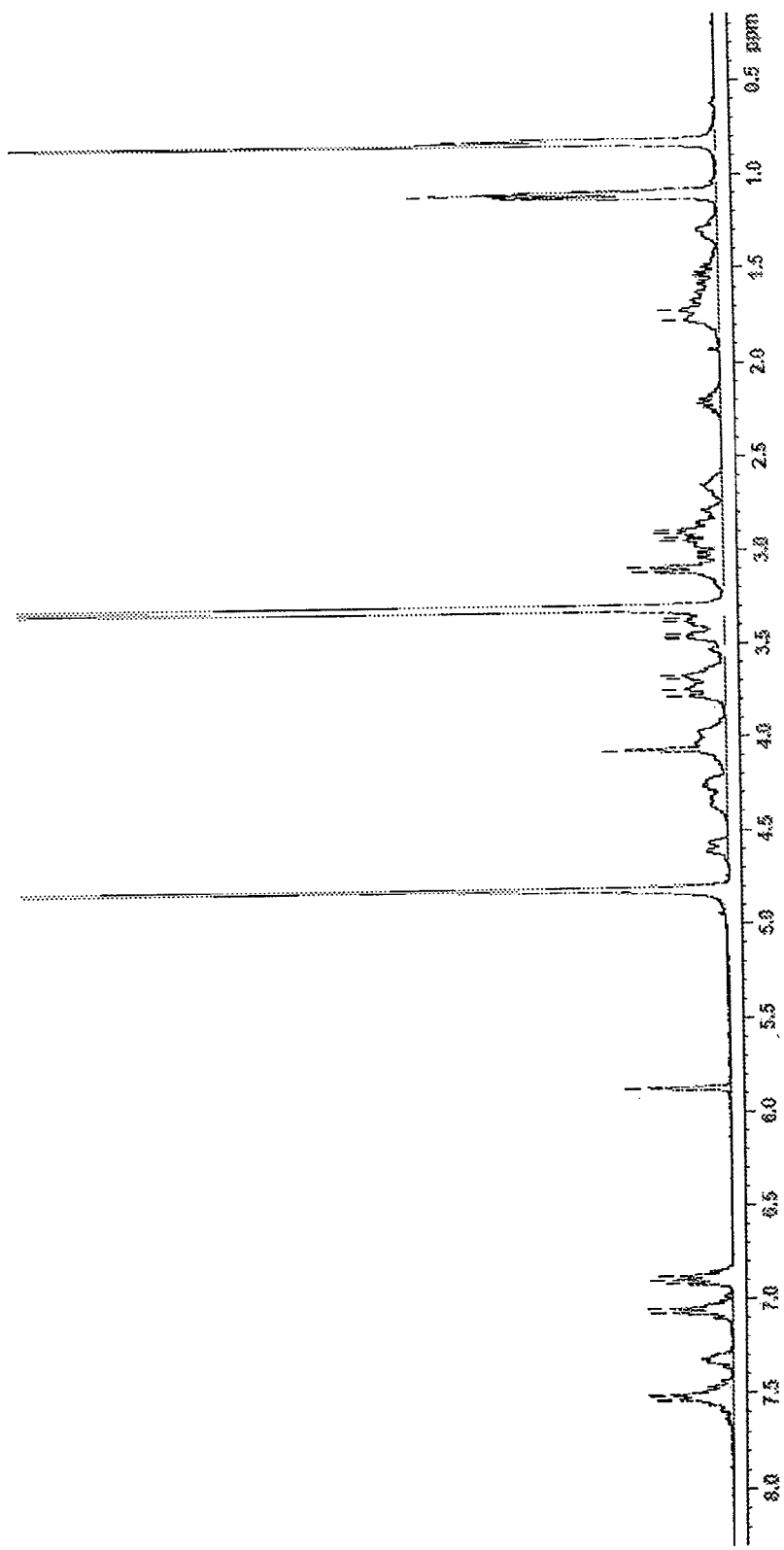
FIG. 51 depicts a $^1$H NMR trace (CD$_3$OD, 300 MHz) of compound I-541.
Figure 52:
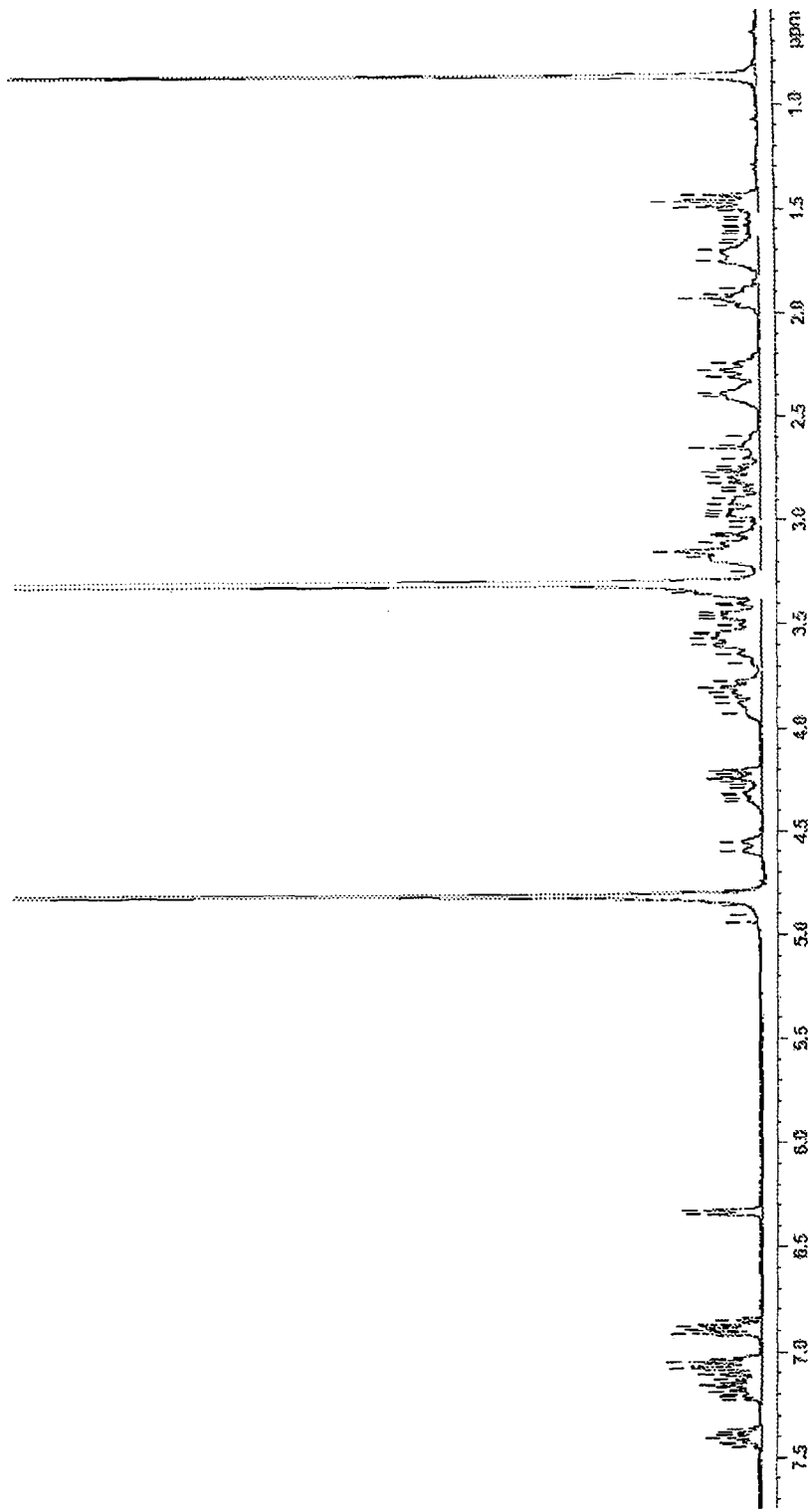
FIG. 52 depicts a $^1$H NMR trace (CD$_3$OD, 300 MHz) of compound I-542.
Figure 53:
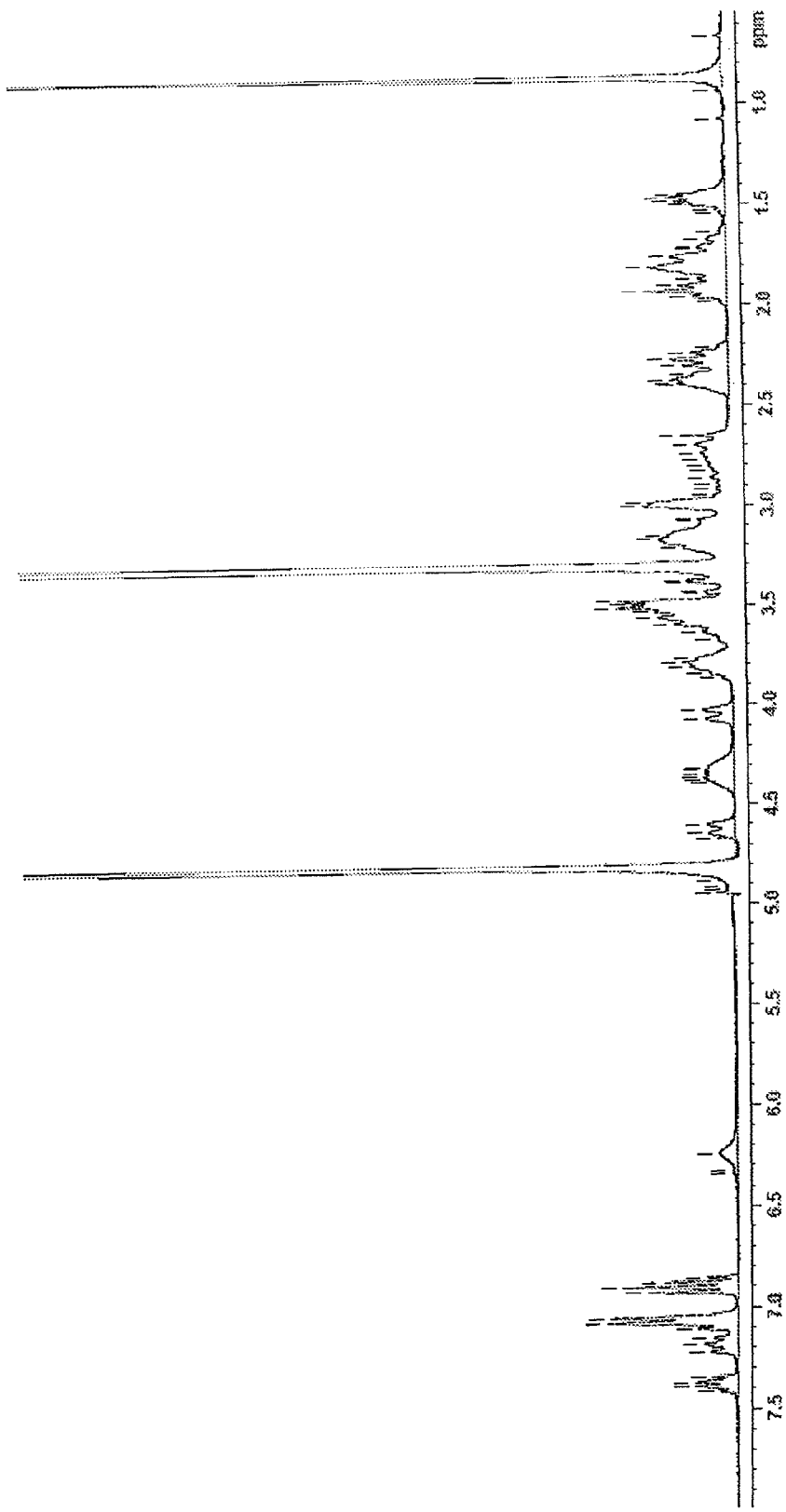
FIG. 53 depicts a $^1$H NMR trace (CD$_3$OD, 300 MHz) of compound I-543.
Figure 54:
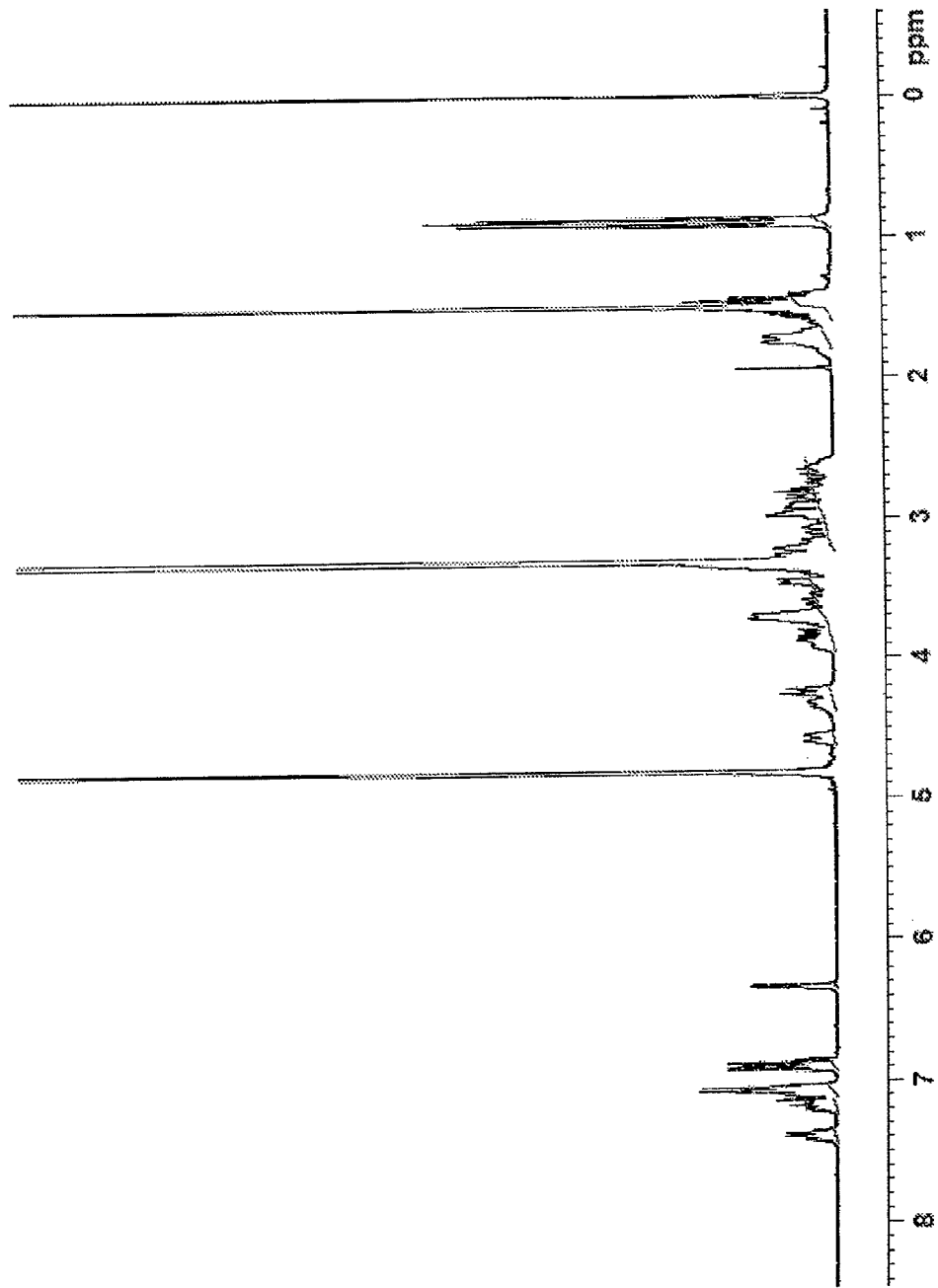
FIG. 54 depicts a $^1$H NMR trace (CD$_3$OD, 300 MHz) of compound I-544.
Figure 55:
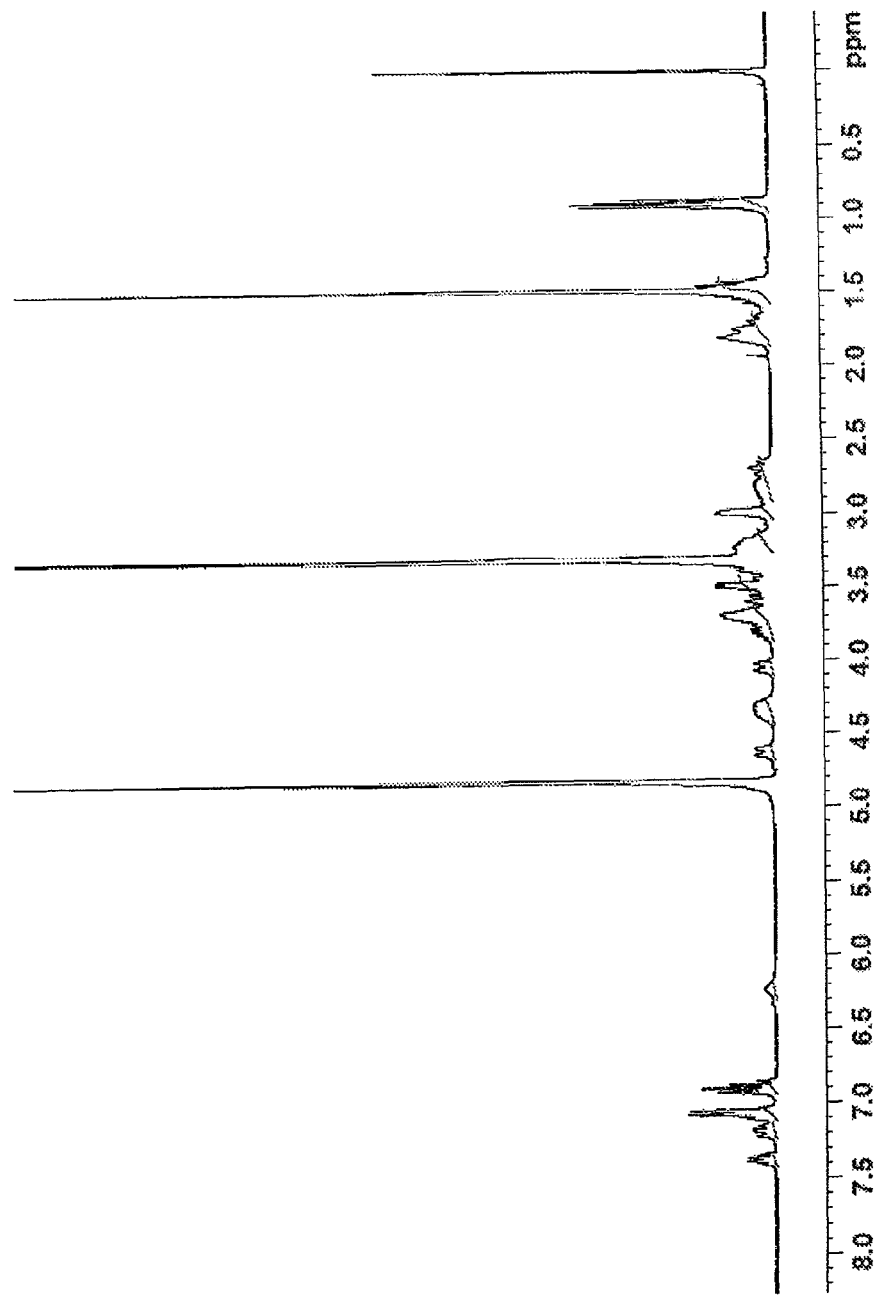
FIG. 55 depicts a $^1$H NMR trace (CD$_3$OD, 300 MHz) of compound I-545.
Figure 56:
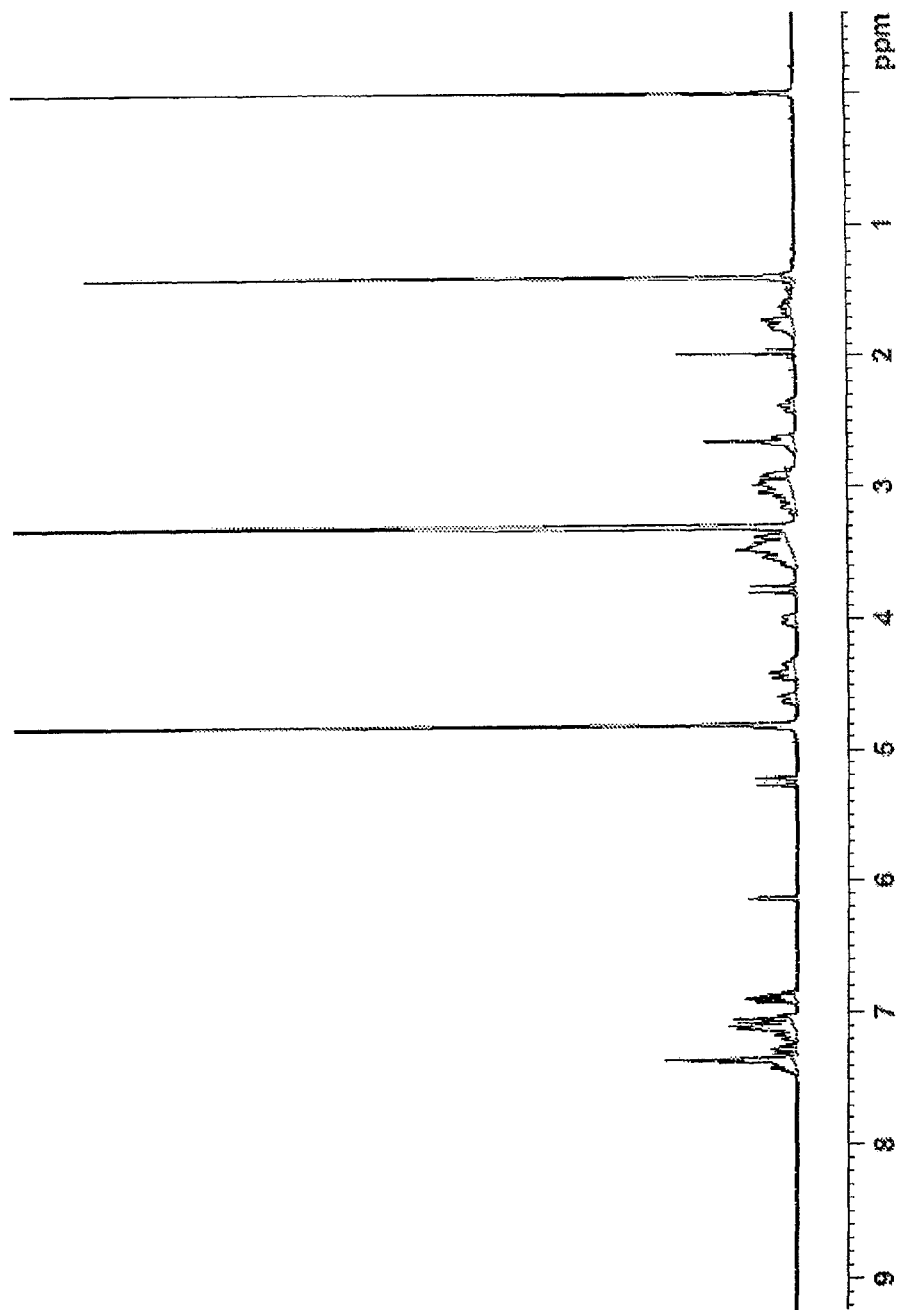
FIG. 56 depicts a $^1$H NMR trace (CD$_3$OD, 300 MHz) of compound I-547.
Figure 57:
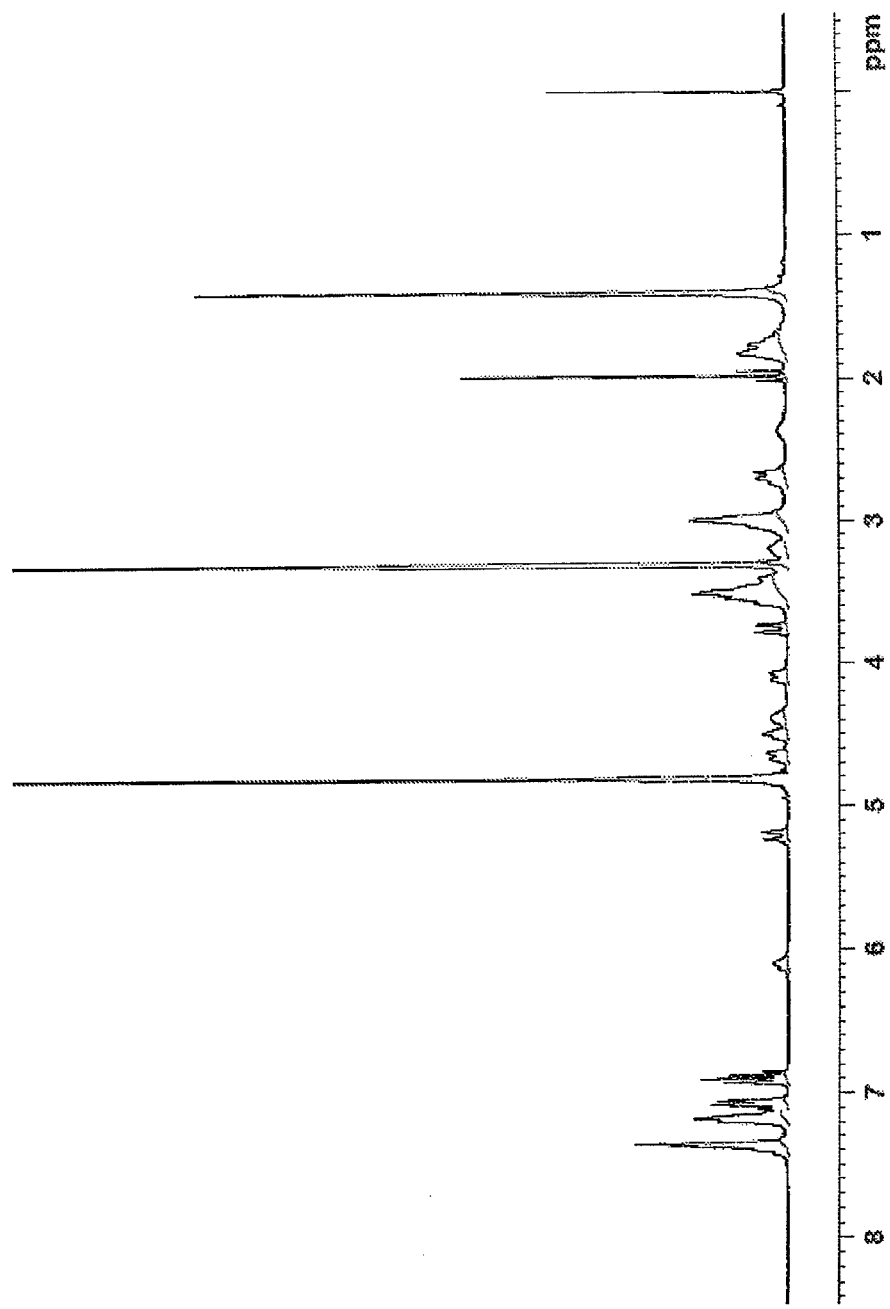
FIG. 57 depicts a $^1$H NMR trace (CD$_3$OD, 300 MHz) of compound I-548.
Figure 58:
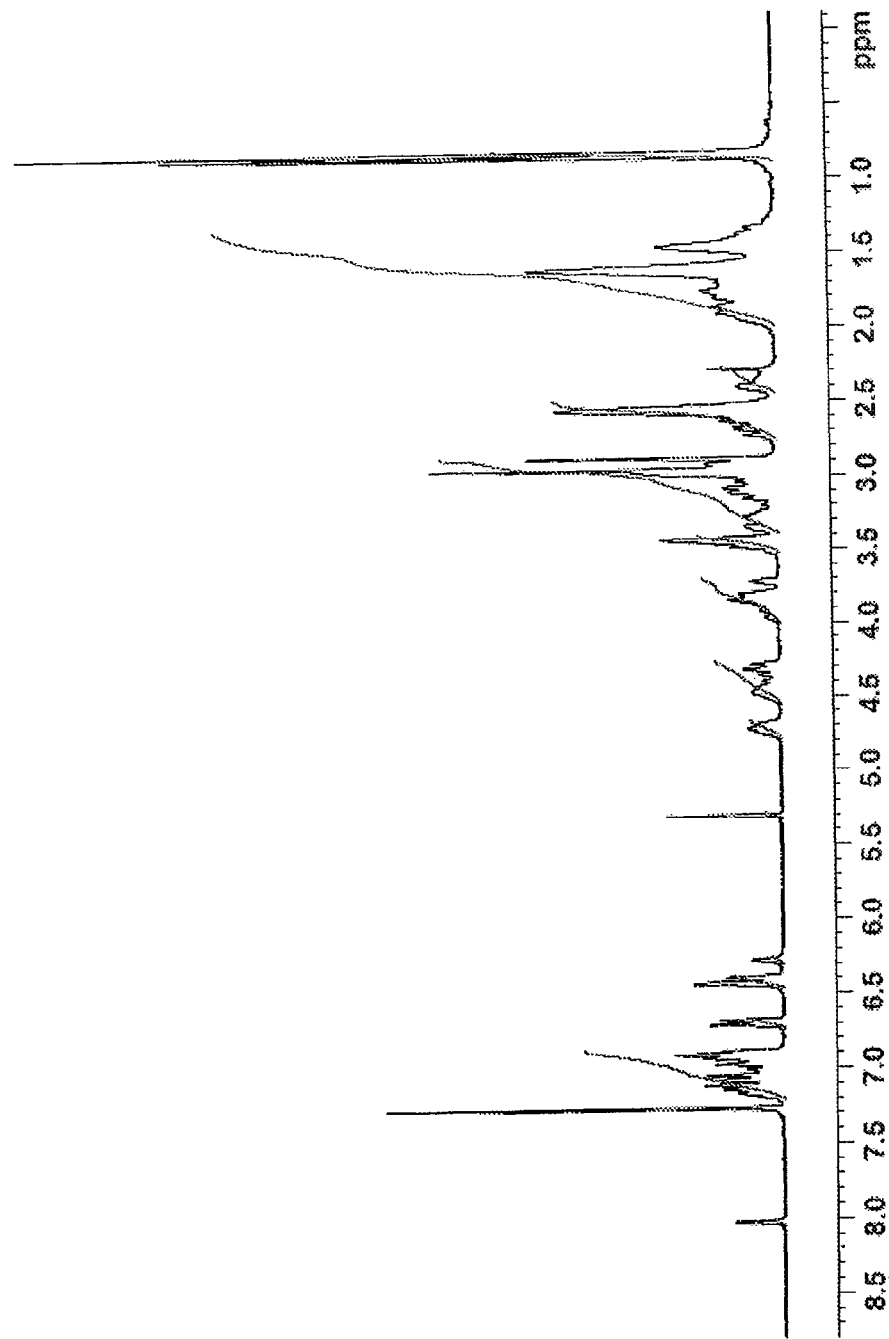
FIG. 58 depicts a $^1$H NMR trace (CDCl$_3$, 300 MHz) of compound I-550.
Figure 59:
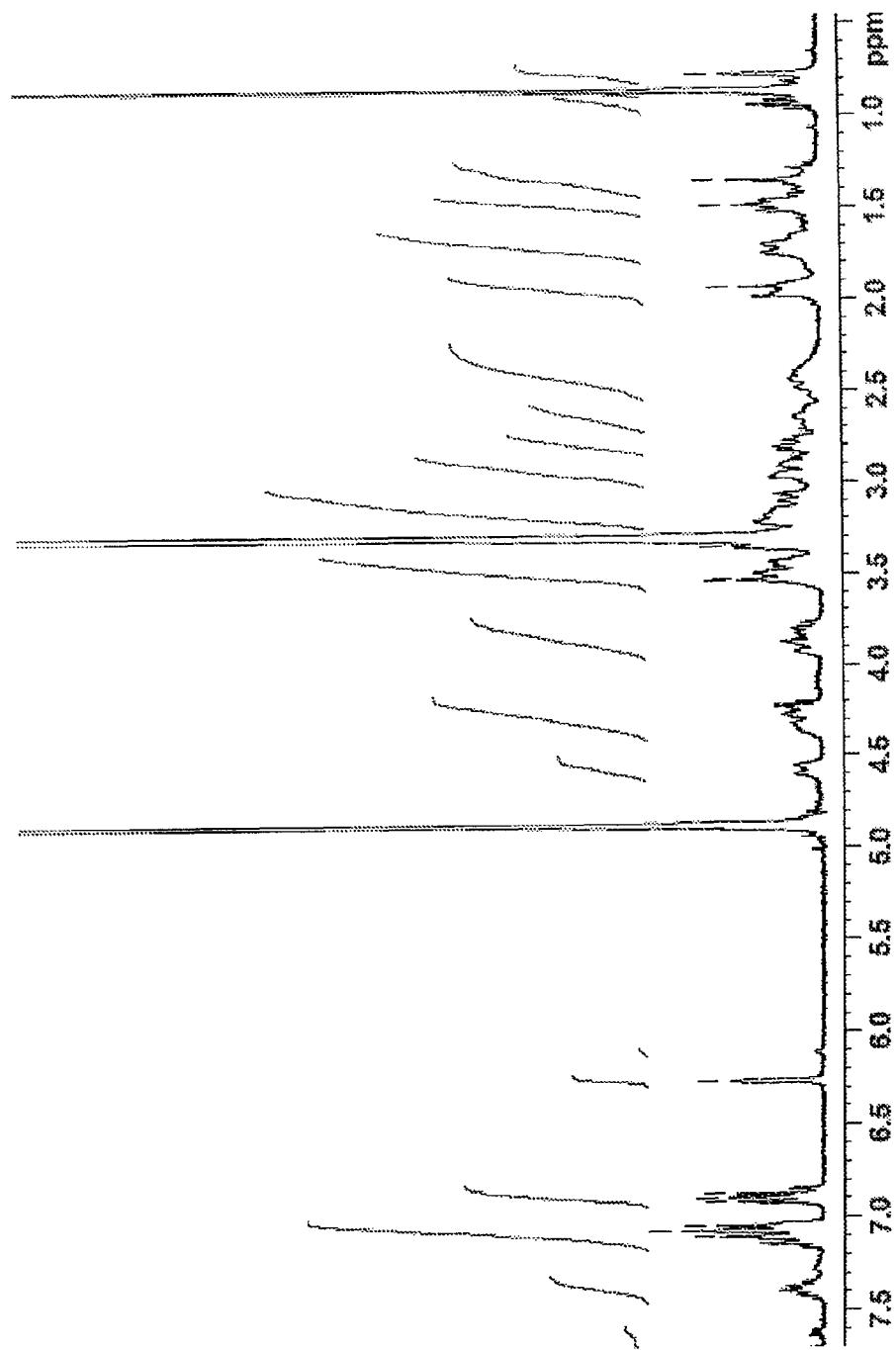
FIG. 59 depicts a $^1$H NMR trace (CD$_3$OD, 300 MHz) of compound I-552.
Figure 60:
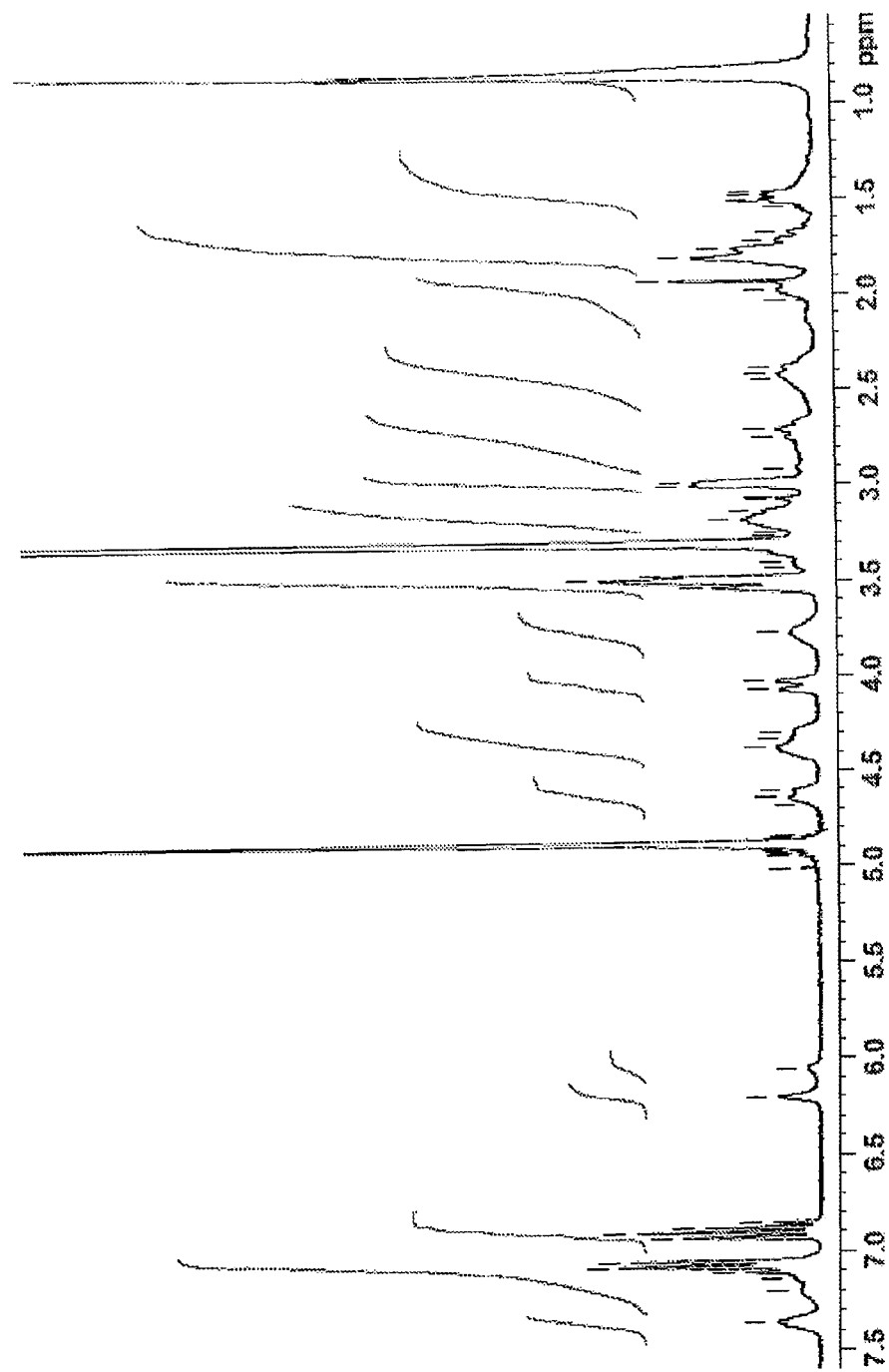
FIG. 60 depicts a $^1$H NMR trace (CD$_3$OD, 300 MHz) of compound I-553.
Figure 61:
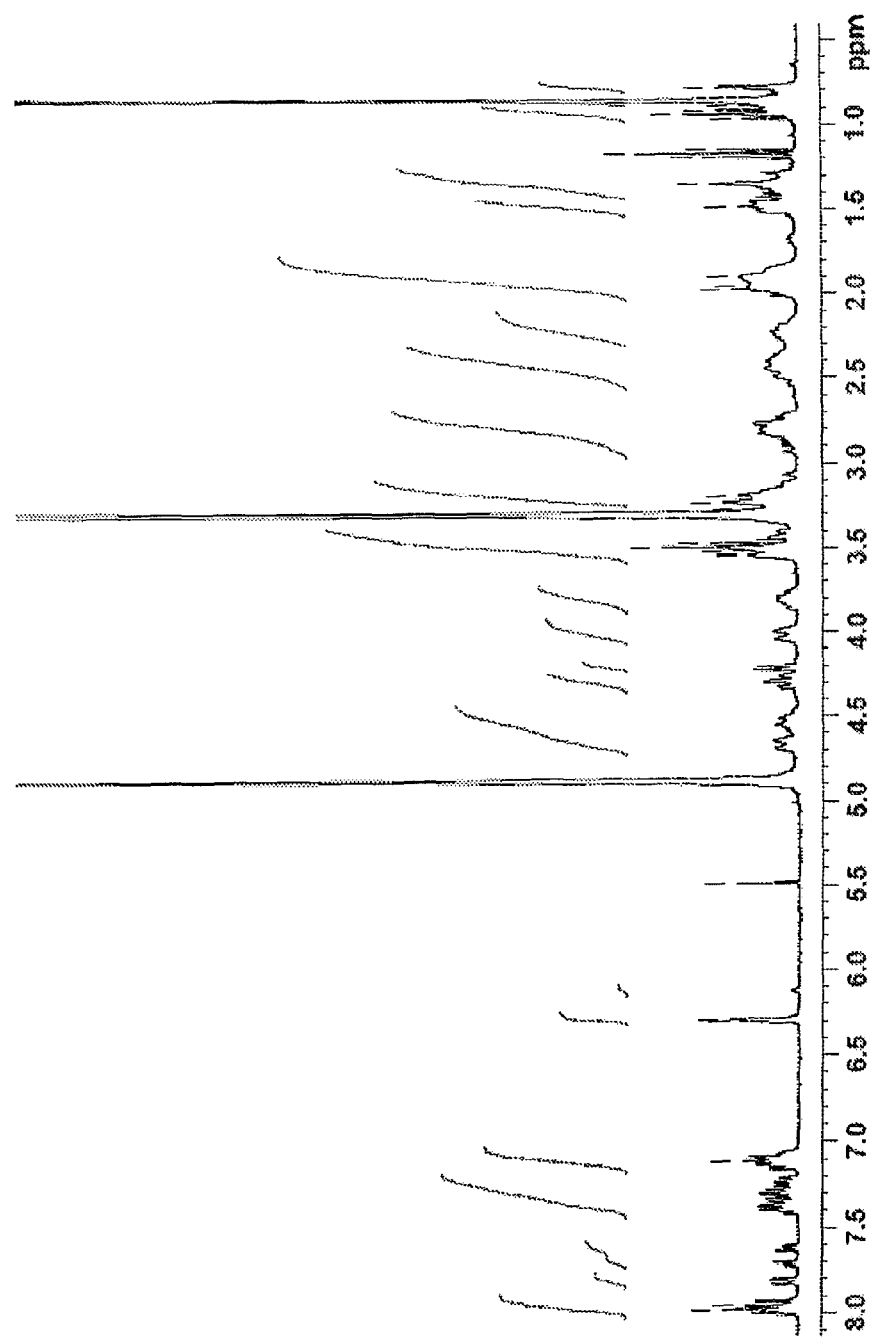
FIG. 61 depicts a $^1$H NMR trace (CD$_3$OD, 300 MHz) of compound I-554.
Figure 62:
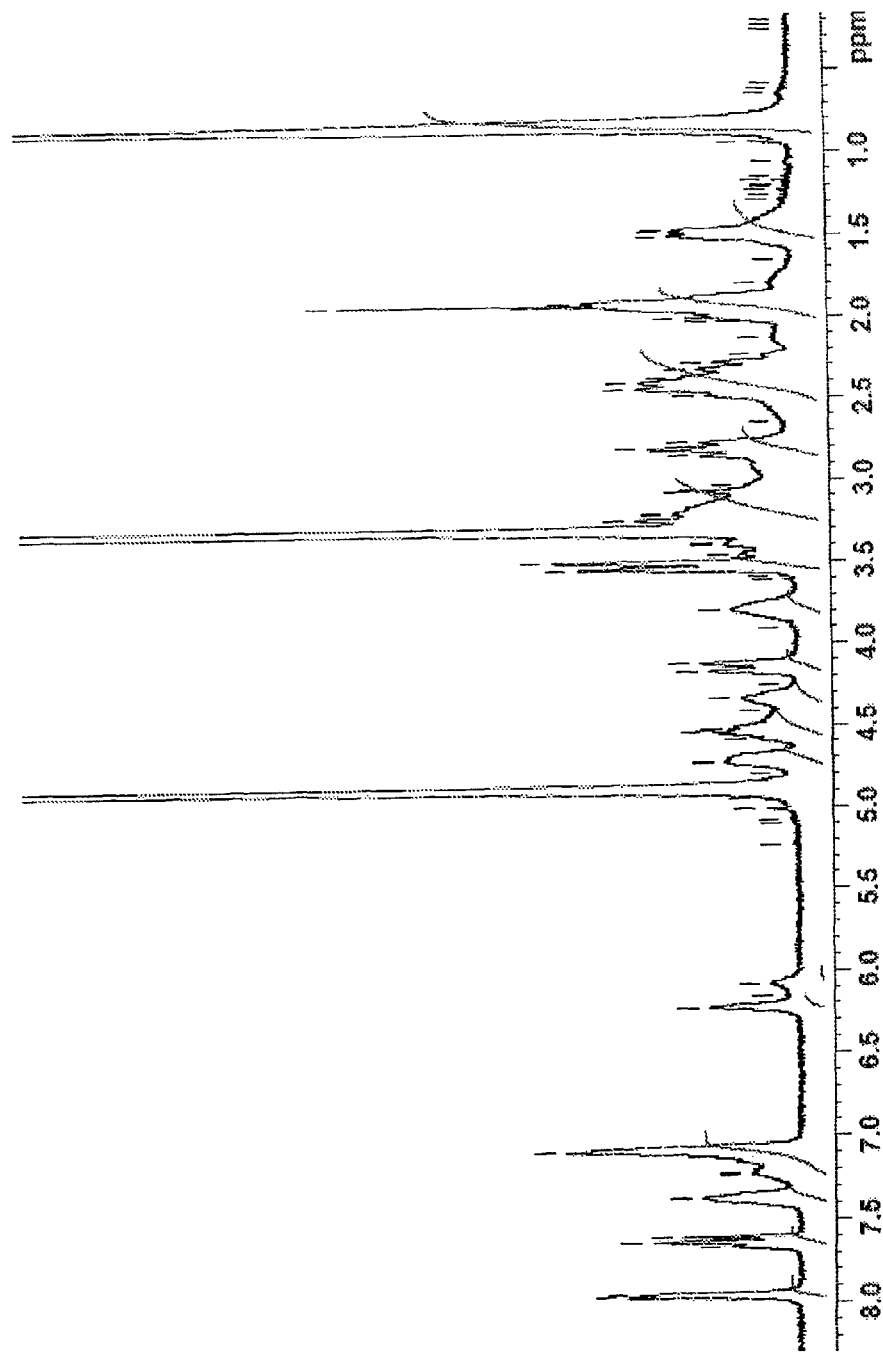
FIG. 62 depicts a $^1$H NMR trace (CD$_3$OD, 300 MHz) of compound I-555.
Figure 63:
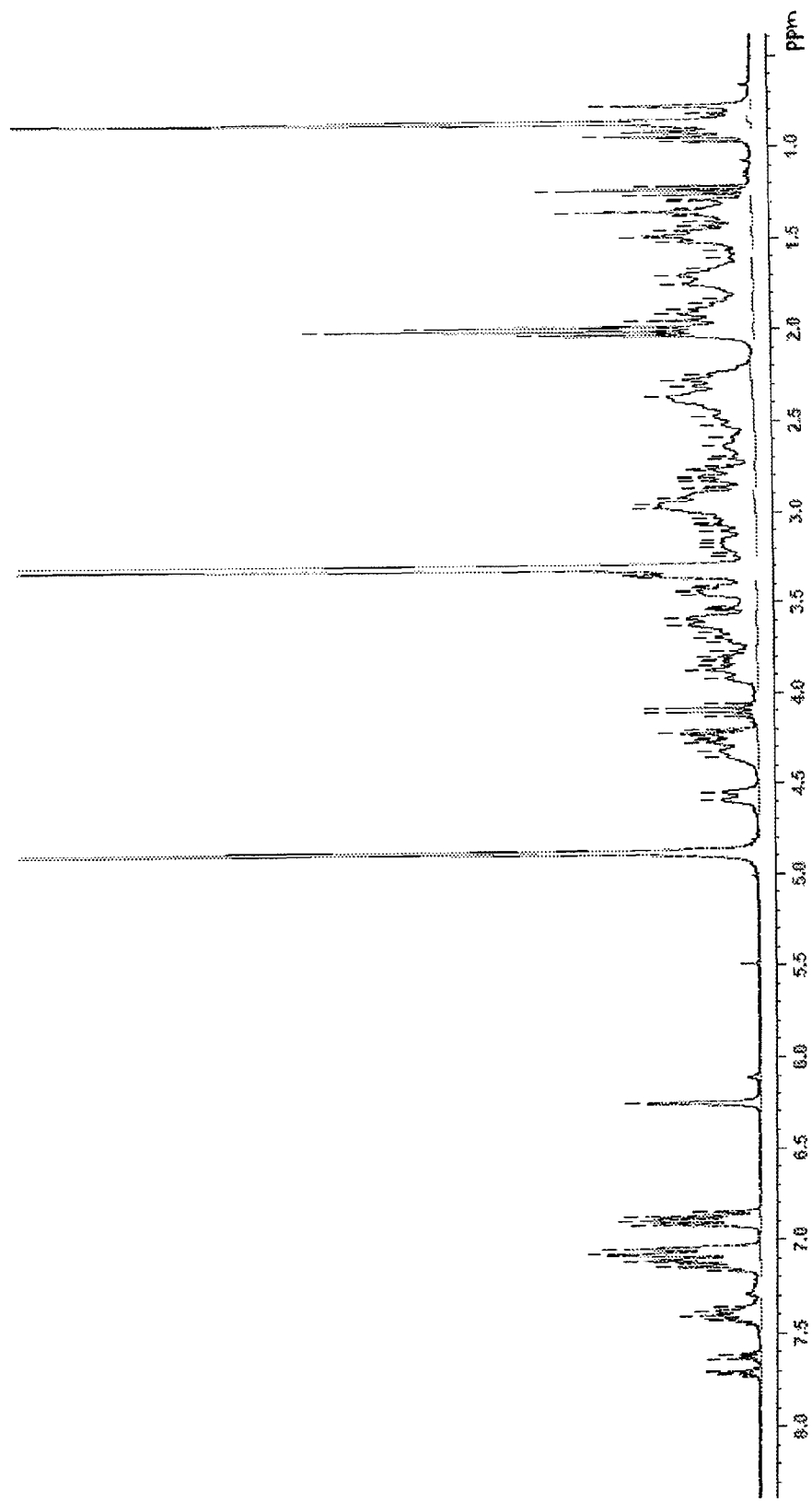
FIG. 63 depicts a $^1$H NMR trace (CD$_3$OD, 300 MHz) of compound I-558.
Figure 64:
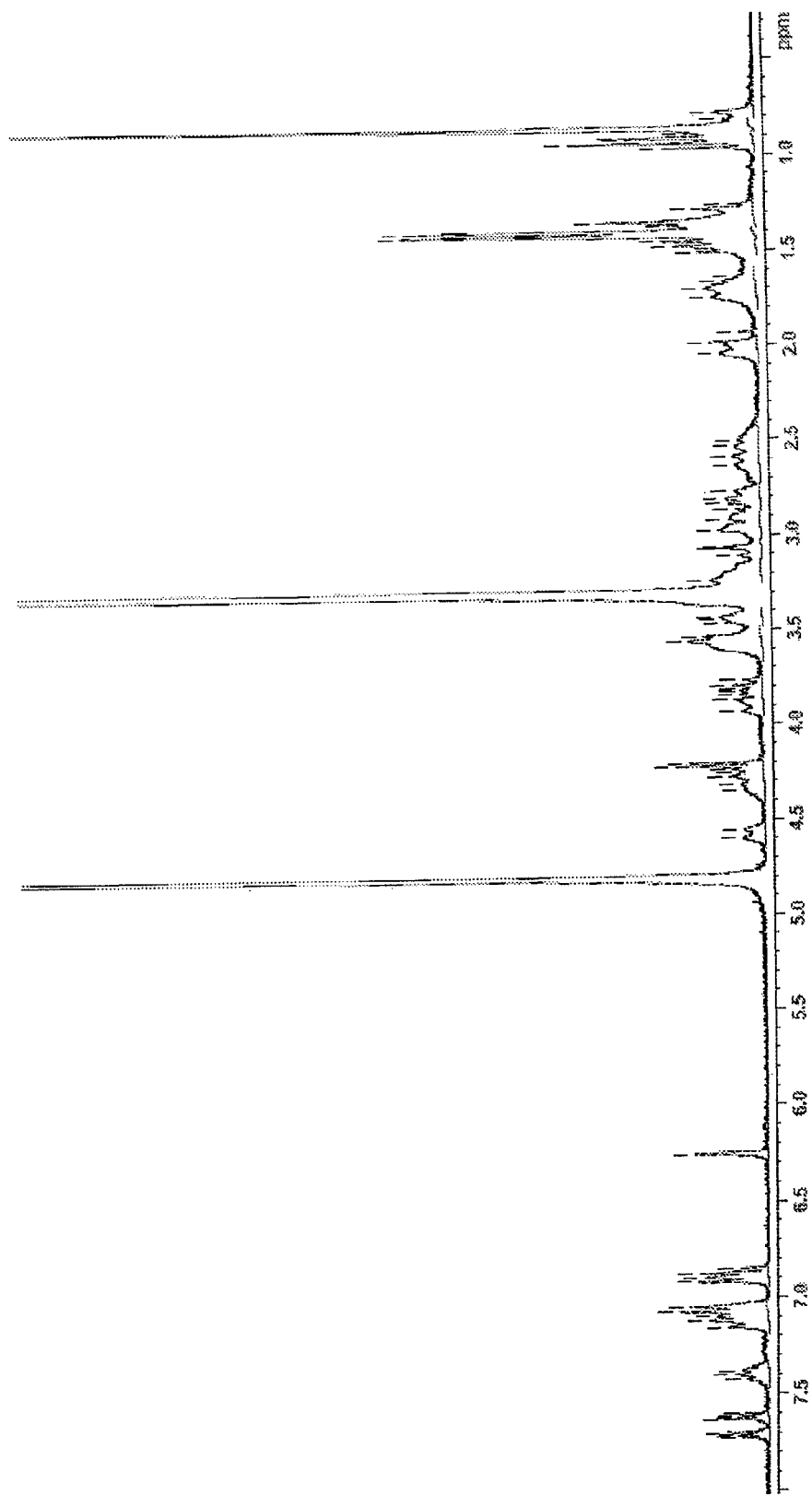
FIG. 64 depicts a $^1$H NMR trace (CD$_3$OD, 300 MHz) of compound I-559.
Figure 65:
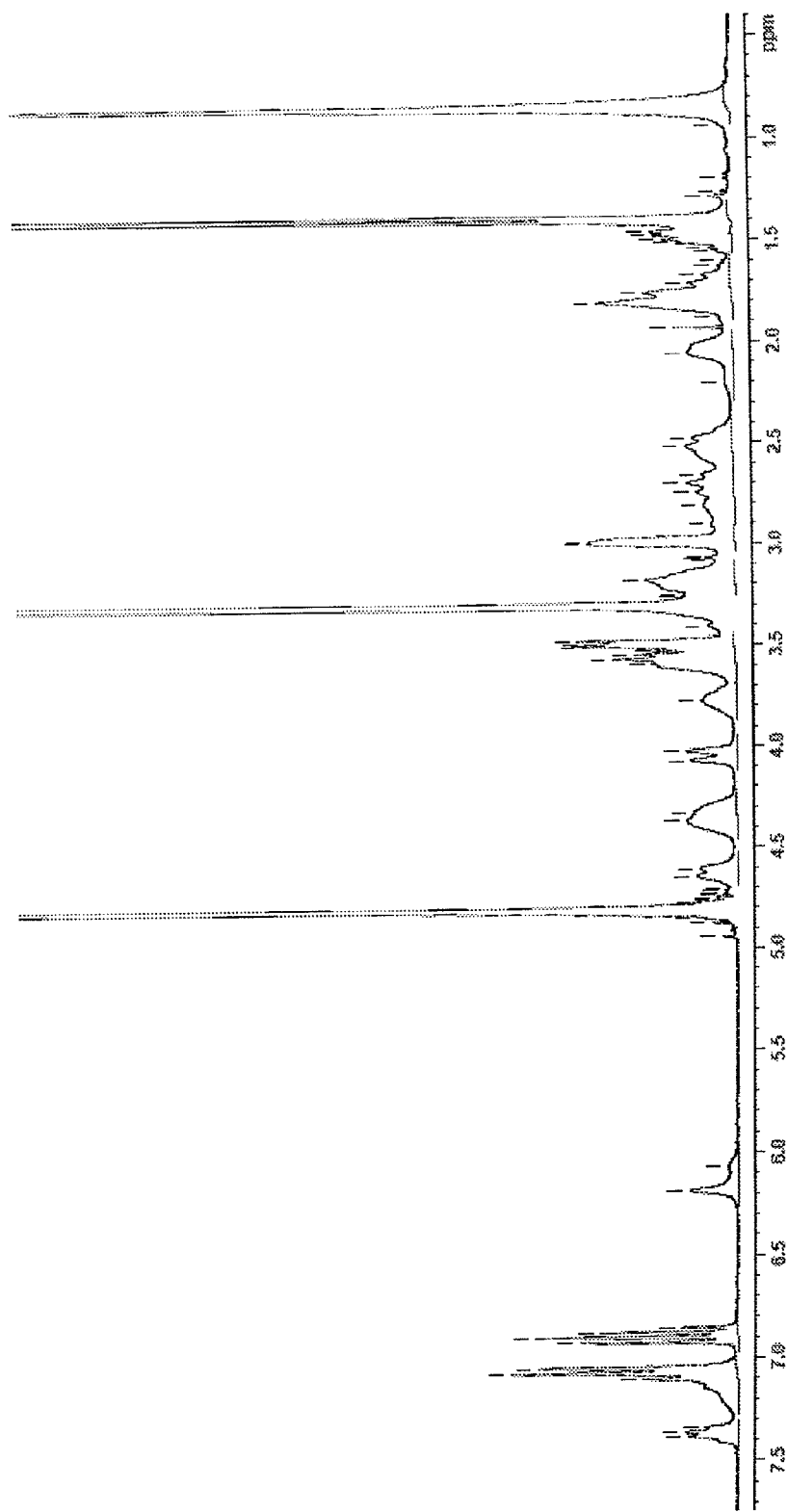
FIG. 65 depicts a $^1$H NMR trace (CD$_3$OD, 300 MHz) of compound I-560.
Figure 66:
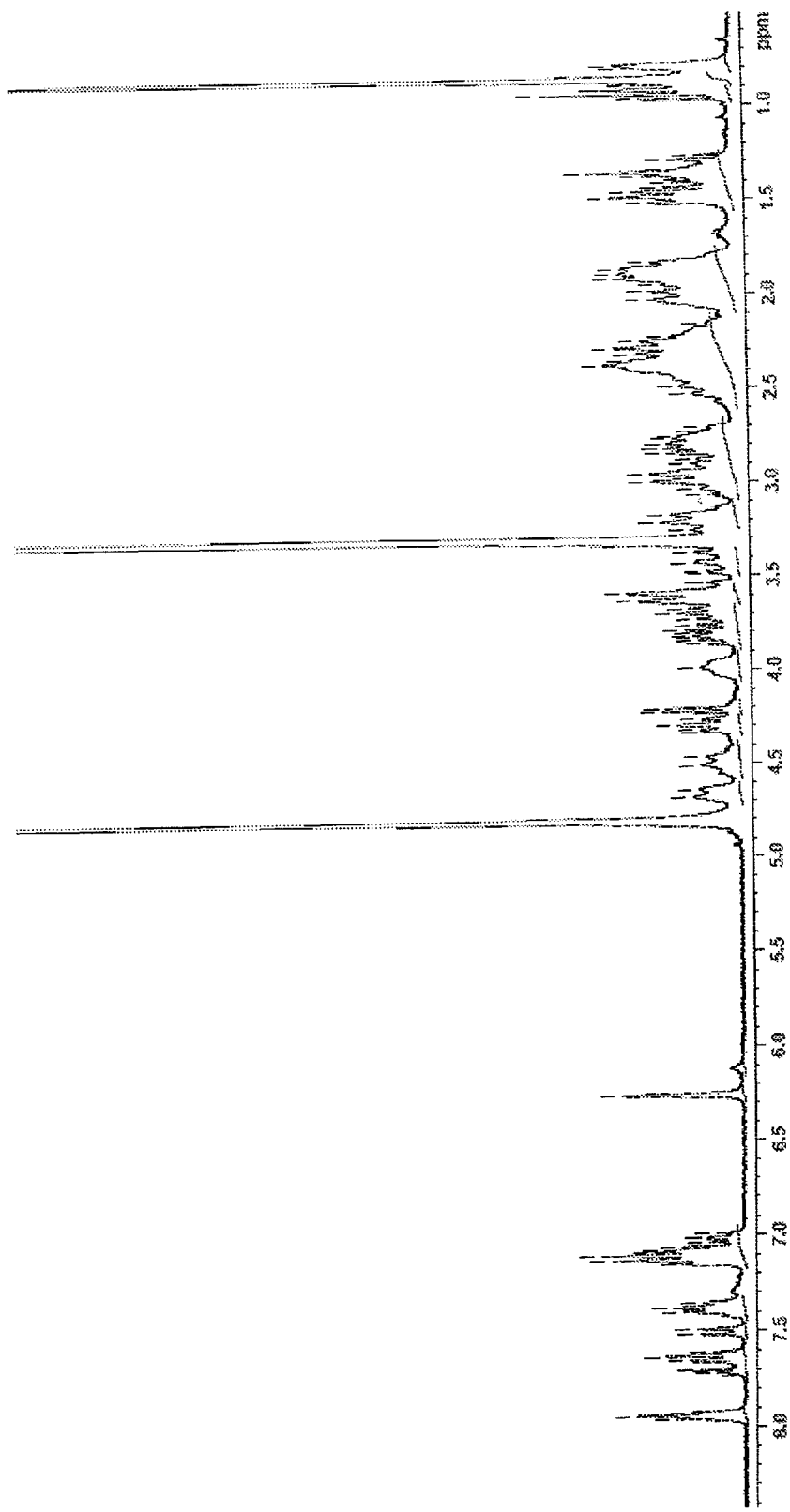
FIG. 66 depicts a $^1$H NMR trace (CD$_3$OD, 300 MHz) of compound I-561.
Figure 67:
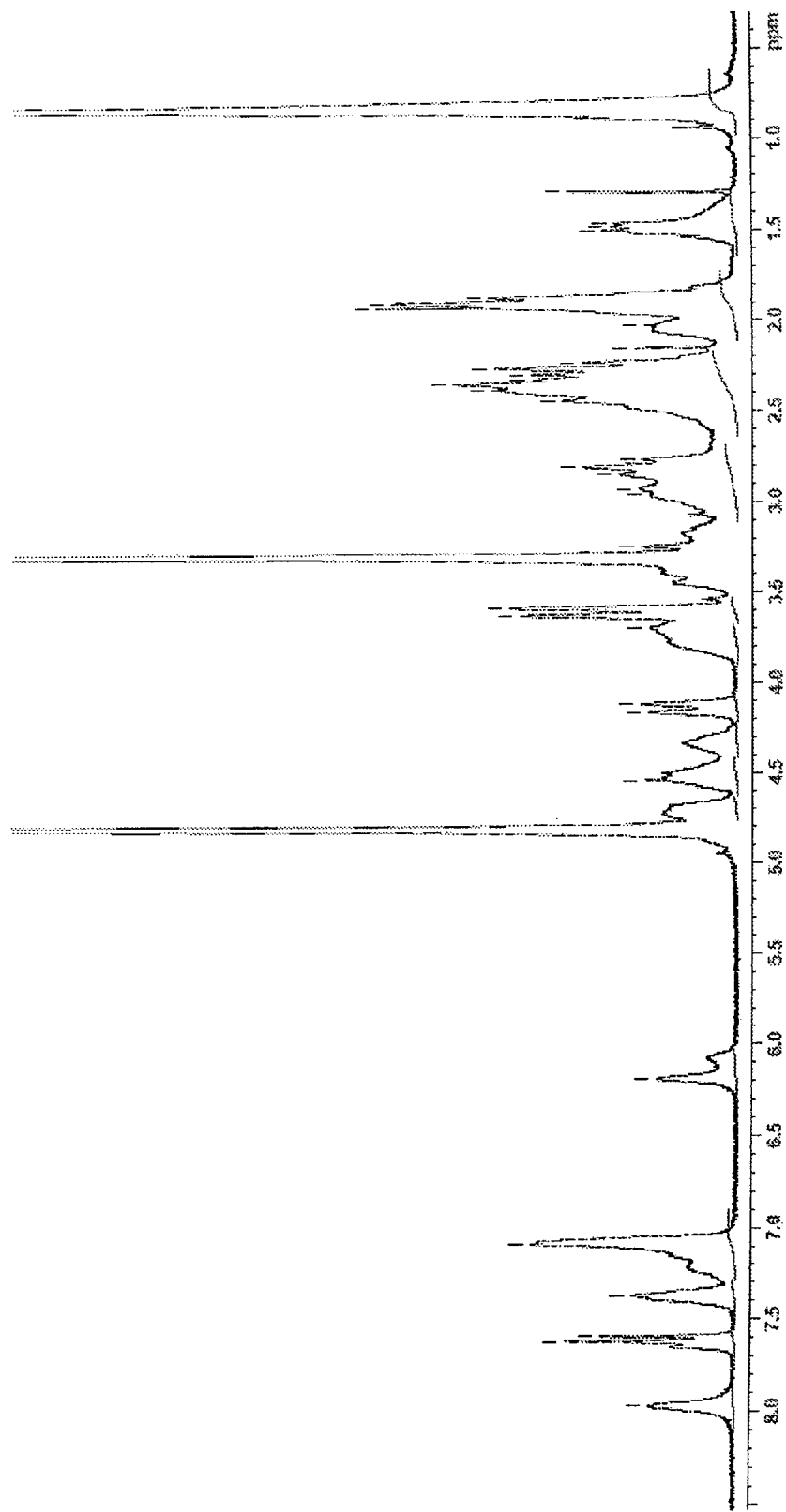
FIG. 67 depicts a $^1$H NMR trace (CD$_3$OD, 300 MHz) of compound I-562.
Figure 68:
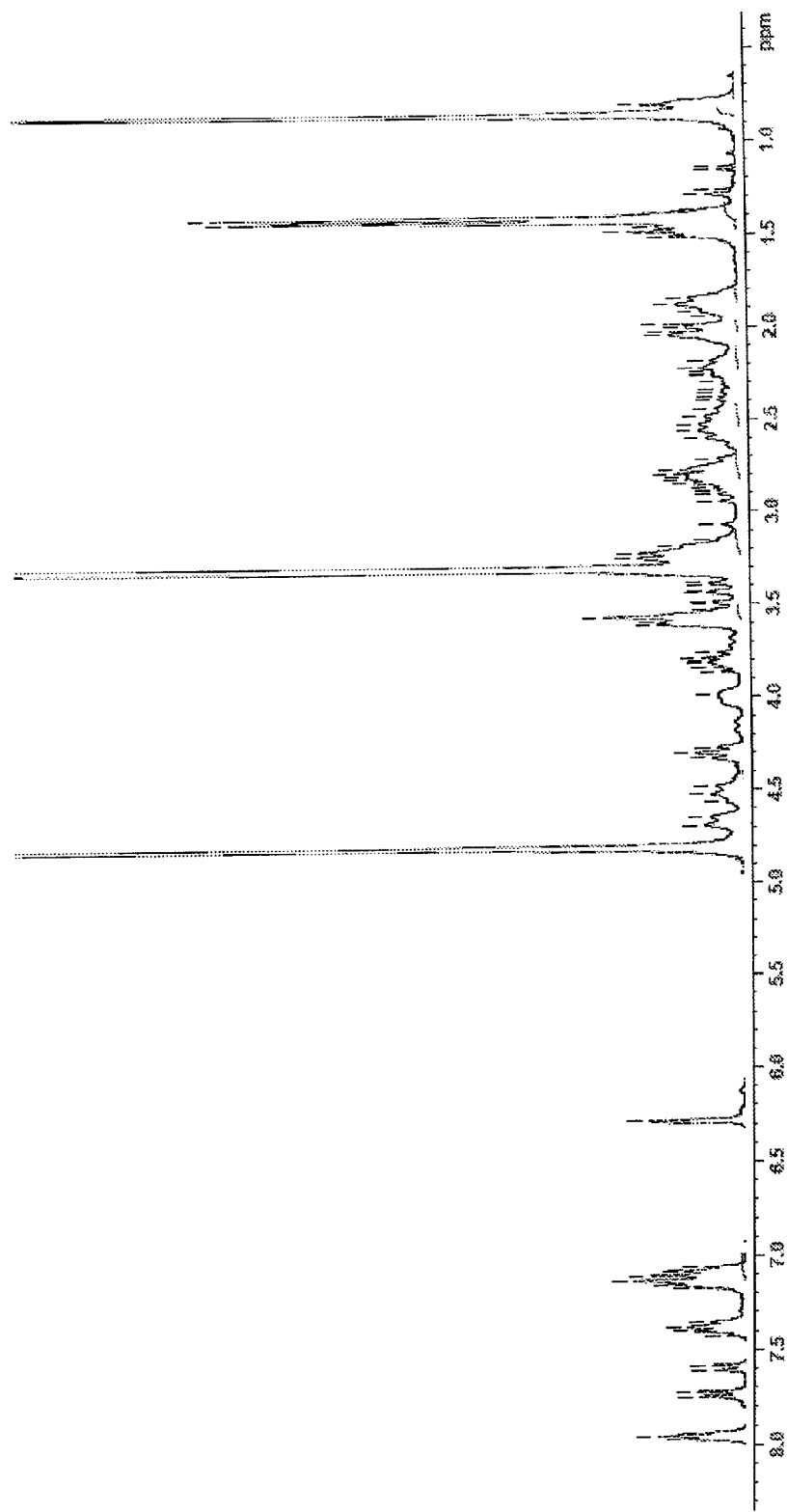
FIG. 68 depicts a $^1$H NMR trace (CDCl$_3$, 300 MHz) of compound I-563.
Figure 69:
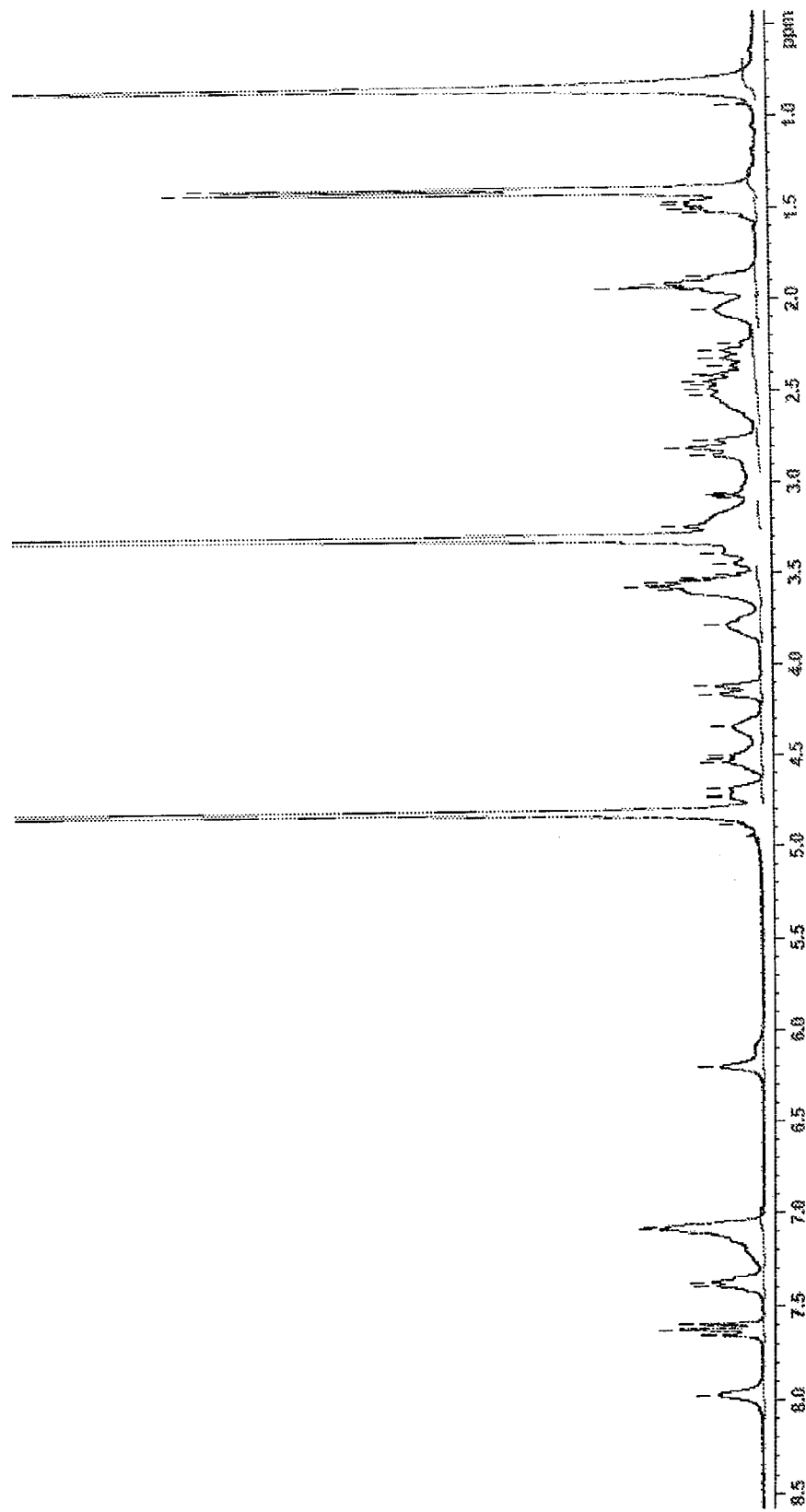
FIG. 69 depicts a $^1$H NMR trace (CD$_3$OD, 300 MHz) of compound I-564.
Figure 70:
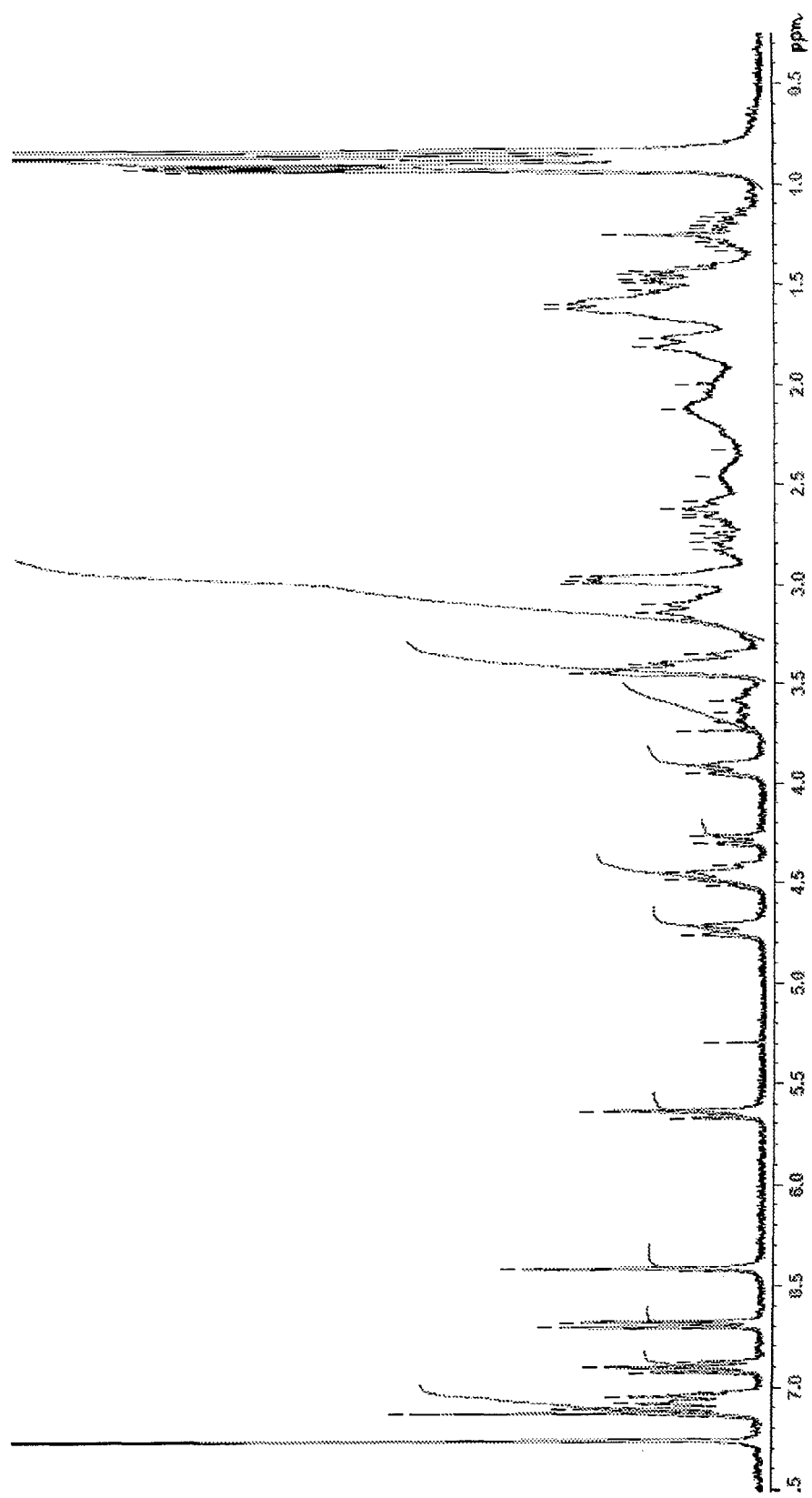
FIG. 70 depicts a $^1$H NMR trace (CDCl$_3$, 300 MHz) of compound I-519.
Figure 71:
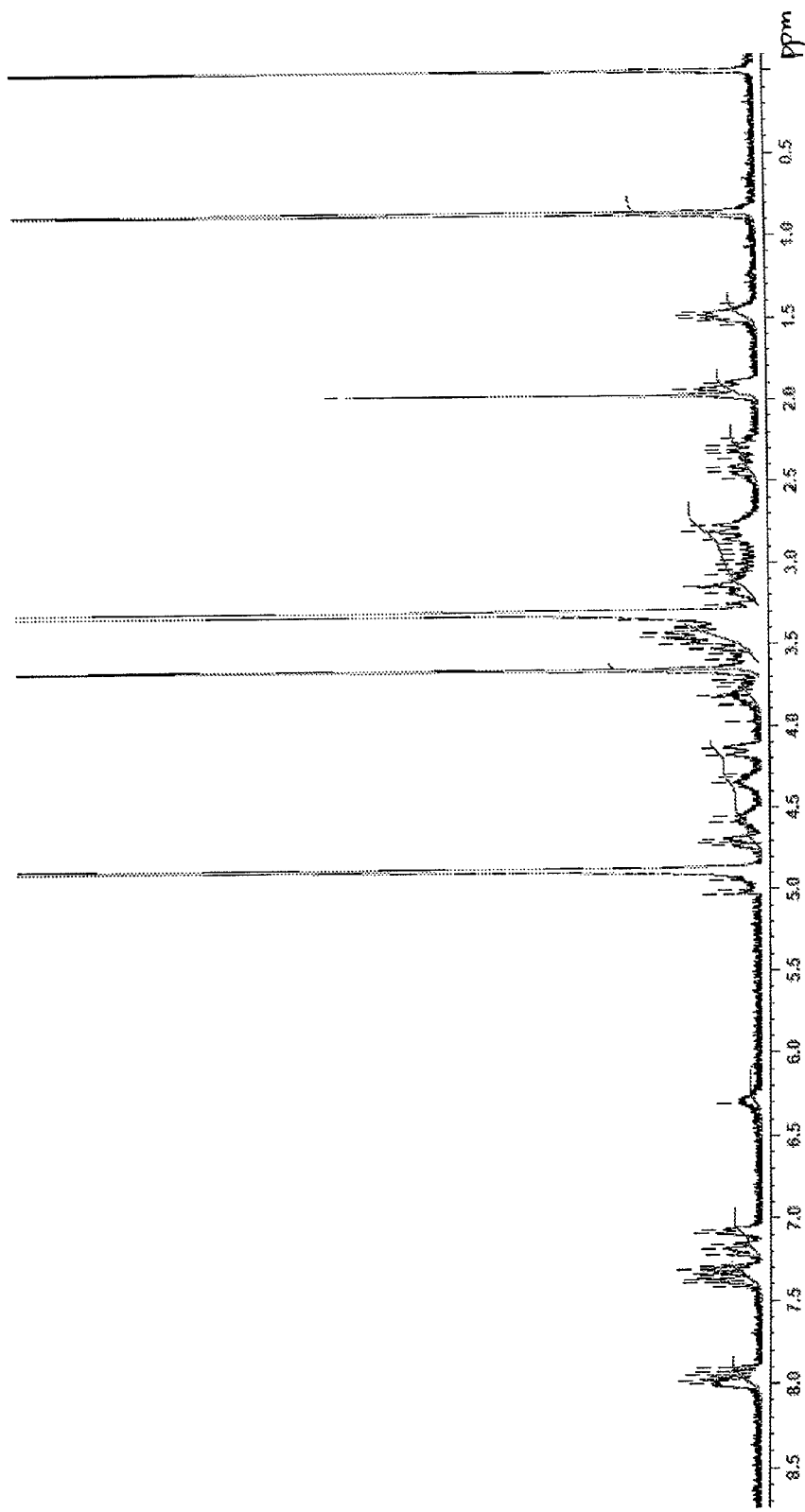
FIG. 71 depicts a $^1$H NMR trace (CD$_3$OD, 300 MHz) of compound I-546.
Figure 72:
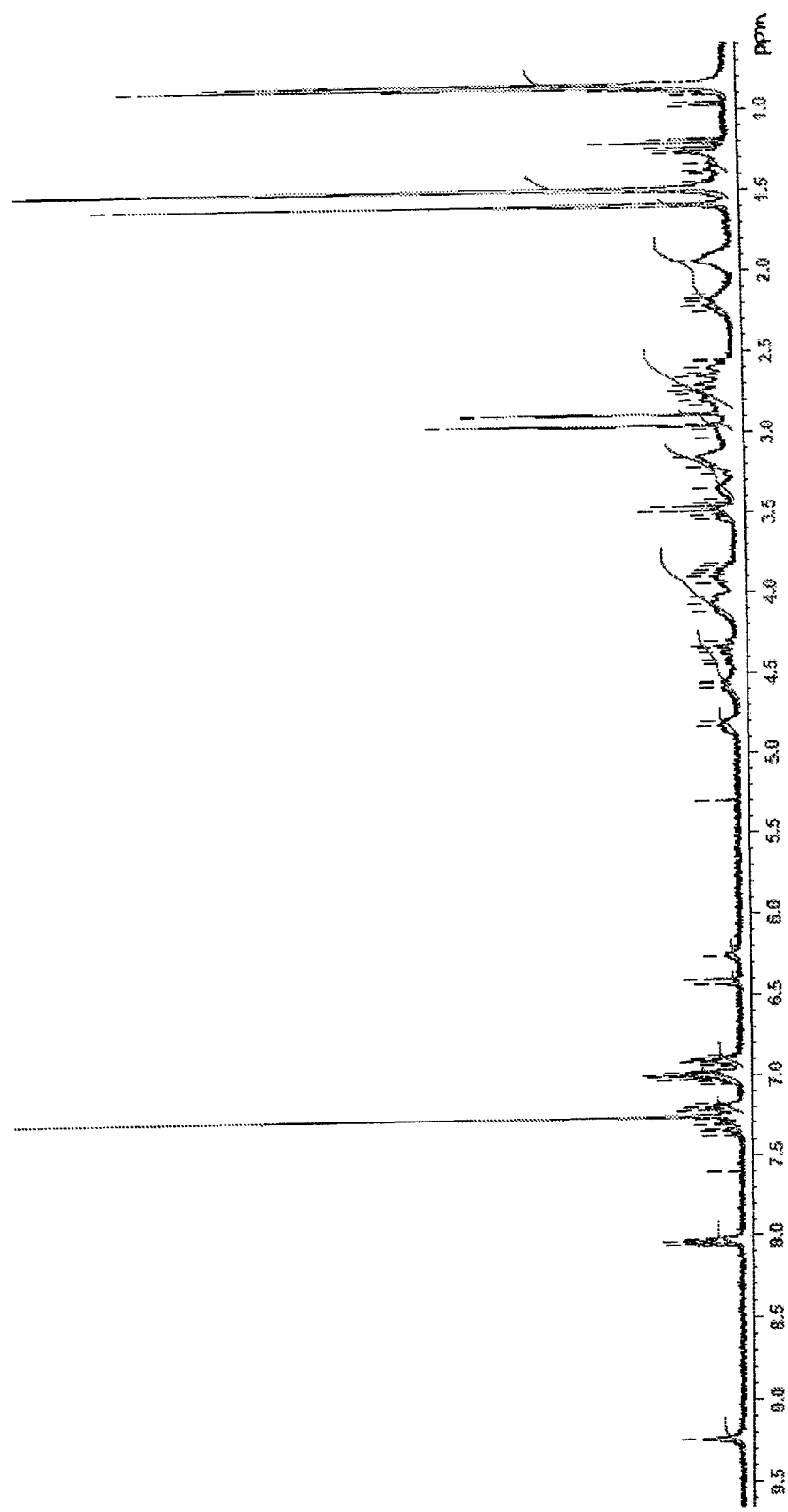
FIG. 72 depicts a $^1$H NMR trace (CDCl$_3$, 300 MHz) of compound I-549.
Figure 73:
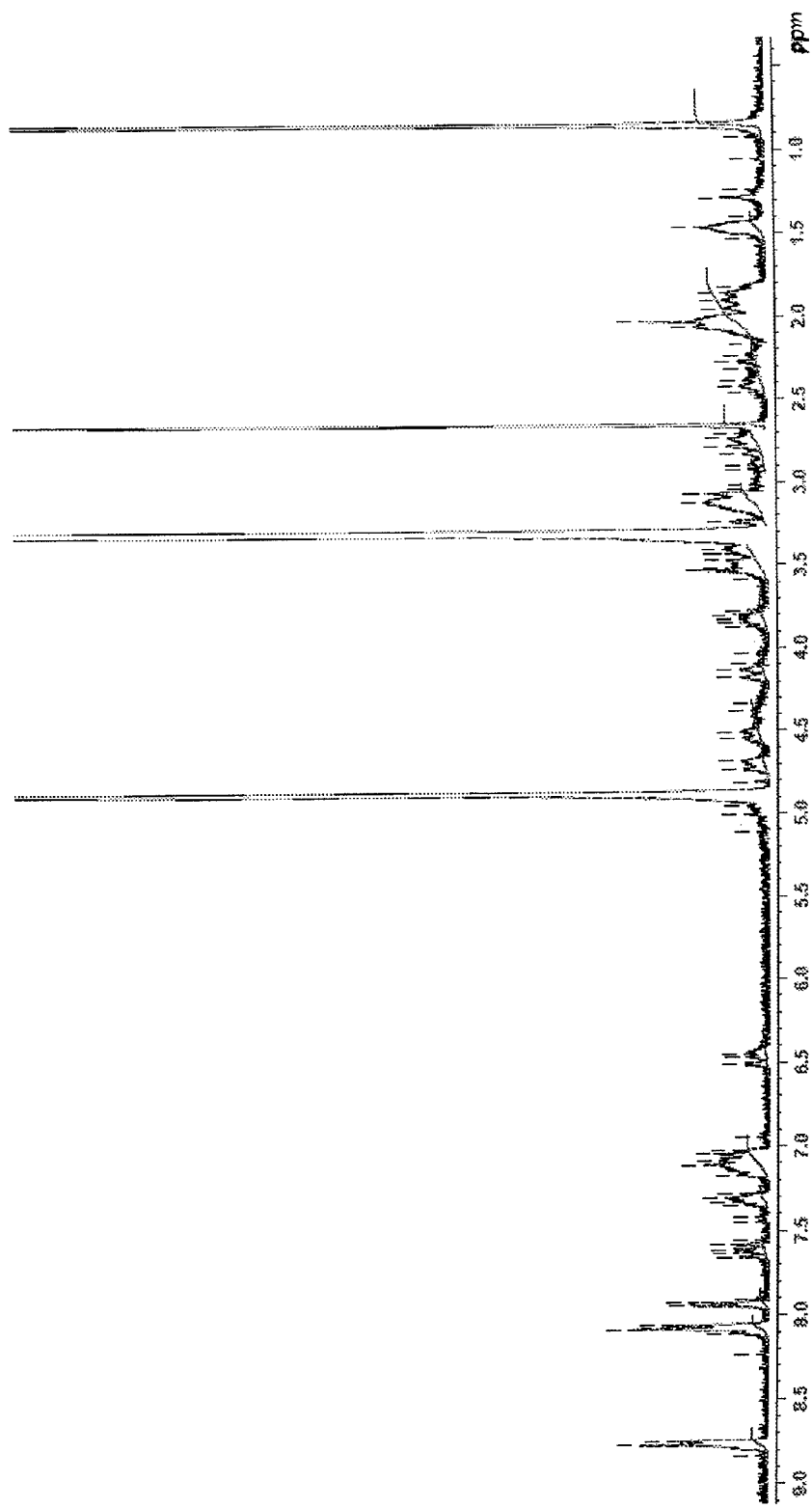
FIG. 73 depicts a $^1$H NMR trace (CD$_3$OD, 300 MHz) of compound I-556.
Figure 74:
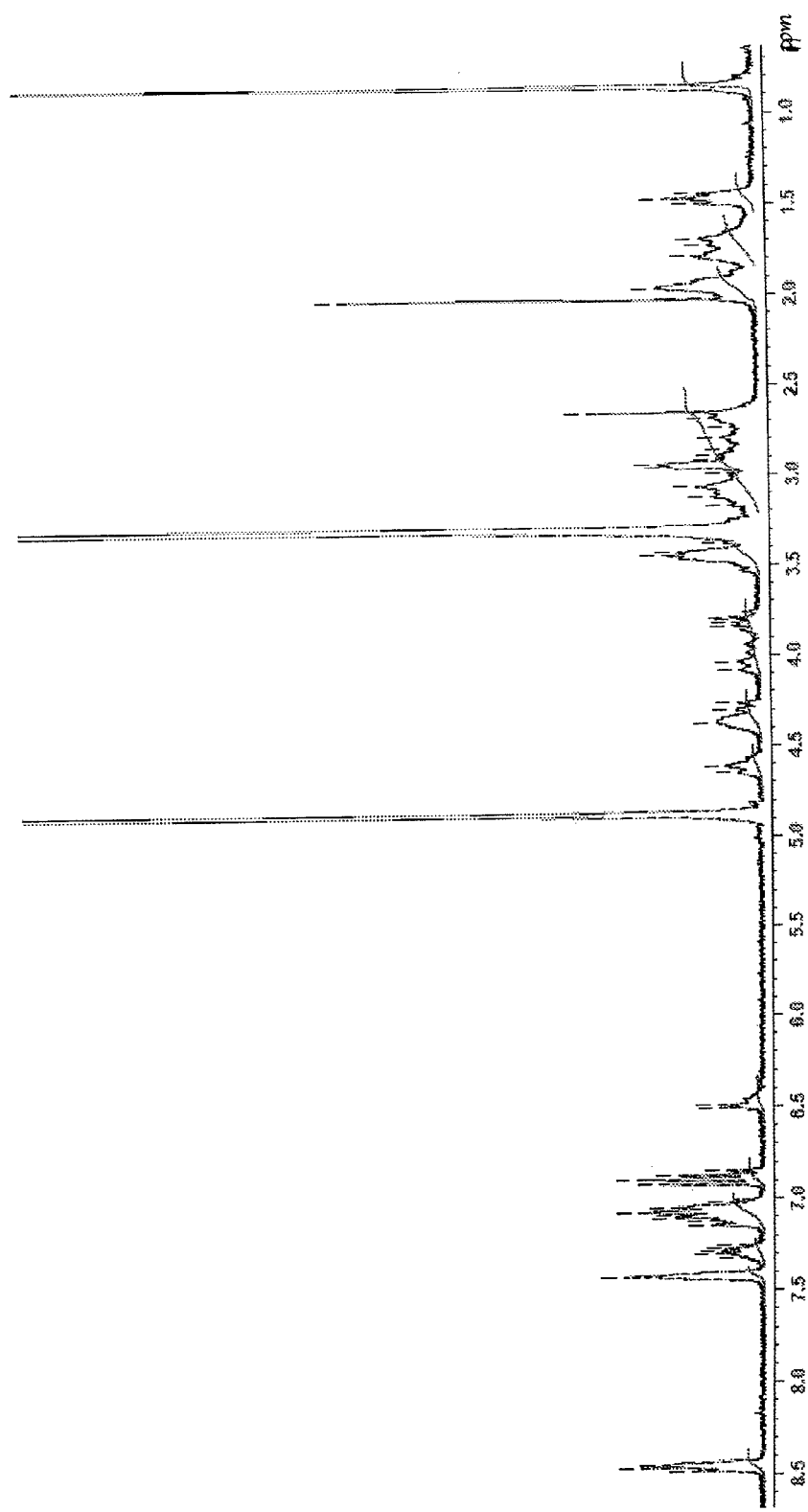
FIG. 74 depicts a $^1$H NMR trace (CD$_3$OD, 300 MHz) of compound I-557.

Compounds of this invention include those described generally above, and are further illustrated by the classes, subclasses, and species disclosed herein. As used herein, the following definitions shall apply unless otherwise indicated.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic or tricyclic $C_8$-$C_{14}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring atom is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, or nitrogen (including, any oxidized forms thereof, e.g., S=O, SO$_2$, etc.; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The terms "haloaliphatic" and "haloalkoxy" means aliphatic or alkoxy, as the case may be, substituted with one or more halo atoms. The term "halogen" or "halo" means F, Cl, Br, or I. Examples of haloaliphatic include —CHF₂, —CH₂F, —CF₃, —CF₂—, or perhaloalkyl, such as, —CF₂CF₃.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halo; —R°; —OR°; —SR°; 1,2-methylene-dioxy; 1,2-ethylenedioxy; phenyl (Ph) optionally substituted with R°; —O(Ph) optionally substituted with R°; —(CH₂)₁₋₂(Ph), optionally substituted with R°; —CH=CH(Ph), optionally substituted with R°; —NO₂; —CN; —N(R°)₂; —NR°C(O)R°; —NR°C(O)N(R°)₂; —NR°CO₂R°; —NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(O)N(R°)₂; —OC(O)N(R°)₂; —S(O)₂R°; —SO₂N(R°)₂; —S(O)R°; —NR°SO₂N(R°)₂; —NR°SO₂R°; —C(=S)N(R°)₂; —C(=NH)—N(R°)₂; or —(CH₂)₀₋₂NHC(O)R° wherein each independent occurrence of R° is selected from hydrogen, optionally substituted C₁₋₆ aliphatic, an unsubstituted 5-6 membered heteroaryl or heterocyclic ring, phenyl, —O(Ph), or —CH₂(Ph), or, notwithstanding the definition above, two independent occurrences of R°, on the same substituent or different substituents, taken together with the atom(s) to which each R° group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of R° are selected from NH₂, NH(C₁₋₄aliphatic), N(C₁₋₄aliphatic)₂, halo, C₁₋₄aliphatic, OH, O(C₁₋₄aliphatic), NO₂, CN, CO₂H, CO₂(C₁₋₄aliphatic), O(haloC₁₋₄ aliphatic), or haloC₁₋₄aliphatic, wherein each of the foregoing C₁₋₄aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHCO₂(alkyl), =NNHSO₂(alkyl), or =NR*, where each R* is independently selected from hydrogen or an optionally substituted C₁₋₆ aliphatic. Optional substituents on the aliphatic group of R* are selected from NH₂, NH(C₁₋₄ aliphatic), N(C₁₋₄ aliphatic)₂, halo, C₁₋₄ aliphatic, OH, O(C₁₋₄ aliphatic), NO₂, CN, CO₂H, CO₂(C₁₋₄ aliphatic), O(halo C₁₋₄ aliphatic), or halo(C₁₋₄ aliphatic), wherein each of the foregoing C₁₋₄aliphatic groups of R* is unsubstituted.

Optional substituents on the nitrogen of a non-aromatic heterocyclic ring are selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R⁺, on the same substituent or different substituents, taken together with the atom(s) to which each R⁺ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R⁺ are selected from NH₂, NH(C₁₋₄ aliphatic), N(C₁₋₄ aliphatic)₂, halo, C₁₋₄ aliphatic, OH, O(C₁₋₄ aliphatic), NO₂, CN, CO₂H, CO₂(C₁₋₄ aliphatic), O(halo C₁₋₄ aliphatic), or halo(C₁₋₄ aliphatic), wherein each of the foregoing C₁₋₄aliphatic groups of R⁺ is unsubstituted.

The term "spirocyclic ring system" refers to a moiety comprising two or more rings, wherein at least one ring has two points of attachment to another ring through a common carbon ring atom.

As detailed above, in some embodiments, two independent occurrences of R° (or R⁺, or any other variable similarly defined herein), are taken together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

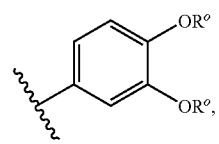

these two occurrences of R° are taken together with the oxygen atoms to which they are bound to form a fused 6-membered oxygen containing ring:

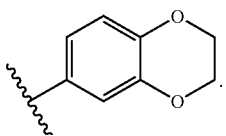

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The term "aryl-C1-C6 aliphatic-" and similar such terms mean that the aryl group is linked to the core molecule by a C1 to C6 aliphatic linker. For instance, the term "aryl-C2-alkyl-" means a —CH$_2$CH$_2$Ph group or a phenylethyl group is attached to the core molecule.

In one embodiment, the present invention provides compounds of formula I:

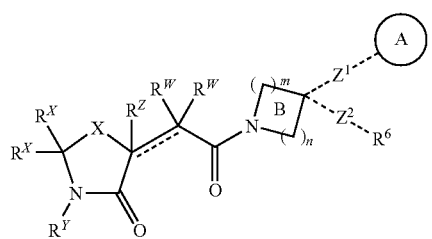

I wherein:
X is S, SO, or SO$_2$;
$Z^1$ is a bond or NR$^7$, O, S, CH$_2$, C(O), or NR$^7$C(O)NR$^7$, wherein R$^7$ is hydrogen, C1-C4 aliphatic or C(O)C1-C4 aliphatic;
$Z^2$ is a bond, O, CH$_2$O, or C(O);
ring A is phenyl or a 4-7 membered heterocyclic or heteroaryl ring or a 10-14 membered bicyclic heteroaryl or heterocyclic ring, wherein said heterocyclic or heteroaryl ring has 1-4 heteroatoms selected from O, N, or S; wherein ring A is optionally substituted with up to 5 R$^1$ substituents;
wherein:
$Z^2$ is a bond, $Z^1$ is a bond, NR$^7$, O, S, CH$_2$, C(O), or NR$^7$C(O)NR$^7$; or wherein:
$Z^1$, $Z^2$, and R$^6$ are absent, ring A is not aromatic, and ring A together with ring B form a spirocyclic ring system;
R$^6$ is hydrogen or C1-C4 aliphatic;
m is 1-3;
n is 1-3; provided that m+n is ≦4;
R$^Y$ is aryl, heteroaryl, cycloaliphatic, C1-C6 aliphatic, aryl-C1-C6 aliphatic-, heteroaryl-C1-C6 aliphatic-, heterocyclyl-C1-C6 aliphatic- or cycloaliphatic-C1-C6 aliphatic-; wherein R$^Y$ is optionally substituted with up to 5 R$^2$ substituents;
R$^X$ is hydrogen, aryl, heteroaryl, C1-C6 aliphatic, aryl-C1-C6 aliphatic-, heteroaryl-C1-C6 aliphatic-, wherein R$^X$ is optionally substituted with up to 5 R$^3$ substituents;
or two R$^X$, taken together with the carbon atom that they are attached to, form a 3-9 membered monocyclic, a 9-14 membered bicyclic, or a 12-14 membered tricyclic aryl, heteroaryl or heterocyclic ring system wherein each heteroaryl or heterocyclic ring has up to 3 heteroatoms selected from O, S, and N; wherein said ring system formed by two R$^X$ is optionally substituted with up to 5 R$^4$ substituents;
R$^Z$ is absent, hydrogen, CN, C1-C6 aliphatic, halo-C1-C6 aliphatic, O—C1-C6 aliphatic, O-(halo-C1-C6 aliphatic), halo, aryl-C1-C6 aliphatic, or heteroaryl-C1-C6 aliphatic;
═══ is a single or a double bond; provided that when it is a double bond, then R$^Z$ and one of R$^W$ is absent;
each R$^W$ is independently absent, hydrogen, halo, oxo, C1-C6 aliphatic, halo-C1-C6 aliphatic, —O—C1-C6 aliphatic, —O-(halo-C1-C6 aliphatic), aryl, aryl-C1-C6 aliphatic-, C3-C7 cycloaliphatic; or
two R$^W$ taken together form an optionally substituted C3-C7 cycloaliphatic or heterocyclic ring, wherein said heterocyclic ring has up to 3 heteroatoms selected from O, S, and N; wherein said ring formed by two R$^W$ is optionally substituted with up to 5 R$^5$ substituents;
wherein each occurrence of R$^1$, R$^2$, R$^3$, R$^4$, and R$^5$ is independently Q-R$^M$;
wherein Q is a bond or is a C1-C6 aliphatic chain wherein up to two non-adjacent methylene units of Q are optionally and independently replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR;
wherein each occurrence of R$^M$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';
wherein each occurrence of R is independently selected from hydrogen or a C$_{1-6}$ aliphatic group optionally substituted with 0-5 occurrences of R$^K$; and each occurrence of R$^K$ is independently selected from —R$^V$, halogen, —NO$_2$, —CN, —OR$^V$, —SR$^V$, —N(R$^V$)$_2$, —NR$^V$COR$^V$, —NR$^V$CON(R$^V$)$_2$, —NR$^V$CO$_2$R$^V$, —COR$^V$, —CO$_2$R$^V$, —OCOR$^V$, —CON(R$^V$)$_2$, —C(═N—CN), —OCON(R$^V$)$_2$, —SOR$^V$, —SO$_2$R$^V$, —SO$_2$N(R$^V$)$_2$, —NR$^V$SO$_2$R$^V$, —NR$^V$SO$_2$N(R$^V$)$_2$, —COCOR$^V$, —COCH$_2$COR$^V$, —OP(O)(OR$^V$)$_2$, —P(O)(OR$^V$)$_2$, —OP(O)$_2$OR$^V$, —P(O)$_2$OR$^V$, —PO(R$^V$)$_2$, or —OPO(R$^V$)$_2$, wherein R$^V$ is hydrogen or unsubstituted C$_{1-6}$ aliphatic; and wherein each occurrence of R' is independently hydrogen, a C$_{1-6}$ aliphatic group optionally substituted with 0-5 occurrences of R$^{M1}$; and each occurrence of R$^{M1}$ is independently selected from —R$^T$, halogen, —NO$_2$, —CN, —OR$^T$, —SR$^T$, —N(R$^T$)$_2$, —NR$^T$COR$^T$, —NR$^T$CON(R$^T$)$_2$, —NR$^T$CO$_2$R$^T$, —COR$^T$, —CO$_2$R$^T$, —OCOR$^T$, —CON(R$^T$)$_2$, —C(═N—CN), —OCON(R$^T$)$_2$, —SOR$^T$, —SO$_2$R$^T$, —SO$_2$N(R$^T$)$_2$, —NR$^T$SO$_2$R$^T$, —NR$^T$SO$_2$N(R$^T$)$_2$, —COCOR$^T$, —COCH$_2$COR$^T$, —OP(O)(OR$^T$)$_2$, —P(O)(OR$^T$)$_2$, —OP(O)$_2$OR$^T$, —P(O)$_2$OR$^T$, —PO(R$^T$)$_2$, or —OPO(R$^T$)$_2$, wherein $R^T$ is hydrogen or unsubstituted $C_{1-6}$ aliphatic; or R' is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur wherein said monocyclic or bicyclic ring is optionally substituted with 0-5 occurrences of $R^U$; and each occurrence of $R^U$ is independently selected from a 3-8-membered saturated, partially unsaturated, or fully unsaturated monocyclic ring optionally substituted with 0-3 occurrences of —$R^{Q1}$ and having 0-3 heteroatoms independently selected from nitrogen, oxygen, or sulfur, or $R^U$ is —$R^Q$, halogen, =O, =$NR^Q$, —$NO_2$, —CN, —$OR^Q$, —$SR^Q$, —$N(R^Q)_2$, —$NR^Q COR^Q$, —$NR^Q CON(R^Q)_2$, —$NR^Q CO_2 R^Q$, —$COR^Q$, —$CO_2 R^Q$, —$OCOR^Q$, —$CON(R^Q)_2$, —C(=N—CN), —$OCON(R^Q)_2$, —$SOR^Q$, —$SO_2 R^Q$, —$SO_2 N(R^Q)_2$, —$NR^Q SO_2 R^Q$, —$NR^Q SO_2 N(R^Q)_2$, —$COCOR^Q$, —$COCH_2 COR^Q$, —OP(O)(OR$^Q$)$_2$, —P(O)(OR$^Q$)$_2$, —OP(O)$_2$OR$^Q$, —P(O)$_2$OR$^Q$, —PO(R$^Q$)$_2$, or —OPO(R$^Q$)$_2$, wherein $R^Q$ and $R^{Q1}$ are hydrogen or unsubstituted $C_{1-6}$ aliphatic; or R and R', two occurrences of R, or two occurrences of R', are taken together with the atom(s) to which they are bound to form a 3-12 membered saturated, partially unsaturated, or fully unsaturated monocyclic or bicyclic ring having 0-4 heteroatoms independently selected from nitrogen, oxygen, or sulfur wherein said monocyclic or bicyclic ring is optionally substituted with 0-5 occurrences of $R^{T1}$; and each occurrence of $R^{T1}$ is independently selected from —$R^S$, halogen, =O, =$NR^S$, —$NO_2$, —CN, —$OR^S$, —$SR^S$, —$N(R^S)_2$, —$NR^S COR^S$, —$NR^S CON(R^S)_2$, —$NR^S CO_2 R^S$, —$COR^S$, —$CO_2 R^S$, —$OCOR^S$, —$CON(R^S)_2$, —C(=N—CN), —$OCON(R^S)_2$, —$SOR^S$, —$SO_2 R^S$, —$SO_2 N(R^S)_2$, —$NR^S SO_2 R^S$, —$NR^S SO_2 N(R^S)_2$, —$COCOR^S$, —$COCH_2 COR^S$, —OP(O)(OR$^S$)$_2$, —P(O)(OR$^S$)$_2$, —OP(O)$_2$OR$^S$, —P(O)$_2$OR$^S$, —PO(R$^S$)$_2$, or —OPO(R$^S$)$_2$, wherein $R^S$ is hydrogen or unsubstituted $C_{1-6}$ aliphatic.

In one embodiment of formula I, $Z^2$ is a bond, $R^6$ is hydrogen, and $Z^1$ is a bond.

In another embodiment of formula I, $Z^2$ is a bond, $R^6$ is hydrogen, and $Z^1$ is $NR^7$, O, S, $CH_2$, C(O), or $NR^7 C(O)NR^7$.

In one embodiment of formula I, $Z^2$—$R^6$ is other than hydrogen and $Z^1$ is a bond.

In one embodiment of formula I, $Z^2$—$R^6$ is other than hydrogen and $Z^1$ is $NR^7$, O, S, $CH_2$, C(O), or $NR^7 C(O)NR^7$.

In one embodiment of formula I, ═══ is a single bond.

In one embodiment of formula I, ═══ is a single bond and both of $R^W$ are hydrogen.

In one embodiment of formula I, $R^Z$, if present, is C1-C6 alkyl, halo-C1-C6 alkyl- or —O—C1-C6 alkyl.

In one embodiment of formula I, $R^Z$, if present, is fluoro, methyl, ethyl, n-propyl, $CF_3$, $CHF_2$, OMe or OEt.

In one embodiment of formula I, at least one $R^W$ is C1-C6 alkyl, halo-C1-C6 alkyl or —O—C1-C6 alkyl.

In one embodiment of formula I, at least one $R^W$ is fluoro, methyl, ethyl, n-propyl, $CF_3$, $CHF_2$, OMe or OEt.

In one embodiment of formula I, one $R^W$ is hydrogen and the other $R^W$ is C1-C6 alkyl, halo-C1-C6 alkyl- or —O—C1-C6 alkyl.

In one embodiment of formula I, one of $R^W$ is hydrogen and the other $R^W$ is fluoro, methyl, ethyl, n-propyl, $CF_3$, $CHF_2$, OMe or OEt.

In one embodiment of formula I, $R^Y$ is C1-C6 aliphatic optionally substituted with one or more halo, OH, —C1-C4 alkoxy, —C1-C4 alkoxy carbonyl, or di-(C1-C4 alkyl) amino-.

In one embodiment of formula I, $R^Y$ is methyl, ethyl, propyl, isopropyl, butyl, t-butyl, 3,3-dimethyl-butyl, 3-methylbutyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino)ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl.

In one embodiment of formula I, $R^Y$ is methyl, ethyl, propyl, isopropyl, butyl, t-butyl, 3,3-dimethyl-butyl, 3-methylbutyl or 2-methyl-propyl.

In one embodiment of formula I, $R^Y$ is C3-C8 cycloaliphatic or a C3-C8 cycloaliphatic substituted C1-C6 aliphatic-.

In one embodiment of formula I, $R^Y$ is C3-C6 cycloalkyl or a C3-C6 cycloalkyl substituted C1-C6 alkyl-.

In one embodiment of formula I, $R^Y$ is cyclopropyl, cyclohexyl, cyclohexylmethyl-, cyclopropylmethyl-, or cyclohexylethyl-.

In one embodiment of formula I, $R^Y$ is pyridyl(C1-C6)-alkyl-, tetrahydrofuranyl(C1-C6 alkyl)-, or N—(C1-C4 alkyl)-pyrrolidinyl-(C1-C6 alkyl)-.

In one embodiment of formula I, tetrahydrofuran-2-yl-methyl-, pyridin-3-yl-methyl-, pyridin-4-yl-ethyl-, pyridin-2-yl-ethyl-, pyridin-4-yl-methyl-, 1H-indazol-5-yl, or 2-(N-methyl)-pyrrolidin-2-yl-ethyl-.

In one embodiment of formula I, $R^Y$ is phenyl or (phenyl)-substituted C1-C6 aliphatic- each optionally substituted with up to 5 $R^2$ substituents independently selected from halogen or a 5-6 membered heterocyclyl ring having 1-3 heteroatoms selected from N, O, or S.

In one embodiment of formula I, $R^Y$ is phenyl, 2,6-difluorophenyl, benzyl, 4-fluorophenylmethyl-, 4-morpholinophenyl-, 2-piperidinylphenyl- or phenylethyl-.

In one embodiment of formula I, one $R^X$ is hydrogen and the other $R^X$ is an aryl or heteroaryl ring optionally substituted with up to 5 $R^3$ substituents independently selected from C1-C6 aliphatic, phenyl, halogen, C3-C6 cycloaliphatic or a 4-7 membered heterocyclic ring wherein said heterocyclic ring is optionally substituted with up to 3 $R^U$ substituents wherein said heteroaryl or heterocyclic ring has up to three heteroatoms selected from N, O, or S.

In one embodiment of formula I, one $R^x$ is hydrogen and the other $R^x$ is phenyl or pyridyl with up to 2 $R^3$ substituents independently selected from halogen or a 4-7 membered heterocyclic ring wherein said heterocyclic ring is optionally substituted with up to 2 $R^U$ substituents wherein said heterocyclic ring has up to three heteroatoms selected from N, O, or S.

In one embodiment of formula I, one $R^X$ is hydrogen and the other $R^X$ is phenyl substituted with a 4-7 membered heterocyclic ring in the 2 position and a halogen in the 3 position.

In one embodiment of formula I, one $R^X$ is hydrogen and the other $R^X$ is phenyl, or phenyl substituted with piperazine, 4-methyl-piperazin-1-yl, 4-ethyl-piperazin-1yl, 4-propyl-piperazin-1yl, 4-butyl-piperazin-1yl, 4-isopropyl-piperazin-1yl, 4-t-butylpiperazin-1yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, or 1-(2,2,2-trifluoroethyl)piperazin-1-yl.

In one embodiment of formula I, one $R^X$ is hydrogen and the other $R^X$ is pyridyl, or pyridyl substituted with piperazine, 4-methyl-piperazin-1-yl, 4-ethyl-piperazin-1yl, 4-propyl-piperazin-1yl, 4-butyl-piperazin-1yl, 4-isopropyl-piperazin- 1yl, 4-t-butylpiperazin-1yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, or 1-(2,2,2-trifluoroethyl)piperazin-1-yl.

In one embodiment of formula I, one $R^X$ is hydrogen and the other $R^X$ is phenyl or heteroaryl optionally substituted with one or more substituents independently selected from C1-C6 aliphatic, cyano, halo, halo-C1-C6 aliphatic-, aryl-C1-C6 aliphatic-, heteroaryl-C1-C6 aliphatic-, aralkyloxy, di(C1-C6 aliphatic)amino-, —O—C1-C6 aliphatic, —S(O)—C1-C6 aliphatic, or —S(O)$_2$—C1-C6 aliphatic.

In one embodiment of formula I, one $R^X$ is hydrogen and the other $R^X$ is a C3-C7 cycloaliphatic or a heterocycloaliphatic ring optionally substituted with up to five $R^3$ substituents and having up to three heteroatoms selected from O, N, or S, wherein said ring is optionally fused to one or more phenyl or heteroaryl rings.

In one embodiment of formula I, said $R^X$ is selected from cyclopentyl, cyclohexyl, cyclohexenyl, cycloheptyl, tetrahydro-2H-pyranyl, tetrahydro-2H-thiopyranyl, 9H-fluoren-9-yl or piperidinyl.

In one embodiment of formula I, two $R^X$, taken together with the carbon atom that they are attached to, form a 3-9 membered monocyclic, a 9-14 membered bicyclic, or a 12-14 membered tricyclic aryl, heteroaryl or heterocyclic ring system wherein each heteroaryl or heterocyclic ring has up to 3 heteroatoms selected from O, S, and N; wherein said ring system formed by two $R^X$ is optionally substituted with up to 5 $R^4$ substituents.

In one embodiment of formula I, said ring system is selected from 9H-fluoroen-9-yl, tetrahydro-2H-pyran-4-yl, tetrahydro-2H-thiopyran-4-yl, cyclobutyl, cyclopentyl, cyclohexyl, cycloheptyl, cyclohexenyl, piperidinyl, or 1-benzyl-piperidin-4-yl.

In another embodiment of formula I, said compound is of formula I-A:

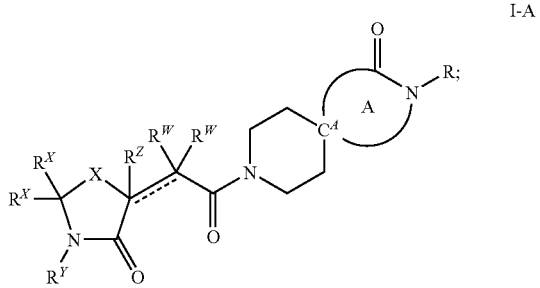

wherein:
ring A is a 4-7 membered heterocyclic ring that forms a spirocyclic ring system with said piperidine ring through carbon atom $C^A$, wherein ring A is optionally fused with a phenyl or heteroaryl ring that is optionally substituted with up to 5 $R^1$ substituents;
wherein said ring A, in addition to the nitrogen ring atom, has up to two additional ring heteroatoms selected from O, N, or S;
wherein ring A, in addition to the oxo group, is optionally substituted with up to 5 $R^1$ substituents;
$R^1$, $R^X$, $R^Y$, $R^Z$, $R^W$, and X are as defined herein.

In one embodiment of formula I-A, ===is a single bond and $R^Z$, if present, is hydrogen.
In one embodiment of formula I-A, ===is a single bond and $R^Z$ is C1-C6 alkyl, halo-C1-C6 alkyl-, or —O—C1-C6 alkyl.
In one embodiment of formula I-A, $R^Z$, if present, is fluoro, methyl, ethyl, n-propyl, $CF_3$, $CHF_2$, OMe or OEt.
In one embodiment of formula I-A, at least one $R^W$ is C1-C6 alkyl, halo-C1-C6 alkyl- or —O—C1-C6 alkyl.
In one embodiment of formula I-A, at least one $R^W$ is fluoro, methyl, ethyl, n-propyl, $CF_3$, $CHF_2$, OMe or OEt.
In one embodiment of formula I-A, ===is a single bond, one $R^W$ is hydrogen and the other $R^W$ is $C_1$-$C_6$ alkyl, halo-C1-C6 alkyl or —O—C1-C6 alkyl.
In one embodiment of formula I-A, one $R^W$ is hydrogen and the other $R^W$ is fluoro, methyl, ethyl, n-propyl, $CF_3$, $CHF_2$, OMe or OEt.
In one embodiment of formula I-A, ===is a single bond and each $R^W$ is hydrogen.
In one embodiment of formula I-A, $R^Y$ is C1-C6 aliphatic optionally substituted with one or more halo, OH, C1-C4 alkoxy, C1-C4 alkoxy carbonyl, or di-(C1-C4 alkyl)amino-.
In one embodiment of formula I-A, $R^Y$ is methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino)ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl.
In one embodiment of formula I-A, $R^Y$ is methyl, ethyl, propyl, isopropyl, butyl, t-butyl, 3,3-dimethyl-butyl, 3-methyl-butyl or 2-methyl-propyl.
In one embodiment of formula I-A, $R^Y$ is C3-C8 cycloaliphatic or a C3-C8 cycloaliphatic substituted C1-C6 aliphatic-.
In one embodiment of formula I-A, $R^Y$ is C3-C6 cycloalkyl or a C3-C6 cycloalkyl substituted C1-C6 alkyl-.
In one embodiment of formula I-A, $R^Y$ is cyclopropyl, cyclohexyl, cyclohexylmethyl-, cyclopropylmethyl-, or cyclohexylethyl-.
In one embodiment of formula I-A, $R^Y$ is pyridyl(C1-C6)alkyl-, tetrahydrofuranyl(C1-C6 alkyl)-, N—(C1-C4 alkyl)-pyrrolidinyl-(C1-C6 alkyl)-.
In one embodiment of formula I-A, $R^Y$ is tetrahydrofuran-2-yl-methyl-, pyridin-3-yl-methyl-, pyridin-4-yl-ethyl-, pyridin-2-yl-ethyl-, pyridin-4-yl-methyl-, 1H-indazol-5-yl, or 2-(N-methyl)-pyrrolidin-2-yl-ethyl-.
In one embodiment of formula I-A, $R^Y$ is phenyl or (phenyl)-substituted C1-C6 aliphatic-optionally substituted with up to 5 $R^2$ substituents independently selected from halogen or a 5-6 membered heterocyclyl ring having 1-3 heteroatoms selected from N, O, or S.
In one embodiment of formula I-A, $R^Y$ is phenyl, 2,6-difluorophenyl, benzyl, 4-fluorophenylmethyl-, 4-morpholinophenyl-, 2-piperidinylphenyl- or phenylethyl-.
In one embodiment of formula I-A, ===is a single bond, one $R^X$ is hydrogen and the other $R^X$ is an aryl or heteroaryl ring optionally substituted with up to 5 $R^3$ substituents independently selected from C1-C6 aliphatic, phenyl, halogen, C3-C6 cycloaliphatic or a 4-7 membered heterocyclic ring with up to 3 $R^U$ substituents wherein said heteroaryl or heterocyclic ring has up to three heteroatoms selected from N, O, or S.
In one embodiment of formula I-A, one $R^X$ is hydrogen and the other $R^X$ is phenyl or pyridyl with up to 2 $R^5$ substituents independently selected from halogen or a 4-7 membered heterocyclic ring with up to 2 R$^U$ substituents wherein said heterocyclic ring has up to three heteroatoms selected from N, O, or S.

In one embodiment of formula I-A, one R$^X$ is hydrogen and the other R$^X$ is phenyl substituted with a 4-7 membered heterocyclic ring in the 2 position and a halogen in the 3 position.

In one embodiment of formula I-A, one R$^X$ is hydrogen and the other R$^X$ is phenyl, or phenyl substituted with piperazine, 4-methyl-piperazin-1-yl, 4-ethyl-piperazin-1yl, 4-propyl-piperazin-1yl, 4-butyl-piperazin-1yl, 4-isopropyl-piperazin-1yl, 4-t-butylpiperazin-1yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, or 1-(2,2,2-trifluoroethyl)piperazin-1-yl.

In one embodiment of formula I-A, one R$^X$ is hydrogen and the other R$^X$ is pyridyl, or pyridyl substituted with piperazine, 4-methyl-piperazin-1-yl, 4-ethyl-piperazin-1yl, 4-propyl-piperazin-1yl, 4-butyl-piperazin-1yl, 4-isopropyl-piperazin-1yl, 4-t-butylpiperazin-1yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, 1-(2,2,2-trifluoroethyl)piperazin-1-yl.

In one embodiment of formula I-A, one R$^X$ is hydrogen and the other R$^X$ is phenyl or heteroaryl optionally substituted with one or more substituents independently selected from C1-C6 aliphatic, cyano, halo, halo-C1-C6 aliphatic-, aryl-C1-C6 aliphatic-, heteroaryl-C1-C6 aliphatic-, aralkyloxy, di(C1-C6 aliphatic)amino-, —O—C1-C6 aliphatic, —S(O)—C1-C6 aliphatic, or —S(O)$_2$—C1-C6 aliphatic.

In one embodiment of formula I-A, at least one R$^X$ is hydrogen and the other R$^X$ is a C3-C7 cycloaliphatic or a heterocycloaliphatic ring optionally substituted with up to five R$^3$ substituents and having up to three heteroatoms selected from O, N, or S, wherein said ring is optionally fused to one or more phenyl or heteroaryl rings.

In one embodiment of formula I-A, said R$^X$ is selected from cyclopentyl, cyclohexyl, cyclohexenyl, cycloheptyl, tetrahydro-2H-pyranyl, tetrahydro-2H-thiopyranyl, 9H-fluoren-9-yl or piperidinyl.

In one embodiment of formula I-A, ═══ is a single bond, two R$^X$, taken together with the carbon atom that they are attached to, form a 3-9 membered monocyclic, a 9-14 membered bicyclic, or a 12-14 membered tricyclic aryl, heteroaryl or heterocyclic ring system wherein each heteroaryl or heterocyclic ring has up to 3 heteroatoms selected from O, S, and N; wherein said ring system formed by two R$^X$ is optionally substituted with up to 5 R$^4$ substituents.

In one embodiment of formula I-A, said ring system is selected from 9H-fluoroen-9-yl, tetrahydro-2H-pyran-4-yl, tetrahydro-2H-thiopyran-4-yl, cyclobutyl, cyclopentyl, cyclohexyl, cycloheptyl, cyclohexenyl, piperidinyl, or 1-benzyl-piperidin-4-yl.

In one embodiment of formula I or I-A, ring A is selected from:

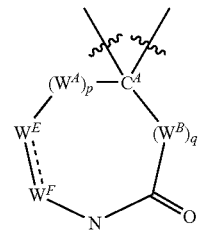

A-i

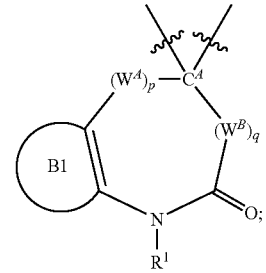

A-ii

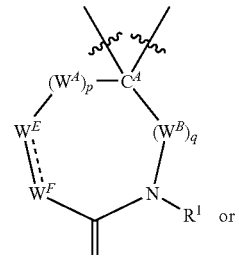

A-iii

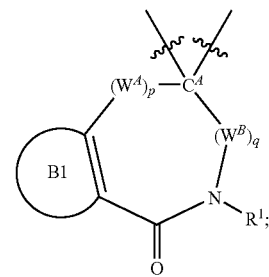

A-iv wherein:
p is 0-2;
q is 0-2; provided that p+q≦2;
each of W$^A$ and W$^B$ is independently selected from NR$^1$, O, S, SO, SO$_2$, C(R$^1$)$_2$, or ═CR$^1$ (when p or q is 2);
W$^E$ is —C(R$^1$)$_2$, ═C(R$^1$)—, ═N—, or —N(R$^1$)—;
W$^F$ is absent or is selected from —C(R$^1$)$_2$, ═C(R$^1$)—, ═N—, or —N(R$^1$)—; provided that both of W$^E$ and W$^F$ are not simultaneously ═N— or —N(R$^1$)—;
ring B1 is a phenyl or 5-6 membered heteroaryl ring optionally substituted with up to 5 R$^1$ substituents; and
R$^1$ is as defined herein.

In another embodiment of formula I or I-A, ring A has formula A-i.

In one embodiment of formula I or I-A, ring A has formula A-ii.

In one embodiment of formula I or I-A, ring A has formula A-iii.

In one embodiment of formula I or I-A, ring A has formula A-iv.

In one embodiment of formula I or I-A, both, $W^E$ and $W^F$ are $=C(R^1)$.

In one embodiment of formula I or I-A, $W^E$ is $=C(R^1)-$ and $W^F$ is $=N-$.

In one embodiment of formula I or I-A, p is 0 and q is 0.
In one embodiment of formula I or I-A, p is 1 and q is 0.
In one embodiment of formula I or I-A, p is 0 and q is 2.
In one embodiment of formula I or I-A, $W^A$ is $NR^1$.
In one embodiment of formula I or I-A, $W^A$ is O.
In one embodiment of formula I or I-A, $W^A$ is $C(R^1)_2$.
In one embodiment of formula I or I-A, $W^A$ is $C(R^1)_2$ and $R^1$ is hydrogen.
In one embodiment of formula I or I-A, $W^B$ is $NR^1$.
In one embodiment of formula I or I-A, $W^B$ is O.
In one embodiment of formula I or I-A, $W^B$ is $C(R^1)_2$.
In one embodiment of formula I or I-A, $W^B$ is $C(R^1)_2$ and $R^1$ is hydrogen.
In one embodiment of formula I or I-A, p is 2 and $W^A$ is $C(R^1)_2-C(R^1)_2$ or $-CR^1=CR^1-$.
In one embodiment of formula I or I-A, q is 2 and $W^B$ is $C(R^1)_2-C(R^1)_2$ or $-CR^1=CR^1-$.

In one embodiment of formula I or I-A, ring A is selected from:

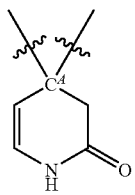
A-i-a

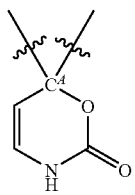
A-i-b

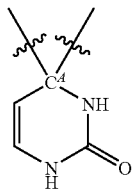
A-i-c

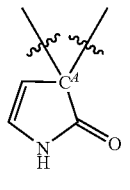
A-i-d

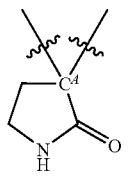
A-i-h

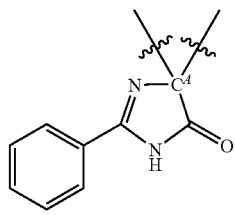
A-i-i

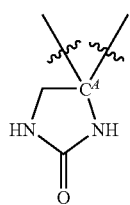
A-i-j

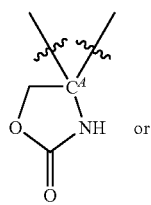
A-i-k or

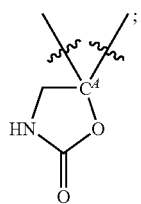
A-i-l

;

wherein said ring is optionally substituted with up to 4 $R^1$ substituents.

In one embodiment of formula I or I-A, ring A is selected from:

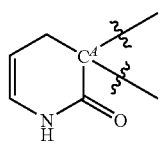
A-i-e

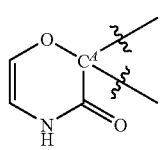
A-i-f or

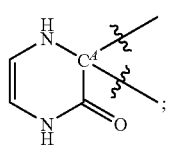
A-i-g

;

wherein said ring is optionally substituted with up to 4 $R^1$ substituents.

In one embodiment of formula I or I-A, ring A is selected from:

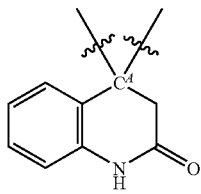
A-ii-a

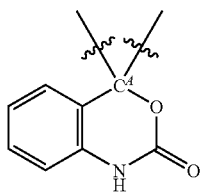
A-ii-b

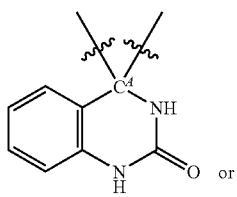
A-ii-c

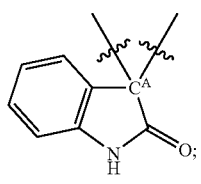
A-ii-d wherein said ring system is optionally substituted with up to 4 $R^1$ substituents.

In one embodiment of formula I or I-A, ring A is selected from:

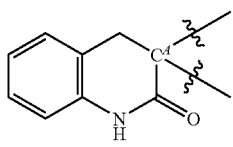
A-ii-e

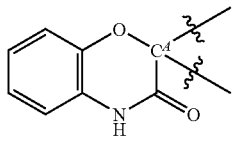
A-ii-f

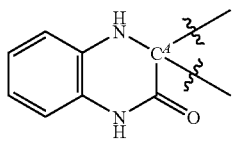
A-ii-g

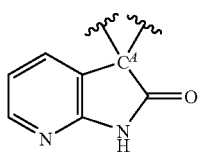
A-ii-h

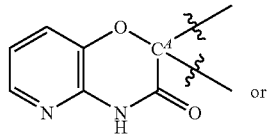
A-ii-i or

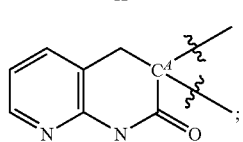
A-ii-j wherein said ring system is optionally substituted with up to 4 $R^1$ substituents.

In another embodiment of formula I or I-A, the compound is of formula I-B:

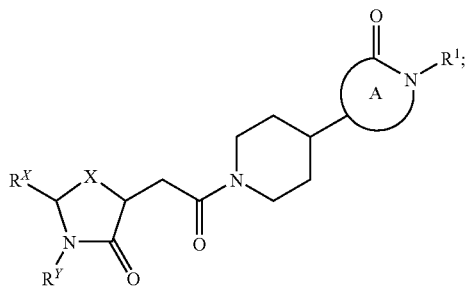
I-B wherein ring A is a 4-7 membered heterocyclic ring optionally fused with an phenyl or heteroaryl ring that is optionally substituted with up to 5 $R^1$ substituents;

wherein said ring A, in addition to the nitrogen ring atom, contains up to two additional ring heteroatoms selected from O, N, or S;

wherein ring A, in addition to the oxo group, is optionally substituted with up to 5 $R^1$ substituents;

$R^1$, $R^X$, $R^Y$, and X are as defined herein.

In one embodiment of formula I-B, $R^Y$ is C1-C6 aliphatic optionally substituted with one or more halo, OH, C1-C4 alkoxy, C1-C4 alkoxy carbonyl, or di-(C1-C4 alkyl)amino-.

In one embodiment of formula I-B, $R^Y$ is methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino) ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl.

In one embodiment of formula I-B, $R^Y$ is methyl, ethyl, propyl, isopropyl, butyl, t-butyl, 3,3-dimethyl-butyl, 3-methyl-butyl or 2-methyl-propyl.

In one embodiment of formula I-B, $R^Y$ is C3-C8 cycloaliphatic or a C3-C8 cycloaliphatic substituted C1-C6 aliphatic-.

In one embodiment of formula I-B, $R^Y$ is C3-C6 cycloalkyl or C3-C6 cycloalkyl substituted C1-C6 alkyl-.

In one embodiment of formula I-B, $R^Y$ is cyclopropyl, cyclohexyl, cyclohexylmethyl-, cyclopropylmethyl-, or cyclohexylethyl-.

In one embodiment of formula I-B, $R^Y$ is pyridyl(C1-C6) alkyl-, tetrahydrofuranyl (C1-C6 alkyl)-, N—(C1-C4 alkyl)-pyrrolidinyl-(C1-C6 alkyl)-.

In one embodiment of formula I-B, $R^Y$ is tetrahydrofuran-2-yl-methyl-, pyridin-3-yl-methyl-, pyridin-4-yl-ethyl-, pyridin-2-yl-ethyl-, pyridin-4-yl-methyl-, 1H-indazol-5-yl, or 2-(N-methyl)-pyrrolidin-2-yl-ethyl-.

In one embodiment of formula I-B, $R^Y$ is phenyl or (phenyl)-substituted C1-C6 aliphatic each optionally substituted with up to 5 $R^2$ substituents independently selected from halogen or a 5-6 membered heterocyclyl ring having 1-3 heteroatoms selected from N, O, or S.

In one embodiment of formula I-B, $R^Y$ is phenyl, 2,6-difluorophenyl, benzyl, 4-fluorophenylmethyl-, 4-morpholinophenyl-, 2-piperidinylphenyl- or phenylethyl-.

In one embodiment of formula I-B, $R^X$ is an aryl or heteroaryl ring optionally substituted with up to 5 $R^3$ substituents independently selected from C1-C6 aliphatic, phenyl, halogen, C3-C6 cycloaliphatic or a 4-7 membered heterocyclic ring with up to 3 $R^U$ substituents wherein said heteroaryl or heterocyclic ring has up to three heteroatoms selected from N, O, or S.

In one embodiment of formula I-B, $R^X$ is phenyl or pyridyl with up to 2 $R^3$ substituents independently selected from halogen or a 4-7 membered heterocyclic ring wherein said heterocyclic ring is optionally substituted with up to 2 $R^U$ substituents wherein said heterocyclic ring has up to three heteroatoms selected from N, O, or S.

In one embodiment of formula I-B, $R^X$ is phenyl substituted with a 4-7 membered heterocyclic ring in the 2 position and a halogen in the 3 position.

In one embodiment of formula I-B, $R^X$ is pyridyl, phenyl, or phenyl substituted with piperazine, 4-methyl-piperazin-1-yl, 4-ethyl-piperazin-1yl, 4-propyl-piperazin-1yl, 4-butyl-piperazin-1yl, 4-isopropyl-piperazin-1yl, 4-t-butylpiperazin-1yl, 4-cyclopropylpiperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl, pyrrolidin-1-yl, 3-dimethylamino-pyrrolidin-1-yl, 4-(piperidin-1-yl)piperidine, pyridyl (1-methylpiperidin-4-yl)piperazin-1-yl, or 1-(2,2,2-trifluoroethyl)piperazin-1-yl.

In one embodiment of formula I-B, $R^X$ is phenyl or heteroaryl optionally substituted with one or more substituents independently selected from C1-C6 aliphatic, cyano, halo, halo-C1-C6 aliphatic-, aryl-C1-C6 aliphatic-, heteroaryl-C1-C6 aliphatic-, aralkyloxy, di(C1-C6 aliphatic)amino-, —O—C1-C6 aliphatic, —S(O)—C1-C6 aliphatic, or —S(O)$_2$—C1-C6 aliphatic.

In one embodiment of formula I-B, $R^X$ is a C3-C7 cycloaliphatic or a heterocycloaliphatic ring optionally substituted with up to five $R^3$ substituents and having up to three heteroatoms selected from O, N, or S, wherein said ring is optionally fused to one or more phenyl or heteroaryl rings.

In one embodiment of formula I-B, said fused ring is selected from cyclopentyl, cyclohexyl, cyclohexenyl, cycloheptyl, tetrahydro-2H-pyranyl, tetrahydro-2H-thiopyranyl, 9H-fluoren-9-yl or piperidinyl.

In one embodiment of formula I-B, ring A is selected from:

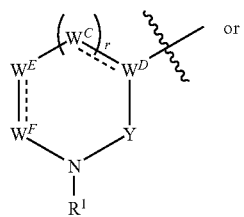

A-v or

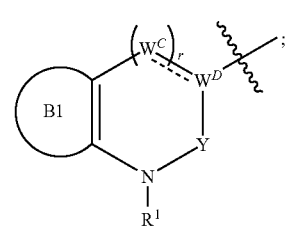

A-vi wherein:
$W^C$ is —C(R$^1$)$_2$, C(O), or =CR$^1$—;
r is 0-2;
$W^D$ is N or =C—;
$W^E$ is —C(R$^1$)$_2$, =C(R$^1$)—, =N—, or —N(R$^1$)—;
$W^F$ is absent or is selected from —C(R$^1$)$_2$, =C(R$^1$)—, =N—, or —N(R$^1$)—; provided that both of $W^E$ and $W^F$ are not simultaneously =N— or —N(R$^1$)—;
Y is C(O), S(O), or S(O)$_2$;
ring B1 is a phenyl or 5-6 membered heteroaryl ring optionally substituted with up to 5 $R^1$ substituents; and ═══ is a single or a double bond;
$R^1$ is as defined herein.

In one embodiment of formula I-B, $W^C$ is —C(R$^1$)$_2$.
In another embodiment of formula I-B, $W^C$ is =CR$^1$—.
In one embodiment of formula I-B, $W^C$ is C(O).
In one embodiment of formula I-B, r is 0.
In one embodiment of formula I-B, r is 1.
In one embodiment of formula I-B, r is 2.
In one embodiment of formula I-B, $W^D$ is N.
In one embodiment of formula I-B, $W^D$ is =C—.
In one embodiment of formula I-B, Y is C(O).
In one embodiment of formula I-B, Y is S(O).
In one embodiment of formula I-B, Y is S(O)$_2$.
In one embodiment of formula I-B, ring A is selected from:

A-v-a

A-v-b

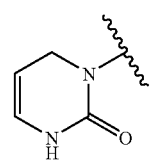

A-v-c

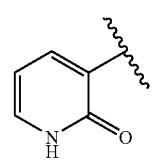

A-v-d

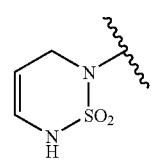

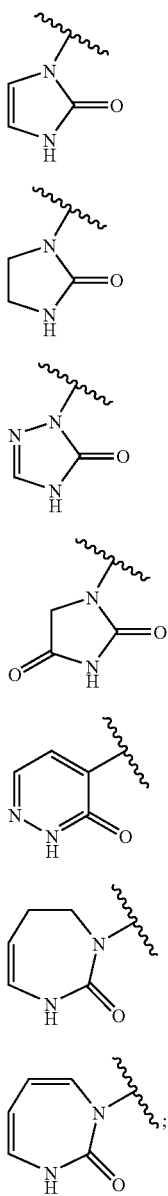
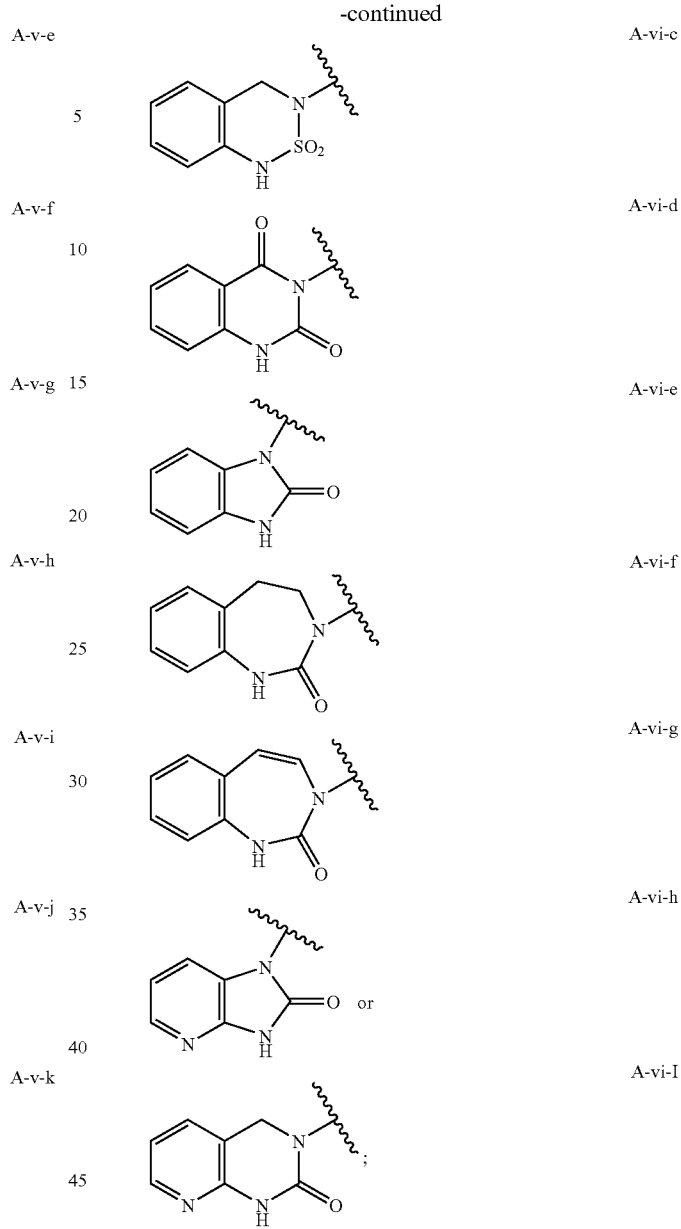

wherein said ring is optionally substituted with up to 4 $R^1$ substituents.

In one embodiment of formula I-B, ring A is selected from:

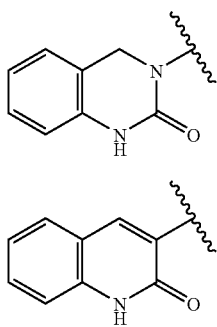

wherein said ring is optionally substituted with up to 4 $R^1$ substituents.

In one embodiment of formula I-B, ring A is optionally substituted with up to 5 substituents selected from C1-C6 aliphatic, C1-C6 aliphatic-oxy, C1-C6 haloaliphatic, CN, halo, oxo, optionally substituted C3-C7 cycloaliphatic, or an optionally substituted ring selected from phenyl, furanyl, pyrrolyl, pyrrolinyl, pyrrolidinyl, imadazolyl, imidazolinyl, imidazolidinyl, pyrazolyl, pyrazolinyl, pyrazolidinyl, pyridyl, pyrimidinyl, piperidinyl, piperazinyl, or morpholinyl.

In one embodiment of formula I-B, in $R^1$, Q is a bond.
In one embodiment of formula I-B, in $R^1$, Q-$R^M$ is Q-R'.
In one embodiment of formula I-B, Q is present and R is hydrogen.
In one embodiment of formula I-B, Q is present and R is $C_1$-$C_6$ aliphatic.
In one embodiment of formula I-B, R is methyl, ethyl, propyl, or butyl.
In one embodiment of formula I-B, R' is hydrogen.

In one embodiment of formula I-B, R' is a C1-C8 aliphatic group, optionally substituted with up to 3 substituents selected from halo, CN, CF₃, CHF₂, OCF₃, or OCHF₂, wherein up to two methylene units of said C1-C8 aliphatic is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂—, or —N(C1-C4 alkyl)SO₂N(C1-C4 alkyl)-.

In one embodiment of formula I-B, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, CF₃, CHF₂, OCF₃, OCHF₂, or C1-C6 alkyl, wherein up to two methylene units of said C1-C6 alkyl is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂—, or —N(C1-C4 alkyl)SO₂N(C1-C4 alkyl)-.

In one embodiment of formula I-B, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, CF₃, CHF₂, OCF₃, OCHF₂, or C₁-C₆ alkyl, wherein up to two methylene units of said C1-C6 alkyl is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂—, or —N(C1-C4 alkyl)SO₂N(C1-C4 alkyl)-.

In one embodiment of formula I-B, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, CF₃, CHF₂, OCF₃, OCHF₂, or C1-C6 alkyl, wherein up to two methylene units of said C1-C6 alkyl is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂—, or —N(C1-C4 alkyl)SO₂N(C1-C4 alkyl)-.

In one embodiment, compounds of the present invention include those in Table 1 and Table 1A.

In another embodiment, compounds of the present invention include those in Table 1.

In another embodiment, compounds of the present invention include those in Table 1A.

In another embodiment, compounds of the present invention include those in Table 1A and Table 1 except for compound numbers 85, 97, and 105.

In another embodiment, compounds of the present invention include those in Table 1 except for compound numbers 85, 97, and 105.

In one embodiment, the present invention provides compounds of formula I':

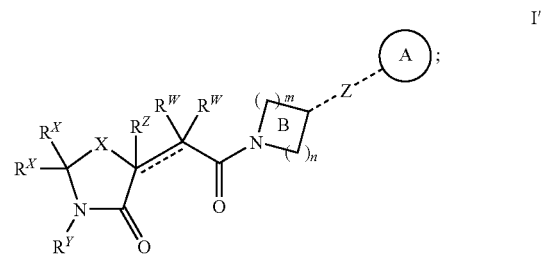

wherein:
X is S, SO, or SO₂;
Z is present or absent;
wherein:
when Z is present, then ring A is attached to ring B through a single bond;
when Z is absent, then ring A together with ring B forms a spirocyclic ring system;
ring A is a 4-7 membered heterocyclic or heteroaryl ring or a 10-14 membered bicyclic heterocyclic ring, wherein ring A has 1-4 heteroatoms selected from O, N, or S;
wherein ring A is optionally substituted with up to 5 $R^1$ substituents;
m is 1-3;
n is 1-3; provided that m+n is ≦4;
$R^Y$ is aryl, heteroaryl, cycloaliphatic, C1-C6 aliphatic, aryl-aliphatic, or cycloaliphatic-aliphatic; wherein $R^Y$ is optionally substituted with up to 5 $R^2$ substituents;
$R^X$ is hydrogen, halo, aryl, heteroaryl, C1-C6 aliphatic, aryl-C1-C6 aliphatic, heteroaryl-C1-C6 aliphatic, wherein $R^X$ is optionally substituted with up to 5 $R^3$ substituents;
or two $R^X$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 $R^3$ substituents;
wherein said ring formed by two $R^X$ is optionally substituted with up to 5 $R^4$ substituents;
$R^Z$ is absent, hydrogen, CN, C1-C6 aliphatic, halo-C1-C6 aliphatic, O—C1-C6 aliphatic, O-(halo-C1-C6 aliphatic), halo, aryl-C1-C6 aliphatic, or heteroaryl-C1-C6 aliphatic;
=== is a single or a double bond; provided that when it is a double bond, then $R^Z$ and one of $R^W$ is absent;
$R^W$ is independently hydrogen, halo, oxo, C1-C6 aliphatic, halo-C1-C6 aliphatic, O—C1-C6 aliphatic, O-(halo-C1-C6 aliphatic), aryl, aryl-C1-C6 aliphatic, C3-C7 cycloaliphatic; or
two $R^W$ taken together form an optionally substituted C3-C7 cycloaliphatic or heterocyclic ring, wherein said heterocyclic ring has up to 3 heteroatoms selected from O, S, and N; wherein said ring formed by two $R^W$ is optionally substituted with up to 5 $R^5$ substituents;
wherein each occurrence of $R^1$, $R^2$, $R^3$, $R^4$, and $R^5$ is independently Q-$R^M$;
wherein Q is a bond or is a C1-C6 aliphatic chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR;
wherein each occurrence of $R^M$ is independently selected from R', halogen, NO₂, CN, OR', SR', N(R')₂, NR'C(O)R', NR'C(O)N(R')₂, NR'CO₂R', C(O)R', CO₂R', OC(O)R', C(O)N(R')₂, OC(O)N(R')₂, SOR', SO₂R', SO₂N(R')₂, NR'SO₂R', NR'SO₂N(R')₂, C(O)C(O)R', or C(O)CH₂C(O)R', wherein each occurrence of R is independently selected from hydrogen or an optionally substituted $C_{1-6}$ aliphatic group;

wherein each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur.

In one embodiment, ===is a double bond and $R^Z$ and one of $R^W$ is absent;

In another embodiment, ===is a single bond. In another embodiment, one or $R^W$ is hydrogen and the other is not. In another embodiment, both of $R^W$ are hydrogen.

In one embodiment, m is 1 and n is 1. In another embodiment, m is 1 and n is 2. Or, m is 2 and n is 1. Or, m is 2 and n is 2.

In another embodiment, $R^Z$ is C1-C6 alkyl or halo-C1-C6 alkyl. Or, $R^Z$ is —O—C1-C6 alkyl. Exemplary $R^Z$ include fluoro, methyl, ethyl, n-propyl, $CF_3$, $CHF_2$, OMe, OEt, etc.

In another embodiment, $R^W$ is C1-C6 alkyl or halo-C1-C6 alkyl. Or, $R^W$ is —O—C1-C6 alkyl. Exemplary $R^W$ include fluoro, methyl, ethyl, n-propyl, $CF_3$, $CHF_2$, OMe, OEt, etc.

In another embodiment, two $R^W$, taken together with the carbon atom they are attached to, form an optionally substituted C3-C9 cycloalkyl or a 3-9 membered heterocyclyl ring. Exemplary such rings include cyclopropyl, cyclopentyl, or cyclohexyl.

In one embodiment, $R^Y$ is C1-C6 aliphatic optionally substituted with one or more halo, OH, C1-C4 alkoxy, C1-C4 alkoxy carbonyl, or di-(C1-C4 alkyl)amino. Exemplary embodiments include methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino)ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl.

In another embodiment, $R^Y$ is C3-C8 cycloaliphatic or C3-C8 cycloaliphatic substituted C1-C6 aliphatic. In one embodiment, $R^Y$ is C3-C6 cycloalkyl or C3-C6 cycloalkyl substituted C1-C6 alkyl. Exemplary embodiments include cyclopropyl, cyclohexyl, cyclohexylmethyl, cyclopropylmethyl, or cyclohexylethyl.

In another embodiment, $R^Y$ is pyridyl(C1-C6)alkyl, tetrahydrofuranyl(C1-C6 alkyl), N—(C1-C4 alkyl)-pyrrolidinyl-(C1-C6 alkyl). Exemplary embodiments include tetrahydrofuran-2-ylmethyl, pyridin-3-yl-methyl, pyridin-4-yl-ethyl, pyridin-2-yl-ethyl, pyridin-4-yl-methyl, 1H-indazol-5-yl, or 2-(N-methyl)-pyrrolidin-2-yl-ethyl.

In another embodiment, $R^Y$ is optionally substituted phenyl or (optionally substituted phenyl)-substituted C1-C6 aliphatic. Exemplary embodiments include phenyl, 2,6-difluorophenyl, benzyl, 4-fluorophenylmethyl, or phenylethyl.

In one embodiment, both $R^X$ are hydrogen.

In one embodiment, $R^X$ is a phenyl or a heteroaryl, such as pyridyl, wherein said phenyl or heteroaryl is optionally substituted with an optionally substituted 3-7 membered heterocyclic or heteroaryl ring having up to three heteroatoms selected from O, S, or N. Exemplary $R^X$ include phenyl, pyridyl, or phenyl substituted with piperazine, 4-methyl-piperazin-1-yl, 4-t-butoxycarbonyl-piperazin-1-yl, 4-hydroxy-piperidinyl, 4-ethoxycarbonyl-piperidin-1-yl, morpholin-4-yl, 1-H-pyrazol-1-yl, imidazol-1-yl or pyridyl.

In another embodiment, $R^X$ is phenyl or heteroaryl optionally substituted with one or more substituents independently selected from C1-C6 aliphatic, cyano, halo, halo-C1-C6 aliphatic, aryl-C1-C6 aliphatic, heteroaryl-C1-C6 aliphatic, aralkyloxy, di(C1-C6 aliphatic)amino, O—C1-C6 aliphatic, S(O)—C1-C6 aliphatic, or $S(O)_2$—C1-C6 aliphatic.

In another embodiment, $R^X$ is an optionally substituted C3-C7 cycloaliphatic or a heterocycloaliphatic ring having up to three heteroatoms selected from O, N, or S, wherein said ring is optionally fused to one or more phenyl or heteroaryl ring. Exemplary rings include cyclopentyl, cyclohexyl, cyclohexenyl, cycloheptyl, tetrahydro-2H-pyranyl, tetrahydro-2H-thiopyranyl, 9H-fluoren-9-yl, piperidinyl, etc.

In another embodiment, two $R^X$, taken together with the carbon atom that they are attached to, form an optionally substituted 3-9 membered cycloaliphatic or heterocyclic, monocyclic, bicyclic, or tricyclic ring. Exemplary embodiments include 9H-fluoroen-9-yl, tetrahydro-2H-pyran-4-yl, tetrahydro-2H-thiopyran-4-yl, cyclobutyl, cyclopentyl, cyclohexyl, cycloheptyl, cyclohexenyl, piperidinyl, or 1-benzyl-piperidin-4-yl.

In another embodiment, the present invention provides compounds of formula I'-A:

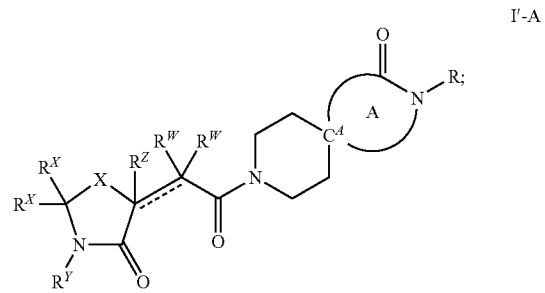

I'-A wherein:

ring A is a 4-7 membered heterocyclic ring that forms a spirocyclic ring system with said piperidine ring through carbon atom $C^A$, wherein said heterocyclic ring is optionally fused with an optionally substituted phenyl or heteroaryl ring;

wherein said ring A, in addition to the nitrogen ring atom, up to two additional ring heteroatoms selected from O, N, or S;

wherein ring A, in addition to the oxo group, is optionally substituted with up to 5 $R^1$ substituents;

$R^1$, $R^X$, $R^Y$, $R^Z$, $R^W$, and X are as defined above.

In one embodiment, ===is a double bond and $R^Z$ and one of $R^W$ is absent;

In another embodiment, ===is a single bond.

In another embodiment, $R^Z$ is C1-C6 alkyl or halo-C1-C6 alkyl. Or, $R^Z$ is —O—C1-C6 alkyl. Exemplary $R^Z$ include methyl, ethyl, n-propyl, $CF_3$, $CHF_2$, OMe, OEt, etc.

In another embodiment, $R^W$ is C1-C6 alkyl or halo-C1-C6 alkyl. Or, $R^W$ is —O—C1-C6 alkyl. Exemplary $R^W$ include methyl, ethyl, n-propyl, $CF_3$, $CHF_2$, OMe, OEt, etc.

In another embodiment, two $R^W$, taken together with the carbon atom they are attached to, form an optionally substituted C3-C9 cycloalkyl or a 3-9 membered heterocyclyl ring. Exemplary such rings include cyclopropyl, cyclopentyl, or cyclohexyl.

In one embodiment, ring A is selected from:

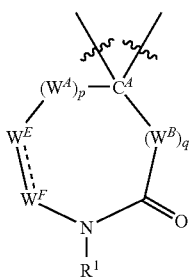

A-i

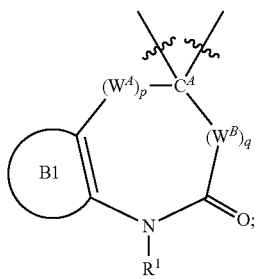

A-ii

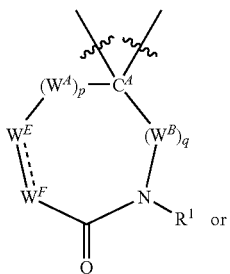

A-iii

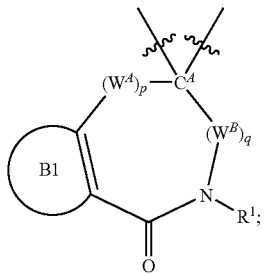

A-iv wherein:
p is 0-2;
q is 0-2; provided that p+q≤2;
each of $W^A$ and $W^B$ is independently selected from $NR^1$, O, S, SO, $SO_2$, $C(R^1)_2$, or $=CR^1$ (when p or q is 2);
$W^E$ is $—C(R^1)_2$, $=C(R^1)—$, $=N—$, or $—N(R^1)—$;
$W^F$ is absent or is selected from $—C(R^1)_2$, $=C(R^1)—$, $=N—$, or $—N(R^1)—$; provided that both of $W^E$ and $W^F$ are not simultaneously $=N—$ or $—N(R^1)—$;
ring B1 is an optionally substituted phenyl or 5-6 membered heteroaryl ring;
$R^1$ is as defined above.

In one embodiment, ring A has formula A-i. In another embodiment, ring A has formula A-ii. Or, ring A has formula A-iii. Or, ring A has formula A-iv.

In one embodiment, both, $W^E$ and $W^F$ are $=C(R^1)$. In another embodiment, $W^E$ is $=C(R^1)—$ and $W^F$ is $=N—$.

In one embodiment, p is 0 and q is 0. In another embodiment, p is 1 and q is 0. In another embodiment, p is 0 and q is 1. In yet another embodiment, both p and q are 1. Or, p is 0 and q is 2. Or, p is 2 and q is 0.

In one embodiment, $W^A$ is $NR^1$. In another embodiment, $W^A$ is O. Or, $W^A$ is $C(R^1)_2$. In one embodiment $R^1$ is hydrogen.

In one embodiment, $W^B$ is $NR^1$. In another embodiment, $W^B$ is O. Or, $W^B$ is $C(R^1)_2$. In one embodiment $R^1$ is hydrogen.

In another embodiment, p is 2 and $W^A$ is $C(R^1)_2—C(R^1)_2$ or $—CR^1=CR^1—$.

In another embodiment, q is 2 and $W^B$ is $C(R^1)_2—C(R^1)_2$ or $—CR^1=CR^1—$.

In one embodiment, ring A is selected from:

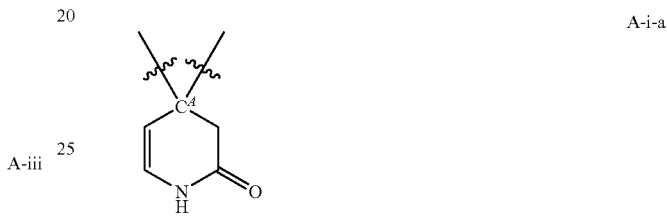

A-i-a

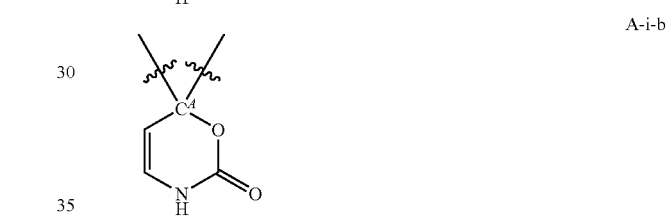

A-i-b

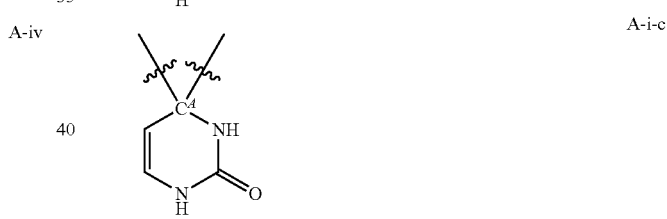

A-i-c

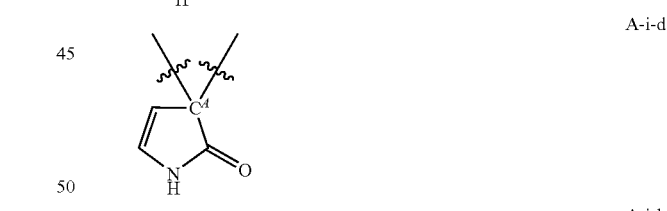

A-i-d

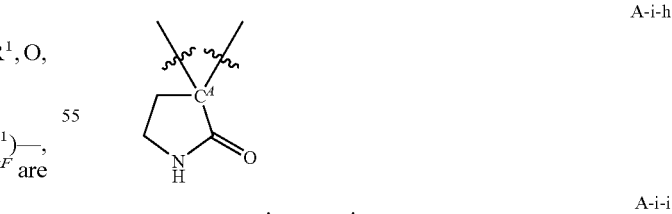

A-i-h

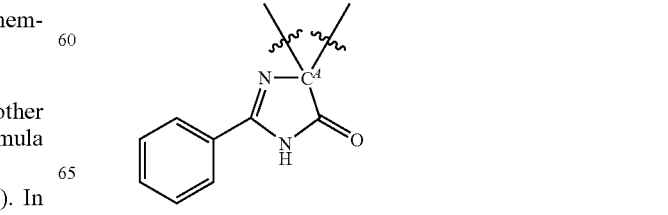

A-i-i

-continued

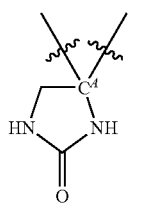
A-i-j

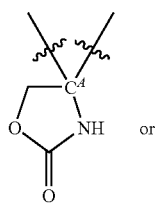
A-i-k
or

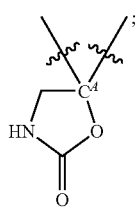
A-i-l
;

wherein said ring is optionally substituted with up to 4 $R^1$ substituents.

In another embodiment, ring A is selected from:

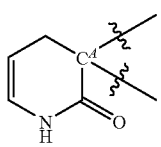
A-i-e

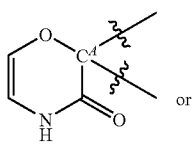
A-i-f
or

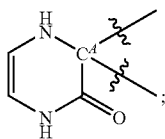
A-i-g
;

wherein said ring is optionally substituted with up to 4 $R^1$ substituents.

In another embodiment, ring A is selected from:

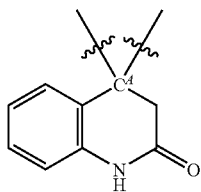
A-ii-a

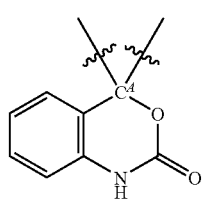
A-ii-b

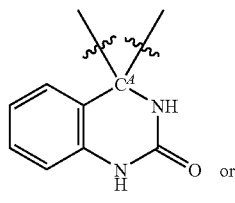
A-ii-c
or

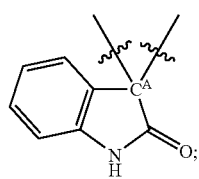
A-ii-d
;

wherein said ring system is optionally substituted with up to 4 $R^1$ substituents.

In another embodiment, ring A is selected from:

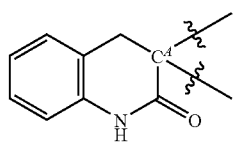
A-ii-e

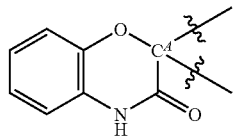
A-ii-f

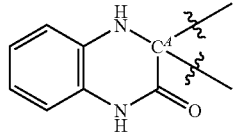
A-ii-g

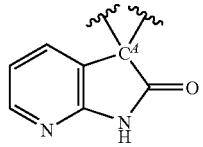
A-ii-h

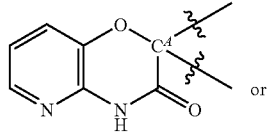
A-ii-i
or

-continued

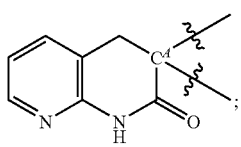

A-ii-j wherein said ring system is optionally substituted with up to 4 R¹ substituents.

In another embodiment, the compounds of the present invention have formula I'-B:

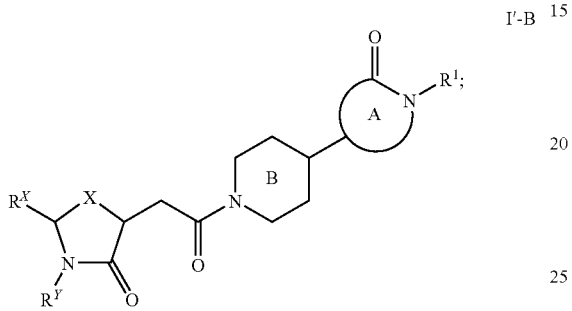

I'-B wherein said ring A, in addition to the nitrogen ring atom, contains up to two additional ring heteroatoms selected from O, N, or S;
wherein ring A, in addition to the oxo group, is optionally substituted with up to 5 R¹ substituents;
R¹, $R^X$, $R^Y$, and X are as defined above.
In one embodiment, ring A is selected from:

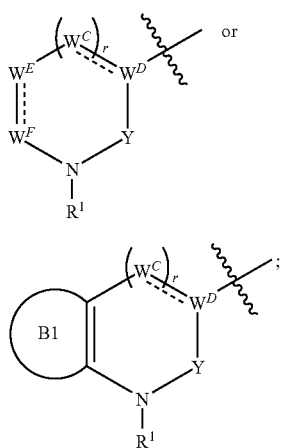

A-v or

A-vi wherein:
$W^C$ is —C(R¹)₂, C(O), or =CR¹—;
r is 0-2;
$W^D$ is N or =C—;
$W^E$ is —C(R¹)₂, =C(R¹)—, =N—, or —N(R¹)—;
$W^F$ is absent or is selected from —C(R¹)₂, =C(R¹)—, =N—, or —N(R¹)—; provided that both of $W^E$ and $W^F$ are not simultaneously =N— or —N(R¹)—;
Y is C(O), S(O), or S(O)₂;
ring B1 is an optionally substituted phenyl or a heteroaryl ring;
═══ is a single or a double bond;

R¹ is as defined above.
In one embodiment, $W^C$ is —C(R¹)₂. Or, $W^C$ is =CR¹—. Or, $W^C$ is C(O).
In one embodiment, r is 0. Or, r is 1. Or, r is 2.
In another embodiment, $W^D$ is N. Or, $W^D$ is =C—.
In one embodiment, Y is C(O). Or, Y is S(O). Or, Y is S(O)₂.
In one embodiment, ring A is selected from:

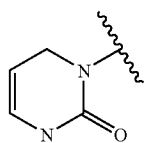

A-v-a

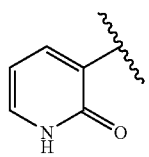

A-v-b

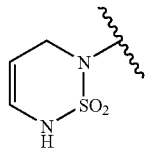

A-v-c

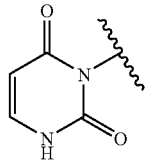

A-v-d

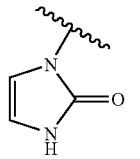

A-v-e

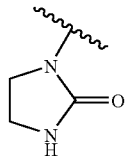

A-v-f

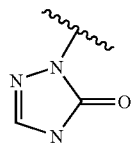

A-v-g

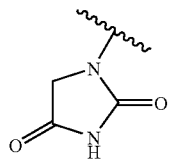

A-v-h

-continued

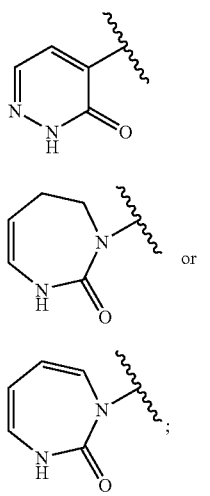

A-v-i

A-v-j

A-v-k wherein said ring is optionally substituted with up to 4 $R^1$ substituents.

In one embodiment, ring A is selected from:

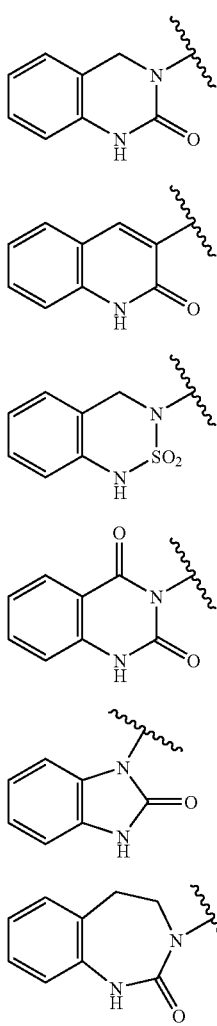

A-vi-a

A-vi-b

A-vi-c

A-vi-d

A-vi-e

A-vi-f

-continued

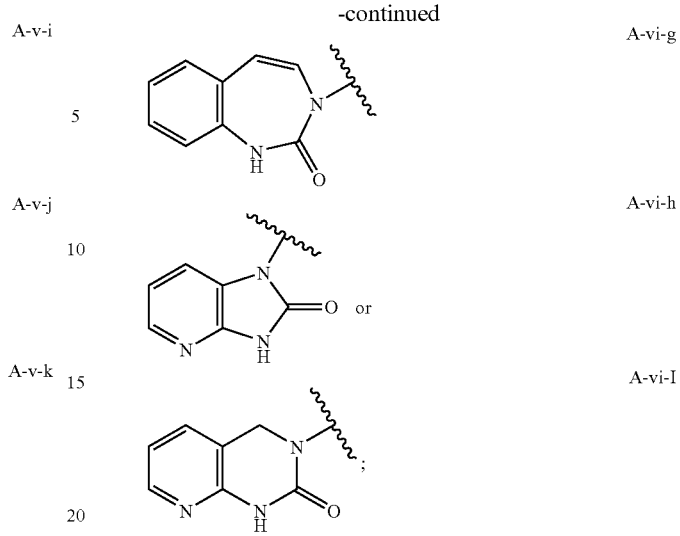

A-vi-g

A-vi-h

A-vi-I wherein said ring is optionally substituted with up to 4 $R^1$ substituents.

In one embodiment, ring A is optionally substituted with up to 5 substituents selected from C1-C6 aliphatic, C1-C6 aliphatic-oxy, C1-C6 haloaliphatic, CN, halo, oxo, optionally substituted C3-C7 cycloaliphatic, or an optionally substituted ring selected from phenyl, furanyl, pyrrolyl, pyrrolinyl, pyrrolidinyl, imadazolyl, imidazolinyl, imidazolidinyl, pyrazolyl, pyrazolinyl, pyrazolidinyl, pyridyl, pyrimidinyl, piperidinyl, piperazinyl, or morpholinyl.

In one embodiment Q is absent. In another embodiment, Q-$R^M$ is R'.

In one embodiment, R is hydrogen. Or, R is C1-C6 aliphatic. Exemplary R includes C1-C6 alkyl, e.g., methyl, ethyl, propyl, or butyl.

In one embodiment, R' is hydrogen.

In one embodiment, R' is a C1-C8 aliphatic group, optionally substituted with up to 3 substituents selected from halo, CN, $CF_3$, $CHF_2$, $OCF_3$, or $OCHF_2$, wherein up to two methylene units of said C1-C8 aliphatic is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In one embodiment, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In one embodiment, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

In one embodiment, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, CF$_3$, CHF$_2$, OCF$_3$, OCHF$_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

In another embodiment, a compound of the present invention is selected from Table 1B.

In another embodiment, the present invention comprises a pharmaceutical composition comprising a compound selected from Table 1B, and a pharmaceutically acceptable carrier, adjuvant, or vehicle.

In another embodiment, the present invention comprises a compound selected from Table 1B, an additional therapeutic agent and a pharmaceutically acceptable carrier, adjuvant, or vehicle.

Exemplary compounds of the present invention are shown in Table 1, Table 1A and Table 1B below.

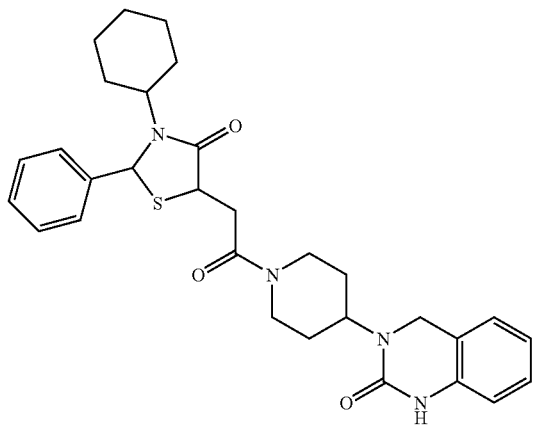

1

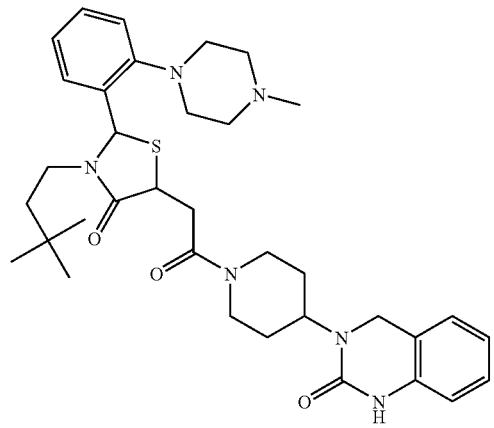

2

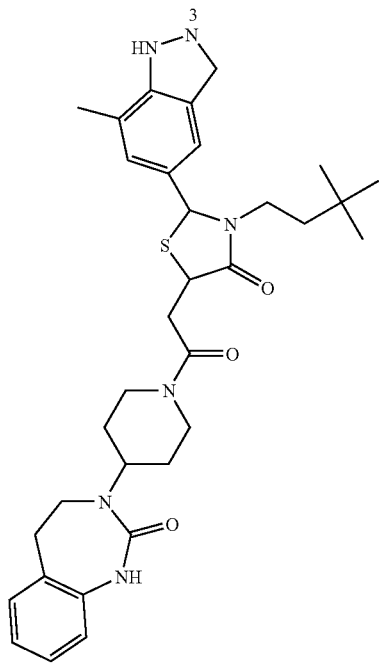
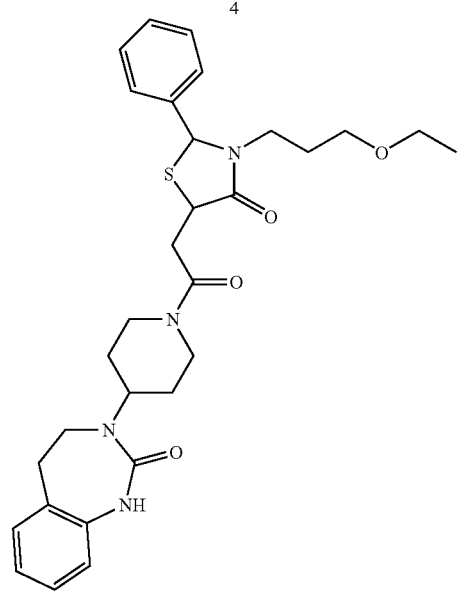

5
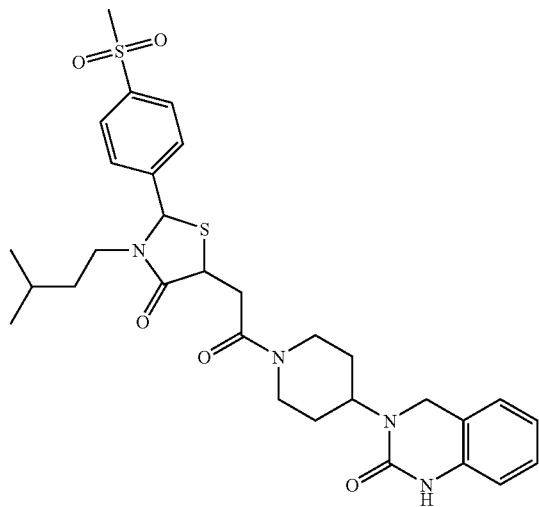
6
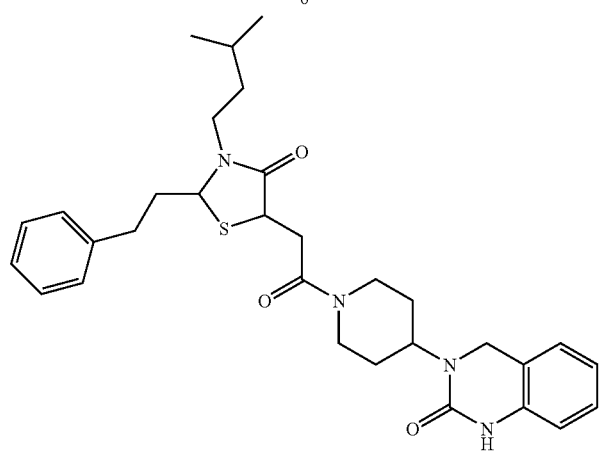
7
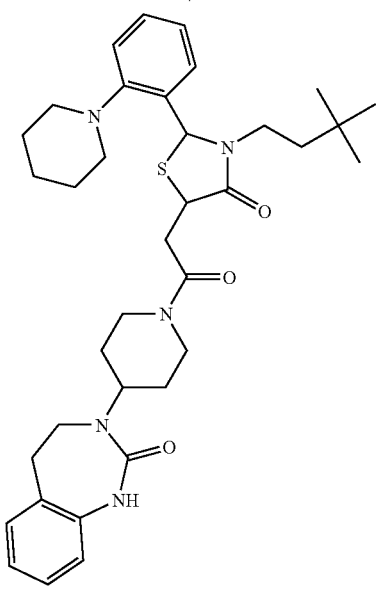

-continued
8
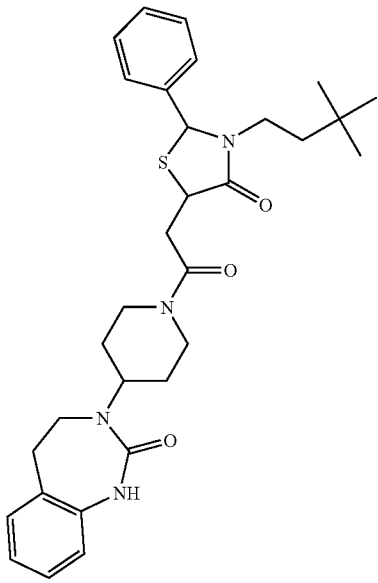
9
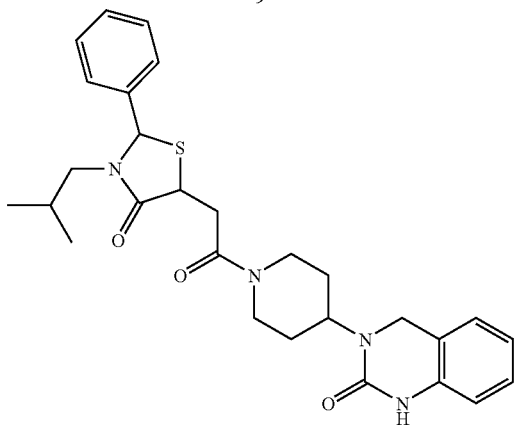
10
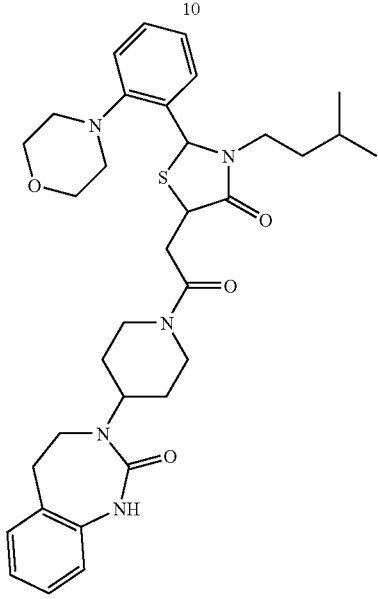

11
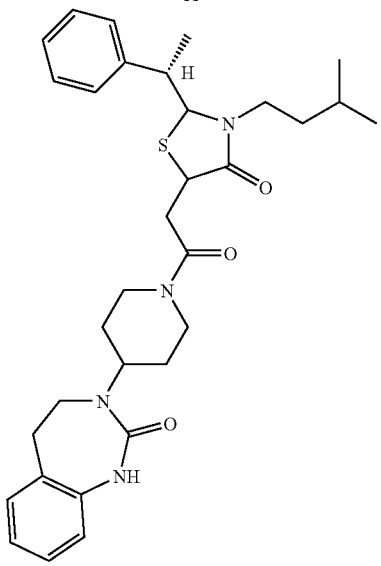
12
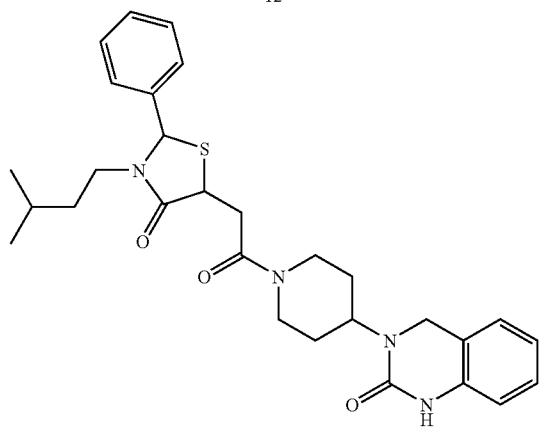
13
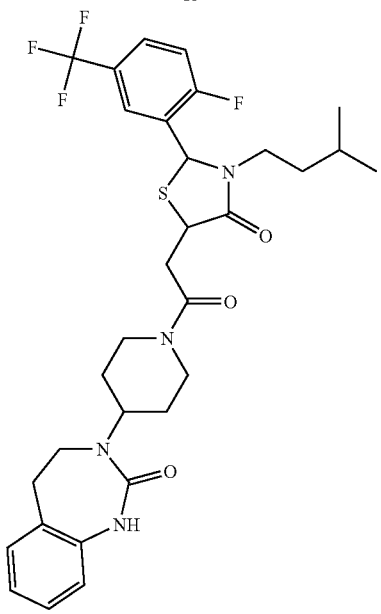

-continued
14
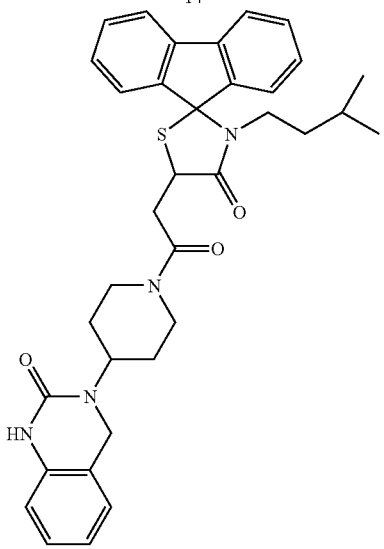
15
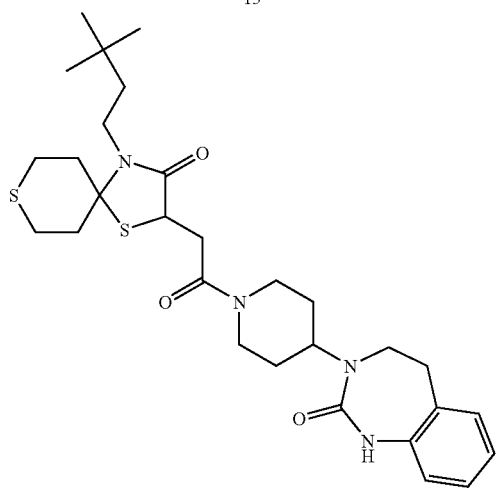
16
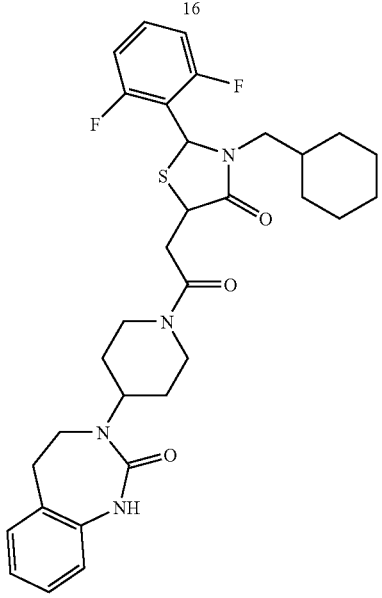

17
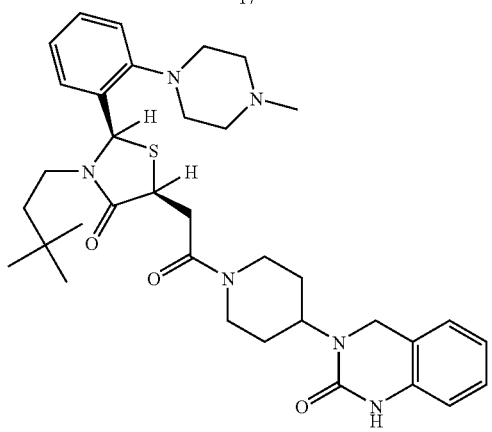
18
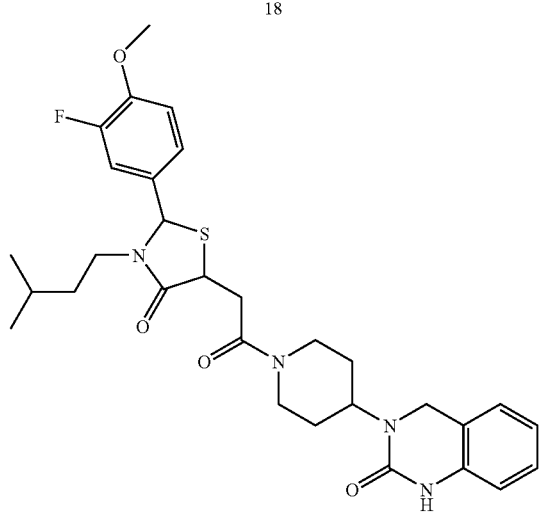
19
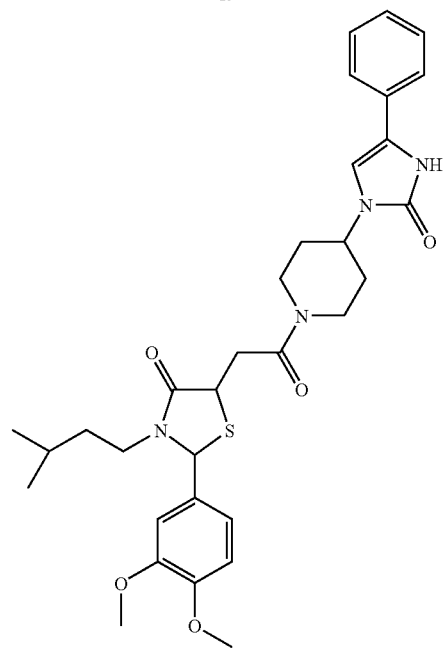

-continued
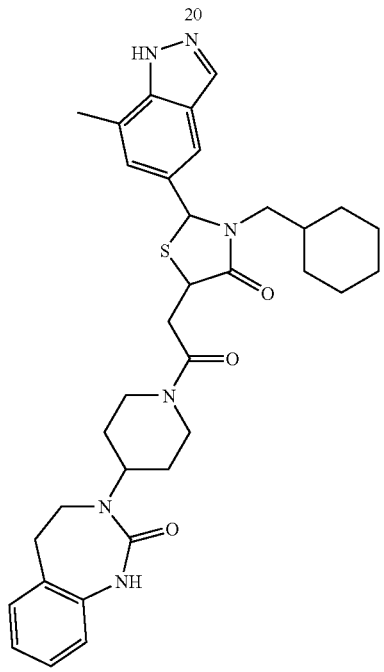
20
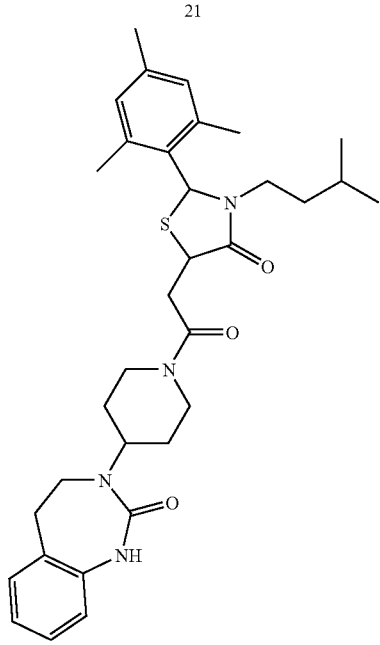
21

22
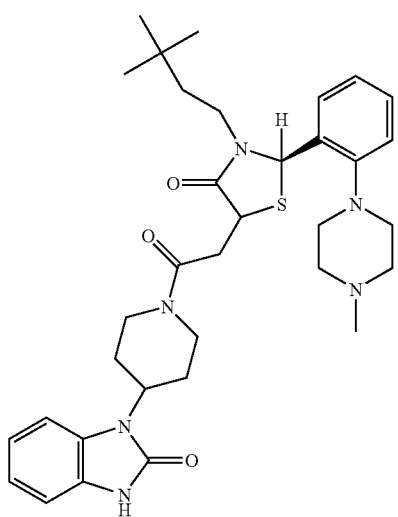
23
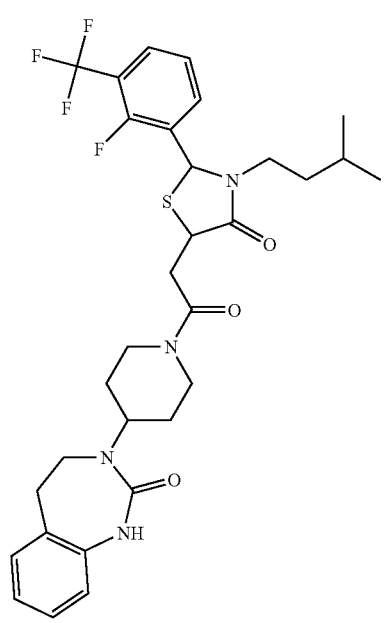

24
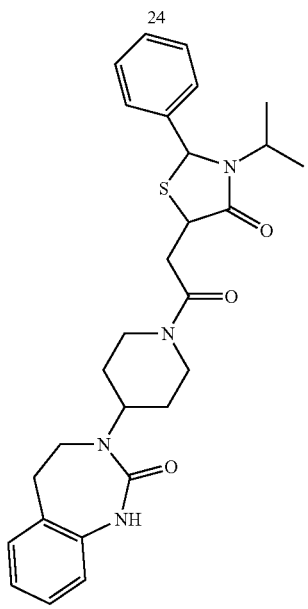
25
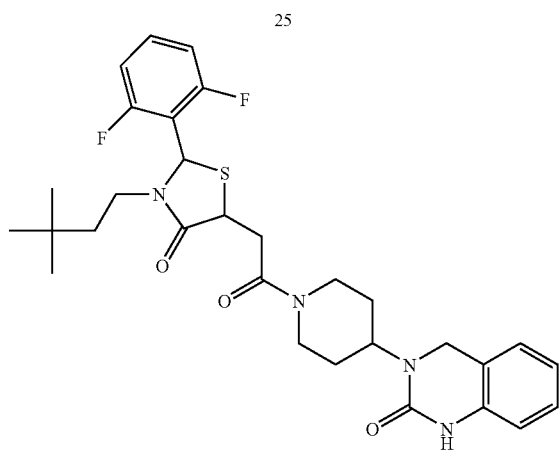
26
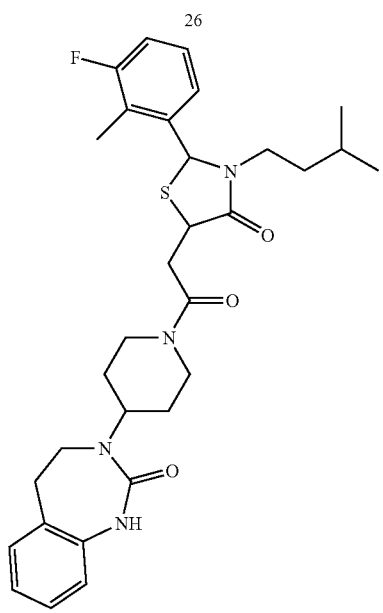

27
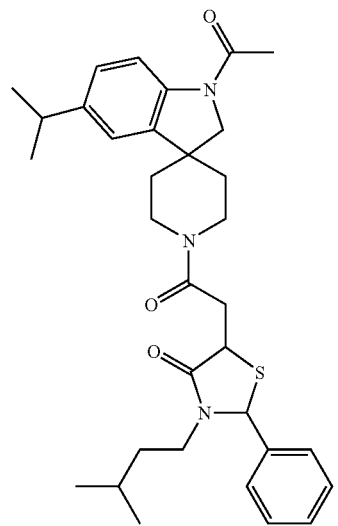
28
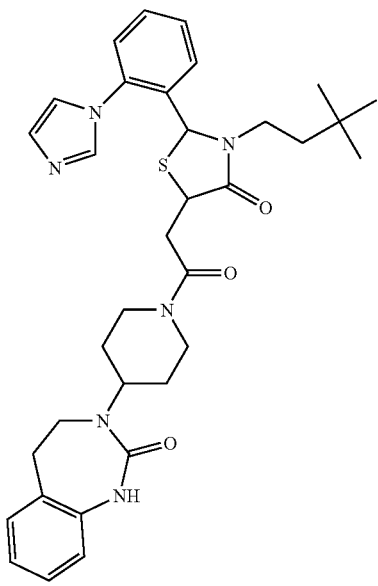
29
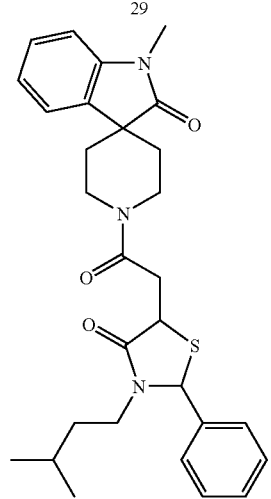

-continued
30
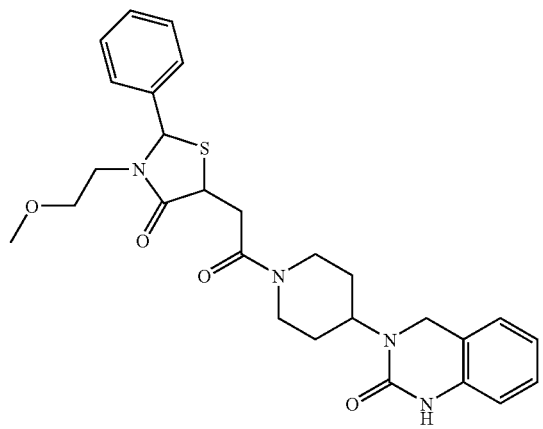
31
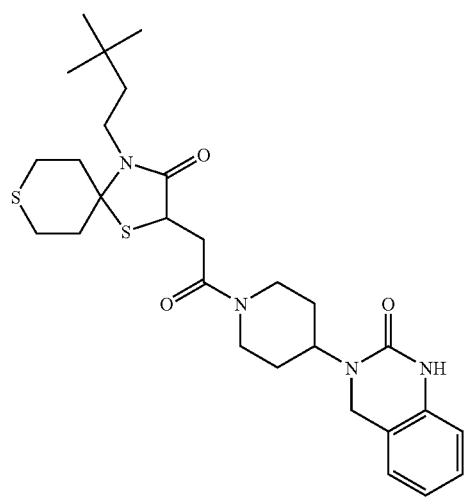
32
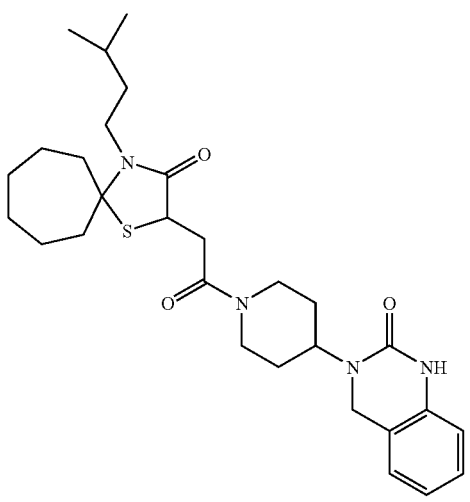

-continued
33
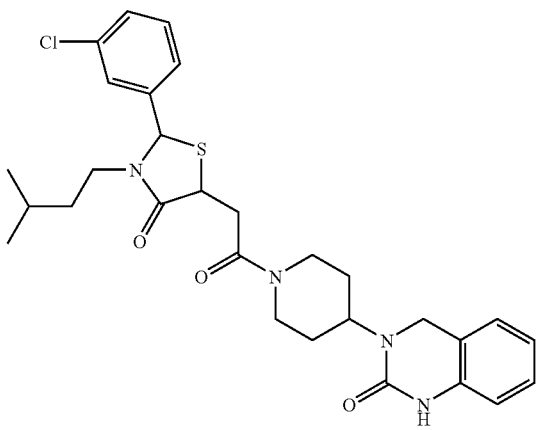
34
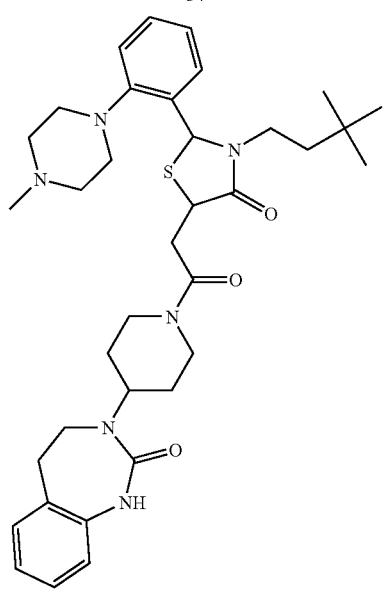
35
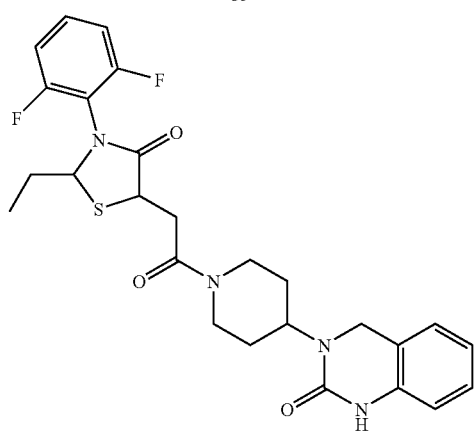

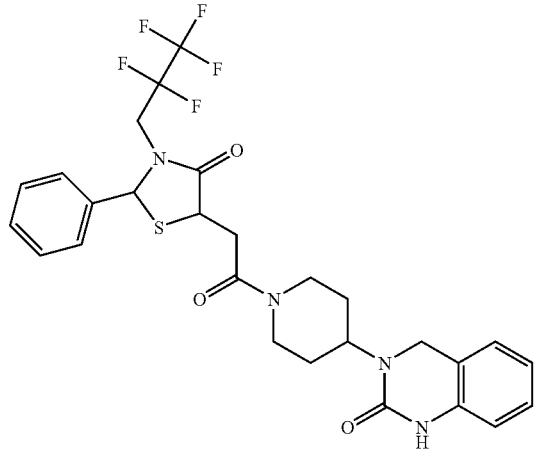
36
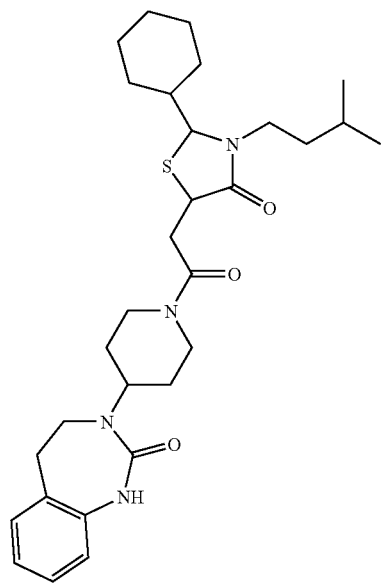
37

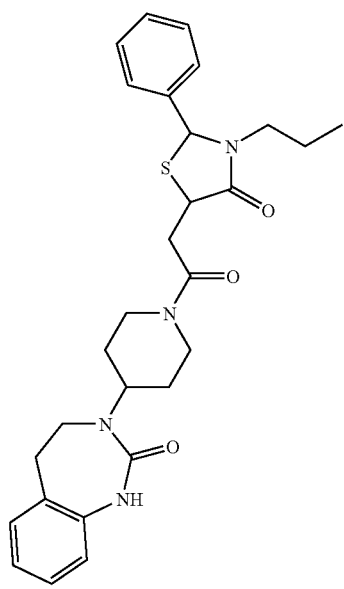
38
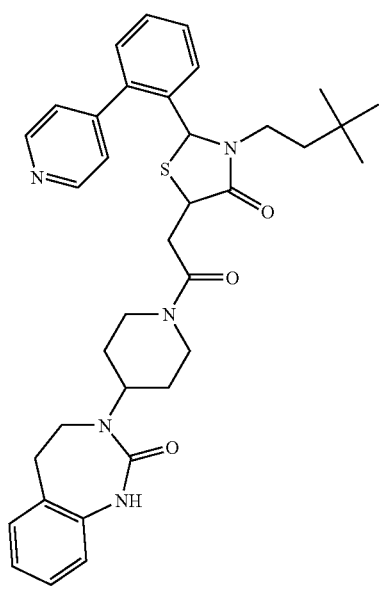
39

-continued
40
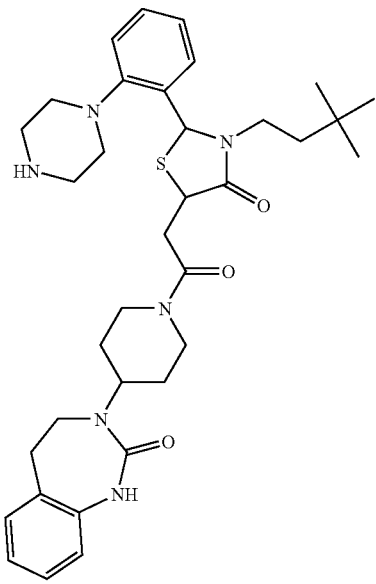
41
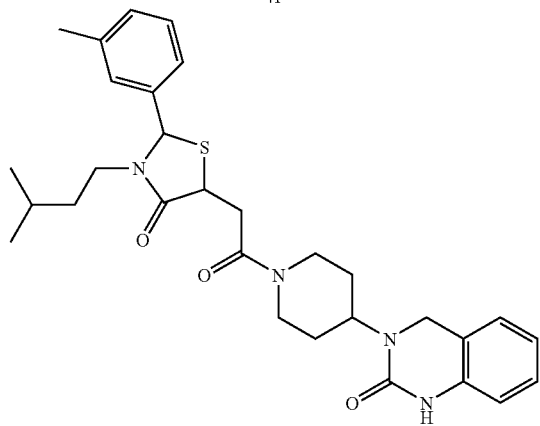
42
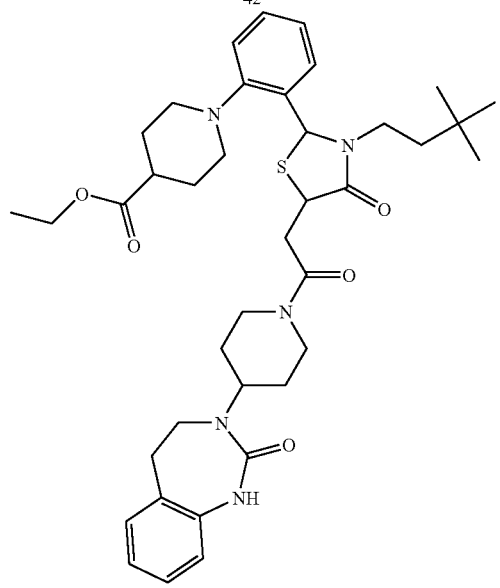

43
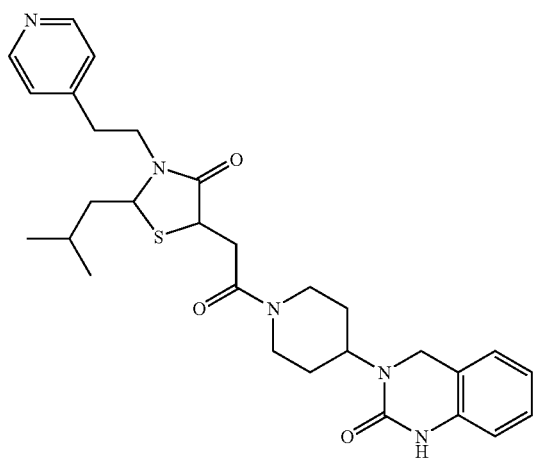
44
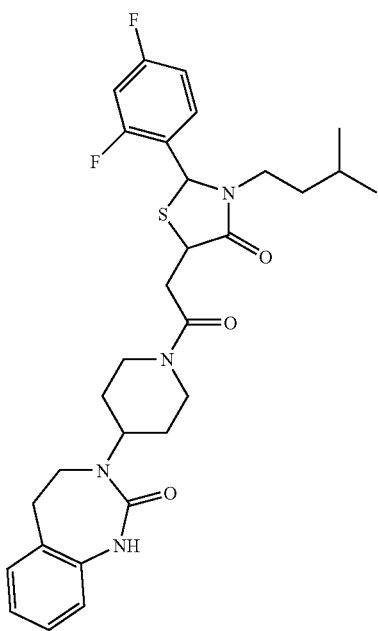

45
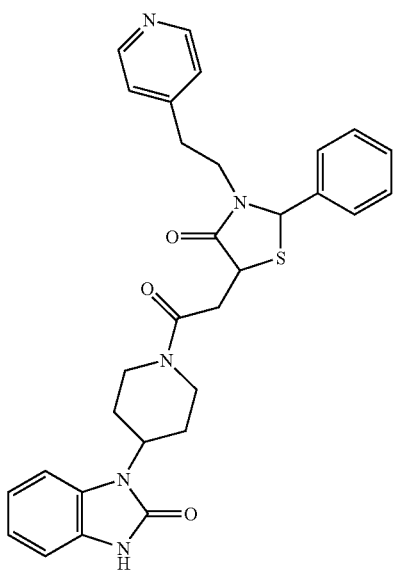
46
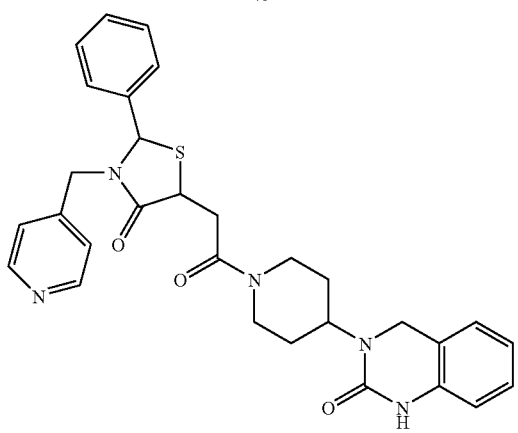
47
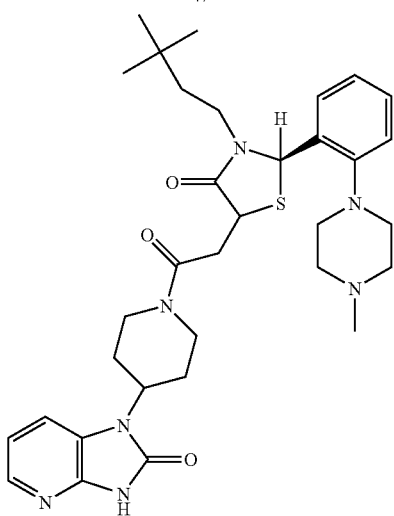

48
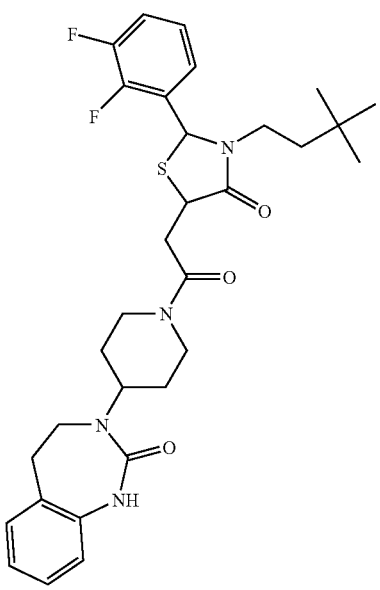
49
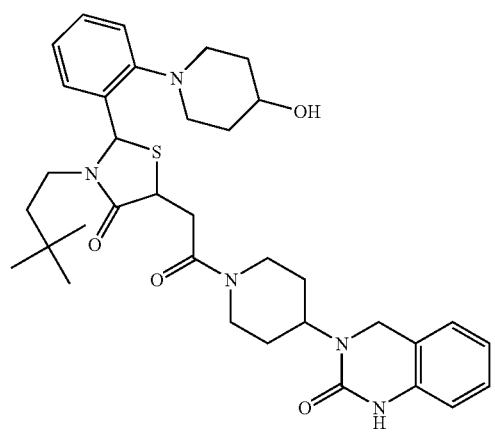
50
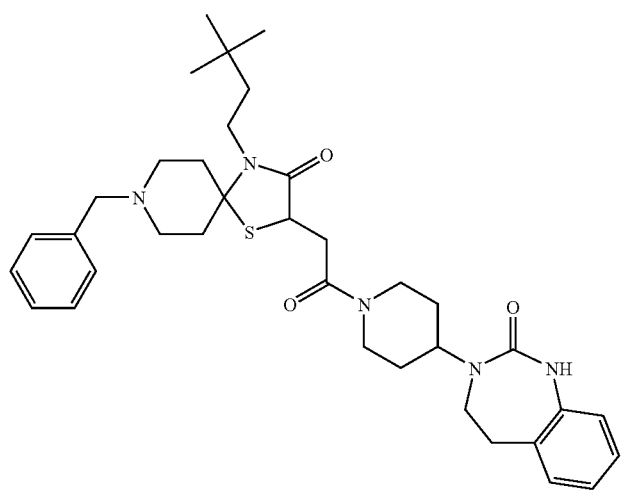

-continued
51
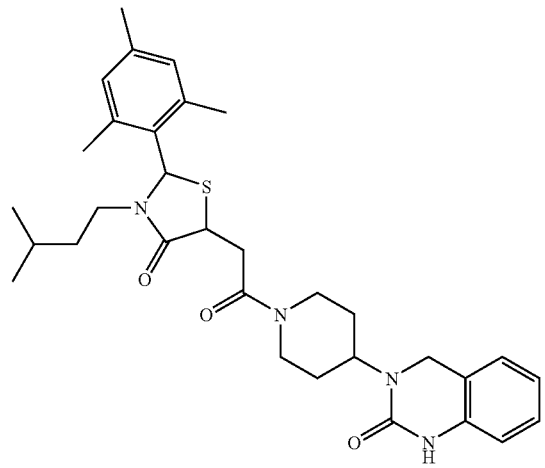
52
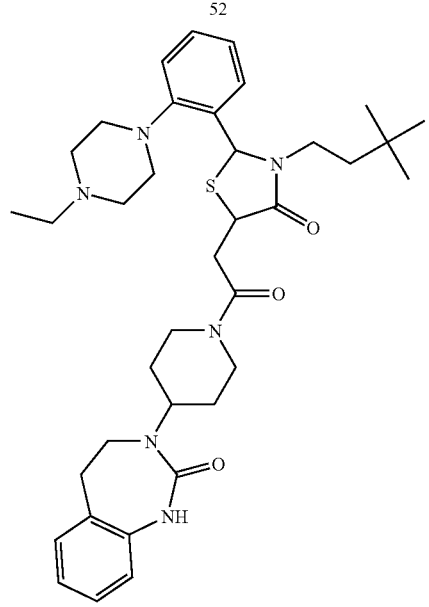

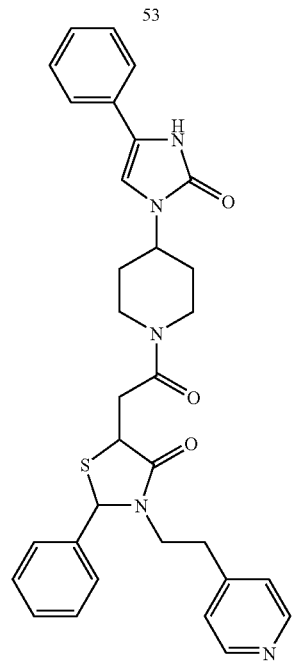
53
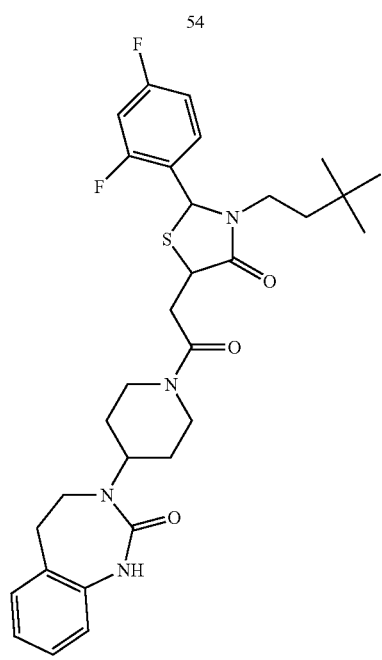
54

55
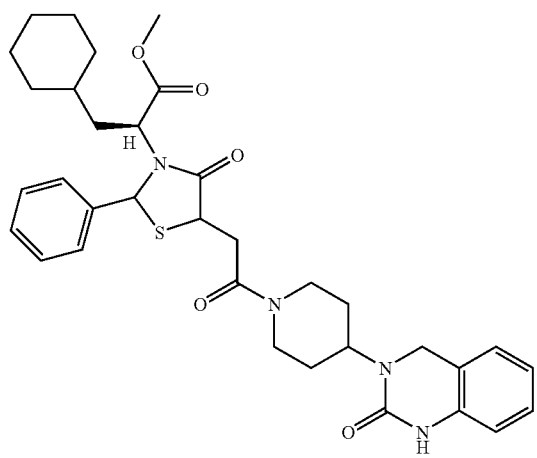
56
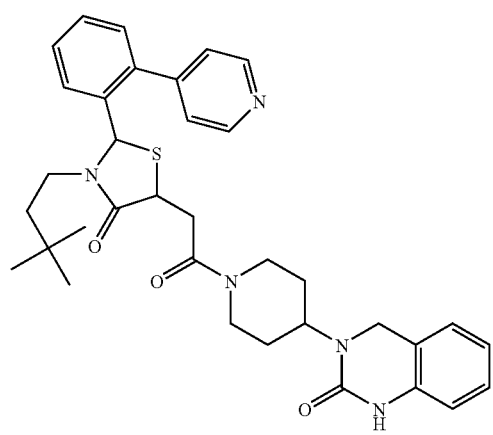
57
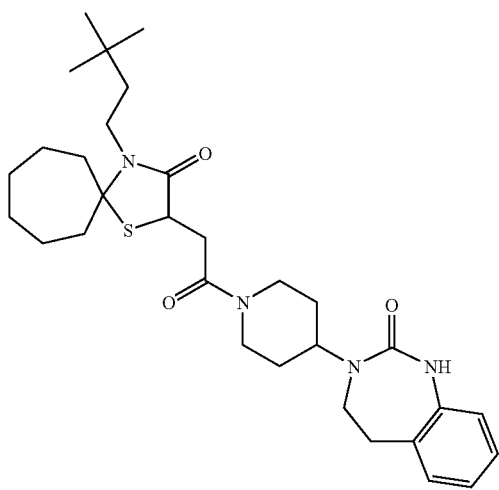

58
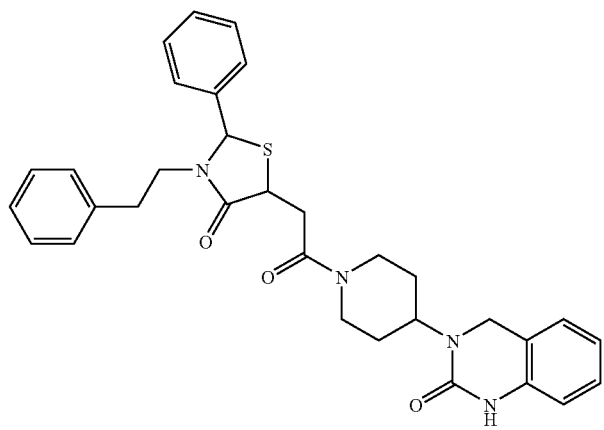
59
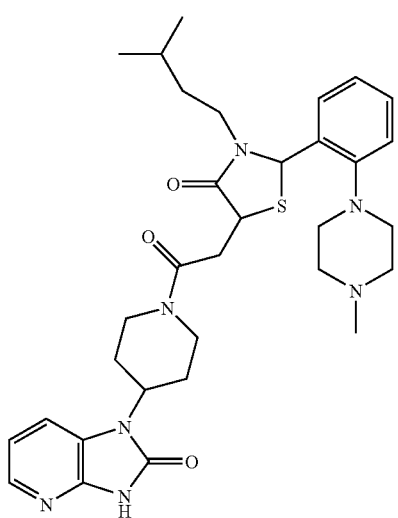
60
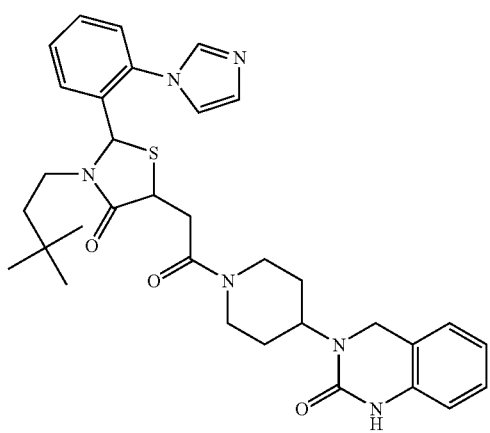

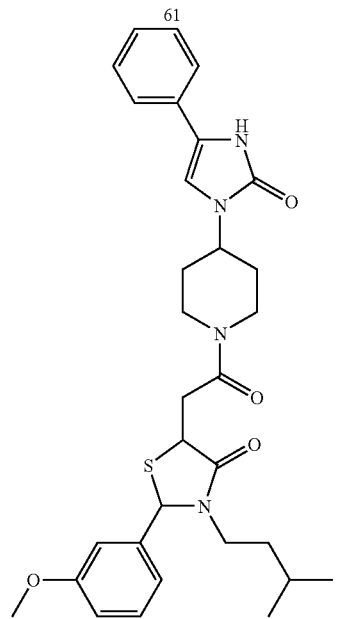
61
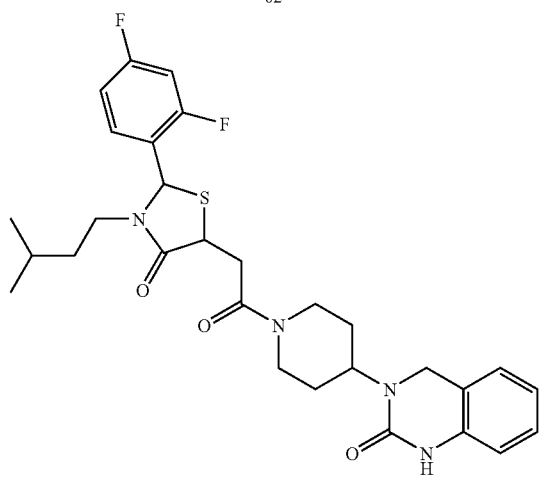
62
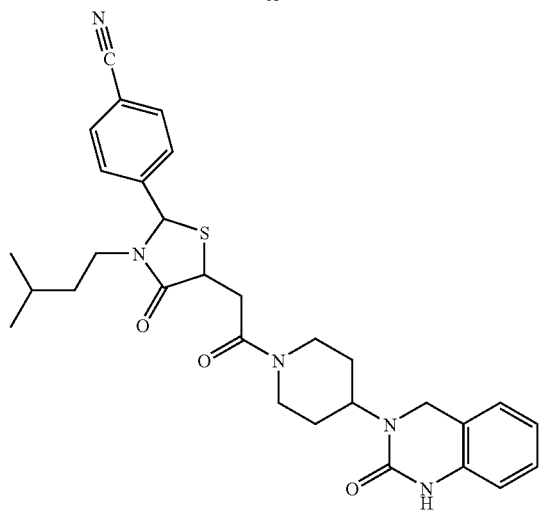
63

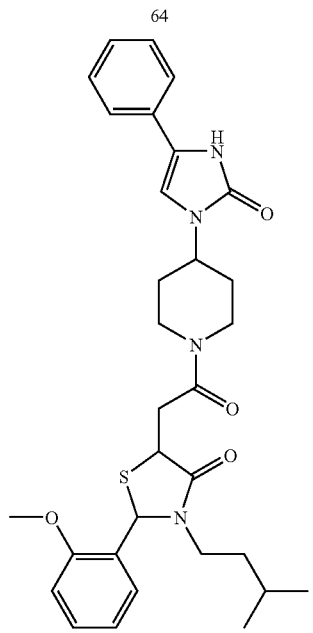
64
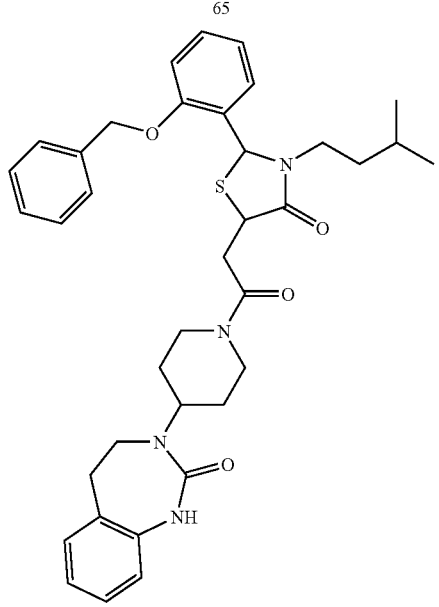
65

66
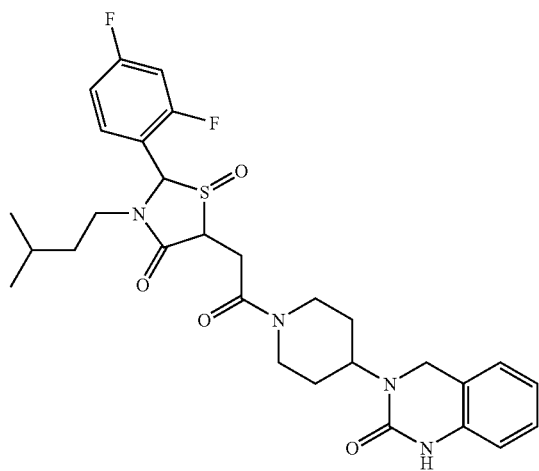
67
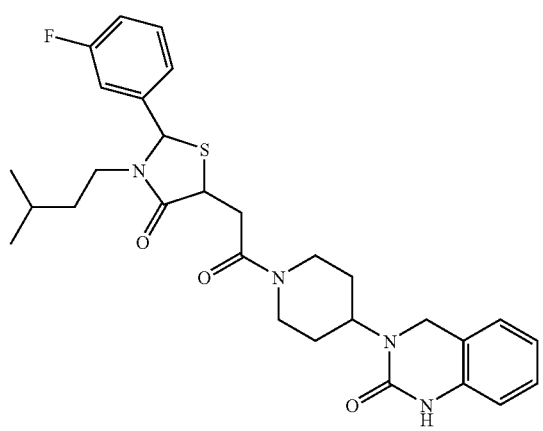
68
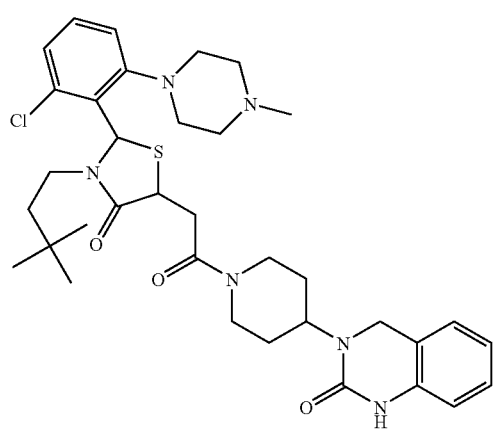

-continued
69
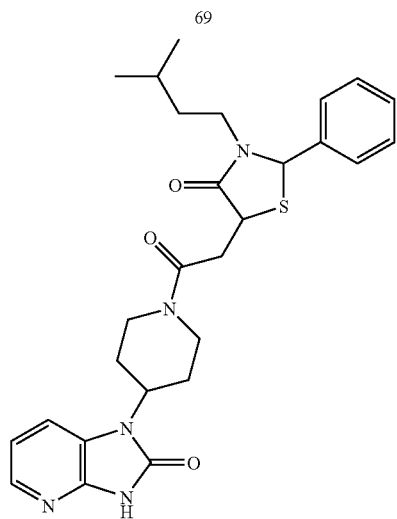
70
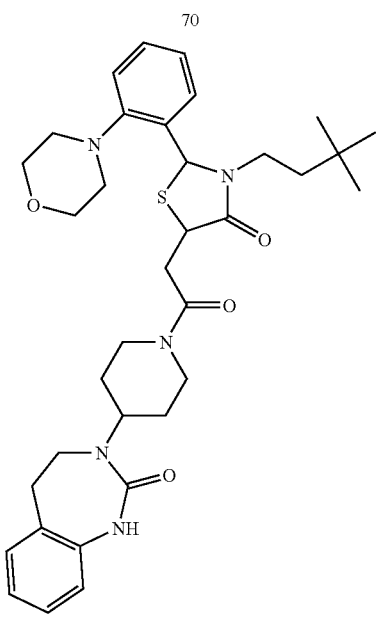
71
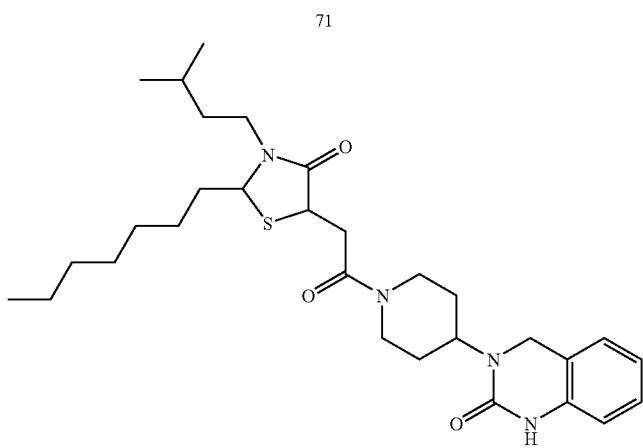

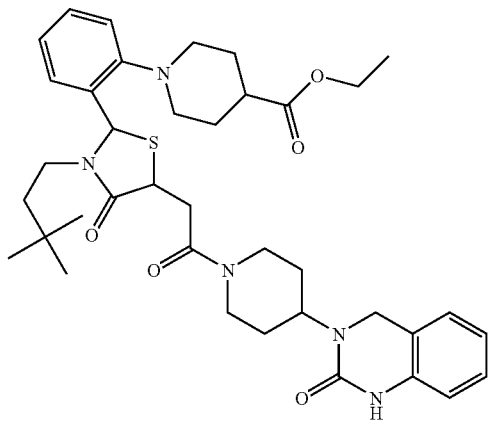
72
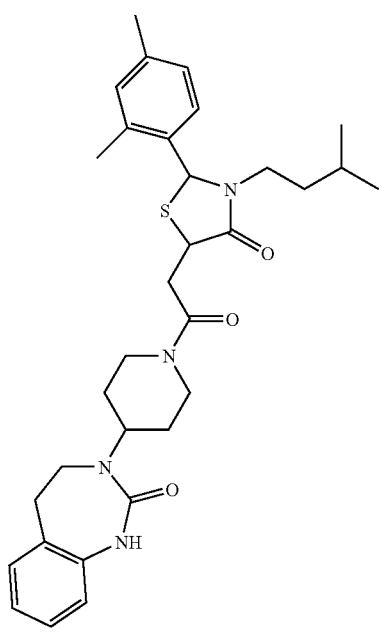
73

74
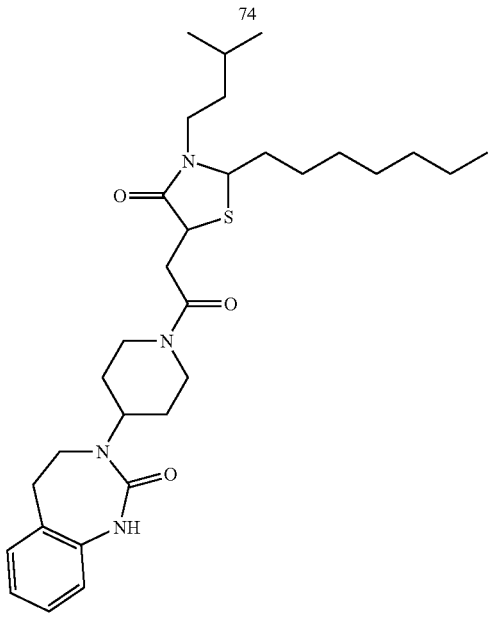
75
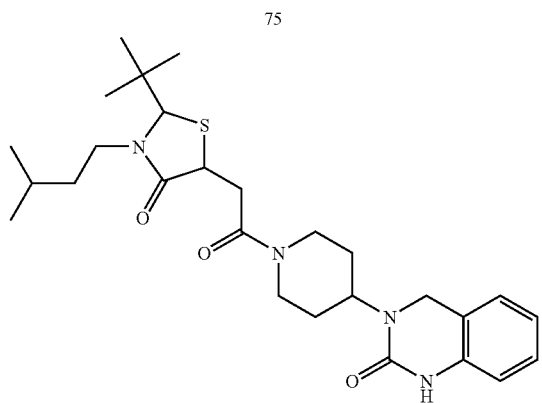
76
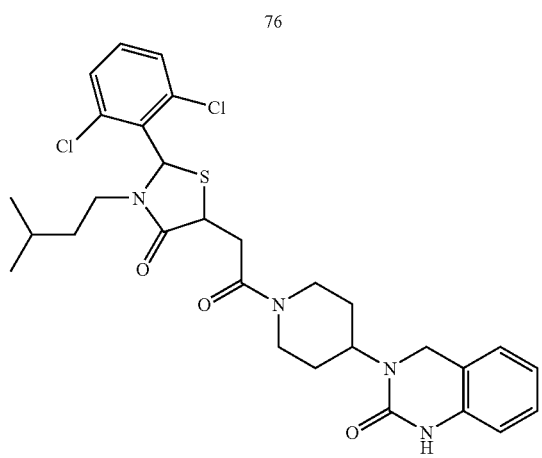

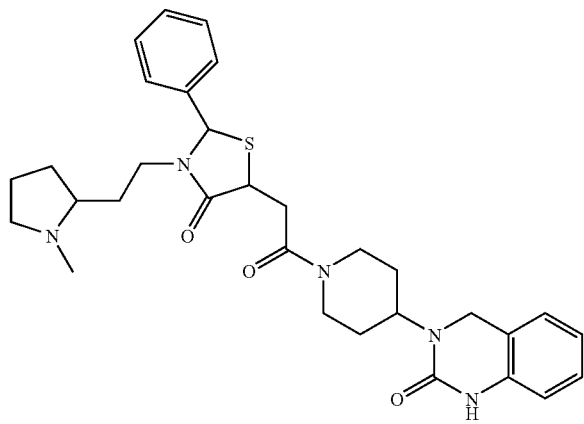
77
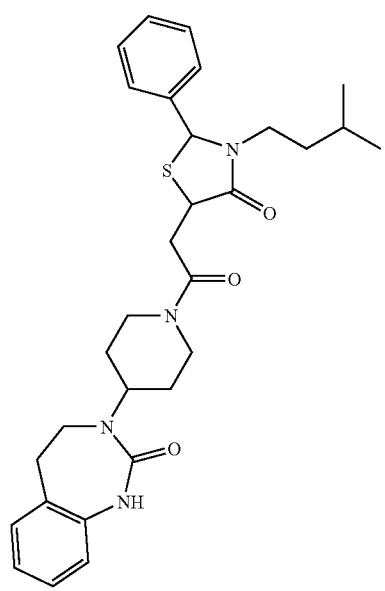
78

79
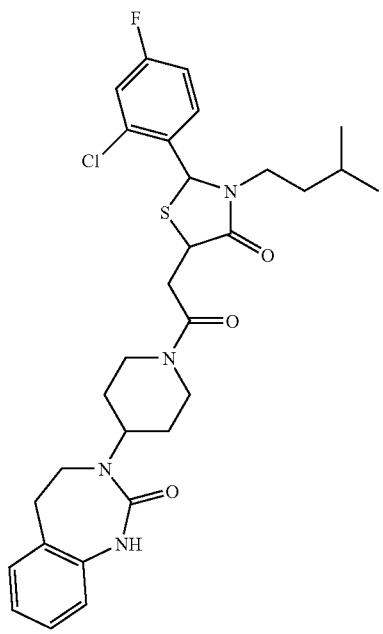
80
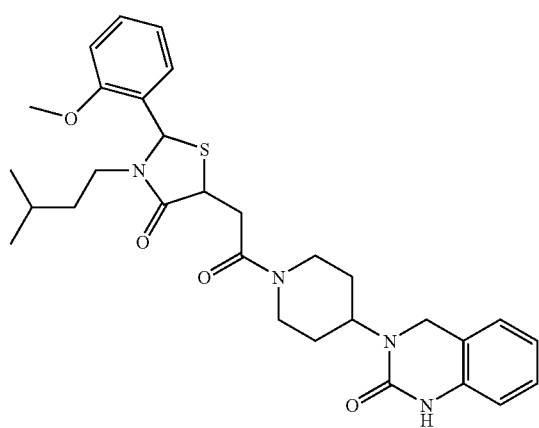

-continued
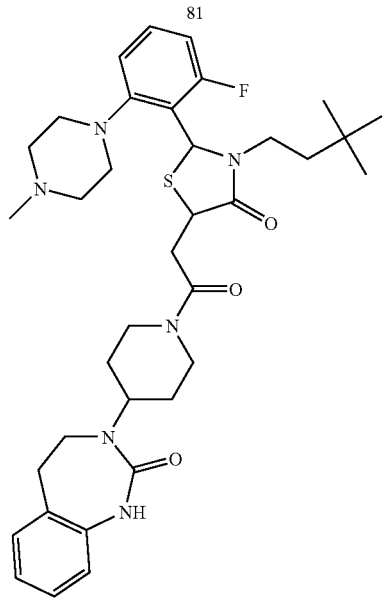
81
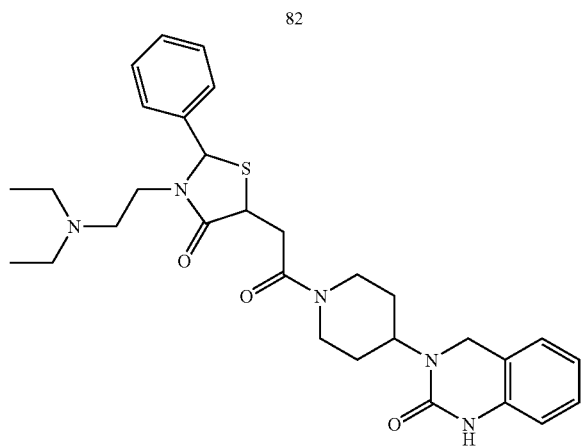
82
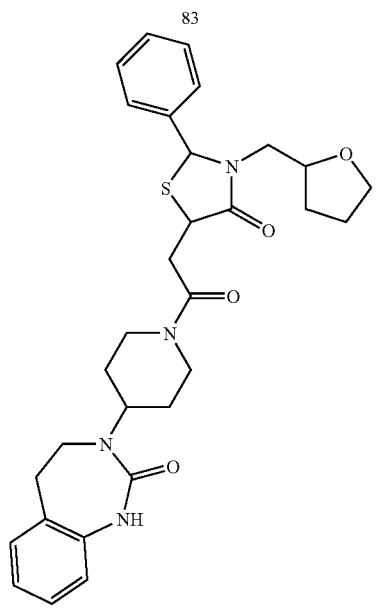
83

84
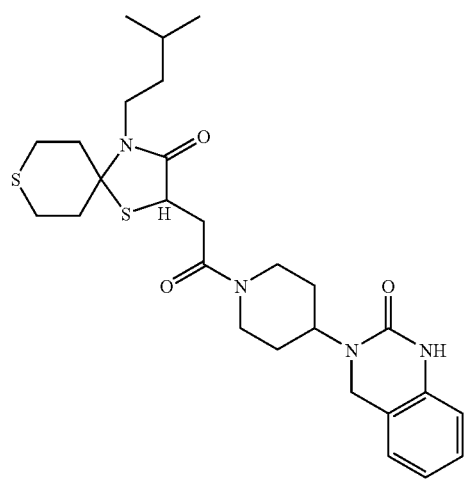
85
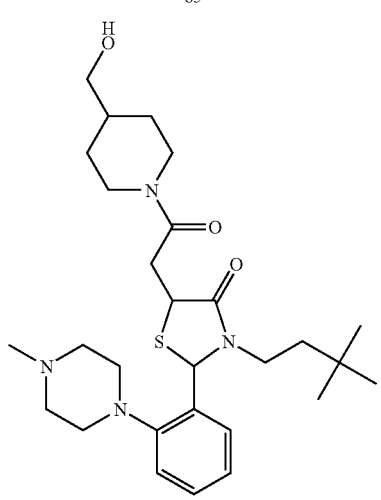
86
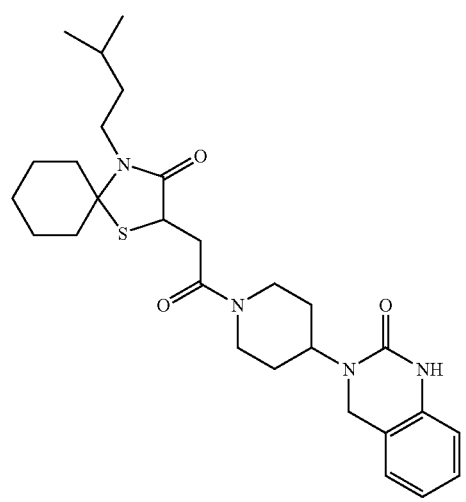

87
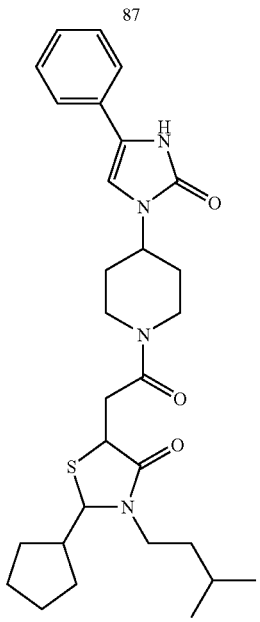
88
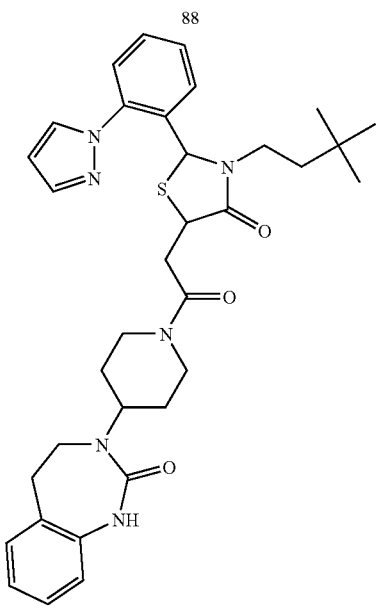

89
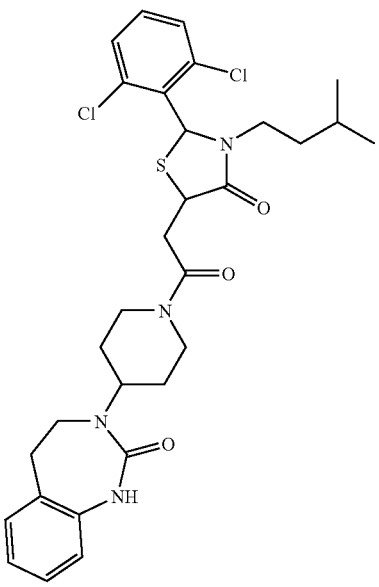
90
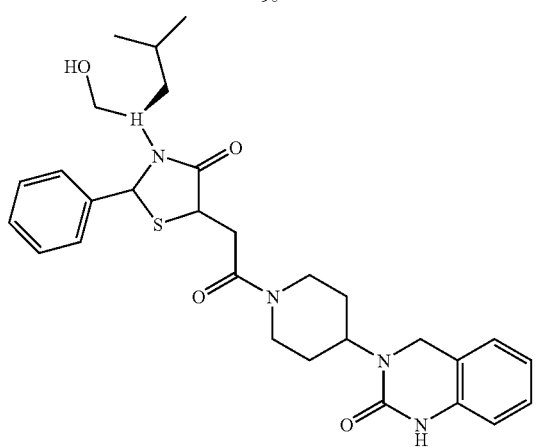
91
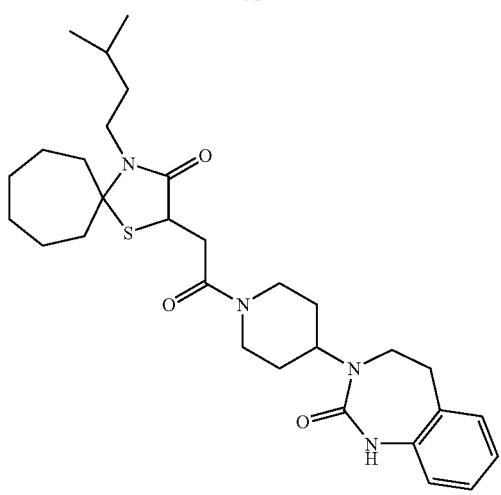

92
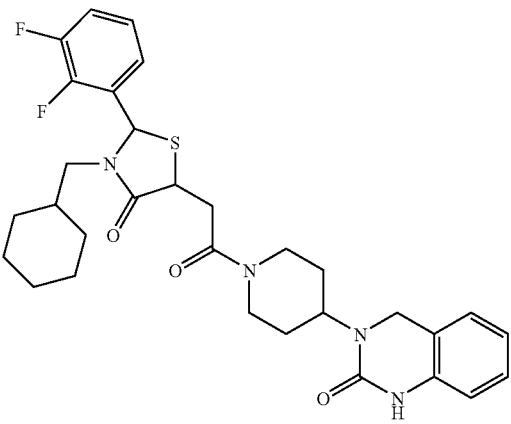
93
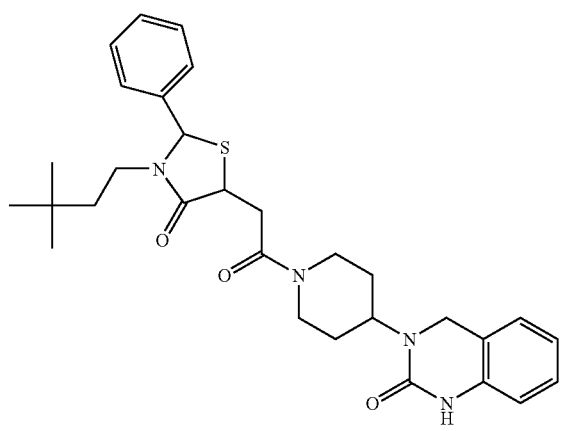
94
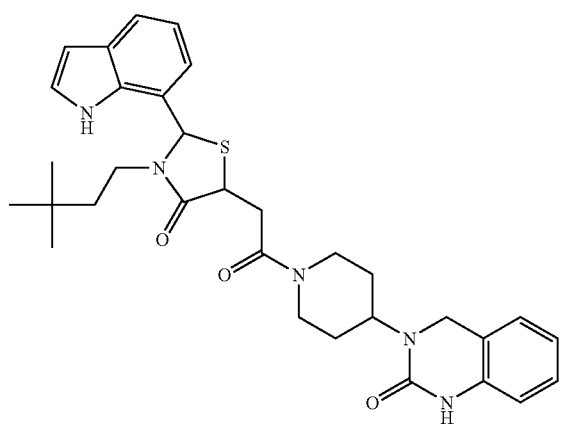

95
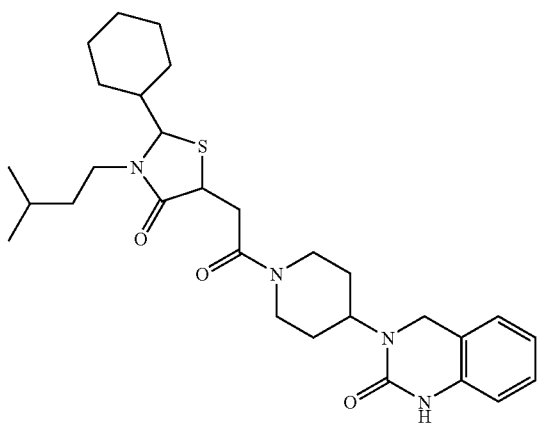
96
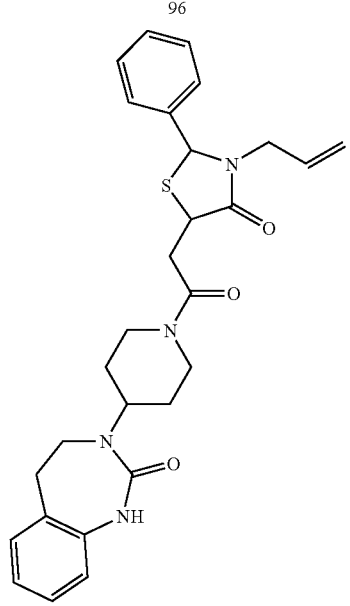
97
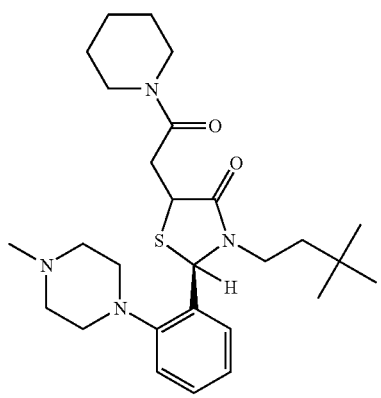

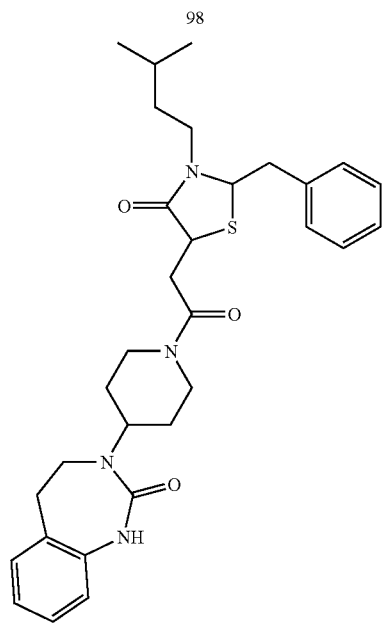
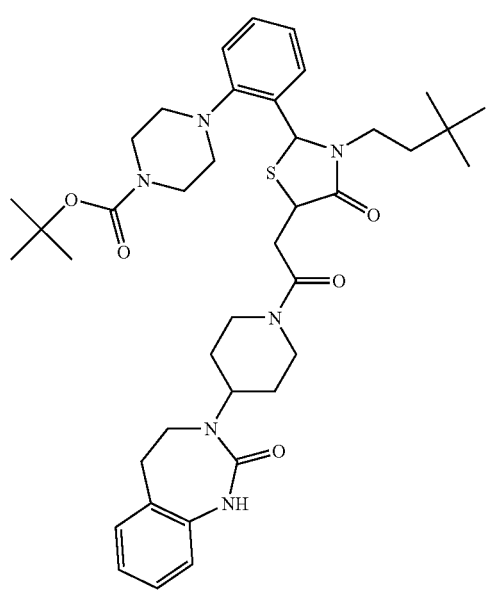

100
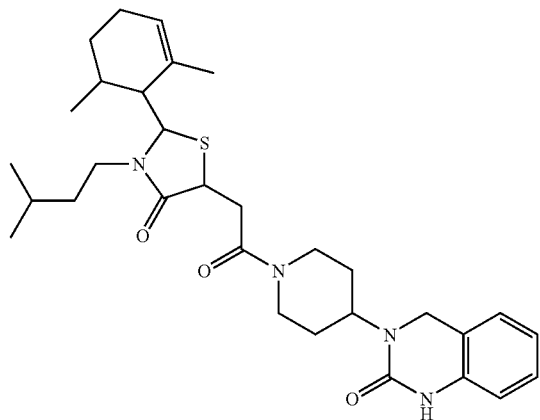
101
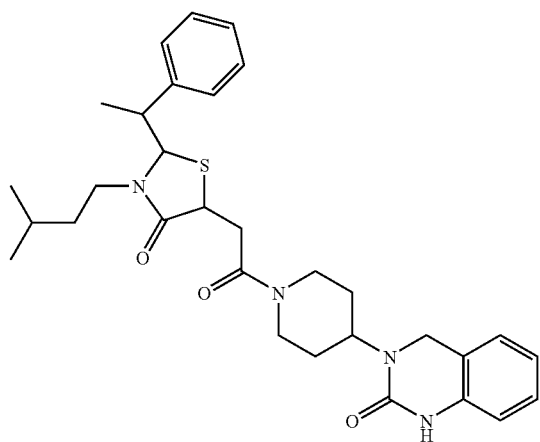
102
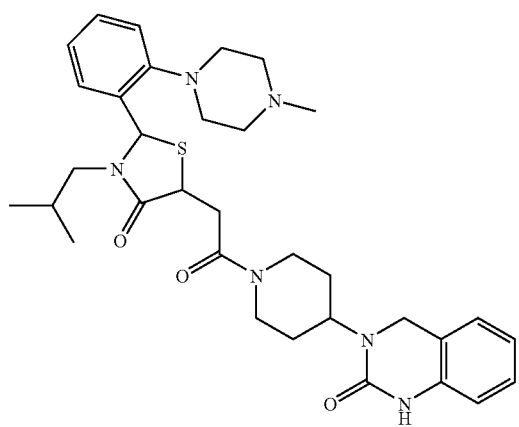

103
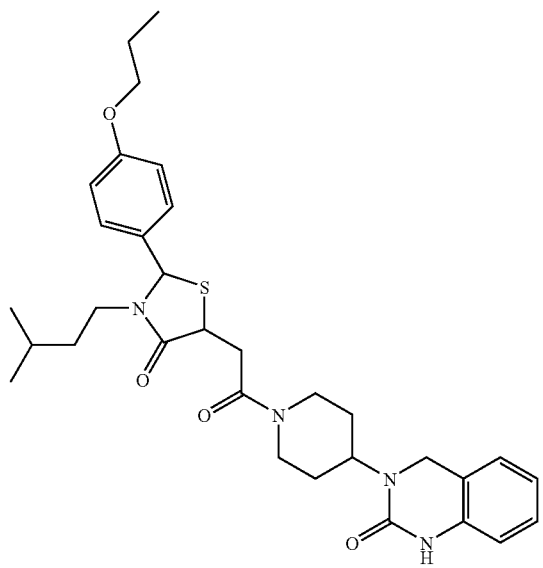
104
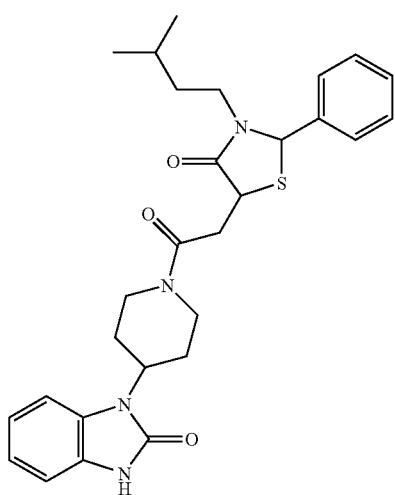
105
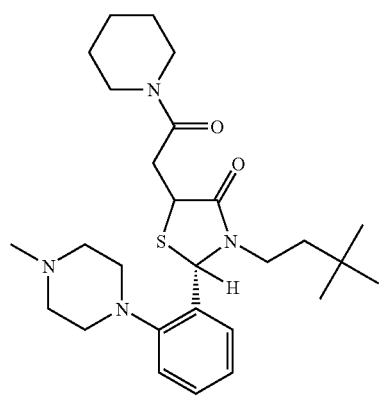

-continued
106
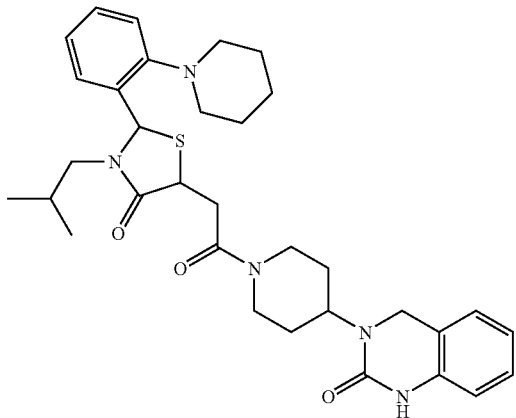
107
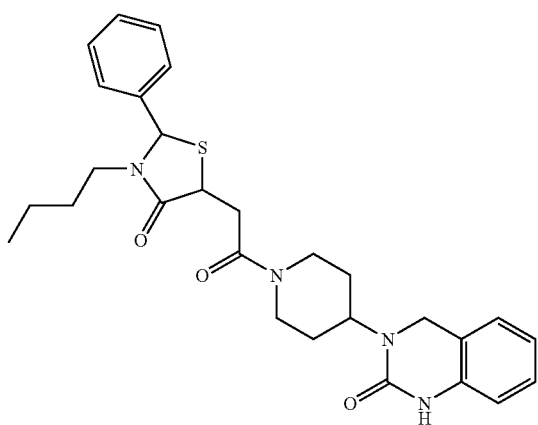
108
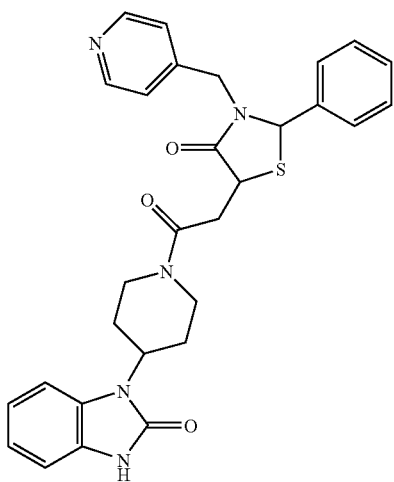

109
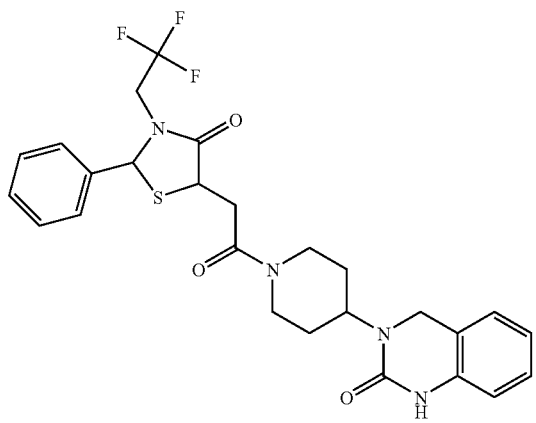
110
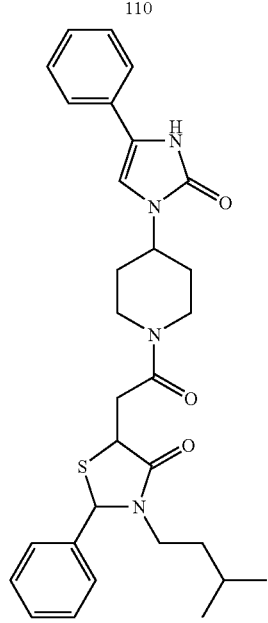
111
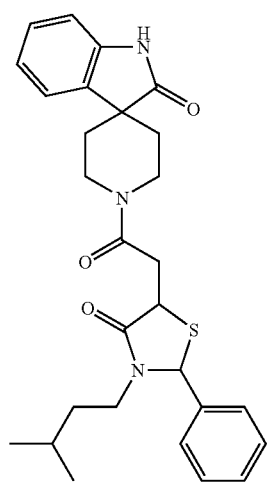

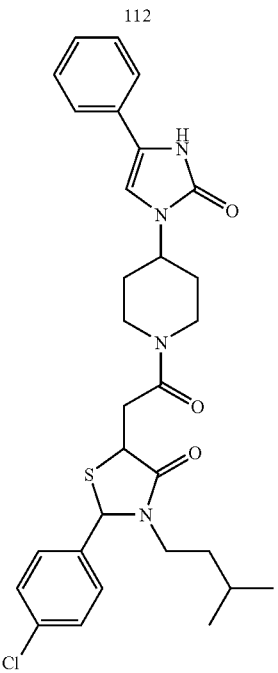
112
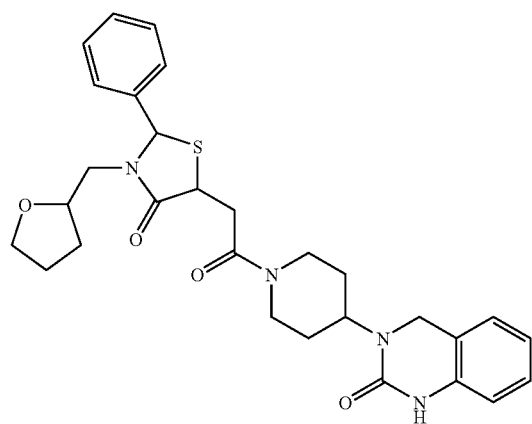
113
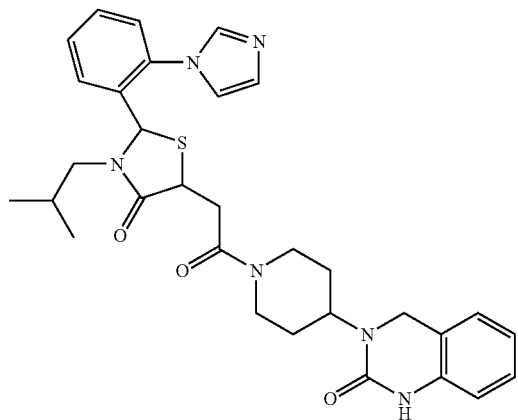
114

115
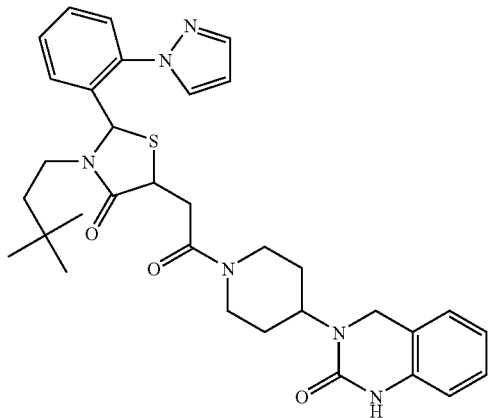
116
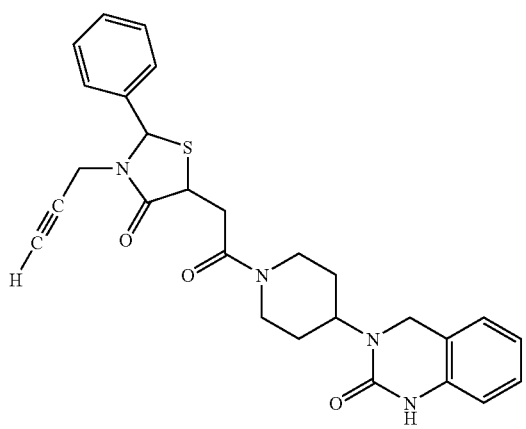
117
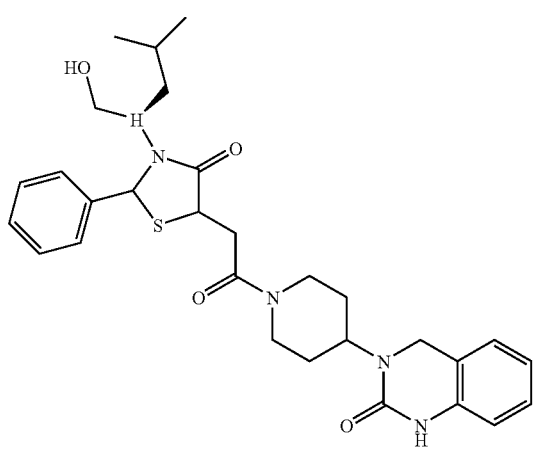

118
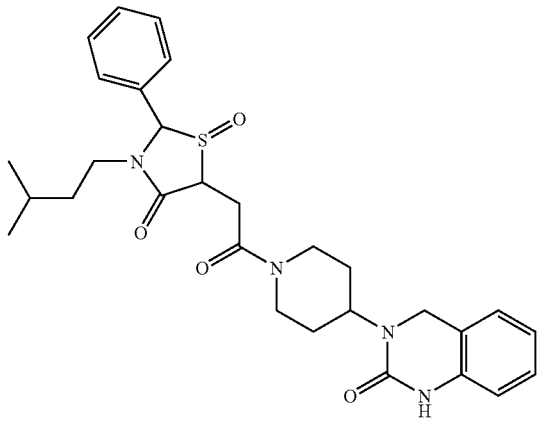
119
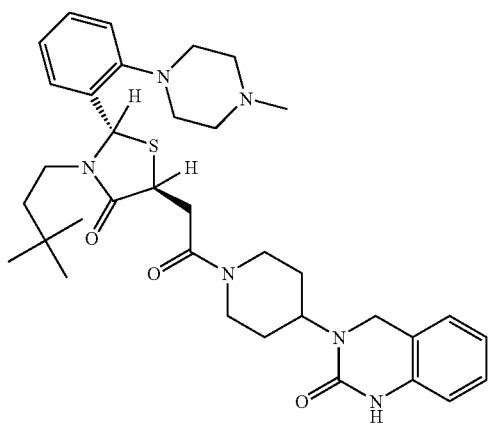
120
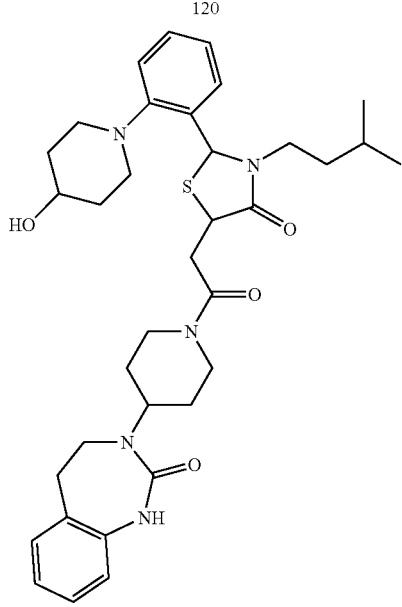

121
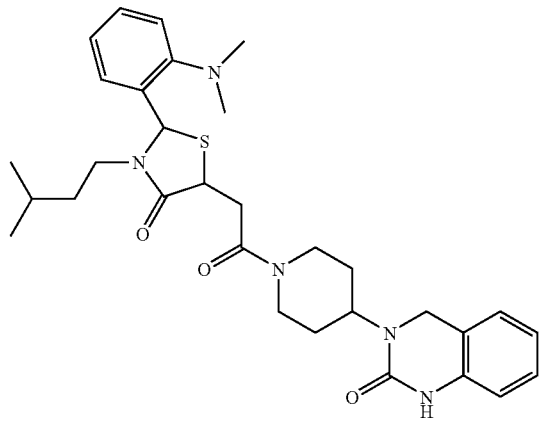
122
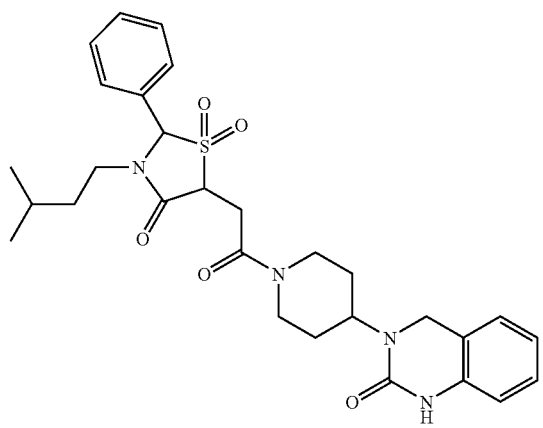
123
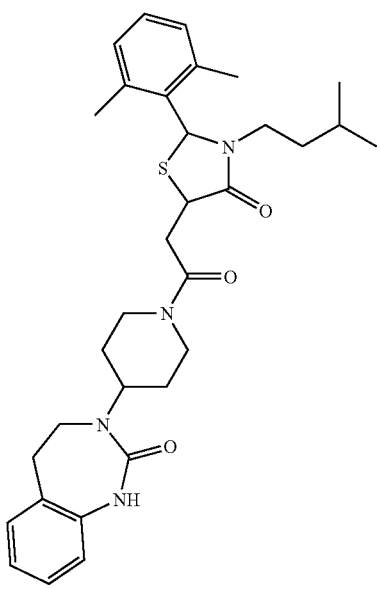

124
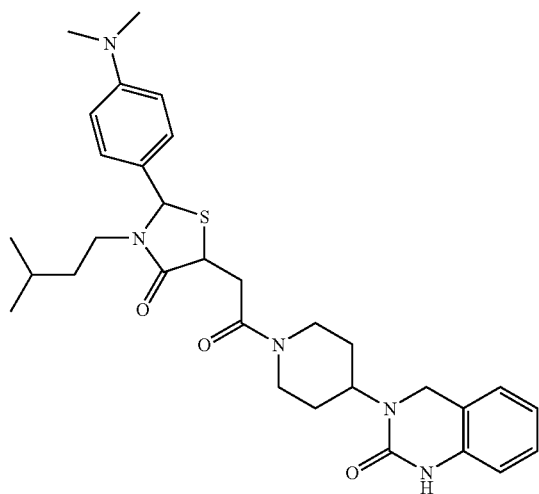
125
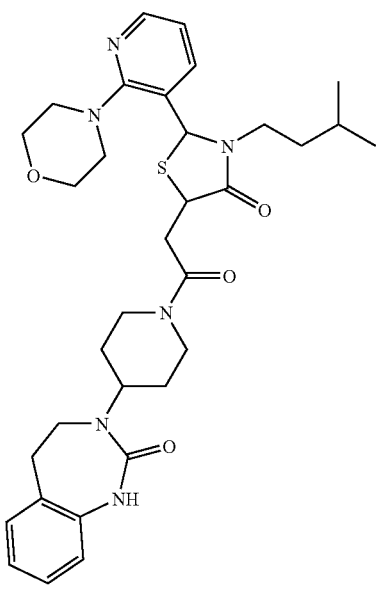
126
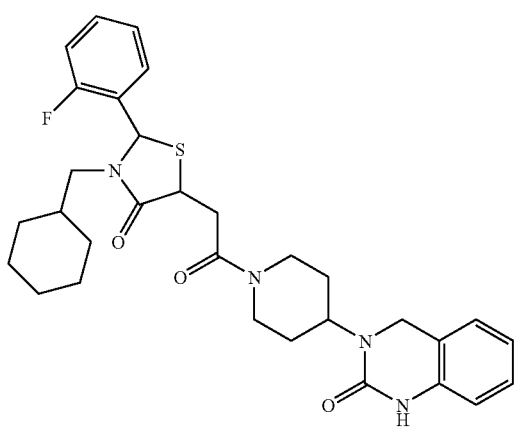

127
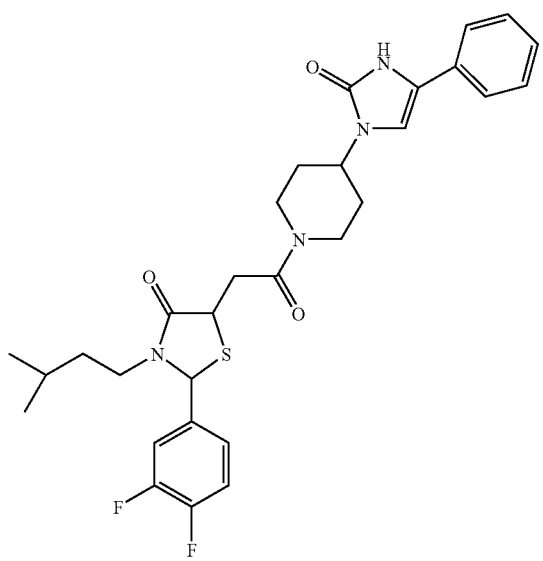
128
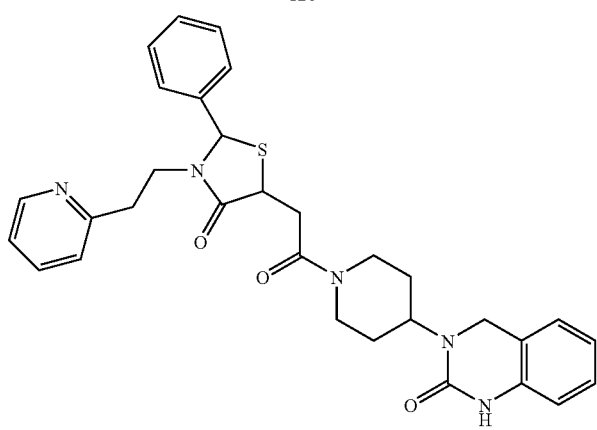
129
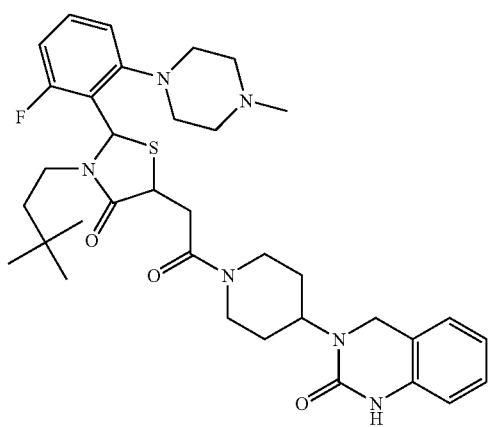

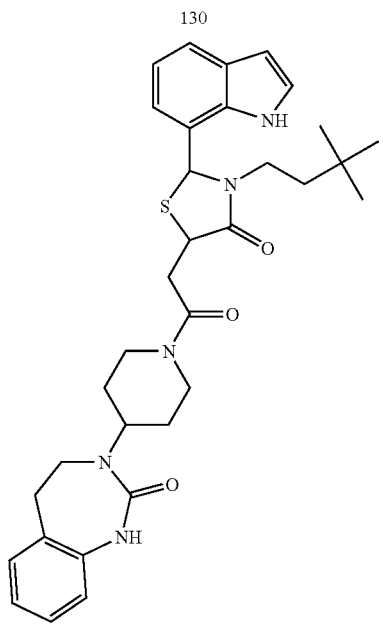
130
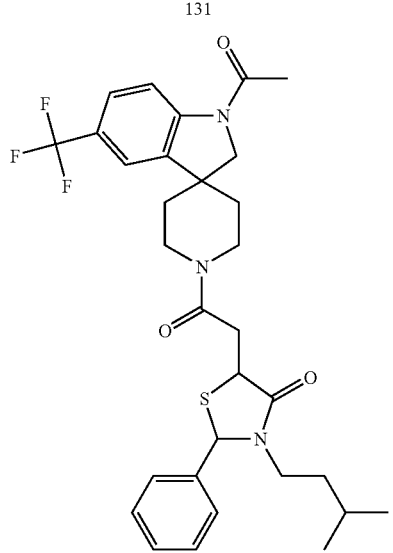
131

-continued
132
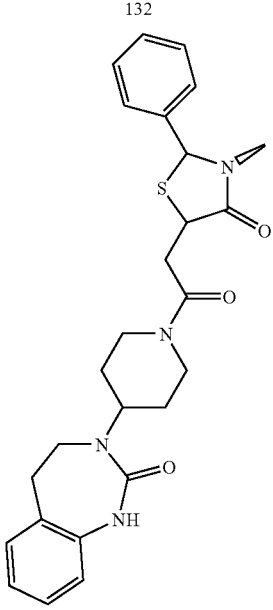
133
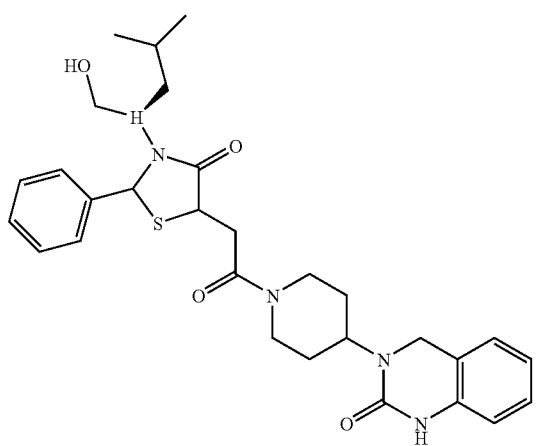
134
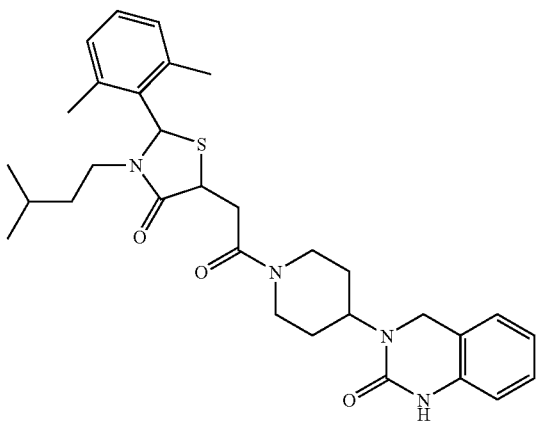

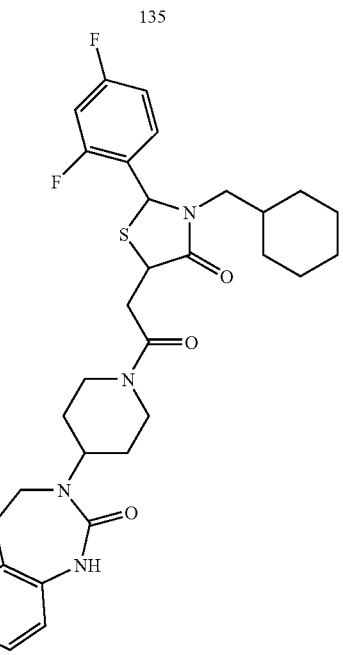
135
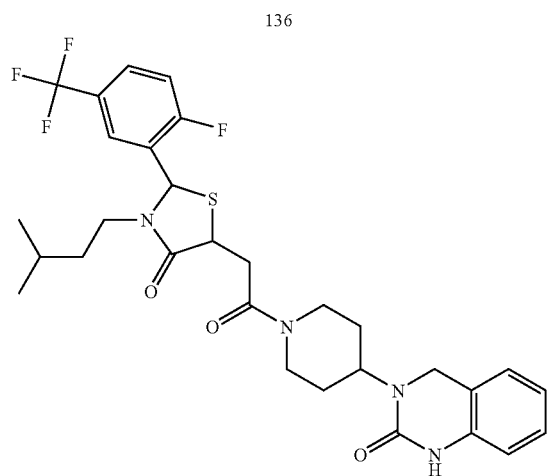
136
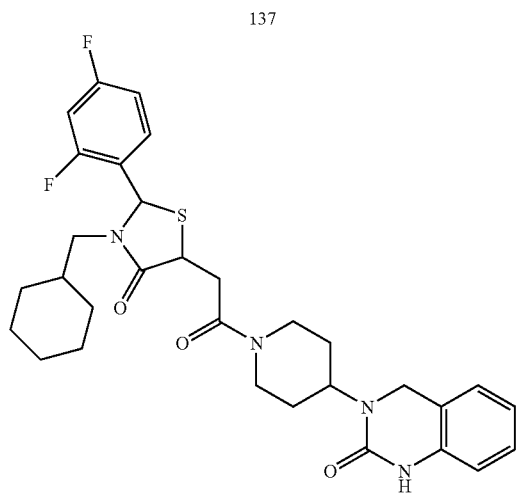
137

-continued
138
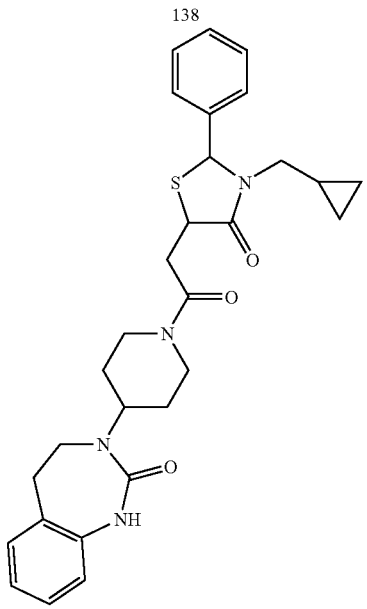
139
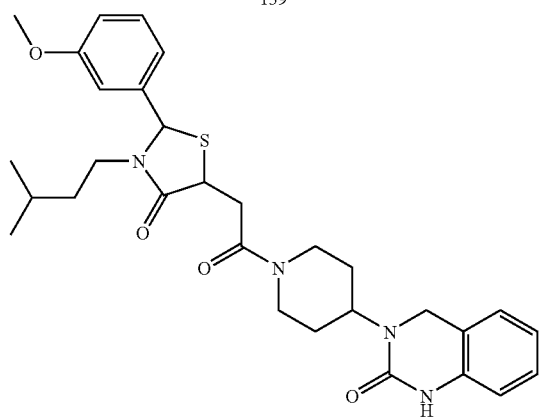
140
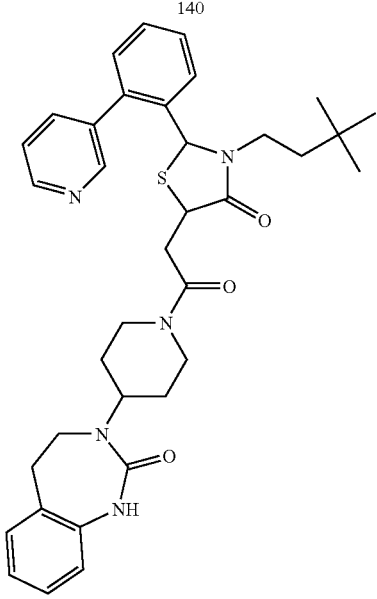

141
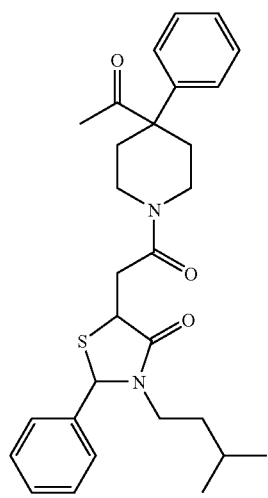
142
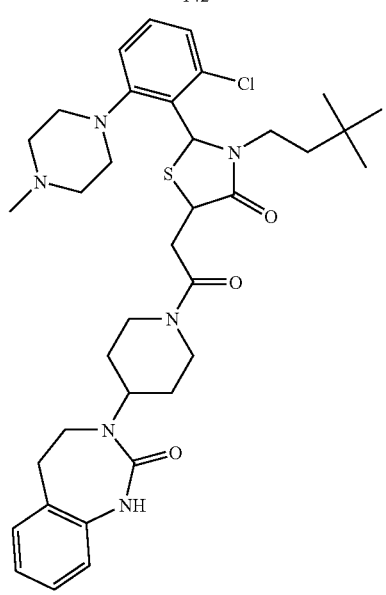

143
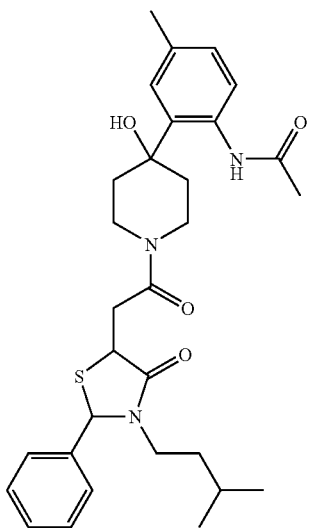
144
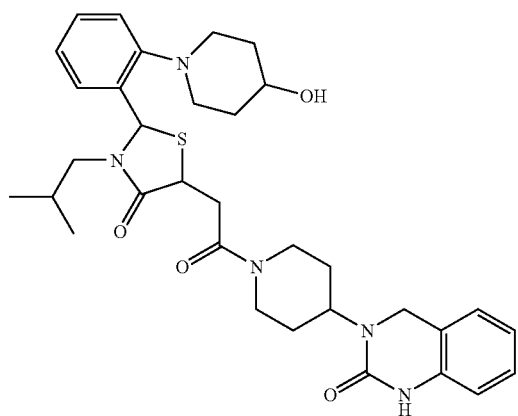
145
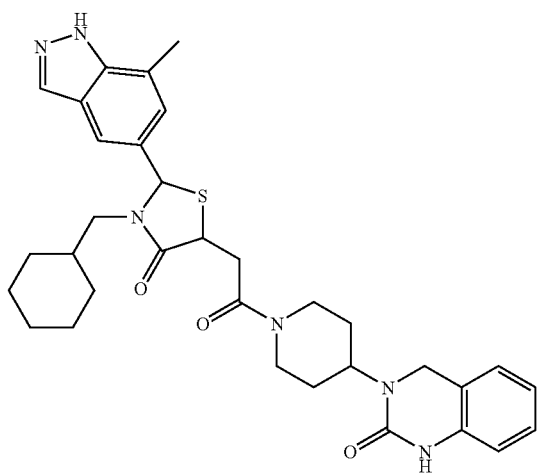

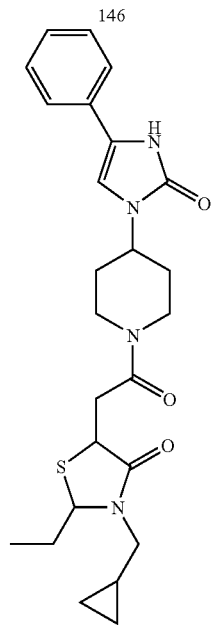
146
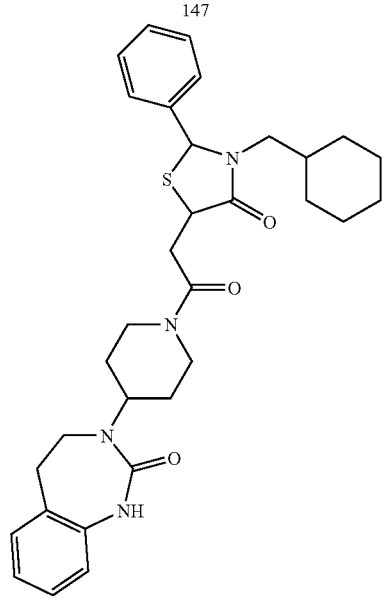
147

-continued
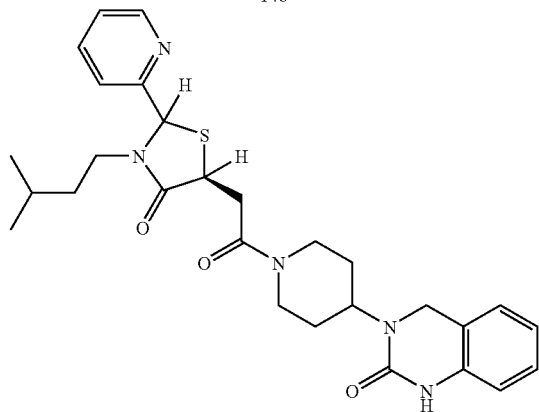
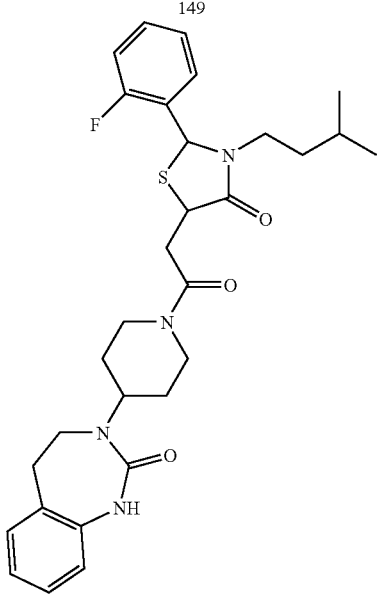
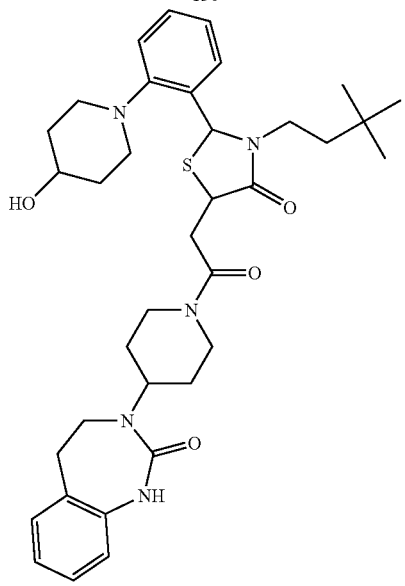

151
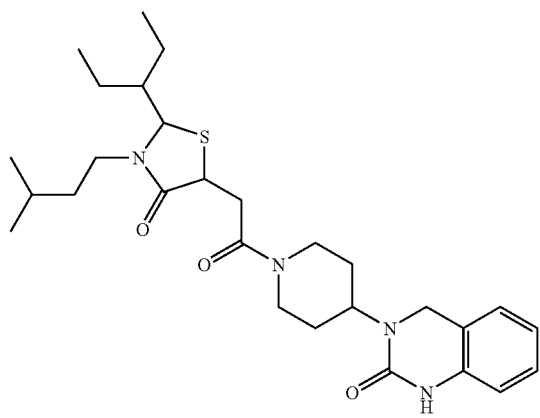
152
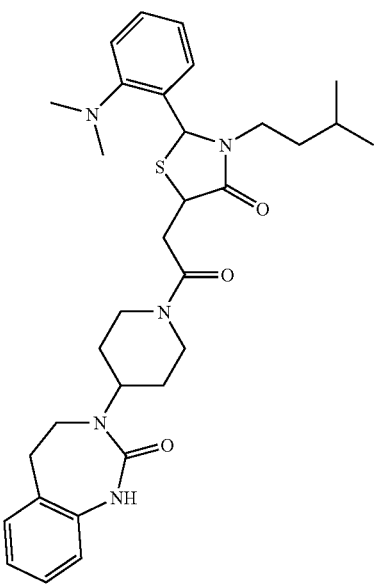
153
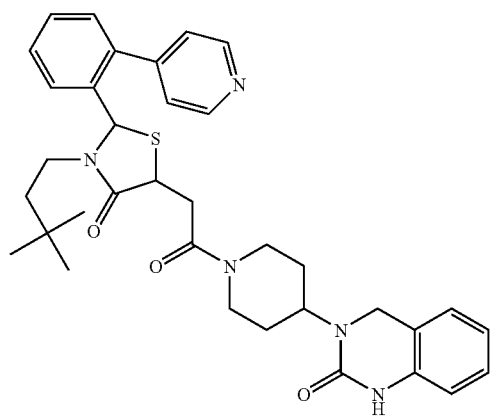

154
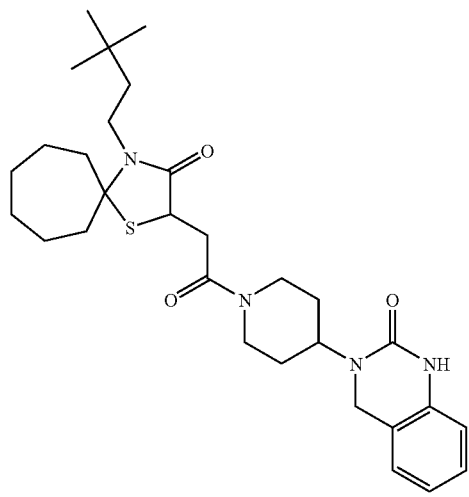
155
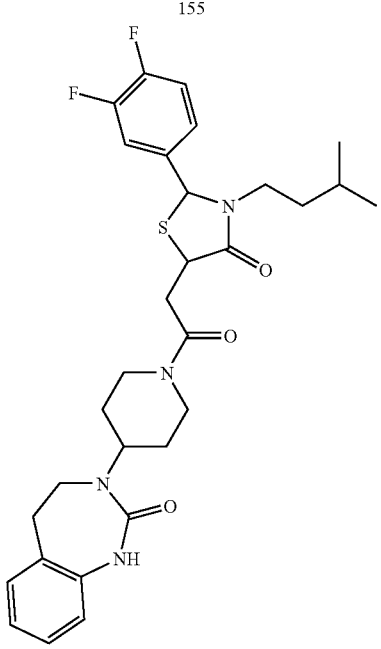
156
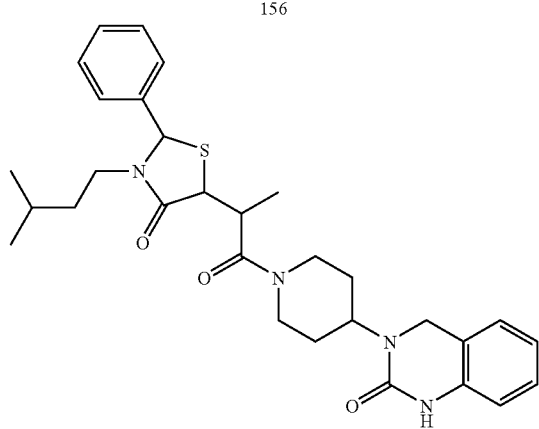

157
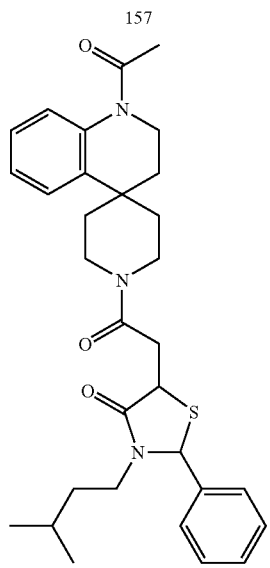
158
159
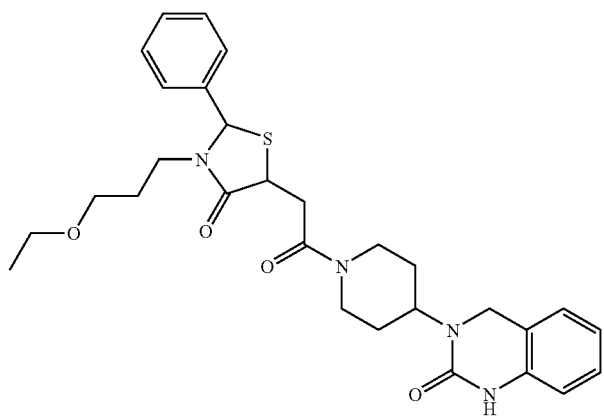

-continued
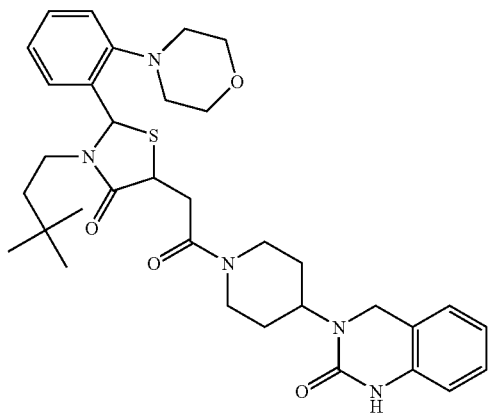
160
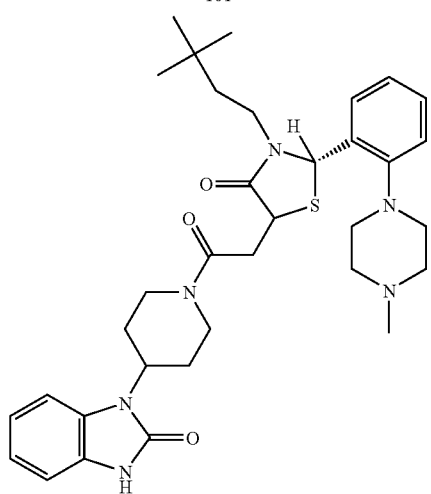
161
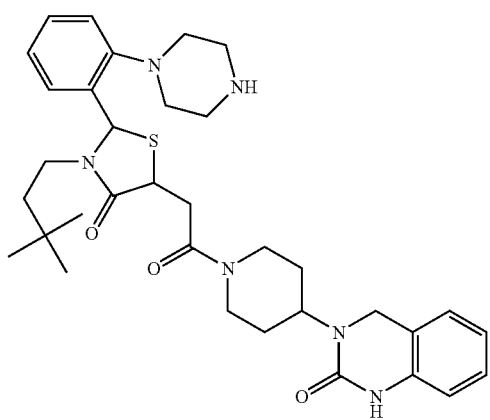
162

163
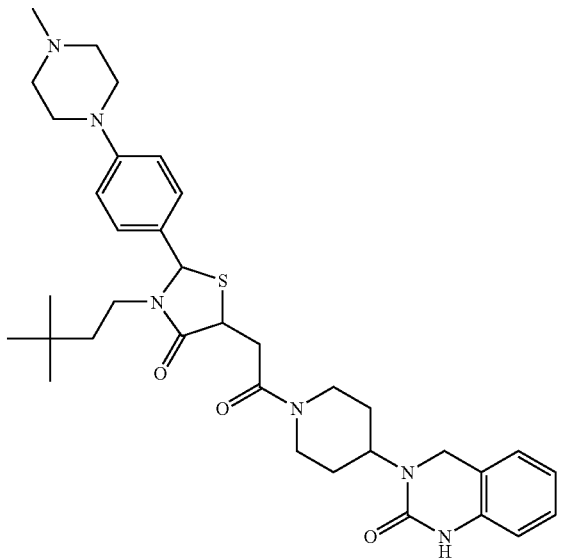
164
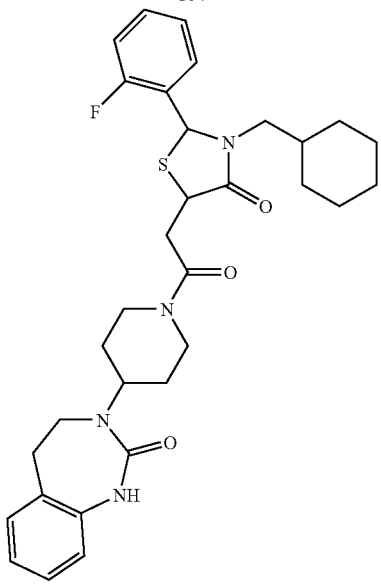
165
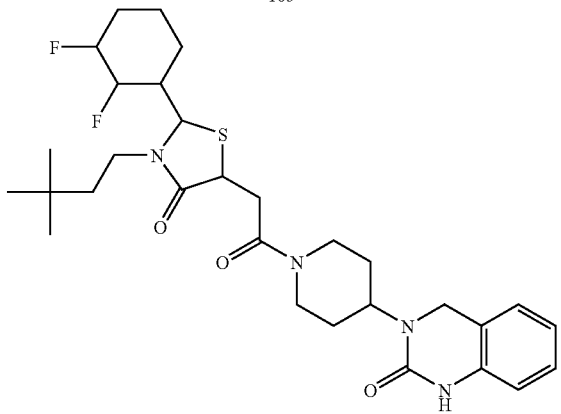

-continued
166
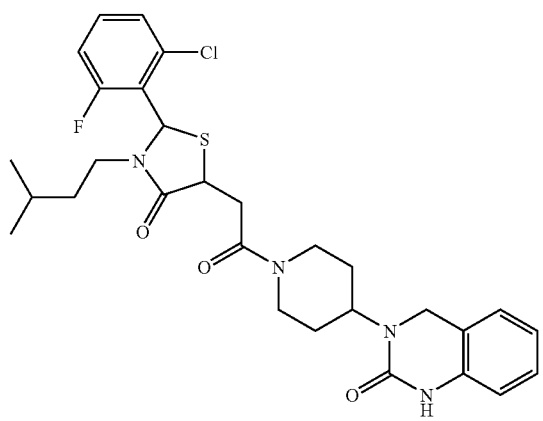
167
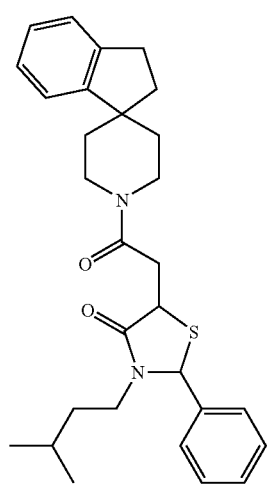
168
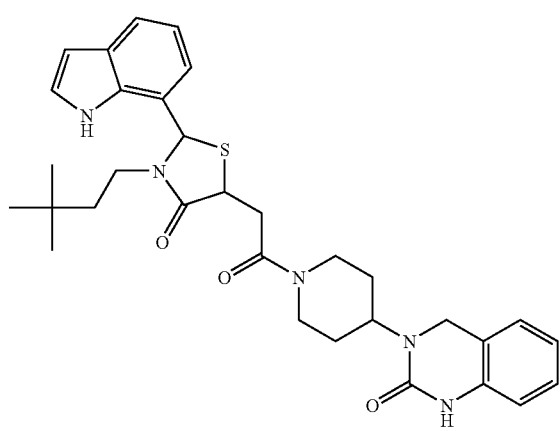

-continued
169
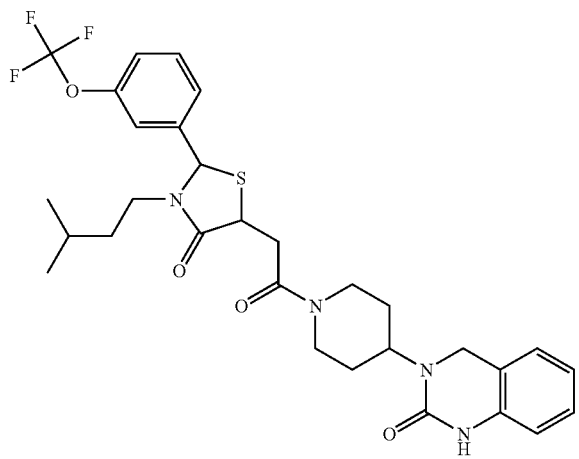
170
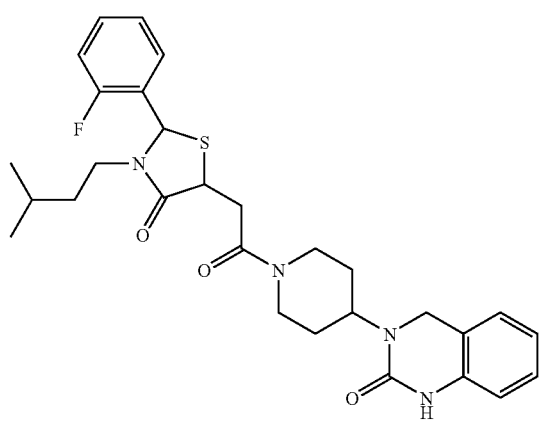
171
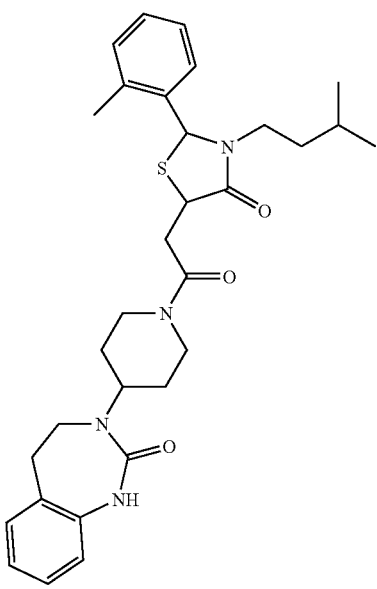

172
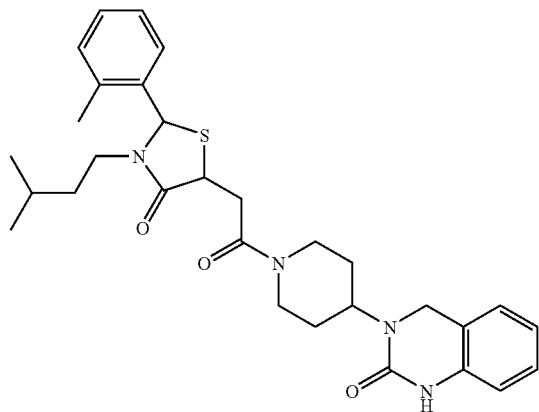
173
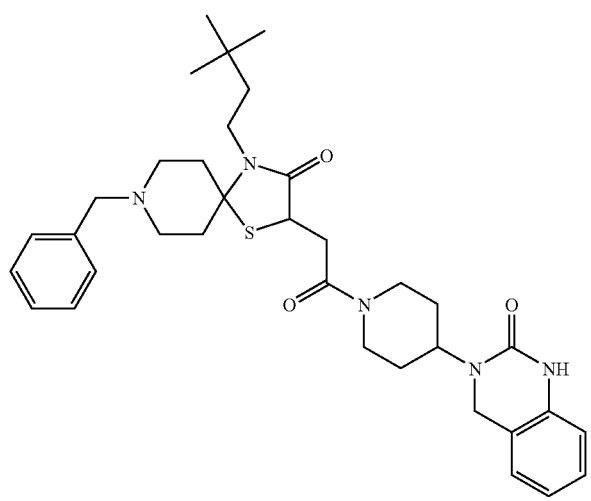
174
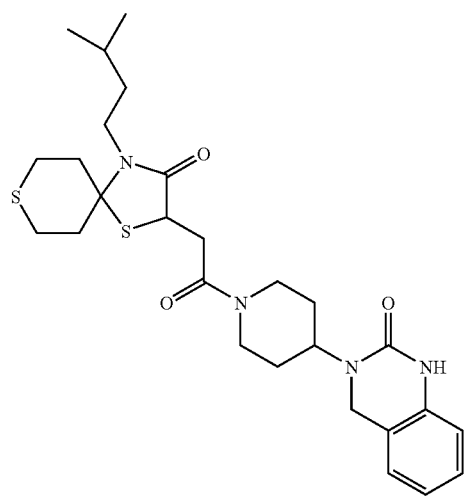

175
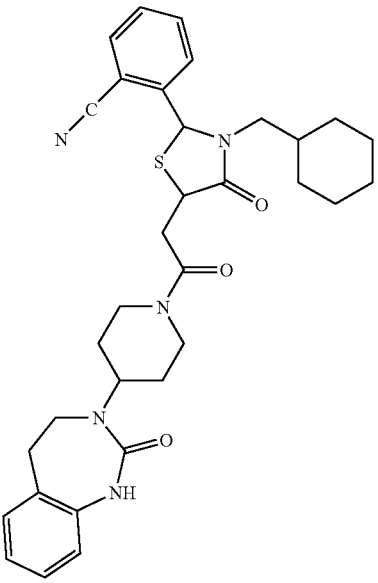
176
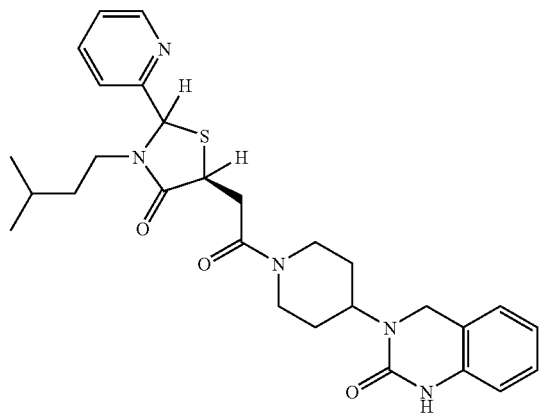
177
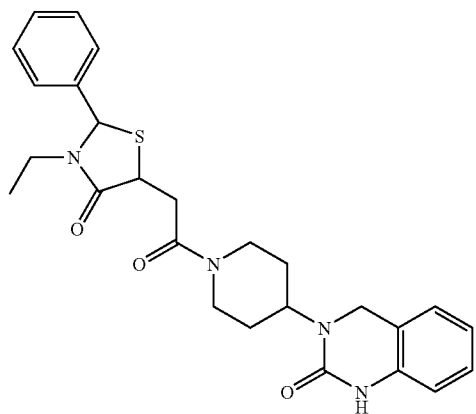

178
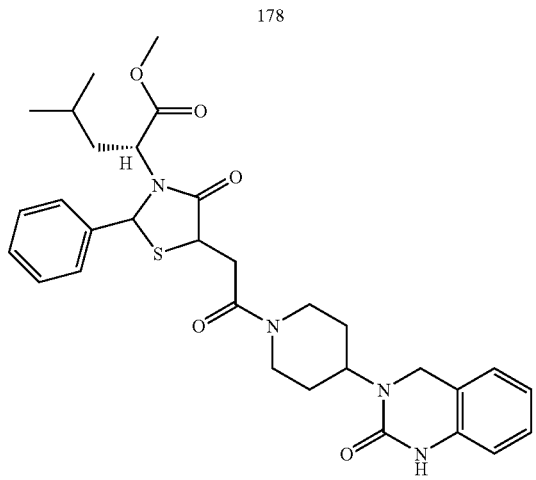
179
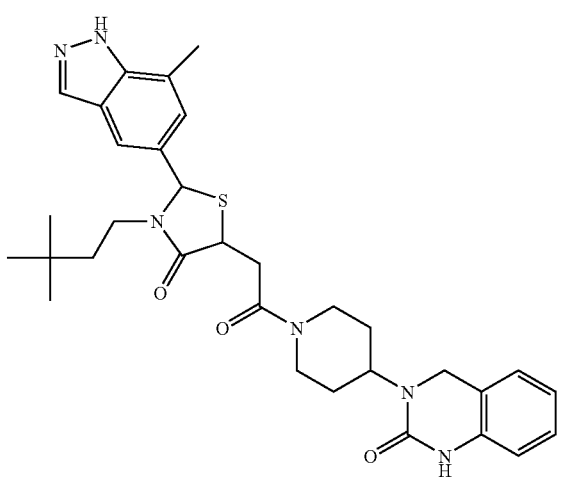
180
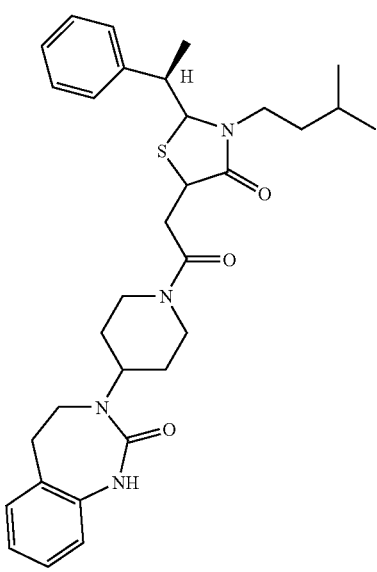

-continued
181
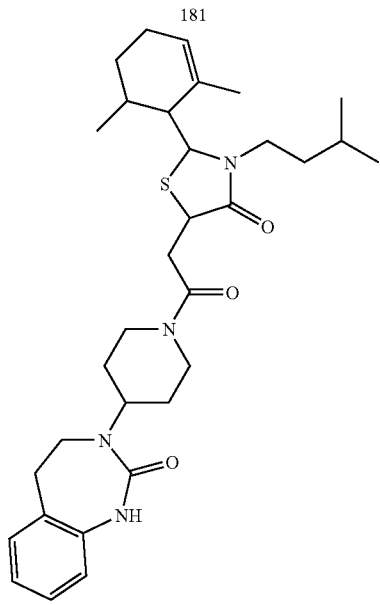
182
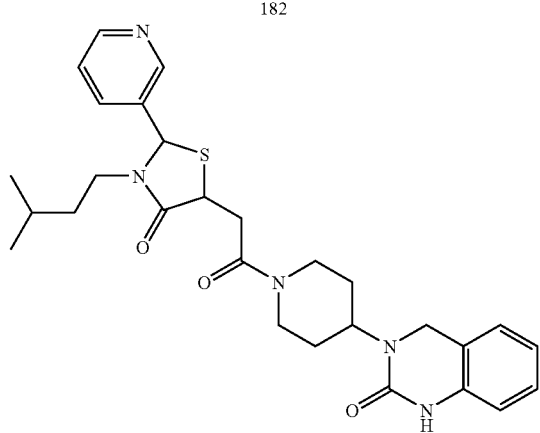
183
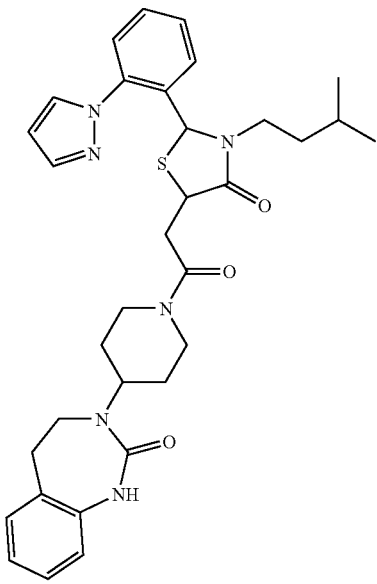

184
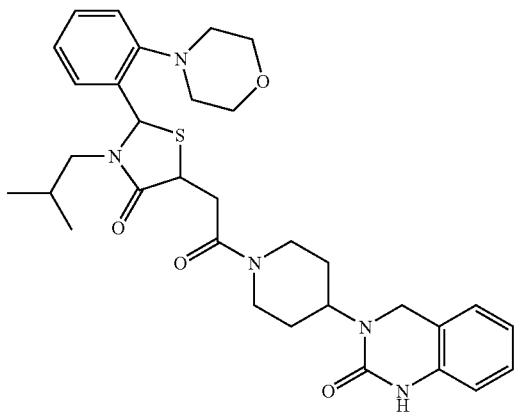
185
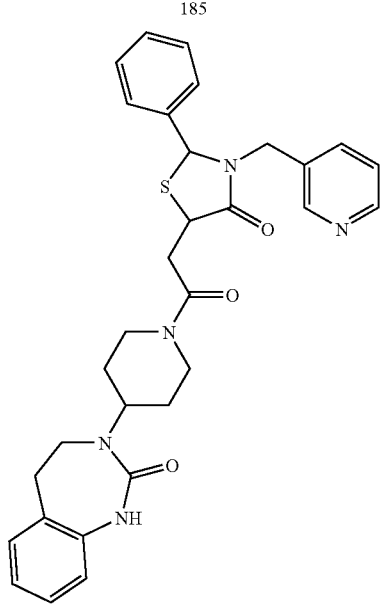
186
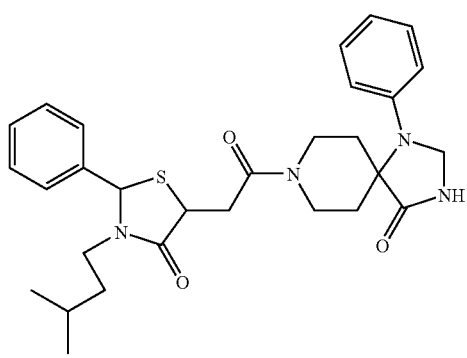

187
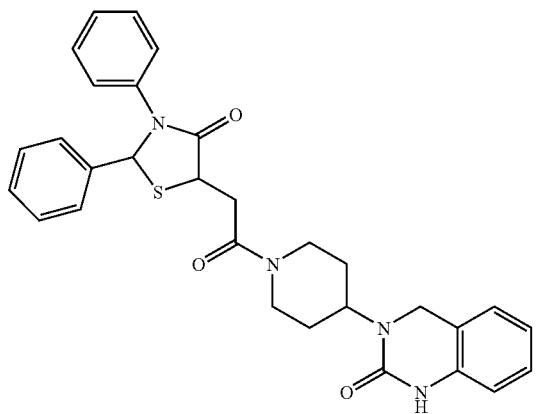
188
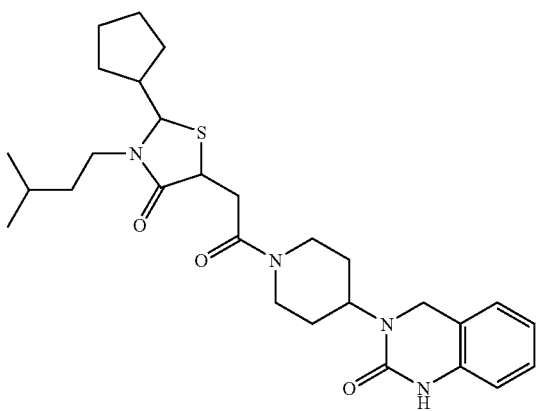
189
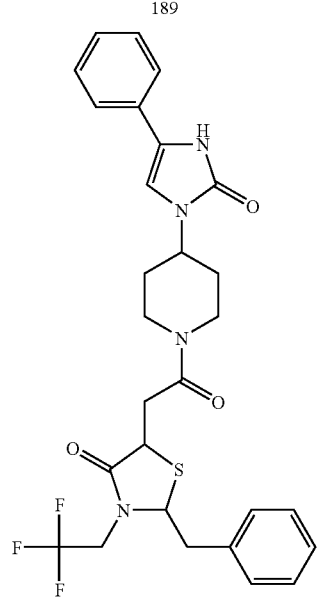

190
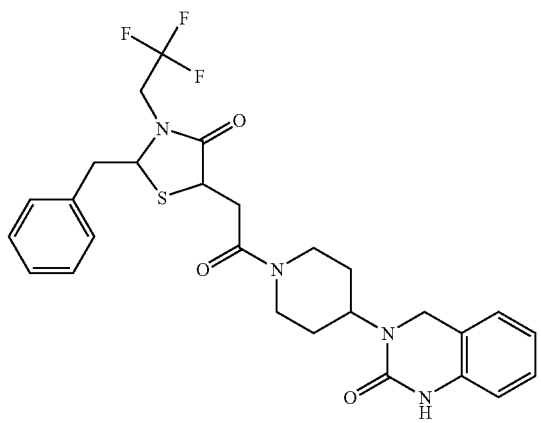
191
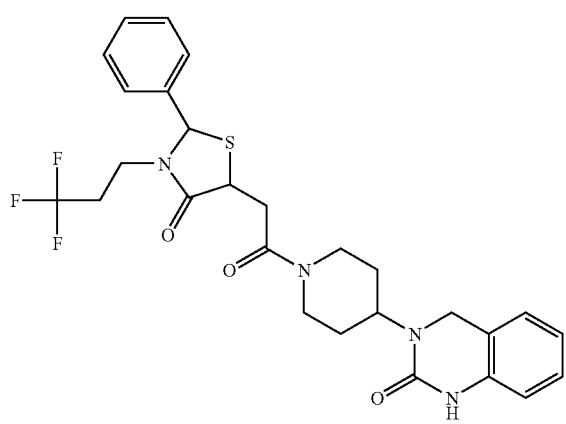
192
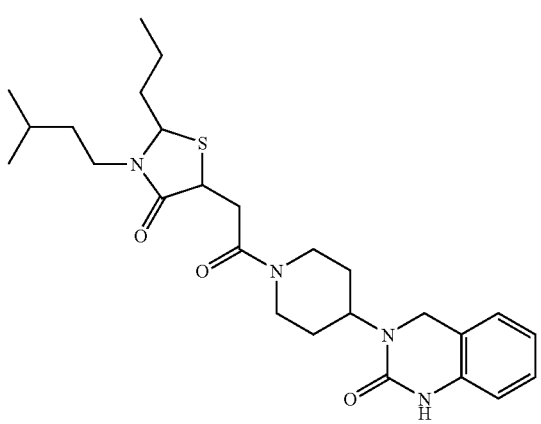

193
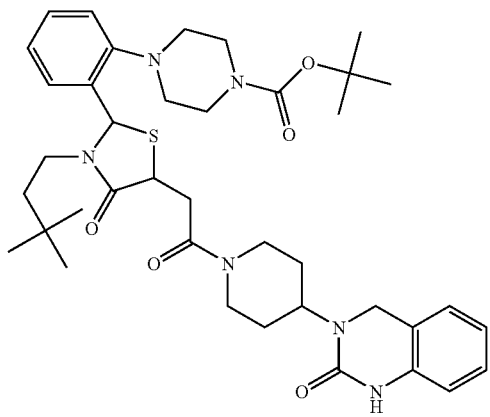
194
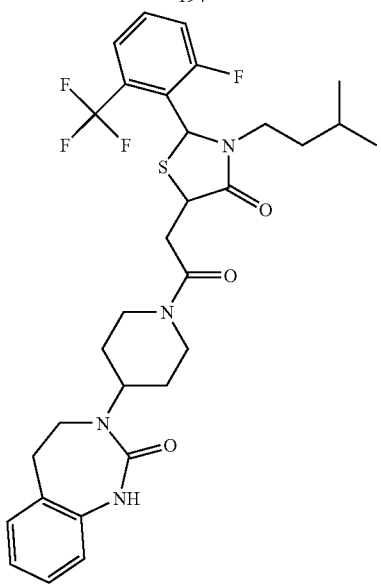
195
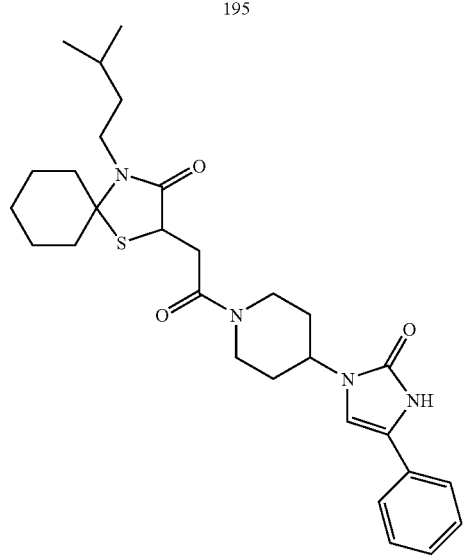

196
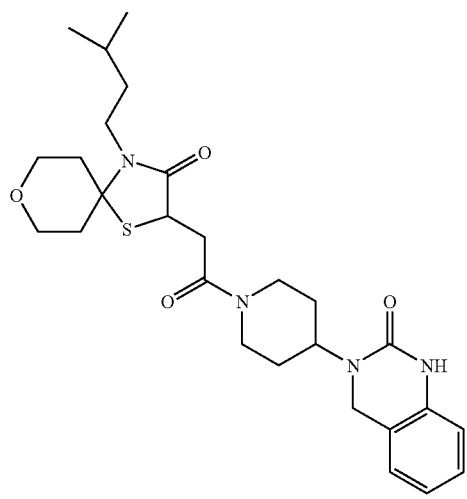
197
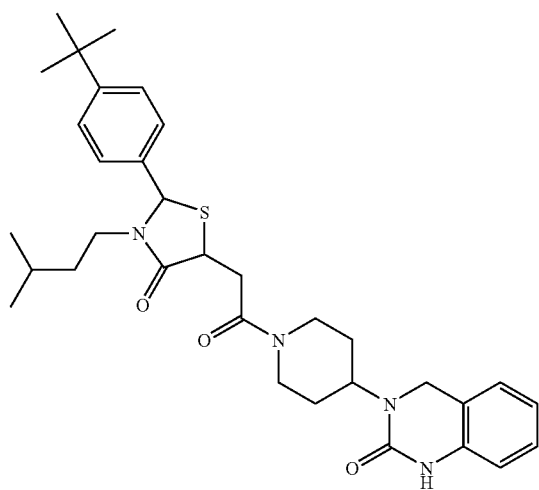
198
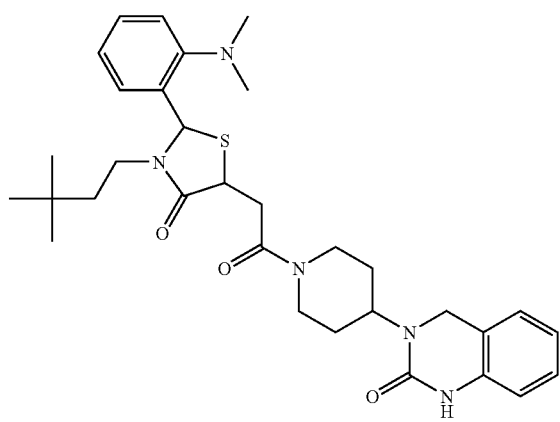

199
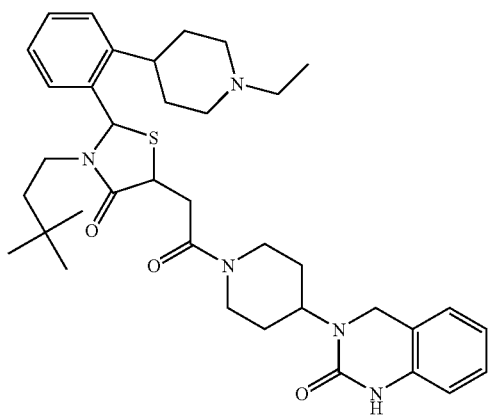
200
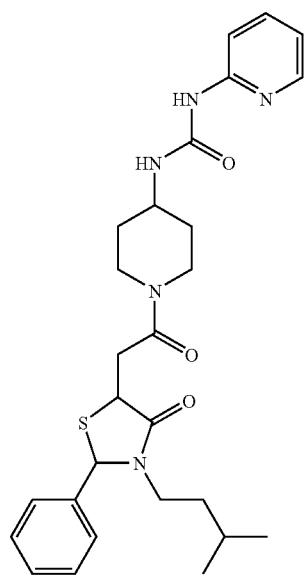
201
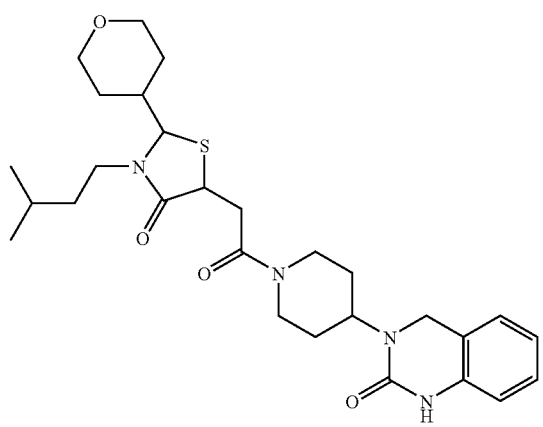

-continued
202
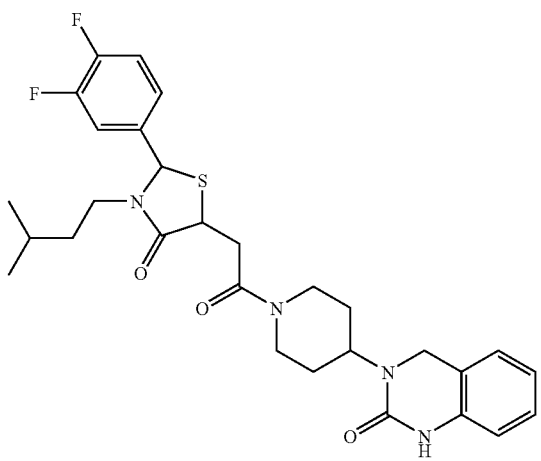
203
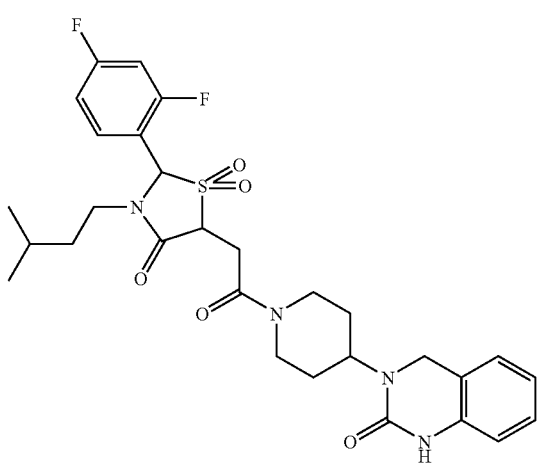
204
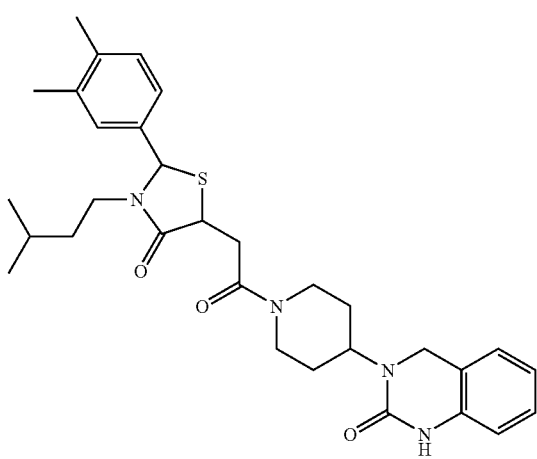

205
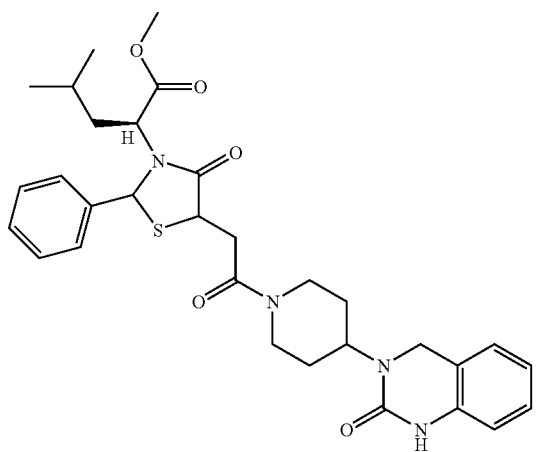
206
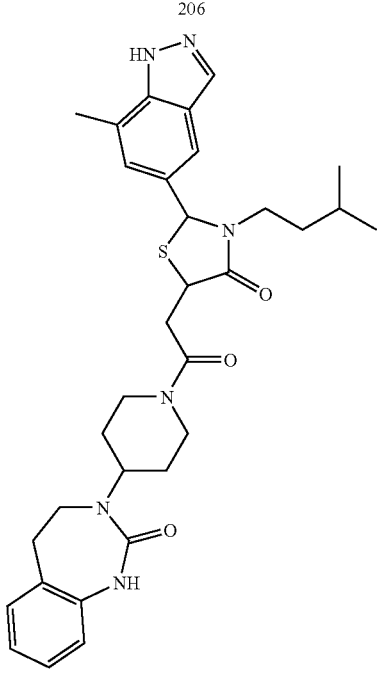

207
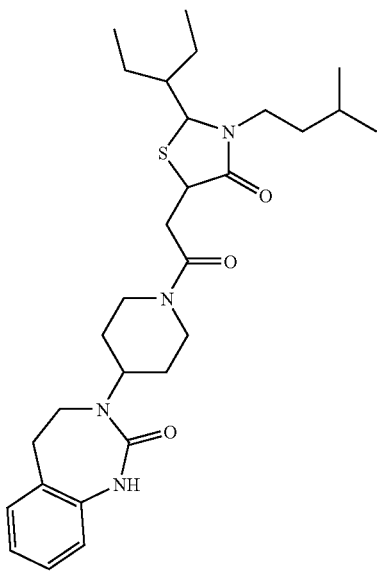
208
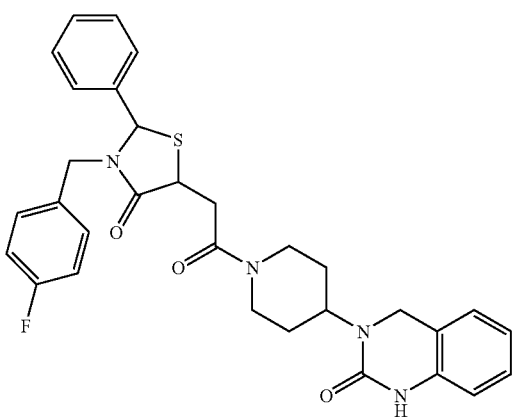
209
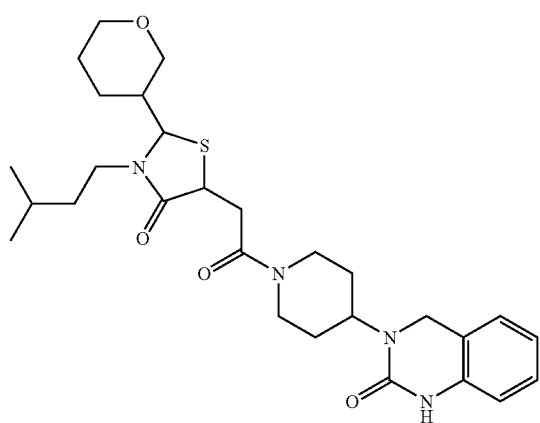

210
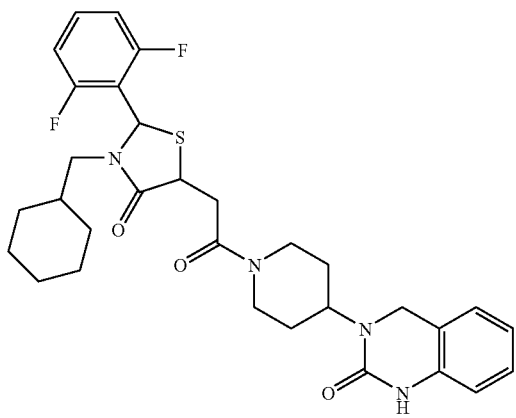
211
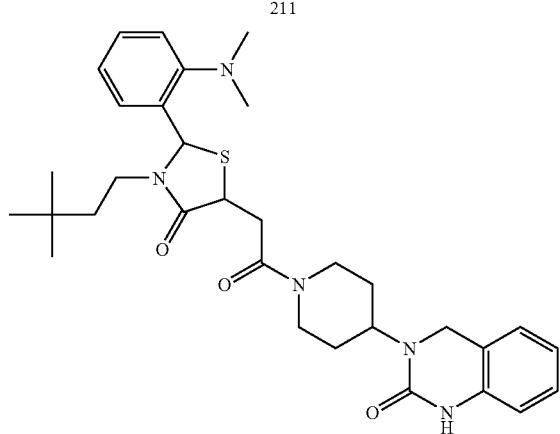
212
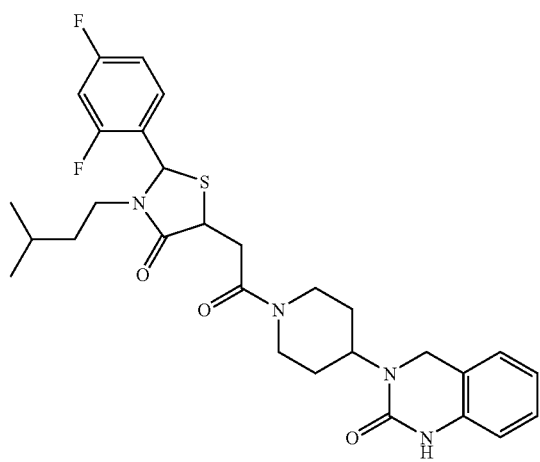

213
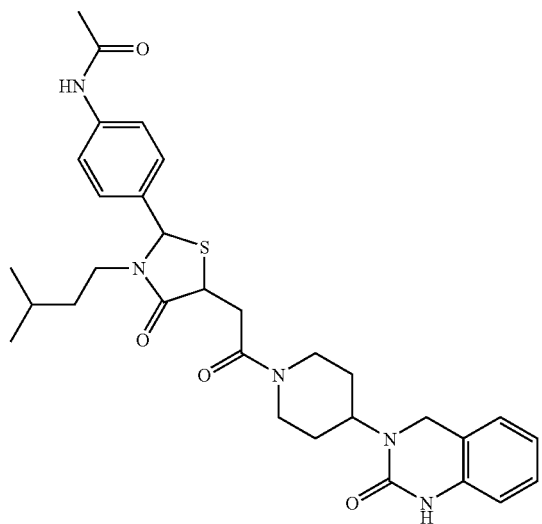
214
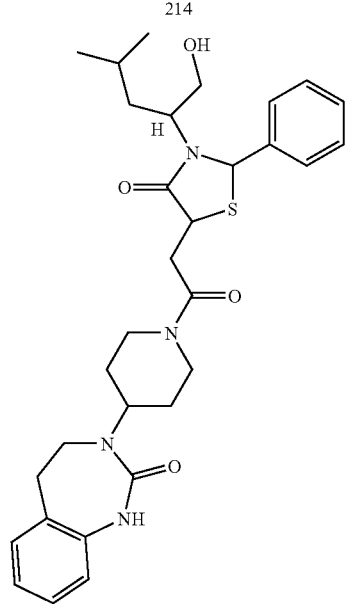

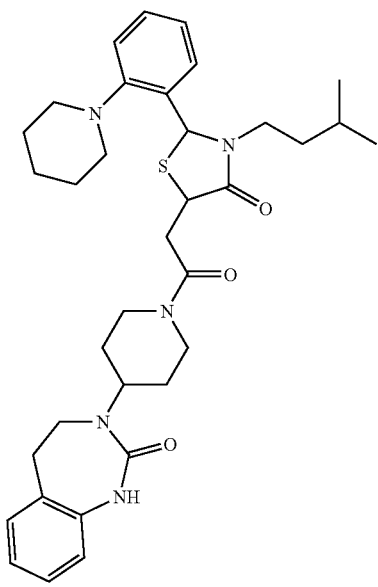
215
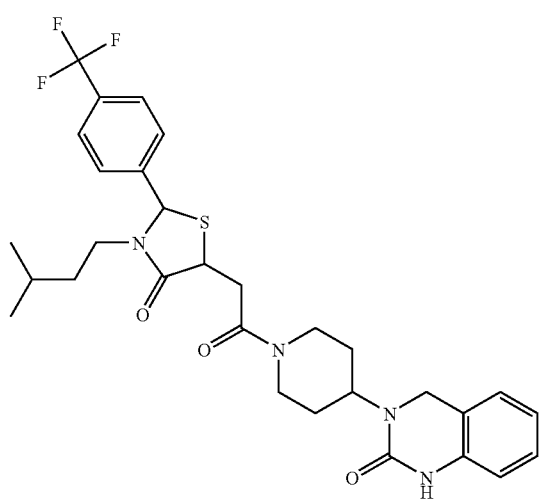
216

217
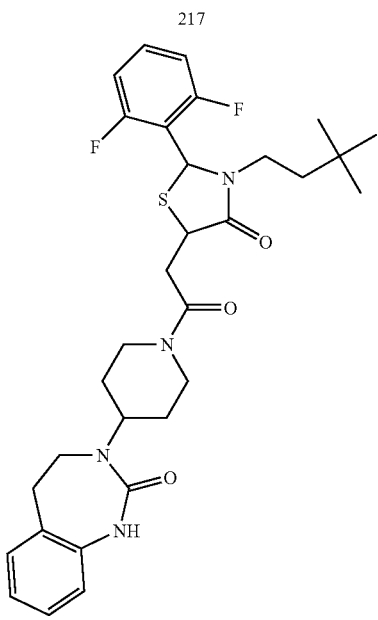
218
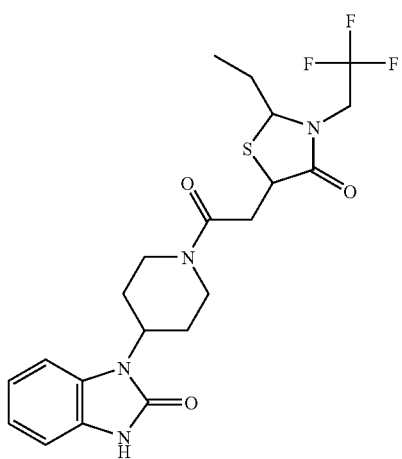
219
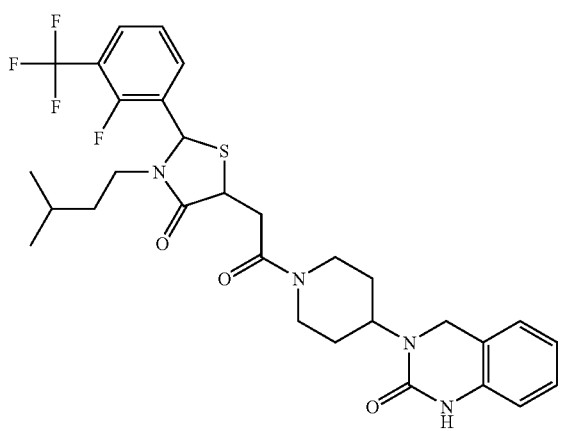

220
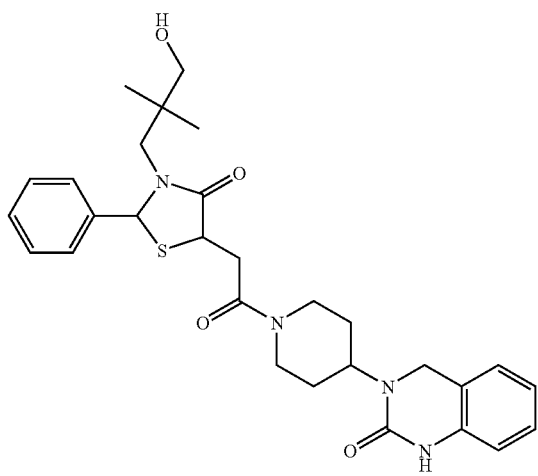
221
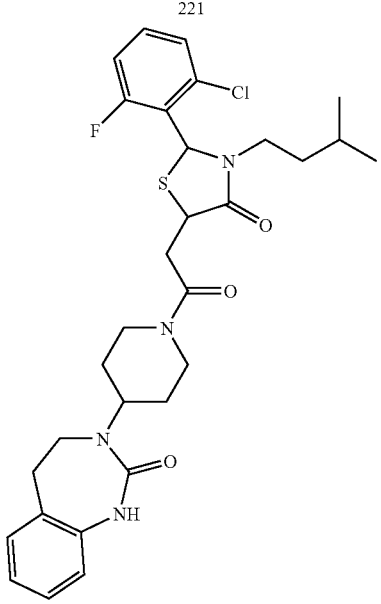
222
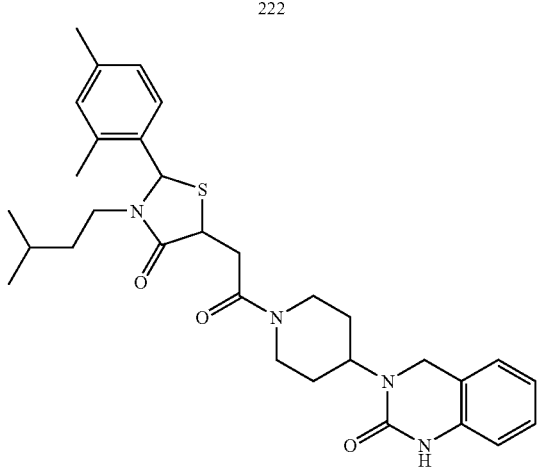

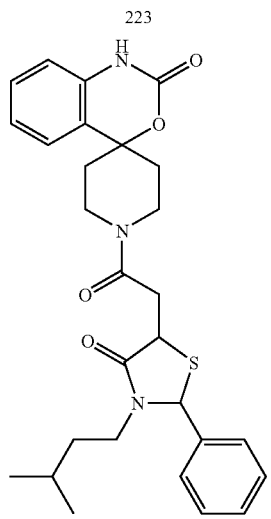
223
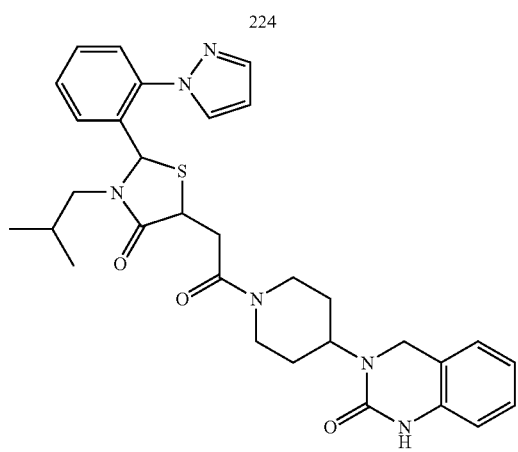
224
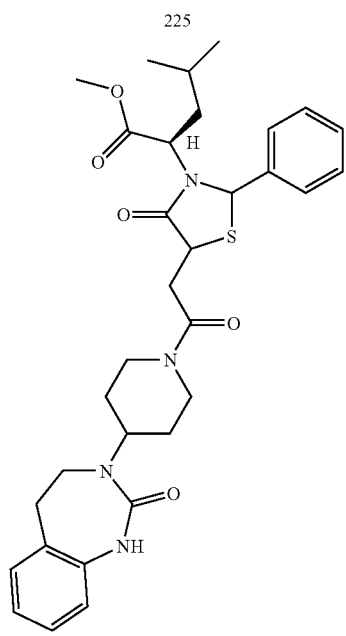
225

-continued
226
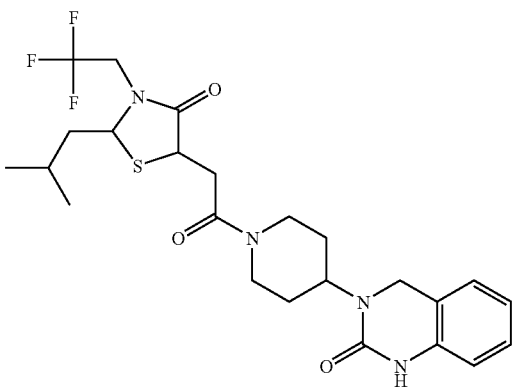
227
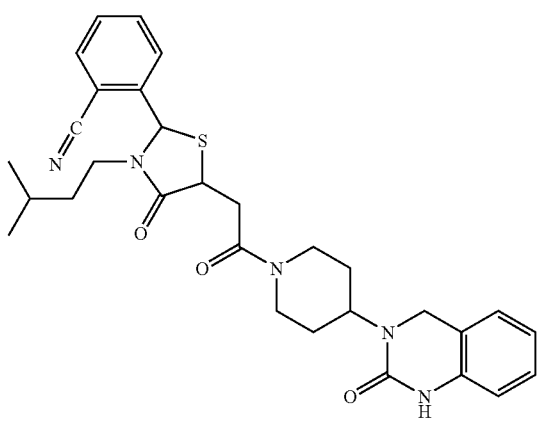
228
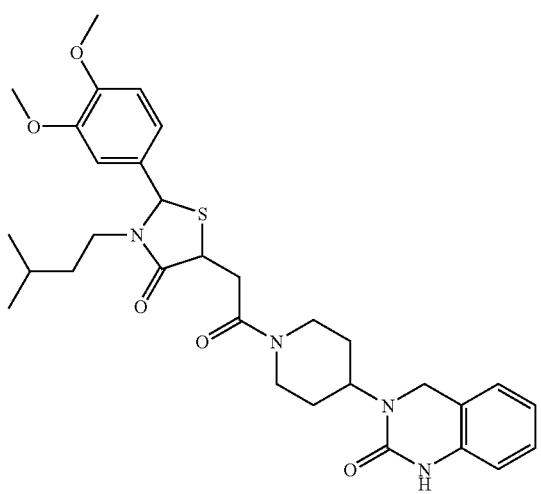

-continued
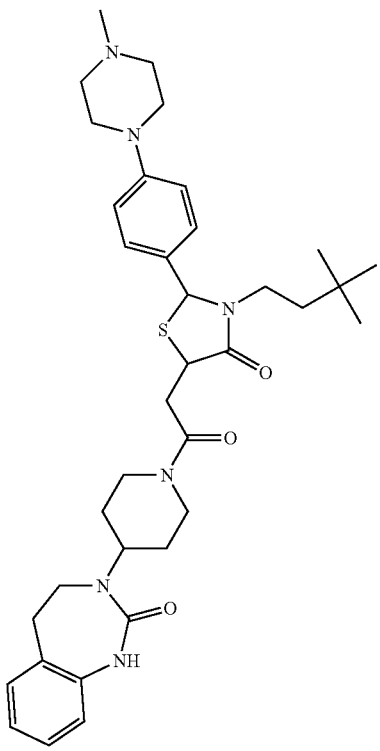
229
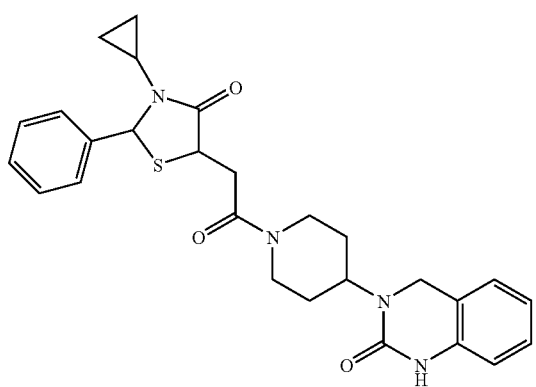
230

-continued
231
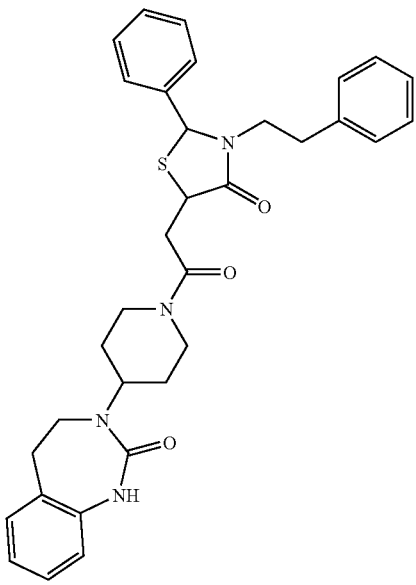
232
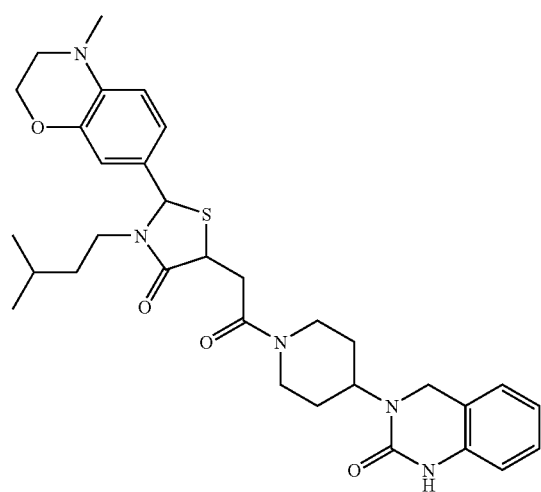

-continued
233
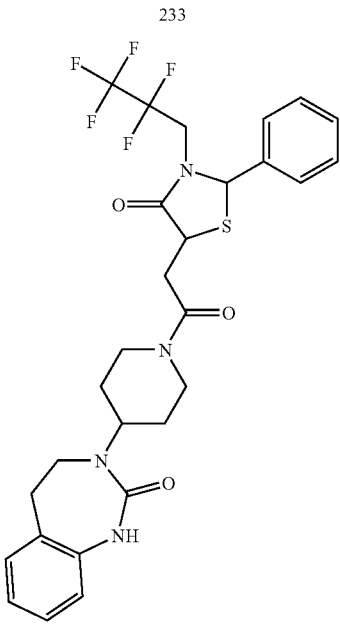
234
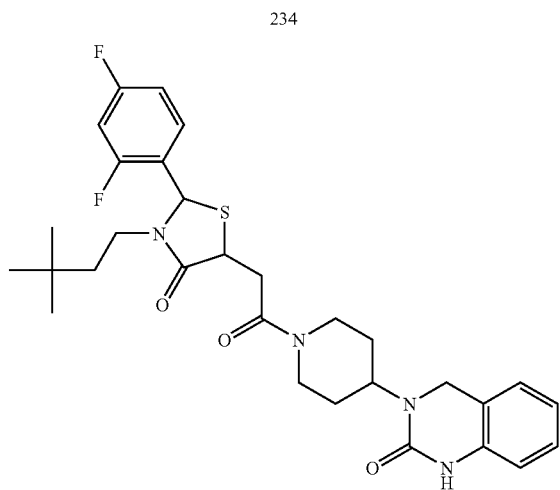
235
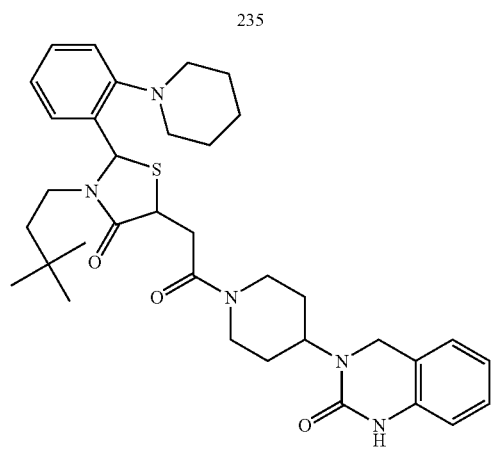

236
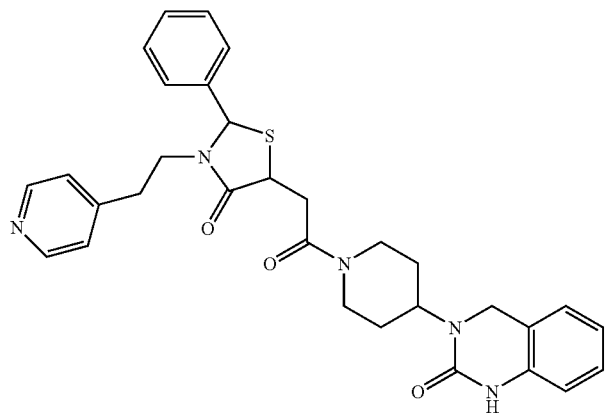
237
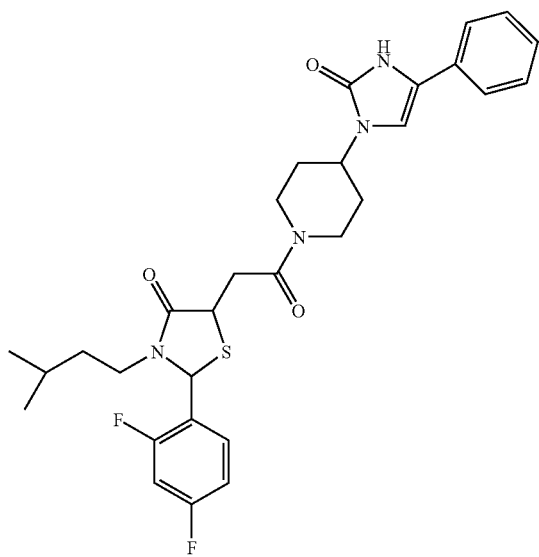
238
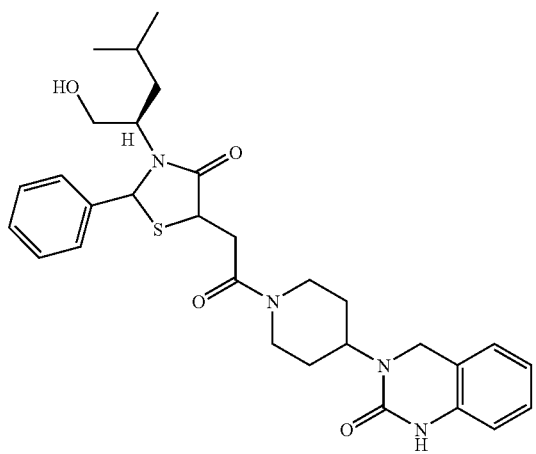

-continued
239
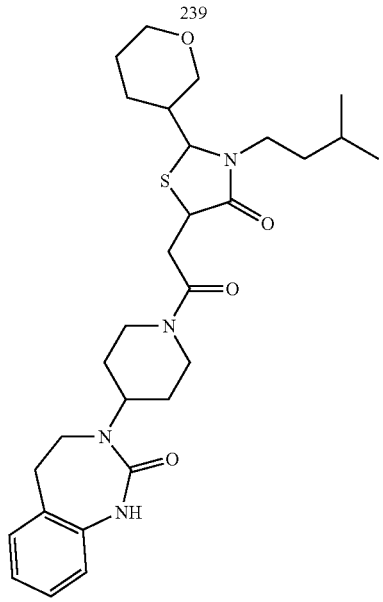
240
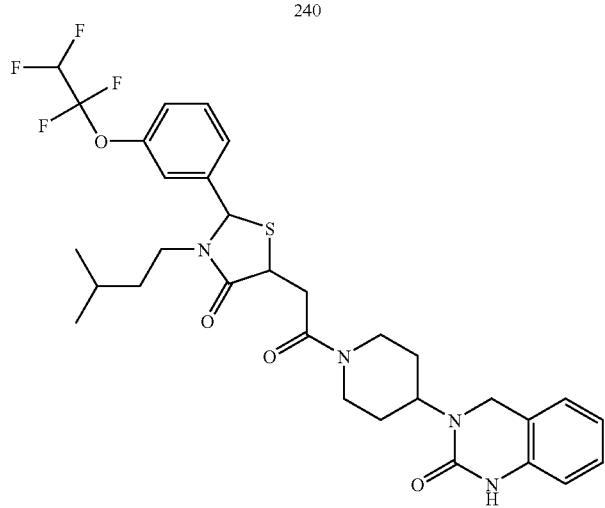
241
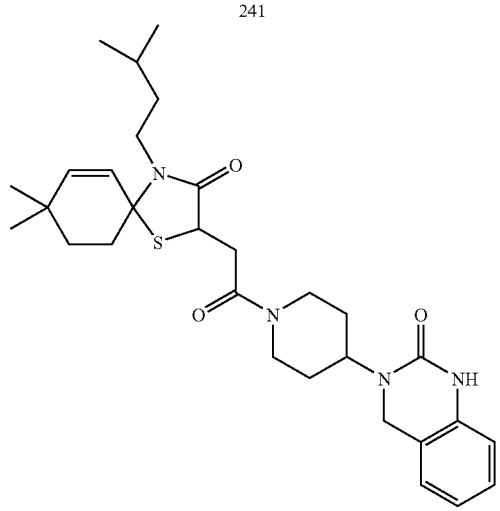

-continued
242
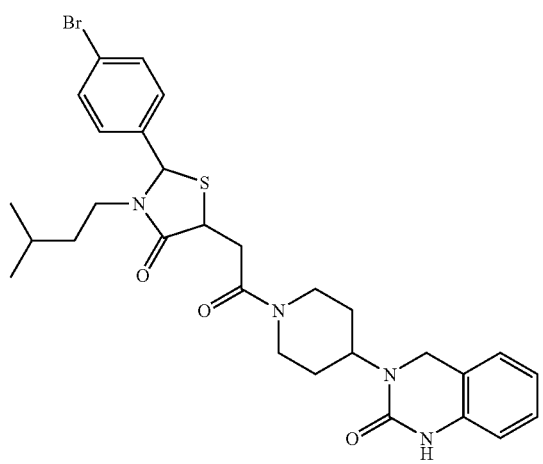
243
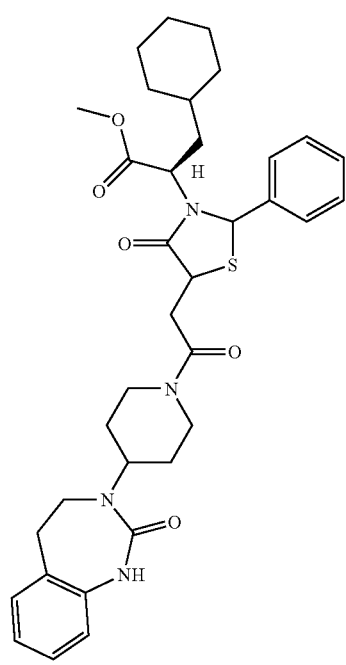

-continued
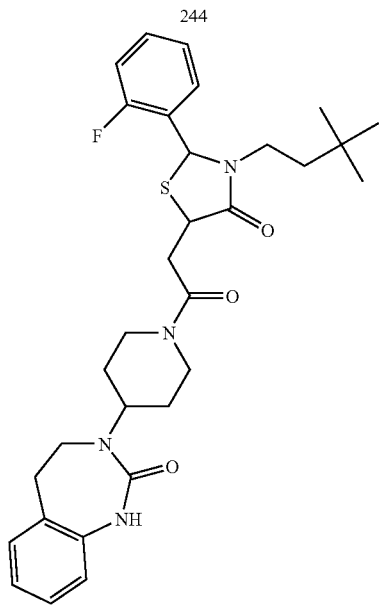
244
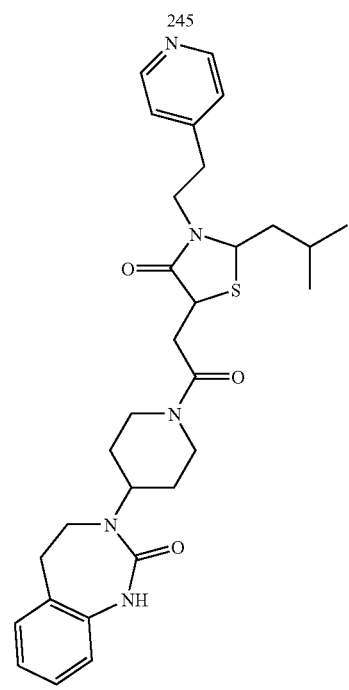
245

246
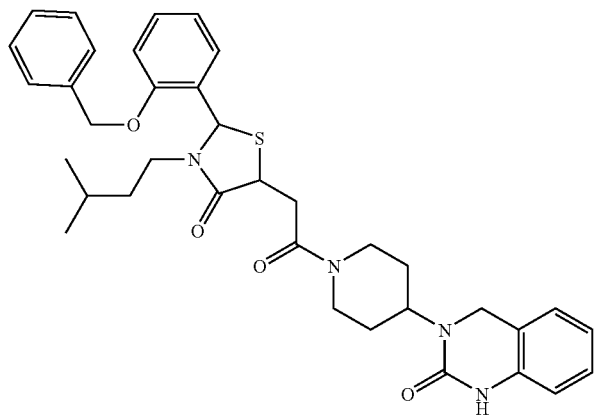
247
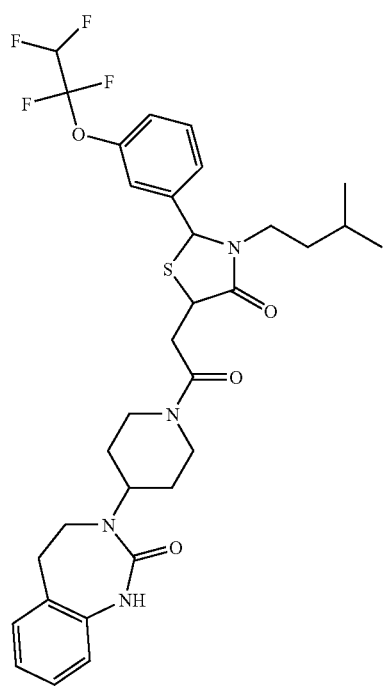

-continued
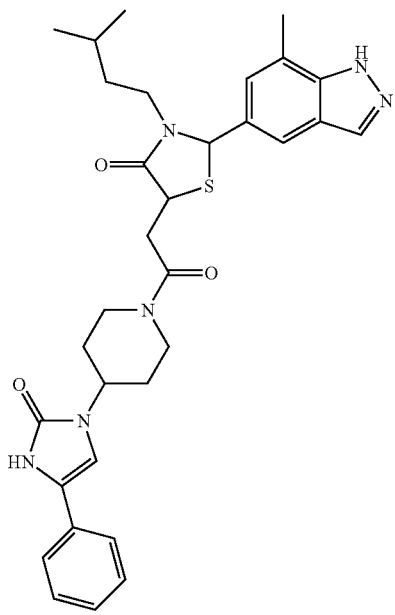

251
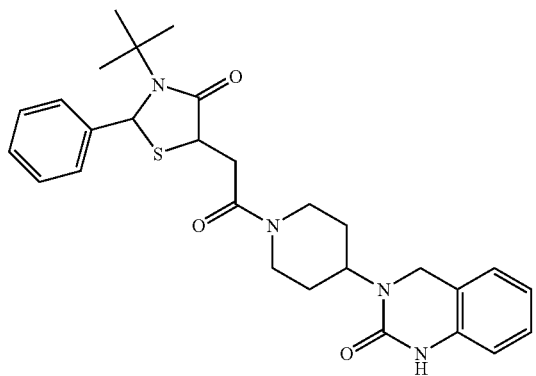
252
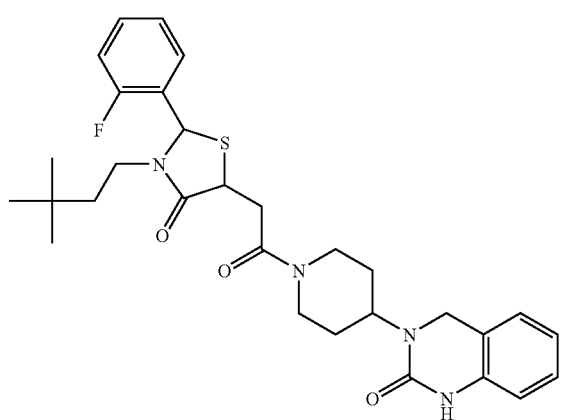
253
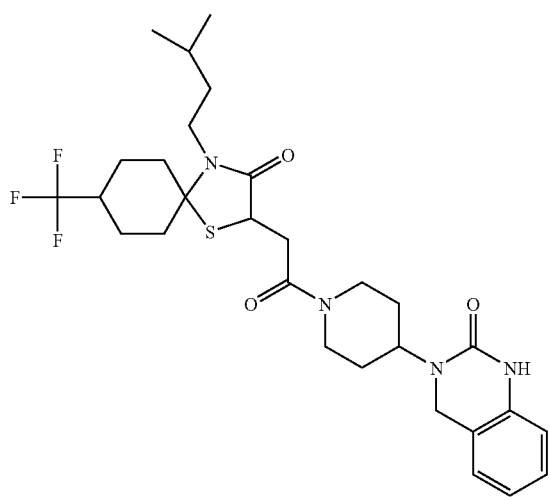

-continued
254
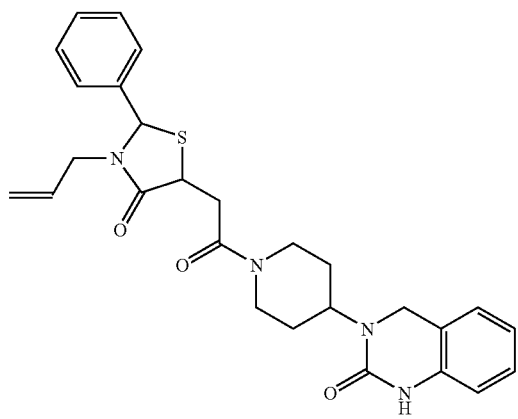
255
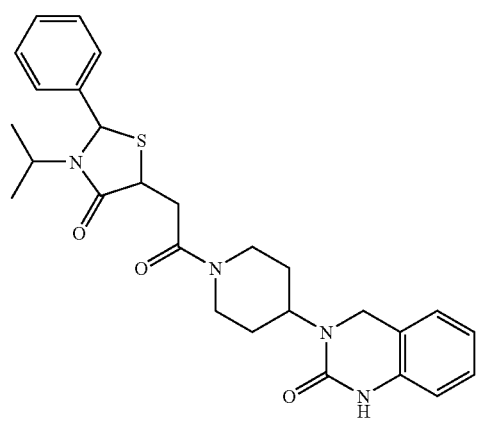
256
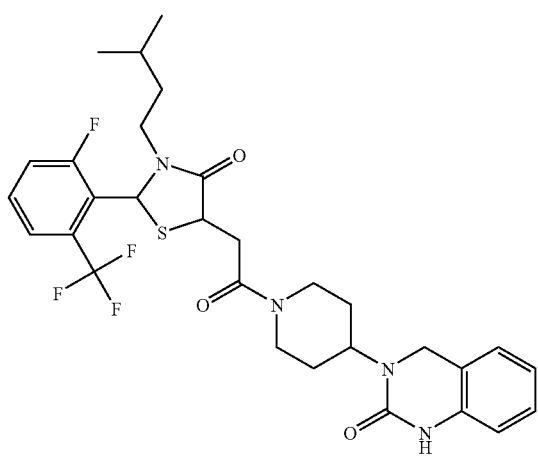

-continued
257
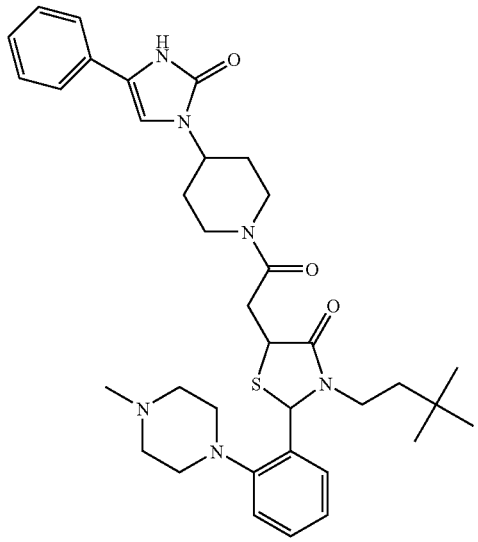
258
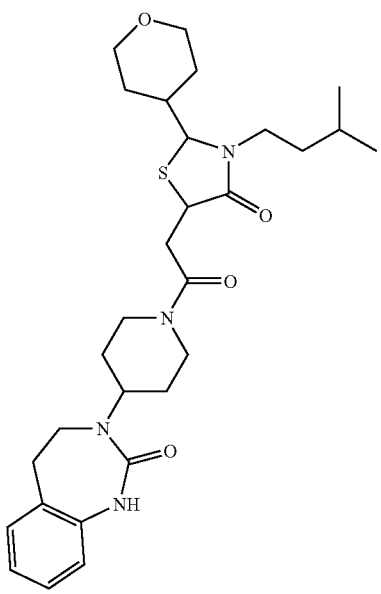
259
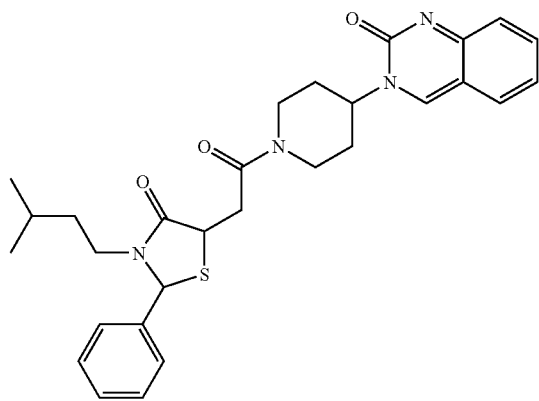

-continued
260
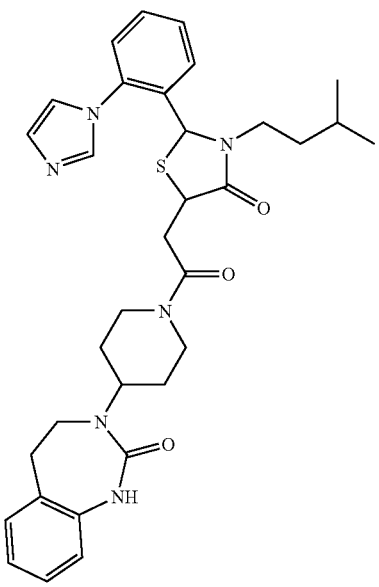
261
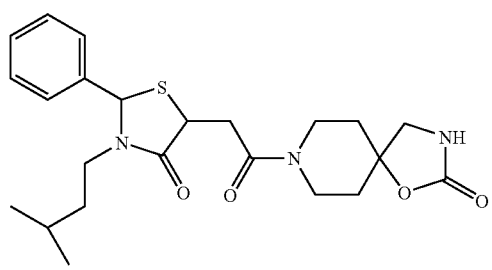
262
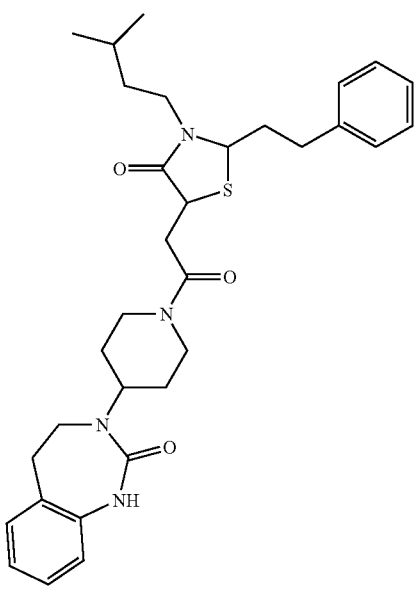

263
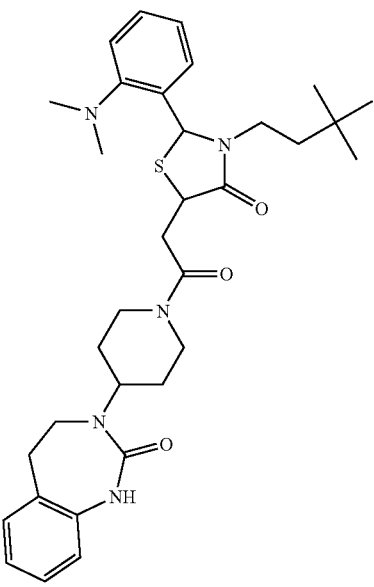
264
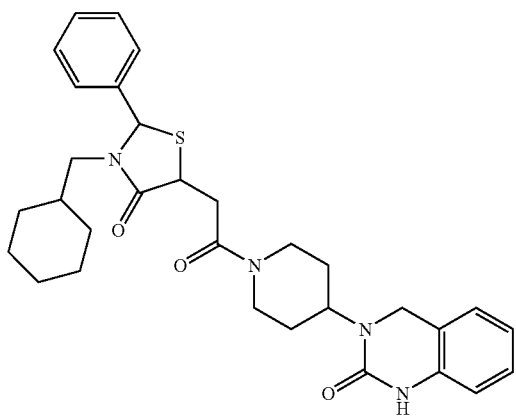
265
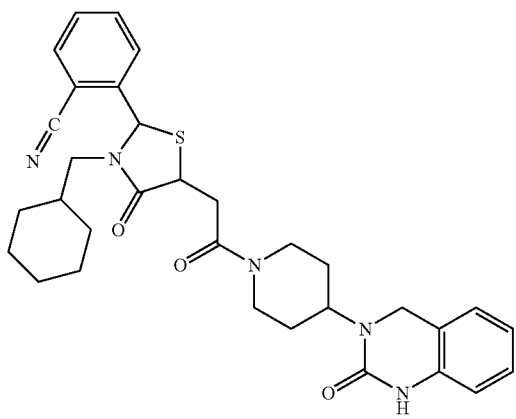

266
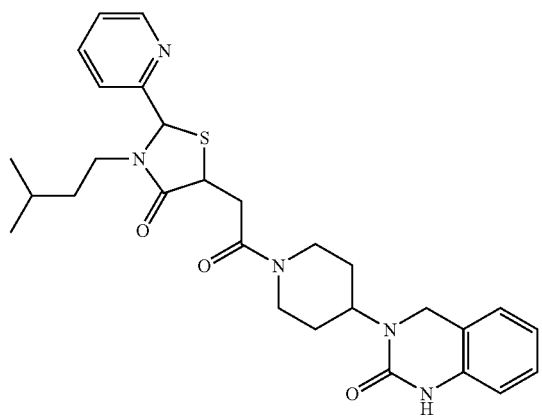
267
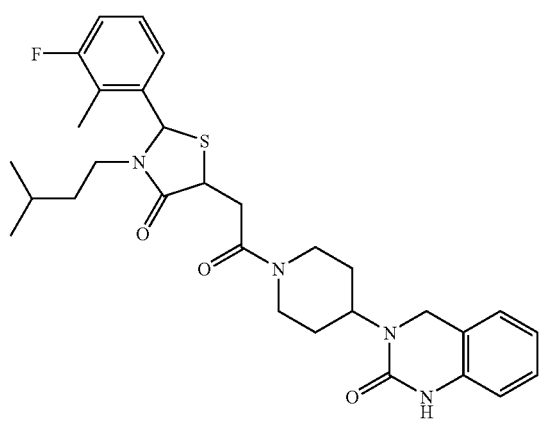
268
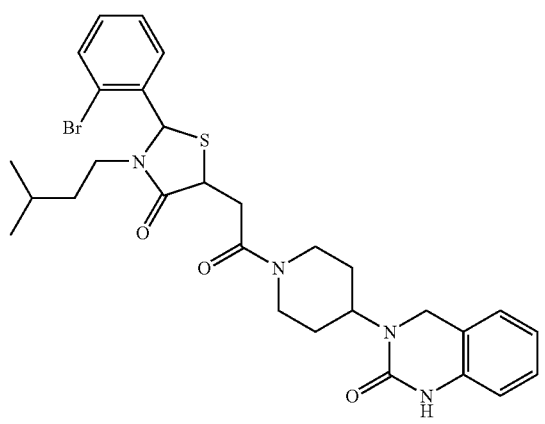

-continued
269
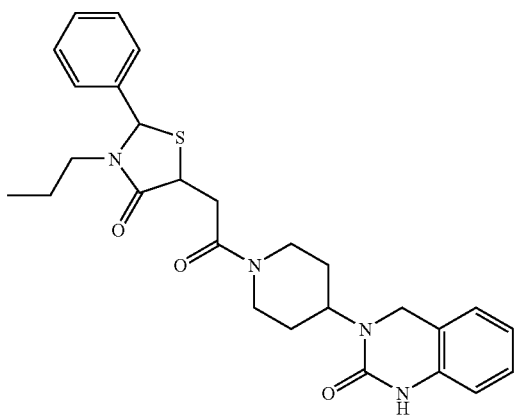
270
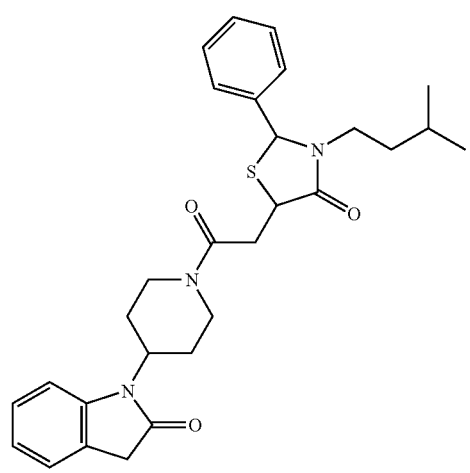
271
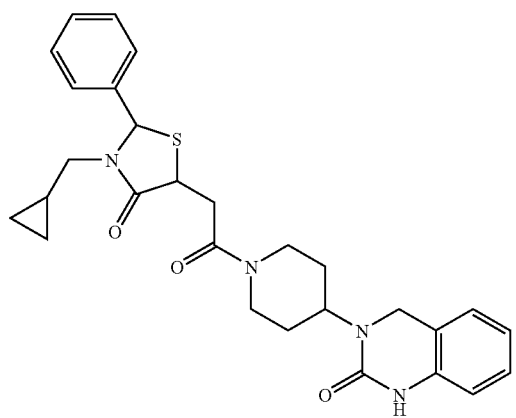

272
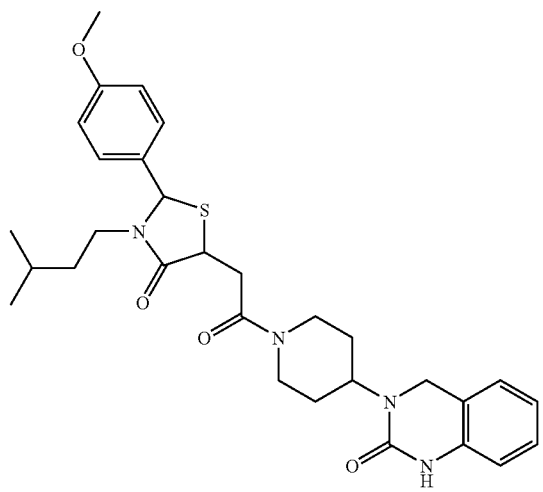
273
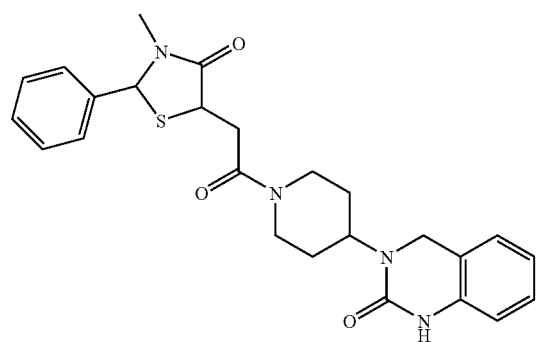
274
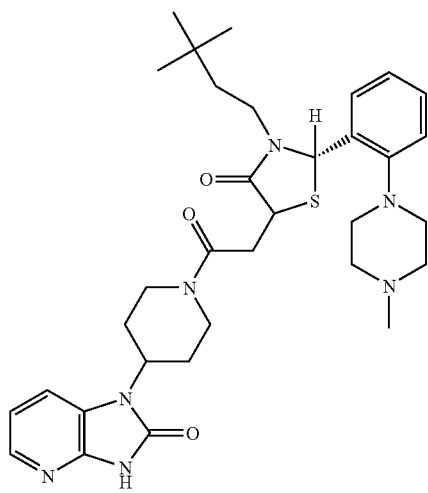

275
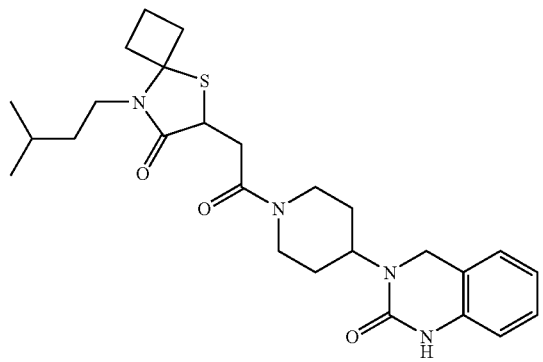
276
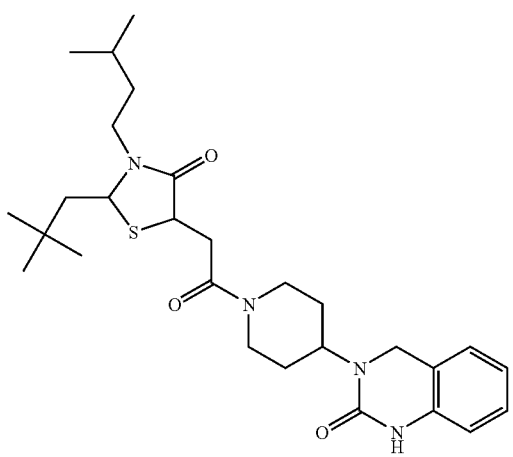
277
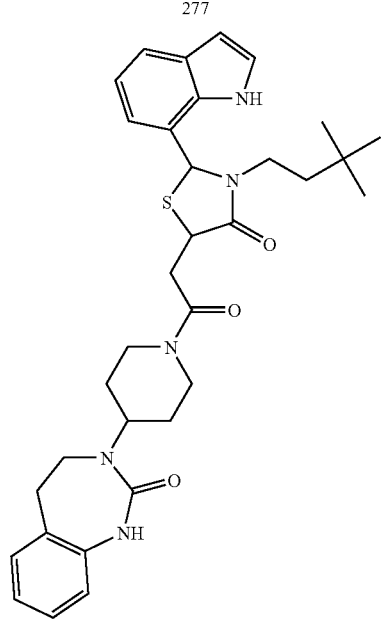

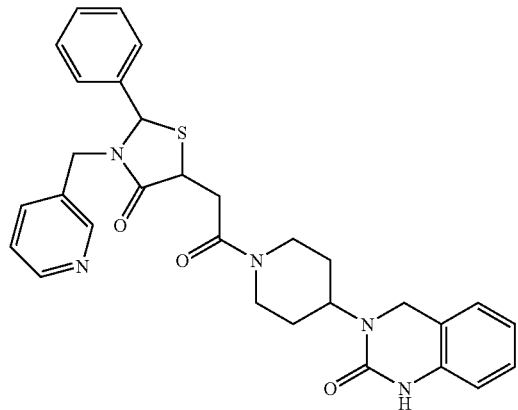
278
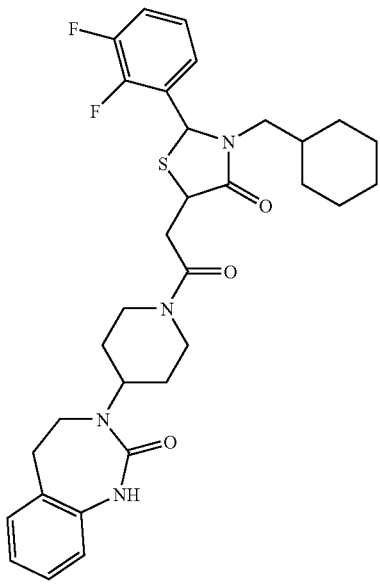
279
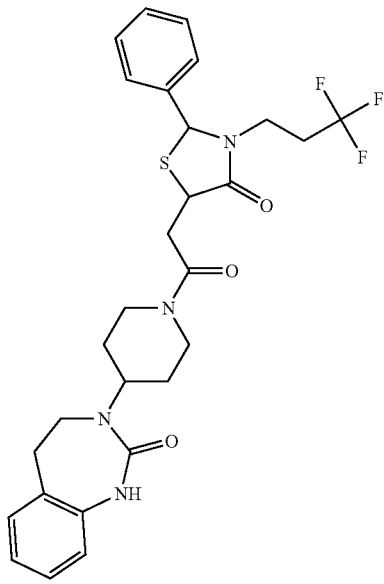
280

281
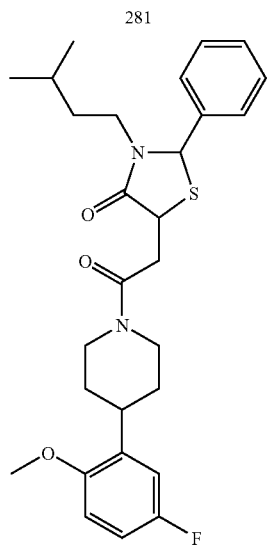
282
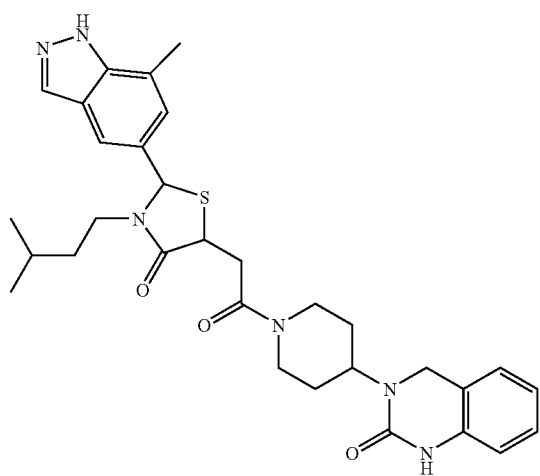
283
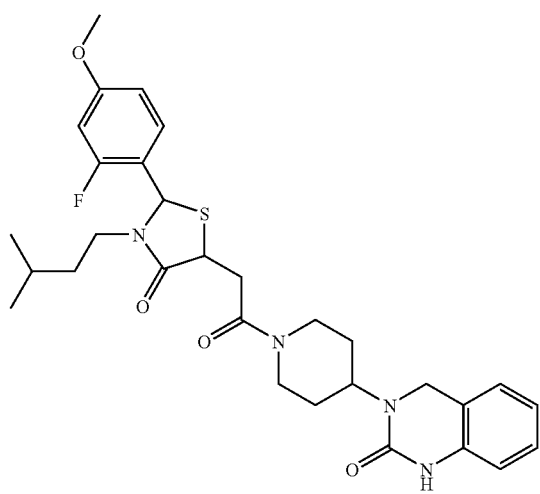

284
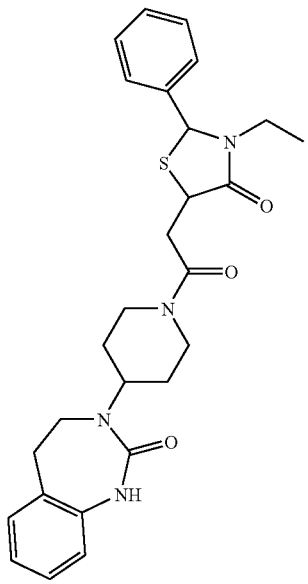
285
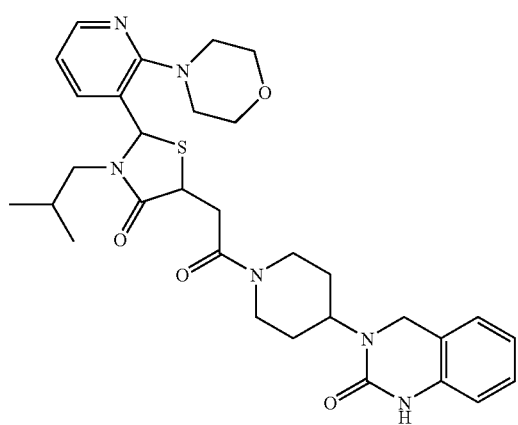

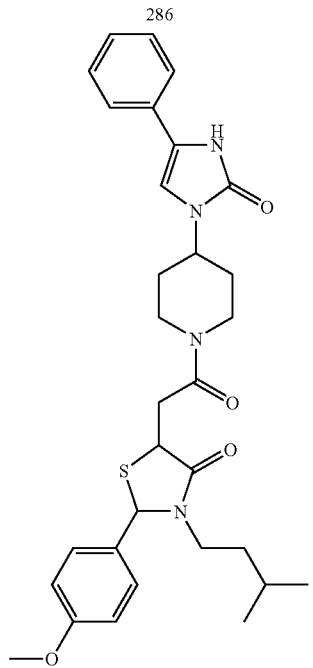
286
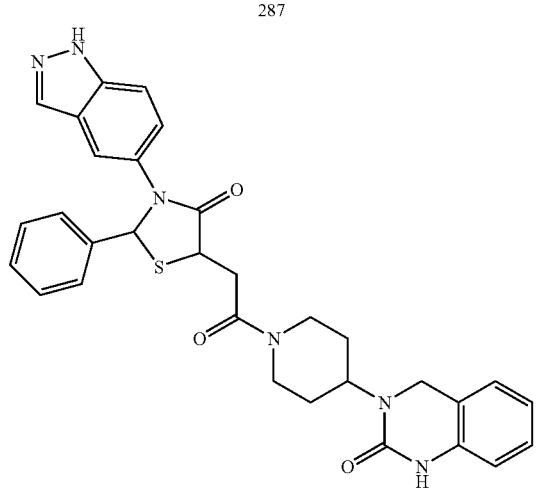
287

TABLE 1A
288
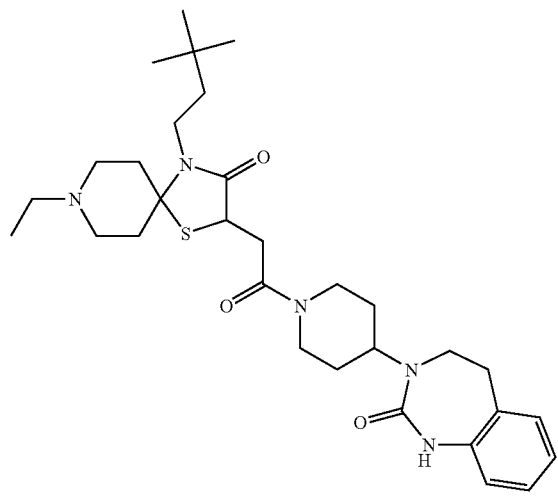
289
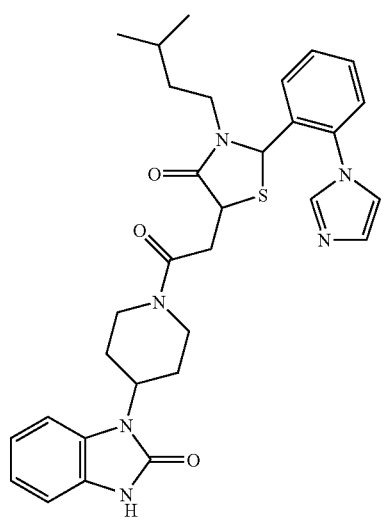
290
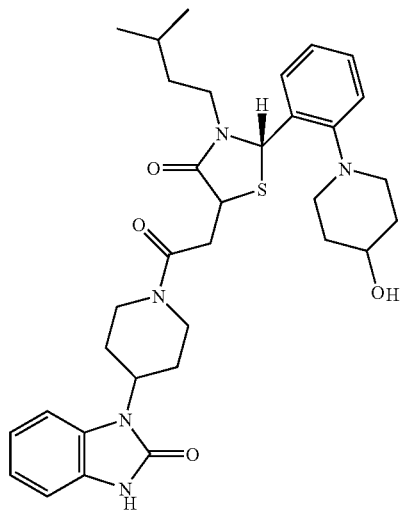
TABLE 1A-continued
291
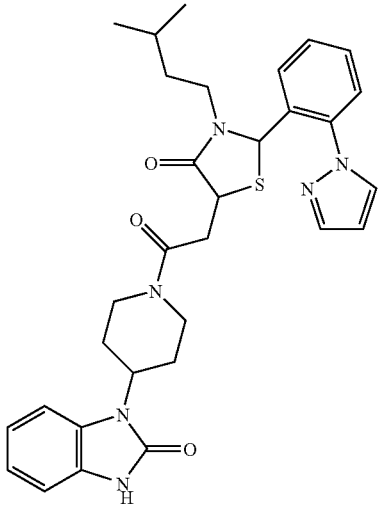
292
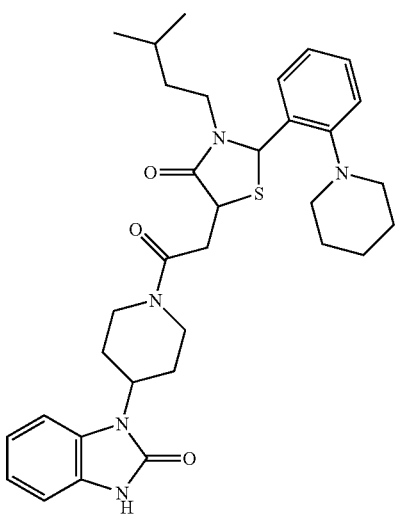
293
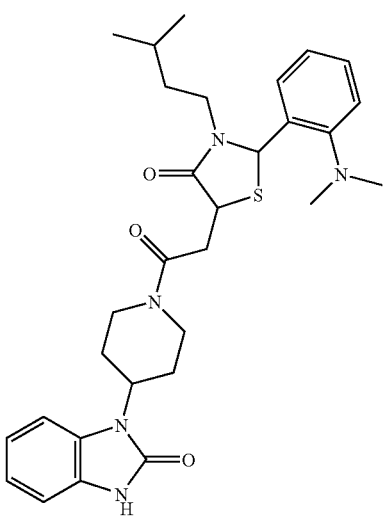

TABLE 1A-continued
294
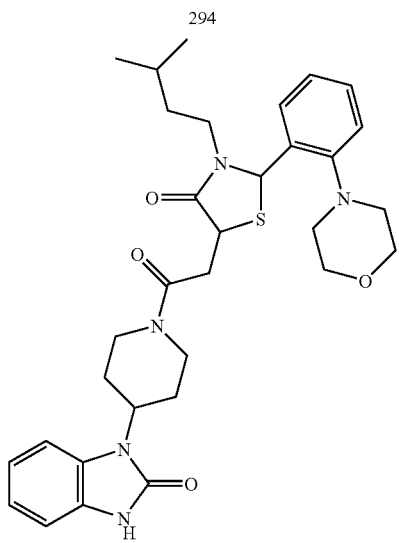
295
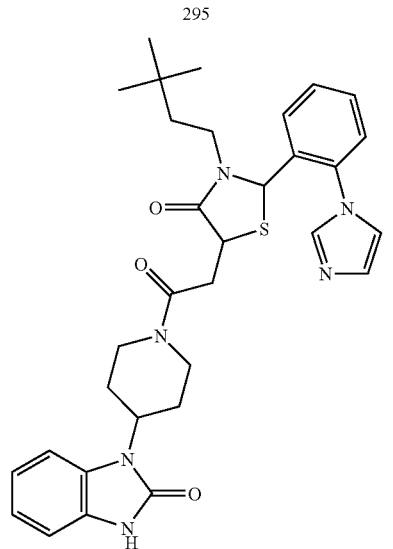
296
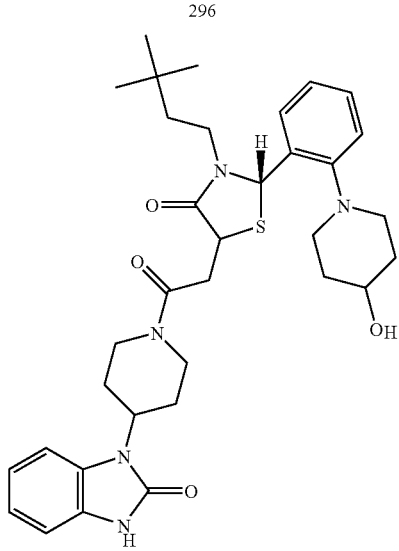
TABLE 1A-continued
297
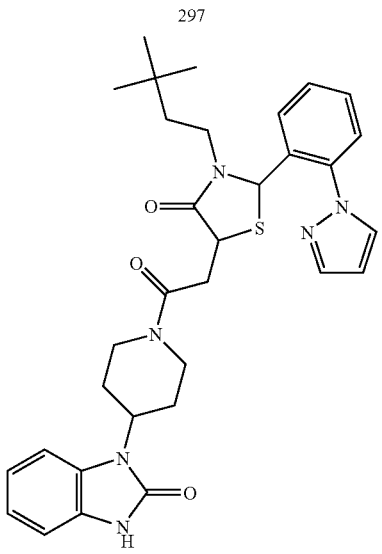
298
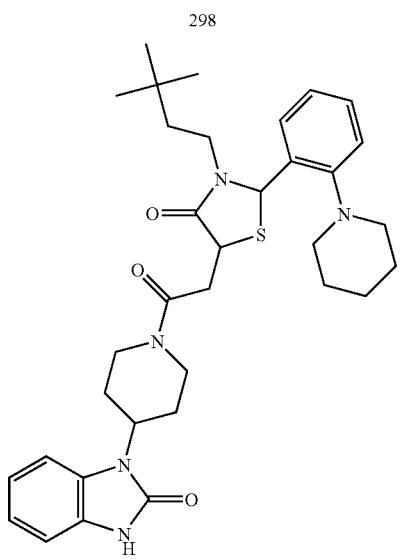
299
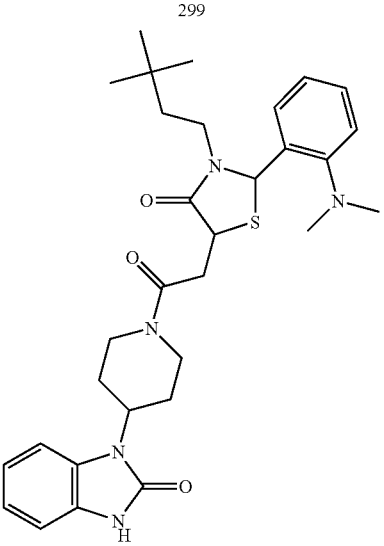

TABLE 1A-continued
300
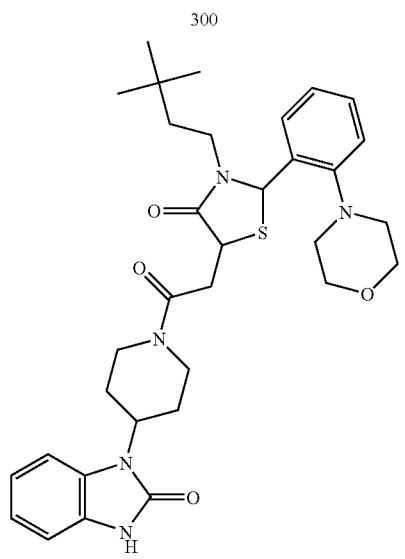
301
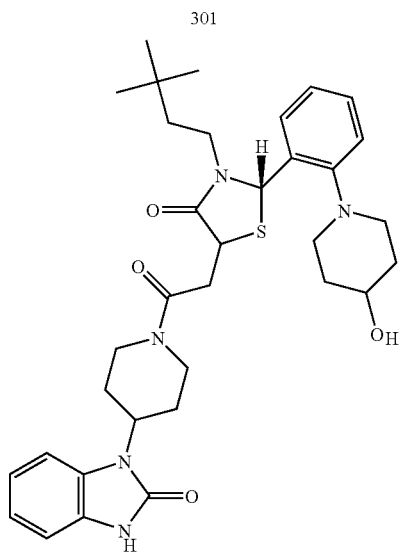
302
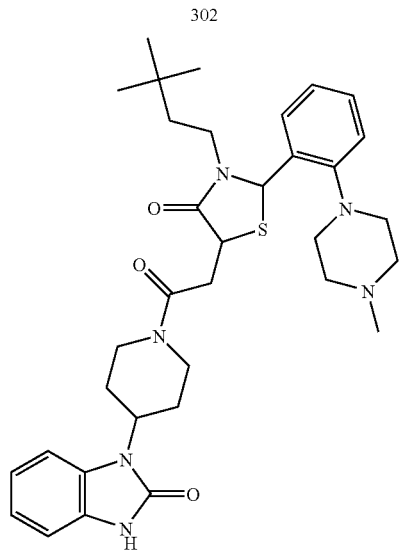
TABLE 1A-continued
303
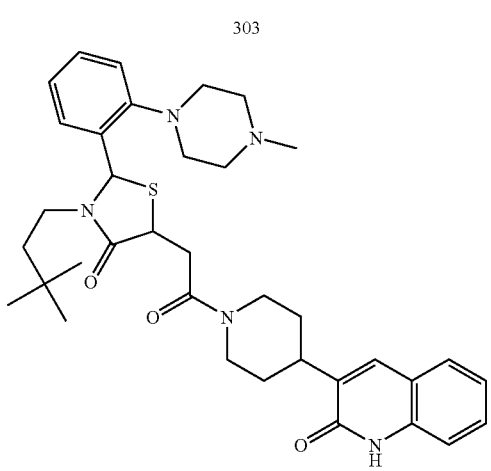
304
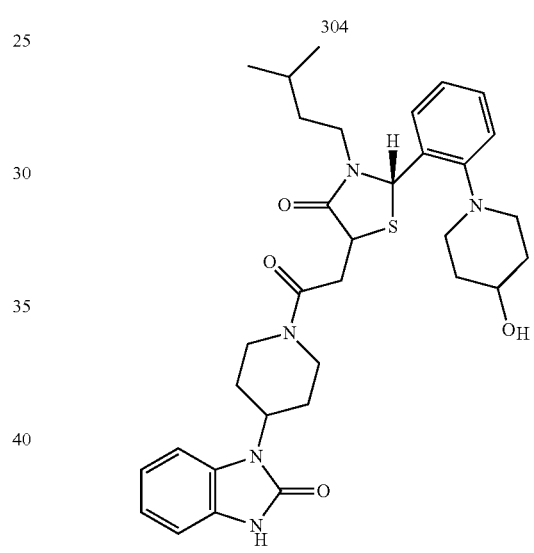
305
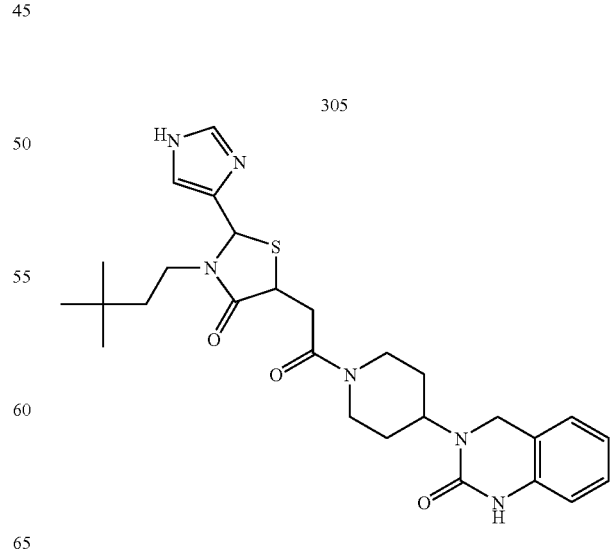

TABLE 1A-continued
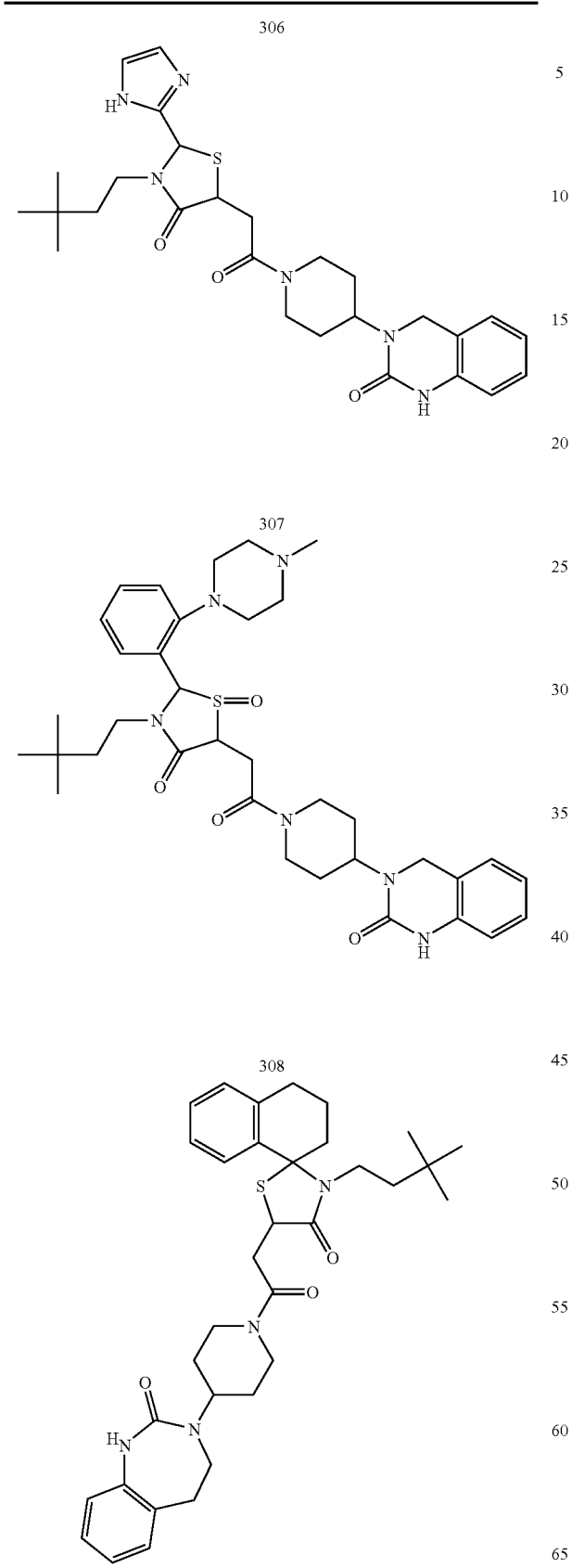
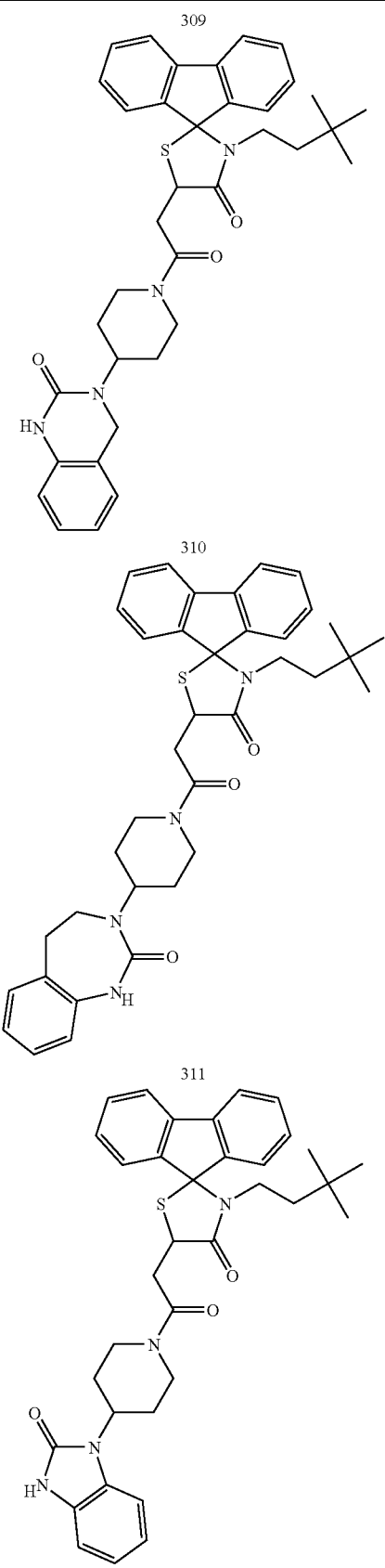

TABLE 1A-continued
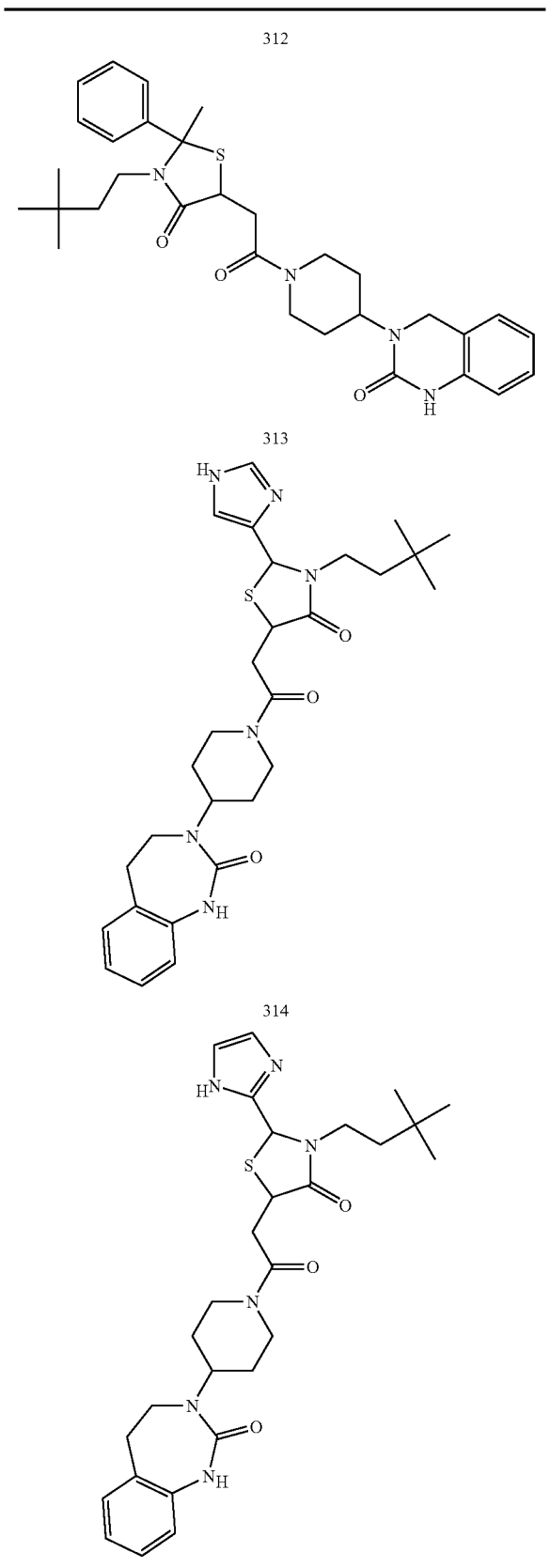
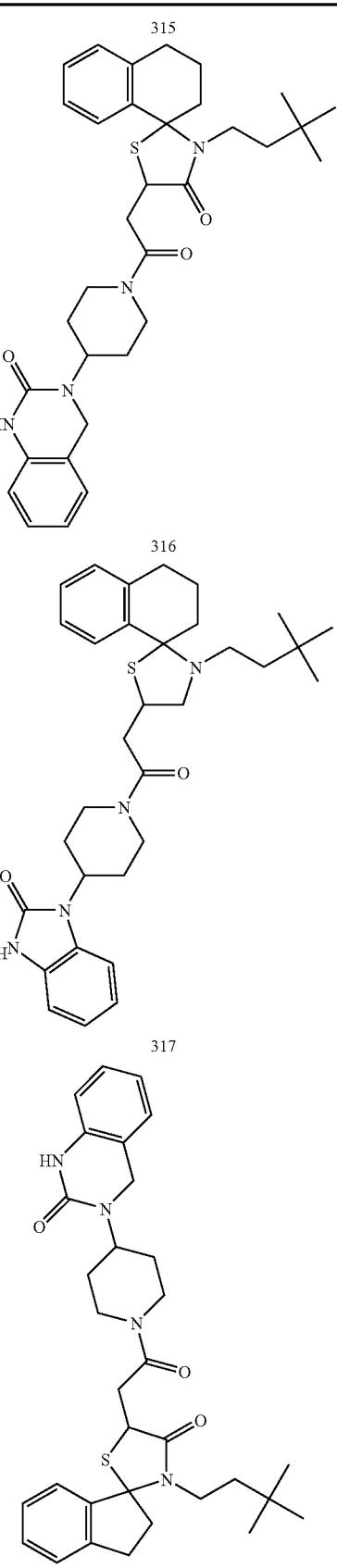

TABLE 1A-continued
318
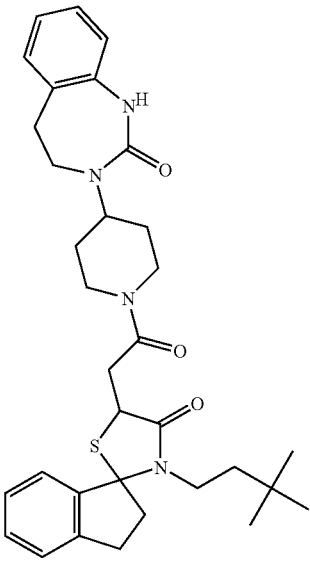
319
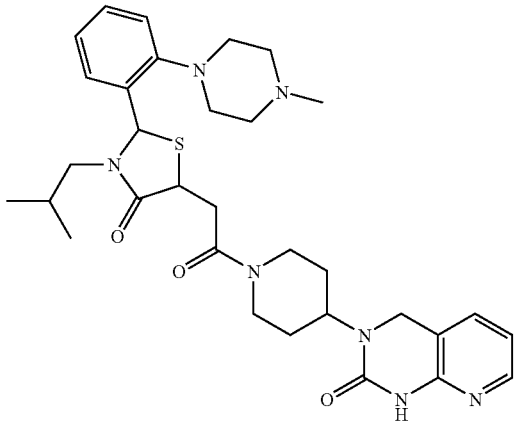
320
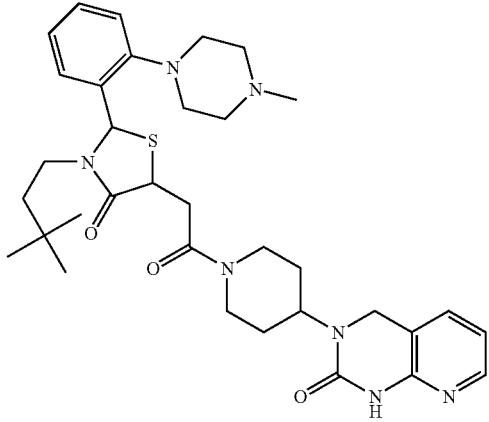
TABLE 1A-continued
321
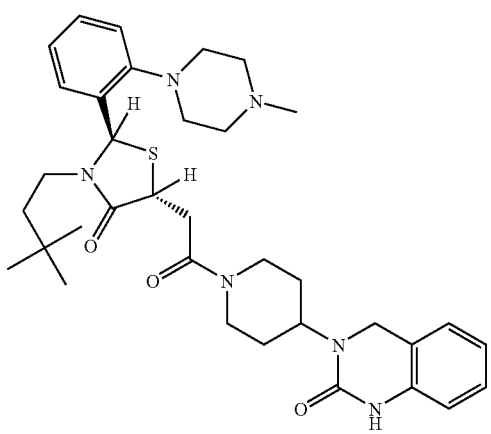
322
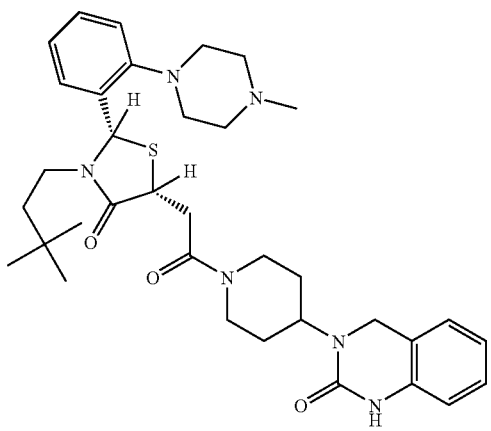
323
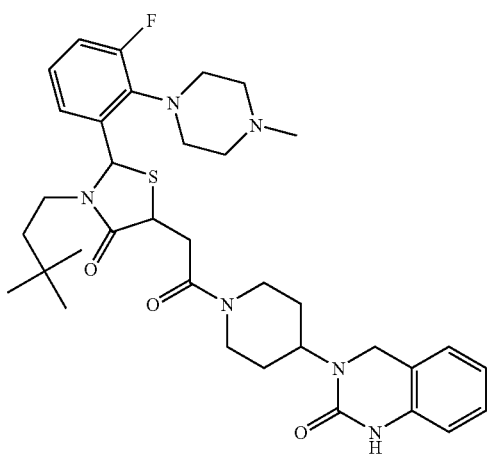

TABLE 1A-continued
324
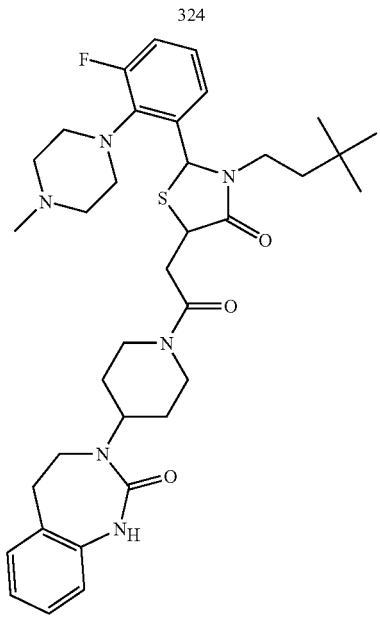
325
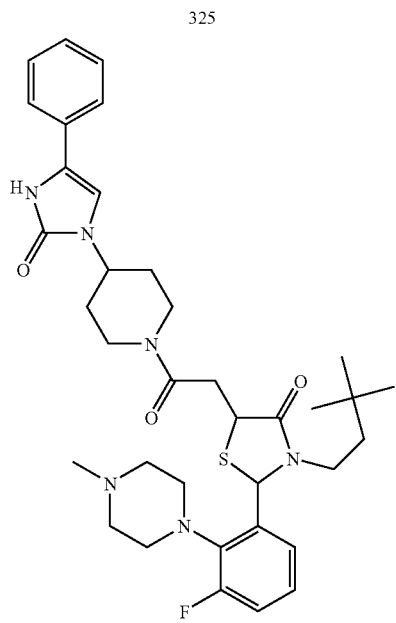
TABLE 1A-continued
326
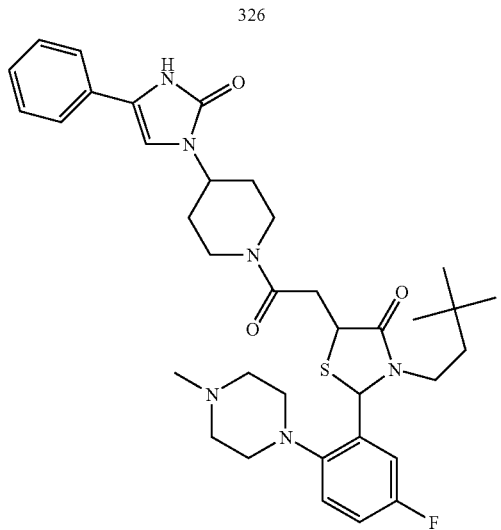
327
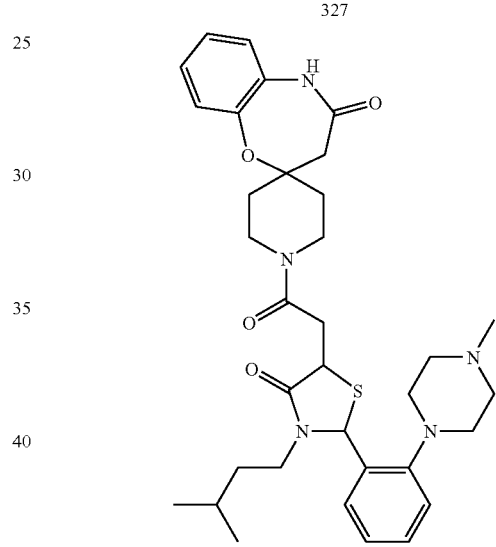
328
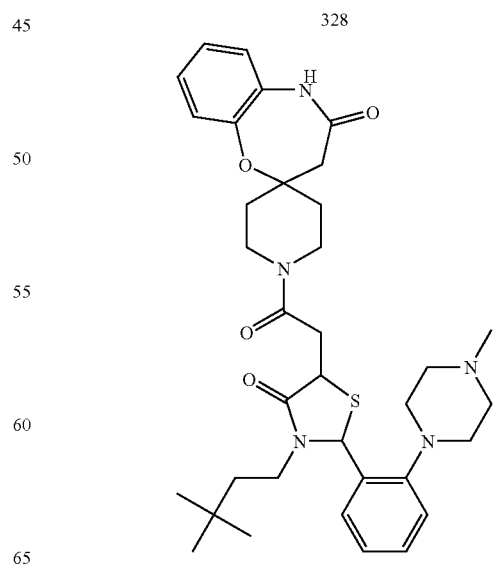

TABLE 1A-continued
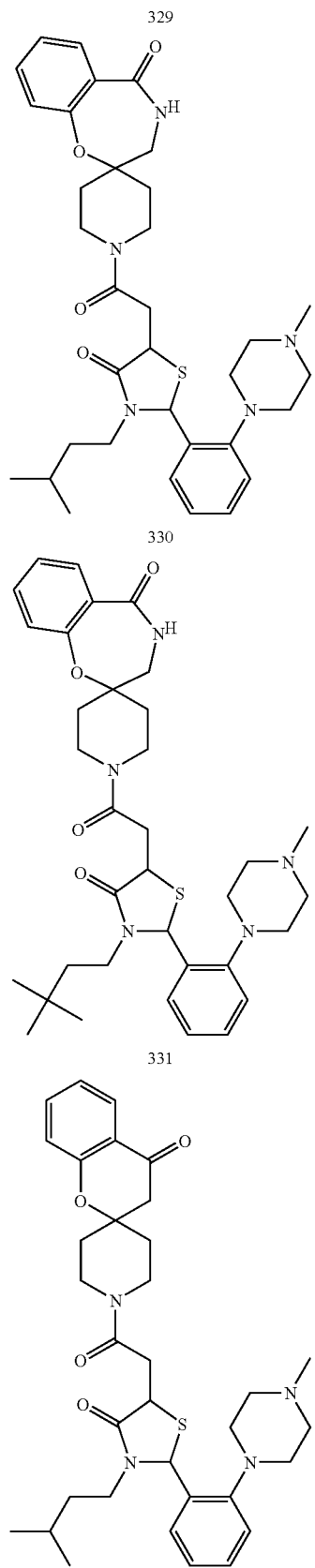
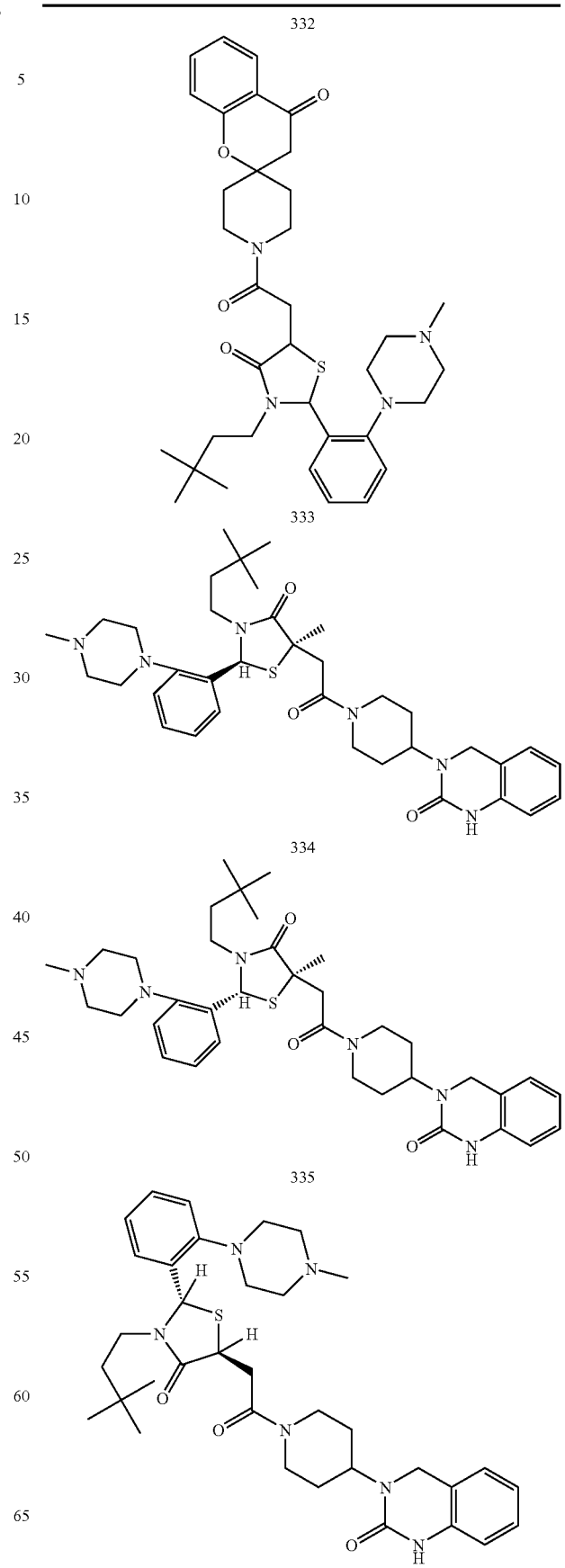

TABLE 1A-continued
336
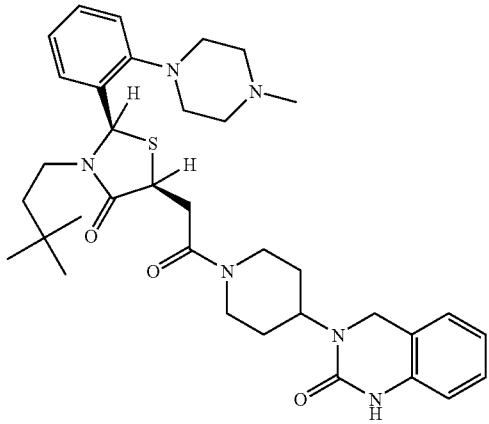
337
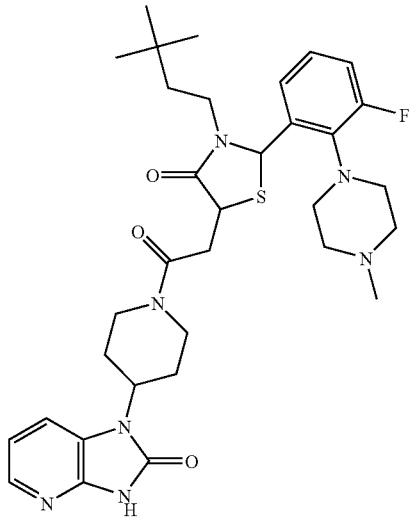
338
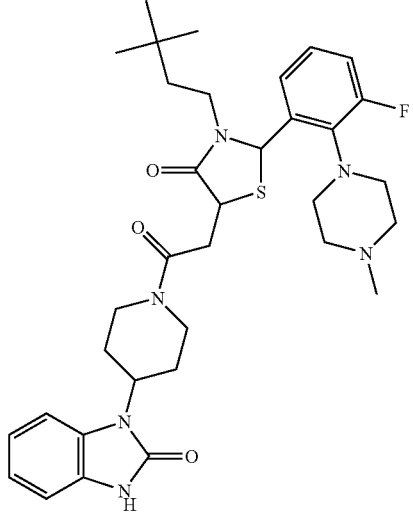
TABLE 1A-continued
339
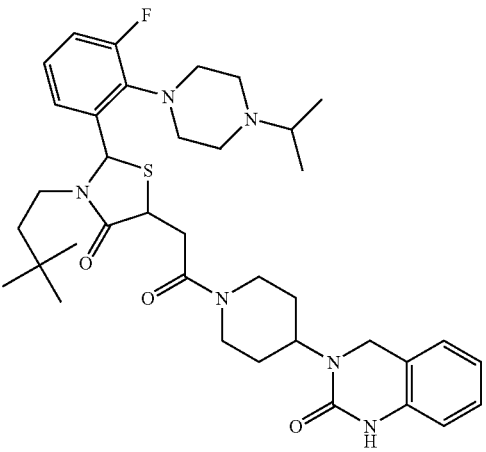
340
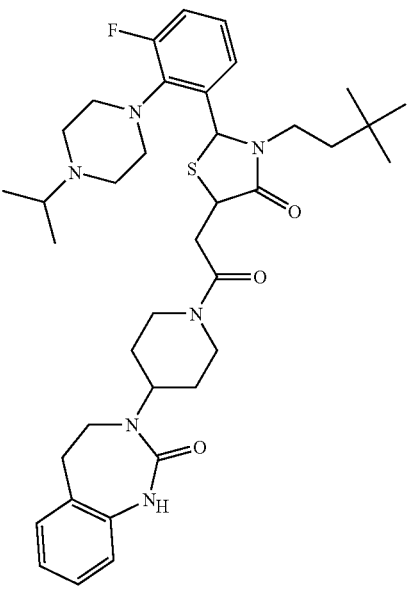
341
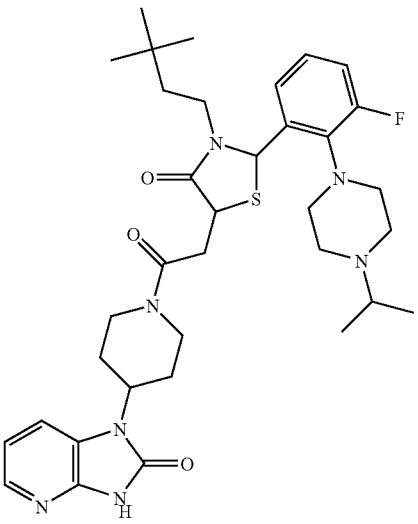

TABLE 1A-continued
342
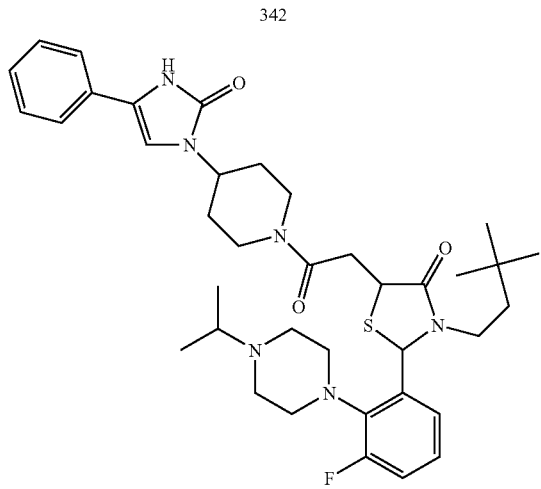
343
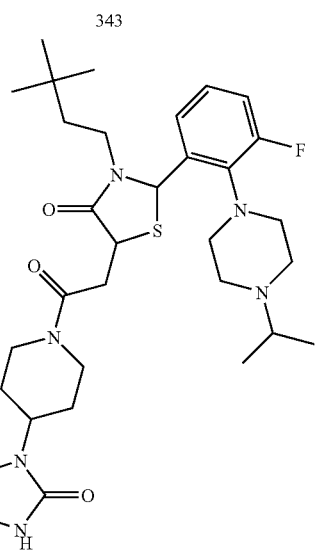
344
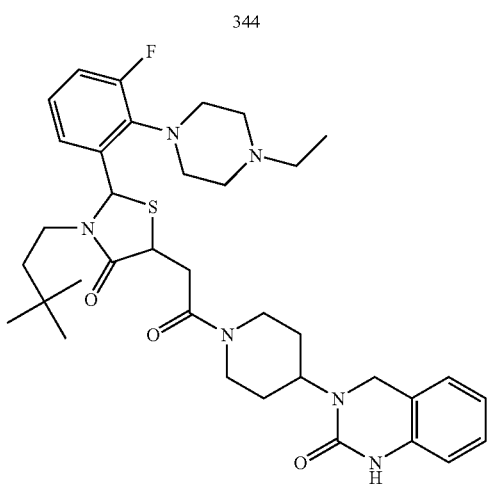
TABLE 1A-continued
345
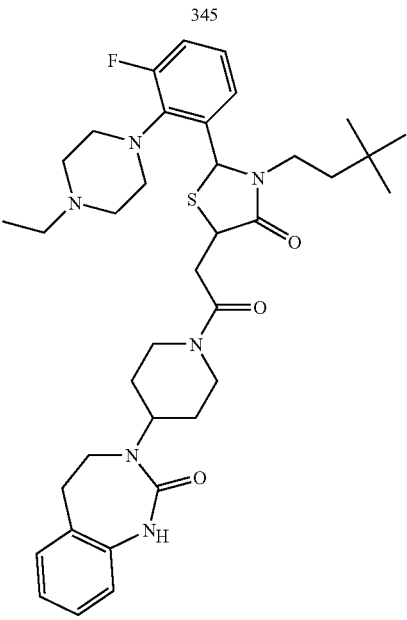
346
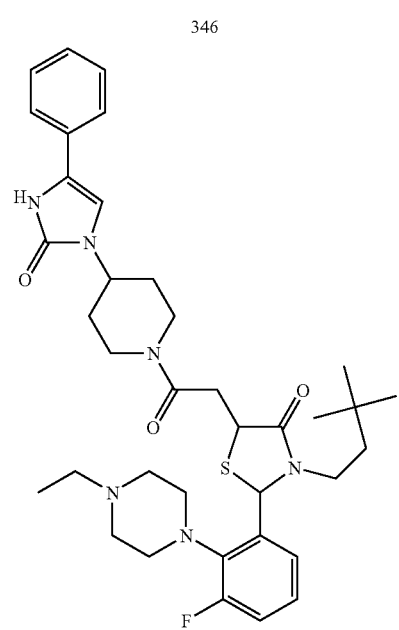

TABLE 1A-continued
347
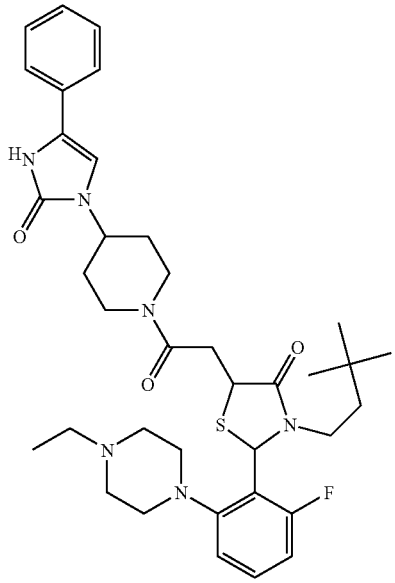
348
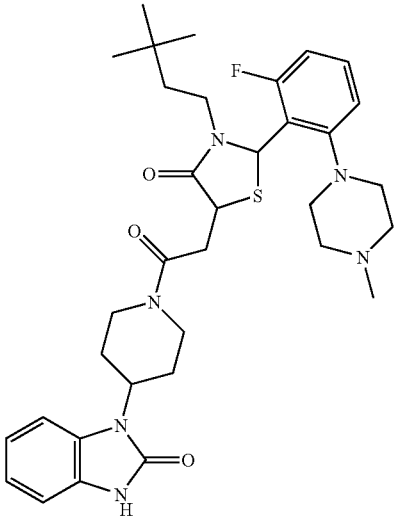
349
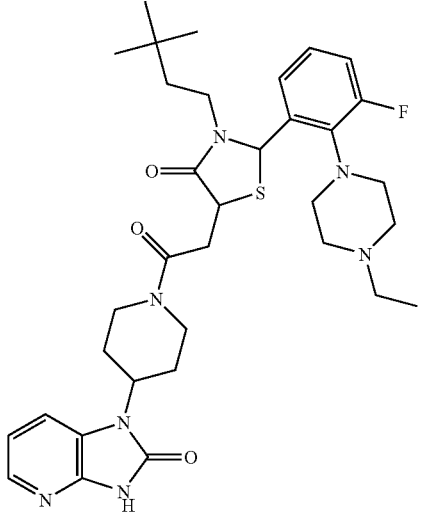
TABLE 1A-continued
350
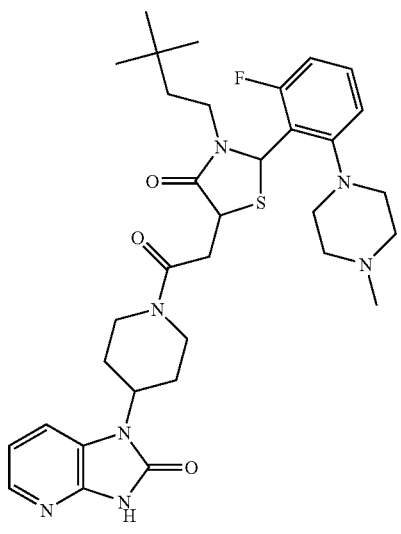
351
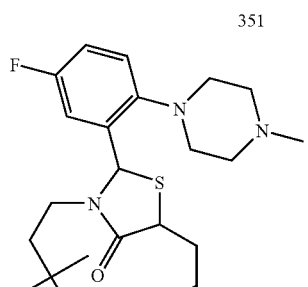
352
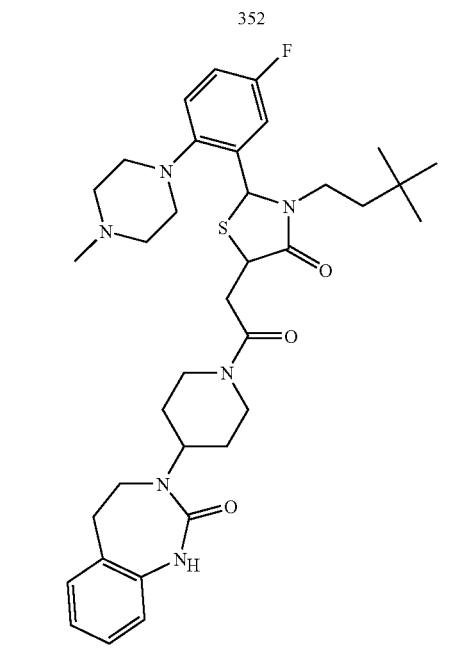

TABLE 1A-continued
353
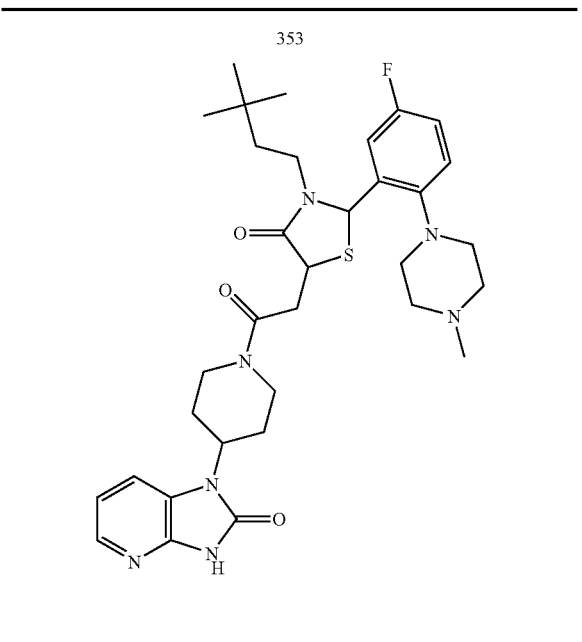
354
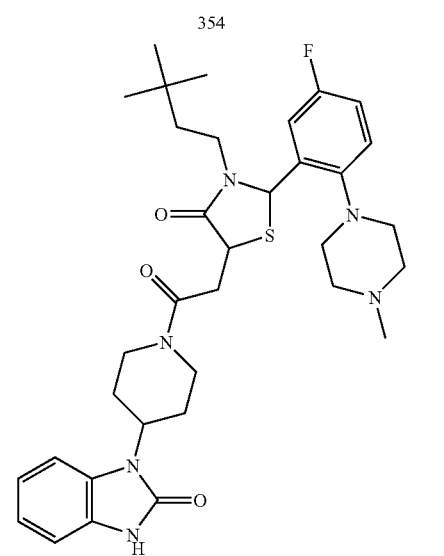
355
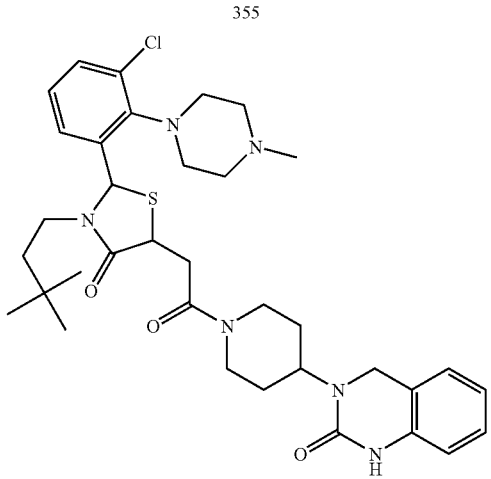
TABLE 1A-continued
356
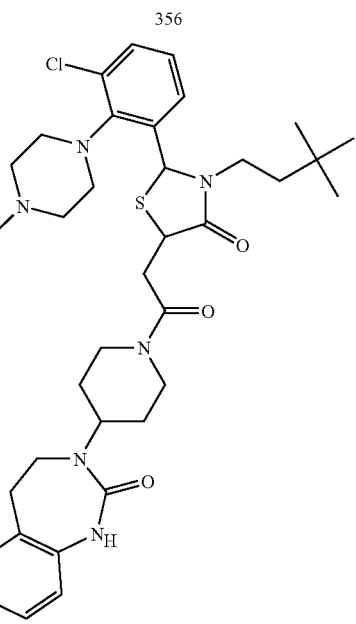
357
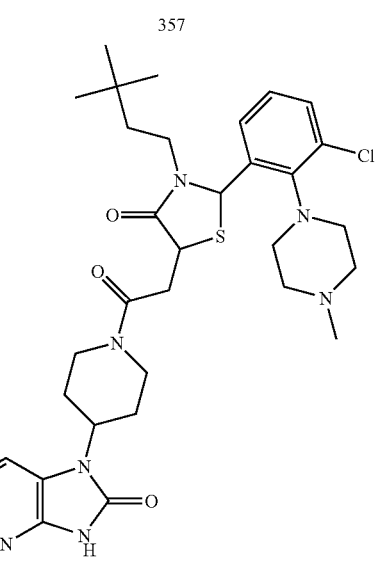

TABLE 1A-continued
358
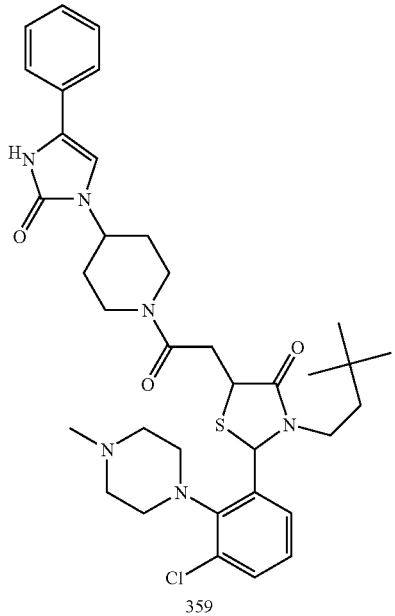
359
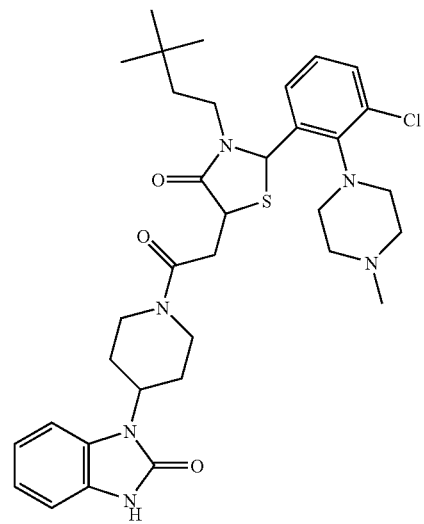
360
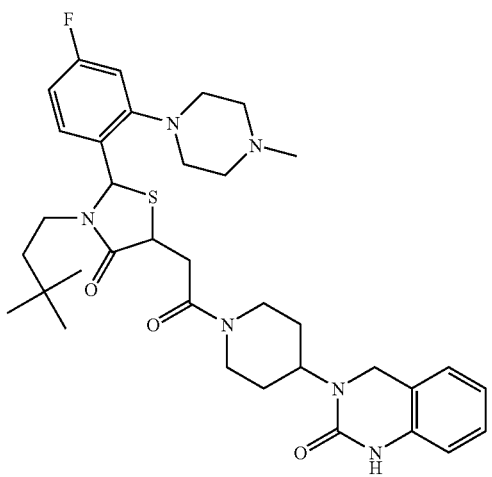
TABLE 1A-continued
361
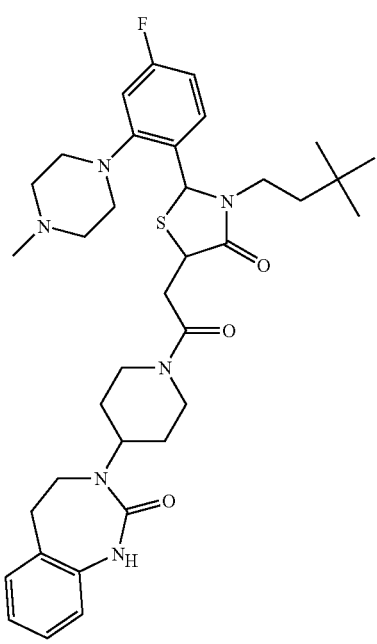
362
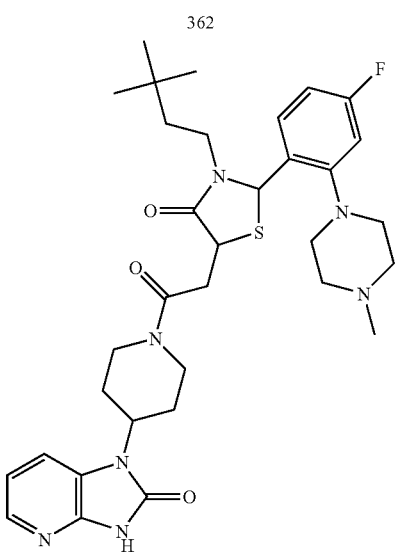

TABLE 1A-continued
363
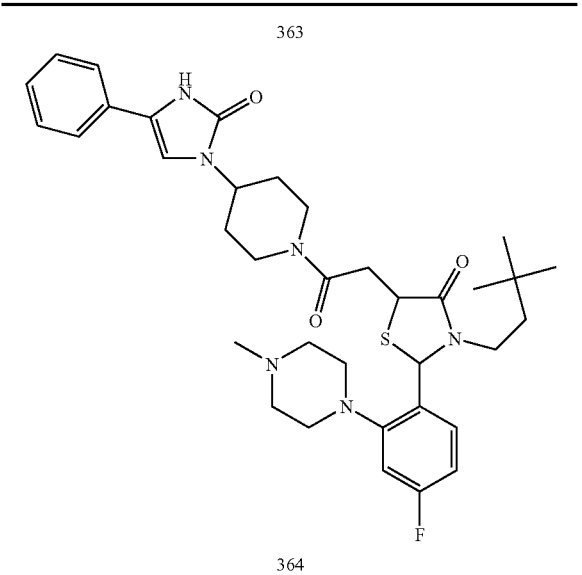
364
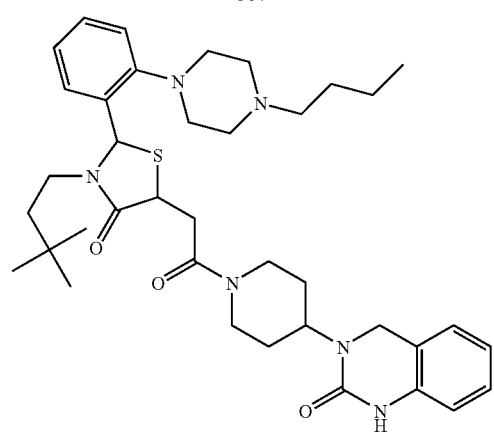
365
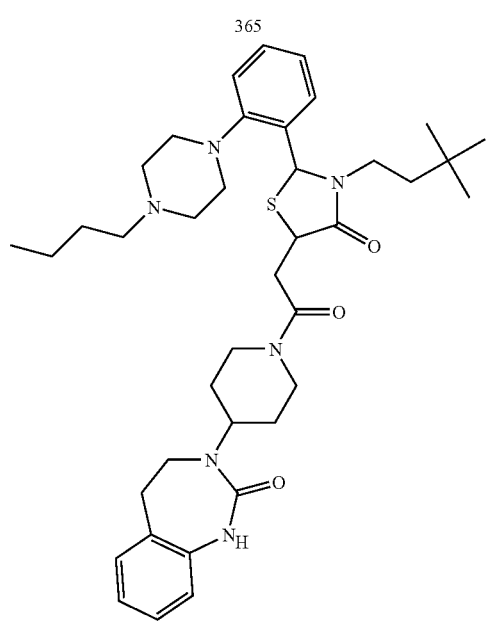
TABLE 1A-continued
366
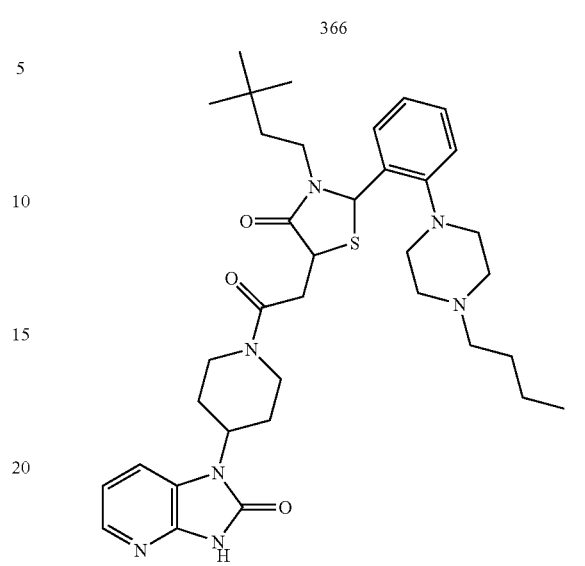
367
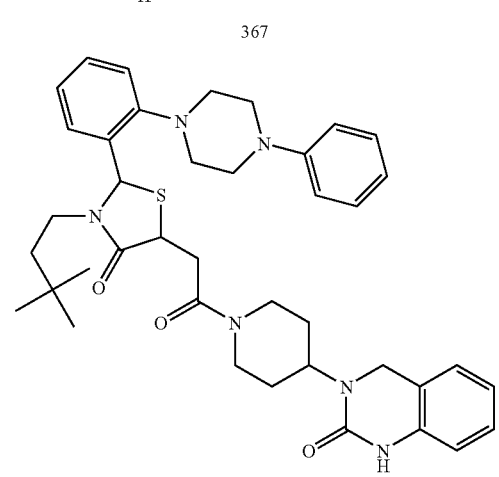
368
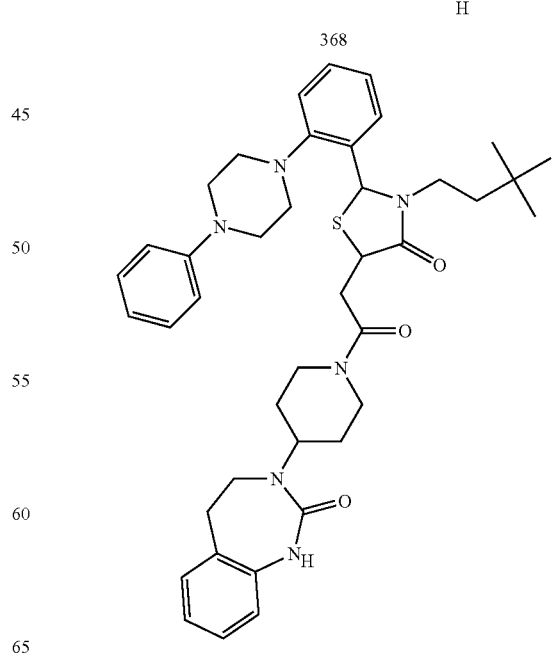

TABLE 1A-continued
369
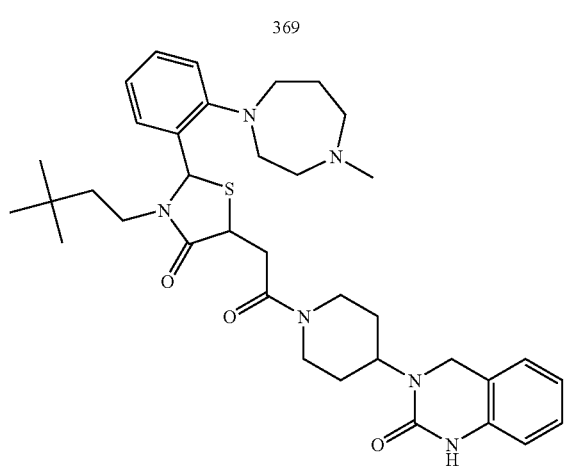
370
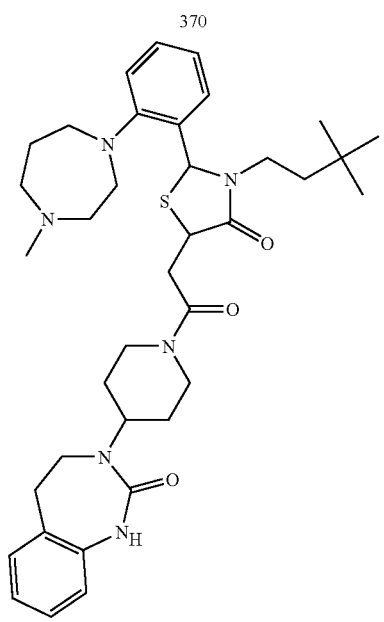
371
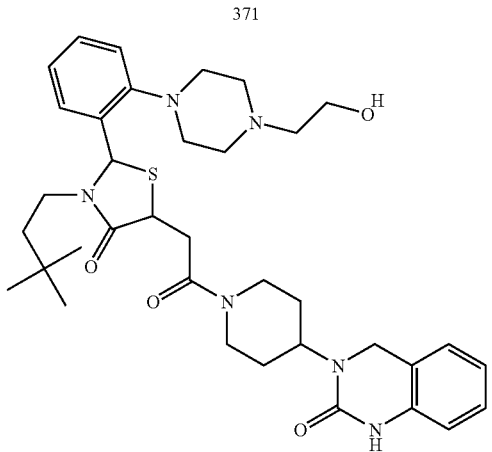
TABLE 1A-continued
372
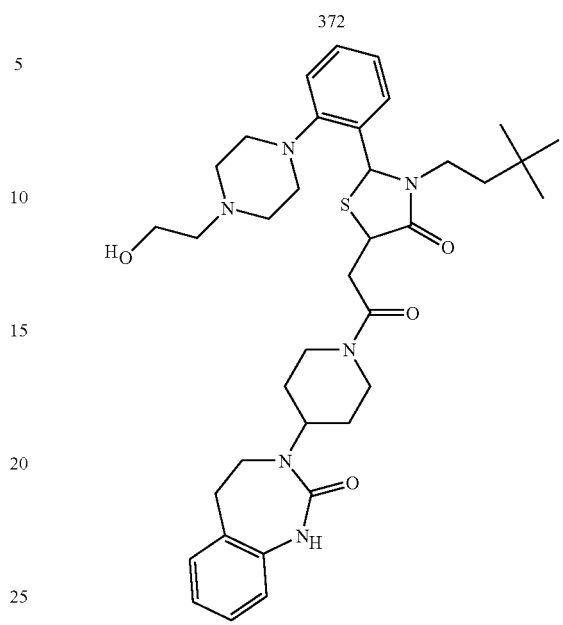
373
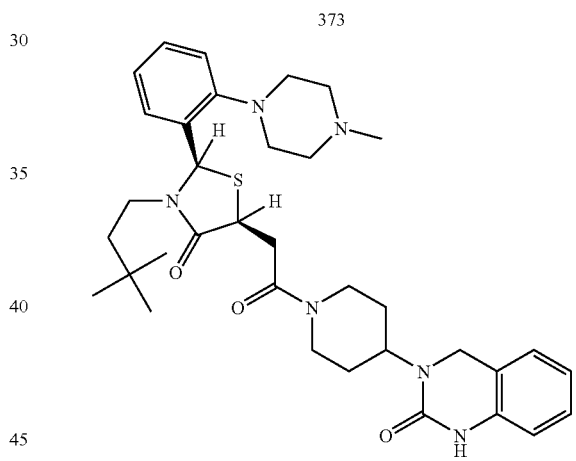
374
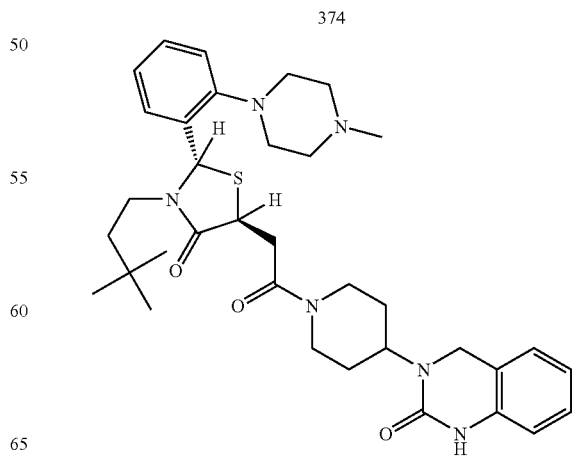

TABLE 1A-continued
375
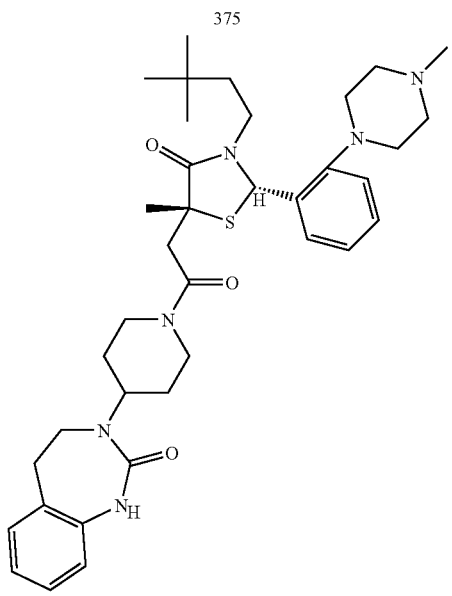
377
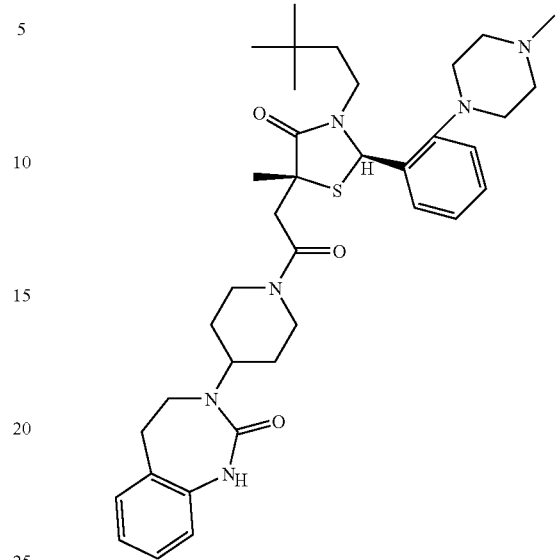
376
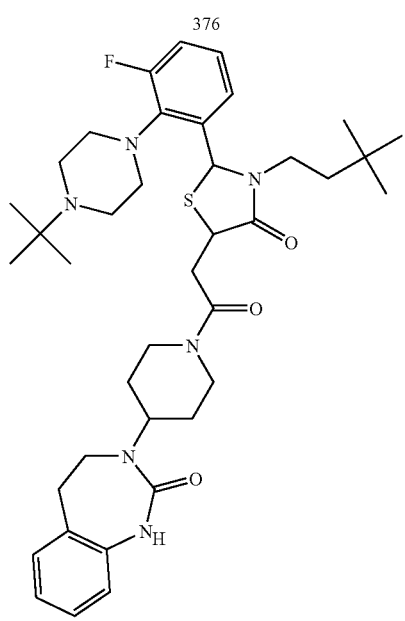
378
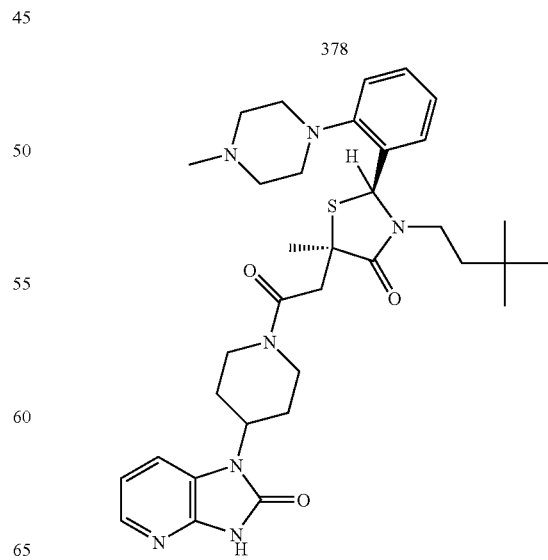

TABLE 1A-continued
379
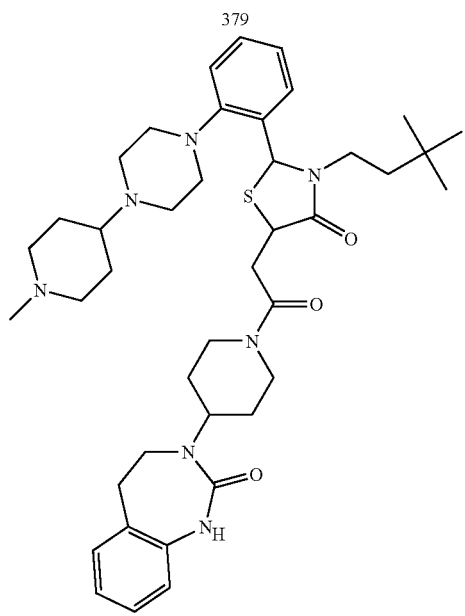
380
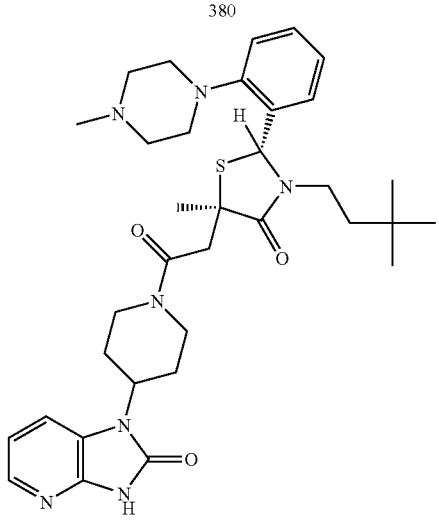
381
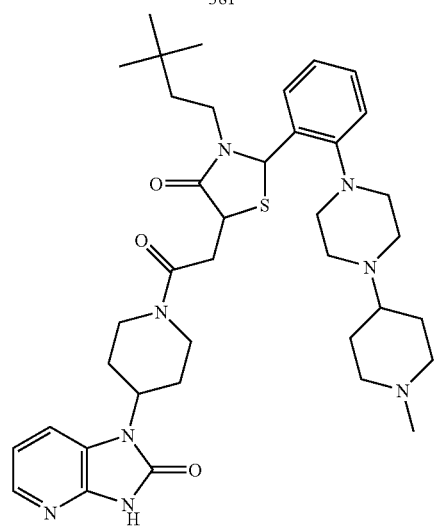
TABLE 1A-continued
382
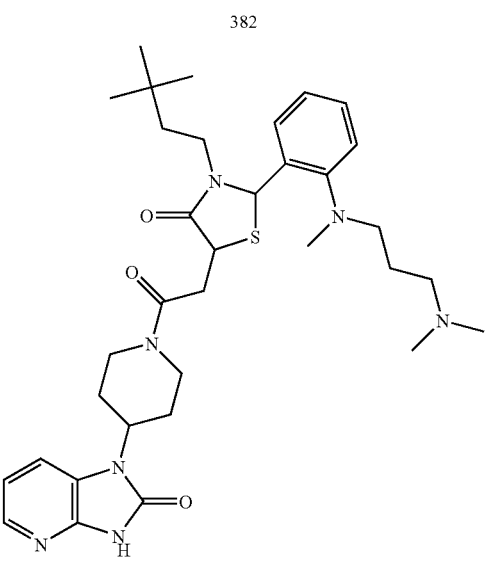
383
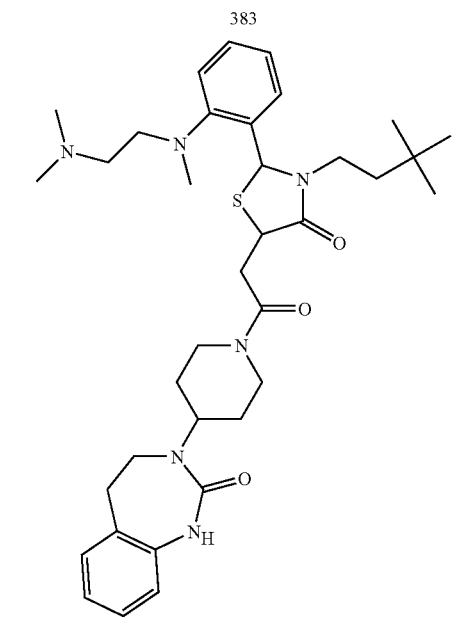

TABLE 1A-continued
384
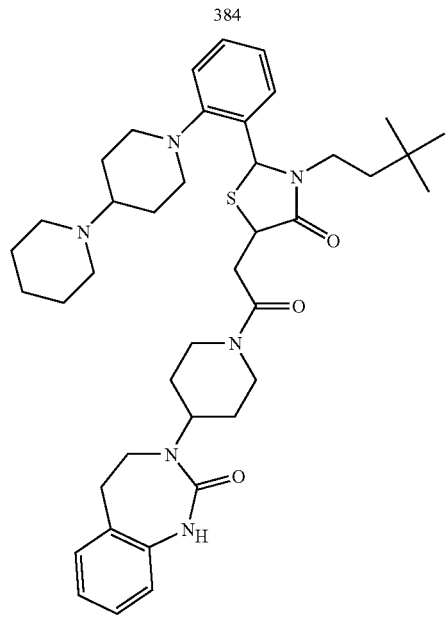
385
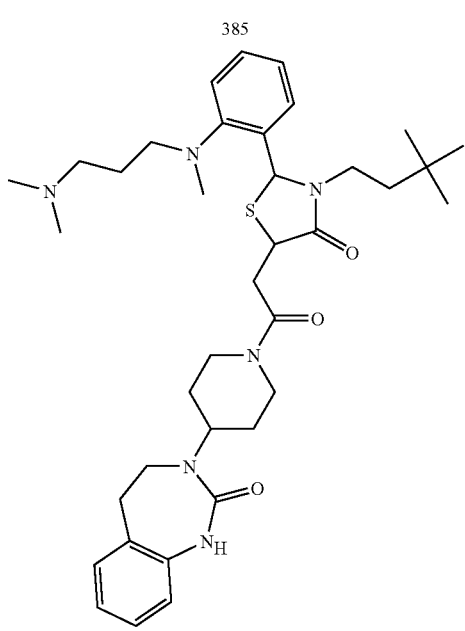
TABLE 1A-continued
386
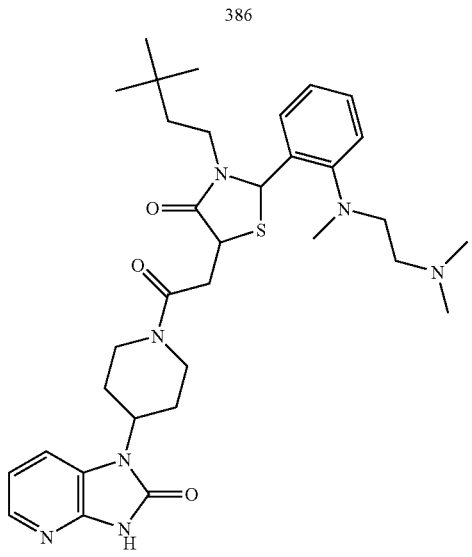
387
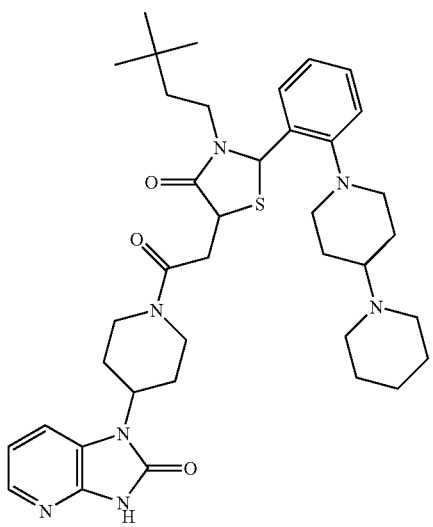

TABLE 1A-continued
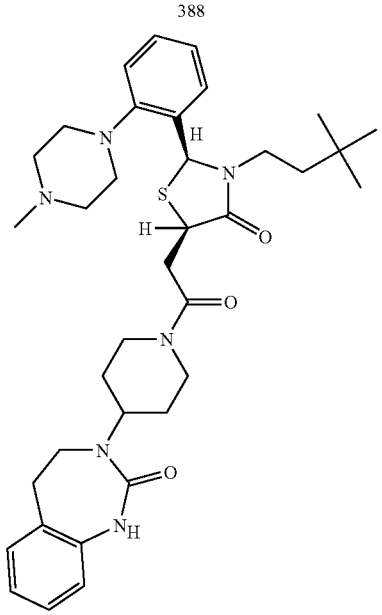
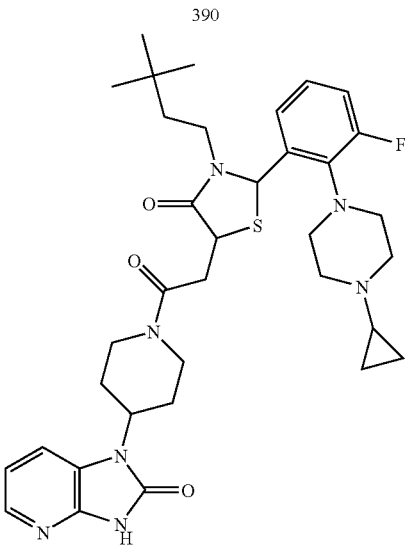
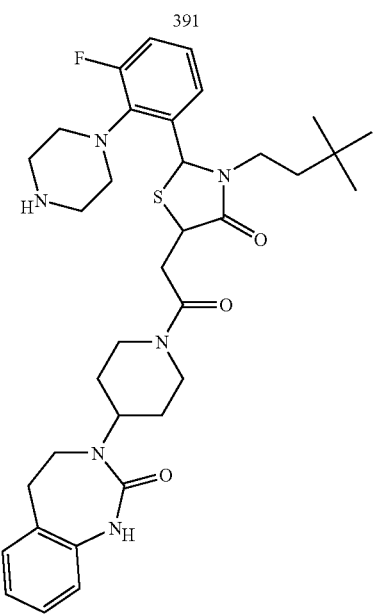

TABLE 1A-continued
392
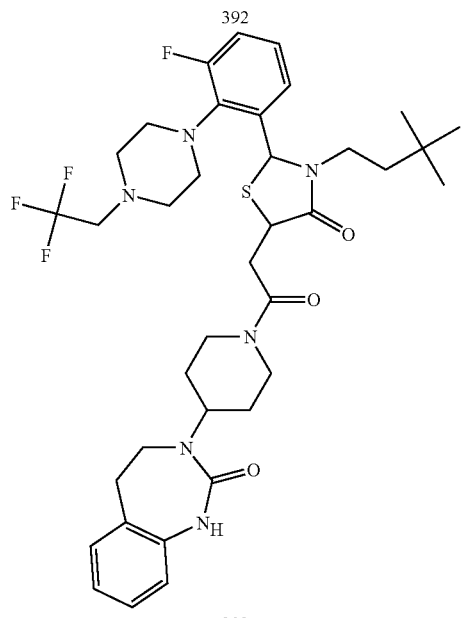
393
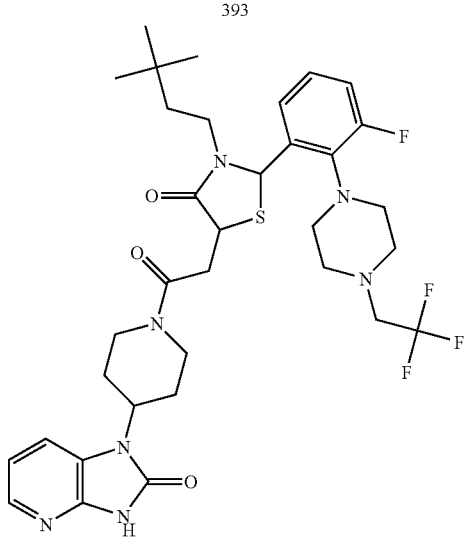
394
TABLE 1A-continued
395
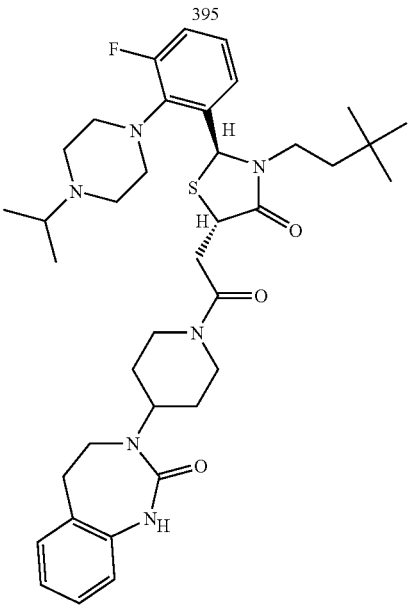
396

TABLE 1A-continued
397
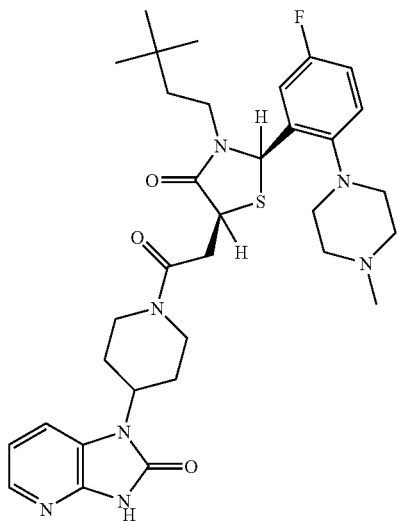
398
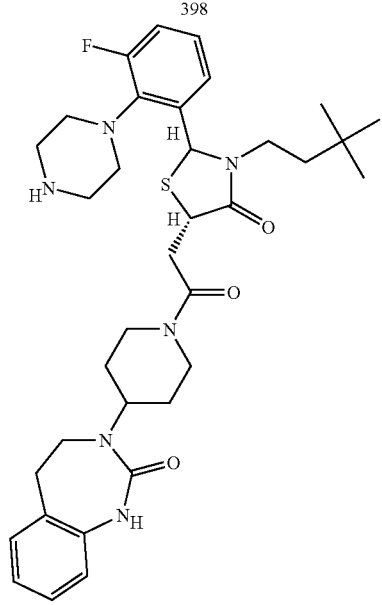
TABLE 1A-continued
399
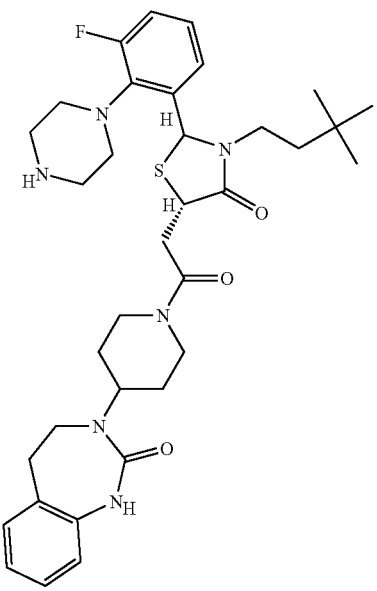
400
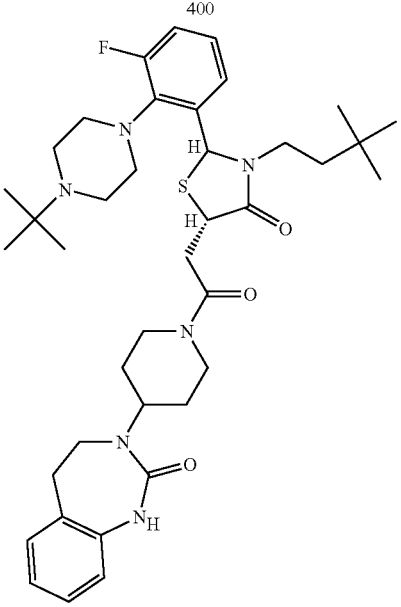

TABLE 1A-continued
401
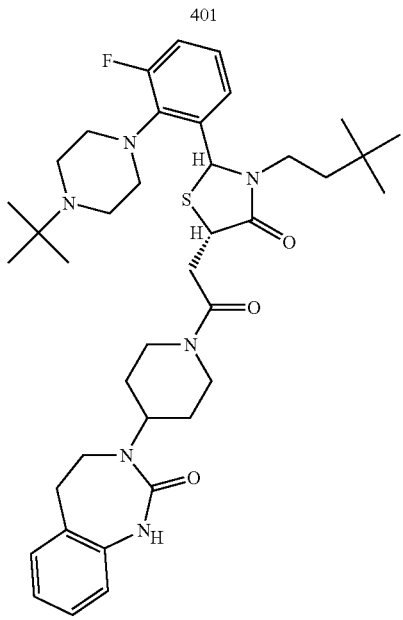
402
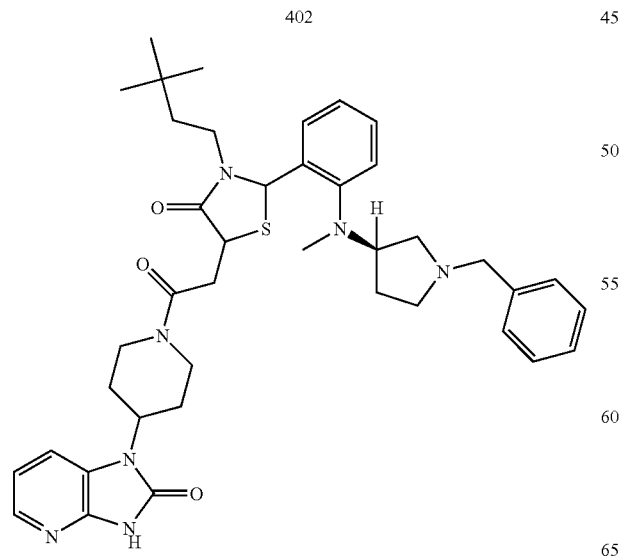
TABLE 1A-continued
403
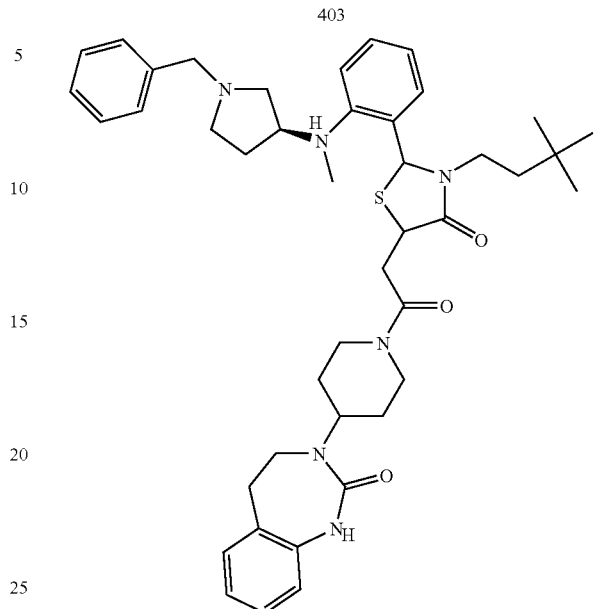
404
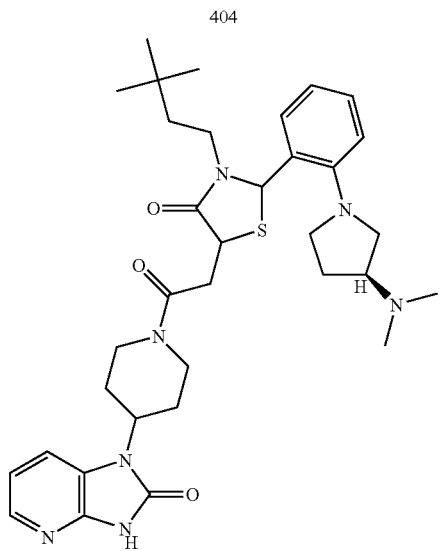

TABLE 1A-continued
405
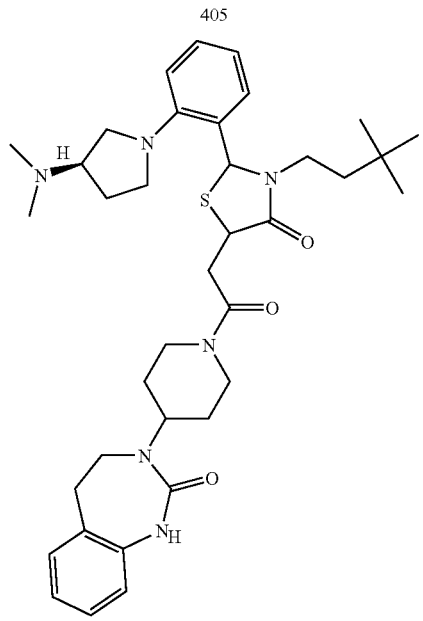
406
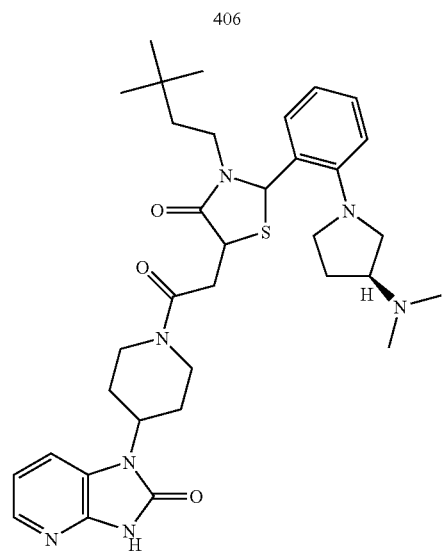
TABLE 1A-continued
407
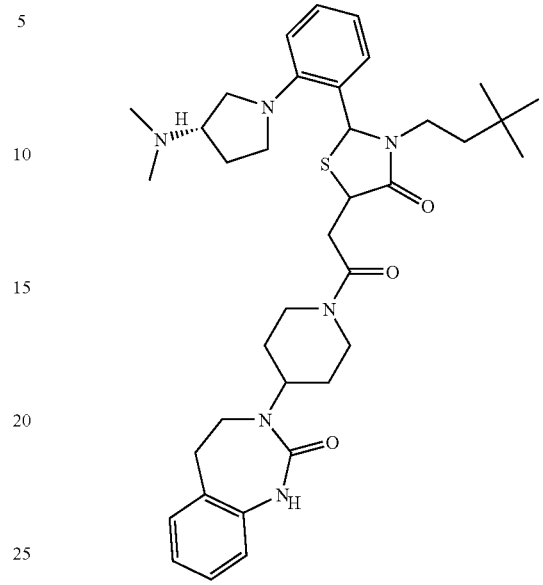
408
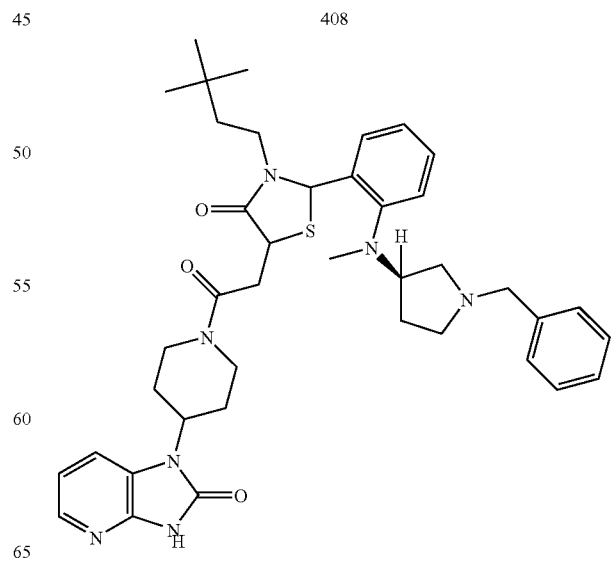

TABLE 1A-continued
409
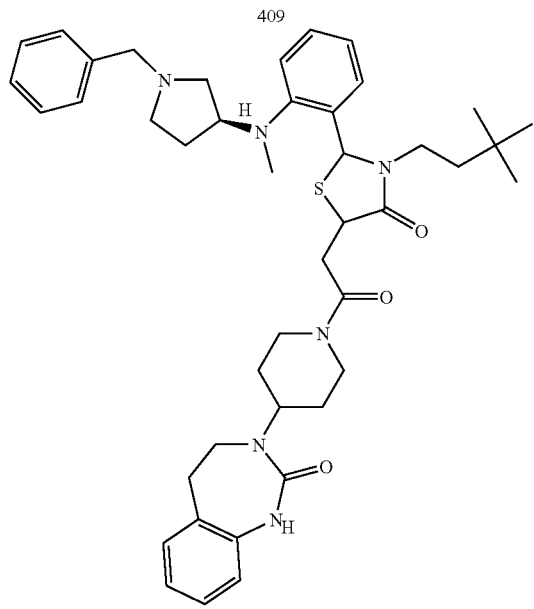
411
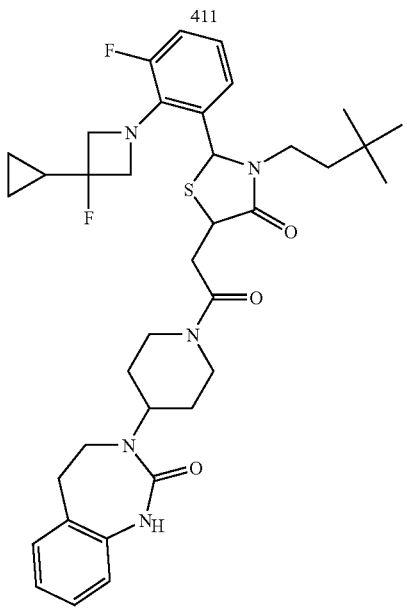
410
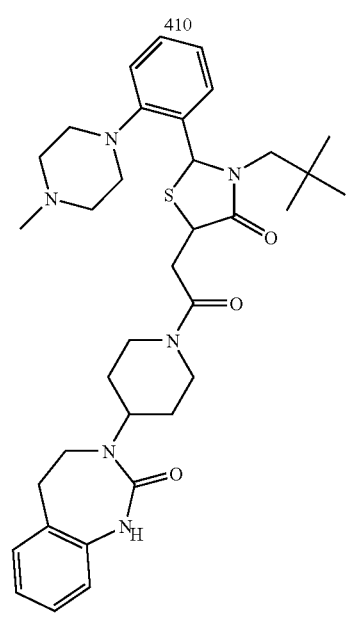
412
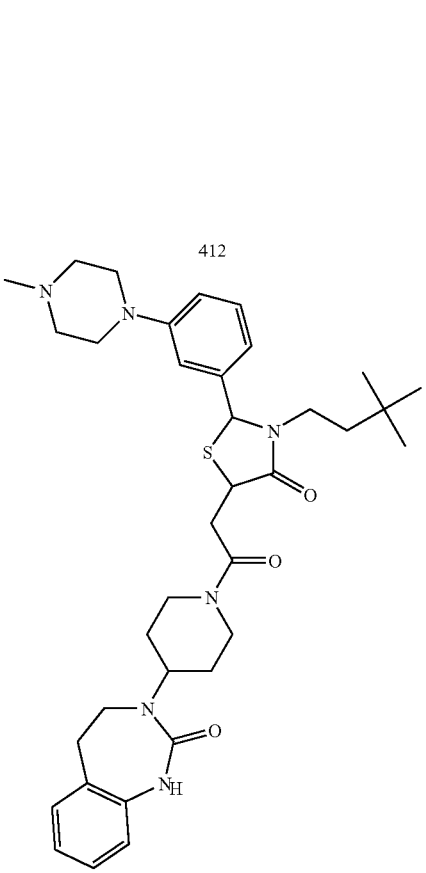

TABLE 1A-continued
413
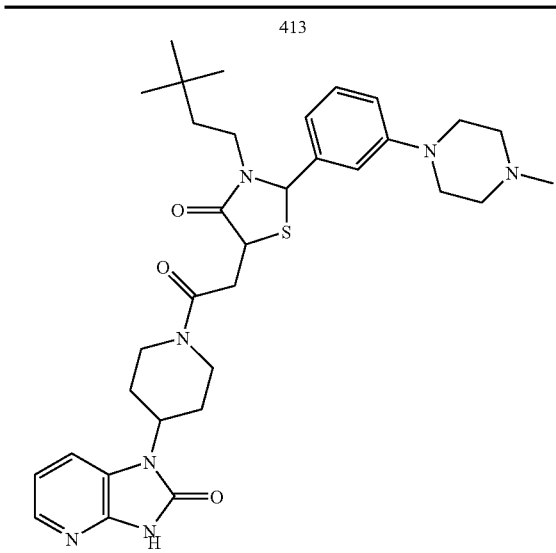
414
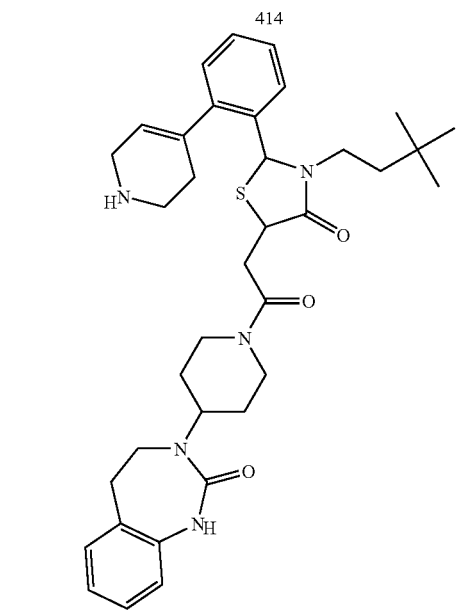
415
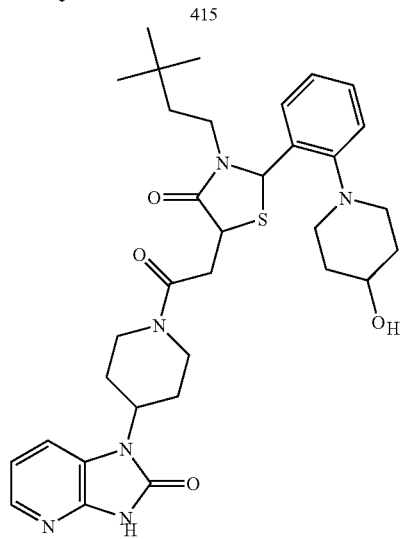
TABLE 1A-continued
416
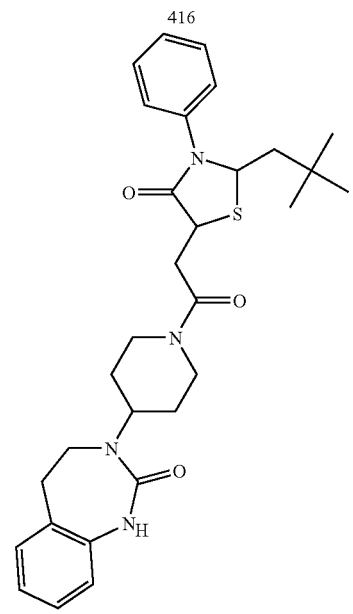
417
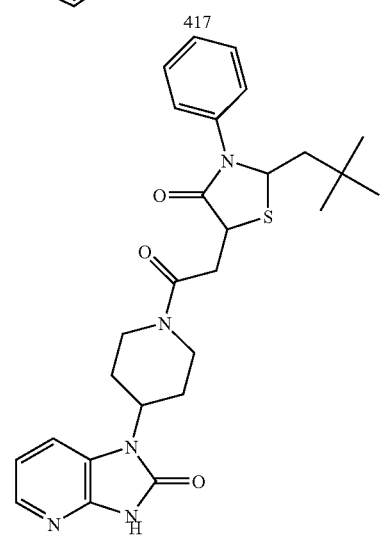
418
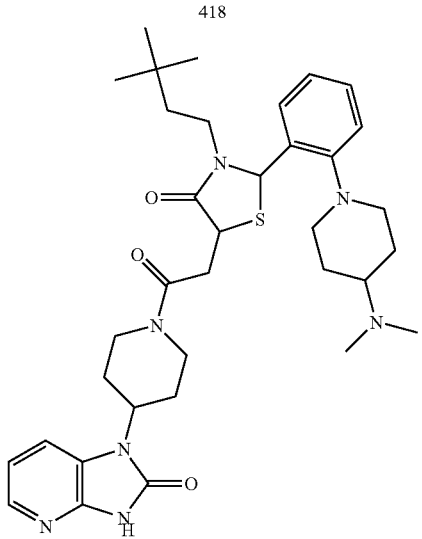

TABLE 1A-continued
419
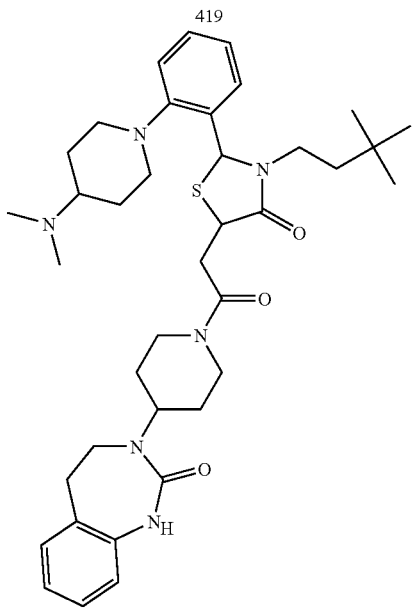
420
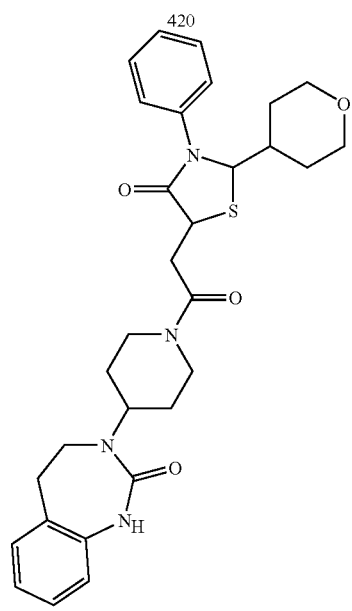
TABLE 1A-continued
421
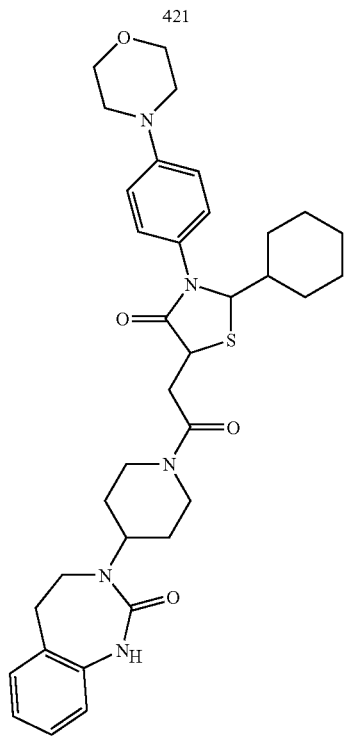
422
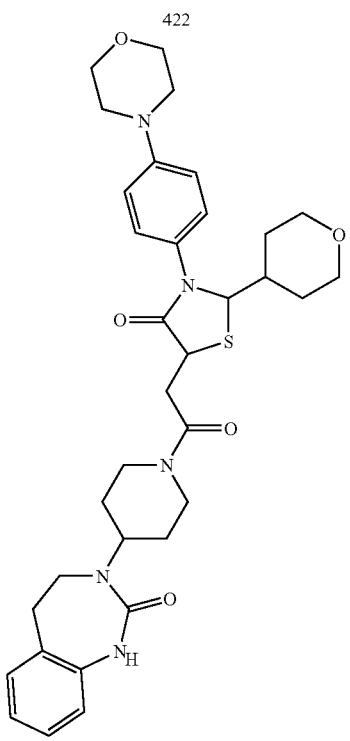

TABLE 1A-continued
423
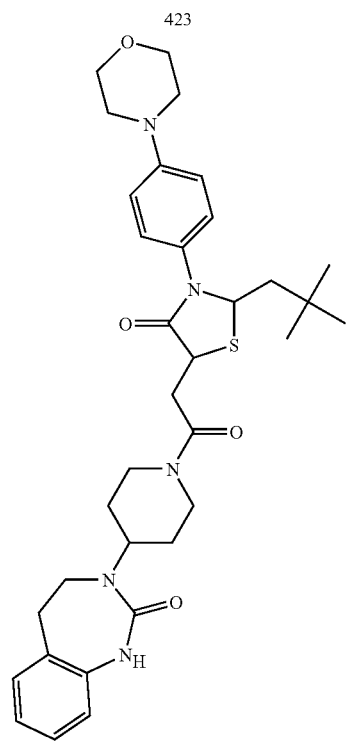
TABLE 1A-continued
425
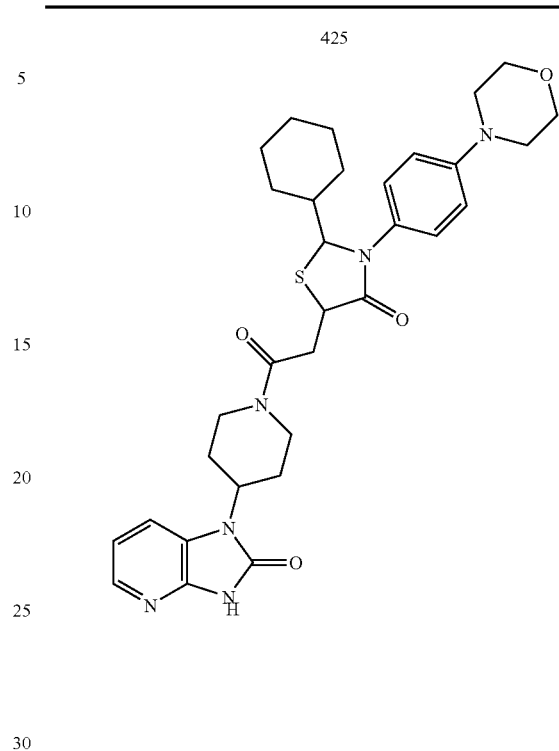
424
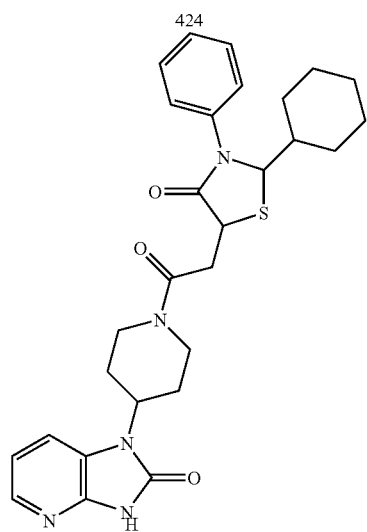
426
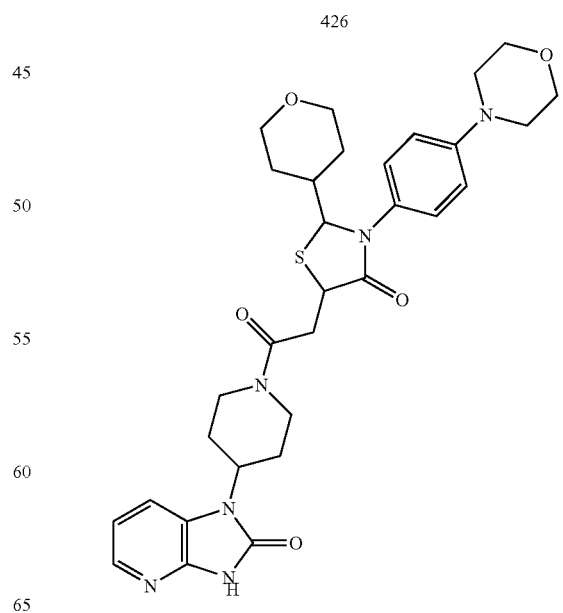

TABLE 1A-continued
427
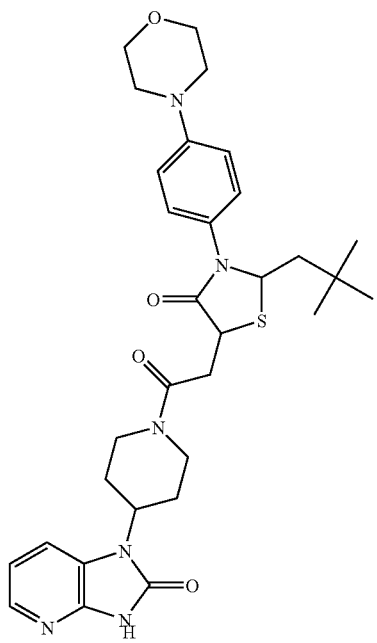
428
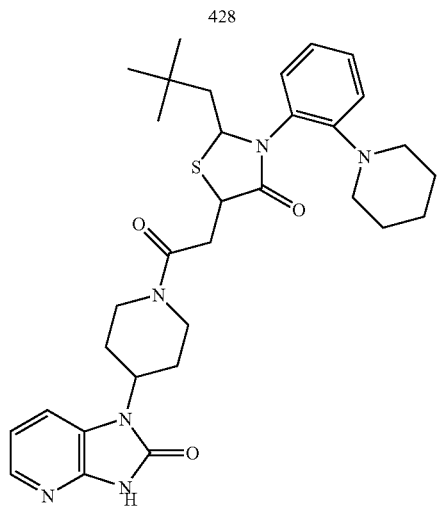
TABLE 1A-continued
429
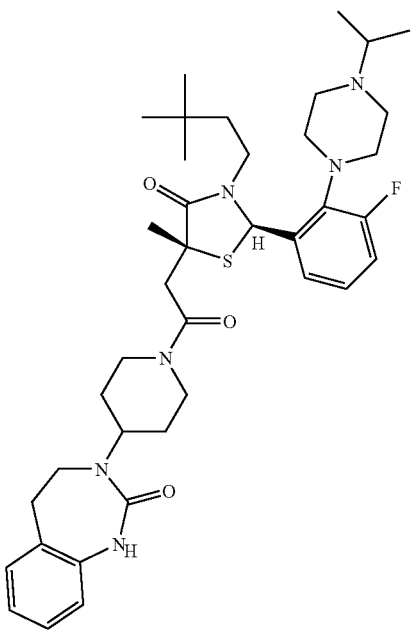
430
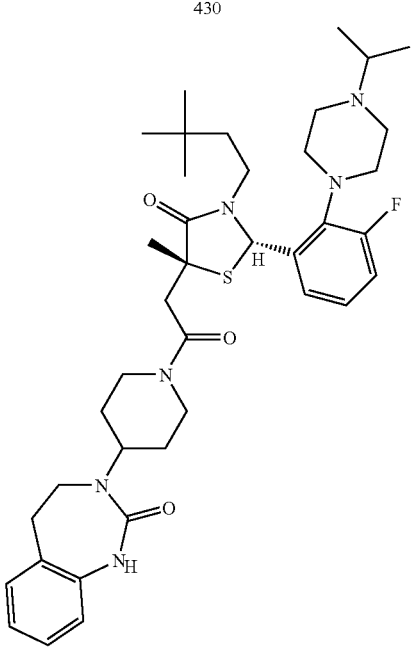

TABLE 1A-continued
431
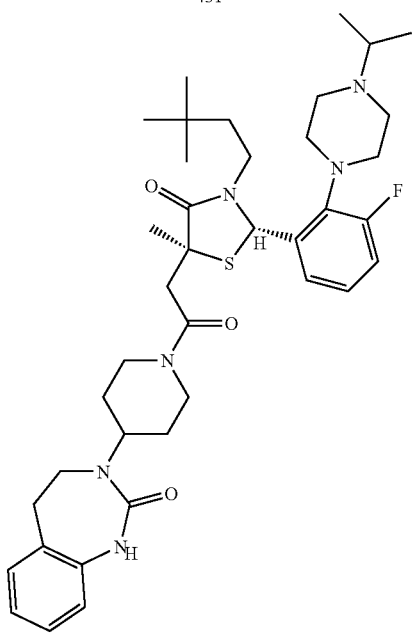
432
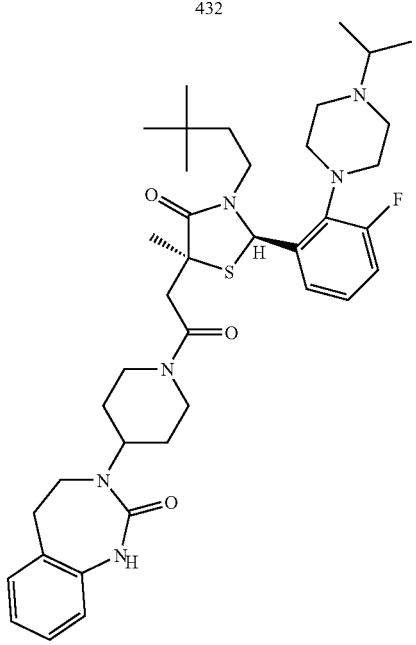
TABLE 1A-continued
433
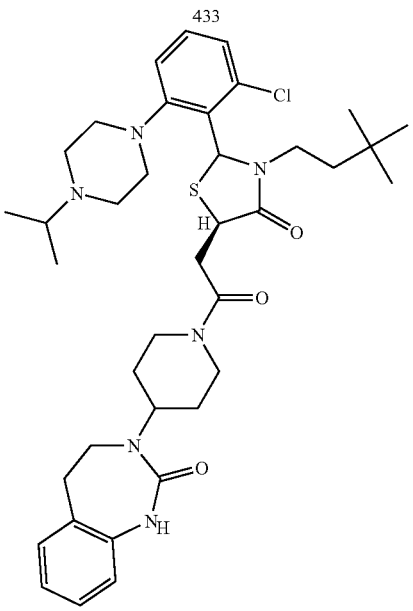
434
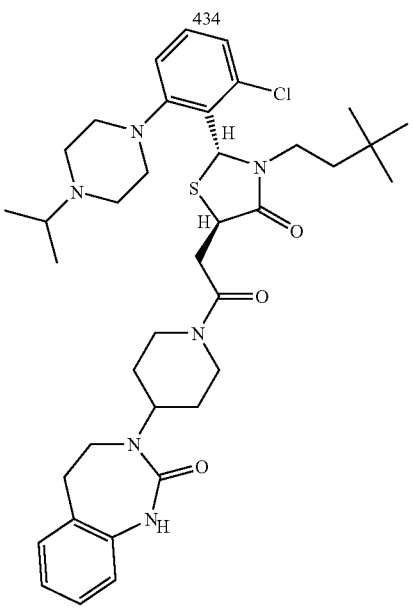

TABLE 1A-continued
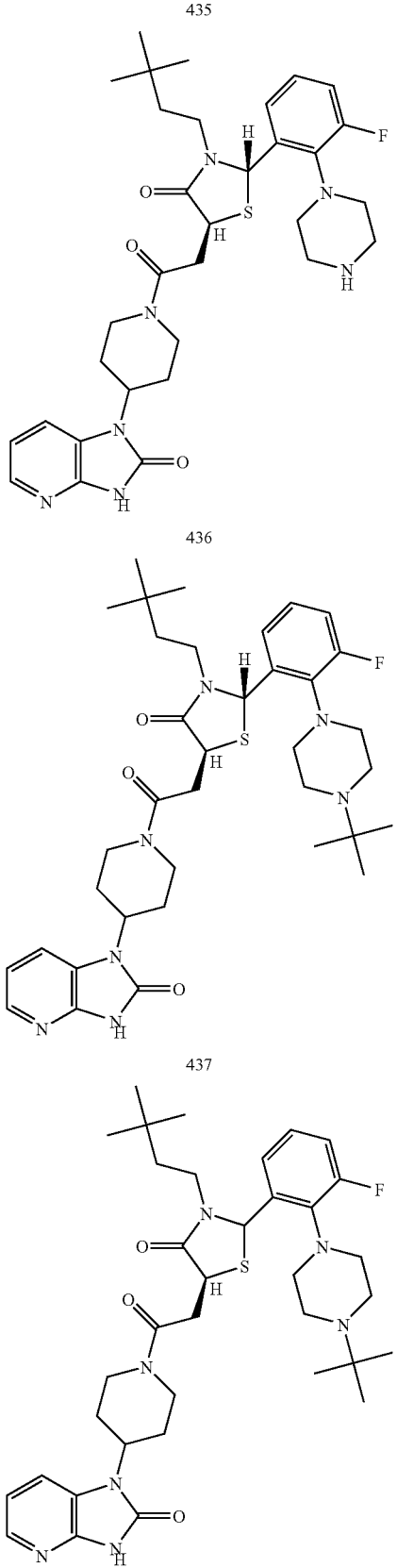
TABLE 1A-continued

TABLE 1A-continued
440
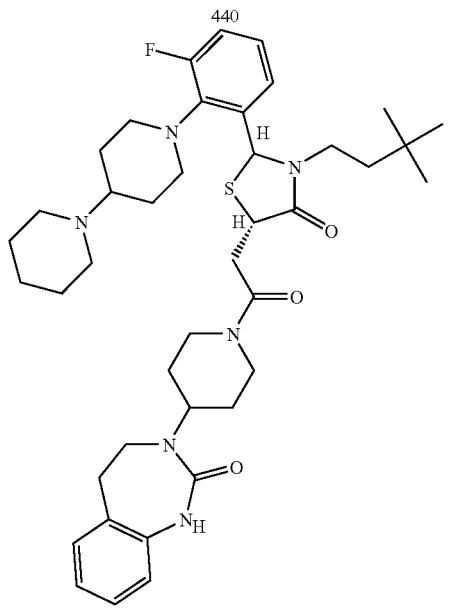
441
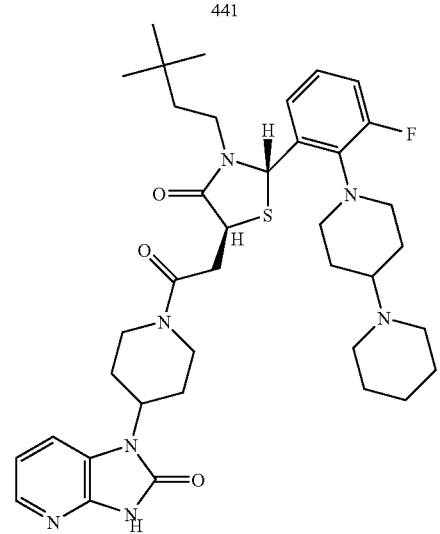
442
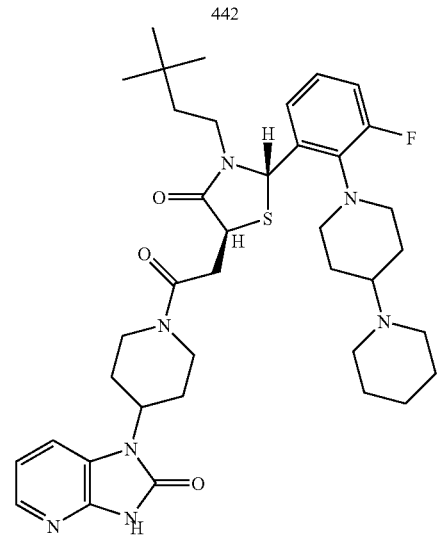
TABLE 1A-continued
443
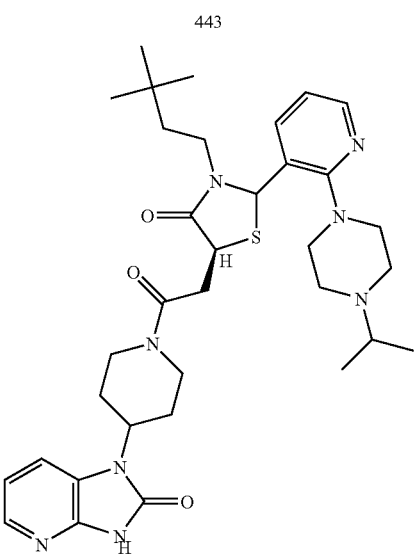
444
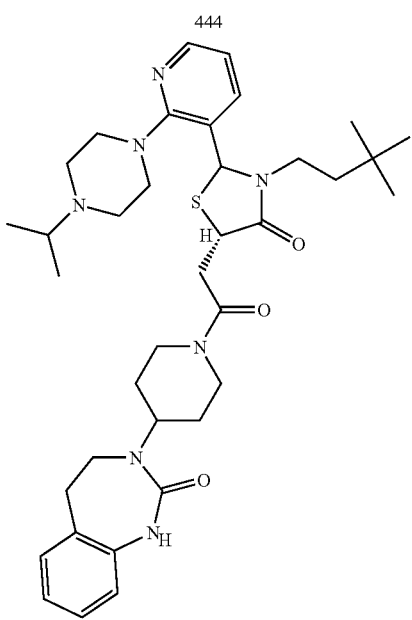

TABLE 1A-continued
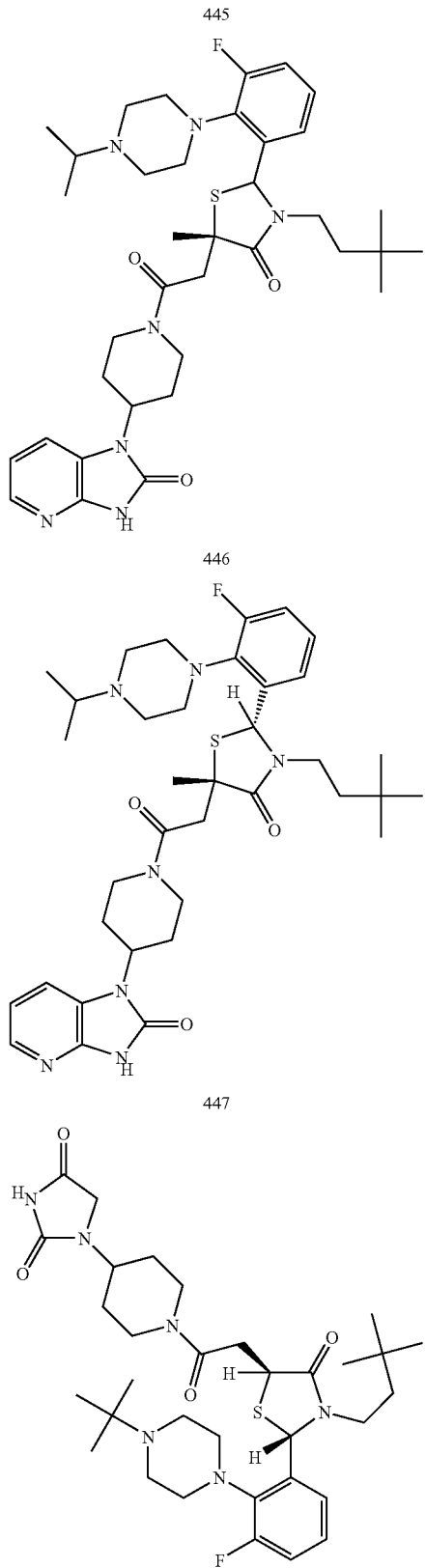
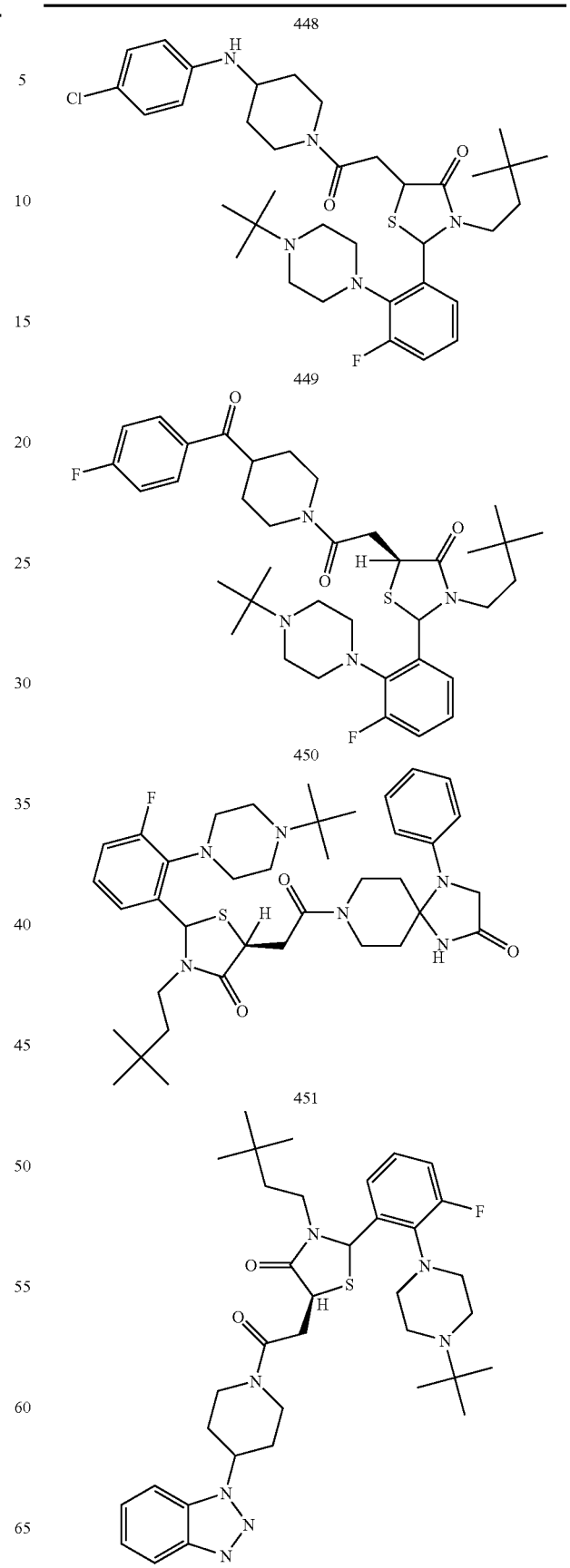

TABLE 1A-continued
452
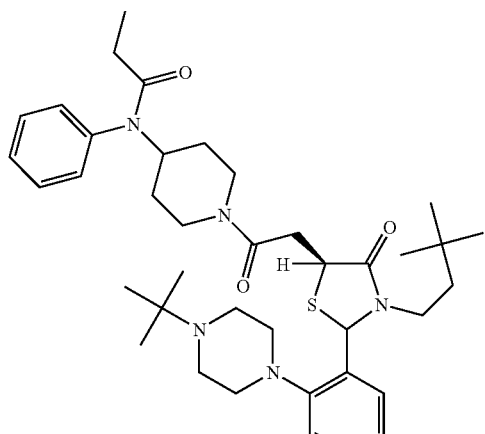
453
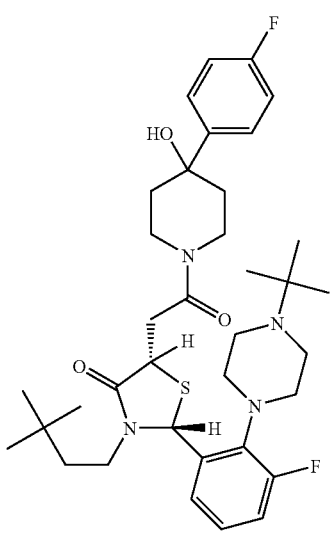
454
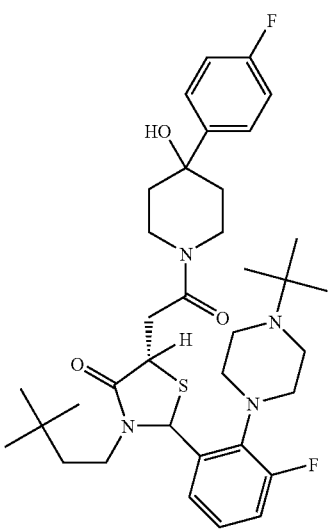
TABLE 1A-continued
455
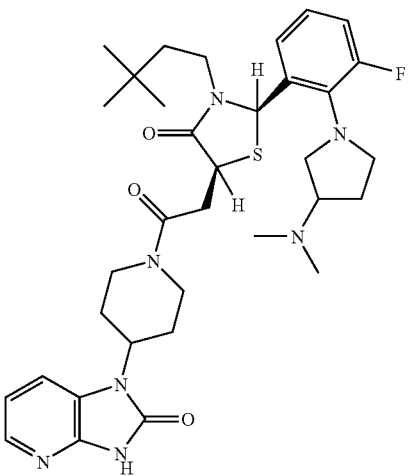
456
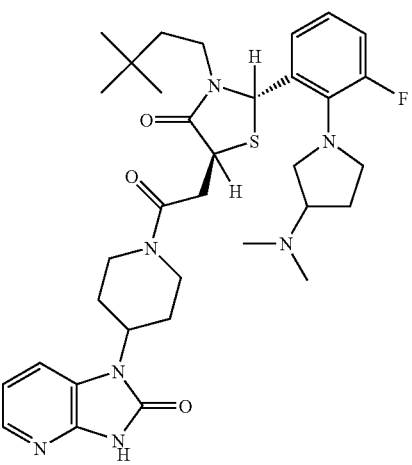
457
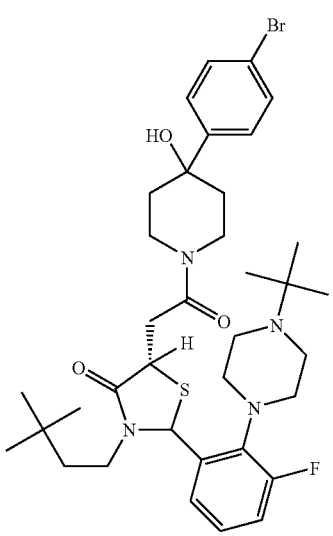

TABLE 1A-continued
458
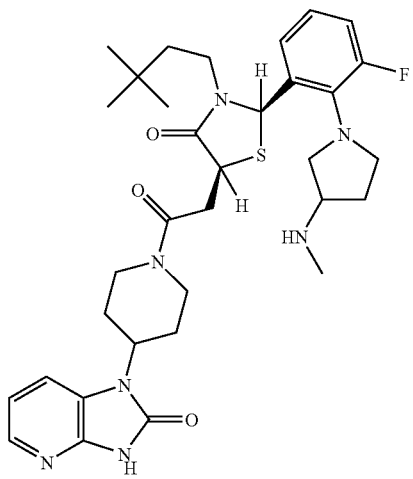
459
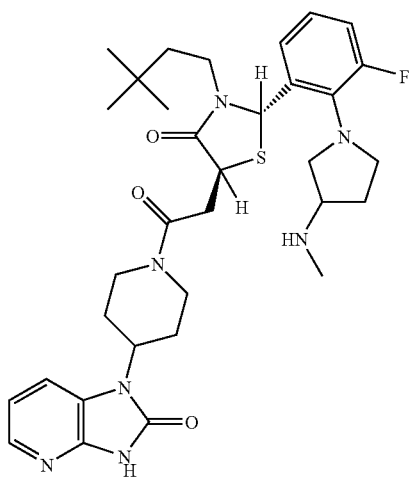
460
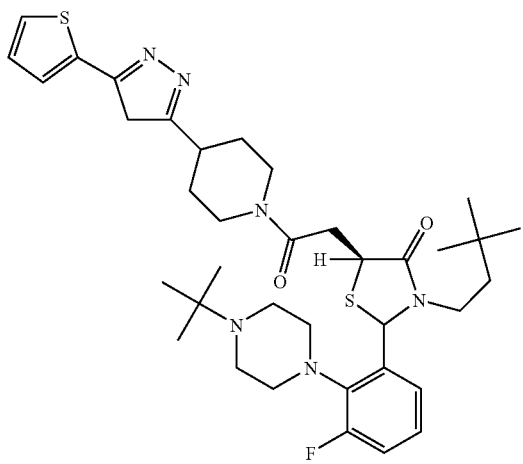
TABLE 1A-continued
461
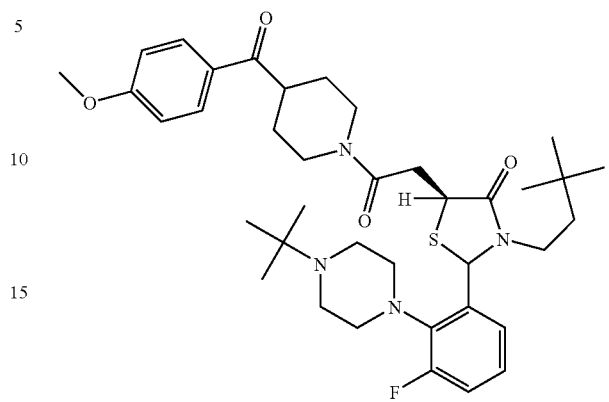
462
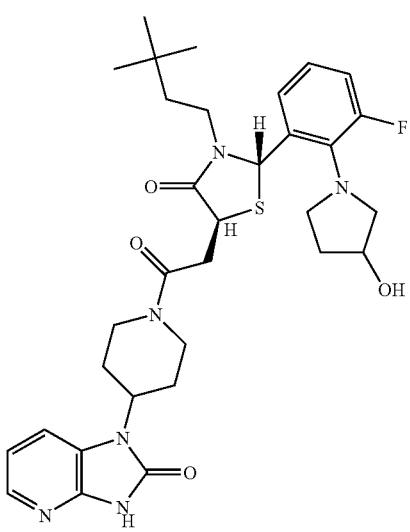
463
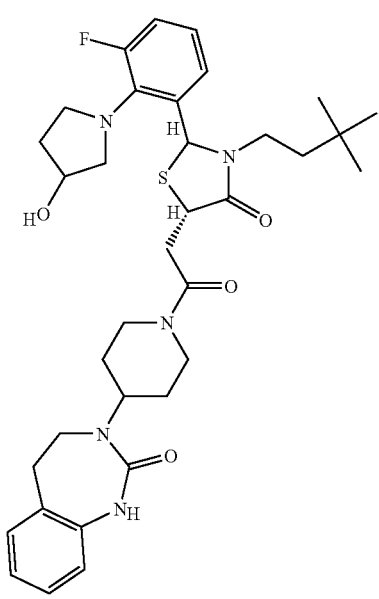

TABLE 1A-continued
464
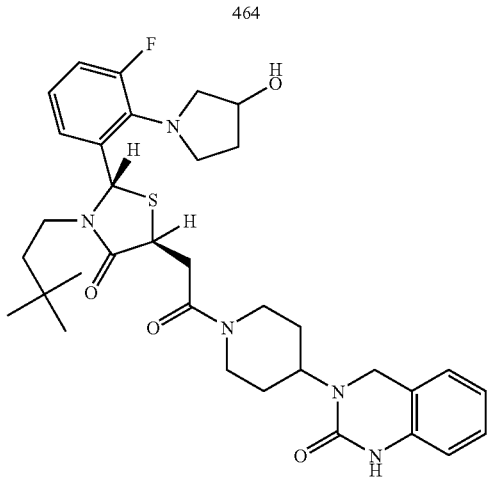
465
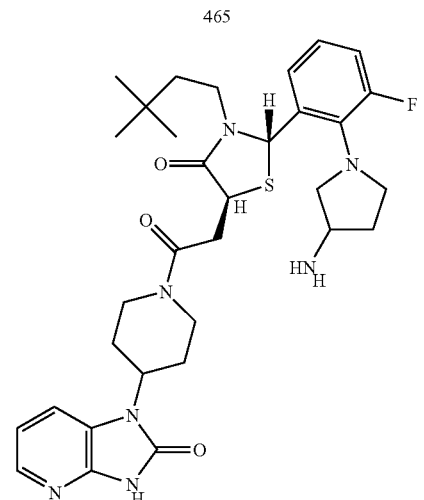
466
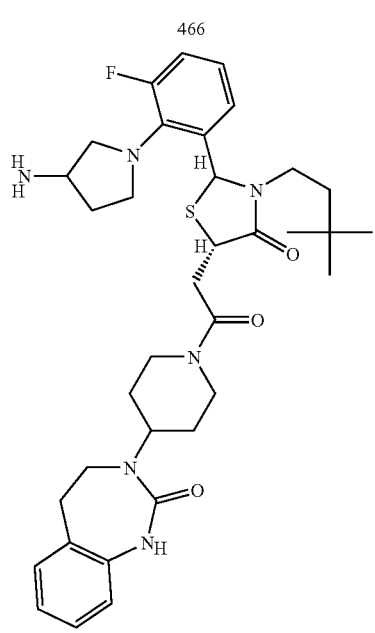
TABLE 1A-continued
467
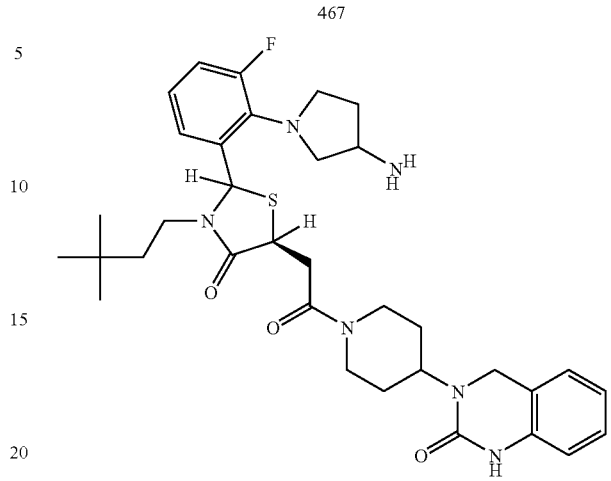
468
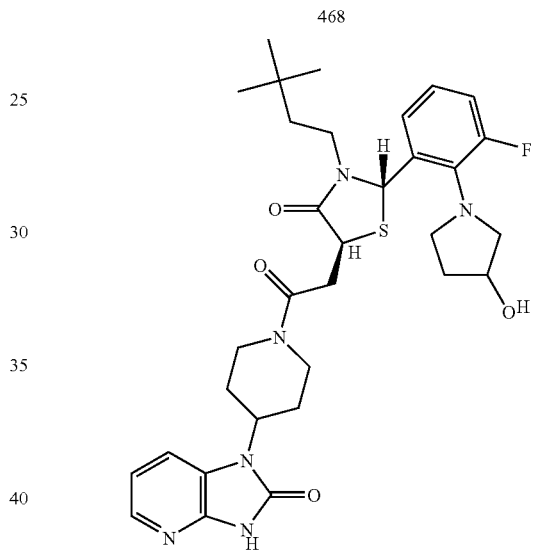
469
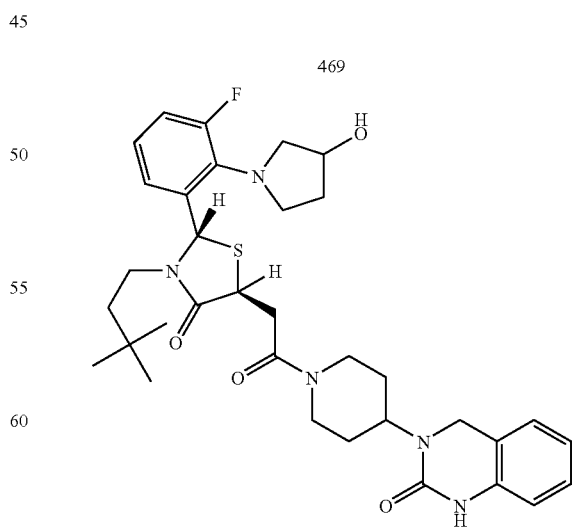

TABLE 1A-continued
470
471
472
473
474
475
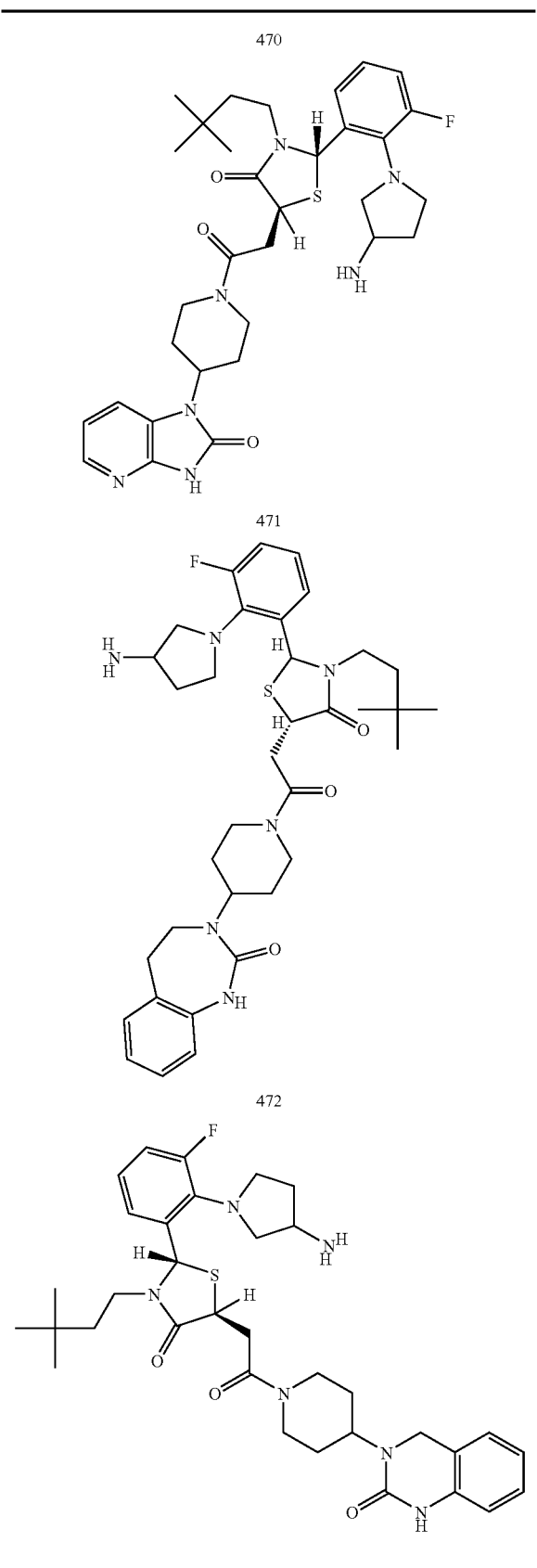

TABLE 1A-continued
476
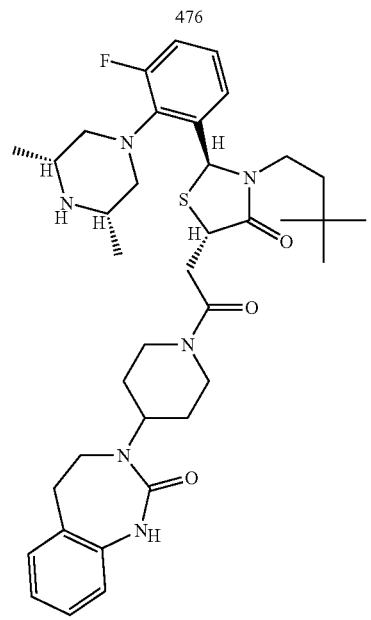
TABLE 1B
478
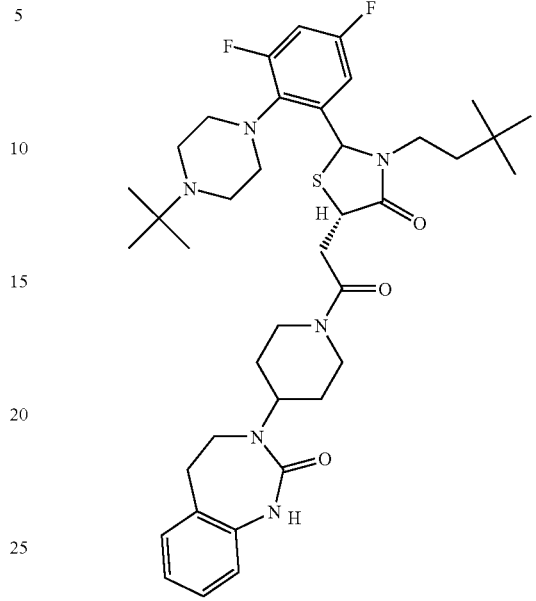
477
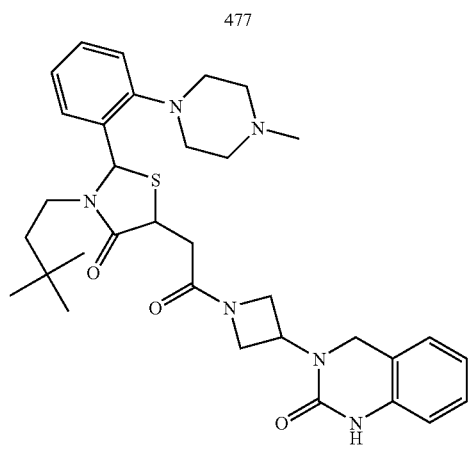
479
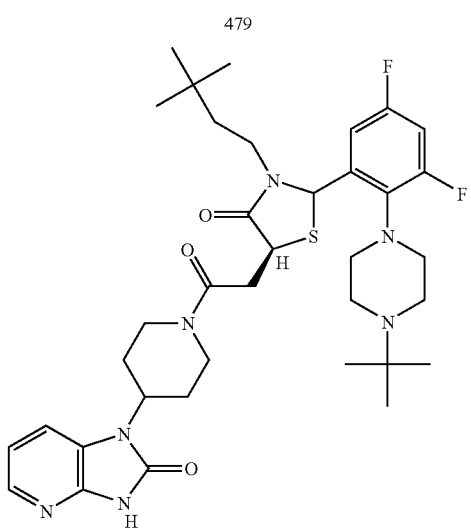

TABLE 1B-continued
480
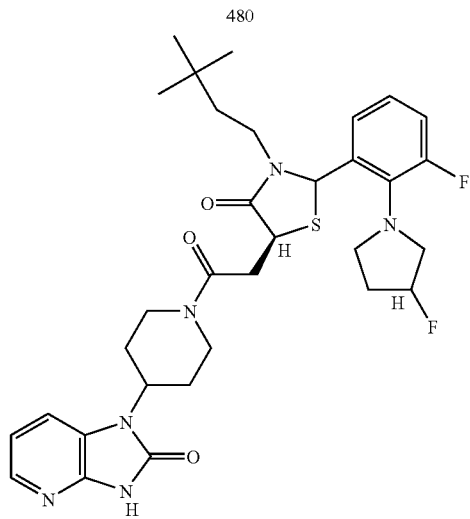
481
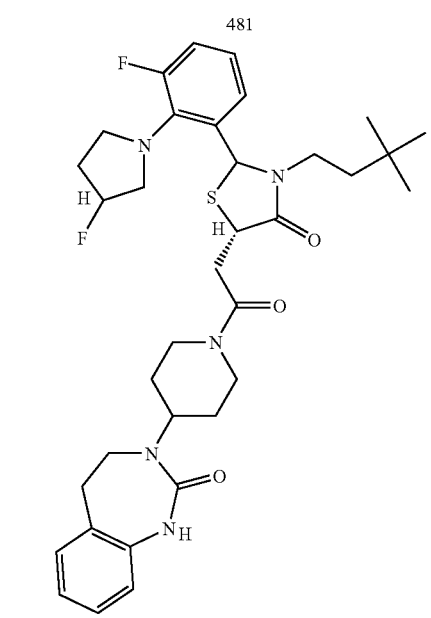
482
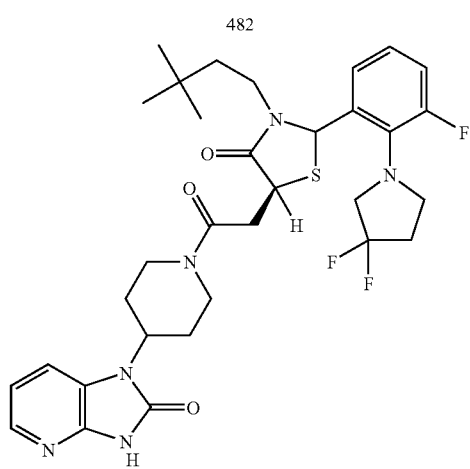
TABLE 1B-continued
483
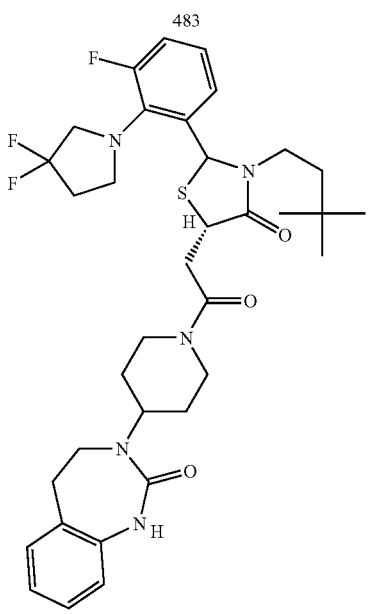
484
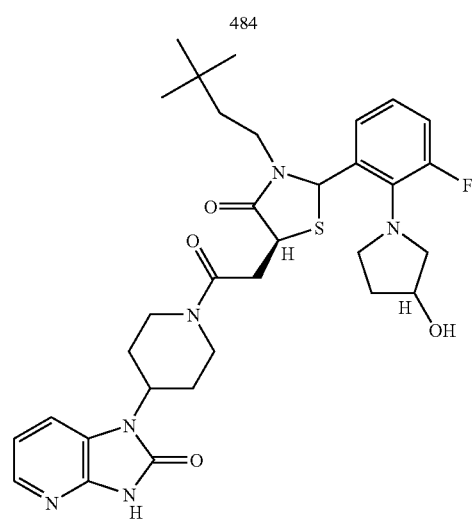

TABLE 1B-continued
485
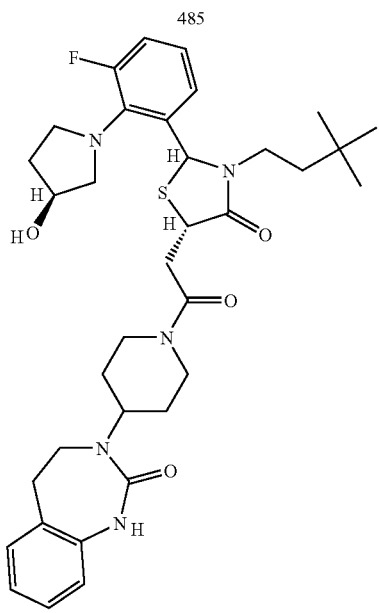
486
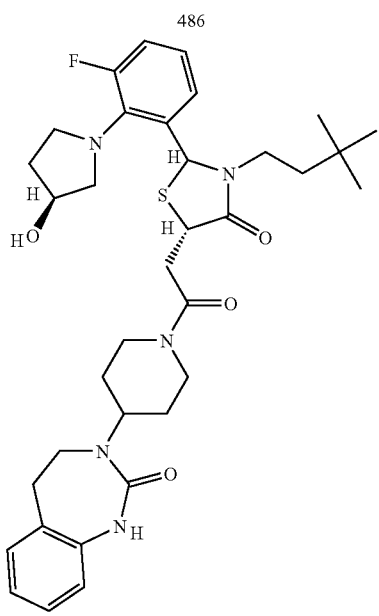
TABLE 1B-continued
487
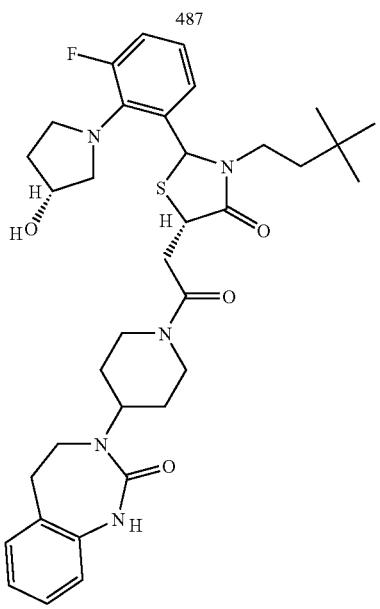
488
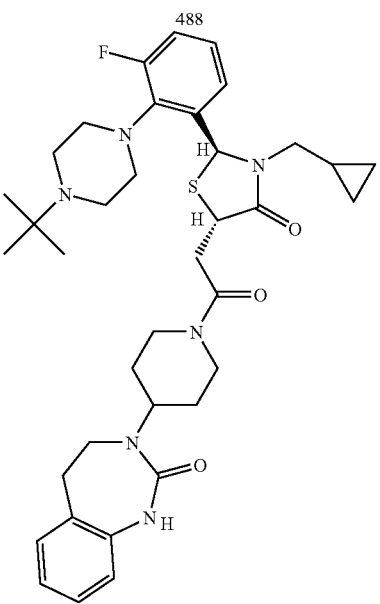

489
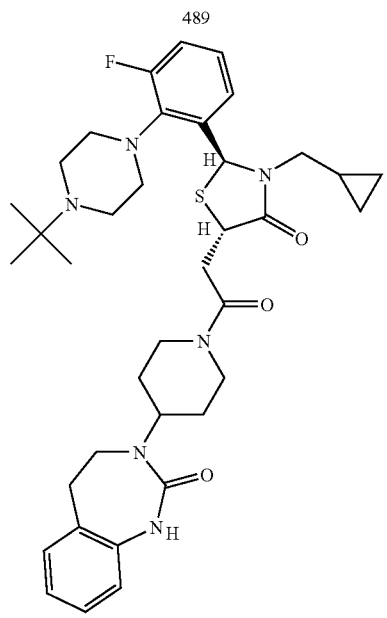
490
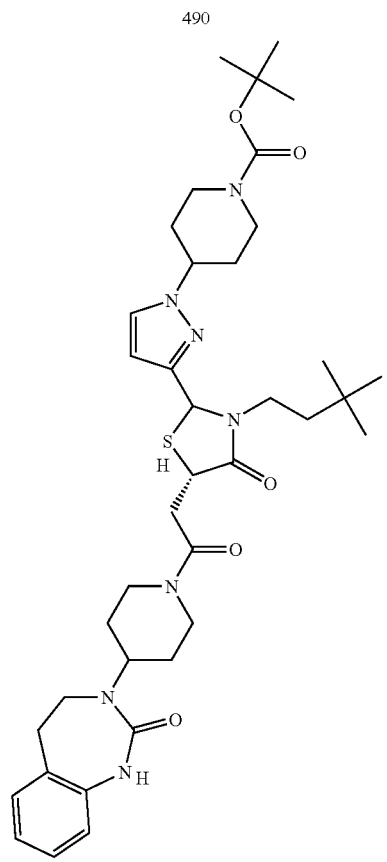
491
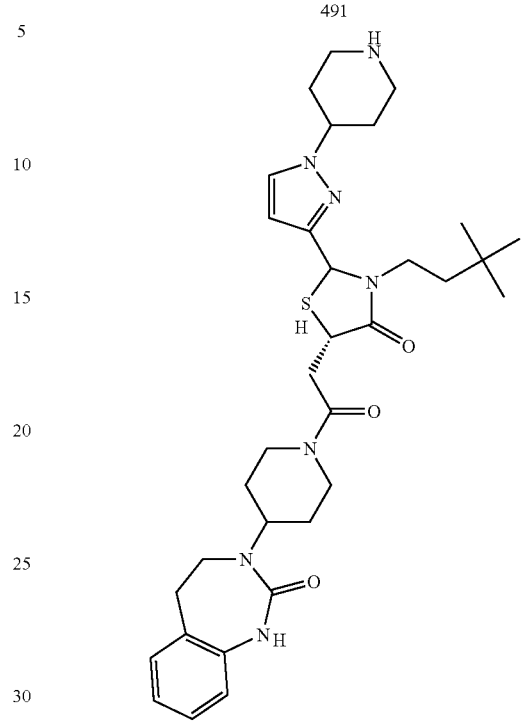
492
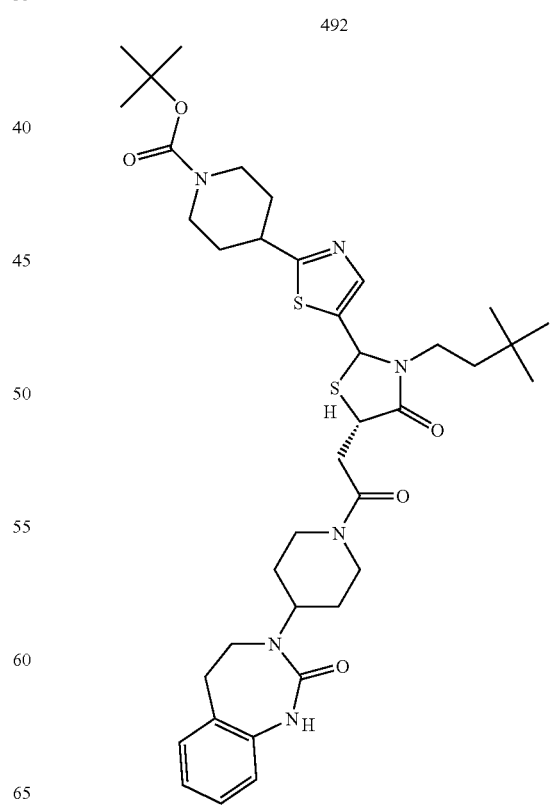

TABLE 1B-continued
493
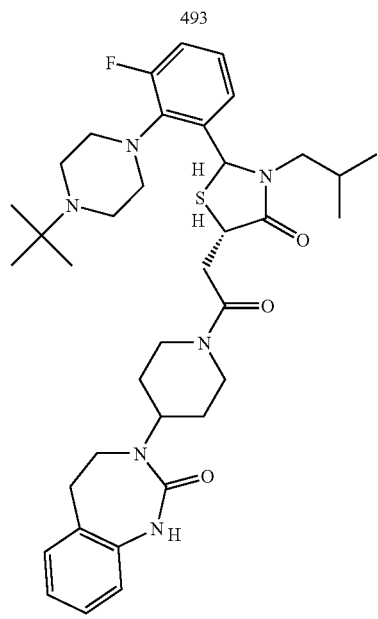
494
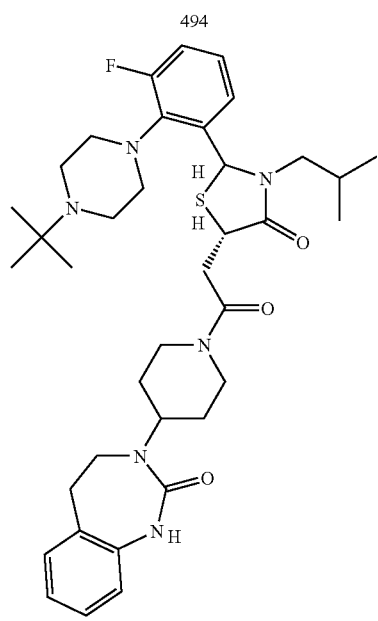
TABLE 1B-continued
495
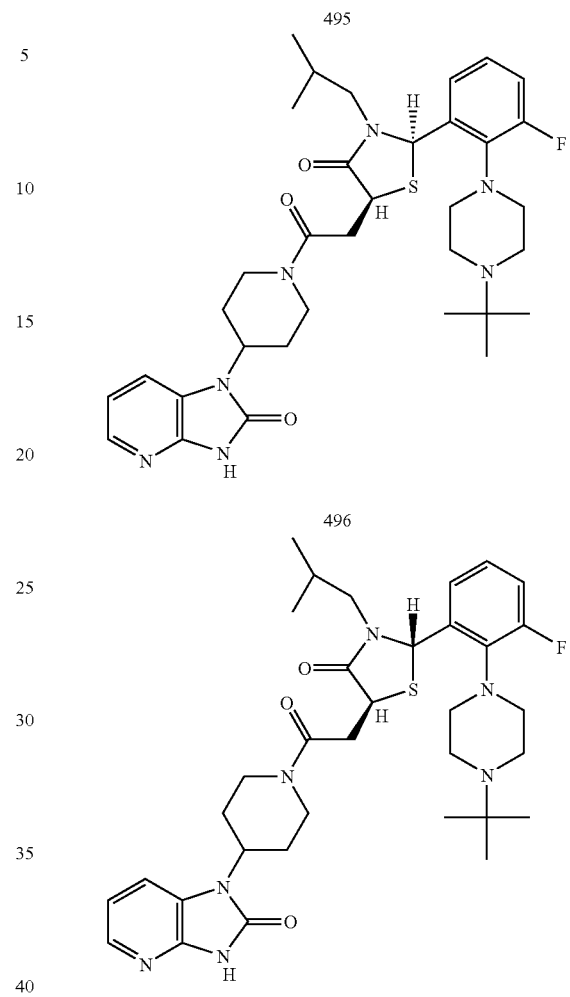
496
497
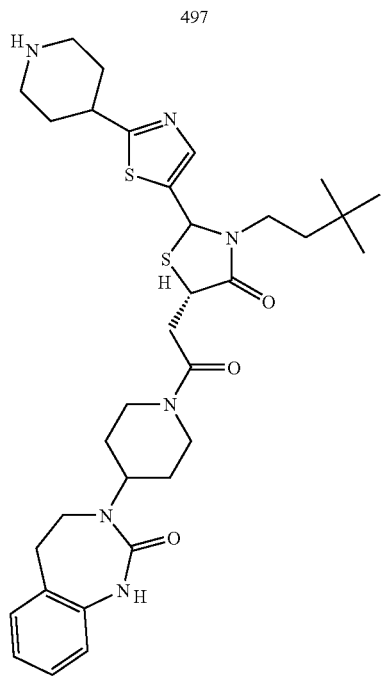

TABLE 1B-continued
498
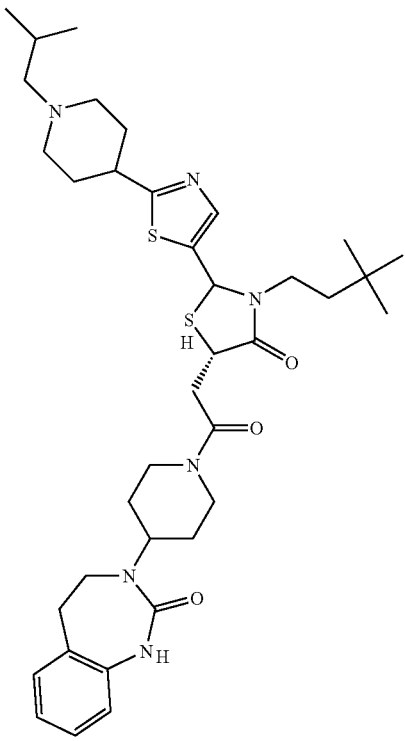
499
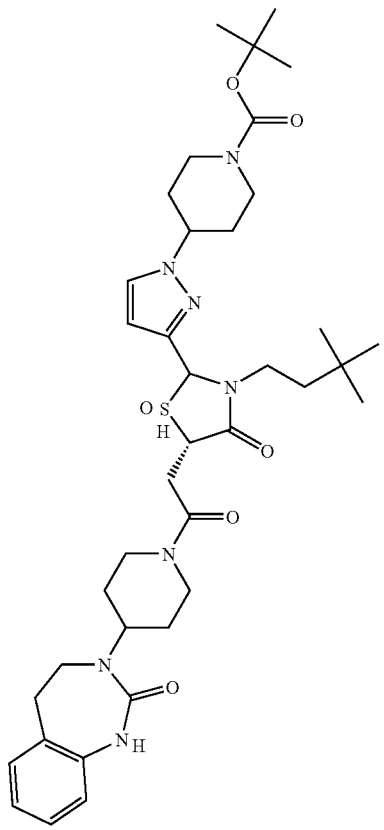
TABLE 1B-continued
500
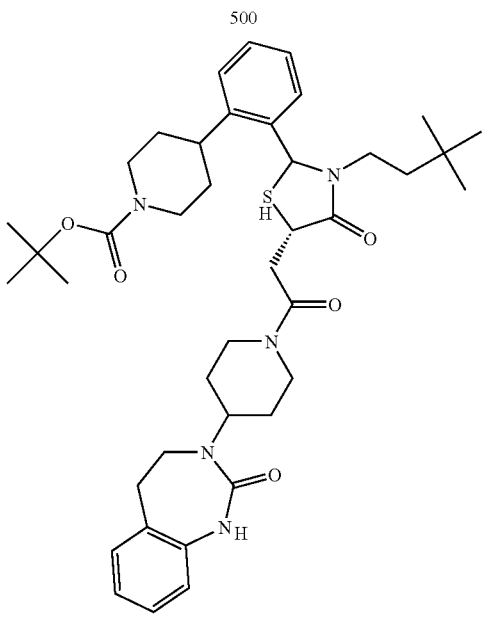
501
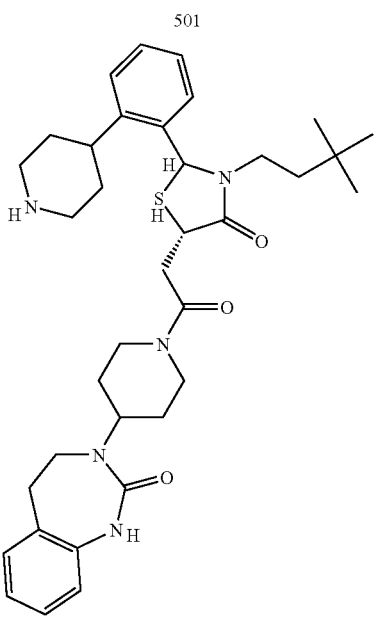

TABLE 1B-continued
502
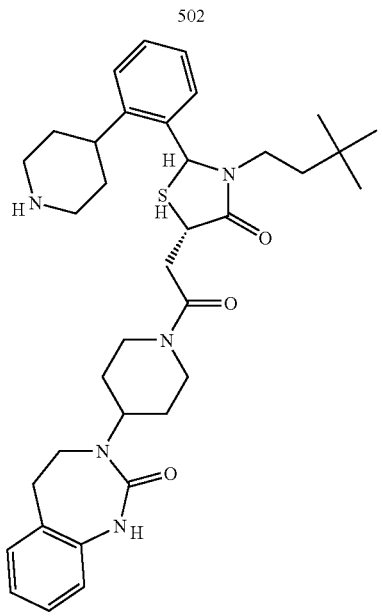
503
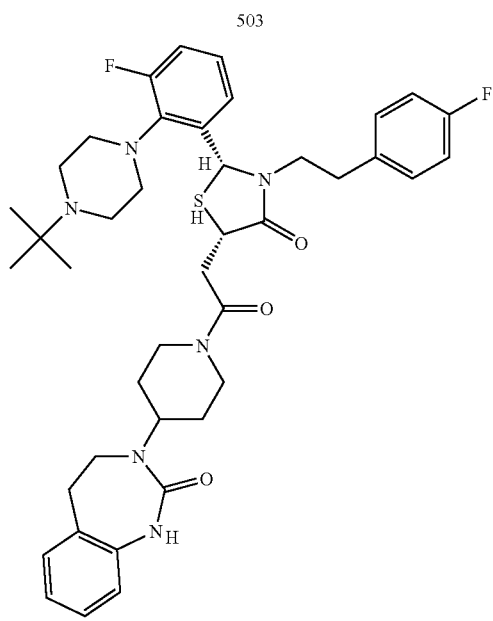
TABLE 1B-continued
504
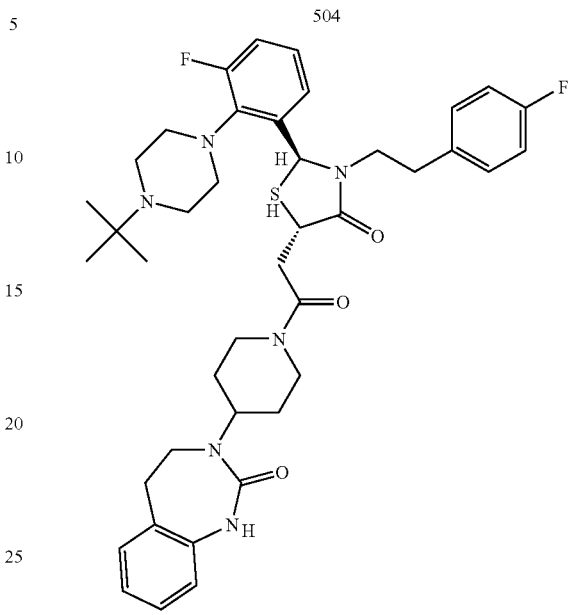
505
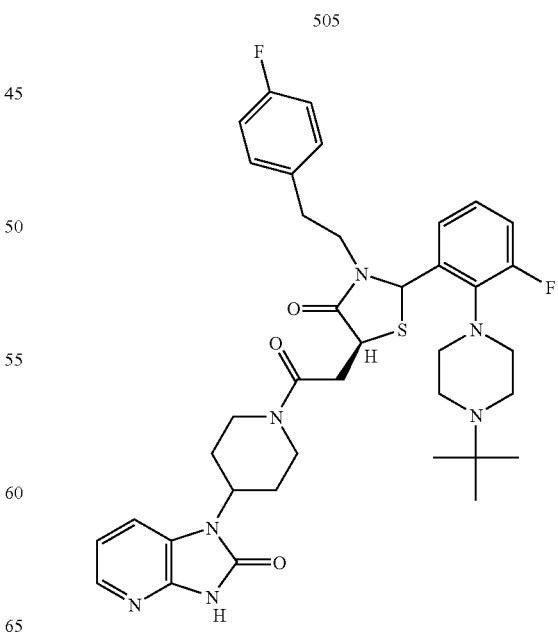

TABLE 1B-continued
506
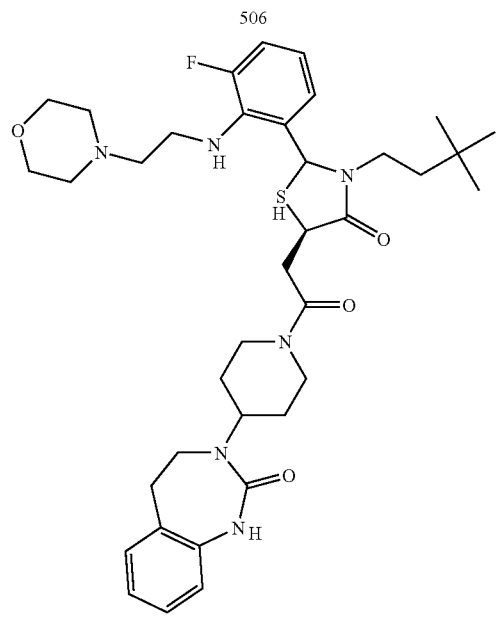
TABLE 1B-continued
508
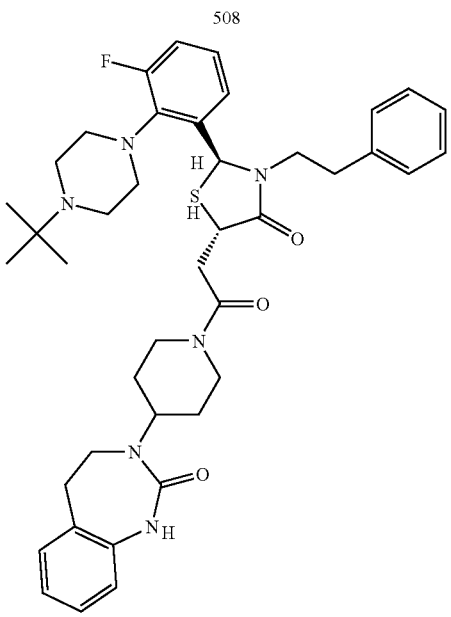
507
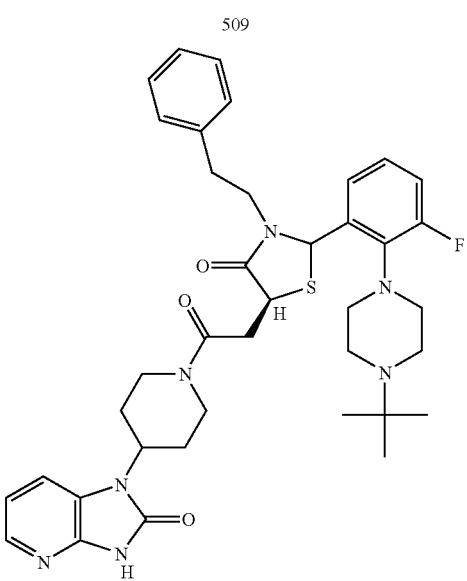
509

TABLE 1B-continued
510
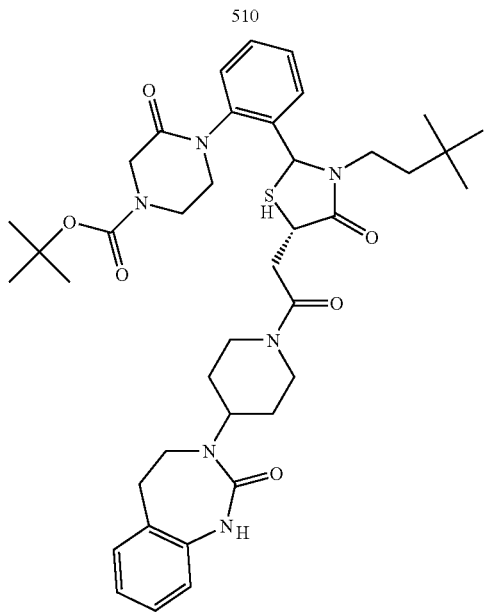
512
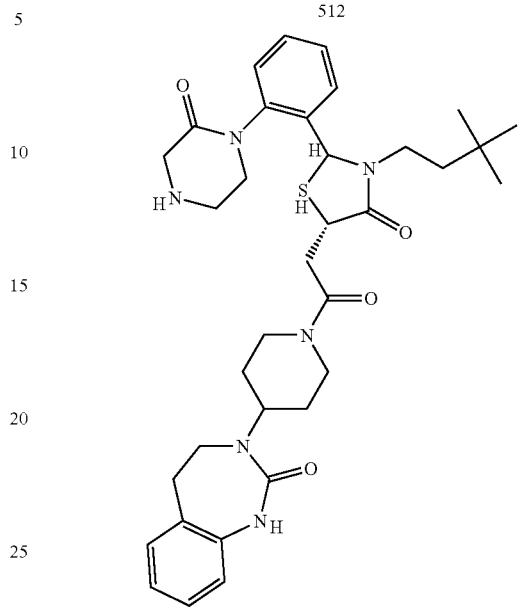
511
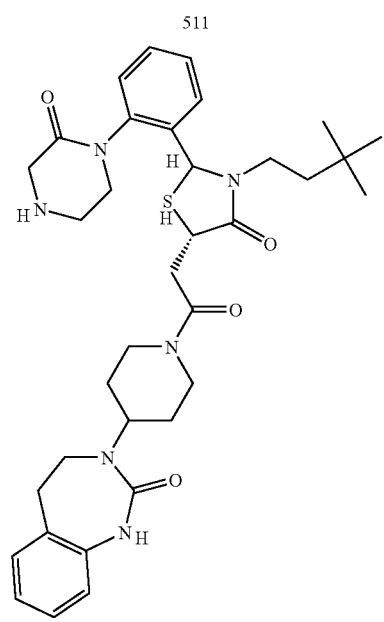
513
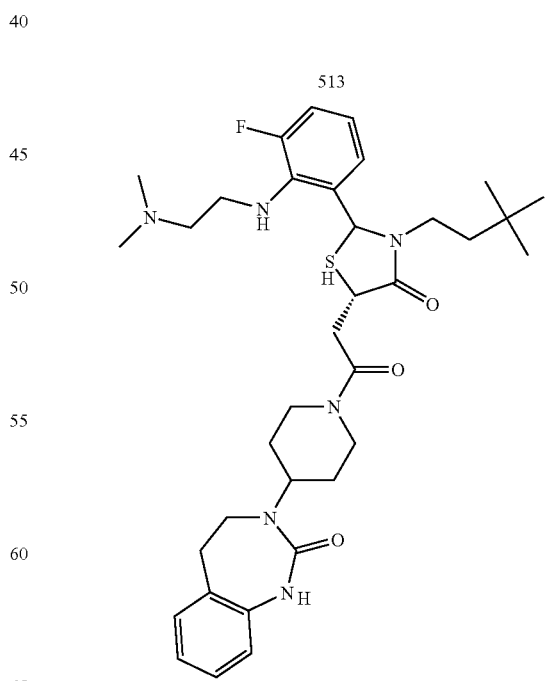

TABLE 1B-continued
514
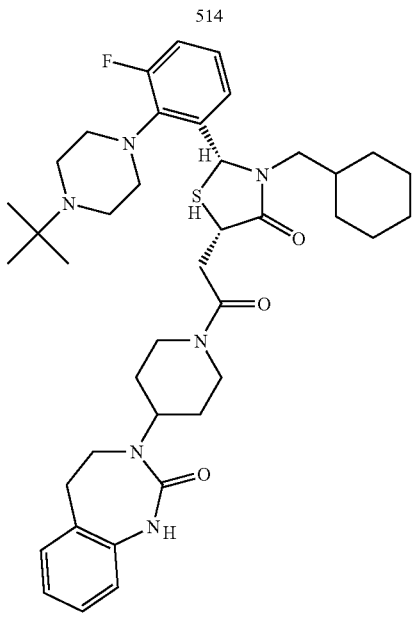
515
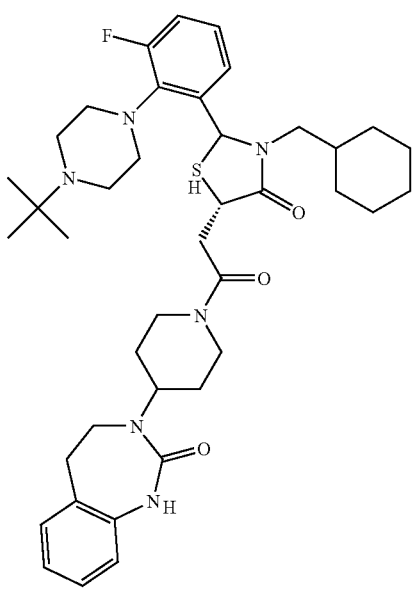
516
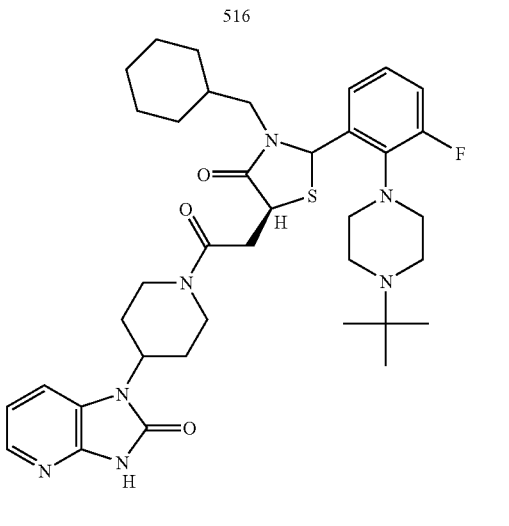
517
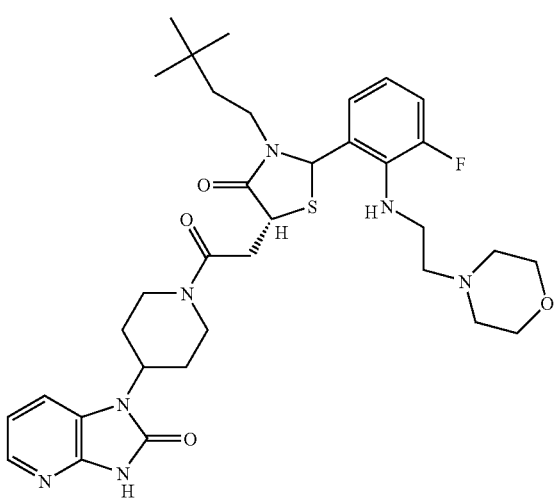
518
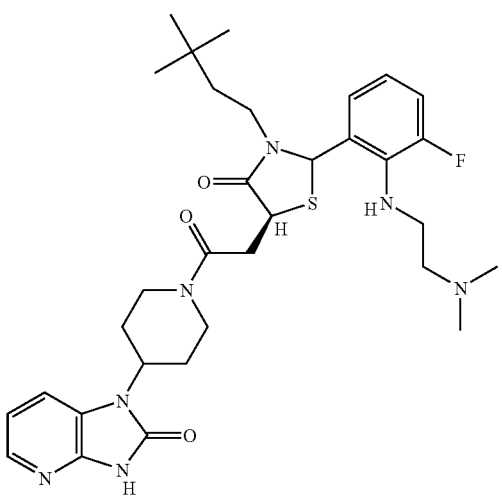

TABLE 1B-continued
519
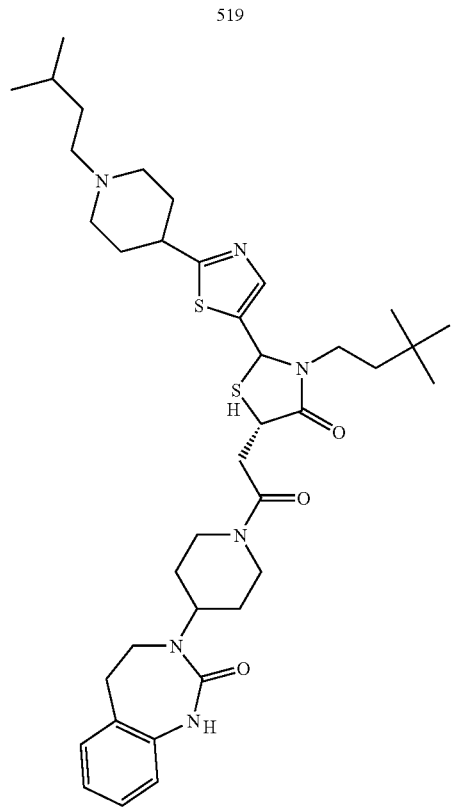
520
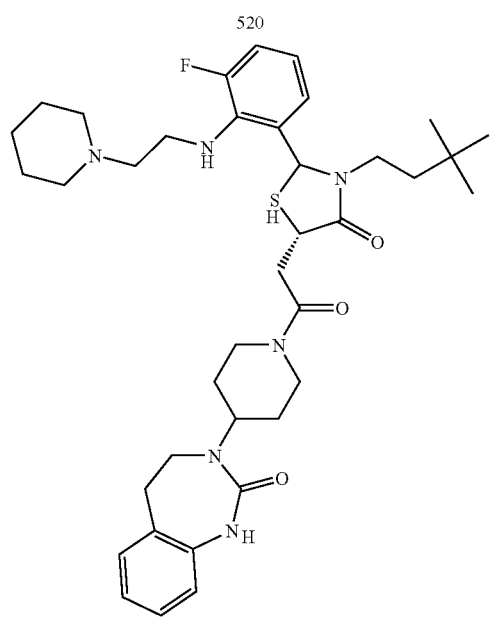
TABLE 1B-continued
521
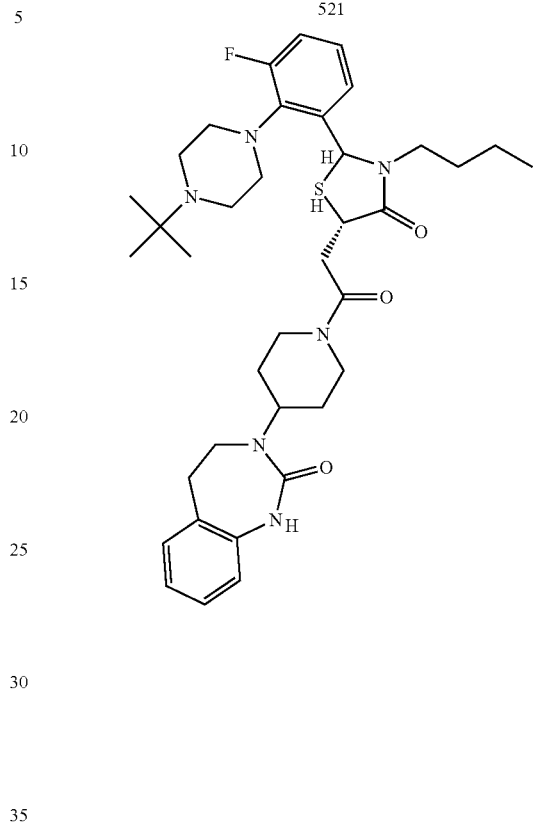
522
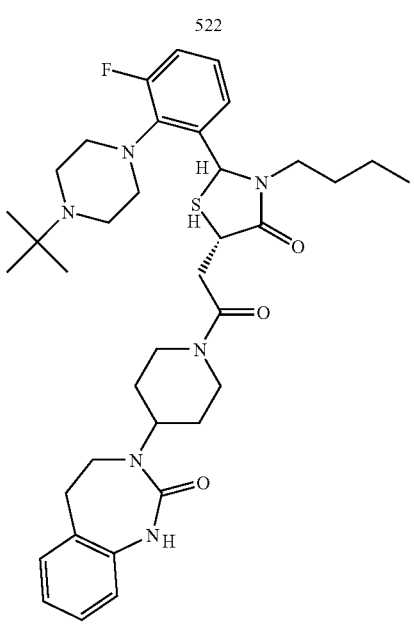

TABLE 1B-continued
523
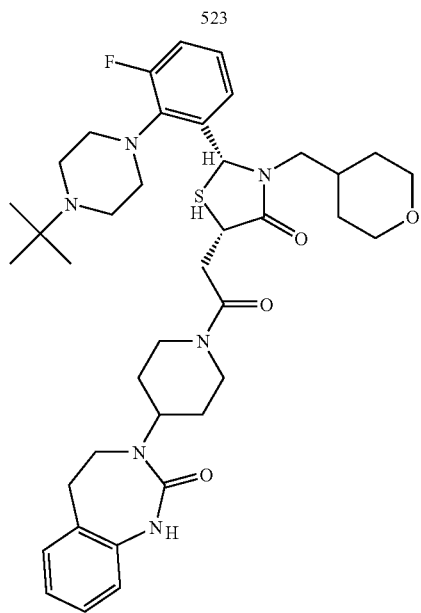
524
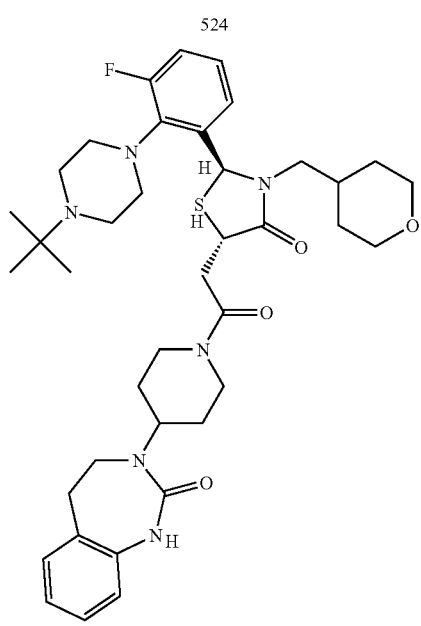
TABLE 1B-continued
525
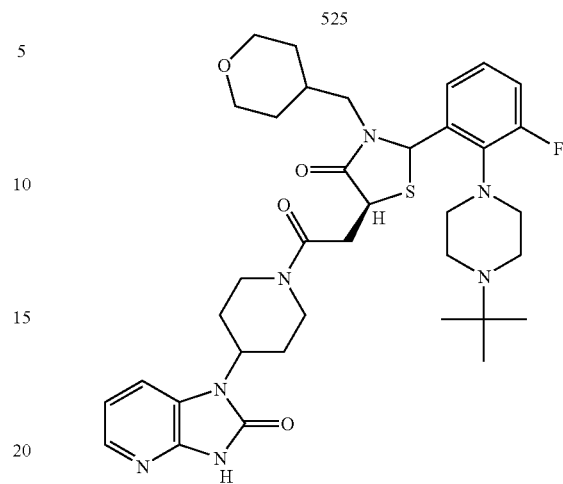
526
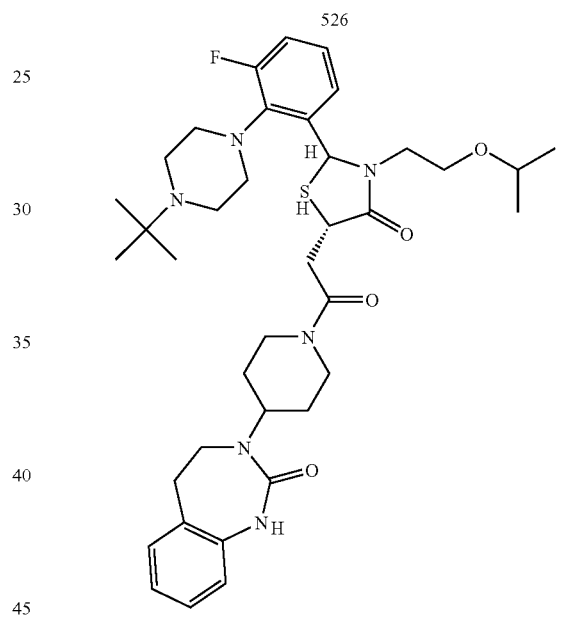
527
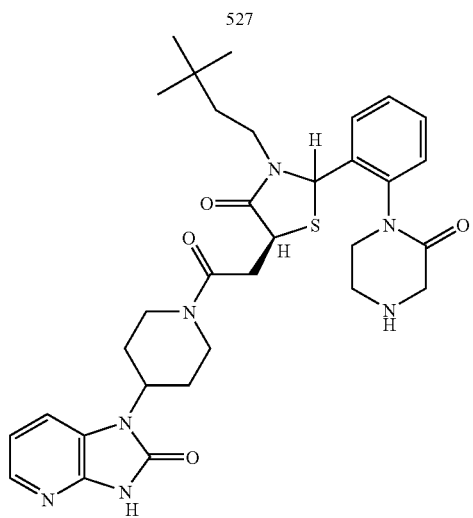

TABLE 1B-continued
528
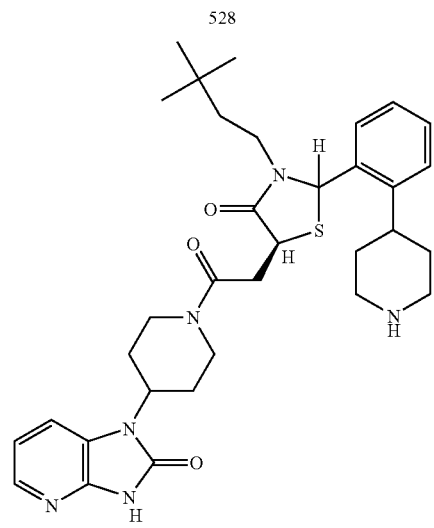
529
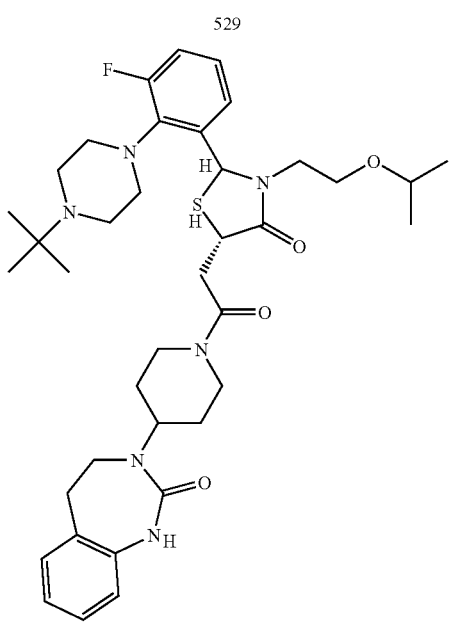
530
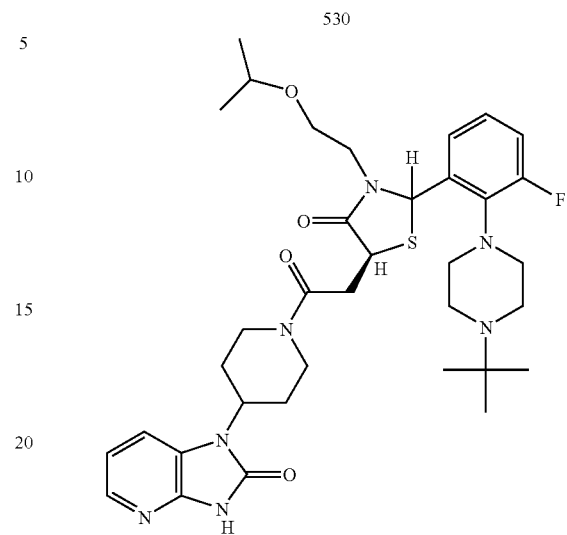
531
532

TABLE 1B-continued
533
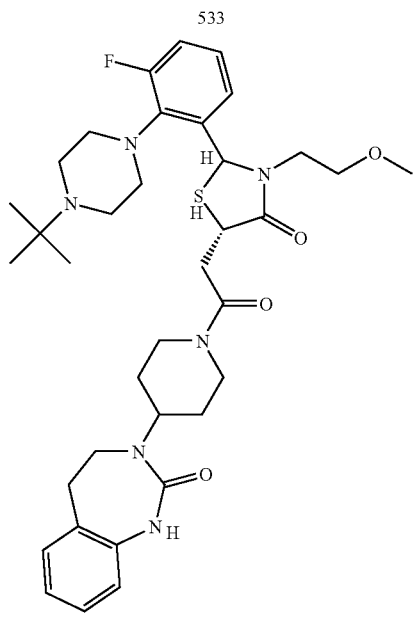
534
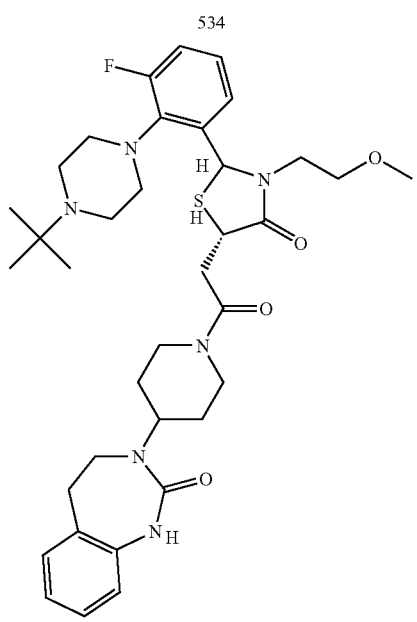
TABLE 1B-continued
535
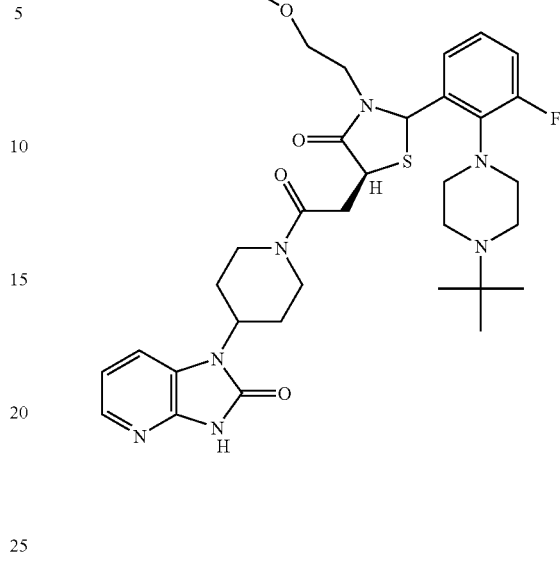
536
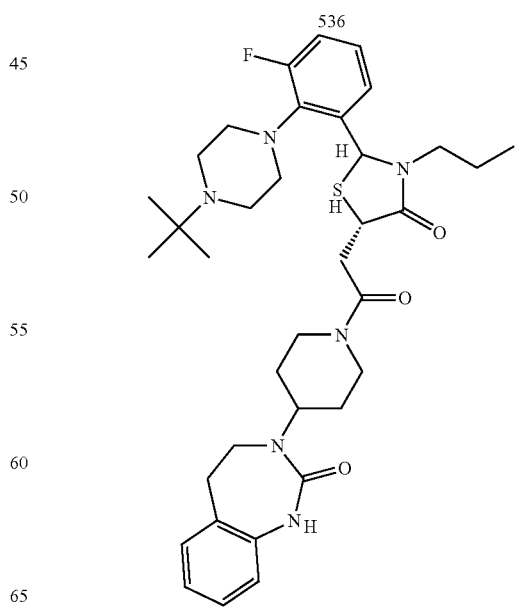

TABLE 1B-continued
537
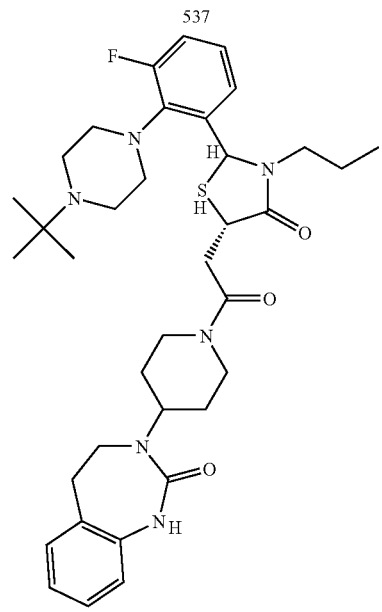
538
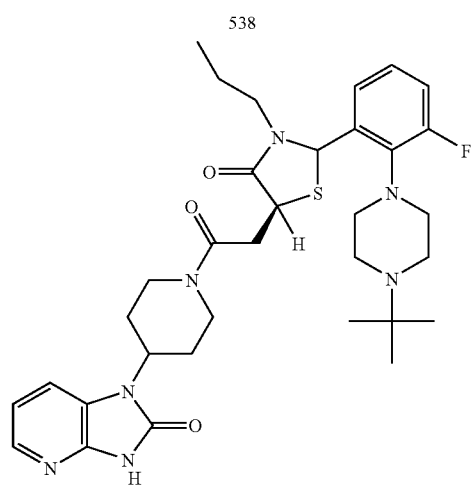
TABLE 1B-continued
539
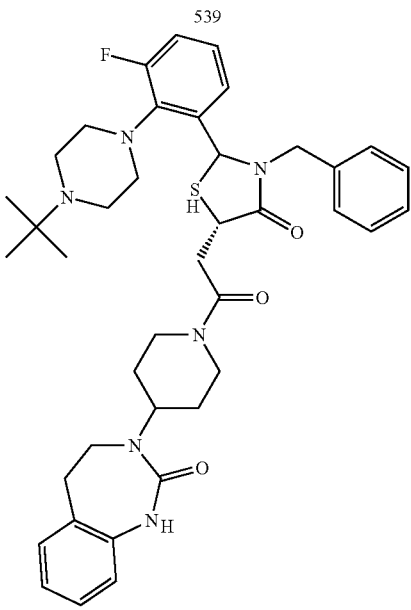
540
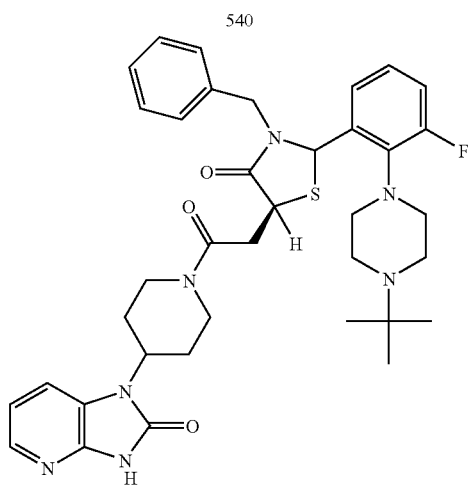

TABLE 1B-continued
541
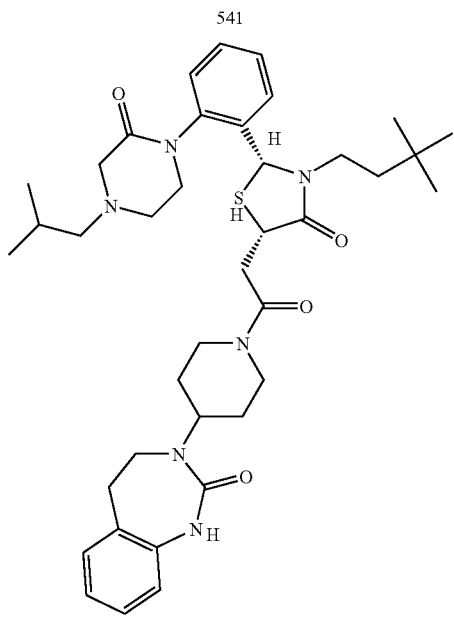
542
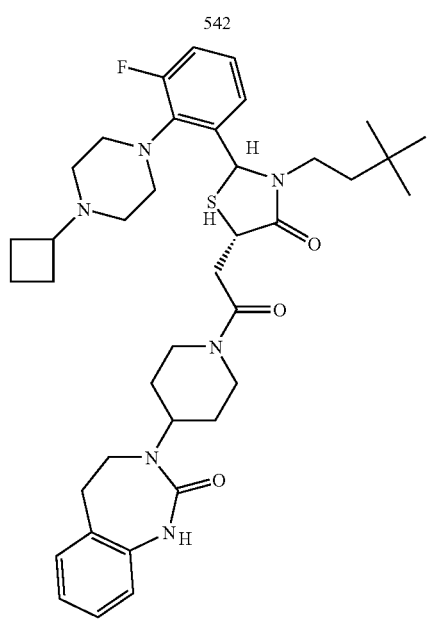
TABLE 1B-continued
543
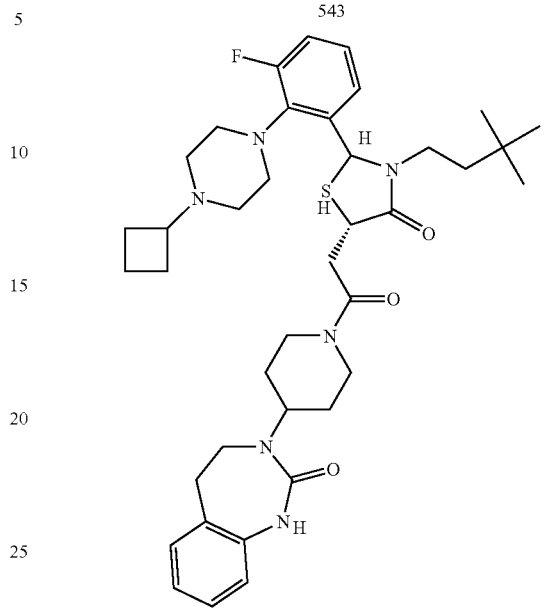
544
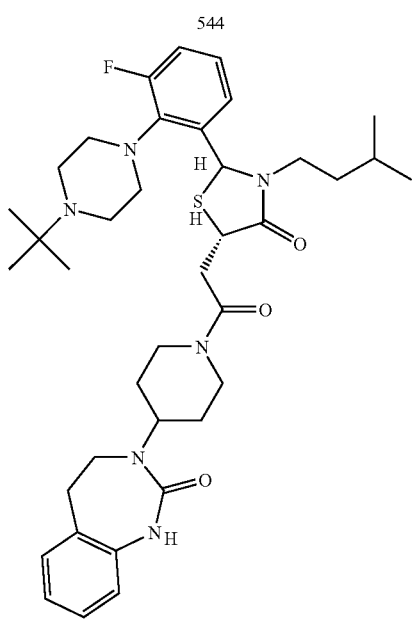

TABLE 1B-continued
545
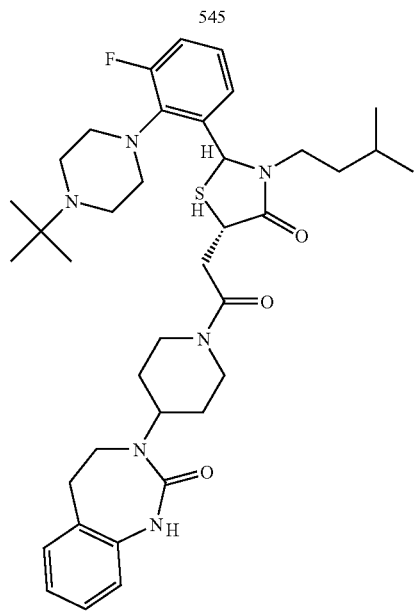
546
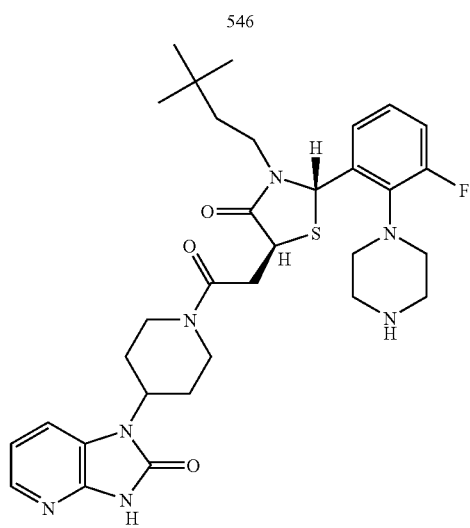
TABLE 1B-continued
547
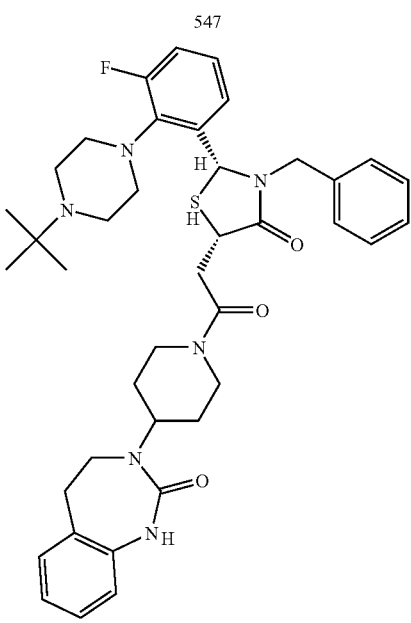
548
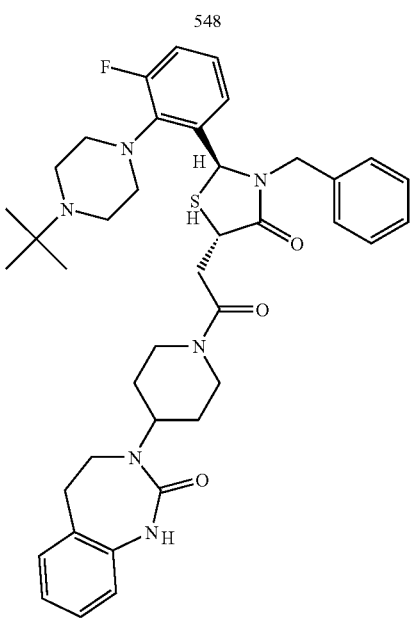

TABLE 1B-continued
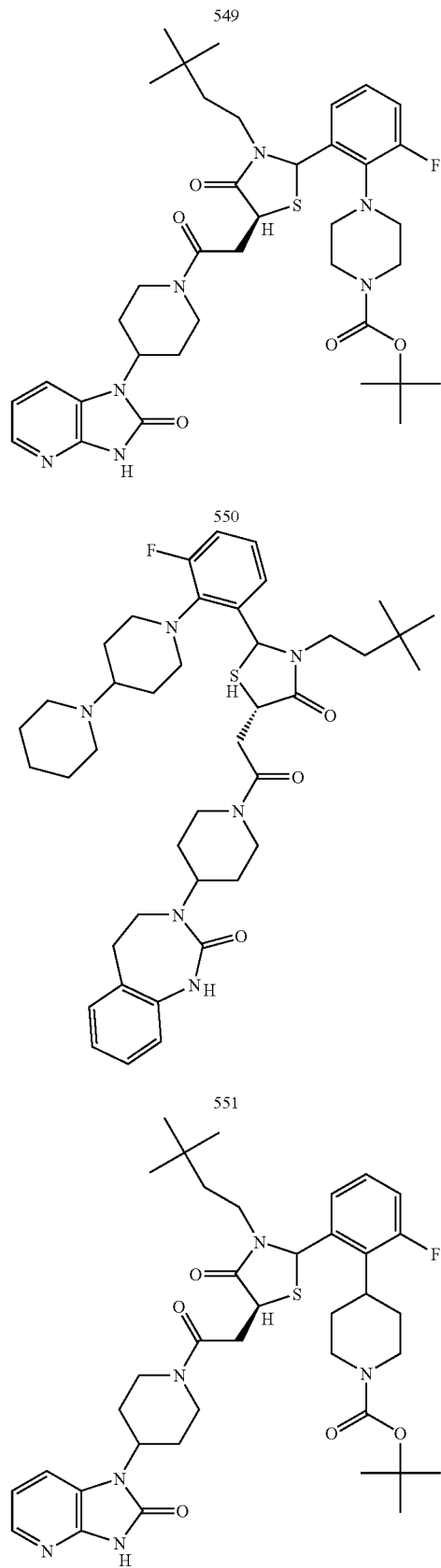
TABLE 1B-continued

TABLE 1B-continued
554
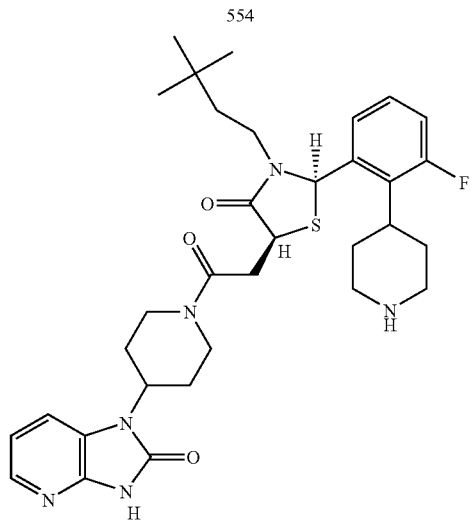
555
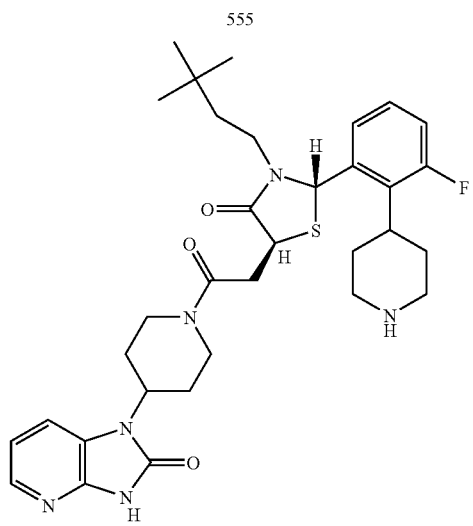
556
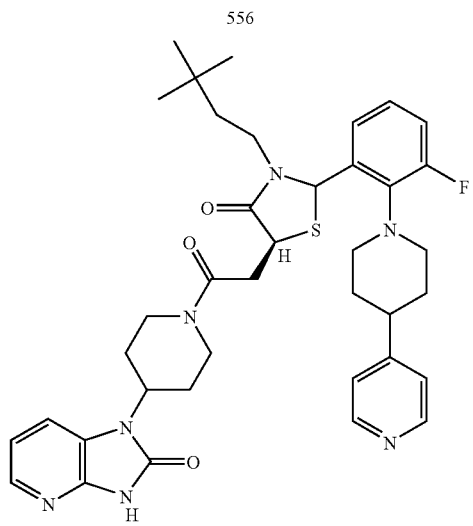
TABLE 1B-continued
557
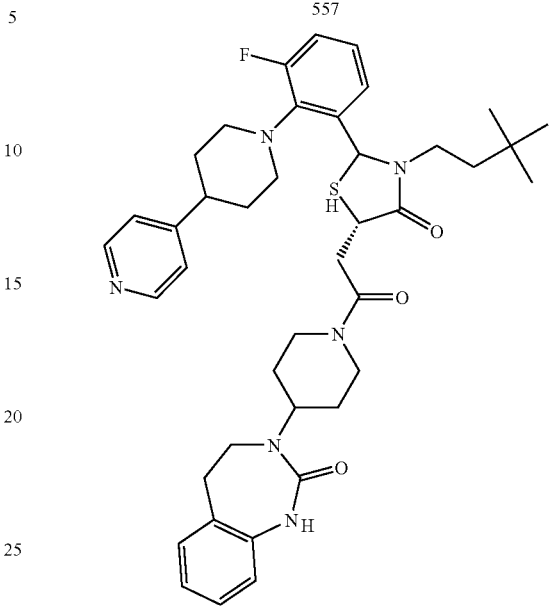
558
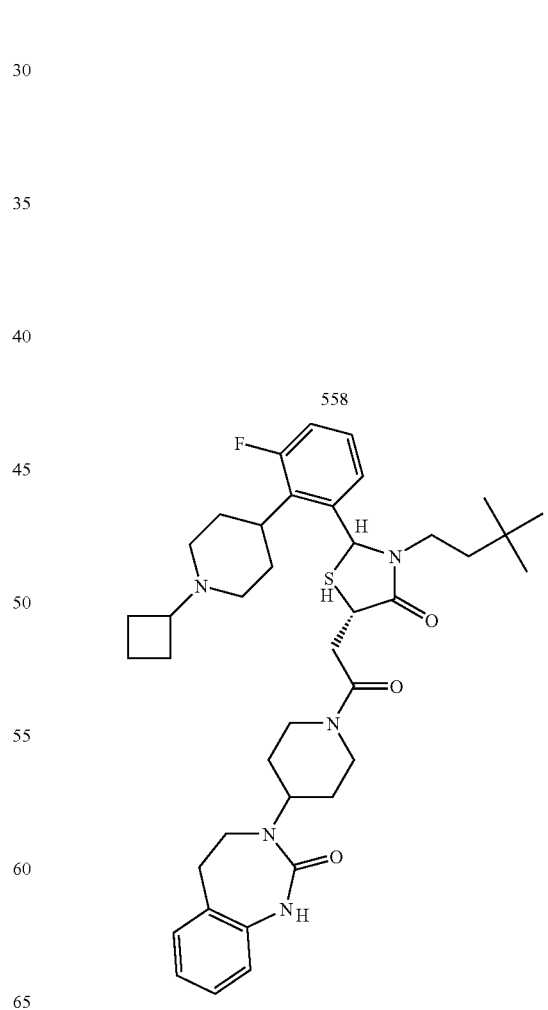

TABLE 1B-continued
559
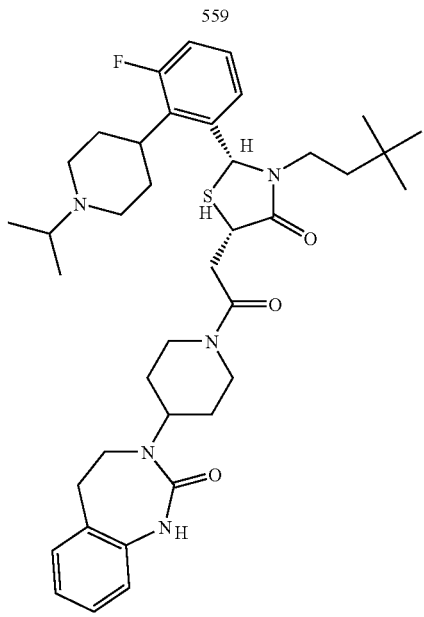
560
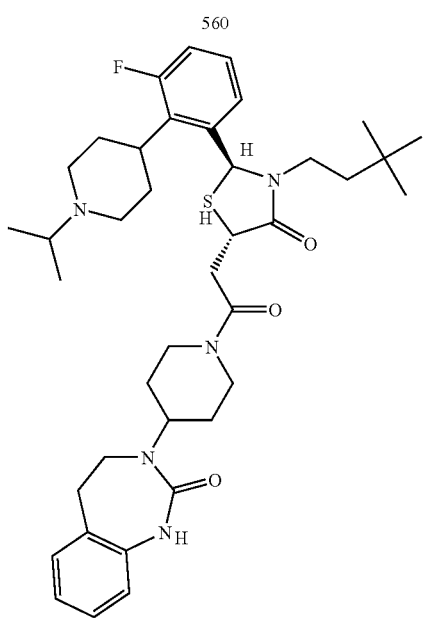
TABLE 1B-continued
561
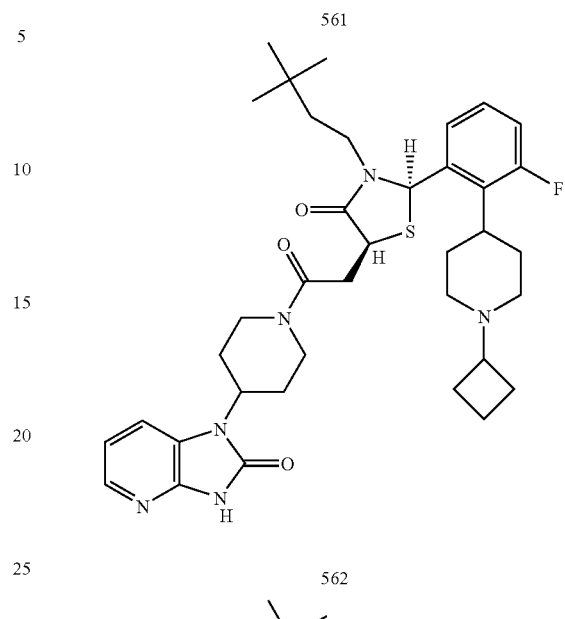
562
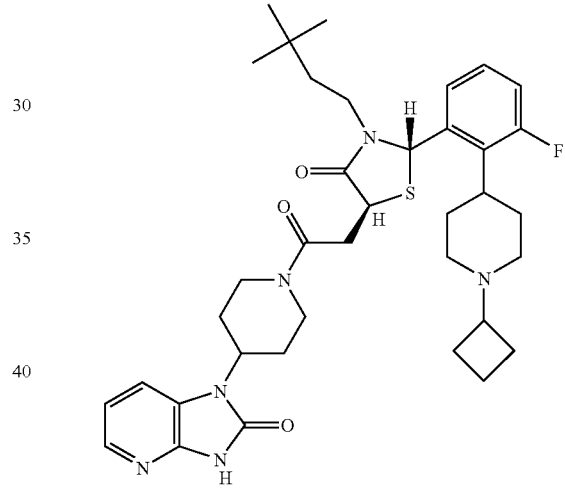
563
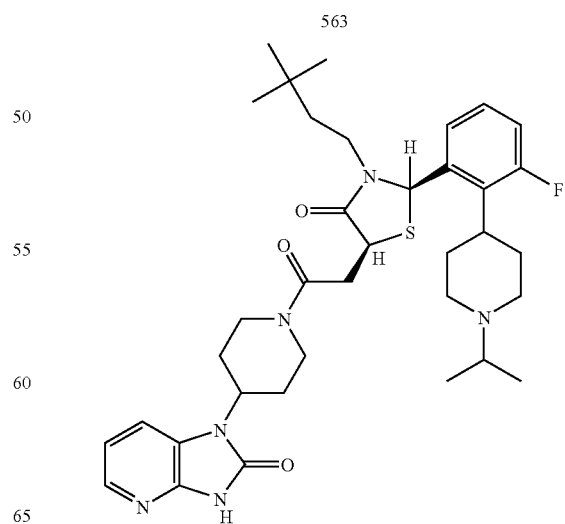

TABLE 1B-continued

564

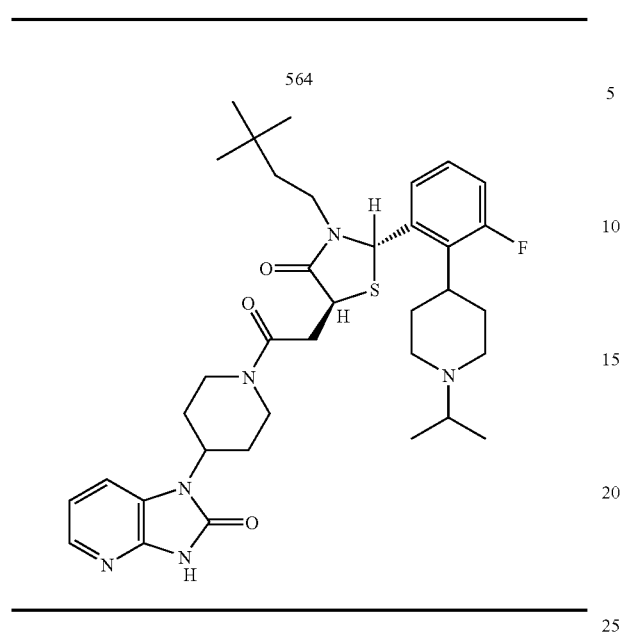

Compounds of the present invention may be readily prepared by methods well known in the art. Synthetic schemes for preparing the compounds of the present invention are shown below for illustrative purposes.

Scheme 1: Preparation of compounds of formula I':

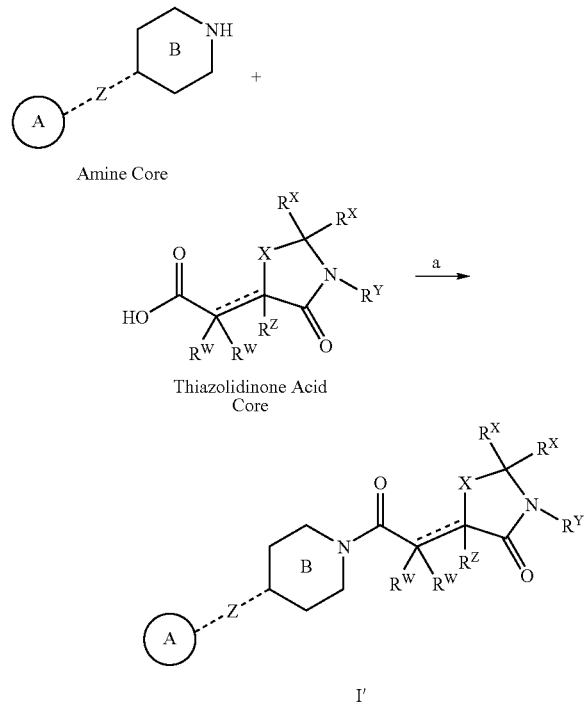

a) HATU, D$^i$PEA, DMF, RT, 16 h.

Compounds of formula I are prepared as shown in Scheme 1 above, wherein an amine core, containing the ring A, and the thiazolidinone acid core are combined under suitable conditions to provide compounds of formula I.

Scheme 1A: Preparation of compounds of formula I:

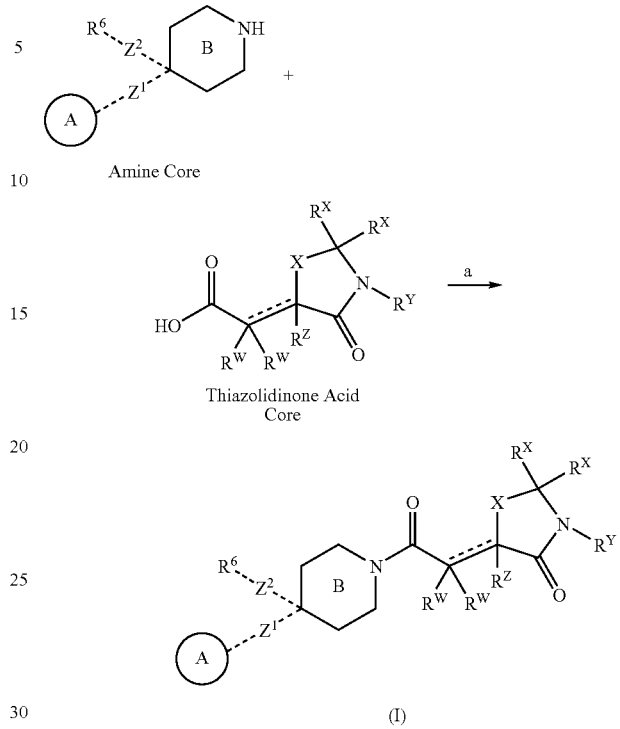

Scheme 2: Preparation of thiazolidinone core acid (Acid-I):

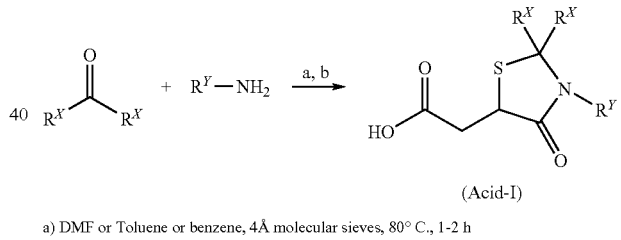

a) DMF or Toluene or benzene, 4Å molecular sieves, 80° C., 1-2 h
b) Mercaptosuccinic acid, 80° C., 16 h Scheme 3: Preparation of thiazolidinone core acid (Acid-II):

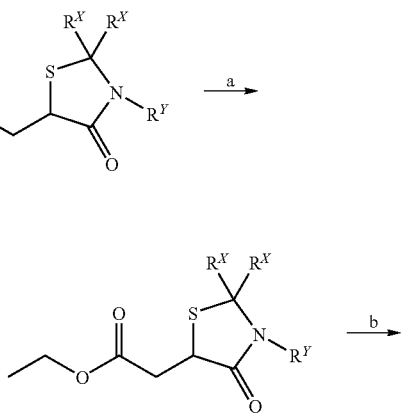

361

-continued

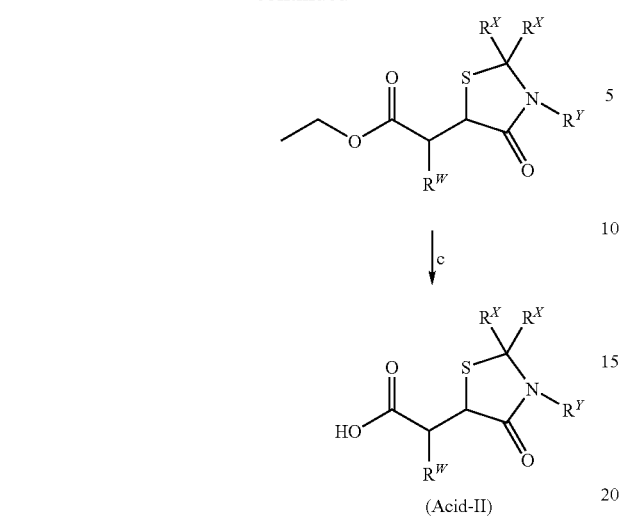

(Acid-II)

a) EtOH/H$_2$SO$_4$, 80° C., 24 h
b) LiHMDS, THF, 15 min, then R$^W$-LG, 0° C. to RT, 16 h
   NaOH (aq.), MeOH; wherein LG is a suitable leaving group.

Scheme 4: Preparation of thiazolidinone core acid (Acid-III):

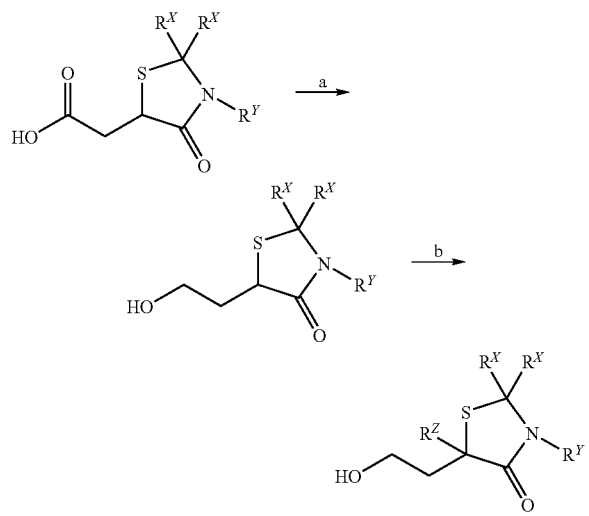

(Acid-III)

a) BOP, D$^i$PEA, THF, 6 h, then NaBH$_4$, RT
b) LiCl, LiHMDS, R$^Z$-LG, -78 C. ° C. to -40° C.; wherein LG is a suitable leaving group
c) Jones oxidation, 0° C.

362

Scheme 5: Preparation of thiazolidinone core acid (Acid-IV):

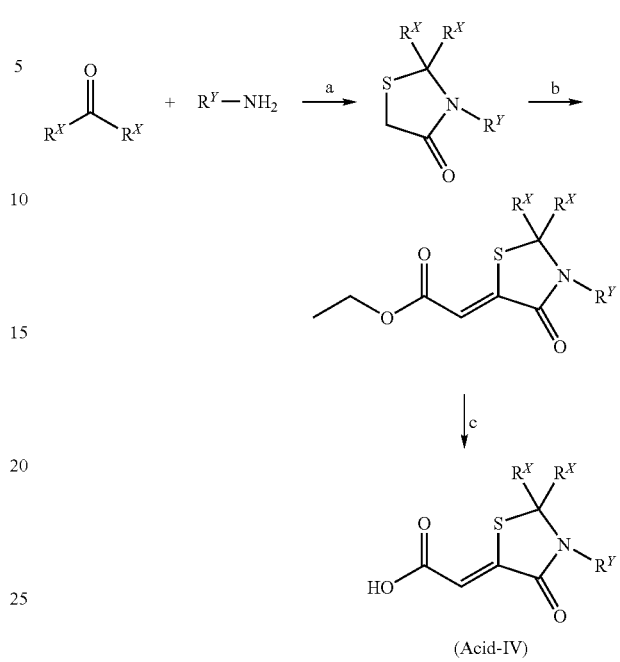

(Acid-IV)

a) THF/trimethoxyorthoformate, thioacetic acid, 80° C., 16 h or DMF, 2 h, 80° C., then thioacetic acid, 80° C., 16 h.
b) LDA, -78 C. ° C. to RT, then ethyl glyoxalate, RT, 16 h
c) NaOH (aq.), MeOH.

Scheme 6: Preparation of thiazolidinone core acid (Acid V):

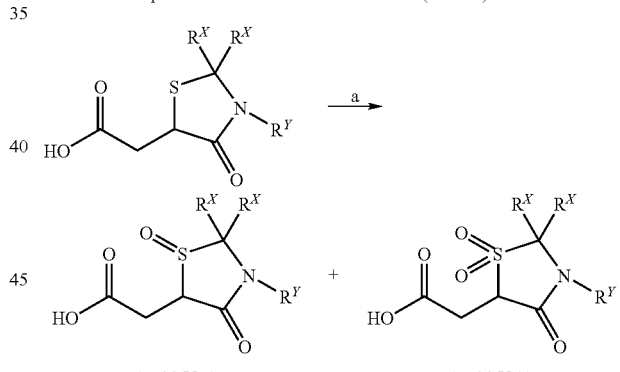

(Acid-V-a)     (Acid-V-b)

a) mCPBA, CHCl$_3$, 0° C. to RT, 16 h

Scheme 7: Preparation of Amine core (C-A-i-d):

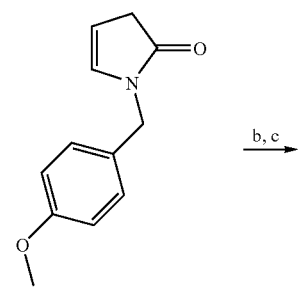

363
-continued

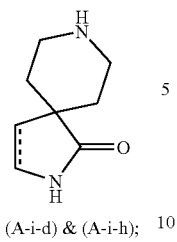

(A-i-d) & (A-i-h);

a) 4-Methoxybenzylchloride, TEA, DMF
b) tert-butyl bis(2-chloroethyl)carbamate, LDA, THF
c) TFA/DCM Amine core C-A-i-e, wherein ring A is A-i-e (see, supra) can be prepared using the method of Scheme 7.

Scheme 8: Preparation of Amine core C-A-ii-c:

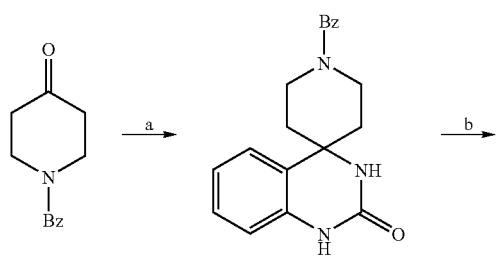

364
-continued

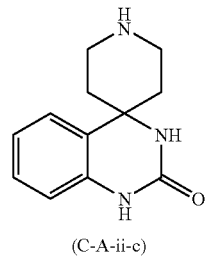

(C-A-ii-c)

a) Polyphosphoric acid, 100° C., then, phenylurea, 150° C.
b) MeOH, HCl, Pd/C, $H_2$ Scheme 9: Preparation of Amine core C-A-ii-d:

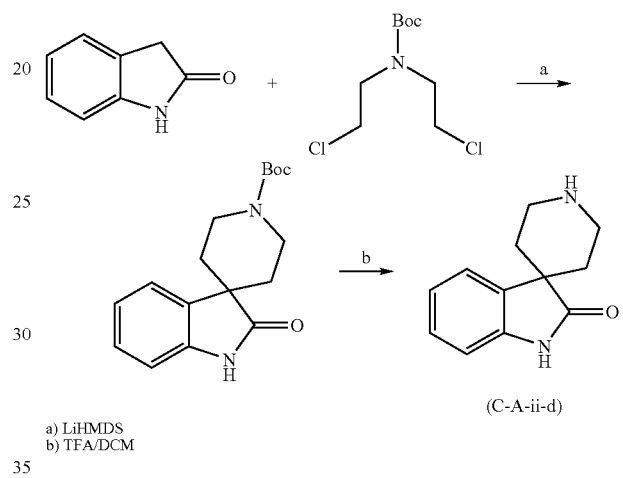

a) LiHMDS
b) TFA/DCM

Scheme 10: Preparation of Amine core C-A-ii-e:

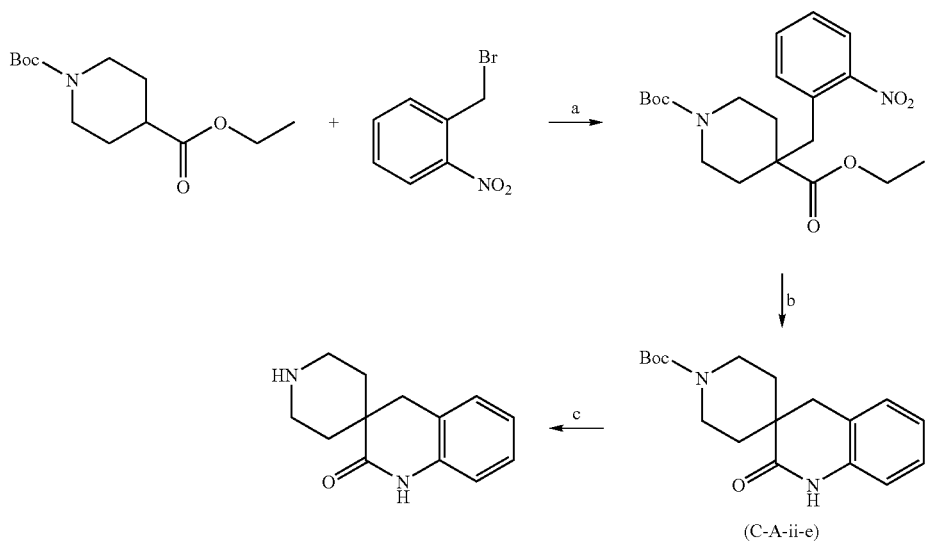

a) NaHMDS
b) $H_2$, Pd/C
c) HCl

Scheme 11: Preparation of Amine core C-A-v-e:

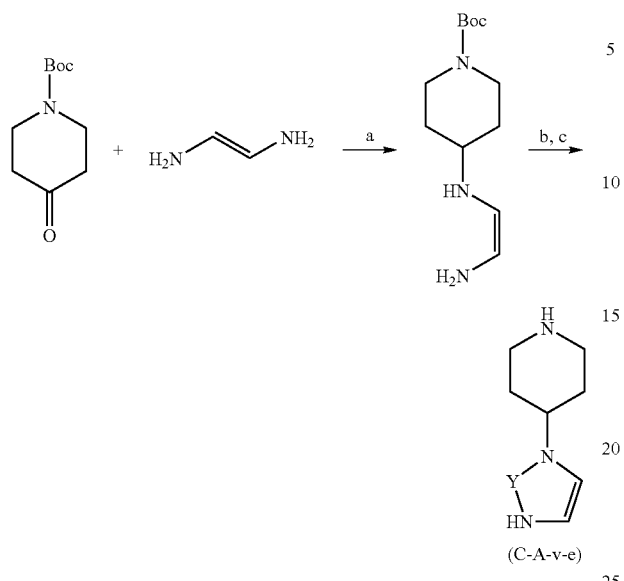

a) NaBH₄CN
b) CDI or SOCl₂ or 1,1'-Sulfonyldiimidazole
c) TFA/DCM

Amine cores C-A-v-a, C-A-v-c, and C-A-v-f, containing ring A embodiments, A-v-a, A-v-c, and A-v-f, respectively, can be readily prepared using the method of Scheme 11.

Scheme 12: Alternative Preparation of Amine core C-A-v-e:

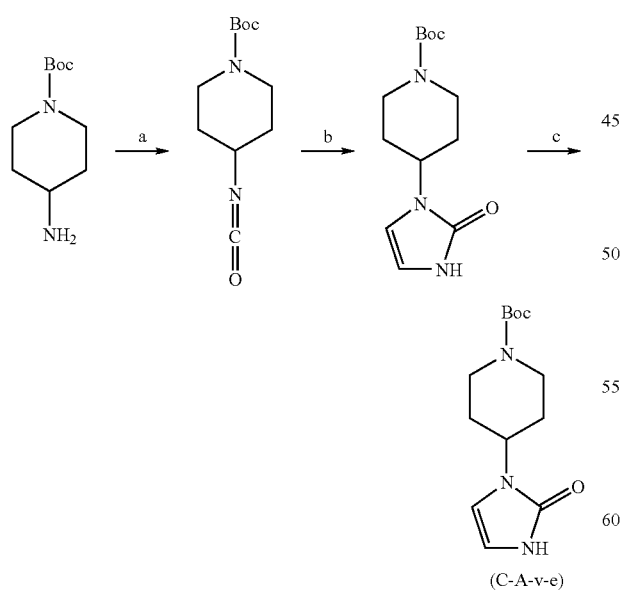

a) COCl₂
b) Aminoacetaldehyde dimethylacetal
c) TFA/DCM

Scheme 13: Preparation of Amine Core C-A-vi-a:

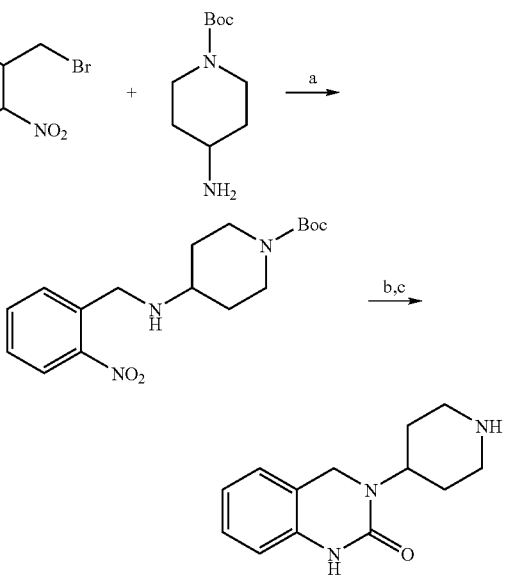

a) TEA, DCM, RT, 16 h
b) CDI, THF/DCM, 16 h.
c) TFA/DCM

Scheme 14: Preparation of Amne core C-A-vi-c:

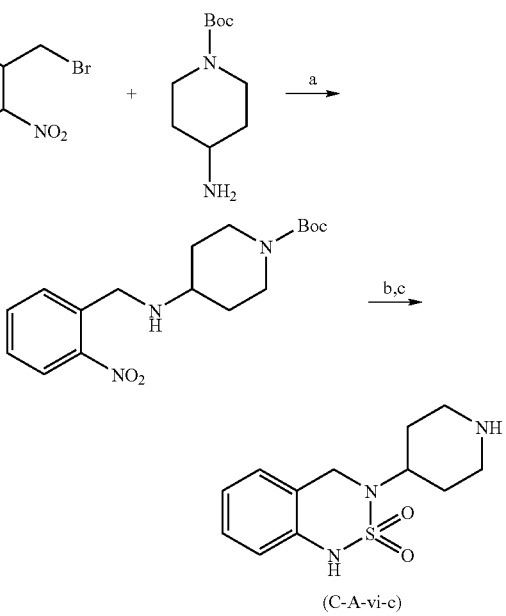

a) TEA, DCM, RT, 16 h
b) 1,1'-Sulfonyldiimidazole, THF/DCM.
c) TFA/DCM

Scheme 15: Preparation of Amine Core C-A-vi-f:
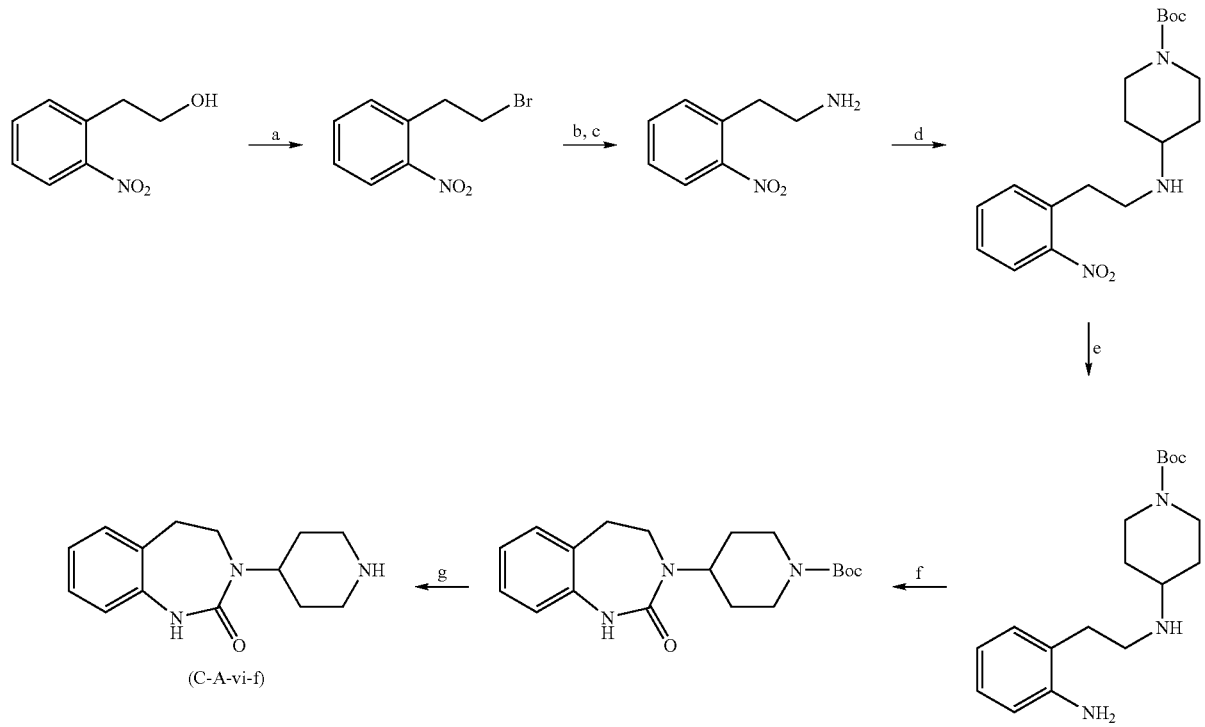
a) PPh₃, CBr₄, DCM, 0° C. to RT, overnight
b) NaN₃, H₂O, CH₃CN
c) 1) PPh₃, toluene, RT, 16 hours;
   2) Acetic acid/48% HBr in Acetic acid, 100° C. 1 h.
d) tert-butyl 4-oxopiperidine-1-carboxylate, NaBH(OAc)₃, AcOH, DMF
e) CDI, THF
f) TFA/DCM
Scheme 16: Preparation of Amine Core A-v-e:
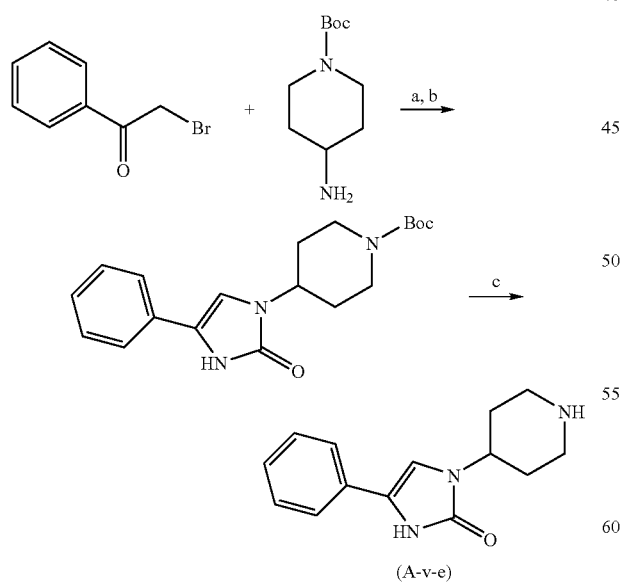
a) DCM, D$^i$PEA
b) NaOCN, AcOH,
c) TFA/DCM
Scheme 17: Preparation of Amine Core A-v-f:
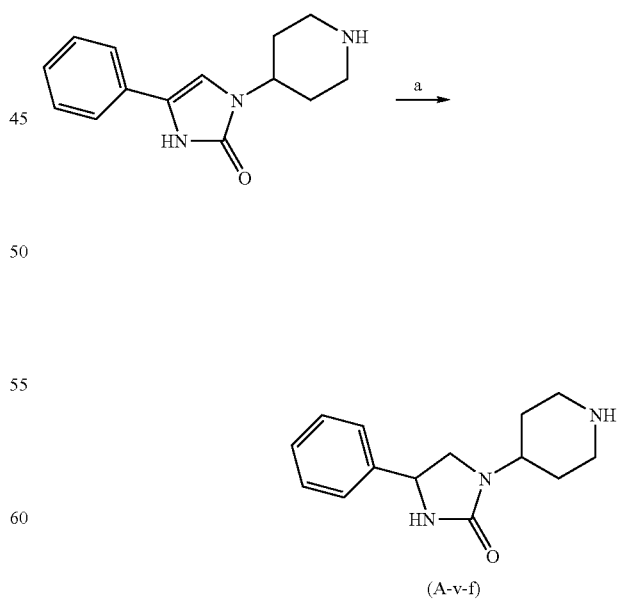
a) H₂, Pd/C, MeOH Scheme 18: Preparation of Amine Core A-v-g:
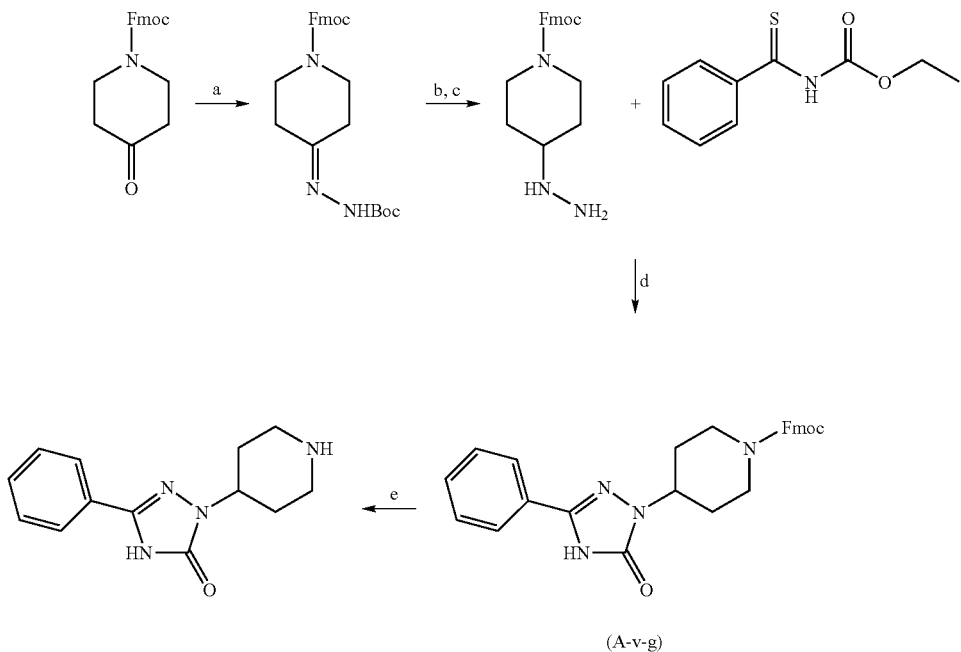
(A-v-g)
a) H$_2$NNHBoc, EtOH
b) PtO$_2$, AcOH, H$_2$
c) TFA
d) D$^i$PEA, THF
e) Et$_2$NH, THF
Scheme 19: Preparation of Amine Core A-vi-h:
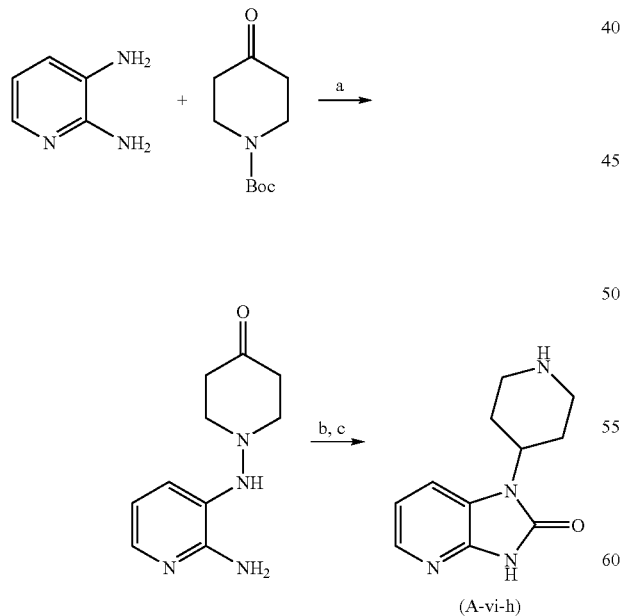
(A-vi-h)
a) NaBH(OAc)$_3$, DCE
b) CDI, CH$_3$CN
c) HCl, Et$_2$O Scheme 20: Preparation of Amine Core A-vi-i:

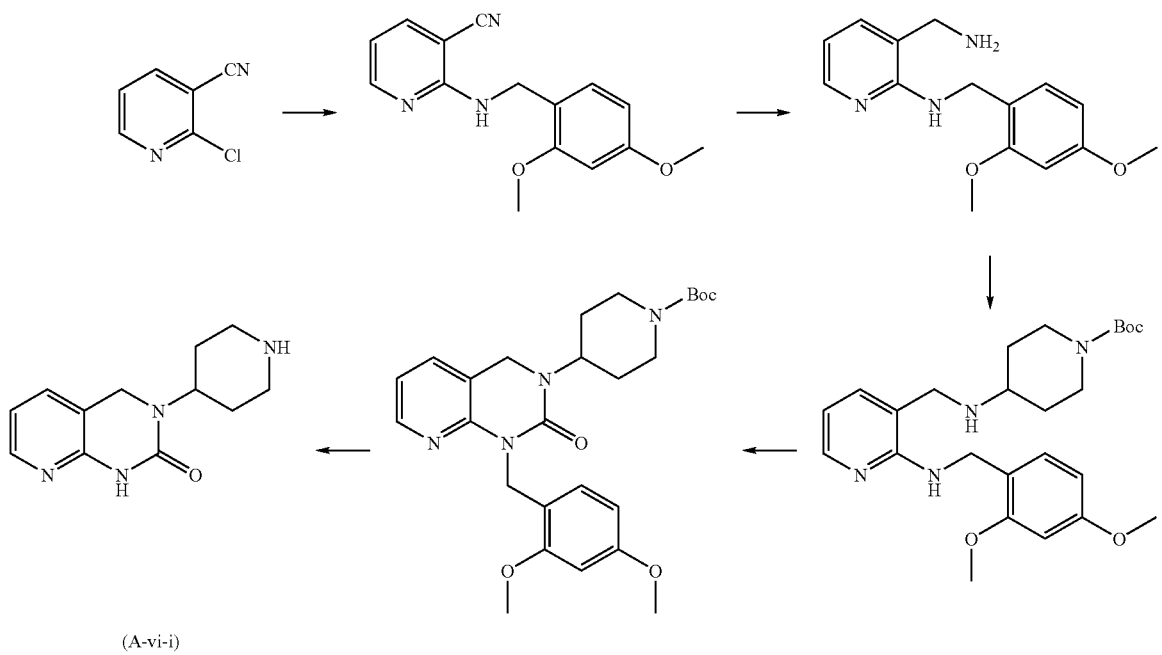

(A-vi-i)
a) 2,4-Dimethoxybenzylamine, DMA, TEA
b) LiAlH₃, THF
c) tert-butyl 4-oxopiperidine-1-carboxylate, NaBH(OAc)3, AcOH, DCE
d) CDI, DMF
e) TFA/DCM Scheme 21: Preparation of Amine Core A-ii-h:

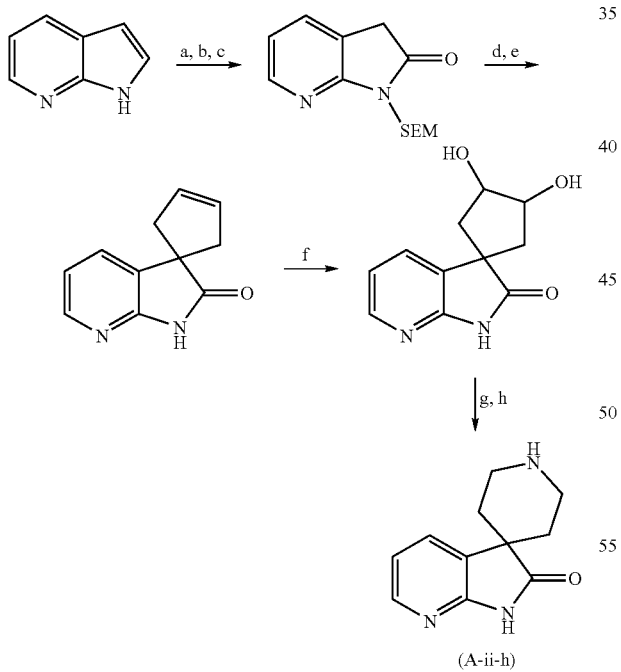

(A-ii-h)

a) NaH, SEM-Cl, DMF
b) Pyridinehydrobromide perbromide, dioxane
c) Zn, AcOH
d) cis-1,4-dichlorobut-2-ene, Cs₂CO₃, DMF
e) TFA/DCM
f) OsO₄, Me₃N-O, DCM
g) NaIO₄, EtOH, H₂O
h) NH₄OH, H₂, Pd/C Scheme 22: Preparation of Amine Core A-ii-i:

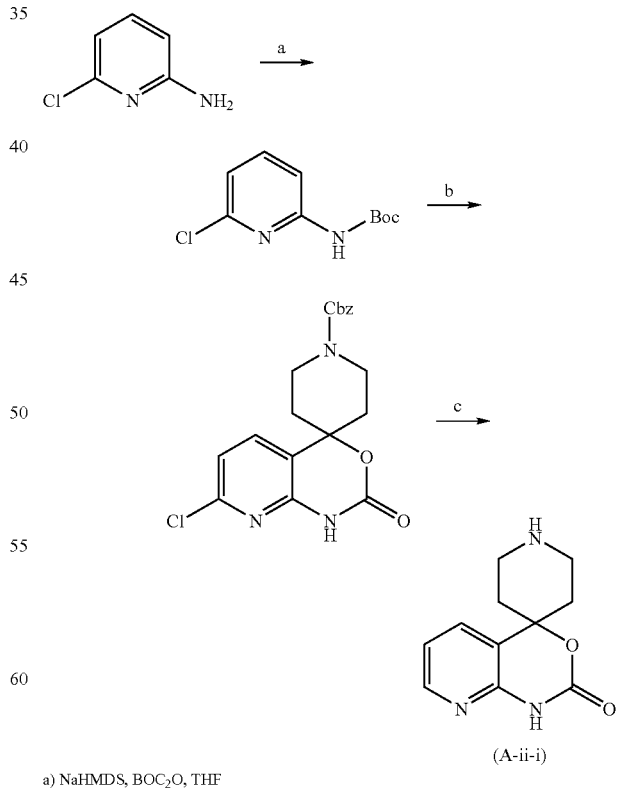

(A-ii-i)

a) NaHMDS, BOC₂O, THF
b) nBuLi, TMEDA, benzyl 4-oxopiperidine-1-carboxylate, THF
c) H₂, Pd/C
d) EtOH Scheme 23: Preparation of Amine Core A-i-h:
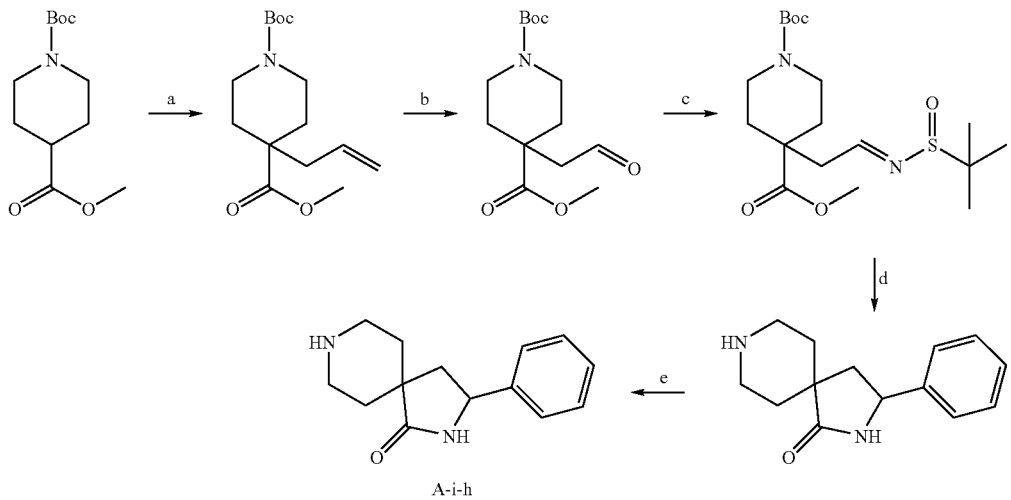
A-i-h
a) KHMDS, allylbromide, THF
b) O₃, MeOH, DCM, then Me₂S
c) $^t$BuSONH₂, CuSO₄, DCE
d) PhLi, Et₂O
e) HCl, MeOH
Scheme 24: Preparation of Amine Core A-ii-j:
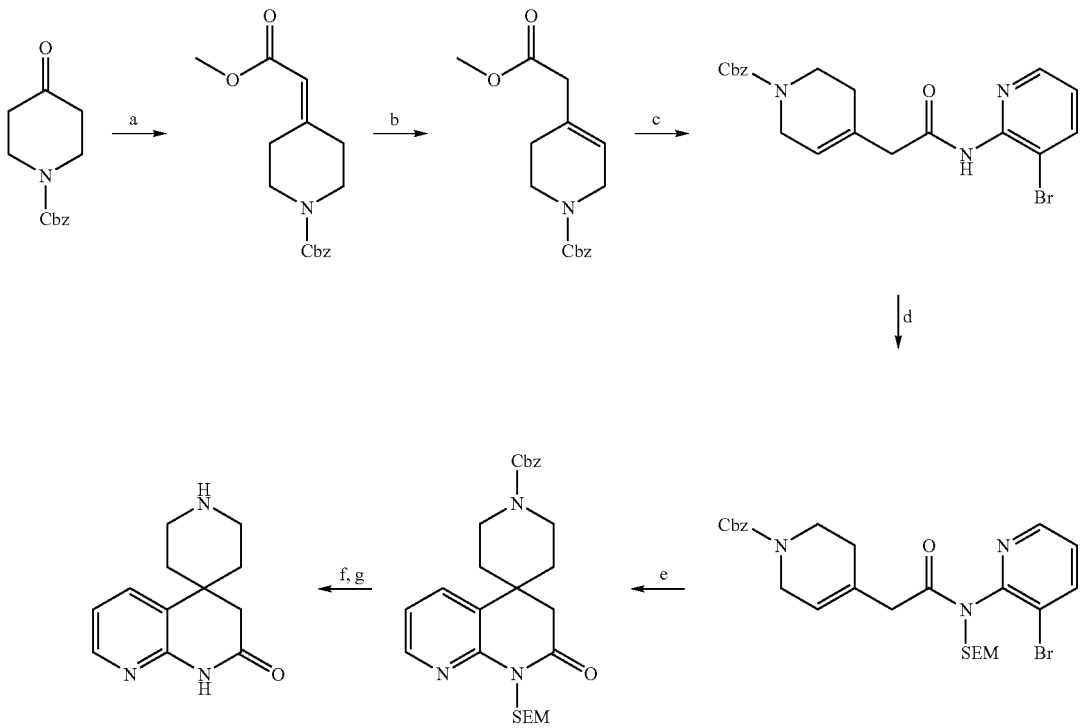
A-ii-j
a) (2-Methoxy-2-oxoethyl)(triphenyl)phosphonium chloride, benzene
b) DBU, DMF
c) 3-bromo-2-aminopyridine, AlMe₃, DCE
d) NaH, SEM-Cl, THF
e) Pd($^t$Bu₃)₂, dicyclohexylmethylamine, dioxane
f) TFA
g) H₂, Pd/C Scheme 25: Preparation of Amine Core A-i-i:
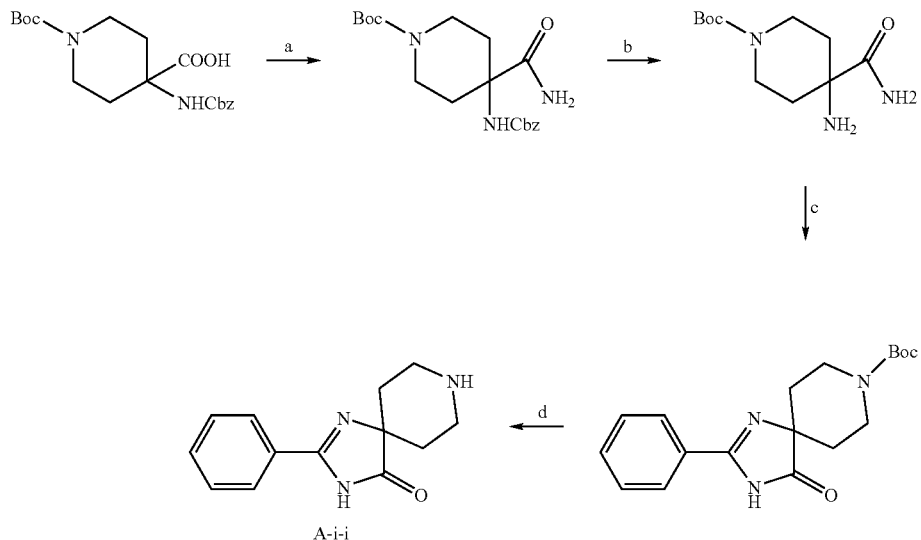
a) EDC, HOBt, NH₃, TEA, DMF
b) H₂, Pd/C, EtOH
c) 1-(Trimethoxymethyl)benzene, toluene
d) TFA/DCM
Scheme 26: Preparation of Amine Core A-i-j:
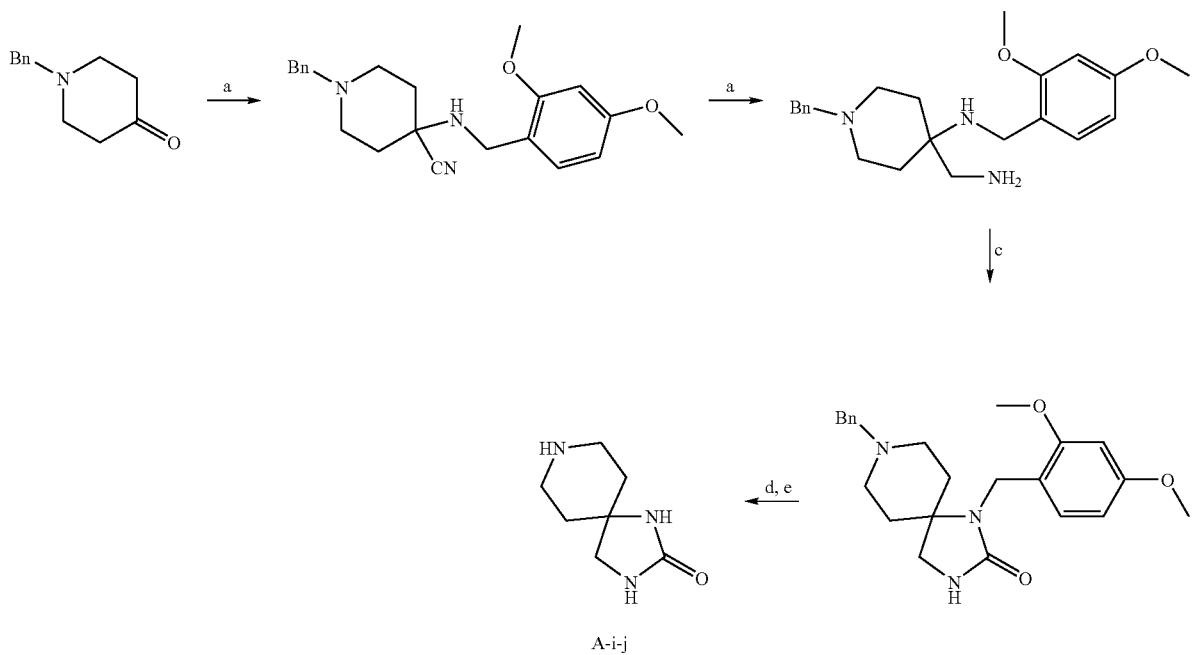
a) 2,4-Dimethoxybenzylamine, TMSCN
b) H₂, Rh/alumina
c) CDI
d) TFA/DCM
e) H₂, Pd/C Scheme 27: Preparation of Amine Core A-i-k:
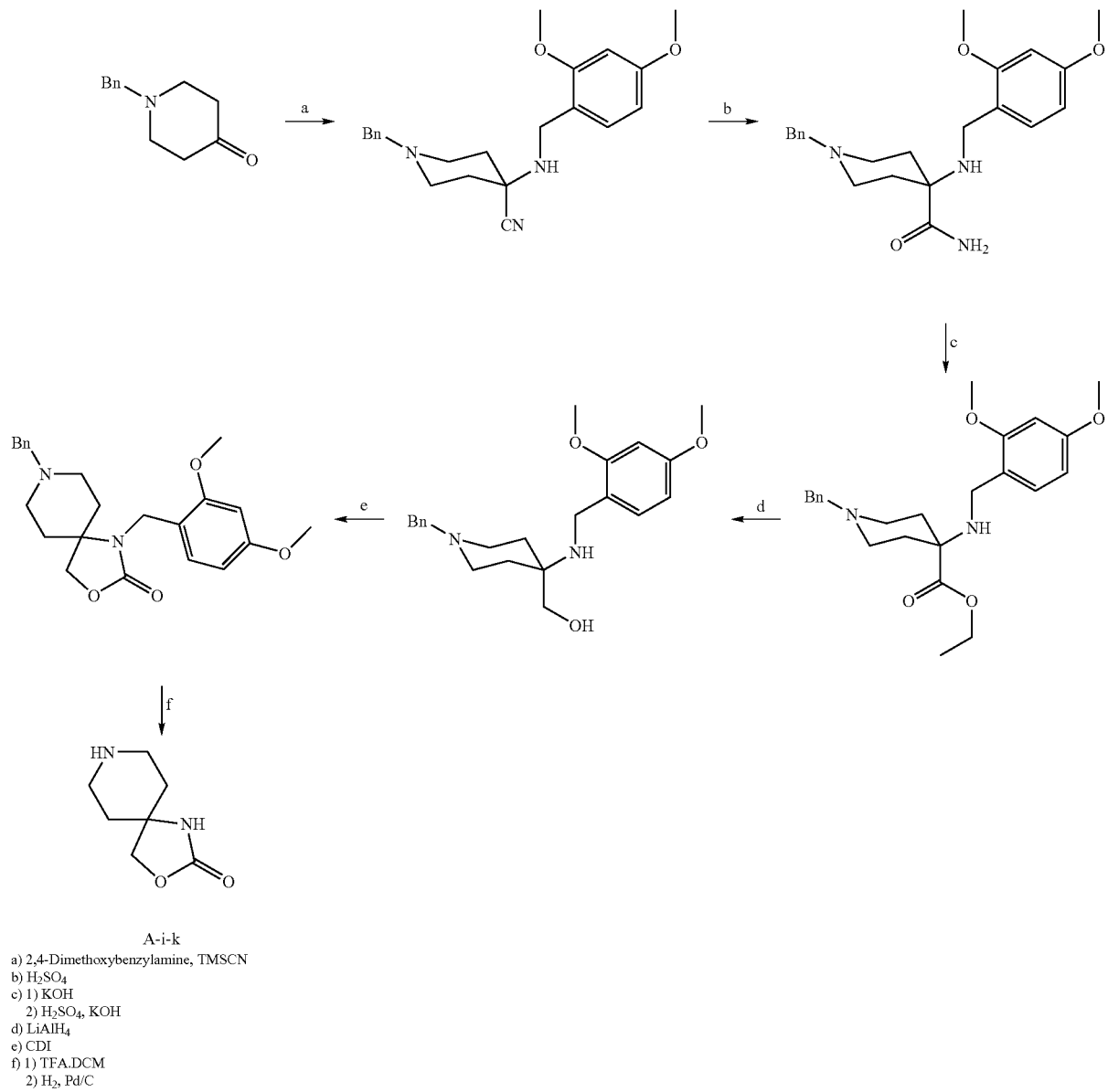
A-i-k
a) 2,4-Dimethoxybenzylamine, TMSCN
b) $H_2SO_4$
c) 1) KOH
   2) $H_2SO_4$, KOH
d) LiAlH$_4$
e) CDI
f) 1) TFA.DCM
   2) $H_2$, Pd/C
Scheme 28: Preparation of Amine Core A-i-l:
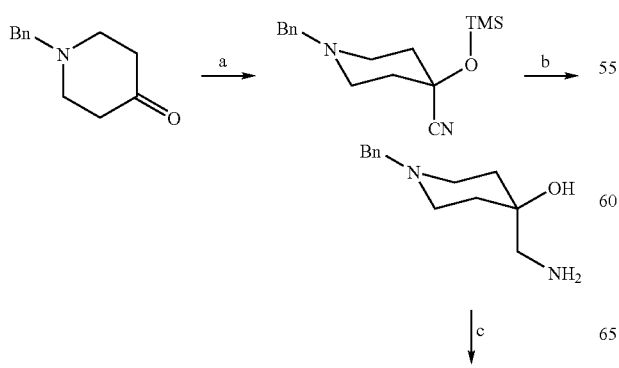

379

-continued

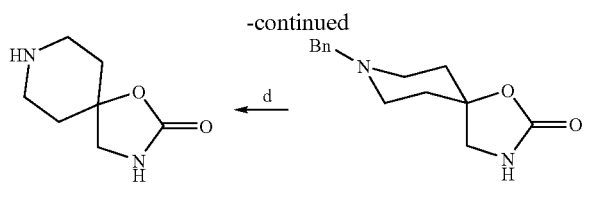

a) TMSCN
b) LiAlH₄
c) COCl₂
d) 1) TFA/DCM
   2) H₂, Pd/C

Amine core A-i-a may be prepared according to the method disclosed in WO2005097795. Amine core A-ii-a may be prepared according to the method disclosed in US2006293281. Amine core A-ii-a wherein the fused 6-membered ring is pyridyl may be prepared according to the method disclosed in WO2007016087. Amine core A-v-b may be prepared according to the method disclosed in WO2006044504. Amine core A-v-i may be prepared according to the method disclosed in WO2006044504. Amine core A-yl-b as the HCl salt may be prepared according to the method disclosed in WO2005056550. Amine core A-yl-d may be prepared according to the method disclosed in Chem. Pharm. Bull., 34(5), pp. 1907-1916 (1986). Amine core A-yl-e is commercially available. Amine core A-v-h may be prepared according to the method disclosed in WO2007016087. Other amine cores not described in the schemes, experimentals, or referenced herein, can be prepared by methods known to one of skill in the art.

Scheme 29: Preparation of Compounds 478 and 479:

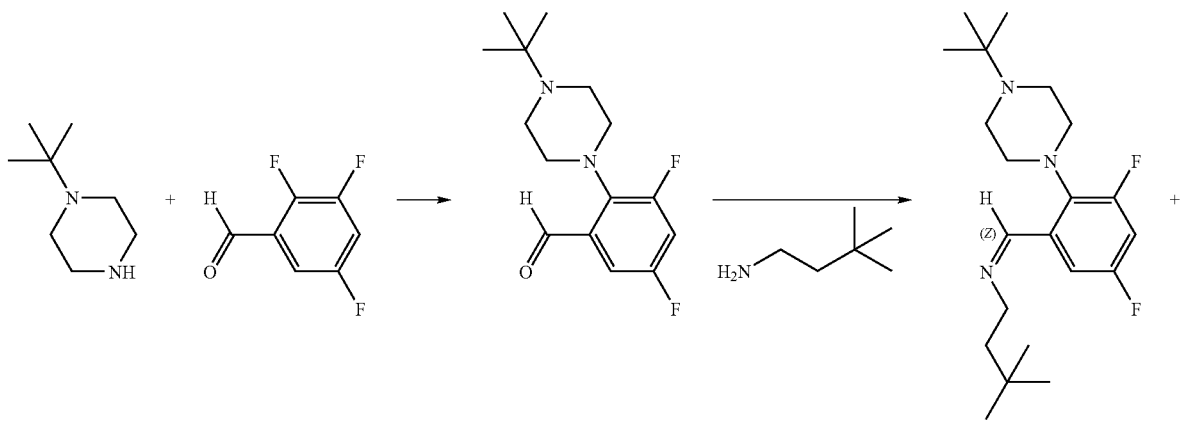

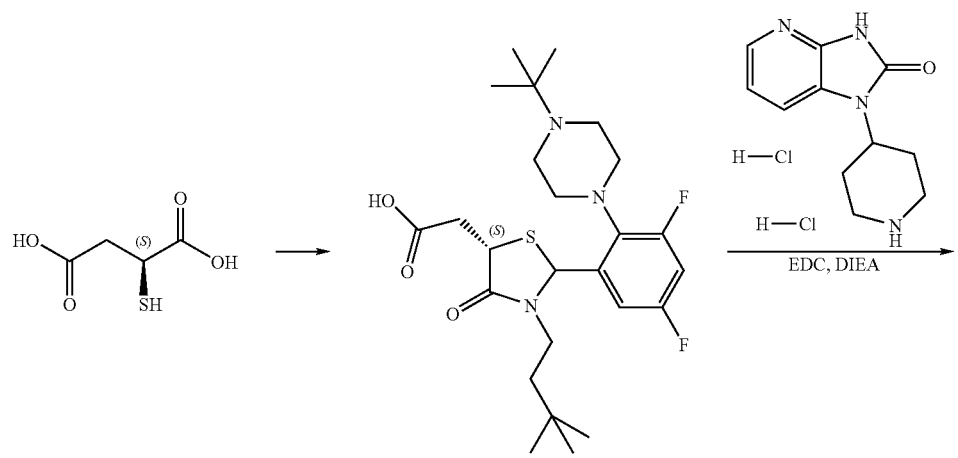

381
-continued
382
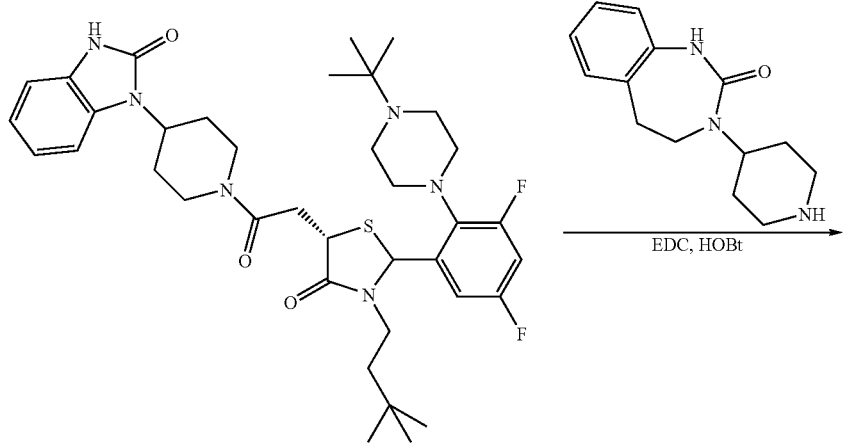
479
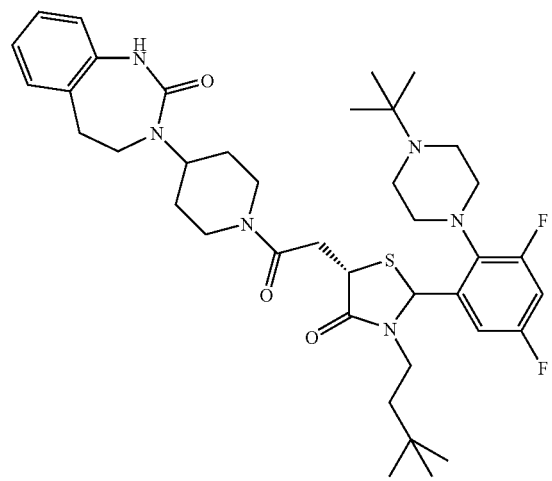
478
Scheme 30: Preparation of Compound 492:
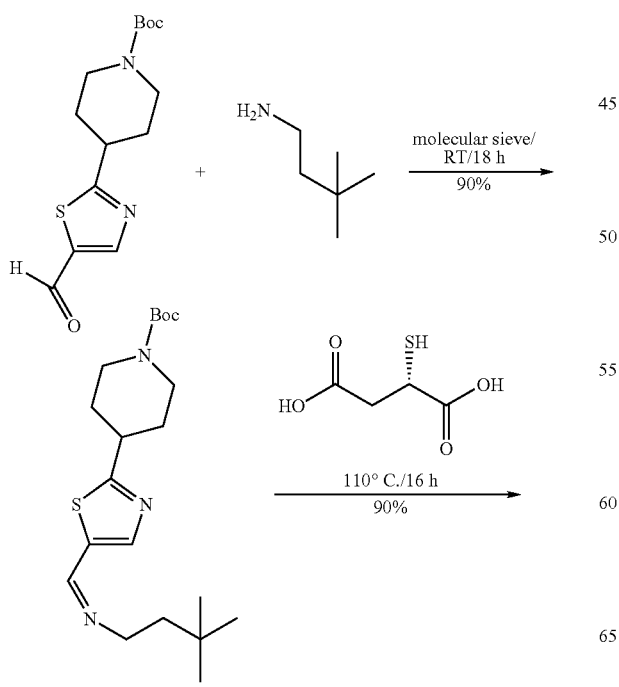

383
-continued
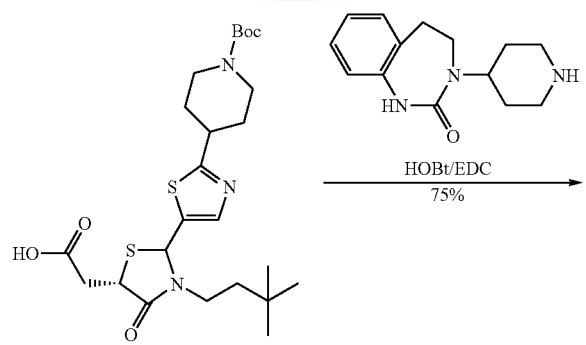
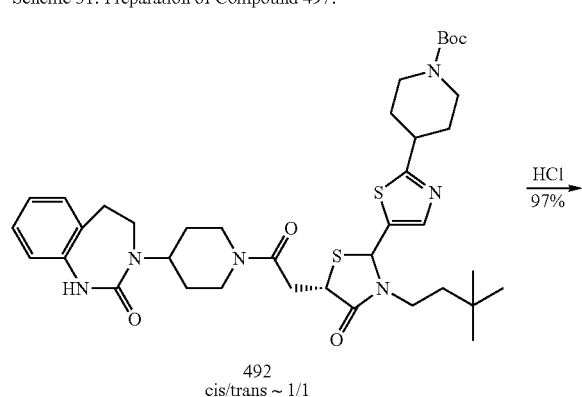
492
cis/trans ~ 1/1
Scheme 31: Preparation of Compound 497:
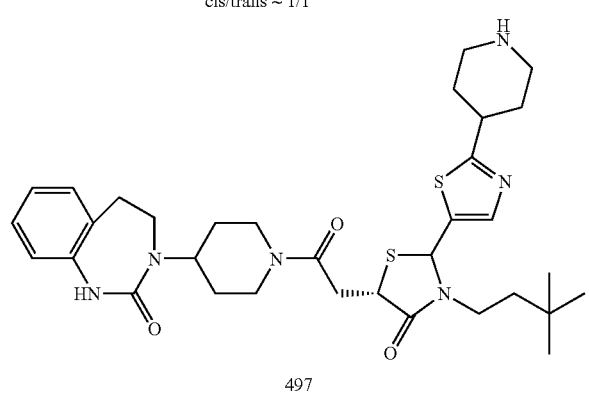
384
Scheme 32: Preparation of Compound 498
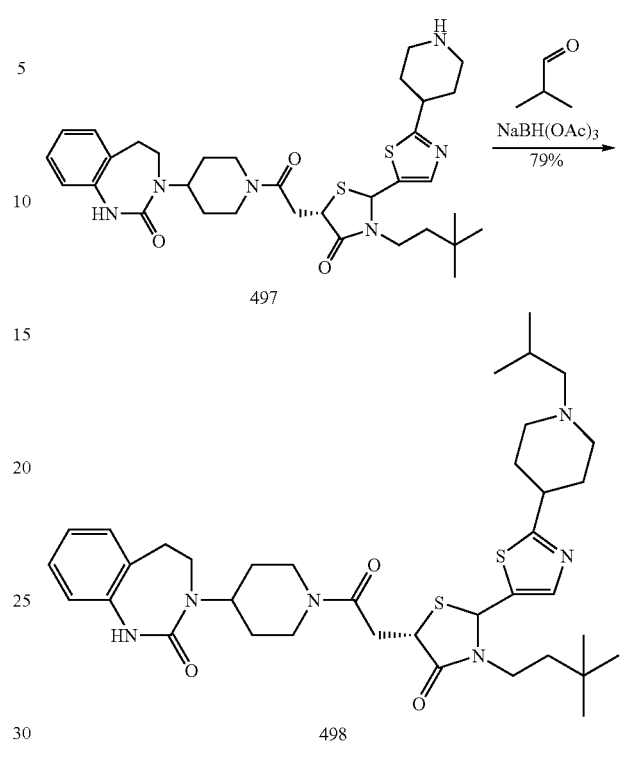
Scheme 33: Preparation of Compounds 480, 481, 482, 483, 484, 485, 486 and 487
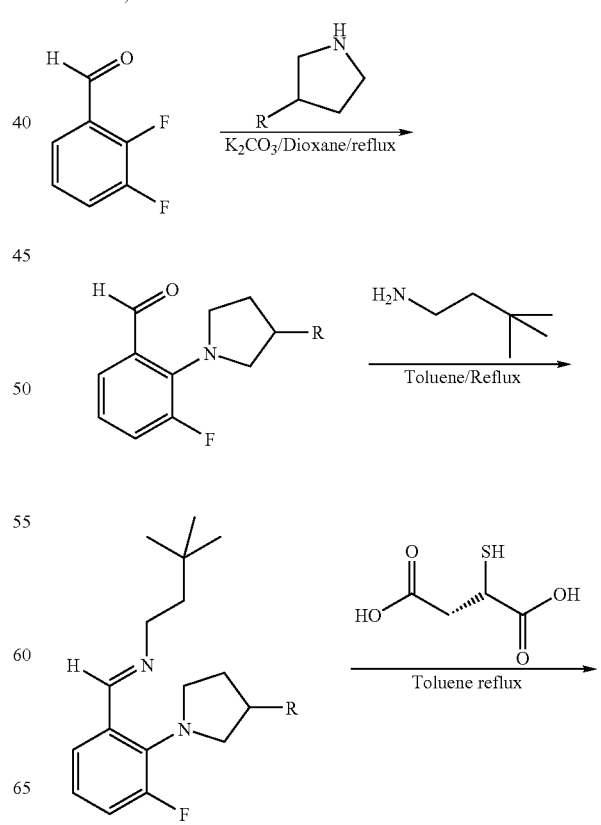

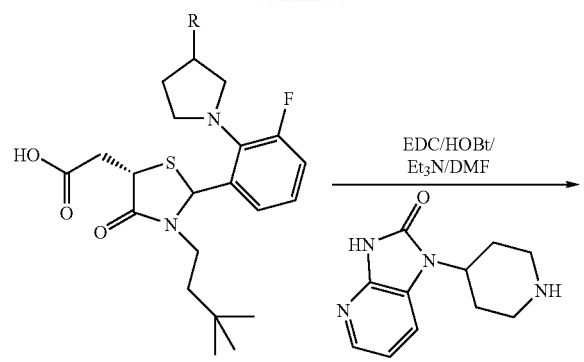
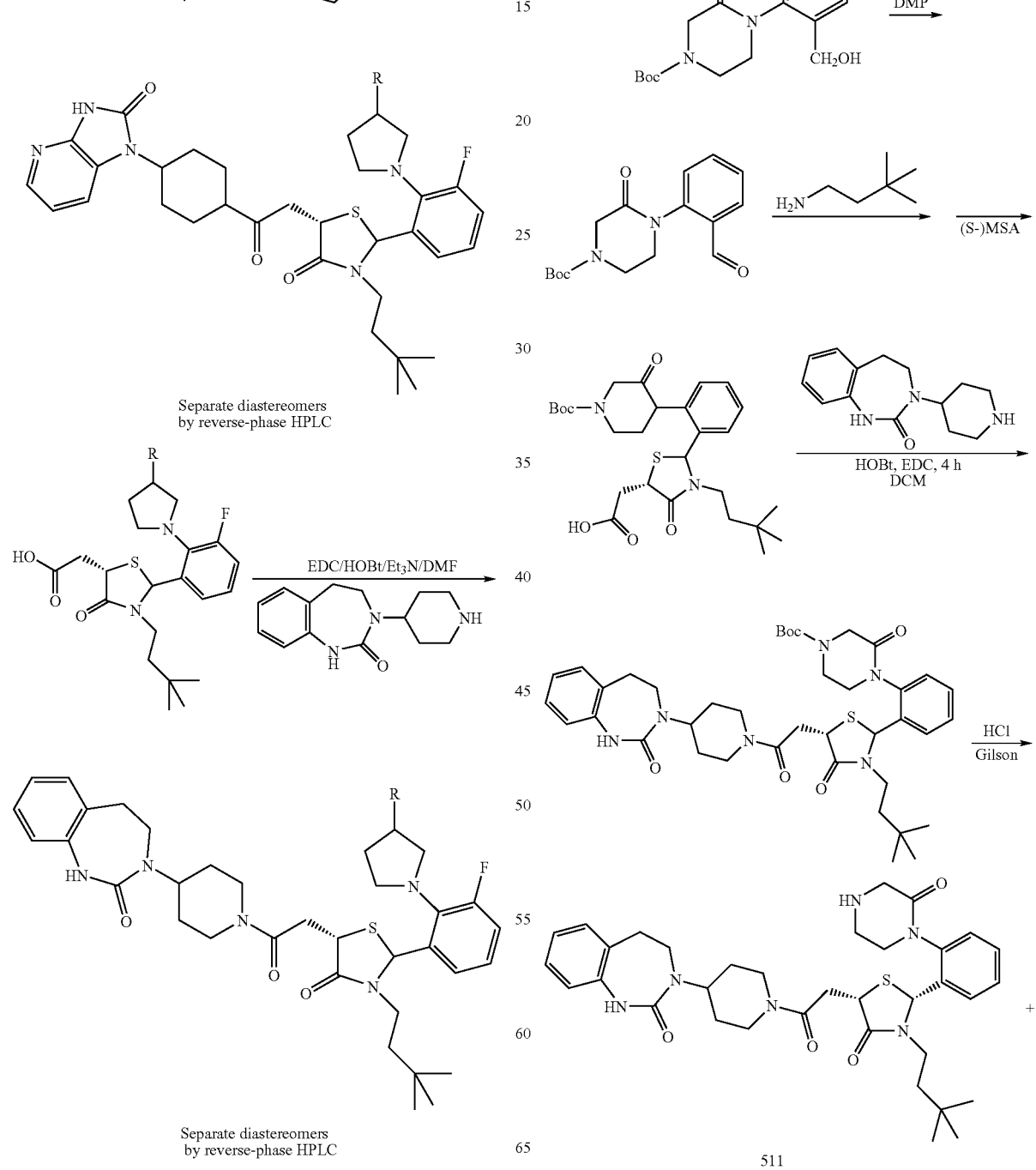
Scheme 34: Preparation of Compounds 511 and 512

387
-continued
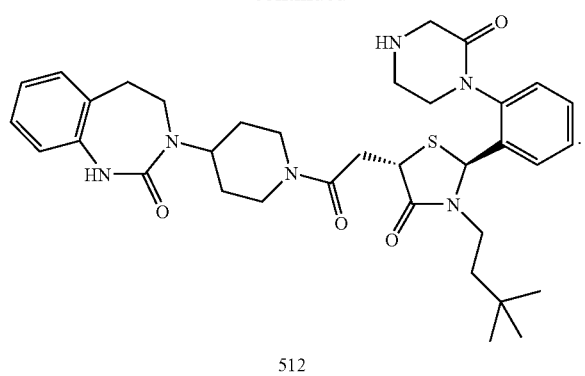
512
Compound 527 was also prepared to similar procedures to those listed in Scheme 34.
Scheme 35: Preparation of Compounds 500.
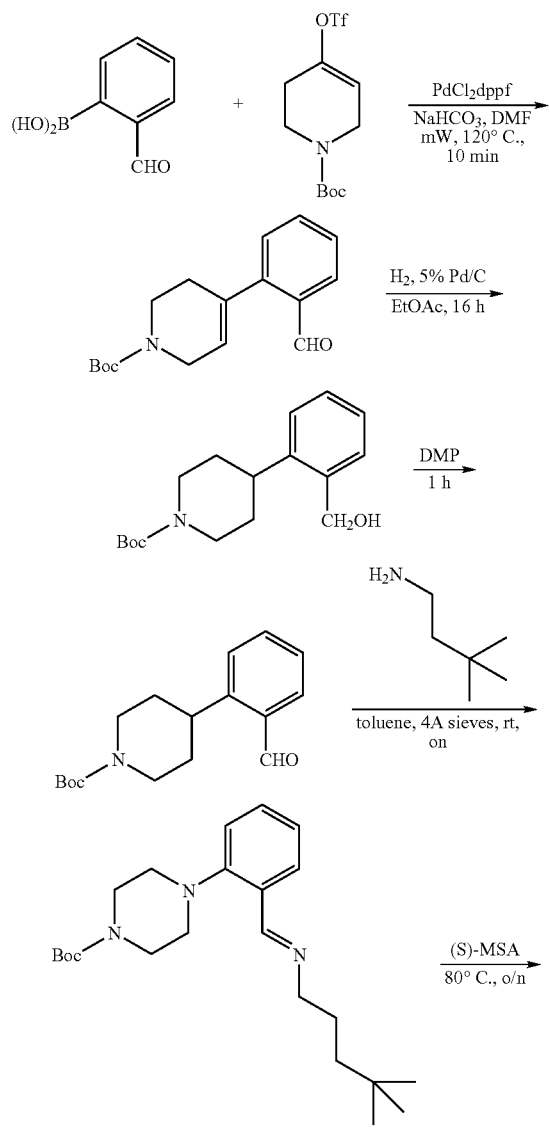
388
-continued
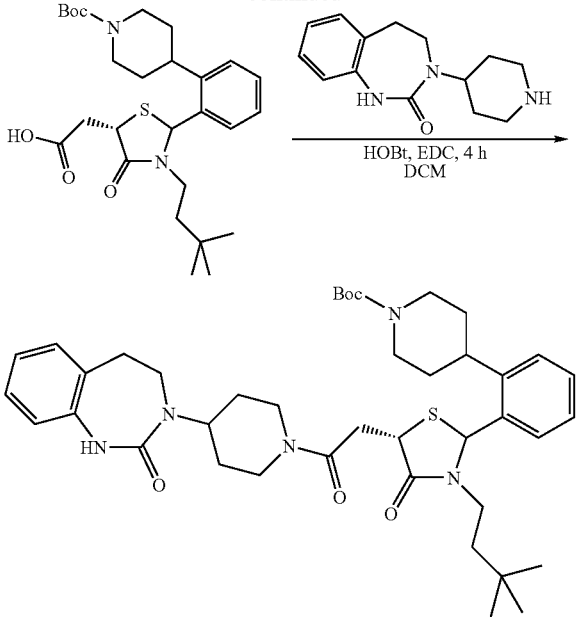
Scheme 36: Preparation of Compounds 552 and 553.
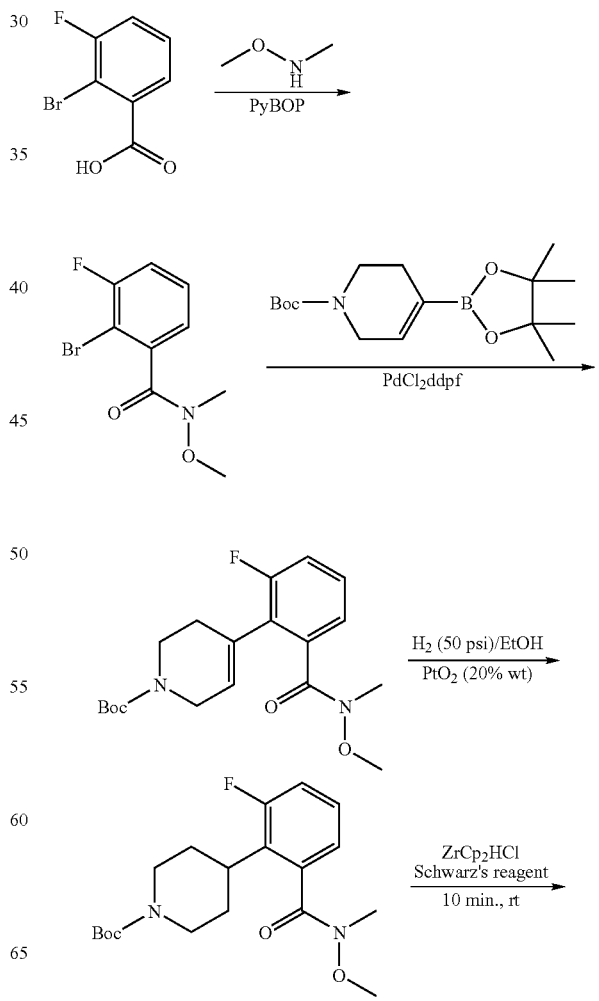

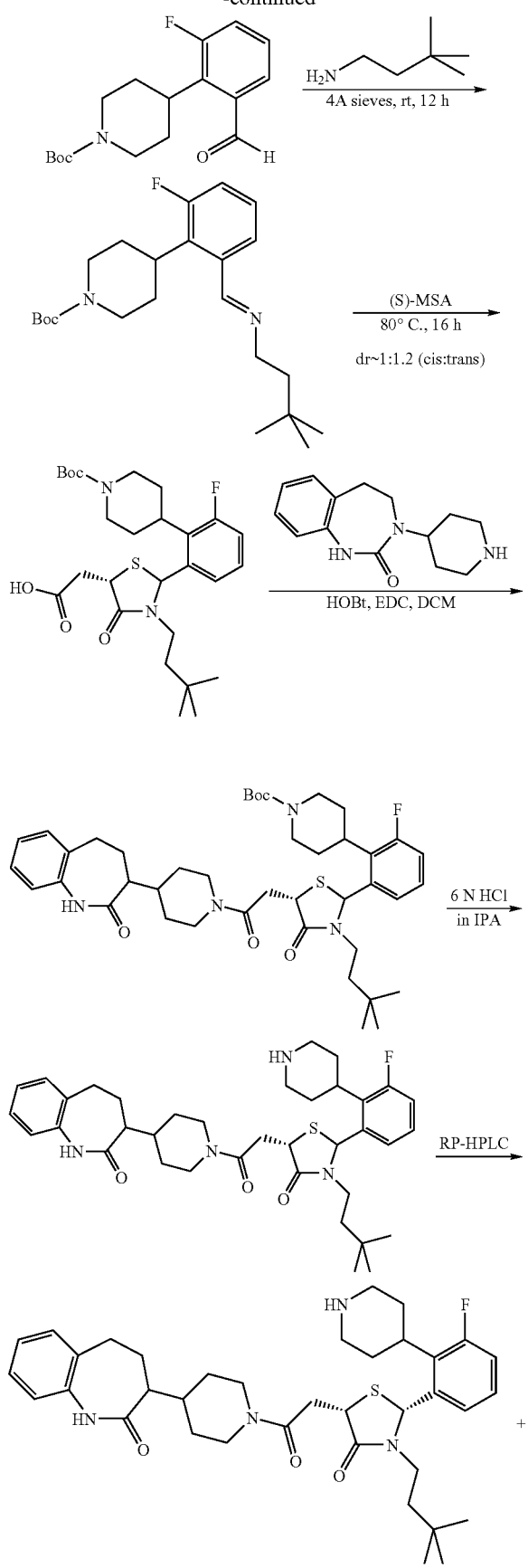

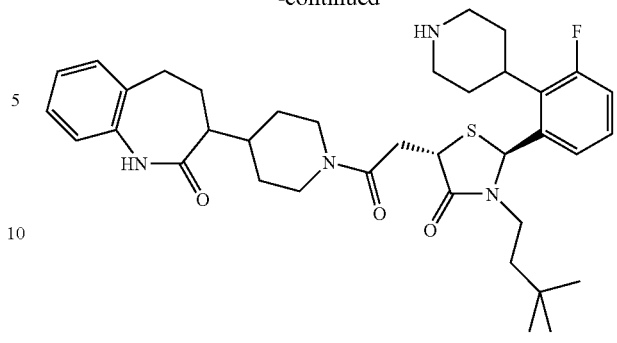

Compounds 551, 554 and 555 were prepared using procedures similar to those in Scheme 36.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an active metabolite or residue thereof. As used herein, the term "active metabolite or residue thereof" means that a metabolite or residue thereof is also an antagonist of CGRP.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The compounds of the present invention are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; encephalitis; brain trauma; epilepsy; neurodegenerative diseases; skin diseases; neurogenic cutaneous redness, skin rosaceousness and erythema; tinnitus; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The compounds of the present invention are further useful in a method for the prevention, treatment, control, amelioration, or reduction of risk of the diseases, disorders and conditions noted herein.

The compounds of the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-inflammatory or analgesic agent or an anti-migraine agent, such as an ergotamine or 5-HT.sub.1 agonists, especially a 5-HT.sub.1B/1D agonist, for example sumatriptan, naratriptan, zolmitriptan, eletriptan, almotriptan, frovatriptan, donitriptan, and rizatriptan; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as aspirin, ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or a steroidal analgesic. Similarly, the instant compounds may be administered with a pain reliever such as acetaminophen, phenacetin, codeine, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; a tricyclic antidepressant, for example amitriptyline, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with ergot alkaloids, for example ergotamine, ergonovine, ergonovine, methylergonovine, metergoline, ergoloid mesylates, dihydroergotamine, dihydroergocornine, dihydroergocristine, dihydroergocryptine, dihydro-I-ergocryptine, dihydro-.theta.-ergocryptine, ergotoxine, ergocornine, ergocristine, ergocryptine, I-ergocryptine, .theta.-ergocryptine, ergosine, ergostane, bromocriptine, or methysergide.

Additionally, the present compounds may be used in conjunction with a beta-adrenergic antagonist such as timolol, propanolol, atenolol, or nadolol, and the like; a MAO inhibitor, for example phenelzine; a calcium channel blocker, for example flunarizine, nimodipine, lomerizine, verapamil, nifedipine, prochlorperazine or gabapentin; neuroleptics such as olanzapine and quetiapine; an anticonvulsant such as topiramate, zonisamide, tonabersat, carabersat or divalproex sodium; an angiotensin II antagonist, for example losartan and candesartan cilexetil; an angiotensin converting enzyme inhibitor such as lisinopril; or botulinum toxin type A.

The present compounds may be used in conjunction with a potentiator such as caffeine, an H2-antagonist, simethicone, aluminum or magnesium hydroxide; a decongestant such as phenylephrine, phenylpropanolamine, pseudoephedrine, oxymetazoline, epinephrine, naphazoline, xylometazoline, propylhexedrine, or levo-desoxy-ephedrine; an antitussive such as codeine, hydrocodone, caramiphen, carbetapentane, or dextromethorphan; a diuretic; a prokinetic agent such as metoclopramide or domperidone, and a sedating or non-sedating antihistamine.

In a particularly preferred embodiment the present compounds are used in conjunction with an anti-migraine agent, such as: an ergotamine; a 5-HT.sub.1 agonist, especially a 5-HT.sub.1B/1D agonist, in particular, sumatriptan, naratriptan, zolmitriptan, eletriptan, almotriptan, frovatriptan, donitriptan and rizatriptan; and a cyclooxygenase inhibitor, such as a selective cyclooxygenase-2 inhibitor, in particular, rofecoxib, etoricoxib, celecoxib, meloxicam, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

In order that the invention described herein may be more fully understood, the following examples are set forth. It should be understood that these examples are for illustrative purposes only and are not to be construed as limiting this invention in any manner.

EXAMPLES

The following definitions describe terms and abbreviations used herein:
Ac acetyl
Bu butyl
Et ethyl
Ph phenyl
Me methyl
Cbz carbobenzyloxy
Bn benzyl
Boc/BOC butyloxycarbonyl
TMS trimethylsilyl
THF tetrahydrofuran
DCM dichloromethane
DCE dichloroethane
EDC 1-(3-dimethylaminopropyl)-3-ethylcarbodiimide hydrochloride
$CH_2Cl_2$ dichloromethane
ppt precipitate
FIA flow injection analysis (Mass Spec)
Rf retention factor (TLC)
EtOAc ethyl acetate
$CH_3CN$ acetonitrile
ACN acetonitrile
EtOH ethanol
MeOH methanol
MTBE methyl tert-butyl ether
DMF N,N-dimethylformamide
DMA N,N-dimethylacetamide
DMSO dimethyl sulfoxide
NMM N-methylmorpholine
DMP Dess Martin periodinane
HOAc acetic acid TFA trifluoroacetic acid
Et₃N triethylamine
DIPEA diisopropylethylamine
DIEA diisopropylethylamine
K₂CO₃ potassium carbonate
Na₂CO₃ sodium carbonate
Cs₂CO₃ cesium carbonate
NaHCO₃ sodium bicarbonate
NaOH sodium hydroxide
Na₂SO₄ sodium sulfate
K₃PO₄ potassium phosphate
NH₄Cl ammonium chloride
LAH lithium aluminum hydride
LiHMDS lithium bis(trimethylsilyl)amide or lithium hexamethyldisilazide
LC/MS liquid chromatography/mass spectra
HPLC high performance liquid chromatography
LC liquid chromatography
Hr or h hours
atm atmospheres
rt or RT room temperature
TLC thin layer chromatography
HCl hydrochloric acid
H₂ water
Pd/C palladium on carbon
H₂SO₄ sulfuric acid
N₂ nitrogen gas
H₂ hydrogen gas
DI de-ionized
i-PrOH isopropyl alcohol
NBS N-bromosuccinimide
Pd[(Ph₃)P]₄ tetrakis(triphenylphosphine)palladium(0)
(S)-MSA (S)-2-mercaptosuccinic acid
PyBOP benzotriazol-1-yl-oxytripyrrolidinophosphonium hexafluorophosphate
CDI 1,1'-carbonyldiimidazole
HATU O-(7-azabenzotriazole-1-yl)-N,N,N,N'-tetramethyluronium hexafluorophosphate
SM starting material
equiv. equivalents
prep preparative
CV column volumes
MS molecular sieves
¹H NMR proton nuclear magnetic resonance
mW microwave General LC/MS Methods LC/MS data were acquired using a PESciex API-150-EX LC/MS, Shimadzu LC-8A pumps, Gilson 215 autosampler, Gilson 819 injection module, 3.0 mL/min flow rate, 10-99% CH₃CN (0.035% TFA)/H₂O (0.05% TFA) gradient, Phenomenex Luna 5u C18 column (50×4.60 mm), Shimadzu SPD-10A UV/Vis detector, Cedex 75 ELSD detector.

Mass Spec Method for Separating Diasteromeric Mixtures:

A Semi-Prep Gilson HPLC was used to purify various diastereomeric mixtures in the present invention using Gilson 322 pumps, a Gilson 215 liquid handler, a Gilson 819 injection module. Flow rate was 15.0 mL/min using a gradient of 20-70% CH3CN (0.1% TFA)/H2O (0.1% TFA) on an Agilent Zorbax, SB-C18 column (21.2×100 mm, 5 um) monitoring with a Gilson 156 UV/Vis detector.

tert-Butyl 4-(1,2-dihydro-2-oxo-5-phenylimidazol-3-yl)piperidine-1-carboxylate

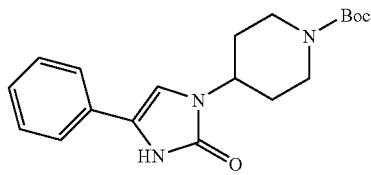

tert-Butyl 4-(1,2-dihydro-2-oxo-5-phenylimidazol-3-yl)piperidine-1-carboxylate was synthesised as described in J. Med. Chem., 2005, 48, 5921. A solution of 2-bromo-1-phenylethanone (5 g, 25 mmol) in DCM (10 ml) was added dropwise to a stirred solution of tert-butyl 4-aminopiperidine-1-carboxylate (6 g, 30 mmol) and DIPEA (9.84 ml, 57.5 ml) in DCM (50 ml) over 1 hour, the reaction mixture was then stirred at room temperature for 16 hours. Sodium cyanate (3.41 g, 52.5 mmol) was added, the reaction mixture was then cooled to 0° C., the pH was brought to pH 4 with acetic acid and the reaction mixtures was stirred from 0° C. to RT over 16 hours. The reaction mixture was poured into water and extracted with DCM (3×). Organics combined, washed with water (3×), brine, dried (MgSO₄) and evaporated to dryness. The residue was triturated with ether, filtered and the solid was washed with ether to give a pale yellow solid (4.04 g, 47%). LC/MS (10% to 99%): M/Z (M+H)⁺ (obs)=344; $t_R$=3.01.

5-Phenyl-3-(piperidin-4-yl)-1H-imidazol-2(3H)-one

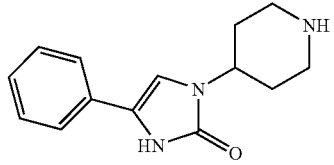

To a solution of tert-butyl 4-(1,2-dihydro-2-oxo-5-phenylimidazol-3-yl)piperidine-1-carboxylate (4 g) in DCM (20 ml) was added TFA (4 ml) and the reaction mixture was stirred at RT for 4 hours. Evaporation gave the TFA salt of the desired product (Quant.). LC/MS (10% to 99%): M/Z (M+H)⁺ (obs)=244; $t_R$=1.06.

tert-Butyl 4-(2-nitrobenzylamino)piperidine-1-carboxylate

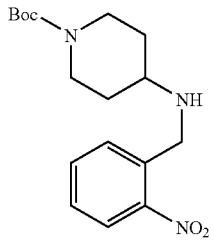

A solution of 1-(bromomethyl)-2-nitrobenzene (13.2 g, 61 mmol) in DCM (60 ml) was added dropwise to a solution of tert-butyl 4-aminopiperidine-1-carboxylate (14.6 g, 73 mmol) and TEA (13.4 ml, 91 mmol) in DCM (100 ml), followed by stirring the reaction mixture for a further 16 hours. The reaction mixture was then poured into water, and the layers separated. The aqueous layer was then extracted with DCM (2×). The organic layers were combined, washed with water (2×), brine, dried (MgSO$_4$) and evaporated to dryness. The residue was taken up in EtOAc and filtered through a large plug of silica. The silica was washed with EtOAc until TLC analysis show no further material was eluting. Evaporation gave the product as an orange oil (24 g, 74%). LC/MS (10% to 99%): M/Z (M+H)$^+$ (obs)=336; $t_R$=2.23.

tert-Butyl 4-(2-aminobenzylamino)piperidine-1-carboxylate

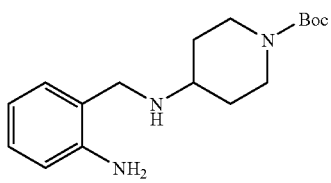

A solution of tert-Butyl 4-(2-nitrobenzylamino)piperidine-1-carboxylate (24 g, 71.6 mmol) in MeOH (150 ml) was stirred under an atmosphere of hydrogen for 24 hours. The reaction mixture was filtered and evaporated to give the crude amine, which was used without further purification.

tert-Butyl 4-(1,2-dihydro-2-oxoquinazolin-3(4H)-yl) piperidine-1-carboxylate

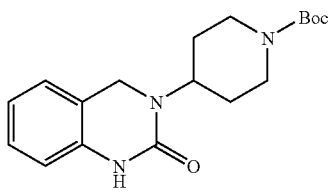

To a solution of tert-butyl 4-(2-nitrobenzylamino)piperidine-1-carboxylate (13.2 g, 43.2 mmol) in THF (400 ml) was added a solution of CDI (7.7 g, 47.5 mmol) in 1:1 DCM:THF (100 ml) dropwise over 1 hour followed by stirring the reaction mixture for a further 16 hours. The reaction mixture was evaporated to give an oil that, when treated with EtOAc, precipitated the desired product. The precipitate was washed with cold EtOAc and dried to give a yellow solid (3.5 g). LC/MS (10% to 99%): M/Z (M+H)$^+$ (obs)=332; $t_R$=3.01.

3,4-Dihydro-3-(piperidin-4-yl)quinazolin-2(1H)-one

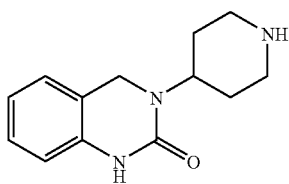

To a solution of tert-Butyl 4-(1,2-dihydro-2-oxoquinazolin-3(4H)-yl)piperidine-1-carboxylate (3.5 g, 10.6 mmol) in DCM (20 ml) was added TFA (15 ml) and the reaction mixture was stirred at RT for 2 h. The reaction mixture was evaporated, then co-evaporated with EtOH (2×), to give the TFA salt of the desired product (Quant.). LC/MS (10% to 99%): M/Z (M+H)$^+$ (obs)=232; $t_R$=0.38.

1-(2-Bromoethyl)-2-nitrobenzene

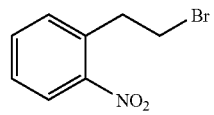

To a solution of 1-(2-hydroxyethyl)-2-nitrobenzene (21 ml, 150 mmol) and triphenylphosphine (39.2 g, 150 mmol) in DCM (400 ml) at 0° C. was add CBr$_4$ (49.5 g, 150 mmol) in portions and the reaction mixture was stirred from 0° C. to RT overnight. The reaction mixture was quenched with sat. aq. Na$_2$CO$_3$, the layers were separated and the organic layer was washed with brine, dried (MgSO$_4$) and evaporated to dryness. The residue was treated with EtOAc and the precipitated Ph$_3$O was filtered and the solvent removed. This was repeated twice more. Purification by column chromatography (0% to 10% EtOAc in Hx) gave an oil that solidified on standing.

2-(2-Nitrophenyl)ethanamine

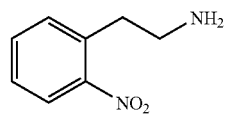

To a solution of 1-(2-Bromoethyl)-2-nitrobenzene (6.96 g, 30.5 mmol) in CH$_3$CN was added a solution of NaN$_3$ (6 g, 91.6 mmol) in water (20 ml) and the reaction mixture was refluxed for 20 hours. The solution was cooled and extracted with DCM (3×). The organics were combined, washed with brine, dried (MgSO$_4$) and evaporated to dryness. The residue was taken up in toluene (160 ml) and to this was added PPh$_3$ (8 g, 30.5 mmol) and the reaction mixture was stirred at RT for 16 hours. The solvent was evaporated to dryness and the residue was treated with acetic acid (30 ml) and 48% HBr in acetic acid (30 ml) at 100° C. for 1 h. The reaction mixture was cooled, concentrated and extracted with DCM. The aqueous was brought to pH~10 with NaOH (aq.) and extracted with EtOAc (3×). The organics were combined, washed with brine, dried (MgSO$_4$) and evaporated to dryness (4.2 g).

tert-Butyl 4-(2-nitrophenethylamino)piperidine-1-carboxylate

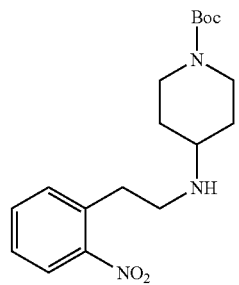

A stirred solution of 2-(2-nitrophenyl)ethanamine (4 g, 24 mmol) and tert-butyl 4-oxopiperidine-1-carboxylate (4.8 g, 24 mmol) in MeOH (48 ml) was brought to pH 5 by the addition of acetic acid. NaBH3CN (2.3 g, 36 mmol) was added and the reaction mixture was stirred at RT for 3 hours. The solvent was evaporated and the residue was taken up in EtOAc and sat. aq. Na$_2$CO$_3$. The layers were separated and the organic layer was washed with brine, dried (Na$_2$SO$_4$) and evaporated to dryness. Purification by column chromatography (0% to 7% MeOH in DCM) gave the desired product. LC/MS (10% to 99%): M/Z (M+H)$^+$ (obs)=350; t$_R$=2.22.

tert-Butyl 4-(2-aminophenethylamino)piperidine-1-carboxylate

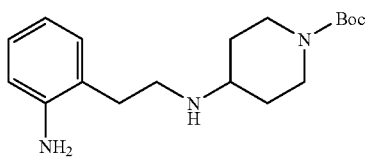

To a solution of tert-butyl 4-(2-nitrophenethylamino)piperidine-1-carboxylate (10.5 g) in EtOH (180 ml) was added 10% Pd/C (1.05 g) and the reaction mixture was stirred at RT under an atmosphere of H$_2$ overnight. The reaction mixture was filtered and the resulting solution was evaporated to dryness giving the desired product (9.6 g). LC/MS (10% to 99%): M/Z (M+H)$^+$ (obs)=320; t$_R$=2.06.

tert-Butyl 4-(1,2,4,5-tetrahydro-2-oxobenzo[d][1,3]diazepin-3-yl)piperidine-1-carboxylate

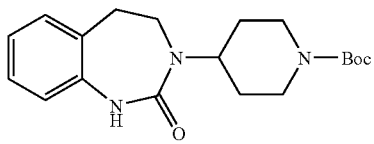

To a solution of tert-butyl 4-(2-aminophenethylamino)piperidine-1-carboxylate (6.9 g, 30 mmol) in DMF (110 ml) was added CDI (4.86 g, 30 mmol) in portions followed by stirring the reaction mixture at RT for 2 h. The reaction mixture was diluted with water and extracted with EtOAc. The organics were combined, washed with water, brine, and evaporated to dryness to give the desired product. LC/MS (10% to 99%): M/Z (M+H)$^+$ (obs)=346; t$_R$=3.24.

4,5-Dihydro-3-(piperidin-4-yl)-1H-benzo[d][1,3]diazepin-2(3H)-one

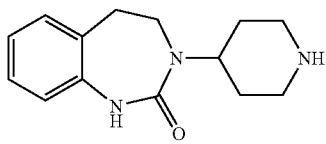

To a solution of tert-butyl 4-(1,2,4,5-tetrahydro-2-oxobenzo[d][1,3]diazepin-3-yl)piperidine-1-carboxylate (10 g, 2.89 mmol) in DCM (5 ml) was added TFA (5 ml) and the reaction mixture was stirred at RT for 1 h. The reaction mixture was evaporated, then co-evaporated with EtOH (2×), to give the TFA salt of the desired product (Quant.). LC/MS (10% to 99%): M/Z (M+H)$^+$ (obs)=246; t$_R$=1.75.

tert-Butyl 4-(2-aminopyridin-3-ylamino)piperidine-1-carboxylate

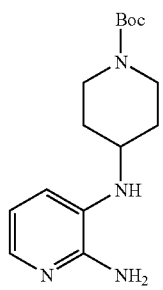

To a solution of 2,3-diaminopyridine (3.0 g, 27.5 mmol) in DCE (45 ml) was added tert-butyl 4-oxopiperidine-1-carboxylate (5.75 g, 28.8 mmol) and the reaction mixture stirred for min at RT before the portion-wise addition of NaBH(Oac)$_3$ (8.7 g, 41.7 mmol) and continued stirring at RT until the reaction judged complete by LCMS. The reaction was quenched with 5% NaOH, the layers separated and the organic layer was dried over Na$_2$SO$_4$. Evaporation gave the desired product as a brown solid (4.96 g). LC/MS (10% to 99%): M/Z (M+H)$^+$ (obs)=293; t$_R$=2.31.

tert-Butyl 4-(2,3-dihydro-2-oxoimidazo[4,5-b]pyridin-1-yl)piperidine-1-carboxylate

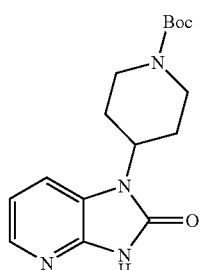

To a solution of tert-Butyl 4-(2-aminopyridin-3-ylamino)piperidine-1-carboxylate (3.0 g, 10.3 mmol) in CH$_3$CN (206 ml) at RT was added CDI (4.2 g, 25.7 mmol) in portions and the reaction mixture was stirred at RT for 16 hours. The reaction mixture was evaporated to dryness and the residue was take up in DCM and water. The layers were separated and the organic layer was washed with brine, dried (Na$_2$SO$_4$) and evaporated to dryness. Purification by column chromatography (1-10% MeOH in DCM) gave the desired solid as a beige solid (3.55 g). LC/MS (10% to 99%): M/Z (M+H)⁺ (obs)= 319; $t_R$=2.31.

1-(Piperidin-4-yl)-1H-imidazo[4,5-b]pyridin-2(3H)-one

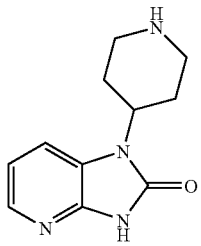

A solution of tert-butyl 4-(2,3-dihydro-2-oxoimidazo[4,5-b]pyridin-1-yl)piperidine-1-carboxylate (3.39 g, 10.7 mmol) in 2N HCl in Et₂O (20 ml) was stirred from 0° C. to RT over 2 h. The solvent was evaporated and the residue triturated with Et₂O, filtered washed with Et₂O and dried to give the bis-HCl Salt of the desired product (2.62 g). LC/MS (10% to 99%): M/Z (M+H)⁺ (obs)=219; $t_R$=0.36.

2-(2,4-Dimethoxybenzylamino)pyridine-3-carbonitrile

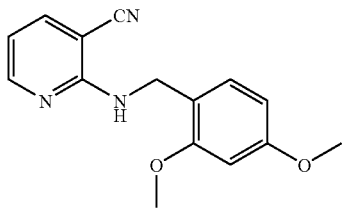

To a solution of 2-chloro-3-cyanopyridine (4.0 g, 28.9 mmol) in DMA (58 ml) was added 2,4-dimethoxybenzealdehyde (5.2 ml, 34.6 mmol) and TEA (4.8 ml (34.6 mmol) and the reaction mixture stirred at 80° C. for 4 hours. The reaction mixture was poured into water and extracted with Et₂O. The organics were combined, dried (Na₂SO₄) and evaporated to dryness. Column chromatography (0.5% to 5% EtOAc (with 0.1% TEA) in DCM) gave the desired product. LC/MS (10% to 99%): M/Z (M+H)⁺ (obs)=270; $t_R$=3.05.

N-(2,4-Dimethoxybenzyl)-3-(aminomethyl)pyridin-2-amine

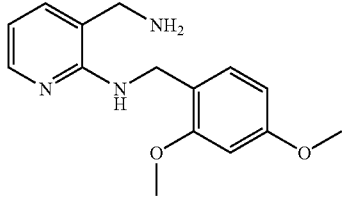

A solution of 2-(2,4-Dimethoxybenzylamino)pyridine-3-carbonitrile (0.55 g, 2.04 mmol) and LiAlH₄ (2.2 ml of 1N, 4.4 mmol) was stirred at RT until the reaction was judged complete by LCMS. The reaction was quenched with sat. aq. Na₂CO₃ and the layers were separated. The organic layer was dried (Na₂SO₄) and the solvents removed under reduced pressure giving the desired product which was used without further purification. LC/MS (10% to 99%): M/Z (M+H)⁺ (obs)= 274; $t_R$=0.28.

tert-Butyl-4-((2-(2,4-dimethoxybenzylamino)pyridin-3-yl)methylamino)piperidine-1-carboxylate

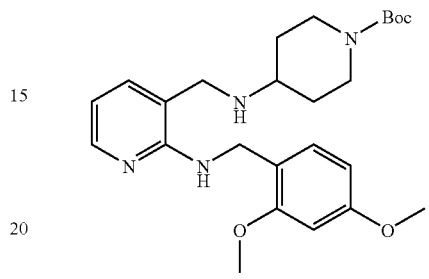

To a stirred solution of N-(2,4-Dimethoxybenzyl)-3-(aminomethyl)pyridin-2-amine (2.04 mmol) and tert-butyl 4-oxopiperidine-1-carboxylate (0.41 g, 2.04 mmol) in DCE (8 ml) and AcOH (115 µL, 2.04 mmol) was added NaBH(OAc)₃ (0.43 g, 2.04 mmol) and the reaction stirred at RT until judged complete by LCMS. The reaction mixture was diluted with DCM and sat. aq. Na₂CO₃, the layers were separated and the organic layer was dried (Na2SO3) and evaporated to dryness. Purification by column chromatography (MeOH/DCM) gave the desired product (0.64 g, 69%). LC/MS (10% to 99%): M/Z (M+H)⁺ (obs)=457; $t_R$=2.19.

tert-Butyl 4-(1-(2,4-dimethoxybenzyl)-1,2-dihydro-2-oxopyrido[2,3-d]pyrimidin-3(4H)-yl)piperidine-1-carboxylate

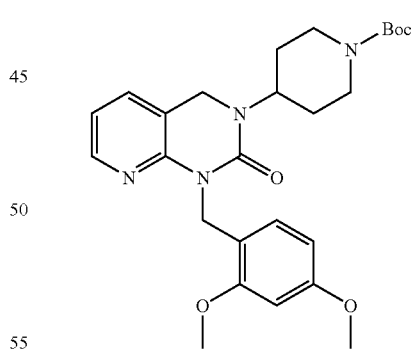

To a solution of tert-butyl 4-((2-(2,4-dimethoxybenzylamino)pyridin-3-yl)methylamino)piperidine-1-carboxylate (2.89 g, 6.33 mmol) in DMF (42 ml) was added CDI (1.23 g, 7.6 mmol) in portions and the reaction mixture was stirred at 120° C. for 2 hours. A further portion of CDI was added (0.82 g) was added and the reaction mixture stirred at 130° C. for 6 hours, followed by stirring at RT for 16 hours. The reaction was diluted with water and extracted with DCM. The organics were combined, dried (NaSO4) and evaporated to dryness. Purification by column chromatography (10 to 80% EtOAc in Hx) gave the desired product (1.17 g). LC/MS (10% to 99%): M/Z (M+H)+ (obs)=483; $t_R$=3.58.

3,4-Dihydro-3-(piperidin-4-yl)pyrido[2,3-d]pyrimidin-2(1H)-one

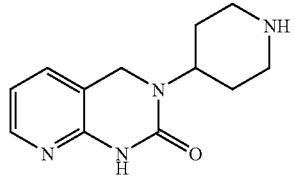

2-(4-Oxo-2-phenyl-3-((pyridin-4-yl)methyl)thiazolidin-5-yl)acetic acid

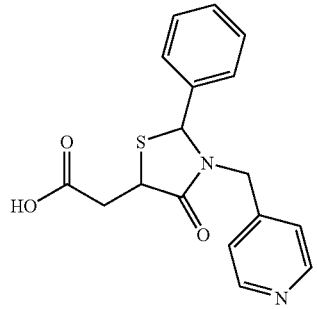

A solution of benzaldehyde (0.75 mmol, 79.6 mg) and 2-(pyridin-4-yl)ethanamine (97.3 mg, 0.9 mmol) in DMF (0.5 ml) with 4 Å molecular sieves was heated at 80° C. for 2 hours. A solution of mercaptosuccinic acid (1.13 mmol, 168 mg) in DMF (0.2 ml) was added and the reaction was heated at 80° C. for an additional 16 hours. The reaction mixture was diluted with water and extracted with EtOAc. The organic layer was washed with 1N HCl, water and evaporated to dryness to give the desired product which was used without further purification. LC/MS (10% to 99%): M/Z (M+H)+ (obs)=329; $t_R$=1.95.

1-(1-(2-(4-Oxo-2-phenyl-3-((pyridin-4-yl)methyl)thiazolidin-5-yl)acetyl)piperidin-4-yl)-1H-benzo[d]imidazol-2(3H)-one (Compound #45)

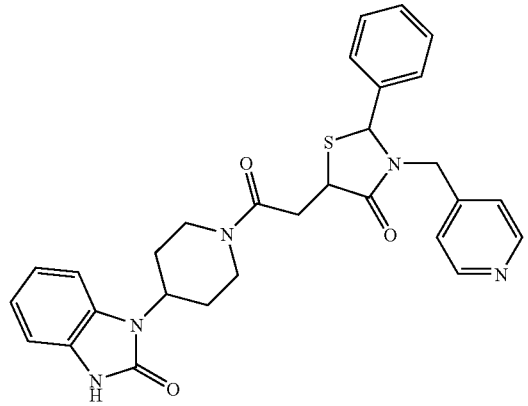

To a solution of 2-(4-oxo-2-phenyl-3-((pyridin-4-yl)methyl)thiazolidin-5-yl)acetic acid (0.15 mmol, 49 mg), 1-(piperidin-4-yl)-1H-benzo[d]imidazol-2(3H)-one (0.15 mmol, 33 mg) and D$^I$PEA (0.375 mmol, 65.3 µl) in 4:1 CH$_3$CN:DMF (0.5 ml) was added HATU (0.18 mmol, 68 mg) and the reaction mixture was stirred at room temperature for 16 h. Purification by preparative reverse phase HPLC using 10%-99% CH$_3$CN (0.035% TFA)/H$_2$O (0.05% TFA) gave the title compound. LC/MS (10% to 99%): M/Z (M+H)+ (obs)= 528.1; $t_R$=2.28. H NMR (400 MHz, CDCl3) δ 9.00 (s, 1H), 8.60 (d, J=6.3 Hz, 2H), 7.40-7.38 (m, 2H), 7.33-7.29 (m, 5H), 7.06-6.92 (m, 4H), 5.55-5.53 (m, 1H), 4.55 (d, J=4.4 Hz, 2H), 4.45-4.42 (m, 3H), 4.07 (d, m, 2H), 3.42-3.41 (m, 1H), 3.20-3.15 (m, 1H), 3.01-2.90 (m, 1H), 2.66 (m, 2H), 1.88 (m, 2H) ppm.

2-(3-Methyl-4-oxo-2-phenylthiazolidin-5-yl)acetic acid

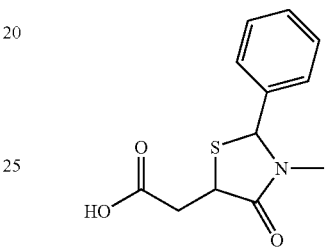

A solution of benzaldehyde (0.75 mmol, 79.6 mg) and methylamine hydrochloride (60.8 mg, 0.9 mmol) in DMF (0.5 ml) with 4 Å molecular sieves was heated at 80° C. for 2 hours. A solution of mercaptosuccinic acid (1.13 mmol, 168 mg) in DMF (0.2 ml) was added and the reaction was heated at 80° C. for an additional 16 hours. The reaction mixture was diluted with water and extracted with EtOAc. The organic layer was washed with 1N HCl, water and evaporated to dryness to give the desired product which was used without further purification.

3,4-Dihydro-3-(1-(2-(3-methyl-4-oxo-2-phenylthiazolidin-5-yl)acetyl)piperidin-4-yl)quinazolin-2(1H)-one (Compound #273)

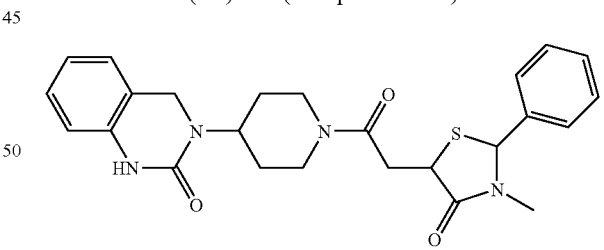

To a solution of 2-(3-methyl-4-oxo-2-phenylthiazolidin-5-yl)acetic acid (0.2 mmol, 50 mg), 3,4-dihydro-3-(piperidin-4-yl)quinazolin-2(1H)-one TFA salt (0.15 mmol, 49 mg) and D$^I$PEA (0.375 mmol, 65.3 µl) in 4:1 CH$_3$CN:DMF (0.5 ml) was added HATU (0.18 mmol, 68 mg) and the reaction mixture was stirred at room temperature for 16 h. Purification by preparative reverse phase HPLC using 10%-99% CH$_3$CN (0.035% TFA)/H$_2$O (0.05% TFA) gave the title compound. LC/MS (10% to 99%): M/Z (M+H)+ (obs)=465.5; $t_R$=2.18. $^1$H NMR (400 MHz, CDCl3) δ 7.34-7.22 (m, 5H), 7.12 (t, J=7.5 Hz, 1H), 7.00 (d, J=7.5 Hz, 2H), 6.95-6.89 (m, 2H), 6.61 (d, J=7.8 Hz, 2H), 5.46-5.41 (m, 1H), 4.70 (m, 1H), 4.56

(m, 1H), 4.26 (m, 3H), 3.86 (m, 1H), 3.50 (m, 1H), 3.32 (m, 1H), 3.12-3.08 (m, 1H), 2.89-2.73 (m, 1H), 1.69 (m, 3H) ppm.

2-(3-Isopropyl-4-oxo-2-phenylthiazolidin-5-yl)acetic acid

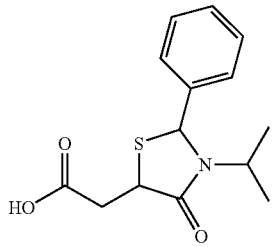

A solution of benzaldehyde (0.75 mmol, 79.6 mg) and isopropylamine (53.1 mg, 0.9 mmol) in DMF (0.5 ml) with 4 Å molecular sieves was heated at 80° C. for 2 hours. A solution of mercaptosuccinic acid (1.13 mmol, 168 mg) in DMF (0.2 ml) was added and the reaction was heated at 80° C. for an additional 16 hours. The reaction mixture was diluted with water and extracted with EtOAc. The organic layer was washed with 1N HCl, water and evaporated to dryness to give the desired product which was used without further purification.

3,4-Dihydro-3-(1-(2-(3-isopropyl-4-oxo-2-phenylthiazolidin-5-yl)acetyl)piperidin-4-yl)quinazolin-2(1H)-one (Compound #255)

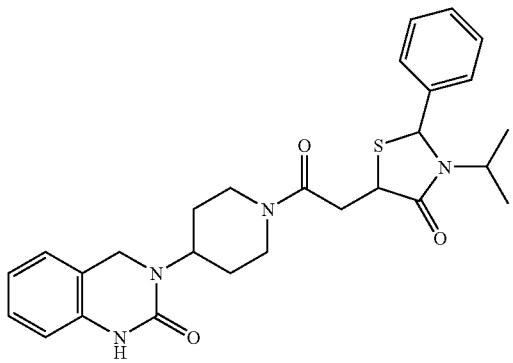

To a solution of 2-(3-isopropyl-4-oxo-2-phenylthiazolidin-5-yl)acetic acid (0.2 mmol, 56 mg), 1-(piperidin-4-yl)-1H-benzo[d]imidazol-2(3H)-one (0.15 mmol, 33 mg) and D$^I$PEA (0.375 mmol, 65.3 µl) in 4:1 CH$_3$CN:DMF (0.5 ml) was added HATU (0.18 mmol, 68 mg) and the reaction mixture was stirred at room temperature for 16 h. Purification by preparative reverse phase HPLC using 10%-99% CH$_3$CN (0.035% TFA)/H$_2$O (0.05% TFA) gave the title compound. LC/MS (10% to 99%): M/Z (M+H)$^+$ (obs)=493.5; t$_R$=3.1. $^1$H NMR (400 MHz, CDCl3) δ 7.31-7.25 (m, 5H), 7.14-7.10 (m, 1H), 7.05 (s, 1H), 7.00 (m, 1H), 6.93-6.89 (m, 1H), 6.62 (d, J=7.8 Hz, 1H), 5.56 (m, 1H), 4.72 (m, 1H), 4.47-4.41 (m, 2H), 4.27-4.19 (m, 2H), 4.02-3.96 (m, 1H), 3.87 (m, 1H), 3.36-3.29 (m, 1H), 3.13-3.10 (m, 1H), 2.70 (m, 2H), 1.70-1.60 (m, 3H), 1.20 (dd, J=2.0, 6.9 Hz, 3H), 0.94 (m, 3H).

2-(3-Isopentyl-4-oxo-2-phenylthiazolidin-5-yl)acetic acid

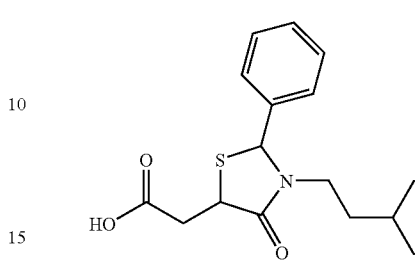

A solution of benzealdehyde (5.06 ml, 50 mmol) and isopentylamine (5.82 ml, 50 mmol) was stirred at 80° C. for 2 hours before the addition of mercaptosuccinic acid (7.51 g, 50 mmol) and a further 16 hours of stirring at 80° C. The reaction mixture was poured into water and extracted with EtOAc. The organics combined, dried and evaporated to dryness. Purification by column chromatography (EtOAc/Hx) gave the desired product as a yellow oil (11.3 g).

Ethyl 2-(3-isopentyl-4-oxo-2-phenylthiazolidin-5-yl)acetate

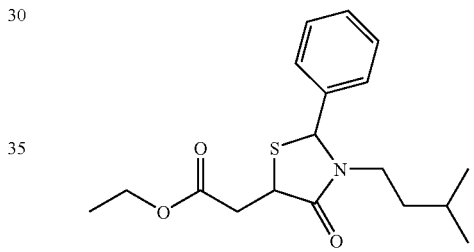

A solution of 2-(3-Isopentyl-4-oxo-2-phenylthiazolidin-5-yl)acetic acid (2.2 g, 7.2 mmol) in EtOH (20 ml) and H$_2$SO$_4$ (1 ml) was refluxed for 16 hours. The solution was evaporated to dryness and the residue was taken up in EtOAc and washed with sat. aq. Na$_2$CO$_3$ (3×), brine and evaporated to give the desired product as an oil.

Ethyl 2-(3-isopentyl-4-oxo-2-phenylthiazolidin-5-yl)propanoate

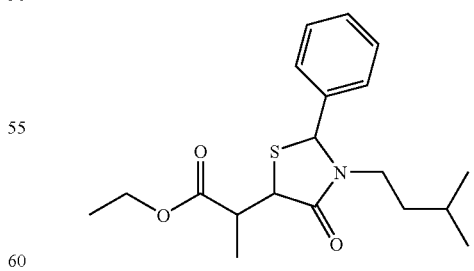

To a stirred solution of ethyl 2-(3-isopentyl-4-oxo-2-phenylthiazolidin-5-yl)acetate (84 mg, 0.25 mmol) in THF at 0° C. was added LiHMDS (0.28 ml of 1 N, 0.28 mmol) dropwise and the reaction mixture was stirred from 0° C. to RT over 16 hours. The reaction mixture was poured in to 1 N HCl and extracted with EtOAc (4×). The organics were combined, dried (MgSO$_4$) and evaporated to dryness. Purification by preparative TLC (7:1; Hx:EtOAc) gave the desired product as an oil (12 mg).

2-(3-Isopentyl-4-oxo-2-phenylthiazolidin-5-yl)propanoic acid

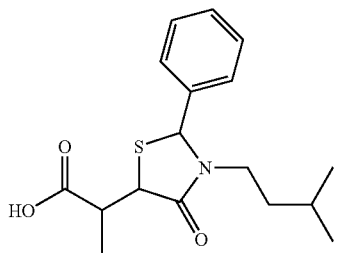

A solution 2-(3-isopentyl-4-oxo-2-phenylthiazolidin-5-yl)propanoic acid (12 mg, 0.034 mmol) and NaOH aq. (0.068 ml of 1N, 0.068 mmol) in MeOH (0.2 ml) was stirred at 60° C. for 16 hours. The solution was neutralized with 1 N HCl (0.068 ml of 1 N), the solvents removed and the crude product used with out further purification.

3-(1-(2-(3-Isopentyl-4-oxo-2-phenylthiazolidin-5-yl)propanoyl)piperidin-4-yl)-3,4-dihydroquinazolin-2(1H)-one (Compound #156)

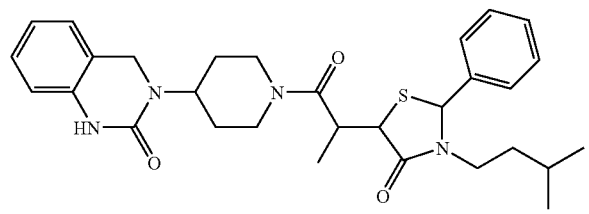

To a solution of 2-(3-Isopentyl-4-oxo-2-phenylthiazolidin-5-yl)propanoic acid (11 mg, 0.034 mmol), 3,4-Dihydro-3-(piperidin-4-yl)quinazolin-2(1H)-one.TFA (17 mg, 0.051 mmol) and D$^i$PEA (24 ul, 0.14 mmol) in DMF (0.2 ml) was added HATU (17 mg, 0.044 mmol) and the reaction mixture was stirred at RT for 16 hours. Purification by preparative reverse phase HPLC using 10%-99% CH$_3$CN (0.035% TFA)/H$_2$O (0.05% TFA) gave the title compound.

3-Isopentyl-2-phenylthiazolidin-4-one

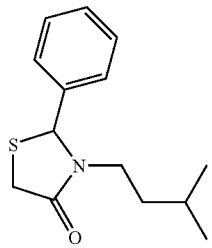

A solution of isopentylamine (0.58 ml, 5 mmol), benzealdehyde (1 ml, 10 mmol) and mercaptoacetic acid (1.05 ml g, 15 mmol) in THF (7 ml) and trimethoxyorthoformate (2 ml) was stirred at 75° C. for 16 hours. The RM was poured in to water and extracted with EtOAc (3×). The organics were combined, washed with 1N HCl (2×), brine, dried (MgSO$_4$) and evaporated to dryness. Purification by column chromatography (10-25% EtOAc in Hx) gave the desired product as an oil (1.07 g, 86%).

Ethyl 2-(3-isopentyl-4-oxo-2-phenylthiazolidin-5-ylidene)acetate

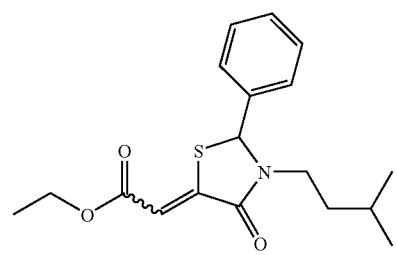

To a stirred solution of 3-isopentyl-2-phenylthiazolidin-4-one (0.25 g, 1 mmol) in THF was added LDA (1.1 ml of ~1 M in THF; freshly prepared from nBuLi and Diisopropylamine) at −78° C. and the reaction mixture was allowed to warm to room temperature. Ethyl glyoxalate (0.24 ml of ~50% w/v in toluene, 1.2 mmol) was added and the reaction mixture was stirred at room temperature for 16 hours. The reaction mixture was poured into 1 N HCl and extracted with EtOAc (3×). The organics were combined, washed with brine, dried (MgSO$_4$) and evaporated to dryness. Purification by column chromatography (5 to 15% EtOAc in Hx) gave the desired product as an oil.

2-(3-Isopentyl-4-oxo-2-phenylthiazolidin-5-ylidene)acetic acid

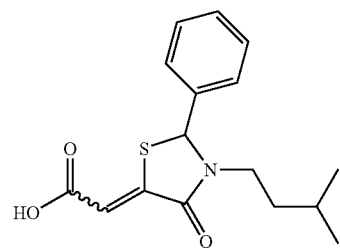

To a solution of ethyl 2-(3-isopentyl-4-oxo-2-phenylthiazolidin-5-ylidene)acetate (0.031 g, 0.1 mmol) and aq. NaOH (0.3 ml of 1 N) in MeOH was stirred at 40° C. for 2 hours. HCl (0.5 ml of 1 N) was added and the MeOH was evaporated. Water and EtOAc was added and the layers separated. The aqueous layer was extracted with EtOAc (2×), all organic layers were combined, dried (MgSO₄) and evaporated to dryness to give the desired product as an orange oil (11 mg, 36%).

3,4-Dihydro-3-(1-(2-(3-isopentyl-4-oxo-2-phenylthiazolidin-5-ylidene)acetyl)piperidin-4-yl)quinazolin-2(1H)-one

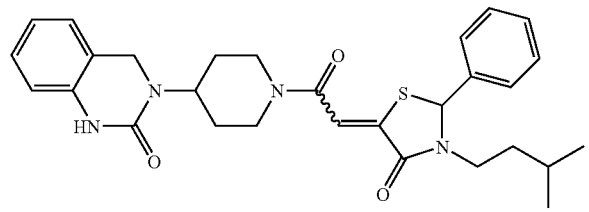

To a solution of 2-(3-isopentyl-4-oxo-2-phenylthiazolidin-5-ylidene)acetic acid (11 mg, 0.036 mmol), 3,4-Dihydro-3-(piperidin-4-yl)quinazolin-2(1H)-one.TFA (18 mg, 0.054 mmol) and D$^i$PEA (22 ul, 0.14 mmol) in DMF (0.2 ml) was added HATU (16 mg, 0.043 mmol) and the reaction mixture was stirred at RT for 16 hours. Purification by preparative reverse phase HPLC using 10%-99% CH₃CN (0.035% TFA)/H₂O (0.05% TFA) gave the title compound.

Preparation A: Synthesis of 1'H-spiro[piperidine-4,4'-quinolin]-2'(3'H)-one

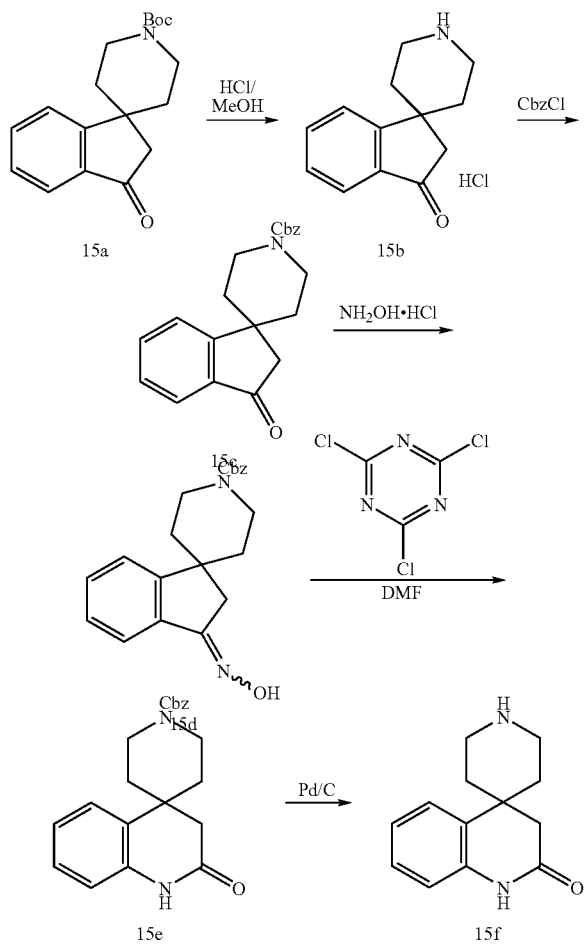

The mixture of tert-butyl 3-oxo-2,3-dihydrospiro[indene-1,4'-piperidine]-1'-carboxylate (20 g, 66.4 mmol) and MeOH/HCl (2.5 mol/L, 100 mL) were stirred overnight. After evaporation the residue was washed by petroleum ether to provide spiro[indene-1,4'-piperidin]-3(2H)-one hydrochloride (15.4 g, 97.6%).

To a solution spiro[indene-1,4'-piperidin]-3(2H)-one hydrochloride (5.0 g, 24.84 mmol) and Et₃N (7.54 g, 74.53 mol) in CH₂Cl₂ (50 mL) was added drop-wise Cbz-Cl (4.66 g, 27.33 mmol) at 0° C. The reaction was allowed to warm to room temperature and stirred overnight. The precipitate was filtered, washed with Et₂O and dried to furnish benzyl 3-oxo-2,3-dihydrospiro[indene-1,4'-piperidine]-1'-carboxylate (6.1 g, yield 99%).

A solution of benzyl 3-oxo-2,3-dihydrospiro[indene-1,4'-piperidine]-1'-carboxylate (3 g, 10.3 mmol) in EtOH (30 mL) containing NH₂OH.HCl (1.43 g, 20.6 mmol) and NaOAc (1.52 g, 18.53 mmol) was heated under reflux for 1.5 h. The solvent was removed by evaporation and the residue was partitioned between CH₂Cl₂ and water. The organic phase was washed with brine, dried over Na₂SO₄, and concentrated to provide benzyl 3-(hydroxyimino)-2,3-dihydrospiro[indene-1,4'-piperidine]-1'-carboxylate (3.14 g, yield 99%), which was used directly in the next step.

2,4,6-trichloro-[1,3,5]-triazine (1.32 g, 7.16 mmol) was added to DMF (9.6 mL) maintained at 25° C. The reaction was monitored by TLC until TCT was consumed. Then benzyl 3-(hydroxyimino)-2,3-dihydrospiro[indene-1,4'-piperidine]-1'-carboxylate (1.6 g, 4.77 mmol) in DMF (17 mL) was added. After the addition, the mixture was stirred at room temperature overnight. Water was added. The mixture was extracted with EtOAc. The combined organic layers were washed with sat. Na₂CO₃, followed by 1N HCl and brine, dried over Na₂SO₄ and concentrated. The residue was purified by prep HPLC to obtain benzyl 2'-oxo-2',3'-dihydro-1'H-spiro[piperidine-4,4'-quinoline]-1-carboxylate (260 mg, yield 16%).

The mixture of benzyl 2'-oxo-2',3'-dihydro-1'H-spiro[piperidine-4,4'-quinoline]-1-carboxylate (1.2 g, 3.4 mmol) and Pd/C (200 mg) in MeOH (20 mL) was hydrogenated under atmosphere pressure at room temperature for 3 h. The catalyst was filtered and the filtrate was concentrated under reduced pressure. The residue was purified by preparative HPLC twice to give 1'H-spiro[piperidine-4,4'-quinolin]-2'(3'H)-one (110 mg, 11%) as a TFA salt. ¹H NMR (CDCl₃) δ 7.65 (d, J=7.5 Hz, 1H), 7.29-7.45 (m, 3H), 3.45 (d, J=12.3 Hz, 2H), 3.20 (t, J=12.3 Hz, 2H), 2.96 (s, 2H), 2.10-2.21 (m, 2H), 1.70 (d, J=14.1 Hz, 2H). MS (ESI) m/z 217.06 [M+H]⁺.

Preparation B: Synthesis of spiro[4H-3,1-benzoxazine-4,4'-piperidin]-2(1H)-one

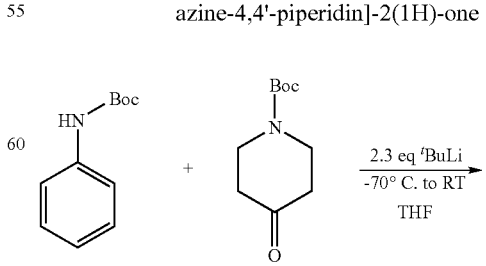

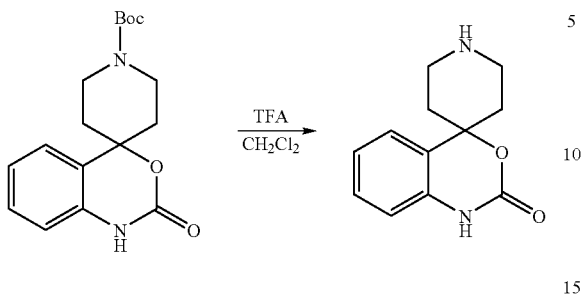

N-Boc-aniline (16.12 g, 83.4 mmol) was dissolved in anhydrous tetrahydrofuran (120 mL) and cooled to −70° C. To this solution was added dropwise, under nitrogen, a 1.7 M solution of tert-butyllithium in pentane (110 mL, 187 mmol) at −70° C. After 30 min at −70° C., the solution was warmed to −20° C. and maintained at that temperature for 2 h. The solution was again cooled to −70° C. and treated dropwise with a solution of N-Boc-4-piperidone (15.98 g, 80.2 mmol) in anhydrous tetrahydrofuran (50 mL). The solution was slowly warmed to room temperature, treated with potassium tert-butoxide (25 mg) and stirred at room temperature overnight under nitrogen. The solution was diluted with diethyl ether (300 mL), cooled in an ice-H$_2$O bath and adjusted to pH 7 with 1.0 NHCl (aq). The layers were separated and the aqueous layer extracted once with diethyl ether (100 mL). The pooled organic layers were washed with H$_2$O and saturated brine, then dried over Na$_2$SO$_4$ and filtered. The filtrate was concentrated under reduced pressure to afford 39.09 g crude product as a viscous pale yellow oil. The crude product was purified via silica gel flash chromatography (25-50% ethyl acetate in hexanes) to afford tert-butyl 2-oxo-1,2-dihydrospiro[benzo[d][1,3]oxazine-4,4'-piperidine]-1'-carboxylate as a pale yellow solid (8.687 g, 34% yield). LC/MS m/z 319.0 [M+H]$^+$, retention time 2.72 min (RP-C$_{18}$, 10-99% CH$_3$CN/0.05% TFA); $^1$H-NMR (400 MHz, CDCl$_3$) δ 9.06 (br s, 1H), 7.28 (m, 1H), 7.12 (m, 2H), 6.91 (d, J=8.5 Hz, 1H), 4.12 (br d, J=9.9 Hz, 2H), 3.36 (br t, J=12.4 Hz, 2H), 2.13 (br d, J=13.1 Hz, 2H), 1.98 (m, 2H), 1.51 (s, 9H).

tert-Butyl 2-oxo-1,2-dihydrospiro[benzo[d][1,3]oxazine-4,4'-piperidine]-1'-carboxylate (6.71 g, 21.1 mmol) was dissolved in dichloromethane (50 mL), treated with trifluoroacetic acid (20 mL) and stirred at room temperature for 45 min. The reaction was concentrated under reduced pressure, re-dissolved in acetonitrile and re-concentrated under reduced pressure. The crude TFA salt was cooled in an ice-H$_2$O bath, dissolved in ice-cold saturated brine (20 mL) and H$_2$O (50 mL) and basified with ice-cold 35% NaOH (aq). A small amount of product (obtained from extraction with 50 mL ethyl acetate) was added to the aqueous layer to initiate crystallization. The suspension obtained was cooled in an ice-H$_2$O bath, filtered, rinsed with ice-cold H$_2$O and dried to afford 3.071 g spiro[benzo[d][1,3]oxazine-4,4'-piperidin]-2(1H)-one free base as a white crystalline solid. An additional 800 mg free base was obtained via extraction of the mother liquor with ethyl acetate (10×50 mL) and subsequent trituration of the crude free base with acetonitrile (overall yield=84%). LC/MS m/z 219.2 [M+H]$^+$, retention time 0.58 min (RP-C$_{18}$, 10-99% CH$_3$CN/0.05% TFA); $^1$H-NMR (400 MHz, DMSO-d$_6$) δ 10.17 (br s, 1H), 7.23 (m, 2H), 7.02 (m, 1H), 6.87 (dd, J=8.2, 1.2 Hz, 1H), 2.89 (m, 2H), 2.82 (m, 2H), 1.84 (m, 4H).

1-Benzyl-4-(2-chloroquinolin-3-yl)piperidin-4-ol

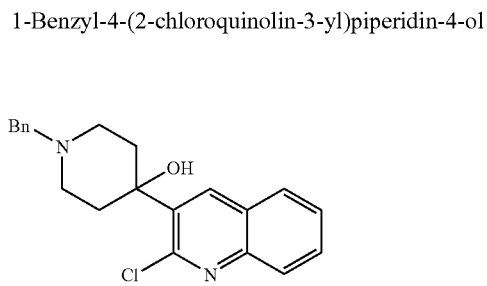

To a solution of LDA (3.4 ml of 2 M in Hept/THF) at −78° C. in THF (5 ml) was added a solution of 2-chloroquinoline (1.0 g. 6.11 mmol) in THF (10 ml) dropwise, and the reaction mixture stirred at −78° C. for 1 hour before a solution of 1-benzylpiperidin-4-one (1.22 g, 6.22 mmol) in THF (2 ml) was added dropwise. The reaction mixture was stirred from −78° C. to RT over two hours, cooled to −20° C., quenched with water and extracted with EtOAc. The organics combined, dried (Na$_2$SO$_4$) and evaporated to dryness. Purification by column chromatography (1 to 15% MeOH in DCM) gave the desired product. LC/MS (10% to 99%): M/Z (M+H)$^+$ (obs)=353; t$_R$=2.24.

3-(1-Benzyl-1,2,3,6-tetrahydropyridin-4-yl)quinolin-2(1H)-one

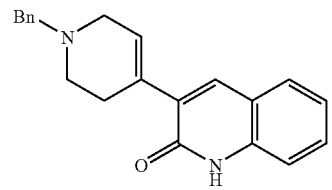

A solution of 1-Benzyl-4-(2-chloroquinolin-3-yl)piperidin-4-ol (1 g, 2.84 mmol) in 6 N HCl (9 ml) was heated at 100° C. for 8 h. The reaction mixture was cooled, water was added and the precipitated product was filtered and dried (0.27 g). LC/MS (10% to 99%): M/Z (M+H)$^+$ (obs)=317; t$_R$=2.18.

3-(Piperidin-4-yl)quinolin-2(1H)-one

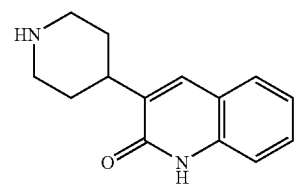

A solution of 3-(1-Benzyl-1,2,3,6-tetrahydropyridin-4-yl)quinolin-2(1H)-one (0.25 g. 0.29 mmol) and 10% Pd/C (130 mg) in MeOH (20 ml) was stirred at 40° C. for 6 hours. The catalyst was filtered and solvent evaporated affording the desired product. LC/MS (10% to 99%): M/Z (M+H)⁺ (obs)= 229; $t_R$=1.27.

2-(4-tert-Butylpiperazin-1-yl)-3,5-difluorobenzaldehyde

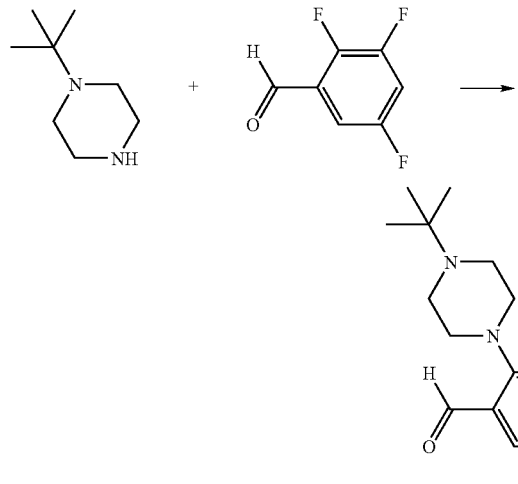

1-tert-Butylpiperazine (2.3 g, 16.2 mmol) and 2,3,5-trifluorobenzaldehyde (2.6 g, 16.2 mmol) were combined in dioxane and heated to 80° C. overnight. The yellow suspension was poured into H₂O/ethyl acetate and the organic layer extracted with 1N HCl. The acidic extract was neutralized with 6N NaOH and extracted with ethyl acetate to yield the crude product as a yellow solid. This solid was purified by silica column to give 2-(4-tert-butylpiperazin-1-yl)-3,5-difluorobenzaldehyde as a yellow solid (0.96 g., 3.4 mmol, 21% yield) ¹H-NMR (300 MHz, CDCl₃) δ 10.52, (1H, s); 7.35 (1H, m); 7.07 (1H, m); 3.22 (4H, m); 2.71 (4H, m); 1.12 (9H, s) ppm.

2-((5S)-2-(2-(4-tert-Butylpiperazin-1-yl)-3,5-difluorophenyl)-3-(3,3-dimethylbutyl)-4-oxothiazolidin-5-yl)acetic acid

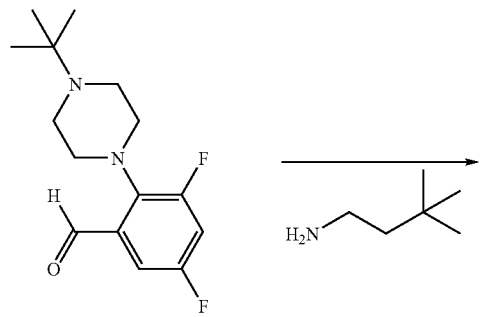

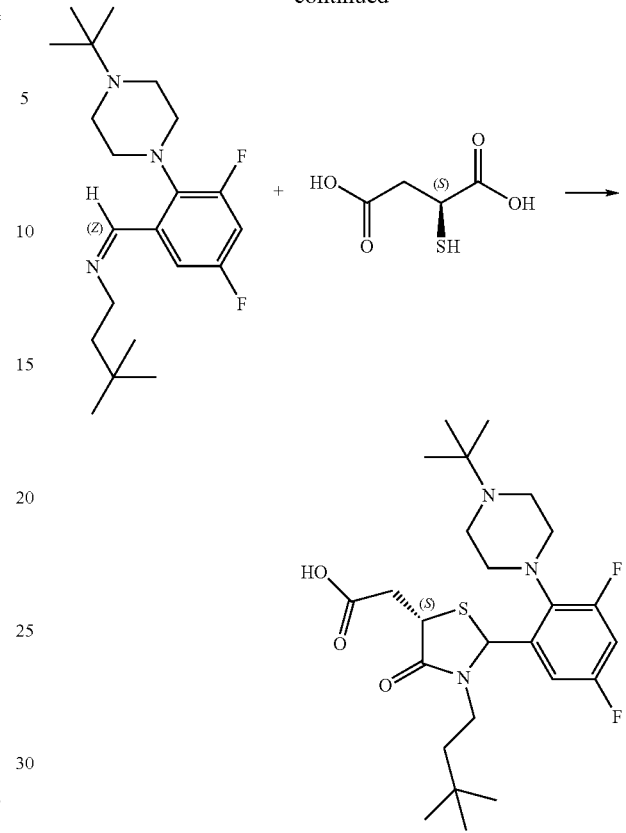

3,3-Dimethylbutan-1-amine (0.7 g, 6.8 mmol) and 2-(4-tert-butylpiperazin-1-yl)-3,5-difluorobenzaldehyde (0.96 g, 3.4 mmol) were combined in toluene and heated to reflux overnight with a Dean-Stark trap attached. The reaction mixture was concentrated to a brown oil. This oil was redissolved in toluene and (S)-2-mercaptosuccinic acid (510 mg, 3.4 mmol) was added. The reaction mixture was heated at 80° C. for 16 hrs., concentrated to an oil, and triturated with ether to give a beige solid, which was filtered off and dried to give 2-((5S)-2-(2-(4-tert-butylpiperazin-1-yl)-3,5-difluorophenyl)-3-(3,3-dimethylbutyl)-4-oxothiazolidin-5-yl)acetic acid (0.45 g, 0.92 mmol, 27% yield) as a solid. LC/MS MH+ 498.45.

(5S)-2-(2-(4-tert-Butylpiperazin-1-yl)-3,5-difluorophenyl)-3-(3,3-dimethylbutyl)-5-(2-oxo-2-(4-(2-oxo-2,3-dihydro-1H-benzo[d]imidazol-1-yl)piperidin-1-yl)ethyl)thiazolidin-4-one (Compound #479)

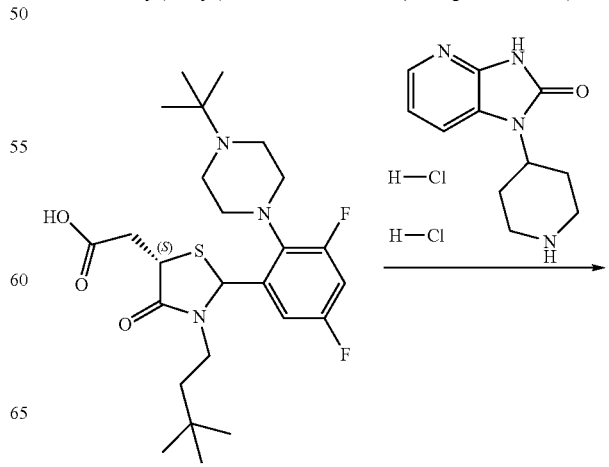

419
-continued

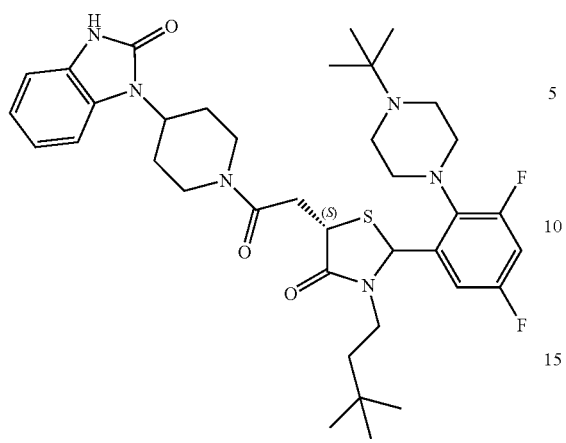

2-((5S)-2-(2-(4-tert-Butylpiperazin-1-yl)-3,5-difluorophenyl)-3-(3,3-dimethylbutyl)-4-oxothiazolidin-5-yl)acetic acid (100 mg, 0.2 mmol), EDC (40 mg, 0.2 mmol), DIEA (52 mg, 0.4 mmol) and 1-(piperidin-4-yl)-1H-imidazo[4,5-b]pyridin-2(3H)-one bis HCl salt (60 mg, 0.2 mmol) were combined in DMF and let stir for 3 days. The mixture was then poured into EtOAc/sat'd NaHCO₃. The organic layer was dried and concentrated to a solid and purified by reverse phase HPLC. Pure fractions were poured into EtOAc/1N NaOH and the organic layer was dried and concentrated to a solid, which was taken up in methanol. Then 4N HCl in dioxane was added. This solution was concentrated to give (5S)-2-(2-(4-tert-butylpiperazin-1-yl)-3,5-difluorophenyl)-3-(3,3-dimethylbutyl)-5-(2-oxo-2-(4-(2-oxo-2,3-dihydro-1H-benzo[d]imidazol-1-yl)piperidin-1-yl)ethyl)thiazolidin-4-one as a white solid (24 mg., 0.03 mmol, 15% yield). LC/MS MH+ 697.97.

(5S)-2-(2-(4-tert-Butylpiperazin-1-yl)-3,5-difluorophenyl)-3-(3,3-dimethylbutyl)-5-(2-oxo-2-(4-(2-oxo-4,5-dihydro-1H-benzo[d][1,3]diazepin-3(2H)-yl)piperidin-1-yl)ethyl)thiazolidin-4-one (Compound #478)

420
-continued

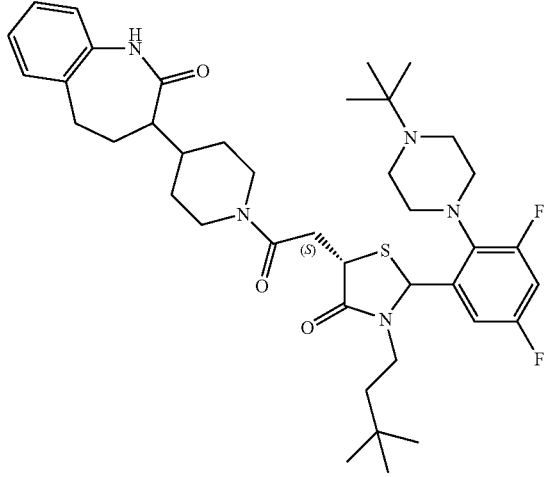

2-((5S)-2-(2-(4-tert-Butylpiperazin-1-yl)-3,5-difluorophenyl)-3-(3,3-dimethylbutyl)-4-oxothiazolidin-5-yl)acetic acid (60 mg, 0.12 mmol), EDC (23 mg, 0.12 mmol), HOBt (18 mg, 0.12 mmol), and 3-(piperidin-4-yl)-4,5-dihydro-1H-benzo[d][1,3]diazepin-2(3H)-one (30 mg, 0.12 mmol) were combined in DMF and let stir for 16 hrs. The reaction mixture was poured into EtOAc/sat'd NaHCO₃ and the organic layer dried and concentrated to a solid, which was purified by flash chromatography to give the product. The HCl salt was made with methanol plus 4N HCl in dioxane, to give (5S)-2-(2-(4-tert-butylpiperazin-1-yl)-3,5-difluorophenyl)-3-(3,3-dimethylbutyl)-5-(2-oxo-2-(4-(2-oxo-4,5-dihydro-1H-benzo[d][1,3]diazepin-3 (2H)-yl)piperidin-1-yl)ethyl)thiazolidin-4-one hydrochloride as a white solid (43 mg, 0.06 mmol, 50% yield). LC/MS MH+ 725.74.

(Z)-tert-Butyl 4-(5-((3,3-dimethylbutylimino)methyl)thiazol-2-yl)piperidine-1-carboxylate

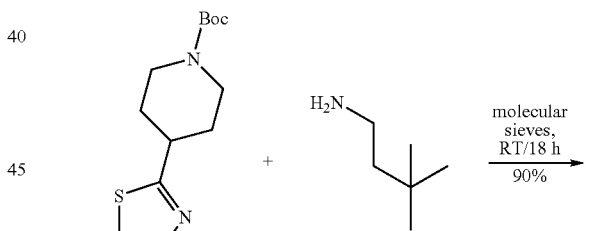

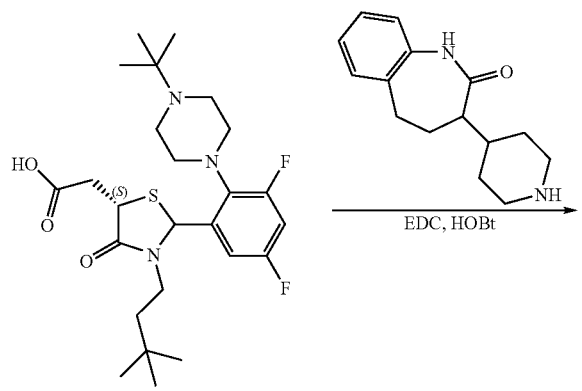

A mixture of t-butyl 4-(5-formylthiazol-2-yl)piperidine-1-carboxylate (250 mg, 0.84 mmol, 1 eq) and 3,3-dimethylbutan-1-amine (94 mg, 0.93 mmol, 1.1 eq) was stirred with molecular sieves at RT for 18 hr. After filtration, the excess solvent was concentrated in vacuo to give (z)-tert-butyl 4-(5-((3,3-dimethylbutylimino)methyl)thiazol-2-yl)piperidine-1-carboxylate (290 mg, 90% yield) with consistent ¹H-NMR data. ¹H NMR (CDCl₃) δ 8.37 (s, 1H), 7.94 (s, 1H), 4.00 (m, 2H), 3.53 (t, J=8.1 Hz, 2H), 2.87 (m, 2H), 2.02 (m, 2H), 1.61-1.46 (m, 5H), 1.47 (s, 9H), 0.94 (s, 9H) ppm.

2-((5S)-2-(2-(1-(tert-Butoxycarbonyl)piperidin-4-yl)thiazol-5-yl)-3-(3,3-dimethylbutyl)-4-oxothiazolidin-5-yl)acetic acid

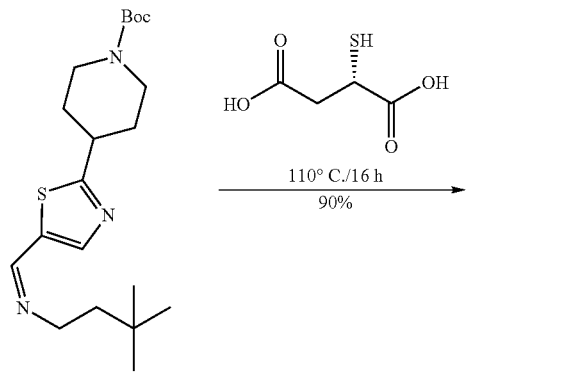

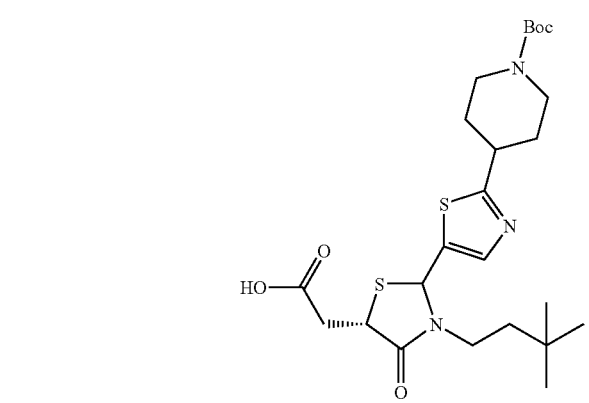

A mixture of (Z)-tert-butyl 4-(5-((3,3-dimethylbutylimino)methyl)thiazol-2-yl)piperidine-1-carboxylate (290 mg, 0.76 mmol, 1 eq) and (S)-2-mercaptosuccinic acid (138 mg, 0.92 mmol, 1.2 eq) in toluene (20 mL) was heated at 110° C. for 18 hr. The excess solvent was concentrated in vacuo and the solids were collected by filtration. The solids were washed with water, toluene and dried to give 2-((5S)-2-(2-(1-(tert-butoxycarbonyl)piperidin-4-yl)thiazol-5-yl)-3-(3,3-dimethylbutyl)-4-oxothiazolidin-5-yl)acetic acid (390 mg, 90% yield). (M+1) 512. ¹H NMR (CDCl₃) δ 7.15 (m, 1H), 5.68 (m, 1H), 4.58-4.11 (m, 3H), 3.62 (m, 1H), 3.39-3.09 (m, 2H), 2.93-2.74 (m, 3H), 2.09 (m, 2H), 1.71-1.64 (m, 2H), 1.47 (s, 9H), 1.44 (m, 1H), 0.85 (s, 9H) ppm.

tert-Butyl 4-(5-((5S)-3-(3,3-dimethylbutyl)-4-oxo-5-(2-oxo-2-(4-(2-oxo-4,5-dihydro-1H-benzo[d][1,3]diazepin-3(2H)-yl)piperidin-1-yl)ethyl)thiazolidin-2-yl)thiazol-2-yl)piperidine-1-carboxylate (Compound #492)

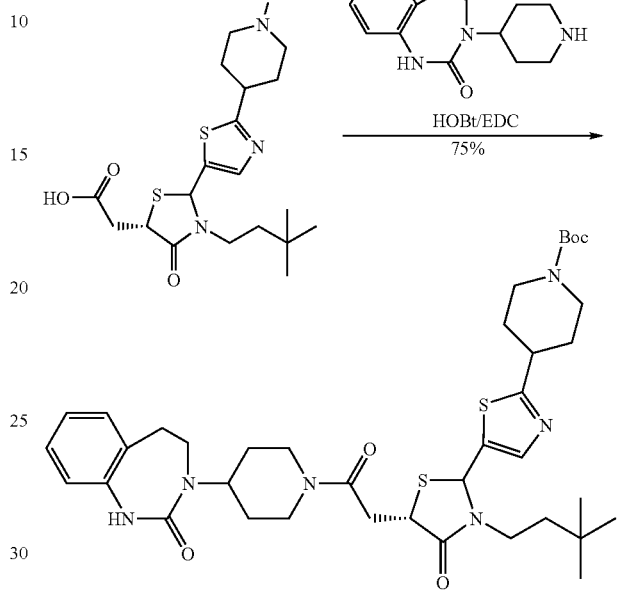

To a solution of 2-((5S)-2-(2-(1-(tert-Butoxycarbonyl)piperidin-4-yl)thiazol-5-yl)-3-(3,3-dimethylbutyl)-4-oxothiazolidin-5-yl)acetic acid (360 mg, 0.7 mmol, 1 eq) in DCM (8 mL) was added HOBt (162 mg, 1.06 mmol, 1.5 eq), EDC (202 mg, 1.06 mmol, 1.5 eq), DIEA (364 mg, 2.8 mmol, 4 eq) and 3-(piperidin-4-yl)-4,5-dihydro-1H-benzo[d][1,3]diazepin-2(3H)-one (207 mg, 0.84 mmol, 1.2 eq). The resulting mixture was stirred at room temperature for 18 hr. The reaction mixture was diluted with DCM (10 mL) and washed with water (5 mL), brine (5 mL), dried (MgSO₄) then concentrated in vacuo. The residue was purified by column chromatography over silica gel eluted with 0 to 10% MeOH in DCM to afford 390 mg of compound I-492 in 75% yield. (M+1) 739. ¹H NMR (CDCl₃) δ 7.19-6.91 (m, 5H), 6.75 (d, J=7.8 Hz, 1H), 5.68 (m, 1H), 4.75 (m, 1H), 4.47 (m, 1H), 4.18 (m, 1H), 3.93 (m, 1H), 3.46-2.67 (m, 11H), 2.08 (m, 6H), 1.71 (m, 6H), 1.47 (m, 9H), 0.85 (m, 9H) ppm.

(5S)-3-(3,3-Dimethylbutyl)-5-(2-oxo-2-(4-(2-oxo-4,5-dihydro-1H-benzo[d][1,3]diazepin-3(2H)-yl)piperidin-1-yl)ethyl)-2-(2-(piperidin-4-yl)thiazol-5-yl)thiazolidin-4-one (Compound #497)

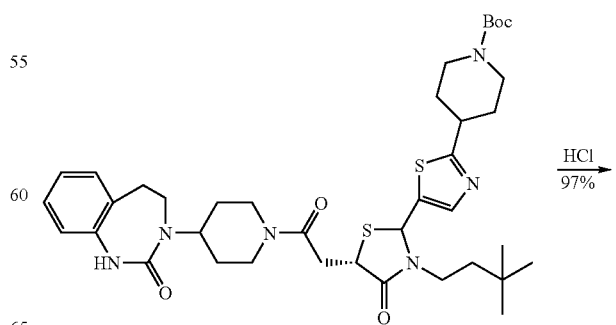

492
cis/trans ~ 1/1

423

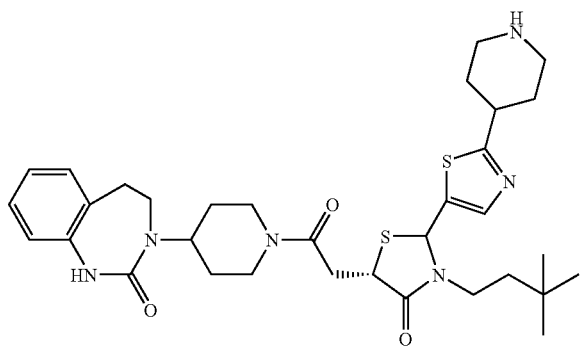

497
(5S)-3-(3,3-Dimethylbutyl)-5-(2-oxo-2-(4-(2-oxo-4,5-di-hydro-1H-benzo[d][1,3]diazepin-3(2H)-yl)piperidin-1-yl)

424 ethyl)-2-(2-(piperidin-4-yl)thiazol-5-yl)thiazolidin-4-one (380 mg, 0.51 mmol, 1 eq) was treated with HCl in dioxane (4M, 8 mL, 32 mmol, 63 eq). MeOH (2 mL) was also added. After 10 min, the excess solvent was concentrated in vacuo to give (5S)-3-(3,3-dimethylbutyl)-5-(2-oxo-2-(4-(2-oxo-4,5-dihydro-1H-benzo[d][1,3]diazepin-3(2H)-yl)piperidin-1-yl)ethyl)-2-(2-(piperidin-4-yl)thiazol-5-yl)thiazolidin-4-one (357 mg, 97% yield). (M+1) 639. $^1$H NMR (CDCl$_3$) δ 7.23-6.92 (m, 5H), 5.66 (m, 1H), 4.76-3.93 (m, 2H), 3.58-2.92 (m, 17H), 2.54 (m, 2H), 2.26 (m, 2H), 1.88-1.71 (m, 4H), 1.59-1.30 (m, 2H), 0.90 (m, 9H) ppm.

(5S)-3-(3,3-Dimethylbutyl)-2-(2-(1-isobutylpiperi-din-4-yl)thiazol-5-yl)-5-(2-oxo-2-(4-(2-oxo-4,5-di-hydro-1H-benzo[d][1,3]diazepin-3(2H)-yl)piperidin-1-yl)ethyl)thiazolidin-4-one (Compound #498)

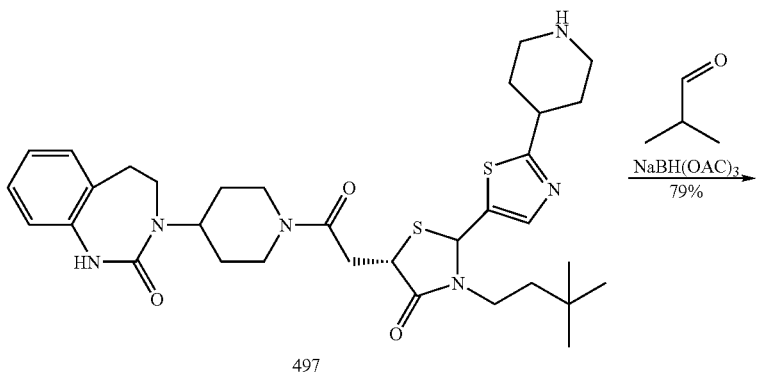

497

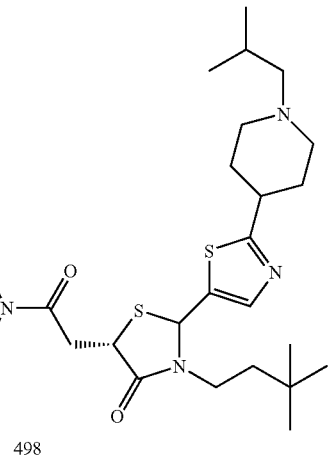

498

To a solution of (5S)-3-(3,3-dimethylbutyl)-5-(2-oxo-2-(4-(2-oxo-4,5-dihydro-1H-benzo[d][1,3]diazepin-3(2H)-yl)piperidin-1-yl)ethyl)-2-(2-(piperidin-4-yl)thiazol-5-yl)thiazolidin-4-one (30 mg, 0.04 mmol, 1 eq) in DCM (3 mL) was added isobutyraldehyde (6 mg; 0.08 mmol, 2 eq) and NaBH(OAc)$_3$ (27 mg, 0.12 mmol, 3 eq). The reaction mixture was stirred at RT for 18 h, then quenched with MeOH (0.1 mL) and sat. NaHCO$_3$ (1 mL). The reaction mixture was diluted with DCM (10 mL) and washed with water (5 mL), brine (5 mL), dried (MgSO$_4$) and then concentrated in vacuo. The residue was purified by column chromatography over silica gel eluted with 2 to 10% MeOH in DCM to afford (5S)-3-(3,3-dimethylbutyl)-2-(2-(1-isobutylpiperidin-4-yl)thiazol-5-yl)-5-(2-oxo-2-(4-(2-oxo-4,5-dihydro-1H-benzo[d][1,3]di-azepin-3(2H)-yl)piperidin-1-yl)ethyl)thiazolidin-4-one (23 mg, 79% yield). (M+1) 695. $^1$H NMR (CDCl$_3$) δ 7.70 (m, 3H), 6.90 (t, J=7.2 Hz, 1H), 6.70 (d, J=7.5 Hz, 1H), 6.49 (NH, 1H), 5.65 (m, 1H), 4.74 (m, 1H), 4.44 (m, 1H), 3.93 (m, 1H), 3.65 (m, 1H), 3.45-3.35 (m, 3H), 3.17-2.59 (m, 9H), 2.09-1.41 (m, 15H), 1.35 (m, 1H), 1.00-0.85 (m, 15H) ppm.

Methyl 2,3-difluorobenzoate

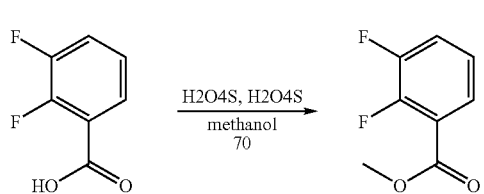

2,3-difluorobenzoic acid (9.47 g, 59.90 mmol) and H$_2$SO$_4$ (0.3 mL) in methanol (100 mL) were heated for 3 days in a 70° C. oil bath. The reaction was cooled to RT, then the solvent was removed under vacuum at 35° C. The crude residue was transferred to a separatory funnel with ether, washed with saturated sodium bicarbonate solution (2×50 mL), brine, dried (MgSO$_4$), filtered and concentrated under vacuum. The residue was redissolved in CH$_2$Cl$_2$, dried (MgSO$_4$), filtered and concentrated under vacuum to yield 8.66 grams of methyl 2,3-difluorobenzoate as a clear liquid.

Methyl 2-(2-(piperidin-1-yl)ethylamino)-3-fluorobenzoate

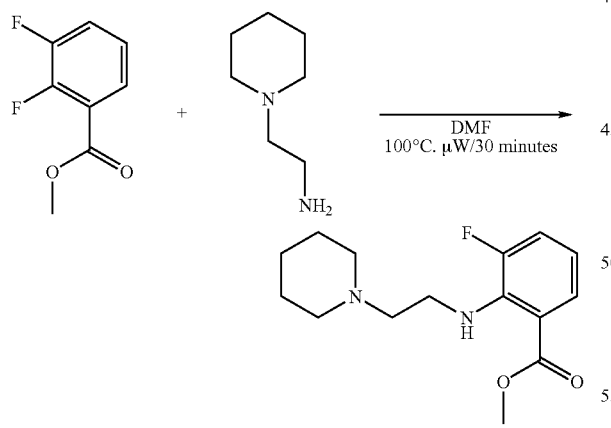

Methyl 2,3-difluorobenzoate (0.816 g, 4.741 mmol) and 2-(piperidin-1-yl)ethanamine (2.7 mL, 18.93 mmol) were dissolved in DMF (15 mL) and heated in a microwave for 30 mins at 100° C. The reaction mixture was transferred to a separatory funnel with EtOAc (75 mL) the organics washed with 10 ml pure water. The layers were separated and the aqueous layer was extracted with EtOAc (2×50 mL). The crude material was purified by silica gel column chromatography eluting with EtOAc/Hexanes to give methyl 2-(2-(piperidin-1-yl)ethylamino)-3-fluorobenzoate (837 mg, 63%). LC/MS: 281.17 (M+1) Rt=1.63 min (10-90% 3/5 min (grad/run) with formic acid).

(2-(2-(Piperidin-1-yl)ethylamino)-3-fluorophenyl)methanol

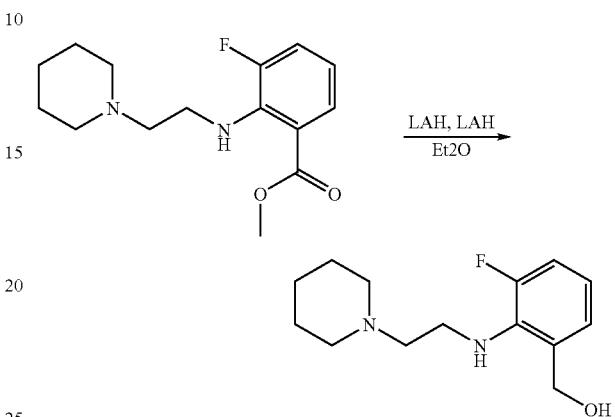

A solution of methyl 2-(2-(piperidin-1-yl)ethylamino)-3-fluorobenzoate (740 mg, 2.640 mmol) in Et$_2$O (30 mL) at −20° C. was treated with LAH (128 mg, 3.372 mmol). After 1.5 hours additional LAH (20 mg, 0.5269 mmol) was added and the reaction was warmed to 0° C. At 0° C., the reaction was diluted with Et$_2$O (80 mL), then NaF and water were added with vigorous stirring until a white ppt formed and the solution cleared. The solution was decanted and evaporated under vacuum. The crude material was purified on a 12 g Redisep ISCO column with 0-10% MeOH in CH$_2$Cl$_2$ over 40 CV to yield (2-(2-(piperidin-1-yl)ethylamino)-3-fluorophenyl)methanol (453 mg, 179.5 mmol) as an off-white solid. FIA: 253.19 (M+1).

2-(2-(Piperidin-1-yl)ethylamino)-3-fluorobenzaldehyde

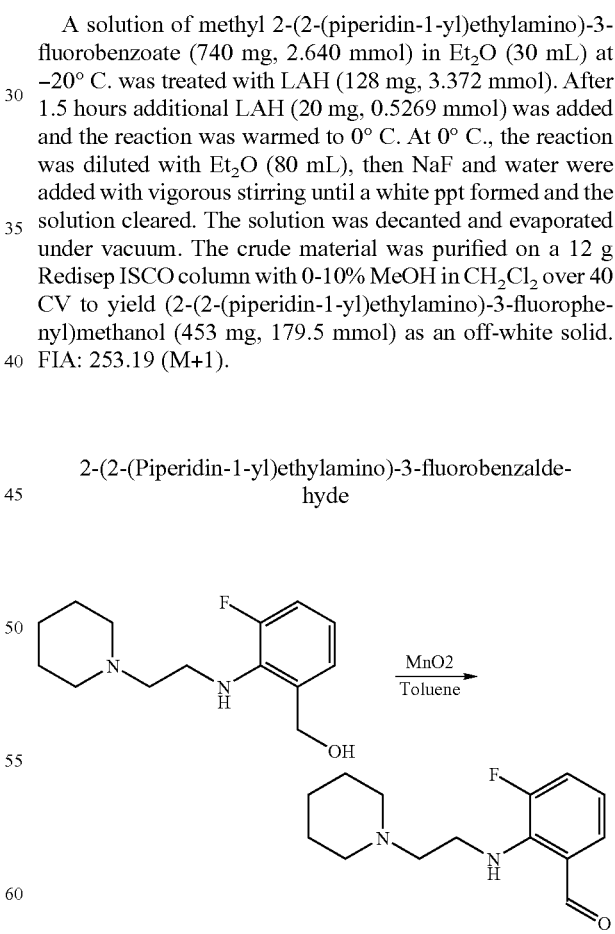

(2-(2-(piperidin-1-yl)ethylamino)-3-fluorophenyl)methanol (453 mg, 1.795 mmol) and MnO$_2$ (692 mg, 7.960 mmol) were heated in toluene (15 mL) at reflux overnight. The suspension was filtered through Celite with CH$_2$Cl$_2$ and concentrated on a rotary evaporator. Crude 2-(2-(piperidin-1-yl)ethylamino)-3-fluorobenzaldehyde was carried on to the next reaction.

2-((E)-(3,3-Dimethylbutylimino)methyl)-6-fluoro-N-(2-(piperidin-1-yl)ethyl)benzenamine

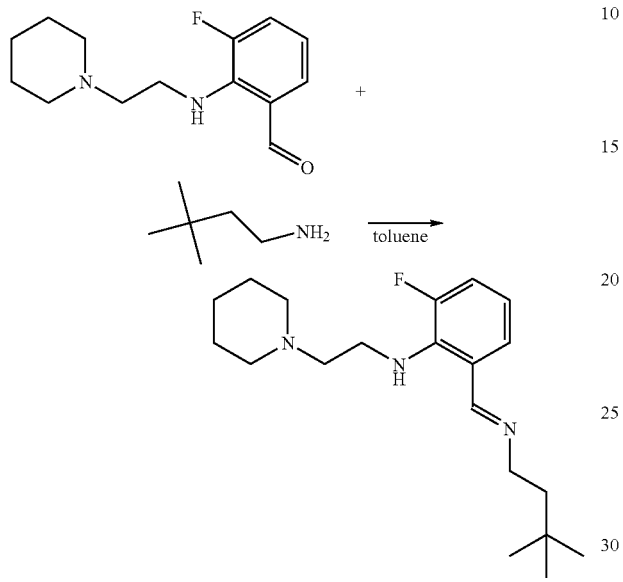

Crude 2-(2-(piperidin-1-yl)ethylamino)-3-fluorobenzaldehyde (372 mg, 1.486 mmol) and 3,3-dimethylbutan-1-amine (225.6 mg, 300.0 µL, 2.229 mmol) were stirred in toluene (7 mL) with 4A MS at RT overnight. The mixture was filtered and the volatiles were removed on rotary evaporator at 40° C. to give 475 mg of crude 2-((E)-(3,3-dimethylbutylimino)methyl)-6-fluoro-N-(2-(piperidin-1-yl)ethyl)benzenamine which was used directly in the next step.

2-((5S)-2-(2-(2-(Piperidin-1-yl)ethylamino)-3-fluorophenyl)-3-(3,3-dimethylbutyl)-4-oxothiazolidin-5-yl)acetic acid

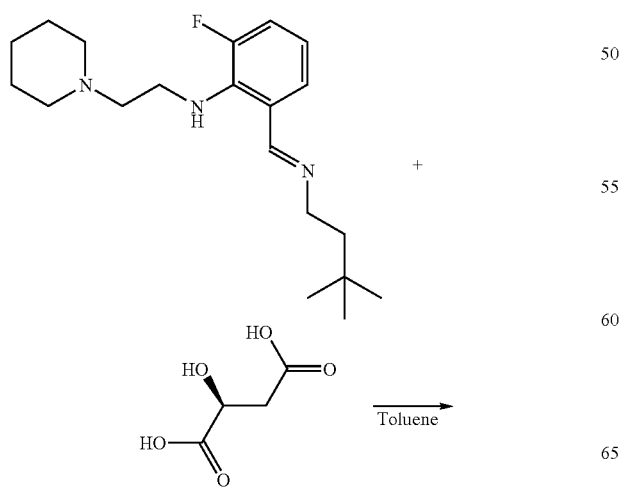

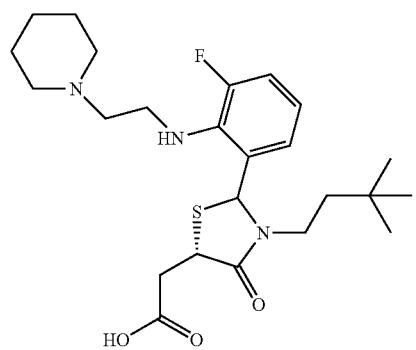

2-((E)-(3,3-dimethylbutylimino)methyl)-6-fluoro-N-(2-(piperidin-1-yl)ethyl)benzenamine (457 mg, 1.370 mmol) and (S)-2-mercaptosuccinic acid (224 mg, 1.492 mmol) were stirred in toluene (14 mL) at 80° C. for 24 hours. The solvent was removed on a rotary evaporator under high vacuum at 35° C. Crude 2-((5S)-2-(2-(2-(piperidin-1-yl)ethylamino)-3-fluorophenyl)-3-(3,3-dimethylbutyl)-4-oxothiazolidin-5-yl)acetic acid was obtained as a brown foam and carried on to the next reaction.

3-(1-(2-((5S)-2-(2-(2-(Piperidin-1-yl)ethylamino)-3-fluorophenyl)-3-(3,3-dimethylbutyl)-4-oxothiazolidin-5-yl)acetyl)piperidin-4-yl)-4,5-dihydro-1H-benzo[d][1,3]diazepin-2(3H)-one (Compound #520)

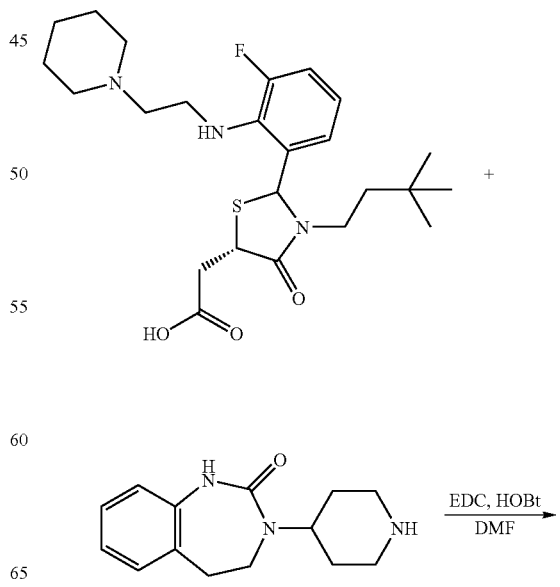

-continued

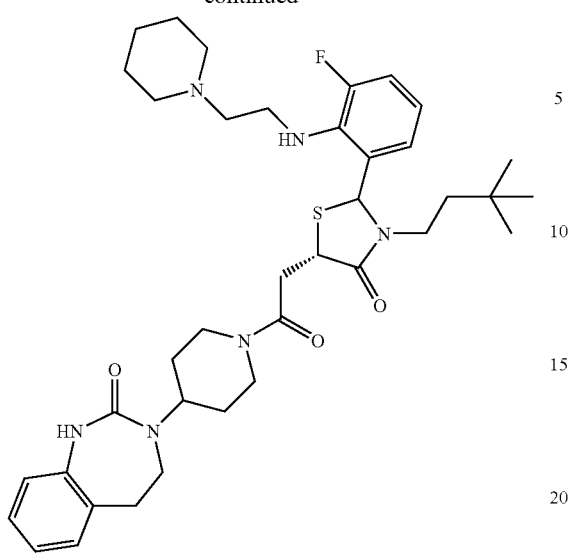

2-((5S)-2-(2-(2-(piperidin-1-yl)ethylamino)-3-fluorophenyl)-3-(3,3-dimethylbutyl)-4-oxothiazolidin-5-yl)acetic acid (319.0 mg, 0.685 mmol), 4,5-dihydro-3-(piperidin-4-yl)-1H-benzo[d][1,3]diazepin-2(3H)-one (336.1 mg, 1.370 mmol), EDC (262.6 mg, 1.370 mmol) and HOBT (209.8 mg, 1.370 mmol) were stirred at RT in DMF (4 mL) overnight. Transferred mixture to a separatory funnel with EtOAc and water. The aqueous layer was extracted with EtOAc (3×), the organic layers were combined, washed with brine, dried (Na₂SO₄) and concentrated in vacuo. The crude was dissolved in DMSO and purified by reverse phase semi-prep chromatography (CH₃CN/water mobile phase) to give 3-(1-(2-((5S)-2-(2-(2-(piperidin-1-yl)ethylamino)-3-fluorophenyl)-3-(3,3-dimethylbutyl)-4-oxothiazolidin-5-yl)acetyl)piperidin-4-yl)-4,5-dihydro-1H-benzo[d][1,3]diazepin-2(3H)-one. LC/MS: 692.34 (M+1) Rt=2.24 min (10-90% 3/5 min (gradient/run) w/formic acid).

1-(1-(2-((5S)-2-(2-(2-(Piperidin-1-yl)ethylamino)-3-fluorophenyl)-3-(3,3-dimethylbutyl)-4-oxothiazolidin-5-yl)acetyl)piperidin-4-yl)-1H-imidazo[4,5-b]pyridin-2(3H)-one (Compound #532)

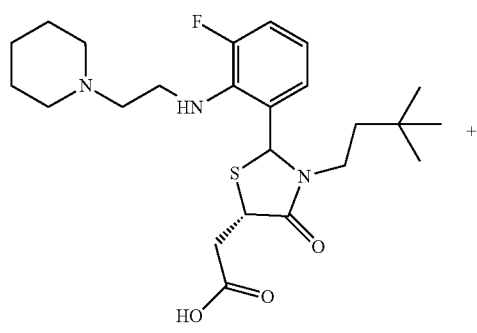

-continued

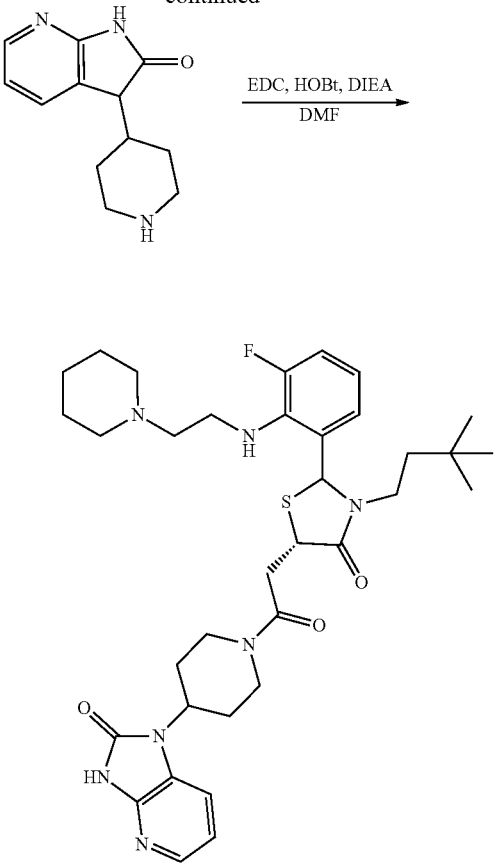

2-((5S)-2-(2-(2-(piperidin-1-yl)ethylamino)-3-fluorophenyl)-3-(3,3-dimethylbutyl)-4-oxothiazolidin-5-yl)acetic acid (319.0 mg, 0.685 mmol), 1-(piperidin-4-yl)-1H-imidazo[4,5-b]pyridin-2(3H)-one (398.9 mg, 1.370 mmol), EDC (262.6 mg, 1.370 mmol), HOBt (209.8 mg, 1.370 mmol) and DIEA (354.1 mg, 477.2 μL, 2.740 mmol) in DMF (4 mL) were stirred at RT overnight. The mixture was transferred to a separatory funnel with water and EtOAc. The aq. layer was extracted with EtOAc, the organics washed with sat bicarb, brine, dried over Na₂SO₄, concentrated and purified by reverse phase semiprep chromatography (CH₃CN/water) to give 1-(1-(2-((5S)-2-(2-(2-(piperidin-1-yl)ethylamino)-3-fluorophenyl)-3-(3,3-dimethylbutyl)-4-oxothiazolidin-5-yl)acetyl)piperidin-4-yl)-1H-imidazo[4,5-b]pyridin-2(3H)-one. LC/MS: 666.37 (M+1) Rt=2.06 min (10-90% 3/5 min (grad/run) w/formic acid).

Methyl 2-(2-(dimethylamino)ethylamino)-3-fluorobenzoate

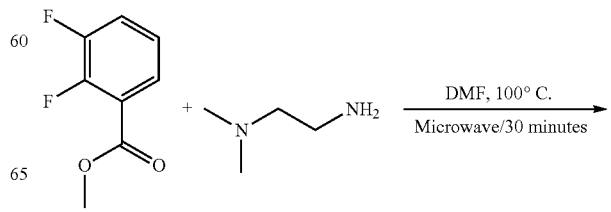

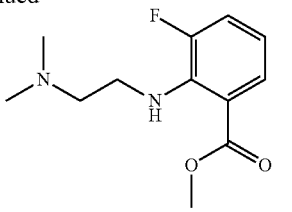

Methyl 2,3-difluorobenzoate (826 mg, 4.799 mmol) and 1,2-ethandiamine N,N-dimethyl (2.1 mL, 19.13 mmol) were stirred in DMF (15 mL) and heated in a microwave for 30 mins at 100° C. The crude material was purified by silica gel column chromatography eluting with EtOAc/Hexanes to yield 344 mg (63%) of methyl 2-(2-(dimethylamino)ethylamino)-3-fluorobenzoate. LC/MS: 241.12 (M+1) Rt=1.49 min (10-90% 3/5 min (grad/run) with formic acid).

(2-(2-(Dimethylamino)ethylamino)-3-fluorophenyl) methanol

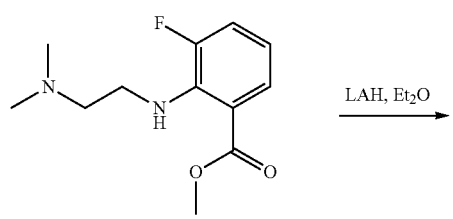

A solution of methyl 2-(2-(dimethylamino)ethylamino)-3-fluorobenzoate (749 mg, 3.117 mmol) in Et$_2$O (30 mL) at −20° C. was treated with LAH (166 mg, 4.374 mmol). After 1.5 hours, additional LAH (15 mg, 0.3952 mmol) was added and the reaction was warmed to 0° C. After 1 hour at 0° C., the reaction was diluted with Et$_2$O (70 mL) and NaF and water were added with vigorous stirring until the reaction was quenched and a white ppt formed. The clear solution was decanted and evaporated under vacuum. The crude material was purified on a 12 g ISCO redisep column (0-10% MeOH in CH$_2$Cl$_2$ as eluent) to yield 543 mg (82%) of (2-(2-(dimethylamino)ethylamino)-3-fluorophenyl)methanol as a clear oil. FIA: 213.08 (M+1).

2-(2-(Dimethylamino)ethylamino)-3-fluorobenzaldehyde

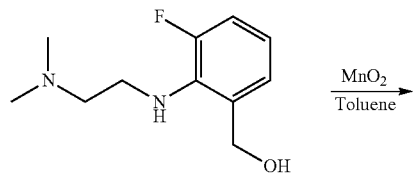

(2-(2-(dimethylamino)ethylamino)-3-fluorophenyl) methanol (536 mg, 2.525 mmol) and MnO$_2$ (878.1 mg, 174.7 µL, 10.10 mmol) were heated to reflux in toluene (13 mL) overnight. The suspension was filtered through Celite with CH$_2$Cl$_2$ and concentrated on a rotary evaporator. The crude product was purified on 12 g Redisep ISCO column eluting with 4-55% EtOAc/Hexanes over 30 CV. 2-(2-(Dimethylamino)ethylamino)-3-fluorobenzaldehyde was identified by $^1$H-NMR and carried on to next reaction.

2-((E)-(3,3-Dimethylbutylimino)methyl)-N-(2-(dimethylamino)ethyl)-6-fluorobenzenamine

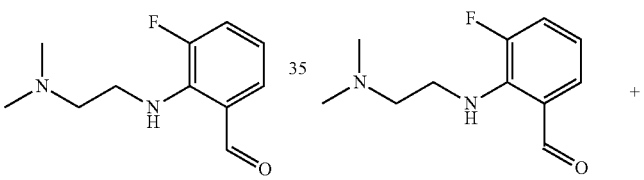

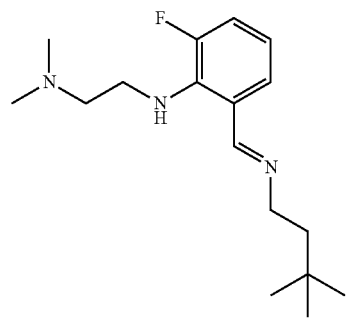

2-(2-(Dimethylamino)ethylamino)-3-fluorobenzaldehyde (157 mg, 0.7467 mmol) and 3,3-dimethylbutan-1-amine (150 µL, 1.115 mmol) were stirred at RT in toluene (5 mL) with 4 Å MS overnight. The suspension was filtered and volatiles removed on a rotary evaporator at 40° C. $^1$H-NMR was consistent with 2-((E)-(3,3-dimethylbutylimino)methyl)-N-(2-

(dimethylamino)ethyl)-6-fluorobenzenamine (175 mg). The crude product was carried on to next reaction.

2-(2-(2-(2-(Dimethylamino)ethylamino)-3-fluorophenyl)-3-(3,3-dimethylbutyl)-4-oxothiazolidin-5-yl)acetic acid

3-(1-(2-((5S)-2-(2-(2-(Dimethylamino)ethylamino)-3-fluorophenyl)-3-(3,3-dimethylbutyl)-4-oxothiazolidin-5-yl)acetyl)piperidin-4-yl)-4,5-dihydro-1H-benzo[d][1,3]diazepin-2(3H)-one (Compound #513)

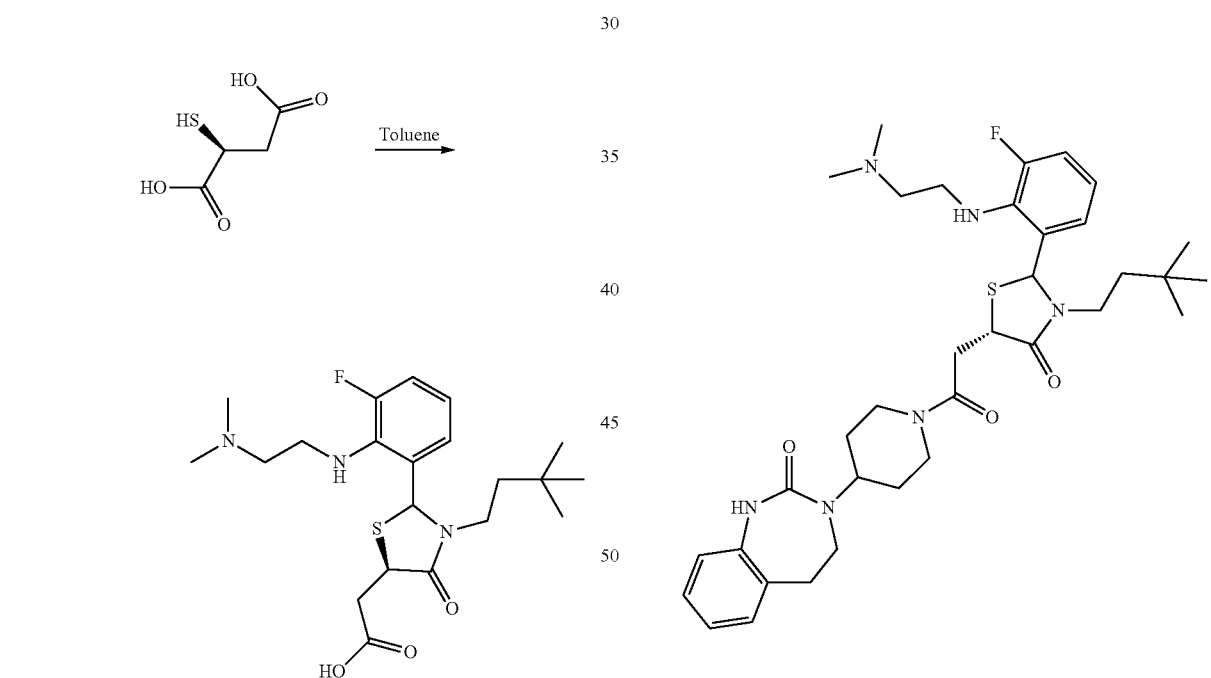

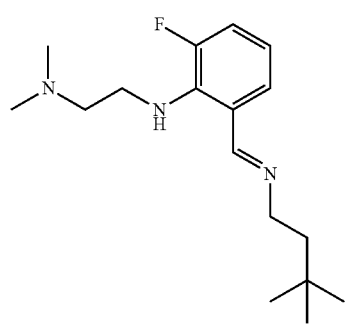

2-((E)-(3,3-dimethylbutylimino)methyl)-N-(2-(dimethylamino)ethyl)-6-fluorobenzenamine (175 mg, 0.5964 mmol) and (S)-2-mercaptosuccinic acid (102 mg, 0.6793 mmol) were stirred in toluene (7 mL) at 80° C. for 24 hours. Crude 2-(2-(2-(2-(dimethylamino)ethylamino)-3-fluorophenyl)-3-(3,3-dimethylbutyl)-4-oxothiazolidin-5-yl)acetic acid was obtained as a brown oil and carried on to the next reaction.

2-(2-(2-(2-(dimethylamino)ethylamino)-3-fluorophenyl)-3-(3,3-dimethylbutyl)-4-oxothiazolidin-5-yl)acetic acid (125.5 mg, 0.295 mmol), 4,5-dihydro-3-(piperidin-4-yl)-1H-benzo[d][1,3]diazepin-2(3H)-one (144.7 mg, 0.5900 mmol), EDC (113.1 mg, 0.5900 mmol), and HOBt (90.35 mg, 0.5900 mmol) in DMF (6 mL) were stirred at RT overnight. The mixture was transferred to a separatory funnel with water, extracted with EtOAc (3×), the organic layers were combined, dried over $Na_2SO_4$ and concentrated to a brown oil. Crude product was purified by ISCO flash chromatography on a 12 g Redisep column eluting with 5-15% MeOH in $CH_2Cl_2$. Obtained 44 mg of desired 3-(1-(2-((5S)-2-(2-(2-(dimethylamino)ethylamino)-3-fluorophenyl)-3-(3,3-dimethylbutyl)-4-oxothiazolidin-5-yl)acetyl)piperidin-4-yl)-4,5-dihydro-1H-benzo[d][1,3]diazepin-2(3H)-one.

1-(1-(2-((5S)-2-(2-(2-(Dimethylamino)ethylamino)-3-fluorophenyl)-3-(3,3-dimethylbutyl)-4-oxothiazolidin-5-yl)acetyl)piperidin-4-yl)-1H-imidazo[4,5-b]pyridin-2(3H)-one (Compound #518)

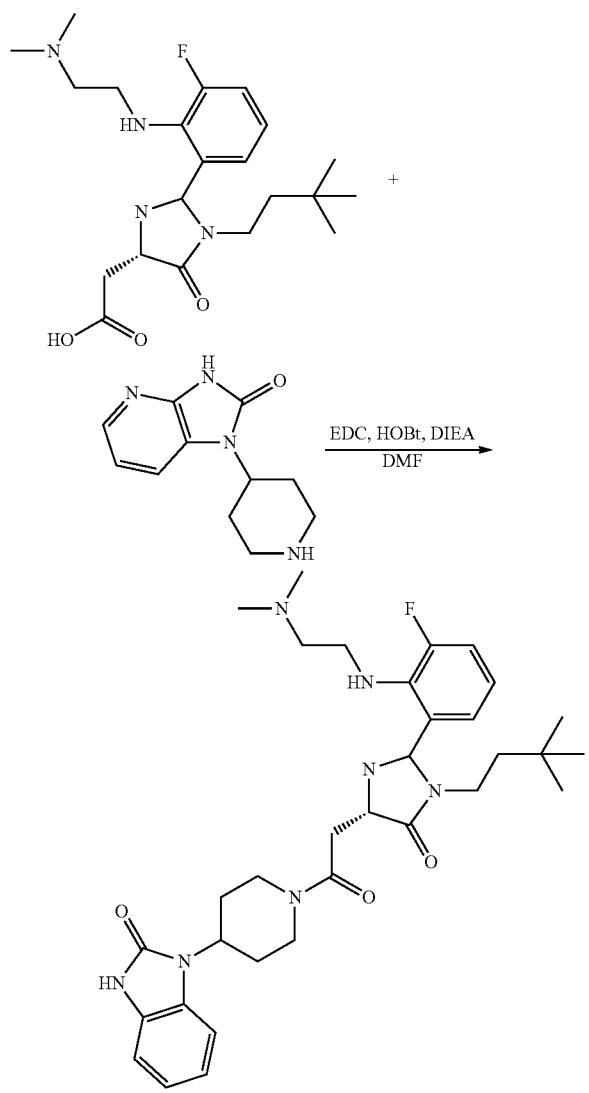

2-(2-(2-(2-(Dimethylamino)ethylamino)-3-fluorophenyl)-3-(3,3-dimethylbutyl)-4-oxothiazolidin-5-yl)acetic acid (125.5 mg, 0.295 mmol), 1-(piperidin-4-yl)-1H-imidazo[4,5-b]pyridin-2(3H)-one (171.8 mg, 0.5900 mmol), EDC (113.1 mg, 0.5900 mmol), HOBt (90.35 mg, 0.5900 mmol), and DIEA (152.5 mg, 205.5 µL, 1.180 mmol) were stirred in DMF (6 mL) at RT overnight. The mixture was diluted with EtOAc and washed with water and a saturated sodium bicarbonate solution. The aqueous layer was back extracted, all organic layers were combined, washed with brine, dried over (MgSO₄), concentrated to an oil. The crude oil was purified by reverse phase column chromatography with ACN/water to give desired 1-(1-(2-((5S)-2-(2-(2-(dimethylamino)ethylamino)-3-fluorophenyl)-3-(3,3-dimethylbutyl)-4-oxothiazolidin-5-yl)acetyl)piperidin-4-yl)-1H-imidazo[4,5-b]pyridin-2(3H)-one.

Methyl 2-(2-morpholinoethylamino)-3-fluorobenzoate

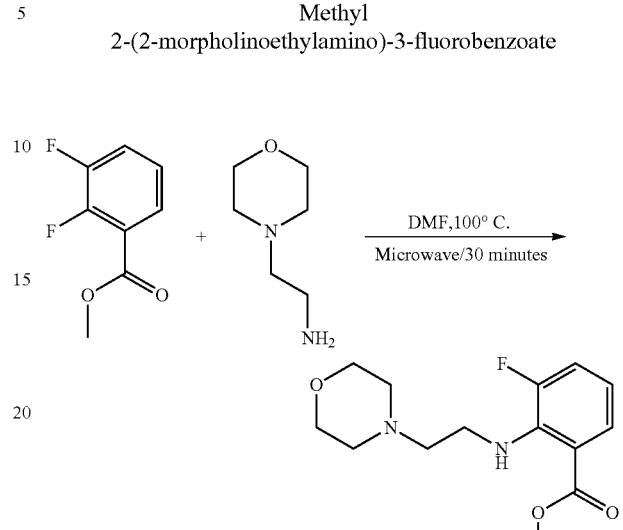

Methyl 2,3-difluorobenzoate (817 mg, 4.746 mmol) and 2-morpholinoethanamine (2.5 mL, 19.20 mmol) were dissolved in DMF (15 mL) and heated in a microwave for 30 mins at 100° C. The crude material was purified by silica gel column chromatography with EtOAc/Hexanes to yield 943 mg (70%) of desired methyl 2-(2-morpholinoethylamino)-3-fluorobenzoate. LC/MS: 283.15 (M+1) Rt=1.48 min (10-90% 3/5 min (grad/run) with formic acid).

(2-(2-Morpholinoethylamino)-3-fluorophenyl)methanol

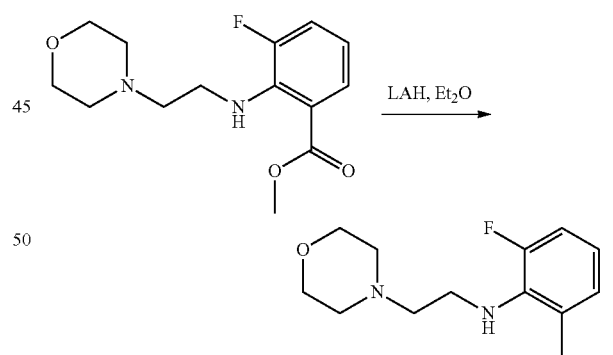

Methyl 2-(2-morpholinoethylamino)-3-fluorobenzoate (943 mg, 3.340 mmol) was dissolved in Et₂O (~40 mL) and cooled to 0° C. The mixture was treated with LAH (203 mg, 5.35 mmol) and stirred at 0° C. The reaction was quenched with NaF (5 g) and water (5 mL), then decanted, dried over Na₂SO₄, and solvent was removed under vacuum. The mixture was diluted with CH₂Cl₂ and EtOAc, dried over MgSO₄, filtered and the solvent was evaporated. The crude product was purified on an ISCO system with EtOAc/Hex (20-80% over 20 column volumes on 12 g redisep column) to give (2-(2-morpholinoethylamino)-3-fluorophenyl)methanol (661 mg, 2.599 mmol) as a colorless oil.

2-(2-Morpholinoethylamino)-3-fluorobenzaldehyde

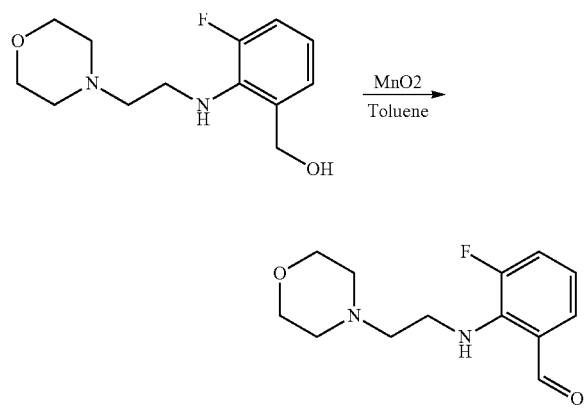

(2-(2-Morpholinoethylamino)-3-fluorophenyl)methanol (695 mg, 2.733 mmol) was stirred with MnO₂ (966 mg, 11.11 mmol) in toluene (12 mL) at 115° C. for 2 days. The reaction was filtered through a plug of Celite with CH₂Cl₂ and the crude product was purified by ISCO chromatography eluting with EtOAc/Hex (12 g redisep column, 5-40% gradient over 30 CV) to give 2-(2-morpholinoethylamino)-3-fluorobenzaldehyde (495 mg). FIA: 253.17 (M+1)

2-((E)-(3,3-Dimethylbutylimino)methyl)-6-fluoro-N-(2-morpholinoethyl)benzenamine

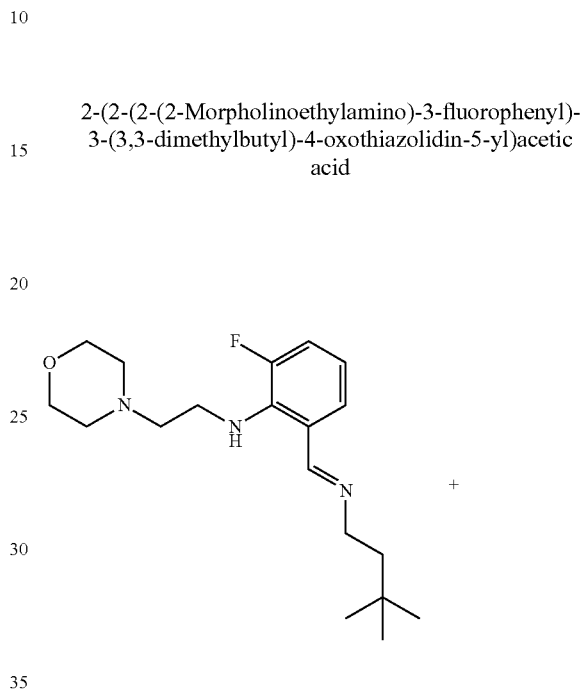

2-(2-Morpholinoethylamino)-3-fluorobenzaldehyde (495 mg, 1.962 mmol), 3,3-dimethylbutan-1-amine (400 μL, 2.973 mmol), and MgSO₄ were added to toluene (15 mL) and the reaction stirred in a 70° C. oil bath overnight. The oil bath temperature was raised to 100° C. for 2.5 hours, then heat was removed, solvent and volatiles removed under high vacuum on a rotary evaporator at 35° C. to give 2-((E)-(3,3-dimethylbutylimino)methyl)-6-fluoro-N-(2-morpholinoethyl)benzenamine. The crude material was carried on to the next reaction. FIA: 336.49 (M+1).

2-(2-(2-(2-Morpholinoethylamino)-3-fluorophenyl)-3-(3,3-dimethylbutyl)-4-oxothiazolidin-5-yl)acetic acid

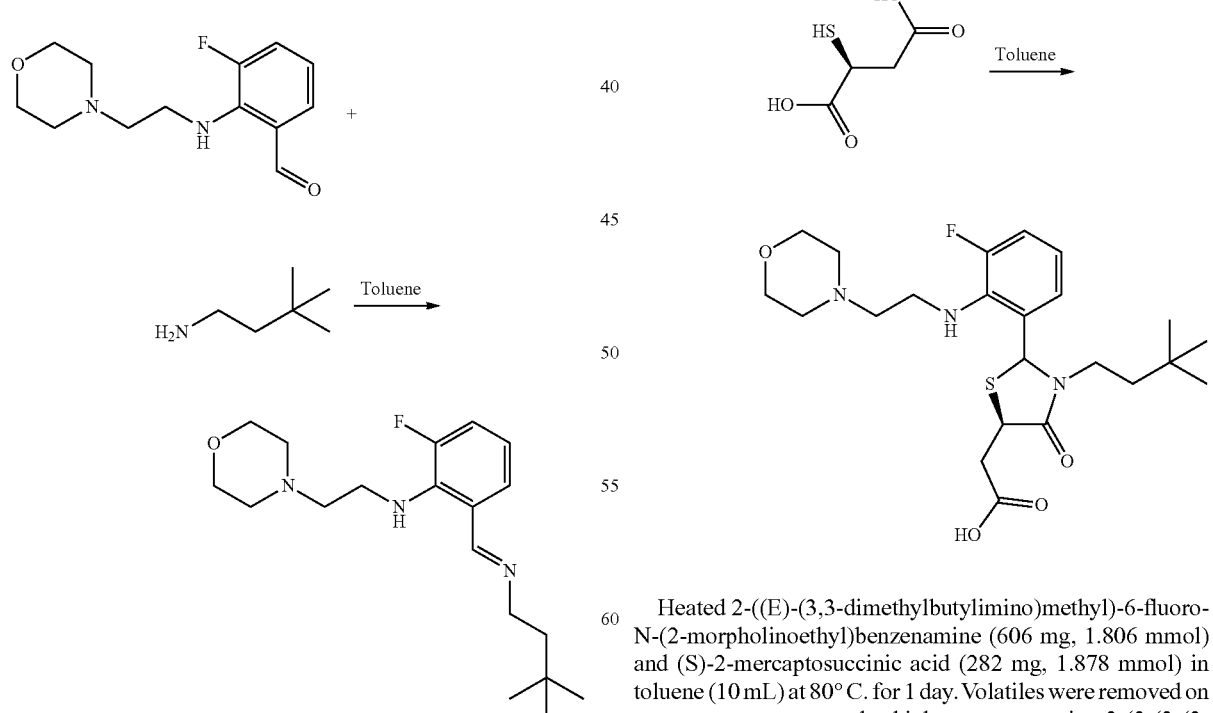

Heated 2-((E)-(3,3-dimethylbutylimino)methyl)-6-fluoro-N-(2-morpholinoethyl)benzenamine (606 mg, 1.806 mmol) and (S)-2-mercaptosuccinic acid (282 mg, 1.878 mmol) in toluene (10 mL) at 80° C. for 1 day. Volatiles were removed on a rotary evaporator under high vacuum to give 2-(2-(2-(2-morpholinoethylamino)-3-fluorophenyl)-3-(3,3-dimethylbutyl)-4-oxothiazolidin-5-yl)acetic acid as a yellow gum which was carried on to the next step as is. LC/MS: 468.39

439

(M+1) Rt=diastereomers at 1.91 and 1.93 min (10-90% 3/5 min (grad/run) w/formic acid).

3-(1-(2-((5S)-2-(2-(2-Morpholinoethylamino)-3-fluorophenyl)-3-(3,3-dimethylbutyl)-4-oxothiazolidin-5-yl)acetyl)piperidin-4-yl)-4,5-dihydro-1H-benzo[d][1,3]diazepin-2(3H)-one (Compound #506)

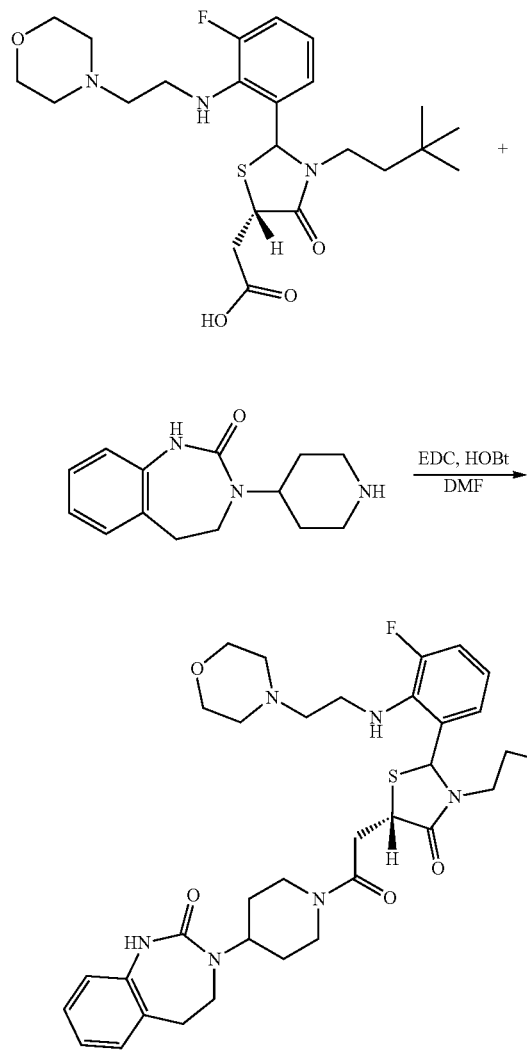

2-(2-(2-(2-Morpholinoethylamino)-3-fluorophenyl)-3-(3,3-dimethylbutyl)-4-oxothiazolidin-5-yl)acetic acid (420.8 mg, 0.9 mmol), 3-(piperidin-4-yl)-4,5-dihydro-1H-benzo[d][1,3]diazepin-2(3H)-one (441 mg, 1.798 mmol), EDC (354 mg, 1.847 mmol), and HOBt (273 mg, 1.783 mmol) were stirred in DMF (5 mL) at RT. The mixture was transferred to a separatory funnel, then diluted with 100 mL EtOAc and washed with a saturated sodium bicarbonate solution. The aqueous layer was extracted 3× with EtOAc. The combined organic layers were washed with brine, dried (Na₂SO₄) and concentrated. The crude material was purified by reverse phase chromatography to give 3-(1-(2-((5S)-2-(2-(2-morpholinoethylamino)-3-fluorophenyl)-3-(3,3-dimethylbutyl)-4-oxothiazolidin-5-yl)acetyl)piperidin-4-yl)-4,5-dihydro-

440

1H-benzo[d][1,3]diazepin-2(3H)-one. LC/MS: 695.33 (M+1) R$_t$=2.20 min (10-90% 3/5 min (grad/run) w/formic acid.

1-(1-(2-((5S)-2-(2-(2-Morpholinoethylamino)-3-fluorophenyl)-3-(3,3-dimethylbutyl)-4-oxothiazolidin-5-yl)acetyl)piperidin-4-yl)-1H-imidazo[4,5-b]pyridin-2(3H)-one (Compound #517)

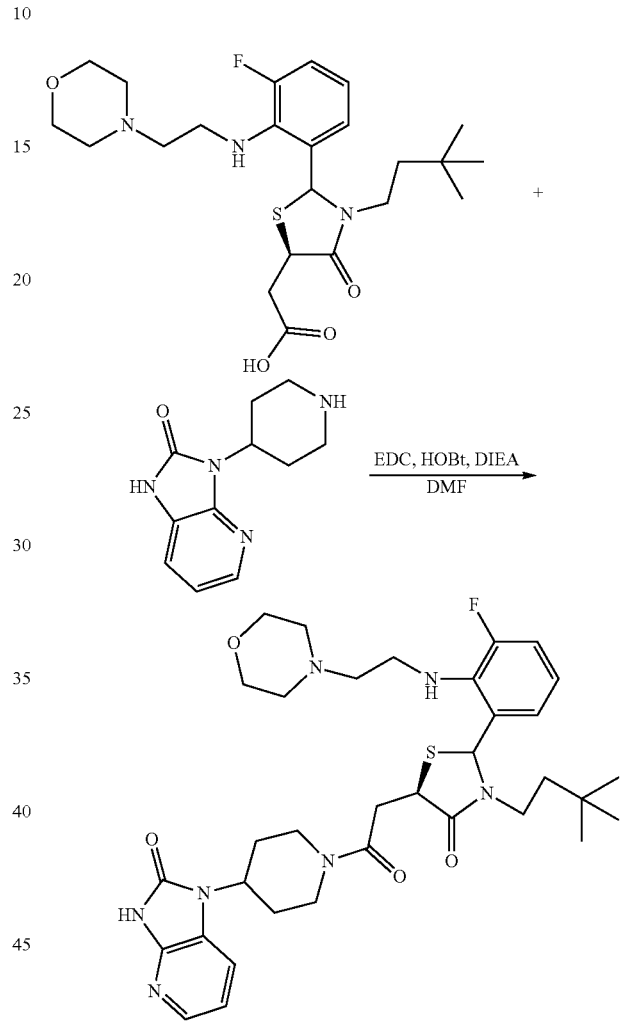

2-(2-(2-(2-Morpholinoethylamino)-3-fluorophenyl)-3-(3,3-dimethylbutyl)-4-oxothiazolidin-5-yl)acetic acid (420.8 mg, 0.9 mmol), 1-(piperidin-4-yl)-1H-imidazo[4,5-b]pyridin-2(3H)-one (545 mg, 1.872 mmol), EDC (360 mg, 1.878 mmol), HOBt (282 mg, 1.841 mmol) and DIEA (730 μL, 4.191 mmol) were stirred in DMF (6 mL) at RT. The mixture was diluted with EtOAc and washed with water and saturated sodium bicarbonate solution. The aqueous layer was back-extracted, the organic layers were combined, then washed with brine, dried (MgSO₄), and concentrated in vacuo. The crude product was purified by reverse phase column chromatography with ACN/water to give 1-(1-(2-((5S)-2-(2-(2-morpholinoethylamino)-3-fluorophenyl)-3-(3,3-dimethylbutyl)-4-oxothiazolidin-5-yl)acetyl)piperidin-4-yl)-1H-imidazo[4,5-b]pyridin-2(3H)-one.

Compounds 488, 489, 493, 494, 503, 504, 508, 514, 515, 521, 522, 523, 524, 526, 529, 533, 536, 537, 539, 544, 545, 547, 548 and 550 were prepared largely according to the procedures listed above for compound 506. Final amide coupling steps for each compound follows immediately below.

Final Amide Coupling Step to Prepare Compounds #488 and #489

Activated the thiazolidinone acid (69 mg, 0.155 mmol, 1.0 equiv) with EDC (35.62 mg, 0.186 mmol, 1.5 equiv) and HOBt (28.5 mg, 0.186 mmol, 1.2 equiv) for 30 min in DMF (2.0 mL). Added 4,5-dihydro-3-(piperidin-4-yl)-1H-benzo[d][1,3]diazepin-2(3H)-one (45.6 mg, 0.186 mmol, 1.2 equiv) and triethylamine (32.4 µL, 0.232 mmol, 1.5 equiv) and stirred o/n. The crude material was partitioned between ethyl acetate and sat'd NaHCO$_3$, the organic layer was dried over sodium sulfate and concentrated in vacuo. The crude product (80 mg) was dissolved in 2.0 mL of DMSO, then purified by reverse-phase chromatography on YMC-Prep C18 3×1250 column eluting with 40-70% acetonitrile/water over 15 minutes. Desired fractions were combined, frozen and lyophilized o/n to give compound 488 (11.0 mg, $^1$H NMR in CDCl$_3$, LC/MS: m/z=677.3, M+1) and compound 489 (10.6 mg, $^1$H-NMR in CDCl$_3$, LC/MS: M/z=677.6, M+1.

Final Amide Coupling Step to Prepare Compounds #493 and #494

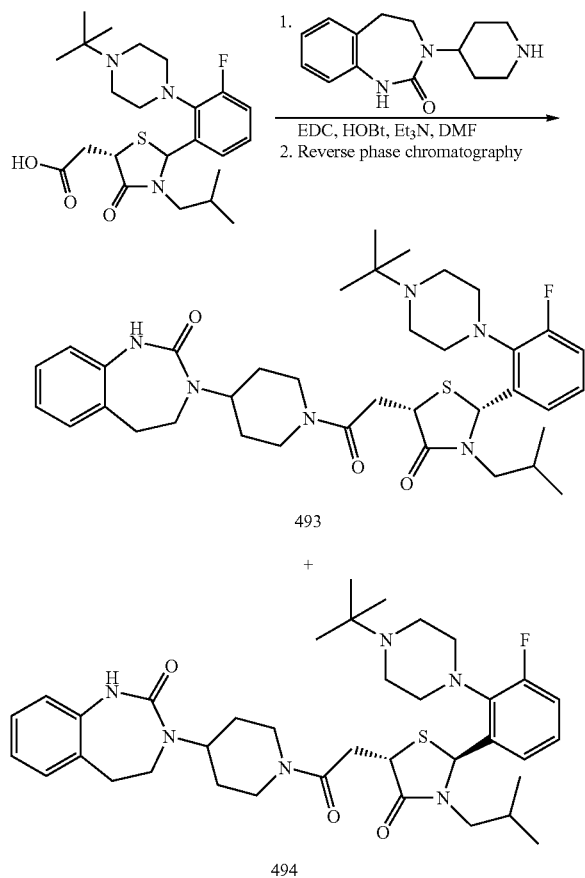

493

+

494

Activated the thiazolidinone acid (250 mg, 0.554 mmol, 1.0 equiv) with EDC (159.2 mg, 0.834 mmol, 1.5 equiv) and HOBt (127.2 mg, 0.834 mmol, 1.5 equiv) for 30 min in DMF (3.0 mL). Added 4,5-dihydro-3-(piperidin-4-yl)-1H-benzo[d][1,3]diazepin-2(3H)-one (203.7 mg, 0.834 mmol, 1.5 equiv) and triethylamine (154.3 µL, 1.107 mmol, 2.0 equiv) and stirred o/n. The crude material was partitioned between ethyl acetate and sat'd NaHCO$_3$, then the organic layer dried over sodium sulfate and concentrated in vacuo. Diasetereomers were separated by reverse-phase chromatography on YMC-Prep C18 3×1250 column eluting with 30-70% acetonitrile/water over 15 minutes. Desired fractions were combined, frozen and lyophilized o/n to give compound 493 (28.1 mg, $^1$H NMR in d6-DMSO, LC/MS: m/z=679.5, M+1) and compound 494 (21.3 mg, $^1$H NMR in d6-DMSO, LC/MS: m/z=679.4, M+1).

Final Amide Coupling Step to Prepare Compounds #495 and #496

Activated the thiazolidinone acid (250 mg, 0.554 mmol, 1.0 equiv) with EDC (159.2 mg, 0.834 mmol, 1.5 equiv) and HOBt (161.2 mg, 0.834 mmol, 1.5 equiv) for 30 min in DMF (3.0 mL). Added 1-(piperidin-4-yl)-1H-imidazo[4,5-b]pyridin-2(3H)-one (203.7 mg, 0.554 mmol, 1.0 equiv) and triethylamine (154.3 µL, 1.107 mmol, 2.0 equiv) and stirred o/n. The crude material was partitioned between ethyl acetate and sat'd NaHCO$_3$, and the organic layer dried over sodium sulfate and concentrated in vacuo. Diasetereomers were separated by reverse-phase chromatography on YMC-Prep C18 3×1250 column eluting with 30-70% acetonitrile/water over 15 minutes. Desired fractions were combined, frozen and lyophilized o/n to give compound 495 (5.4 mg, $^1$H NMR in d4-Methanol, LC/MS: m/z=652.6, M+1) and compound 496 (77.1 mg, LC/MS: m/z=652.6, M+1).

Final Amide Coupling Step to Prepare Compounds #503 and #504

Activated the thiazolidinone acid (241.2 mg, 0.466 mmol, 1.0 equiv) with EDC (134.0 mg, 0.699 mmol, 1.5 equiv) and HOBt (107.0 mg, 0.699 mmol, 1.5 equiv) for 30 min in DMF (2.0 mL). Added 4,5-dihydro-3-(piperidin-4-yl)-1H-benzo[d][1,3]diazepin-2(3H)-one (114.3 mg, 0.466 mmol, 1.0 equiv) and triethylamine (129.9 µL, 0.932 mmol, 2.0 equiv) and stirred o/n. The crude material was partitioned between ethyl acetate and sat'd NaHCO$_3$, then the organic layer dried over sodium sulfate and concentrated in vacuo. Diasetereomers were separated by reverse-phase chromatography on a YMC-Prep C18 3×1250 column eluting with 30-70% acetonitrile/water over 15 minutes. Desired fractions were combined, frozen and lyophilized o/n to give compound 503 (21.1 mg, $^1$H NMR in d4-Methanol, LC/MS: m/z=745.4, M+1) and compound 504 (19.8 mg, $^1$H NMR in d4-Methanol, LC/MS: m/z=745.3, M+1).

Final Amide Coupling Step to Prepare Compound #508

Activated the thiazolidinone acid (285.0 mg, 0.570 mmol, 1.0 equiv) with EDC (164.0 mg, 0.856 mmol, 1.5 equiv) and HOBt (131.0 mg, 0.856 mmol, 1.5 equiv) for 30 min in DMF (2.0 mL). Added 4,5-dihydro-3-(piperidin-4-yl)-1H-benzo[d][1,3]diazepin-2(3H)-one (209.9 mg, 0.856 mmol, 1.5 equiv) and triethylamine (159.1 µL, 1.14 mmol, 2.0 equiv) and stirred o/n. The crude material was partitioned between ethyl acetate and sat'd NaHCO$_3$, then the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 508 (10.0 mg, $^1$H NMR in d4-Methanol, LC/MS: m/z=727.5, M+1).

Final Amide Coupling Step to Prepare Compound #509

Activated the thiazolidinone acid (285.0 mg, 0.570 mmol, 1.0 equiv) with EDC (164.0 mg, 0.856 mmol, 1.5 equiv) and HOBt (131.0 mg, 0.856 mmol, 1.5 equiv) for 30 min in DMF (2.0 mL). Added 1-(piperidin-4-yl)-1H-imidazo[4,5-b]pyridin-2(3H)-one (249.1 mg, 0.856 mmol, 1.5 equiv) and triethylamine (159.1 µL, 1.14 mmol, 2.0 equiv) and stirred o/n. The crude material was partitioned between ethyl acetate and sat'd NaHCO$_3$, the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 509 (6.4 mg, $^1$H NMR in d4-Methanol), LC/MS: m/z=700.3, M+1).

Final Amide Coupling Step to Prepare Compounds #514 and #515

Activated the thiazolidinone acid (431.2 mg, 0.877 mmol, 1.0 equiv) with EDC (336.2 mg, 1.75 mmol, 2.0 equiv) and HOBt (268.6 mg, 1.75 mmol, 2.0 equiv) for 30 min in DMF (2.0 mL). Added 4,5-dihydro-3-(piperidin-4-yl)-1H-benzo[d][1,3]diazepin-2(3H)-one (430.3 mg, 1.75 mmol, 2.0 equiv) and triethylamine (245 μL, 1.75 mmol, 2.0 equiv) and stirred o/n. The crude material was partitioned between ethyl acetate and sat'd NaHCO$_3$, the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 514 (8.0 mg, $^1$H NMR in d4-Methanol, LC/MS: m/z=719.3 M+1) and compound 515 (10.8 mg, $^1$H NMR in d4-Methanol, LC/MS: m/z=719.5, M+1).

Final Amide Coupling Step to Prepare Compound #516

Activated the thiazolidinone acid (431.2 mg, 0.877 mmol, 1.0 equiv) with EDC (336.2 mg, 1.75 mmol, 2.0 equiv) and HOBt (268.6 mg, 1.75 mmol, 2.0 equiv) for 30 min in DMF (2.0 mL). Added 1-(piperidin-4-yl)-1H-imidazo[4,5-b]pyridin-2(3H)-one (510.7 mg, 1.75 mmol, 2.0 equiv) and triethylamine (245 μL, 1.75 mmol, 2.0 equiv) and stirred o/n. The crude material was partitioned between ethyl acetate and sat'd NaHCO$_3$, the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 516 (6.18 mg, $^1$H NMR in d4-Methanol, LC/MS: 692.3, M+1).

Final Amide Coupling Step to Prepare Compounds #521 and #522

Activated the thiazolidinone acid (350 mg, 0.775 mmol, 1.0 equiv) with EDC (297.1 mg, 1.55 mmol, 2.0 equiv) and HOBt (237.4 mg, 1.55 mmol, 2.0 equiv) for 30 min in DMF (2.0 mL). Added 4,5-dihydro-3-(piperidin-4-yl)-1H-benzo[d][1,3]diazepin-2(3H)-one (380.2 mg, 1.55 mmol, 2.0 equiv) and triethylamine (216.0 μL, 1.55 mmol, 2.0 equiv) and stirred o/n. The crude material was partitioned between ethyl acetate and sat'd NaHCO$_3$, the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 521 (25.7 mg, $^1$H NMR in d4-Methanol, LC/MS: m/z=679.4, M+1) and compound 522 (30.6 mg, $^1$H NMR in d4-Methanol, LC/MS: m/z=679.4, M+1).

Final Amide Coupling Step to Prepare Compounds #523 and #524

Activated the thiazolidinone acid (241.0 mg, 0.464 mmol, 1.0 equiv) with EDC (177.8 mg, 0.928 mmol, 2.0 equiv) and HOBt (142.1 mg, 0.928 mmol, 2.0 equiv) for 30 min in DMF (2.0 mL). Added 4,5-dihydro-3-(piperidin-4-yl)-1H-benzo[d][1,3]diazepin-2(3H)-one (227.6 mg, 0.928 mmol, 2.0 equiv) and triethylamine (129.3 μL, 0.928 mmol, 2.0 equiv) and stirred o/n. The crude material was partitioned between ethyl acetate and sat'd NaHCO$_3$, the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 523 (3.8 mg, $^1$H NMR in d4-Methanol, LC/MS: m/z=721.3, M+1) and compound 524 (6.6 mg, $^1$H NMR in d4-Methanol, LC/MS: m/z=721.4, M+1).

Final Amide Coupling Step to Prepare Compounds #526 and #529

Activated the thiazolidinone acid (162.2 mg, 0.320 mmol, 1.0 equiv) with EDC (122.7 mg, 0.640 mmol, 2.0 equiv) and HOBt (98.0 mg, 0.640 mmol, 2.0 equiv) for 30 min in DMF (2.0 mL). Added 4,5-dihydro-3-(piperidin-4-yl)-1H-benzo[d][1,3]diazepin-2(3H)-one (157.0, 0.640 mmol, 2.0 equiv) and triethylamine (89.2 μL, 0.640 mmol, 2.0 equiv) and stirred o/n. The crude material was partitioned between ethyl acetate and sat'd NaHCO$_3$, the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 526 (11.9 mg, $^1$H NMR in d4-Methanol, LC/MS: m/z=709.4 M+1) and compound 529 (16.2 mg, $^1$H NMR in d4-Methanol, LC/MS: m/z=709.4, M+1).

Final Amide Coupling Step to Prepare Compounds #530 and #531

Activated the thiazolidinone acid (162.2 mg, 0.320 mmol, 1.0 equiv) with EDC (122.7 mg, 0.640 mmol, 2.0 equiv) and HOBt (98.0 mg, 0.640 mmol, 2.0 equiv) for 30 min in DMF (2.0 mL). Added 1-(piperidin-4-yl)-1H-imidazo[4,5-b]pyridin-2(3H)-one (186.3 mg, 0.640 mmol, 2.0 equiv) and triethylamine (89.2 μL, 0.640 mmol, 2.0 equiv) and stirred o/n. The crude material was partitioned between ethyl acetate and sat'd NaHCO$_3$, the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 530 (3.13 mg, $^1$H NMR in d4-Methanol, LC/MS: m/z=682.3 M+1) and compound 531 (2.0 mg, $^1$H NMR in d4-Methanol, LC/MS: m/z/=682.3, M+1).

Final Amide Coupling Step to Prepare Compound #533

Activated the thiazolidinone acid (337.7 mg, 0.707 mmol, 1.0 equiv) with EDC (271.3 mg, 1.42 mmol, 2.0 equiv) and HOBt (216.7 mg, 1.42 mmol, 2.0 equiv) for 30 min in DMF (2.0 mL). Added 4,5-dihydro-3-(piperidin-4-yl)-1H-benzo[d][1,3]diazepin-2(3H)-one (347.1 mg, 1.42 mmol, 2.0 equiv) and triethylamine (197.2 μL, 1.42 mmol, 2.0 equiv) and stirred o/n. The crude material was partitioned between ethyl acetate and sat'd NaHCO$_3$, the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 533 (31.8 mg, $^1$H NMR in d4-Methanol, LC/MS: m/z=681.4, M+1).

Final Amide Coupling Step to Prepare Compound #535

Activated the thiazolidinone acid (337.7 mg, 0.707 mmol, 1.0 equiv) with EDC (271.3 mg, 1.42 mmol, 2.0 equiv) and HOBt (216.7 mg, 1.42 mmol, 2.0 equiv) for 30 min in DMF (2.0 mL). Added 1-(piperidin-4-yl)-1H-imidazo[4,5-b]pyridin-2(3H)-one (412.0 mg, 1.42 mmol, 2.0 equiv) and triethylamine (197.2 μL, 1.42 mmol, 2.0 equiv) and stirred o/n. The crude material was partitioned between ethyl acetate and sat'd NaHCO₃, the organic layer dried over sodium sulfate and concentrated in vacuo. Separated diastereomers by reverse-phase chromatography on a YMC-Prep C18 3×1250 column eluting with 30-70% acetonitrile/water over 15 minutes. Desired fractions were combined, frozen and lyophilized o/n to give compound 535 (26.4 mg, ¹H NMR in d4-Methanol, LC/MS: m/z=681.3, M+1).

Final Amide Coupling Step to Prepare Compounds #536 and #537

Activated the thiazolidinone acid (178.5 mg, 0.408 mmol, 1.0 equiv) with EDC (156.4 mg, 0.816 mmol, 2.0 equiv) and HOBt (124.9 mg, 0.816 mmol, 2.0 equiv) for 30 min in DMF (2.0 mL). Added 4,5-dihydro-3-(piperidin-4-yl)-1H-benzo[d][1,3]diazepin-2(3H)-one (200.1 mg, 0.816 mmol, 2.0 equiv) and triethylamine (113.7 µL, 0.816 mmol, 2.0 equiv) and stirred o/n. The crude material was partitioned between ethyl acetate and sat'd NaHCO₃, the organic layer dried over sodium sulfate and concentrated in vacuo. Separated diastereomers by reverse-phase chromatography on a YMC-Prep C18 3×1250 column eluting with 30-50% acetonitrile/water over 15 minutes. Desired fractions were combined, frozen and lyophilized o/n to give compound 536 (3.5 mg, ¹H NMR in d4-Methanol, LC/MS: m/z=665.5, M+1) and compound 537 (11.3 mg, ¹H NMR in d4-Methanol, LC/MS: m/z=665.4, M+1).

Final Amide Coupling Step to Prepare Compound #538

Activated the thiazolidinone acid (178.5 mg, 0.408 mmol, 1.0 equiv) with EDC (156.4 mg, 0.816 mmol, 2.0 equiv) and HOBt (124.9 mg, 0.816 mmol, 2.0 equiv) for 30 min in DMF (2.0 mL). Added 1-(piperidin-4-yl)-1H-imidazo[4,5-b]pyridin-2(3H)-one (237.5 mg, 0.816 mmol, 2.0 equiv) and triethylamine (113.7 µL, 0.816 mmol, 2.0 equiv) and stirred o/n. The crude material was partitioned between ethyl acetate and sat'd NaHCO₃, the organic layer dried over sodium sulfate and concentrated in vacuo. Separated diastereomers by reverse-phase chromatography on a YMC-Prep C18 3×1250 column eluting with 30-50% acetonitrile/water over 15 minutes. Desired fractions were combined, frozen and lyophilized o/n to give compound 538 (2.9 mg, ¹H NMR in d4-Methanol, LC/MS: 638.3, M+1).

Final Amide Coupling Step to Prepare Compound #539

Activated the thiazolidinone acid (179.0 mg, 0.369 mmol, 1.0 equiv) with EDC (141.3 mg, 0.737 mmol, 2.0 equiv) and HOBt (112.9 mg, 0.737 mmol, 2.0 equiv) for 30 min in DMF (2.0 mL). Added 4,5-dihydro-3-(piperidin-4-yl)-1H-benzo[d][1,3]diazepin-2(3H)-one (112.9 mg, 0.737 mmol, 2.0 equiv) and triethylamine (102.8 µL, 0.737 mmol, 2.0 equiv) and stirred o/n. The crude material was partitioned between ethyl acetate and sat'd NaHCO₃, the organic layer dried over sodium sulfate and concentrated in vacuo. Separated diastereomers by reverse-phase chromatography on a YMC-Prep C18 3×1250 column eluting with 30-50% acetonitrile/water over 15 minutes. Desired fractions were combined, frozen and lyophilized o/n to give compound 539 (2.9 mg, ¹H NMR in d4-Methanol, LC/MS: m/z=713.3, M+1).

Final Amide Coupling Step to Prepare Compounds #544 and #545

Activated the thiazolidinone acid (107.2 mg, 0.207 mmol, 1.0 equiv) with EDC (79.4 mg, 0.414 mmol, 2.0 equiv) and HOBt (63.5 mg, 0.414 mmol, 2.0 equiv) for 30 min in DMF (2.0 mL). Added 4,5-dihydro-3-(piperidin-4-yl)-1H-benzo[d][1,3]diazepin-2(3H)-one (101.7 mg, 0.414 mmol, 2.0 equiv) and triethylamine (57.8 µL, 0.414 mmol, 2.0 equiv) and stirred o/n. The crude material was partitioned between ethyl acetate and sat'd NaHCO₃, the organic layer dried over sodium sulfate and concentrated in vacuo. Separated diastereomers by reverse-phase chromatography on a YMC-Prep C18 3×1250 column eluting with 30-50% acetonitrile/water over 15 minutes. Desired fractions were combined, frozen and lyophilized o/n to give compound 544 (7.5 mg, ¹H NMR in d4-Methanol, LC/MS: m/z=693.4, M+1) and compound 545 (8.6 mg, ¹H NMR in d4-Methanol, LC/MS: m/z=693.4, M+1).

Final Amide Coupling Step to Prepare Compounds #547 and #548

Activated the thiazolidinone acid (560 mg, 1.15 mmol, 1.0 equiv) with EDC (442.1 mg, 2.31 mmol, 2.0 equiv) and HOBt (353.1 mg, 2.31 mmol, 2.0 equiv) for 30 min in DMF (4.0 mL). Added 4,5-dihydro-3-(piperidin-4-yl)-1H-benzo[d][1,3]diazepin-2(3H)-one (565.7 mg, 2.31 mmol, 2.0 equiv) and triethylamine (321.3 µL, 2.31 mmol, 2.0 equiv) and stirred o/n. The crude material was partitioned between ethyl acetate and sat'd NaHCO₃, the organic layer dried over sodium sulfate and concentrated in vacuo. Separated diastereomers by reverse-phase chromatography on a YMC-Prep C18 3×1250 column eluting with 25-50% acetonitrile/water over 15 minutes. Desired fractions were combined, frozen and lyophilized o/n to give compound 547 (39.1 mg, ¹H NMR in d4-Methanol, LC/MS: m/z=713.3, M+1) and compound 548 (15.8 mg, ¹H NMR in d4-Methanol, LC/MS: m/z=713.3, M+1).

Final Amide Coupling Step to Prepare Compound #550

Activated the thiazolidinone acid (6.31 g, 12.48 mmol, 1.0 equiv) with EDC (5.26 g, 27.5 mmol, 2.2 equiv) and HOBt (3.71 g, 27.5 mmol, 2.2 equiv) for 30 min in DMF (63.0 mL). Added 4,5-dihydro-3-(piperidin-4-yl)-1H-benzo[d][1,3]diazepin-2(3H)-one (3.67 g, 14.98 mmol, 1.2 equiv) and N-methylmorpholine (5.5 mL, 59.9 mmol, 4.0 equiv) and stirred o/n. The crude material was partitioned between ethyl acetate and sat'd NaHCO₃, the organic layer dried over sodium sulfate and concentrated in vacuo. The crude product was purified by silica gel chromatography eluting with 7% MeOH/CH₂Cl₂. Product fractions were combined and concentrated in vacuo to give compound 550 as a beige crystalline solid (5.36 g, ¹H NMR in CDCl₃, LC/MS: m/z=733.4, M+1).

Compounds 495, 496, 516, 530, 531, 535 and 538 were prepared largely according to the procedures listed above for compound 517.

N-(2-(3,3-Difluoropyrrolidin-1-yl)-3-fluorobenzylidene)-3,3-dimethylbutan-1-amine

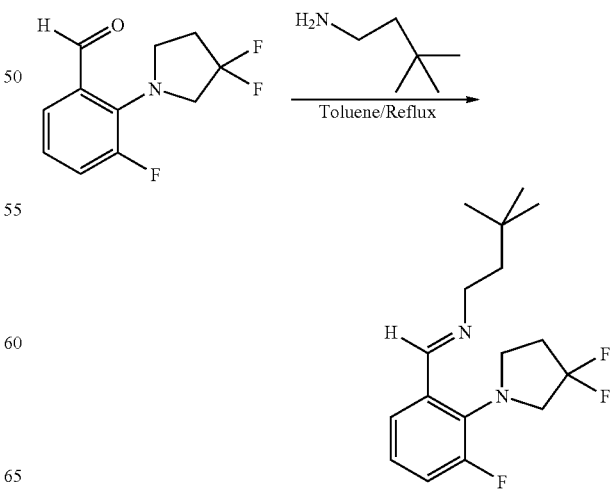

2-(3,3-Difluoropyrrolidin-1-yl)-3-fluorobenzaldehyde (400 mg, 1.745 mmol) was taken in toluene (15 mL) and 3,3-dimethylbutan-1-amine (176.6 mg, 234.8 µL, 1.745 mmol) was added. The reaction mixture was refluxed overnight with a Dean Stark trap to remove the water. The reaction mixture was then concentrated and used in the next step without further purification.

2-((5S)-2-(3-Fluoro-2-(3,3-difluoropyrrolidin-1-yl)phenyl)-3-(3,3-dimethylbutyl)-4-oxothiazolidin-5-yl) acetic acid

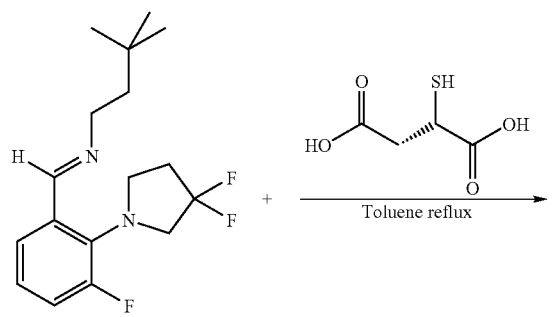

N-(2-(3,3-Difluoropyrrolidin-1-yl)-3-fluorobenzylidene)-3,3-dimethylbutan-1-amine (400.2 mg, 1.281 mmol) was taken in toluene and (S)-2-mercaptosuccinic acid (192.3 mg, 1.281 mmol) was added. The reaction mixture was refluxed overnight with a Dean Stark trap to remove the water. Then the reaction mixture was concentrated, triturated with ether and dried overnight to give 2-((5S)-2-(3-fluoro-2-(3,3-difluoropyrrolidin-1-yl)phenyl)-3-(3,3-dimethylbutyl)-4-oxothiazolidin-5-yl)acetic acid which was used directly in the next step. The product was identified by LC/MS. LC/MS: m/z=445.5M+1.

3-Fluoro-2-(3-fluoropyrrolidin-1-yl)benzaldehyde

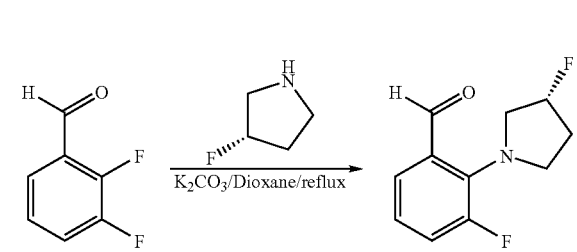

2,3-Difluorobenzaldehyde (1.0 g, 7.037 mmol) was taken up in dry dioxane (20 ml) in a tube and (S)-3-fluoropyrrolidine (627.1 mg, 7.037 mmol) and $K_2CO_3$ (676.4 mg, 10.56 mmol) were added and the mixture refluxed overnight. The reaction mixture was diluted with ethyl acetate, filtered, concentrated to dryness and purified on an ISCO system eluting with Hexane/ethyl acetate (10-100) to give 400 mg of 3-fluoro-2-(3-fluoropyrrolidin-1-yl) benzaldehyde.

N-(3-Fluoro-2-(3-fluoropyrrolidin-1-yl)benzylidene)-3,3-dimethylbutan-1-amine

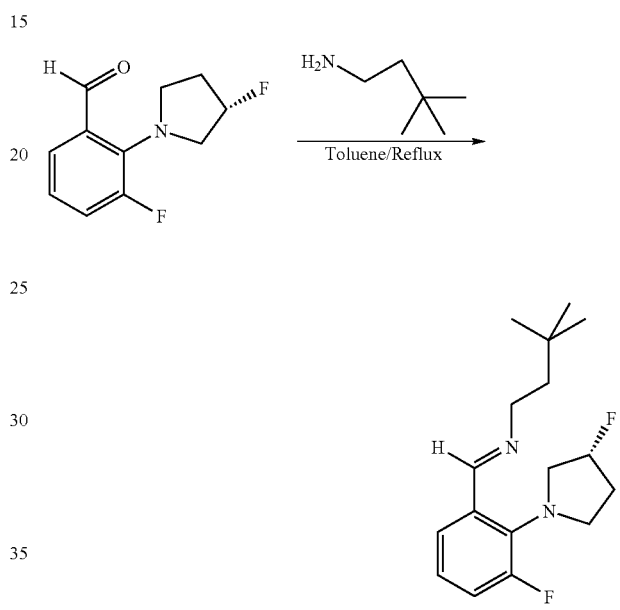

3-Fluoro-2-(3-fluoropyrrolidin-1-yl)benzaldehyde (403.8 mg, 1.912 mmol) was taken in toluene (15 mL) and 3,3-dimethylbutan-1-amine (193.5 mg, 257.3 µL, 1.912 mmol) was added. The reaction mixture was refluxed overnight with a Dean Stark trap to remove the water. The reaction mixture was concentrated to give crude N-(3-fluoro-2-(3-fluoropyrrolidin-1-yl)benzylidene)-3,3-dimethylbutan-1-amine which was used directly in the next step without further purification.

2-((5R)-3-(3,3-Dimethylbutyl)-2-(3-fluoro-2-((S)-3-fluoropyrrolidin-1-yl)phenyl)-4-oxothiazolidin-5-yl) acetic acid

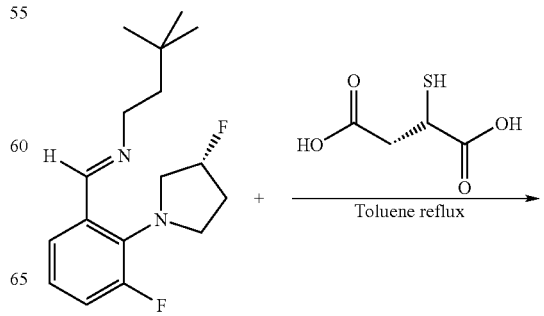

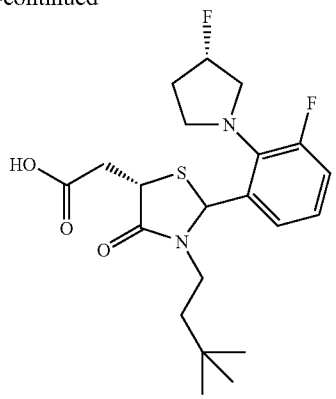

N-(3-Fluoro-2-(3-fluoropyrrolidin-1-yl)benzylidene)-3,3-dimethylbutan-1-amine (400 mg, 1.359 mmol) was taken in toluene and (S)-2-mercaptosuccinic acid (204.1 mg, 1.359 mmol) was added. The reaction mixture was refluxed overnight with a Dean Stark trap to remove the water. Then the reaction mixture was concentrated, triturated with ether and dried overnight to give crude 2-((5R)-3-(3,3-dimethylbutyl)-2-(3-fluoro-2-((S)-3-fluoropyrrolidin-1-yl)phenyl)-4-oxothiazolidin-5-yl)acetic acid which was used directly in the next step. The product was identified by HPLC and LC/MS. (LC/MS: m/z=427.2 M+1).

The procedures described directly above were used to prepare the thiazolidinone acetic acid intermediates for compounds 484, 485, 486 and 487. The final amide bond coupling reactions to prepare compounds 480, 481, 482, 483, 484, 485, 486 and 487 were also accomplished using the procedures described above (e.g, see procedure for compound 494).

3-(1-(2-((2R,5S)-2-(2-(1-Cyclobutylpiperidin-4-yl)-3-fluorophenyl)-3-(3,3-dimethylbutyl)-4-oxothiazolidin-5-yl)acetyl)piperidin-4-yl)-4,5-dihydro-1H-benzo[d][1,3]diazepin-2(3H)-one (Compound #542)

3-(1-(2-((2S,5S)-2-(2-(1-Cyclobutylpiperidin-4-yl)-3-fluorophenyl)-3-(3,3-dimethylbutyl)-4-oxothiazolidin-5-yl)acetyl)piperidin-4-yl)-4,5-dihydro-1H-benzo[d][1,3]diazepin-2(3H)-one (Compound #543)

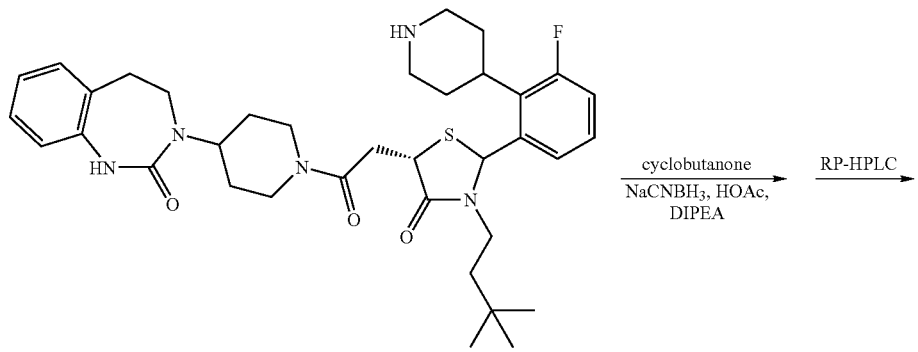

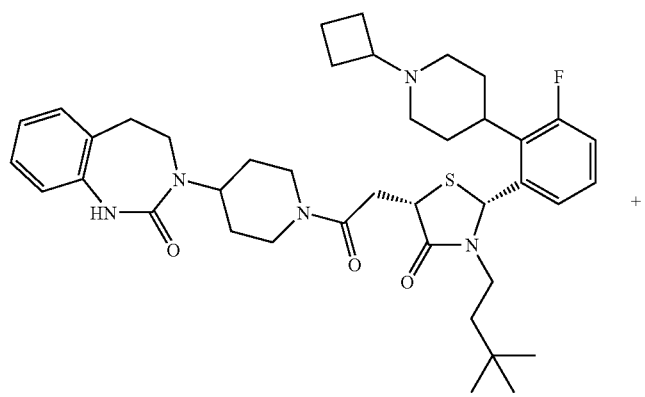

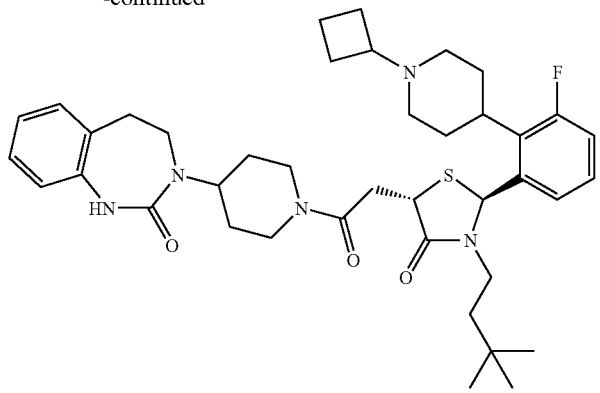

To a solution of amine thiazolidinone starting material (130 mg, 0.19 mmol) in dichloroethane (2 mL) was added cyclobutanone (40 mg, 3 eq.), then NaBH(OAc)₃(120 mg, 3 eq.), and AcOH (17 uL, 3 eq.). The reaction mixture was stirred for 18 h at room temperature (no further evolution after 2 h by HPLC: small amount ~5% of SM). The reaction was stirred with MeOH (100 uM) for 5 min, then concentrated in vacuo. The residue was diluted in DCM, washed with sat. aq. NaHCO₃, then concentrated in vacuo. The residue was then diluted in DMSO and purified by prep-HPLC (Gilson, 100 uL injections, 35-50% ACN in water over 30 min, 254 detection). The pure fractions for the cis and the trans diastereomers were combined and lyophilized. The cis diastereomer was then salted as its mono-HCl salt.

Cis diastereomer/#542(HCl salt): 11.3 mg as a white solid, Rt=7.09 min (35 to 50% ACN in water over 8 min, YMC 3×1250 column), purity ~98% at 254; LC/MS ES+1: 705.4. ¹H NMR (CD3OD).

Trans diastereomer/#543 (TFA salt): 15.1 mg as a white solid, Rt=7.49 min (35 to 50% ACN in water over 8 min, YMC 3×1250 column), purity ~98% at 254; LC/MS ES+1: 705.4. ¹H NMR (CD3OD).

Compounds 558, 559, 560, 561, 562, 563 and 564 were also prepared according to the procedures described above.

tert-Butyl 4-(2-formylphenyl)-5,6-dihydropyridine-1 (2H)-carboxylate

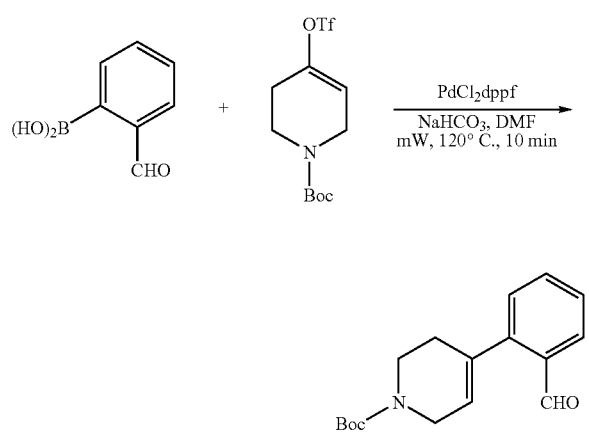

To the commercially available boronic acid (620 mg, 1.87 mmol) and the triflate (280.5 mg, 1.87 mmol, 1 eq.) in DMF (9 mL) was added a saturated aqueous solution of NaHCO₃ (4.7 mL, 1.2 M). PdCl₂(dppf)₂ (136.9 mg, 0.1 eq, 0.187 mmol) was added, and the reaction was stirred for 10 minutes at 120° C. under microwave conditions. After warming to room temperature, EtOAc (~50 mL) and water (40 ml) were added, the phases were separated and the organics washed with brine, dried (MgSO₄), filtered and concentrated. The crude brown material was chromatographed using a 24 g ISCO column, eluting with 0 to 20% EtOAc/hexanes. The pure fractions were combined to provide 377 mg (70%) of desired tert-butyl 4-(2-formylphenyl)-5,6-dihydropyridine-1 (2H)-carboxylate as a clear oil. LCMS ES+1: 288.17. This intermediate was used without further purification in the next step tert-Butyl 4-(2-(hydroxymethyl)phenyl)piperidine-1-carboxylate

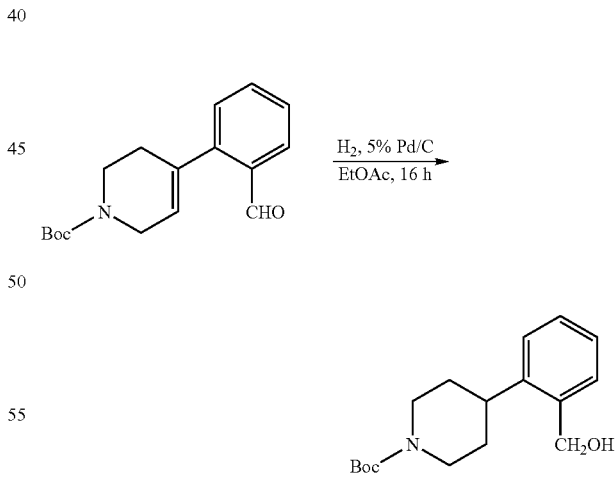

A mixture of tert-butyl 4-(2-formylphenyl)-5,6-dihydropyridine-1(2H)-carboxylate (305 mg, 1.06 mmol, 1 eq.)), 5% Pd/C (30 mg) and EtOAc (10 mL) was stirred at room under 1 atm of H₂ for 18 h. Mainly benzyl alcohol was observed by LC/MS and HPLC (Rt=4.21 min). The catalyst was filtered off, the filtrate was concentrated in vacuo, and purified by ISCO chromatography (24 g, Si35, 10 to 25% EtOAC in Hexanes, Rf~0.6 in 1:1 Hex:EtOAc, to give 432 mg (52%) of tert-butyl 4-(2-(hydroxymethyl)phenyl)piperidine-1-carboxylate as a thick, colorless oil.

tert-Butyl 4-(2-formylphenyl)piperidine-1-carboxylate

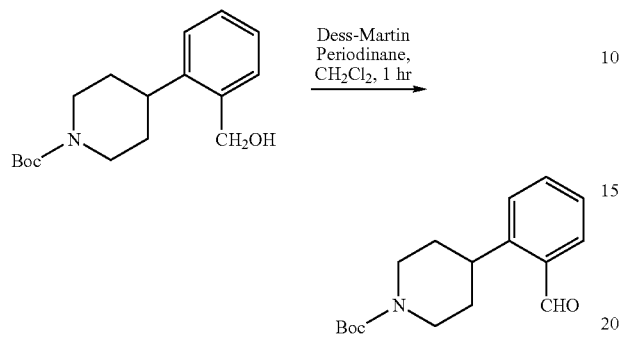

tert-Butyl 4-(2-(hydroxymethyl)phenyl)piperidine-1-carboxylate (216 mg, 0.74 mmol, 1 eq.) and Dess Martin periodinane (377 mg, 1.2 eq., 0.89 mmol) were stirred in DCM (7 mL) for 1 h. HPLC and LCMS showed completion of the reaction. Sodium thiosulfate was then added and the biphasic mixture was stirred for 10 min, then the mixture was diluted with EtOAc (50 mL), the biphasic mixture was separated, the organics were dried (MgSO$_4$), conc in vacuo and purified by ISCO chromatography (8 g SiO$_2$, 0 to 15% EtOAc in Hexanes). Remaining DMP side product was observed so the residue was taken up in DCM, the insolubles filtered off, the filtrate concentrated and purified by ISCO chromatography (12 g SiO$_2$, 0 to 10% EtOAc in Hexanes) to give, after concentration, 229 mg of tert-butyl 4-(2-formylphenyl)piperidine-1-carboxylate as a clear oil (still contains some DMP side product) which was used in the next step without further purification. LC/MS ES+1-Boc: 190.08.

tert-Butyl 4-(2-((E)-(3,3-dimethylbutylimino)methyl)phenyl)piperidine-1-carboxylate

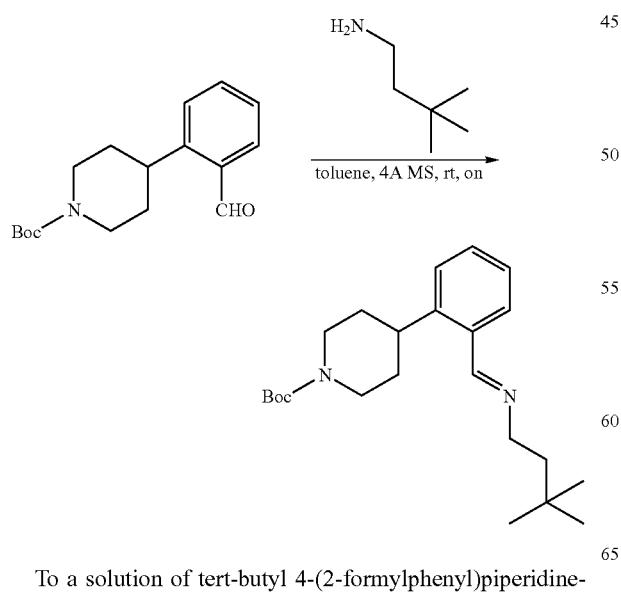

To a solution of tert-butyl 4-(2-formylphenyl)piperidine-1-carboxylate (229 mg, 0.79 mmol) in toluene (4 mL) was added 3,3 dimethylbutylamine (88.09 mg, 117.1 µL, 0.8705 mmol) and 4 Å molecular sieves. The resulting suspension was stirred at rt overnight. Filtered out molecular sieves and concentrated the mixture with a flow of N$_2$ to give 282 mg of tert-butyl 4-(2-((E)-(3,3-dimethylbutylimino)methyl)phenyl)piperidine-1-carboxylate as an thick off-white oil which was used without further purification for the next step.

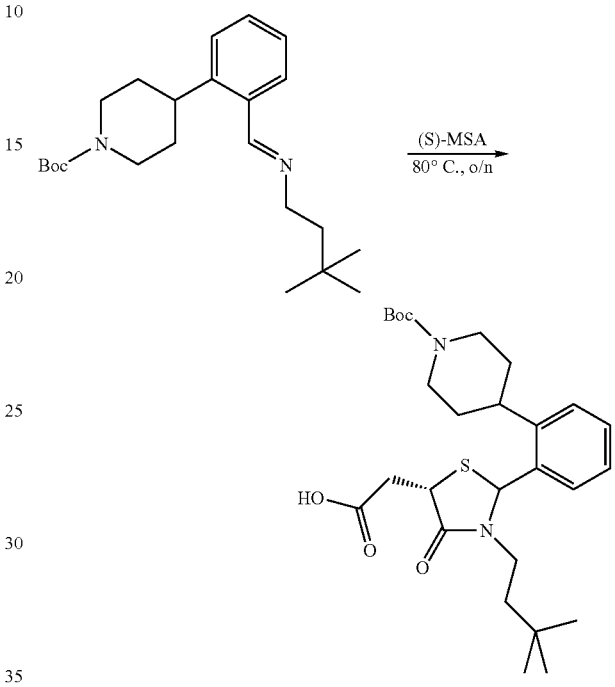

To a solution of tert-butyl 4-(2-((E)-(3,3-dimethylbutylimino)methyl)phenyl) piperidine-1-carboxylate (262 mg, 0.70 mmol, 1 eq.) in toluene (7 mL) was added (S)-2-mercaptosuccinic acid (126.7 mg, 1.2 eq., 0.844 mmol). The reaction mixture was stirred at 80° C. for 16 h and cooled to rt. Some sticky solid on the wall of the flask was observed. The solvent was concentrated in vacuo and the residue was triturated with Et$_2$O and stirred for 10 min. The insolubles were filtered off to give 210 mg (59%) of a white solid which was fairly clean desired product by HPLC, LC/MS (~90%+ pure) ES+1: 505.66, ES-1: 503.71. This crude material was used without further purification for the next step.

Compound #500

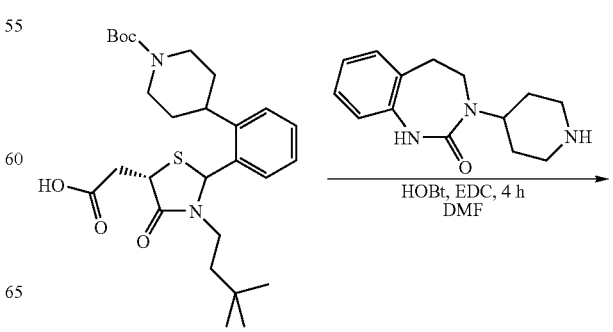

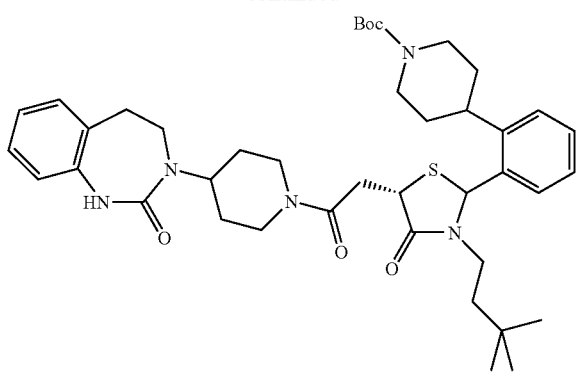

Thiazolidinone acid (110 mg, 0.218 mmol, 1 eq.), EDC (62.6 mg, 1.5 eq., 0.32 mmol), HOBt (44 mg, 1.5 eq, 0.32 mmol) in DMF (2 mL) were stirred at rt for 1 h. Unreacted acid was detected by HPLC so another 1.5 eq of both EDC and HOBt were added to the dark reaction solution. After a total of 1 h50, full activation was observed by HPLC. 4,5-dihydro-3-(piperidin-4-yl)-1H-benzo[d][1,3]diazepin-2 (3H)-one (66.8 mg, 1.25 eq., 0.27 mmol) was then added, followed by N-methylmorpholine (NMM, 71.9 uL, 3 eq., 0.65 mmol)). The dark reaction mixture was stirred at rt for 4 h. The crude was diluted with EtOAc (30 mL), washed with NaHCO$_3$, brine, dried (MgSO$_4$) and concentrated in vacuo. The crude residue was purified by ISCO Companion (8 g Supra Si35, 10 to 75 to 90% EtOAc in Hexanes) to give 72.0 mg of compound 500 as a white solid and as a mixture of the two diastereomers.

4,5-Dihydro-3-(1-(2-((2S,5S)-3-(3,3-dimethylbutyl)-4-oxo-2-(2-(piperidin-4-yl)phenyl)thiazolidin-5-yl)acetyl)piperidin-4-yl)-1H-benzo[d][1,3]diazepin-2 (3H)-one (Compound #502)

4,5-Dihydro-3-(1-(2-((2R,5S)-3-(3,3-dimethylbutyl)-4-oxo-2-(2-(piperidin-4-yl)phenyl)thiazolidin-5-yl)acetyl)piperidin-4-yl)-1H-benzo[d][1,3]diazepin-2 (3H)-one (Compound #501)

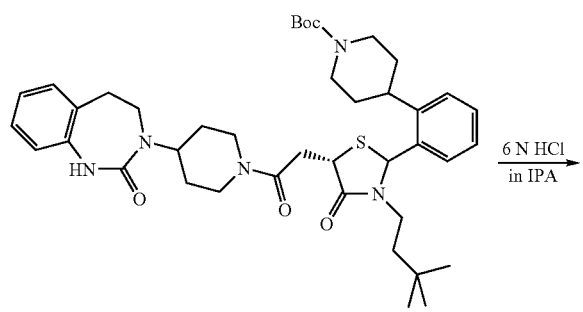

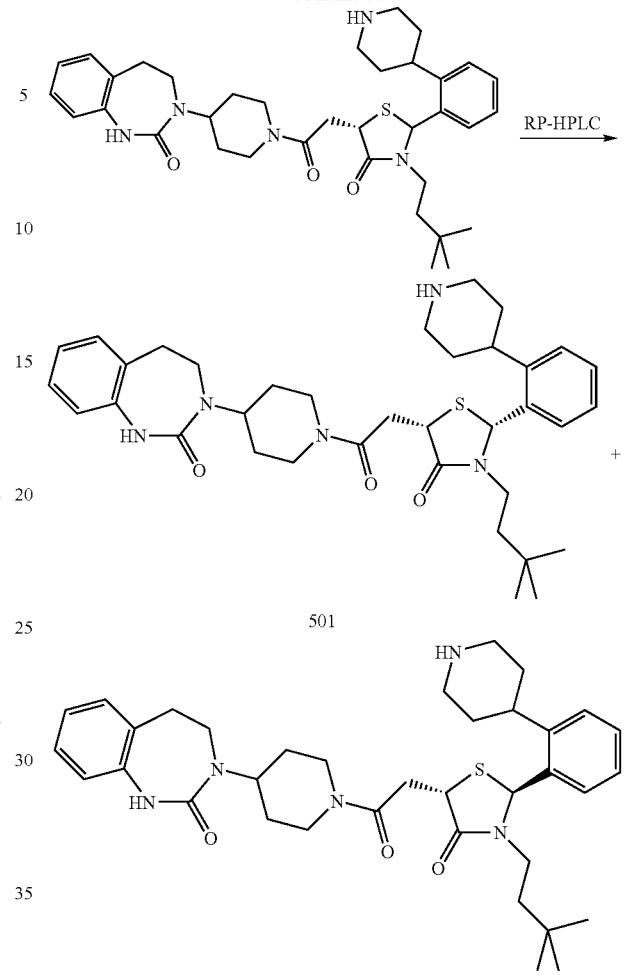

To a solution of Boc-thiazolidinone (70 mg, 0.0956 mmol) in dioxane (1 mL) was added HCl in dioxane (4N, 2 mL, 8 mmol). The solution was stirred for 20 min and monitored by HPLC, then concentrated in vacuo. The residue was diluted in DMSO and purified by prep-HPLC (Gilson, 150 uL injections, 30-70% ACN in water over 15 min, 220 detection). The pure fractions for each diastereomer were combined and lyophilized to give both desired compounds. Cis-diastereomer/#501 (TFA salt): white solid, 24.9 mg, Rt=6.04 min (30 to 60% ACN in water over 8 min, YMC 3×1250 column), purity ~98% at 254; LC/MS MSES+1: 632.68, Rt=2.07 min. $^1$H-NMR (300.0 MHz, MeOD) δ 7.37 (m, 4H), 7.10-7.03 (m, 2H), 6.92-6.85 (m, 2H), 6.28 (s, 1H), 4.60 (m, 1H), 4.53-4.27 (m, 2H), 4.00-3.96 (m, 1H), 3.75-3.65 (m, 1H), 3.59-3.41 (m, 5H), 3.36-3.30 (m, 1H), 3.24-3.09 (m, 4H), 2.95-2.89 (m, 3H), 2.85-2.75 (m, 1H), 2.15-1.88 (m, 5H), 1.76-1.55 (m, 5H), 1.47-1.40 (m, 2H), 0.82 (s, 9H) ppm. Trans-diastereomer/#502 (TFA salt): white solid, 19.8 mg, Rt=6.40 min (30 to 60% ACN in water over 8 min, YMC 3×1250 column), purity ~95% at 254; LC/MS MSES+1: 632.35, Rt=2.12 min. $^1$H-NMR (300.0 MHz, MeOD) δ 7.38-7.32 (m, 4H), 7.06 (d, J=8.3 Hz, 2H), 6.93-6.88 (m, 2H), 6.21 (br m, 1H), 4.67-4.61 (m, 1H), 4.36 (m, 1H), 4.05 (m, 1H), 3.67 (m, 1H), 3.54-3.48 (m, 4H), 3.32-3.16 (m, 4H), 3.00 (m, 3H), 2.71 (m, 2H), 2.03 (m, 4H), 1.93-1.65 (m, 4H), 1.43 (m, 2H), 0.82 (s, 9H) ppm.

Compounds 528, 552 and 553 were also prepared according to the above procedure.

2-Bromo-3-fluoro-N-methoxy-N-methylbenzamide

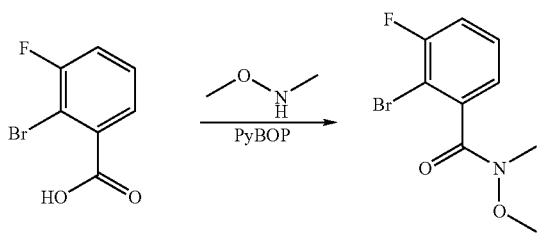

2-Bromo-3-fluorobenzoic acid (9.27 g), 1-N,O-dimethylhydroxylamine hydrochloride (4.129 g, 42.33 mmol), and PyBOP (22.03 g, 1 eq., 42.33 mmol) were suspended in DCM (400 mL). DIEA was then added and the resulting solution was stirred at room temp. for 14 h (no SM left by TLC). The solution was then washed with water, 1N aq HCl and aq sat. NaHCO$_3$ in succession. The organics were dried (MgSO$_4$) and concentrated in vacuo. The residue was purified by ISCO (330 g SiO$_2$, attached) to give 8.3 g (75%) of 2-bromo-3-fluoro-N-methoxy-N-methylbenzamide as a white solid. Rf~0.5 (1:1 Hex:EtOAc); LC/MS ES+1: 261.99.

tert-Butyl 4-(2-(N-methoxy-N-methylcarbamoyl)-6-fluorophenyl)-5,6-dihydropyridine-1(2H)-carboxylate

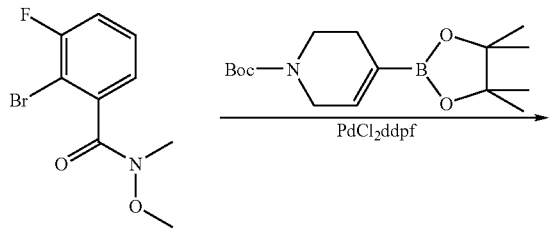

To a degassed mixture of 2-bromo-3-fluoro-N-methoxy-N-methylbenzamide (1.65 g, 6.3 mmol) and pinacol boronate (1.95 mmol, 1 eq., 6.3 mmol) in DMF (10 mL) was added NaHCO$_3$ (795 mg, 1.5 eq.) and water (2 mL). PdCl$_2$(dppf)$_2$ (461 mg, 0.1 eq., 0.63 mmol) was added, and the reaction was stirred for 10 minutes at 120° C. under microwave conditions. After cooling to room temperature, EtOAc (~100 mL) and water (2×100 ml) were added, the phases were separated and the organics washed with brine, dried (MgSO$_4$), filtered and concentrated. The crude brown material was chromatographed using an ISCO system (120 g SiO$_2$, 0 to 30% EtOAc in Hexanes) to give 1.93 g (84%), of tert-butyl 4-(2-(N-methoxy-N-methylcarbamoyl)-6-fluorophenyl)-5,6-dihydropyridine-1(2H)-carboxylate as an oil. LC/MS ES+1 365.19.

tert-Butyl 4-(2-(N-methoxy-N-methylcarbamoyl)-6-fluorophenyl)piperidine-1-carboxylate

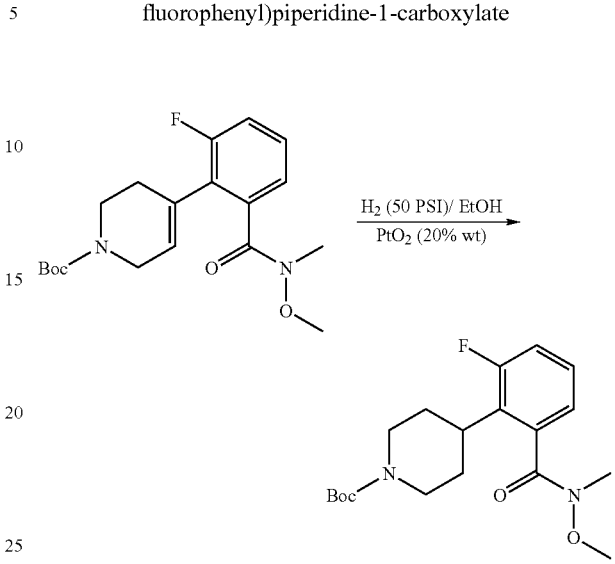

A solution of tert-butyl 4-(2-(N-methoxy-N-methylcarbamoyl)-6-fluorophenyl)-5,6-dihydropyridine-1(2H)-carboxylate (450 mg, 1.235 mmol) and PtO$_2$ (180 mg) in EtOH (19 mL) was shaken in a Parr flask for 1 h15 under 51 psi of H$_2$. The reaction was monitored by LC/MS. Unreacted SM was detected, so another 150 mg of PtO$_2$ (total: 450 mg, 30 wt %) was then added and the mixture was hydrogenated under 50 psi for another 3 h. Mostly desired product was detected after 4 h by LC/MS (Rt=2.83 min). The catalyst was filtered off and the solution was concentrated in vacuo to yield 435 mg of tert-butyl 4-(2-(N-methoxy-N-methylcarbamoyl)-6-fluorophenyl)piperidine-1-carboxylate as a clear thick oil which was used as is for the next step. LC/MS ES+1: 367.38.

tert-Butyl 4-(2-fluoro-6-formylphenyl)piperidine-1-carboxylate

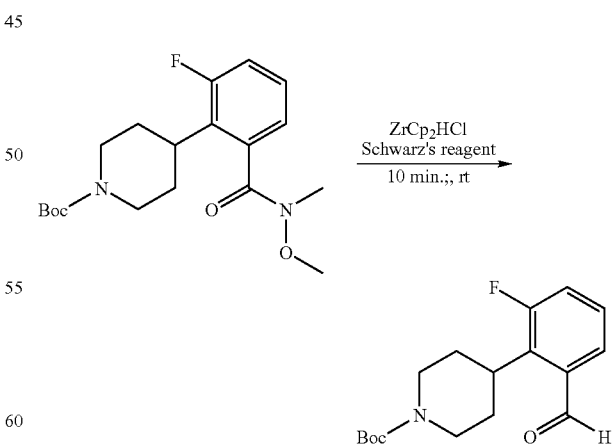

Cp$_2$Zr(H)Cl (1.45 g, 5.61 mmol, 1.5 eq.) was suspended in THF (25 mL) under N$_2$ at room temperature in a flame-dried flask. To this suspension was added tert-butyl 4-(2-(N-methoxy-N-methylcarbamoyl)-6-fluorophenyl)piperidine-1-carboxylate (1.37 g, 3.739 mmol) in THF (50 mL). The reaction was stirred under N₂ for 15 min until the mixture turned clear (monitored by TLC: no SM detected). SiO₂ was then added and the mixture was concentrated and purified by ISCO flash chromatography (SiO₂, 5 to 30% EtOAc in Hexanes) to give 652 mg of tert-butyl 4-(2-fluoro-6-formylphenyl)piperidine-1-carboxylate as a white solid (57% over 2 steps). LC/MS ES+1: 308.17.

tert-Butyl 4-(2-((E)-(3,3-dimethylbutylimino)methyl)-6-fluorophenyl)piperidine-1-carboxylate

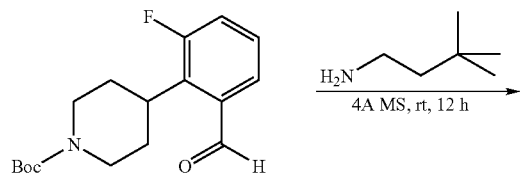

To a solution of tert-butyl 4-(2-fluoro-6-formylphenyl)piperidine-1-carboxylate (1.0 g, 4.23 mmol) in toluene (14 mL) was added 3,3 dimethylbutylamine (428.0 mg, 569.1 µL, 4.230 mmol) and 4 Å molecular sieves. The resulting solution was stirred at rt overnight. The molecular sieves were filtered off and the mixture concentrated in vacuo to give 1.5 g of tert-butyl 4-(2-((E)-(3,3-dimethylbutylimino)methyl)-6-fluorophenyl)piperidine-1-carboxylate as an off-white solid (1.5 g). The material was used without further purification for the next step. ¹H-NMR in CD₃CN of the crude was consistent for the product with a diagnostic peak of the imine proton @ 8.74 ppm.

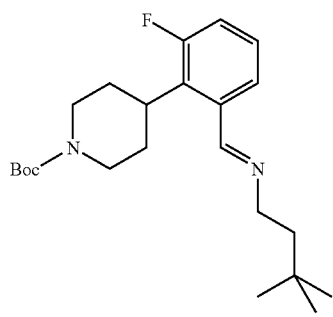

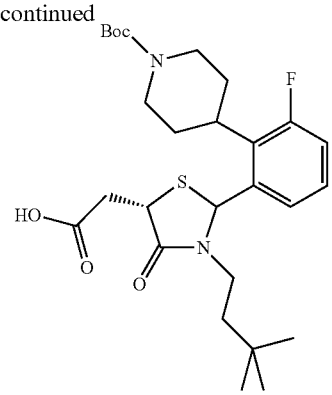

To a solution of tert-butyl 4-(2-((E)-(3,3-dimethylbutylimino)methyl)-6-fluorophenyl)piperidine-1-carboxylate (1.5 g, 3.84 mmol) in toluene (17 mL) was added (S)-2-mercaptosuccinic acid (692 mg, 4.61 mmol, 1.2 eq.). The reaction mixture was stirred at 85° C. for 18 h, then cooled to rt. Some sticky solid on the wall of the flask was observed. The solvent was concentrated in vacuo and the residue was triturated with Et₂O and stirred for 10 min. The mixture was filtered and the resulting white solid was dried for 2 h to give 1.49 g (74% over two steps) of thiazolidinone acid as a white solid which was used without further purification in the next step. LC/MS MSES+1: 523.51; ES−1: 521.65.

Compound #500

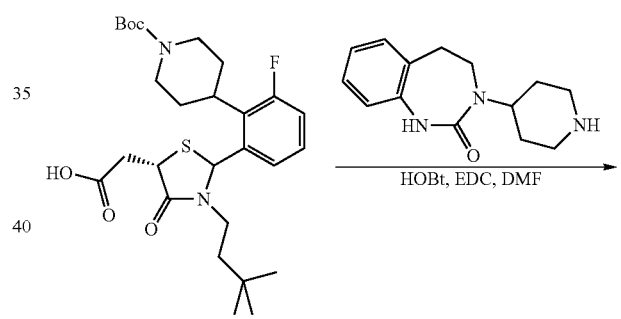

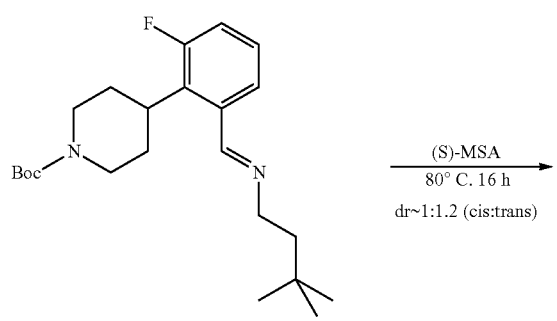

The starting thiazolidinone acid (1.0 g, 1.91 mmol), EDC (623 mg, 3.25 mmol, 1.7 eq.) and HOBt (439 mg, 3.25 mmol, 1.7 eq.) in DCM (10 mL) were stirred at rt for 50 min. 4,5-dihydro-3-(piperidin-4-yl)-1H-benzo[d][1,3]diazepin-2(3H)-one (586.6 mg, 2.39 mmol, 1.25 eq.) was then added, followed by NMM (631 uL, 5.74 mmol, 3 eq.). The dark reaction mixture was stirred at rt for 90 min. The crude was purified by ISCO flash chromatography (120 g SiO₂, 25 to 75% EtOAc in Hexanes). No clean separation of diastereomers was observed. The fractions were collected and concentrated in vacuo to give 783 mg of compound #500 as a mixture of two diastereomers. LC/MS ES+1: 750.41.

Compound 551 was also made according to the procedure described above.

3-(1-(2-((2R,5S)-2-(3-fluoro-2-(piperidin-4-yl)phenyl)-3-(3,3-dimethylbutyl)-4-oxothiazolidin-5-yl)acetyl)piperidin-4-yl)-4,5-dihydro-1H-benzo[d][1,3]diazepin-2(3H)-one (Compound #552)

3-(1-(2-((2S,5S)-2-(3-fluoro-2-(piperidin-4-yl)phenyl)-3-(3,3-dimethylbutyl)-4-oxothiazolidin-5-yl)acetyl)piperidin-4-yl)-4,5-dihydro-1H-benzo[d][1,3]diazepin-2(3H)-one (Compound #553)

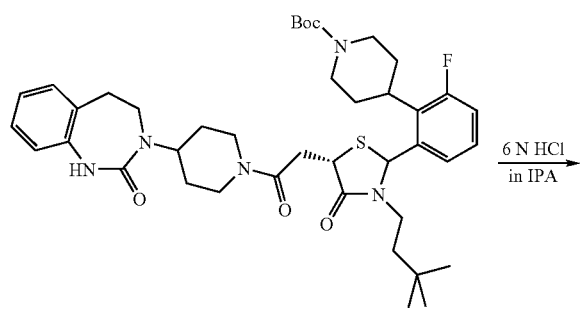

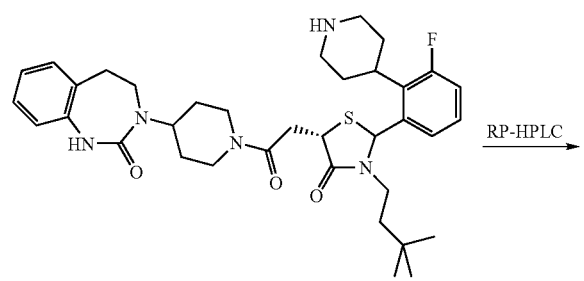

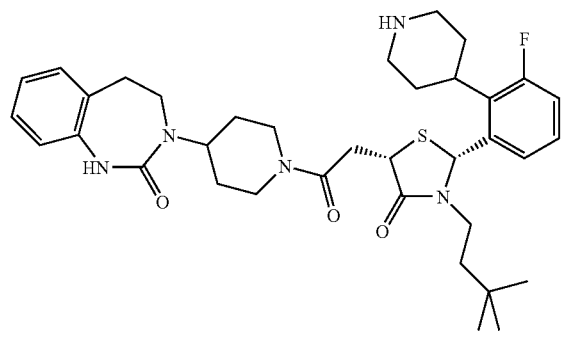

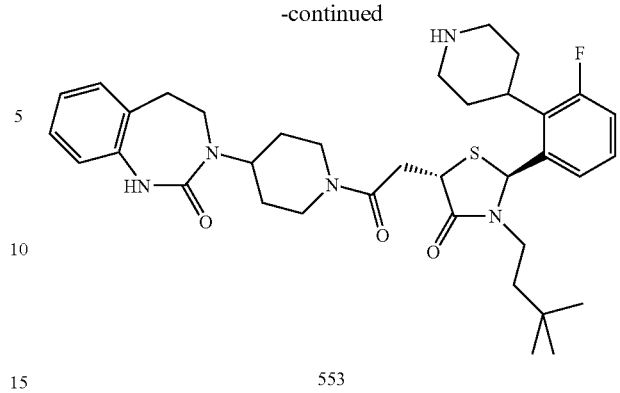

553

To a solution of Boc-thiazolidinone (783 mg, 1.04 mmol) in MeOH (6 mL) was added 6N HCl in iPrOH (6 mL, excess). The resulting reaction solution was stirred at rt for 8 h. The solution was concentrated in vacuo to yield the desired product as a white solid (678 mg) and as a mixture of two diastereomers. The material was used without further purification for the next step. LC/MS MSES+1: 650.35, Rt=2.05 min.

A solution of the mixture (98 mg) in MeOH (2.2 mL) was purified by prep-HPLC (Gilson, 100 uL injections, 25-55% ACN in water over 30 min, 254 detection). The pure fractions for the cis diastereomer were combined, basified with sat aq NaHCO$_3$ and extracted with EtOAc (2×). The combined organics were acidified with 6HCl in IPA, concentrated in vacuo, redissolved in (1:1) CH$_3$CN/water and lyophilized. The pure fractions for the trans diastereomer were combined and directly lyophilized. Cis-diastereomer/#552 (HCl-salt): white solid, 23.3 mg, Rt=7.13 min (25 to 55% ACN in water over 8 min, YMC 3×1250 column), purity ~98% at 254; LC/MS MS/ES ES+1: 650.36, Rt=2.13. $^1$HNMR (300.0 MHz, MeOD) δ 7.40 (m, 1H), 7.10-7.05 (m, 4H), 6.89 (m, 2H), 6.26 (s, 1H), 4.58 (m, 1H), 4.25 (m, 3H), 3.92-3.75 (m, 2H), 3.5 (m, 4H), 3.22-3.04 (m, 5H), 2.95-2.26 (m, 8H), 1.95 (m, 2H), 1.72 (m, 3H), 1.58-1.32 (m, 5H), 1.35 (s, 9H) ppm. Trans-diastereomer/#553 (TFA salt): white solid, 29.6 mg, Rt=7.73 min (25 to 55% ACN in water over 8 min, YMC 3×1250 column), purity ~98% at 254; LC/MS MS ES+1: 650.35, Rt=2.19 min. $^1$H NMR (300.0 MHz, MeOD) δ 7.36 (m, 1H), 7.11-7.05 (m, 4H), 6.88 (m, 2H), 6.20-6.02 (br m, 1H), 4.62 (m, 1H), 4.38 (m, 2H), 4.05 (1H), 3.54-3.48 (m, 4H), 3.18 (m, 3H), 3.07 (m, 2H), 2.95-2.61 (m, 2H), 2.41 (m, 2H), 1.98 (m, 2H), 1.89-1.62 (m, 4H), 1.52-1.47 (m, 2H), 0.86 (s, 9H) ppm.

Compounds 554 and 555 were also prepared according to the procedure described above.

Analytical data for certain compounds of the present invention are shown below in Table 2.

TABLE 2

| Cmpd # | LC/MS M + 1 | LC/RT min |
|---|---|---|
| 1 | 533.5 | 3.36 |
| 2 | 633. | 1.45 |
| 3 | 603.5 | 3.35 |
| 4 | 551.5 | 3.22 |
| 5 | 599.5 | 3.07 |
| 6 | 549.5 | 1.98 |
| 7 | 632.7 | 2.34 |
| 8 | 549.5 | 3.63 |
| 9 | 507.5 | 3.24 |
| 10 | 620.5 | 1.89 |

TABLE 2-continued

| Cmpd # | LC/MS M + 1 | LC/RT min |
|---|---|---|
| 11 | 563.5 | 3.77 |
| 12 | 521. | 3.31 |
| 13 | 621.5 | 3.77 |
| 14 | 595.5 | 3.8 |
| 15 | 559.3 | 3.72 |
| 16 | 597.5 | 3.62 |
| 17 | 633. | 1.47 |
| 18 | 569.5 | 3.37 |
| 19 | 593.5 | 3.17 |
| 20 | 615.5 | 3.23 |
| 21 | 577.7 | 3.94 |
| 22 | 619.7 | 1.39 |
| 23 | 621.5 | 3.8 |
| 24 | 507.3 | 3.25 |
| 25 | 571.5 | 3.72 |
| 26 | 567.5 | 3.72 |
| 27 | 562.4 | 3.28 |
| 28 | 615.7 | 1.41 |
| 29 | 506.4 | 2.96 |
| 30 | 509.7 | 2.91 |
| 31 | 545.7 | 3.64 |
| 32 | 527.3 | 1.98 |
| 33 | 555.3 | 3.55 |
| 34 | 647. | 1.46 |
| 35 | 529.3 | 3.12 |
| 36 | 583.3 | 1.86 |
| 37 | 541.7 | 3.8 |
| 38 | 507.5 | 3.25 |
| 39 | 626.7 | 1.53 |
| 40 | 633.5 | 1.42 |
| 41 | 535.5 | 3.54 |
| 42 | 704.7 | 2.23 |
| 43 | 536.3 | 2.24 |
| 44 | 571.3 | 3.57 |
| 45 | 542.5 | 2.13 |
| 46 | 542.5 | 2.39 |
| 47 | 620.5 | 1.27 |
| 48 | 585.3 | 3.82 |
| 49 | 634.5 | 1.74 |
| 50 | 632.7 | 1.49 |
| 51 | 563.7 | 2.08 |
| 52 | 661.7 | 1.47 |
| 53 | 568.5 | 2.22 |
| 54 | 585.3 | 3.84 |
| 55 | 619.5 | 3.68 |
| 56 | 612.5 | 1.52 |
| 57 | 555.5 | 2.13 |
| 58 | 555.3 | 3.37 |
| 59 | 606.4 | 2.39 |
| 60 | 601.5 | 1.37 |
| 61 | 563.5 | 3.34 |
| 62 | 573.4 | 3.06 |
| 63 | 546.5 | 3.27 |
| 64 | 563.5 | 3.36 |
| 65 | 641.3 | 3.89 |
| 66 | 573.4 | 3.05 |
| 67 | 539.5 | 3.45 |
| 68 | 667.5 | 1.42 |
| 69 | 508.6 | 3.1 |
| 70 | 634.5 | 1.93 |
| 71 | 543.5 | 2.31 |
| 72 | 690.5 | 2.16 |
| 73 | 563.5 | 3.82 |
| 74 | 557.5 | 4.15 |
| 75 | 501.5 | 3.5 |
| 76 | 589.5 | 1.98 |
| 77 | 562.5 | 2.41 |
| 78 | 535.5 | 3.51 |
| 79 | 587.3 | 3.79 |
| 80 | 551.5 | 3.47 |
| 81 | 665.7 | 1.46 |
| 82 | 550.5 | 2.42 |
| 83 | 549.5 | 3.12 |
| 84 | 531. | 1.78 |
| 85 | 517.5 | 1.21 |
| 86 | 513.3 | 3.53 |
| 87 | 525.5 | 3.5 |
| 88 | 615.5 | 1.88 |
| 89 | 603.5 | 3.77 |
| 90 | 551.5 | 3.22 |
| 91 | 541.5 | 2.05 |
| 92 | 583.5 | 3.6 |
| 93 | 535.5 | 3.51 |
| 94 | 574.5 | 2. |
| 95 | 527.3 | 1.96 |
| 96 | 505.3 | 3.2 |
| 97 | 487.5 | 1.41 |
| 98 | 549.7 | 3.63 |
| 99 | 733.7 | 2.26 |
| 100 | 553.5 | 2.08 |
| 101 | 549.5 | 1.89 |
| 102 | 619.5 | 2.58 |
| 103 | 579.5 | 3.64 |
| 104 | 507. | 3.22 |
| 105 | 487.5 | 1.37 |
| 106 | 604.7 | 2.21 |
| 107 | 507.5 | 3.27 |
| 108 | 528.1 | 2.28 |
| 109 | 533.3 | 3.11 |
| 110 | 533. | 3.28 |
| 111 | 492.5 | 3.43 |
| 112 | 567.5 | 3.53 |
| 113 | 535.5 | 2.95 |
| 114 | 587.5 | 1.32 |
| 115 | 601.5 | 1.84 |
| 116 | 489.5 | 3. |
| 117 | 551.5 | 3.12 |
| 118 | 537.4 | 2.95 |
| 119 | 633. | 1.41 |
| 120 | 634.5 | 1.74 |
| 121 | 564.7 | 1.84 |
| 122 | 553.6 | 3.16 |
| 123 | 563.7 | 3.79 |
| 124 | 564.7 | 2.91 |
| 125 | 621.5 | 3.22 |
| 126 | 565.5 | 3.55 |
| 127 | 569.5 | 3.44 |
| 128 | 556.5 | 2.39 |
| 129 | 651.5 | 1.39 |
| 130 | 588.5 | 2.13 |
| 131 | 588.4 | 3.22 |
| 132 | 479.3 | 3.02 |
| 133 | 551.5 | 3.22 |
| 134 | 549.5 | 1.98 |
| 135 | 597.5 | 3.65 |
| 136 | 607.3 | 1.96 |
| 137 | 583.5 | 3.58 |
| 138 | 519.5 | 3.28 |
| 139 | 551.5 | 3.44 |
| 140 | 626.5 | 1.58 |
| 141 | 493.1 | 3.76 |
| 142 | 681.7 | 1.47 |
| 143 | 538.7 | 3.52 |
| 144 | 620.7 | 1.68 |
| 145 | 601.5 | 3.15 |
| 146 | 469.5 | 2.56 |
| 147 | 561.5 | 3.7 |
| 148 | 522. | 1.52 |
| 149 | 553.5 | 3.57 |
| 150 | 648.7 | 1.79 |
| 151 | 515.7 | 1.96 |
| 152 | 578.5 | 1.89 |
| 153 | 612.5 | 1.46 |
| 154 | 541.7 | 2.06 |
| 155 | 571.5 | 3.6 |
| 156 | 535. | 3.52 |
| 157 | 534.4 | 2.77 |
| 158 | 555.3 | 3.6 |
| 159 | 537.5 | 3.06 |
| 160 | 620.5 | 1.89 |
| 161 | 619.7 | 1.38 |
| 162 | 619.7 | 1.36 |
| 163 | 633.5 | 1.37 |
| 164 | 579.5 | 3.62 |

TABLE 2-continued

| Cmpd # | LC/MS M + 1 | LC/RT min |
|---|---|---|
| 165 | 571.5 | 3.75 |
| 166 | 573.5 | 1.91 |
| 167 | 477.3 | 4.08 |
| 168 | 574.5 | 2.05 |
| 169 | 605.5 | 3.61 |
| 170 | 539.5 | 3.38 |
| 171 | 549.5 | 3.62 |
| 172 | 535.5 | 3.45 |
| 173 | 618.7 | 1.41 |
| 174 | 531.5 | 3.37 |
| 175 | 586.5 | 3.47 |
| 176 | 522. | 1.52 |
| 177 | 479.5 | 3. |
| 178 | 579.5 | 3.39 |
| 179 | 589.5 | 3.3 |
| 180 | 563.7 | 3.67 |
| 181 | 567.5 | 3.95 |
| 182 | 522.5 | 2.54 |
| 183 | 601.7 | 1.83 |
| 184 | 606.5 | 1.83 |
| 185 | 556.5 | 2.48 |
| 186 | 521.6 | 2.67 |
| 187 | 527.3 | 3.19 |
| 188 | 513.5 | 3.52 |
| 189 | 559.3 | 3.13 |
| 190 | 547.3 | 3.15 |
| 191 | 547.5 | 1.74 |
| 192 | 487.5 | 1.82 |
| 193 | 719.7 | 2.21 |
| 194 | 621.5 | 3.79 |
| 195 | 525.5 | 3.41 |
| 196 | 515.7 | 3.07 |
| 197 | 577.7 | 3.84 |
| 198 | 578.5 | 1.64 |
| 199 | 647.7 | 1.41 |
| 200 | 510.8 | 2.76 |
| 201 | 529.5 | 1.56 |
| 202 | 557.5 | 3.44 |
| 203 | 589.4 | 3.21 |
| 204 | 549.5 | 3.58 |
| 205 | 579.5 | 3.39 |
| 206 | 589.7 | 3.15 |
| 207 | 529.5 | 3.79 |
| 208 | 559.5 | 3.38 |
| 209 | 529.5 | 1.61 |
| 210 | 583.5 | 3.53 |
| 211 | 578.5 | 1.92 |
| 212 | 557.5 | 3.44 |
| 213 | 578.4 | 2.95 |
| 214 | 565.5 | 3.22 |
| 215 | 618.7 | 2.28 |
| 216 | 589.5 | 3.57 |
| 217 | 585.3 | 3.77 |
| 218 | 471.3 | 2.79 |
| 219 | 607.5 | 1.99 |
| 220 | 537.5 | 3. |
| 221 | 587.5 | 3.7 |
| 222 | 549.5 | 1.98 |
| 223 | 508.2 | 2.53 |
| 224 | 587.5 | 1.78 |
| 225 | 593.5 | 3.53 |
| 226 | 513.3 | 3.29 |
| 227 | 546.5 | 3.28 |
| 228 | 581.3 | 3.27 |
| 229 | 647.7 | 1.42 |
| 230 | 491.3 | 2.97 |
| 231 | 569.5 | 3.5 |
| 232 | 592.5 | 3.38 |
| 233 | 597.3 | 1.91 |
| 234 | 571.5 | 3.77 |
| 235 | 618.7 | 2.28 |
| 236 | 556.5 | 2.2 |
| 237 | 569.5 | 3.43 |
| 238 | 551.5 | 3.13 |
| 239 | 543.5 | 3.3 |
| 240 | 637.4 | 3.61 |
| 241 | 539.5 | 3.57 |

TABLE 2-continued

| Cmpd # | LC/MS M + 1 | LC/RT min |
|---|---|---|
| 242 | 601.3 | 3.64 |
| 243 | 633.5 | 3.8 |
| 244 | 567.5 | 3.79 |
| 245 | 550.5 | 2.53 |
| 246 | 627.5 | 2.06 |
| 247 | 651.5 | 3.69 |
| 248 | 587.5 | 3.02 |
| 249 | 518.2 | 3.49 |
| 250 | 523.5 | 3.04 |
| 251 | 507.5 | 3.24 |
| 252 | 553.3 | 3.72 |
| 253 | 581.3 | 3.6 |
| 254 | 491.3 | 3.06 |
| 255 | 493.5 | 3.1 |
| 256 | 607.5 | 1.98 |
| 257 | 645.7 | 1.38 |
| 258 | 543.5 | 3.25 |
| 259 | 519. | 3.07 |
| 260 | 601.5 | 1.34 |
| 261 | 446.5 | 3.03 |
| 262 | 563.7 | 3.75 |
| 263 | 592.7 | 1.98 |
| 264 | 547.5 | 3.57 |
| 265 | 572.7 | 3.4 |
| 266 | 522.5 | 2.96 |
| 267 | 553.5 | 1.91 |
| 268 | 601.3 | 3.61 |
| 269 | 493.3 | 3.13 |
| 270 | 506.4 | 2.77 |
| 271 | 505.5 | 3.14 |
| 272 | 551.5 | 3.41 |
| 273 | 465.5 | 2.88 |
| 274 | 620.7 | 1.24 |
| 275 | 485.5 | 3.31 |
| 276 | 515.7 | 1.98 |
| 277 | 588.7 | 2.05 |
| 278 | 542.5 | 2.35 |
| 279 | 597.5 | 3.65 |
| 280 | 561.5 | 1.78 |
| 281 | 499.1 | 3.98 |
| 282 | 575.5 | 3.05 |
| 283 | 569.5 | 3.45 |
| 284 | 493.5 | 3.13 |
| 285 | 607.5 | 1.54 |
| 286 | 563.5 | 3.32 |
| 287 | 567.5 | 2.85 |
| 288 | 570.5 | 1.33 |
| 289 | 573.5 | 1.27 |
| 290 | 606.5 | 1.62 |
| 291 | 573.5 | 1.73 |
| 292 | 590.7 | 2.16 |
| 293 | 550.5 | 1.79 |
| 294 | 592.7 | 1.79 |
| 295 | 587.5 | 1.34 |
| 296 | 620.7 | 1.71 |
| 297 | 587.5 | 1.79 |
| 298 | 604.5 | 2.23 |
| 299 | 564.5 | 1.88 |
| 300 | 606.5 | 1.86 |
| 301 | 620.7 | 1.78 |
| 302 | 619 | 1.42 |
| 303 | 630 | 1.49 |
| 304 | 606.5 | 1.71 |
| 305 | 525.5 | 1.24 |
| 306 | 525.5 | 1.25 |
| 307 | 649.7 | 1.41 |
| 308 | 589.5 | 2.13 |
| 309 | 609.5 | 2.18 |
| 310 | 623.7 | 2.23 |
| 311 | 595.5 | 2.12 |
| 312 | 549.7 | 2 |
| 313 | 539.5 | 1.32 |
| 314 | 539.6 | 1.31 |
| 315 | 575.7 | 2.08 |
| 316 | 561.5 | 2.02 |
| 317 | 561.5 | 2.04 |
| 318 | 575.5 | 2.09 |

TABLE 2-continued

| Cmpd # | LC/MS M + 1 | LC/RT min |
|---|---|---|
| 319 | 620.4 | 1.61 |
| 320 | 634.4 | 1.68 |
| 321 | 633.7 | 1.47 |
| 322 | 633.7 | 1.5 |
| 323 | 651.5 | 1.42 |
| 324 | 665.5 | 1.48 |
| 325 | 663.7 | 1.42 |
| 326 | 663.7 | 1.45 |
| 327 | 620.5 | 1.32 |
| 328 | 634.7 | 1.41 |
| 329 | 620.5 | 1.3 |
| 330 | 634.5 | 1.35 |
| 331 | 605.5 | 1.48 |
| 332 | 619.7 | 1.56 |
| 333 | 647.7 | 1.41 |
| 334 | 647.7 | 1.49 |
| 335 | 633.5 | 1.45 |
| 336 | 633.5 | 1.47 |
| 337 | 638.5 | 1.26 |
| 338 | 637.5 | 1.39 |
| 339 | 679.7 | 1.49 |
| 340 | 693.7 | 1.52 |
| 341 | 666.5 | 1.34 |
| 342 | 691.5 | 1.51 |
| 343 | 665.7 | 1.41 |
| 344 | 665.5 | 1.42 |
| 345 | 679.7 | 1.46 |
| 346 | 677.7 | 1.44 |
| 347 | 663.7 | 1.39 |
| 348 | 637.7 | 1.34 |
| 349 | 652.5 | 1.26 |
| 350 | 638.5 | 1.18 |
| 351 | 651.5 | 1.46 |
| 352 | 665.5 | 1.49 |
| 353 | 638.5 | 1.26 |
| 354 | 637.7 | 1.42 |
| 355 | 667.5 | 1.47 |
| 356 | 681.7 | 1.52 |
| 357 | 654.7 | 1.29 |
| 358 | 679.7 | 1.46 |
| 359 | 653.7 | 1.41 |
| 360 | 651.5 | 1.45 |
| 361 | 665.5 | 1.5 |
| 362 | 638.5 | 1.29 |
| 363 | 663.7 | 1.44 |
| 364 | 675.7 | 1.56 |
| 365 | 689.5 | 1.63 |
| 366 | 662.5 | 1.38 |
| 367 | 695.7 | 2.02 |
| 368 | 709 | 2.01 |
| 369 | 647.7 | 1.52 |
| 370 | 661.7 | 1.55 |
| 371 | 663.7 | 1.45 |
| 372 | 677.7 | 1.5 |
| 373 | 633 | 1.42 |
| 374 | 633 | 1.42 |
| 375 | 661.6 | 1.53 |
| 376 | 707 | 1.56 |
| 377 | 661.6 | 1.61 |
| 378 | 634.6 | 1.26 |
| 379 | 730.9 | 1.31 |
| 380 | 634.6 | 1.37 |
| 381 | 703.9 | 1.16 |
| 382 | 636.7 | 1.33 |
| 383 | 649.7 | 1.48 |
| 384 | 715.7 | 1.61 |
| 385 | 663.7 | 1.54 |
| 386 | 622.7 | 1.28 |
| 387 | 688.7 | 1.43 |
| 388 | 647.7 | 1.43 |
| 389 | 691.7 | 1.53 |
| 390 | 664.7 | 1.32 |
| 391 | 651.7 | 1.47 |
| 392 | 733.7 | 2.07 |
| 393 | 706.7 | 1.82 |
| 394 | 638.5 | 0.95 |
| 395 | 693.6 | 1.63 |

TABLE 2-continued

| Cmpd # | LC/MS M + 1 | LC/RT min |
|---|---|---|
| 396 | 693.6 | 1.7 |
| 397 | 638.5 | 1.24 |
| 398 | 651.7 | 1.47 |
| 399 | 651.7 | 1.47 |
| 400 | 707.7 | 1.58 |
| 401 | 707.7 | 1.53 |
| 402 | 710.9 | 1.5 |
| 403 | 737.7 | 1.68 |
| 404 | 634.5 | 1.32 |
| 405 | 661.7 | 1.49 |
| 406 | 634.5 | 1.3 |
| 407 | 661.5 | 1.49 |
| 408 | 710.7 | 1.51 |
| 409 | 737.7 | 1.69 |
| 410 | 633.5 | 1.4 |
| 411 | 680.7 | 2.29 |
| 412 | 647.7 | 1.5 |
| 413 | 620.5 | 1.27 |
| 414 | 630 | 1.5 |
| 415 | 621.6 | 1.59 |
| 416 | 535.5 | 1.92 |
| 417 | 508.5 | 1.62 |
| 418 | 648.7 | 1.3 |
| 419 | 675.7 | 1.52 |
| 420 | 549.6 | 1.51 |
| 421 | 632.4 | 1.88 |
| 422 | 634.6 | 1.44 |
| 423 | 620.6 | 1.83 |
| 424 | 520.4 | 1.65 |
| 425 | 605.4 | 1.52 |
| 426 | 607.4 | 1.12 |
| 427 | 593.4 | 1.52 |
| 428 | 591.6 | 1.7 |
| 429 | 707.4 | 1.77 |
| 430 | 707.4 | 1.91 |
| 431 | 707.4 | 1.77 |
| 432 | 707.4 | 1.87 |
| 433 | 709 | 1.49 |
| 434 | 709 | 1.49 |
| 435 | 623 | 1.21 |
| 436 | 680 | 1.29 |
| 437 | 680 | 1.29 |
| 438 | 682 | 1.3 |
| 439 | 733.6 | 1.68 |
| 440 | 733.6 | 1.7 |
| 441 | 706.6 | 1.45 |
| 442 | 706.4 | 1.5 |
| 443 | 649.7 | 1.21 |
| 444 | 676.5 | 1.44 |
| 445 | 680 | 1.48 |
| 446 | 680 | 1.33 |
| 447 | 645.5 | 1.98 |
| 448 | 672.6 | 2.42 |
| 449 | 669.5 | 3.2 |
| 450 | 693.6 | 2.75 |
| 451 | 664.5 | 2.98 |
| 452 | 694.7 | 3.12 |
| 453 | 657 | 3.05 |
| 454 | 657.5 | 3.1 |
| 455 | 652.5 | 1.98 |
| 456 | 652.5 | 1.98 |
| 457 | 717.1 | 2.68 |
| 458 | 638.5 | 1.94 |
| 459 | 638.5 | 2 |
| 460 | 695.2 | 2.3 |
| 461 | 681.3 | 2.45 |
| 462 | 625.4 | 2.87 |
| 463 | 652.4 | 3.31 |
| 464 | 637.3 | 3.29 |
| 465 | 624.5 | 1.91 |
| 466 | 651.2 | 2.13 |
| 467 | 637.5 | 1.97 |
| 468 | 625.4 | 2.94 |
| 469 | 638.5 | 3.2 |
| 470 | 624.5 | 1.98 |
| 471 | 651.2 | 2.21 |
| 472 | 637.2 | 2.13 |

TABLE 2-continued

| Cmpd # | LC/MS M + 1 | LC/RT min |
|---|---|---|
| 473 | 652.5 | 1.94 |
| 474 | 679.5 | 2.13 |
| 475 | 652.5 | 1.98 |
| 476 | 679.5 | 2.16 |
| 477 | 605 | 1.36 |
| 478 | 725.7 | 2.24 |
| 479 | 698 | 2.08 |
| 480 | 627.6 | 3.35 |
| 481 | 654.5 | 3.8 |
| 482 | 645.5 | 3.46 |
| 483 | 672.5 | 3.83 |
| 484 | 625.5 | 2.99 |
| 485 | 652.5 | 3.4 |
| 486 | 652.5 | 3.33 |
| 487 | 652.5 | 3.35 |
| 488 | 677.3 | 1.91 |
| 489 | 677.6 | 2 |
| 490 | 722 | 3.38 |
| 491 | 622 | 1.92 |
| 492 | 739 | 3.76 |
| 493 | 679.3 | 2.02 |
| 494 | 679.3 | 2.05 |
| 495 | 652.6 | 3.27 |
| 496 | 652.6 | 3.39 |
| 497 | 639 | 2 |
| 498 | 695 | 2.04 |
| 499 | 738 | 3.17 |
| 500 | 732.4 | 3.99 |
| 501 | 632.7 | 2.07 |
| 502 | 632.4 | 2.12 |
| 503 | 745.4 | 4.44 |
| 504 | 745.3 | 4.44 |
| 505 | 718.3 | 3.75 |
| 506 | 695.4 | 2.17 |
| 507 | 727.5 | 4.33 |
| 508 | 727.5 | 4.41 |
| 509 | 700.3 | 1.87 |
| 510 | 747.3 | 3.34 |
| 511 | 647.7 | 1.98 |
| 512 | 647.3 | 2 |
| 513 | 653.36 | 2.13 |
| 514 | 719.3 | 2.17 |
| 515 | 719.5 | 2.21 |
| 516 | 692.3 | 2 |
| 517 | 668.3 | 1.95 |
| 518 | 626.6 | 1.95 |
| 519 | 709 | 2.15 |
| 520 | 693.4 | 2.21 |
| 521 | 679.4 | 2 |
| 522 | 679.4 | 2.05 |
| 523 | 721.3 | 1.87 |
| 524 | 721.4 | 1.91 |
| 525 | 694.3 | 1.65 |
| 526 | 709.4 | 1.95 |
| 527 | 620.4 | 1.76 |
| 528 | 605.4 | 1.88 |
| 529 | 709.4 | 2 |
| 530 | 682.3 | 1.74 |
| 531 | 682.3 | 1.78 |
| 532 | 666.4 | 2.03 |
| 533 | 681.4 | 1.82 |
| 534 | 681.3 | 1.87 |
| 535 | 654.4 | 1.61 |
| 536 | 665.5 | 1.95 |
| 537 | 665.4 | 1.97 |
| 538 | 638.3 | 1.74 |
| 539 | 713.3 | 2.08 |
| 540 | 686.2 | 1.87 |
| 541 | 703.4 | 2.4 |
| 542 | 705.4 | 2.22 |
| 543 | 705.4 | 2.24 |
| 544 | 693.4 | 2.08 |
| 545 | 693.4 | 2.13 |
| 546 | 624 | 1.92 |
| 547 | 713.4 | 2.04 |
| 548 | 713.4 | 2.08 |
| 549 | 724 | 3.76 |
| 550 | 733.4 | 2.26 |
| 551 | | |
| 552 | 650.4 | 2.08 |
| 553 | 650.4 | 2.19 |
| 554 | 623.5 | 1.94 |
| 555 | 623.3 | 1.97 |
| 556 | 700 | 2.24 |
| 557 | 727 | 2.5 |
| 558 | 704.34 | 2.2 |
| 559 | 692.3 | 2.19 |
| 560 | 692.3 | 2.21 |
| 561 | 677.2 | 2.01 |
| 562 | 677.3 | 2.04 |
| 563 | 665.2 | 1.99 |
| 564 | 665.3 | 2.02 |

Measuring CGRP Functional Antagonism Using SK-N-MC-BLA (4C10):

CGRP functional antagonism was characterized in a cell based transcriptional assay using a recombinant SK-N-MC line. To introduce the transcriptional reporter system, SK-N-MC cell line was transduced with a retroviral vector containing β-lactamase gene downstream of cAMP responsive promoter. The expression of β-lactamase is triggered by cAMP increase that is a downstream event of activation of endogenous CGRP receptor. Single clones were separated using Fluorescent Activated Cell Sorting (FACS) based on CGRP induced β-lactamase activity. β-lactamase activity was measured using a fluorescence energy transfer (FRET) dye, CCF4. CCF4 is a substrate of β-lactamase (Zlokarnik G, et al., Science, 279 (5347): 84-88, 1998) and cleaved into a product with different fluorescent signal from that of the parent. 4C10 clone was selected for dose dependent β-lactamase expression to different concentrations of CGRP and consistent pharmacology with previously published values. To evaluate functional antagonist activity of compounds in SK-N-MC (4C10) line, compounds were evaluated for their inhibition of β-lactamase expression in the presence of CGRP.

SK-N-MC (4C10) was cultured in Minimal Essential Media (MEM) (Invitrogen) supplemented with 1 mM non-essential amino acids solution (Invitrogen), 100 units/ml Penicillin-Streptomycin (Invitrogen), 1 mM sodium pyruvate (Invitrogen) and 10% fetal bovine serum. For the β-lactamase assay, low serum, 1% FBS in MEM was used. 30,000 cells were plated into each wells of poly-D-lysine coated 384-well plate (Becton Dickinson) a day prior to the assay. SK-N-MC (4C10) was preincubated with compounds for 30 min before the addition of 200 pM CGRP. The assay was incubated for 3 hours at 37° C. to allow β-lactamase expression. CCF4 dye was added and incubated for 2 hours at room temperature. The fluorescent signals were read using a fluorescence plate reader, Topology Compensatory Plate Reader (tcPR) at excitation wavelength, 400 nm and emission wavelengths, 460 nm for the product and 535 nm for the parent. The ratio of values at 460 to 535 nm was used to calculate percent of activation. Curve fitting and IC50 calculation were carried about using MOD3.

$I^{125}$-CGRP Binding Displacement Assay to Calculate $K_i$ of Compounds.

Purified SK-N-MC membrane was purchased from Perkin Elmer. The membrane was thawed quickly and placed on ice. The compounds were diluted with CGRP binding solution (25 mM Tris-HCl, pH7.4, 5 mM MgCl2, 0.1% BSA and 0.05% Tween). The membrane was diluted 1:20 with the binding solution and homogenized with Tissue Matster-50 Homogenizer (Omni International) for 30 sec. The homogenized membrane was added to compounds in the binding solution. After 10 minutes incubation at room temperature, the final concentration of 46 pM, I125-iodotyrosyl-Calcitonin-Gene-Related Peptide (GE healthcare) was added to the membrane and compounds. After 2 hour incubation at room temperature, the reaction was stopped by rapid filtration through 0.5% PEI treated GF/C filter plate (Perkin Elmer) and the filter plate was washed with ice-cold washing solution (50 mM Tris HCl, pH7.4, 5 mM MgCl2 and 0.1% BSA) using cell harvestor (Tomtec). The radioactivity of the filter plates were read on Topcount (Packard). The nonspecific binding was determined in the control reaction where 1 uM unlabelled CGRP was preincubated with the membrane prior to I125-CGRP addition. The total binding was determined in the control reaction of the membrane and I125-CGRP in the absence of compound. The percent displacement of I125-CGRP with compounds was calculated using nonspecific and total binding controls. The curve fitting was carried out using MOD3. Ki of compound was calculated by the equation of Cheng and Prusoff (Cheng Y., Prusoff W. H., Biochem. Pharmacol. 22: 3099-3108, 1973) using Kd of CGRP for the membrane and the amount of I125-CGRP used for the assay.

Exemplary compounds of the present invention in Table 1 were found to be antagonists of CGRP in the $I^{125}$-CGRP binding assay and in the CGRP functional antagonism assay described above.

$IC_{50}$ and Ki data for selected compounds of the present invention are shown below in Table 3. In Table 3, for both the $IC_{50}$ column and the Ki column, the symbols have the following meaning: "A" means <1 μM; "B" means between 1 μM and 5 μM; "C" means >5 μM and "ND" means no data.

TABLE 3

| Cmpd # | IC50 | Ki |
| --- | --- | --- |
| 1 | A | A |
| 2 | A | A |
| 3 | A | A |
| 4 | A | ND |
| 5 | B | ND |
| 6 | A | ND |
| 7 | A | ND |
| 8 | A | A |
| 9 | A | A |
| 10 | A | A |
| 11 | A | ND |
| 12 | A | A |
| 13 | A | ND |
| 14 | A | A |
| 15 | A | A |
| 16 | A | A |
| 17 | ND | A |
| 18 | B | ND |
| 19 | C | C |
| 20 | A | A |
| 21 | A | ND |
| 22 | B | ND |
| 23 | A | ND |
| 24 | B | ND |
| 25 | A | ND |
| 26 | A | ND |
| 27 | C | ND |
| 28 | A | A |
| 29 | C | ND |
| 30 | B | A |
| 31 | A | ND |
| 32 | A | ND |
| 33 | A | A |
| 34 | A | ND |
| 35 | B | ND |
| 36 | A | ND |
| 37 | A | A |
| 38 | A | ND |
| 39 | ND | ND |
| 40 | ND | ND |
| 41 | A | A |
| 42 | ND | ND |
| 43 | B | A |
| 44 | A | A |
| 45 | C | ND |
| 46 | B | ND |
| 47 | A | ND |
| 48 | A | A |
| 49 | A | A |
| 50 | ND | ND |
| 51 | A | ND |
| 52 | ND | ND |
| 53 | C | C |
| 54 | A | A |
| 55 | B | ND |
| 56 | ND | ND |
| 57 | A | ND |
| 58 | A | A |
| 59 | A | ND |
| 60 | A | A |
| 61 | B | C |
| 62 | A | A |
| 63 | A | A |
| 64 | B | A |
| 65 | A | ND |
| 66 | A | A |
| 67 | A | A |
| 68 | ND | ND |
| 69 | A | ND |
| 70 | A | A |
| 71 | C | ND |
| 72 | ND | ND |
| 73 | A | ND |
| 74 | B | ND |
| 75 | B | ND |
| 76 | A | A |
| 77 | C | ND |
| 78 | A | A |
| 79 | A | A |
| 80 | A | A |
| 81 | ND | ND |
| 82 | B | ND |
| 83 | A | ND |
| 84 | A | A |
| 85 | C | ND |
| 86 | B | ND |
| 87 | B | B |
| 88 | A | A |
| 89 | A | ND |
| 90 | B | ND |
| 91 | A | ND |
| 92 | A | ND |
| 93 | A | A |
| 94 | C | ND |
| 95 | A | ND |
| 96 | B | ND |
| 97 | C | ND |
| 98 | B | ND |
| 99 | ND | ND |
| 100 | A | ND |
| 101 | C | ND |
| 102 | A | A |
| 103 | C | ND |
| 104 | C | C |
| 105 | C | C |
| 106 | A | A |
| 107 | A | A |
| 108 | C | ND |
| 109 | B | A |
| 110 | C | C |
| 111 | C | ND |
| 112 | C | ND |
| 113 | A | A |

TABLE 3-continued

| Cmpd # | IC50 | Ki |
|---|---|---|
| 114 | A | A |
| 115 | A | A |
| 116 | B | A |
| 117 | B | ND |
| 118 | B | A |
| 119 | ND | A |
| 120 | A | A |
| 121 | A | ND |
| 122 | C | A |
| 123 | A | ND |
| 124 | B | ND |
| 125 | A | ND |
| 126 | A | ND |
| 127 | B | C |
| 128 | B | A |
| 129 | ND | ND |
| 130 | B | ND |
| 131 | C | ND |
| 132 | B | ND |
| 133 | C | ND |
| 134 | A | ND |
| 135 | A | ND |
| 136 | A | ND |
| 137 | A | ND |
| 138 | A | ND |
| 139 | B | ND |
| 140 | ND | ND |
| 141 | C | ND |
| 142 | ND | ND |
| 143 | C | ND |
| 144 | A | A |
| 145 | A | A |
| 146 | C | ND |
| 147 | A | A |
| 148 | B | A |
| 149 | A | A |
| 150 | A | A |
| 151 | A | ND |
| 152 | A | ND |
| 153 | ND | ND |
| 154 | A | ND |
| 155 | A | ND |
| 156 | A | ND |
| 157 | C | ND |
| 158 | B | ND |
| 159 | A | A |
| 160 | A | A |
| 161 | A | ND |
| 162 | ND | ND |
| 163 | ND | ND |
| 164 | B | ND |
| 165 | A | ND |
| 166 | A | ND |
| 167 | C | ND |
| 168 | B | ND |
| 169 | B | A |
| 170 | A | A |
| 171 | A | A |
| 172 | A | A |
| 173 | ND | ND |
| 174 | A | A |
| 175 | A | A |
| 176 | B | A |
| 177 | B | ND |
| 178 | B | ND |
| 179 | A | ND |
| 180 | B | ND |
| 181 | A | ND |
| 182 | A | A |
| 183 | A | A |
| 184 | A | A |
| 185 | A | ND |
| 186 | C | ND |
| 187 | B | A |
| 188 | A | A |
| 189 | C | ND |
| 190 | C | B |
| 191 | A | ND |
| 192 | A | ND |
| 193 | ND | ND |
| 194 | A | A |
| 195 | B | C |
| 196 | B | ND |
| 197 | C | ND |
| 198 | A | A |
| 199 | ND | ND |
| 200 | C | ND |
| 201 | B | ND |
| 202 | A | A |
| 203 | B | A |
| 204 | B | B |
| 205 | B | ND |
| 206 | A | ND |
| 207 | A | ND |
| 208 | A | A |
| 209 | A | ND |
| 210 | A | ND |
| 211 | B | A |
| 212 | A | A |
| 213 | B | ND |
| 214 | B | ND |
| 215 | A | ND |
| 216 | ND | ND |
| 217 | A | ND |
| 218 | C | ND |
| 219 | B | ND |
| 220 | ND | ND |
| 221 | A | ND |
| 222 | A | ND |
| 223 | C | ND |
| 224 | A | A |
| 225 | A | A |
| 226 | B | A |
| 227 | A | A |
| 228 | B | ND |
| 229 | ND | ND |
| 230 | C | B |
| 231 | A | ND |
| 232 | B | ND |
| 233 | A | ND |
| 234 | A | ND |
| 235 | B | ND |
| 236 | B | A |
| 237 | A | C |
| 238 | B | ND |
| 239 | A | ND |
| 240 | B | A |
| 241 | B | ND |
| 242 | B | ND |
| 243 | B | ND |
| 244 | A | A |
| 245 | C | ND |
| 246 | A | ND |
| 247 | B | ND |
| 248 | A | C |
| 249 | A | ND |
| 250 | C | ND |
| 251 | C | B |
| 252 | A | ND |
| 253 | B | ND |
| 254 | B | ND |
| 255 | B | A |
| 256 | A | A |
| 257 | A | ND |
| 258 | B | ND |
| 259 | A | A |
| 260 | A | A |
| 261 | C | ND |
| 262 | B | ND |
| 263 | A | A |
| 264 | A | A |
| 265 | A | A |
| 266 | A | A |
| 267 | A | ND |

TABLE 3-continued

| Cmpd # | IC50 | Ki |
|---|---|---|
| 268 | A | A |
| 269 | B | ND |
| 270 | C | ND |
| 271 | A | A |
| 272 | B | ND |
| 273 | B | ND |
| 274 | A | ND |
| 275 | C | ND |
| 276 | B | ND |
| 277 | A | ND |
| 278 | A | A |
| 279 | A | A |
| 280 | A | ND |
| 281 | C | ND |
| 282 | A | A |
| 283 | B | A |
| 284 | B | ND |
| 285 | A | ND |
| 286 | B | C |
| 287 | B | B |
| 288 | A | A |
| 289 | A | A |
| 290 | A | A |
| 291 | A | ND |
| 292 | B | ND |
| 293 | A | ND |
| 294 | A | ND |
| 295 | A | A |
| 296 | A | A |
| 297 | A | A |
| 298 | A | ND |
| 299 | A | A |
| 300 | A | ND |
| 301 | A | A |
| 302 | A | A |
| 303 | A | A |
| 304 | ND | A |
| 305 | B | ND |
| 306 | C | C |
| 307 | A | A |
| 308 | A | ND |
| 309 | B | ND |
| 310 | A | ND |
| 311 | B | ND |
| 312 | A | ND |
| 313 | A | ND |
| 314 | C | ND |
| 315 | A | A |
| 316 | C | ND |
| 317 | B | A |
| 318 | A | ND |
| 319 | A | ND |
| 320 | A | ND |
| 321 | A | ND |
| 322 | B | ND |
| 323 | A | ND |
| 324 | A | A |
| 325 | A | ND |
| 326 | ND | ND |
| 327 | ND | ND |
| 328 | A | A |
| 329 | ND | ND |
| 330 | B | A |
| 331 | A | A |
| 332 | C | ND |
| 333 | B | ND |
| 334 | A | ND |
| 335 | A | A |
| 336 | A | A |
| 337 | ND | ND |
| 338 | A | ND |
| 339 | ND | ND |
| 340 | C | C |
| 341 | A | A |
| 342 | B | ND |
| 343 | ND | ND |
| 344 | A | ND |
| 345 | A | A |
| 346 | A | ND |
| 347 | A | A |
| 348 | B | C |
| 349 | A | A |
| 350 | A | A |
| 351 | B | A |
| 352 | A | ND |
| 353 | A | A |
| 354 | A | A |
| 355 | ND | ND |
| 356 | A | ND |
| 357 | A | A |
| 358 | C | ND |
| 359 | ND | ND |
| 360 | A | ND |
| 361 | B | ND |
| 362 | B | ND |
| 363 | A | A |
| 364 | C | ND |
| 365 | A | A |
| 366 | A | ND |
| 367 | A | A |
| 368 | ND | ND |
| 369 | B | ND |
| 370 | A | ND |
| 371 | A | A |
| 372 | C | ND |
| 373 | B | ND |
| 374 | B | B |
| 375 | A | A |
| 376 | A | ND |
| 377 | B | ND |
| 378 | A | ND |
| 379 | A | ND |
| 380 | A | A |
| 381 | C | ND |
| 382 | A | ND |
| 383 | B | ND |
| 384 | C | ND |
| 385 | B | ND |
| 386 | ND | ND |
| 387 | A | ND |
| 388 | C | ND |
| 389 | A | A |
| 390 | C | ND |
| 391 | C | C |
| 392 | C | ND |
| 393 | A | ND |
| 394 | A | A |
| 395 | C | ND |
| 396 | B | ND |
| 397 | C | C |
| 398 | C | ND |
| 399 | C | ND |
| 400 | A | A |
| 401 | A | A |
| 402 | A | A |
| 403 | B | A |
| 404 | B | ND |
| 405 | B | A |
| 406 | ND | A |
| 407 | A | A |
| 408 | A | ND |
| 409 | C | A |
| 410 | A | ND |
| 411 | B | ND |
| 412 | A | ND |
| 413 | A | ND |
| 414 | B | C |
| 415 | B | A |
| 416 | ND | ND |
| 417 | B | ND |
| 418 | C | ND |
| 419 | B | ND |
| 420 | C | ND |
| 421 | A | ND |
| 422 | A | ND |
| 423 | A | ND |

TABLE 3-continued

| Cmpd # | IC50 | Ki |
|---|---|---|
| 424 | A | ND |
| 425 | A | ND |
| 426 | B | ND |
| 427 | ND | ND |
| 428 | C | ND |
| 429 | ND | ND |
| 430 | C | ND |
| 431 | A | A |
| 432 | A | A |
| 433 | C | ND |
| 434 | A | A |
| 435 | B | A |
| 436 | A | A |
| 437 | A | A |
| 438 | A | ND |
| 439 | A | ND |
| 440 | ND | ND |
| 441 | A | ND |
| 442 | A | ND |
| 443 | A | ND |
| 444 | C | ND |
| 445 | B | ND |
| 446 | A | A |
| 447 | A | A |
| 448 | A | ND |
| 449 | ND | ND |
| 450 | ND | ND |
| 451 | B | ND |
| 452 | A | ND |
| 453 | A | ND |
| 454 | C | ND |
| 455 | B | ND |
| 456 | B | A |
| 457 | A | A |
| 458 | A | A |
| 459 | A | A |
| 460 | ND | ND |
| 461 | A | A |
| 462 | A | A |
| 463 | B | A |
| 464 | B | ND |
| 465 | B | ND |
| 466 | A | ND |
| 467 | B | ND |
| 468 | A | ND |
| 469 | A | A |
| 470 | A | A |
| 471 | A | A |
| 472 | A | ND |
| 473 | C | ND |
| 474 | B | A |
| 475 | A | A |
| 476 | C | ND |
| 477 | C | A |
| 478 | A | A |
| 479 | A | A |
| 480 | B | A |
| 481 | B | A |
| 482 | B | A |
| 483 | C | A |
| 484 | A | A |
| 485 | B | A |
| 486 | A | A |
| 487 | A | A |
| 488 | A | A |
| 489 | A | A |
| 490 | C | A |
| 491 | A | A |
| 492 | B | A |
| 493 | A | A |
| 494 | A | A |
| 495 | A | A |
| 496 | A | A |
| 497 | A | A |
| 498 | A | A |
| 499 | ND | ND |
| 500 | C | A |
| 501 | A | A |
| 502 | A | A |
| 503 | A | A |
| 504 | A | A |
| 505 | A | A |
| 506 | A | A |
| 507 | A | A |
| 508 | A | A |
| 509 | A | A |
| 510 | A | A |
| 511 | A | A |
| 512 | A | A |
| 513 | A | A |
| 514 | A | A |
| 515 | A | A |
| 516 | A | A |
| 517 | A | A |
| 518 | A | A |
| 519 | A | A |
| 520 | A | A |
| 521 | A | A |
| 522 | A | A |
| 523 | A | A |
| 524 | A | A |
| 525 | A | A |
| 526 | A | A |
| 527 | A | A |
| 528 | A | A |
| 529 | A | A |
| 530 | A | A |
| 531 | A | A |
| 532 | A | A |
| 533 | A | A |
| 534 | A | A |
| 535 | A | A |
| 536 | A | ND |
| 537 | A | ND |
| 538 | A | A |
| 539 | A | A |
| 540 | A | A |
| 541 | A | A |
| 542 | A | A |
| 543 | A | A |
| 544 | A | A |
| 545 | A | A |
| 546 | A | ND |
| 547 | A | A |
| 548 | A | A |
| 549 | B | A |
| 550 | A | A |
| 551 | C | B |
| 552 | A | A |
| 553 | B | A |
| 554 | A | A |
| 555 | B | A |
| 556 | A | A |
| 557 | ND | A |
| 558 | ND | A |
| 559 | ND | ND |
| 560 | ND | ND |
| 561 | ND | ND |
| 562 | ND | ND |
| 563 | ND | ND |
| 564 | ND | ND |

What is claimed is:
1. A compound selected from:
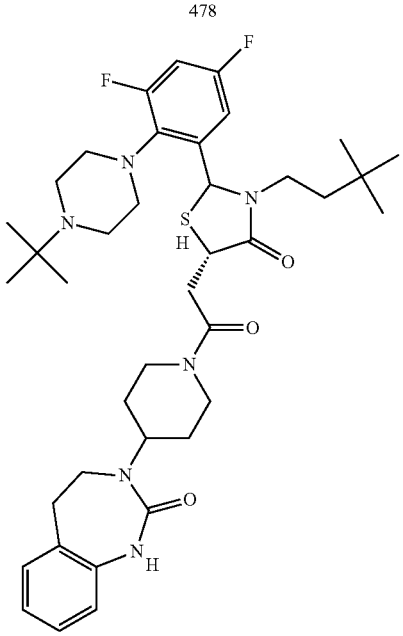
478
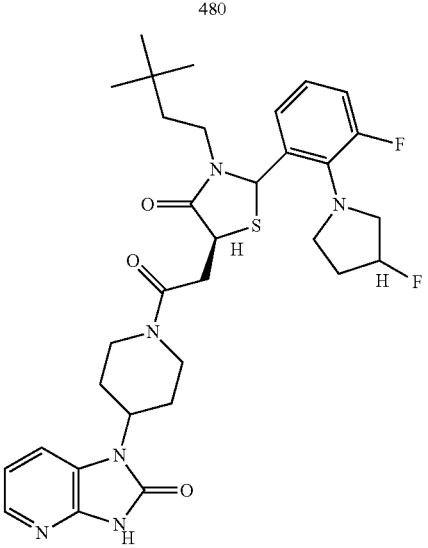
480
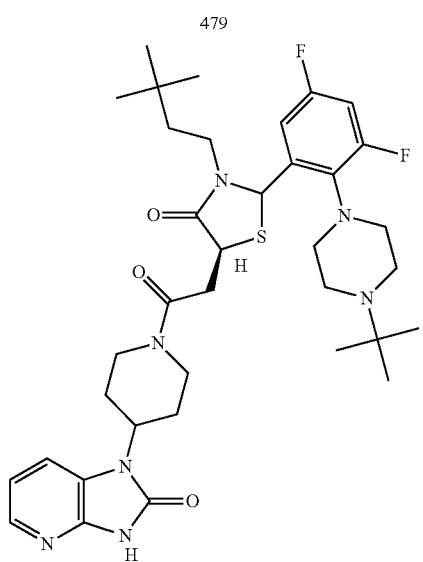
479
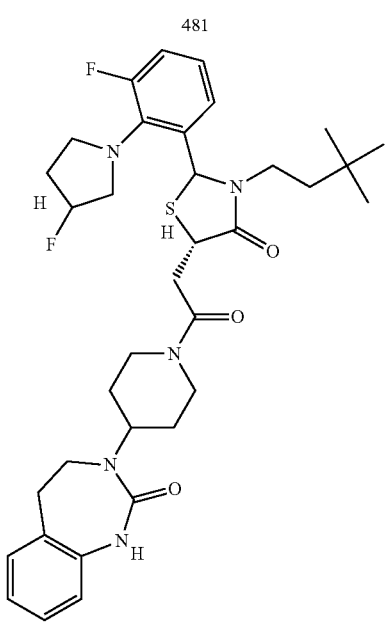
481

481
-continued
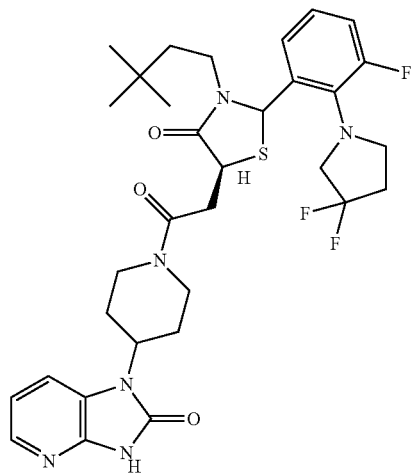
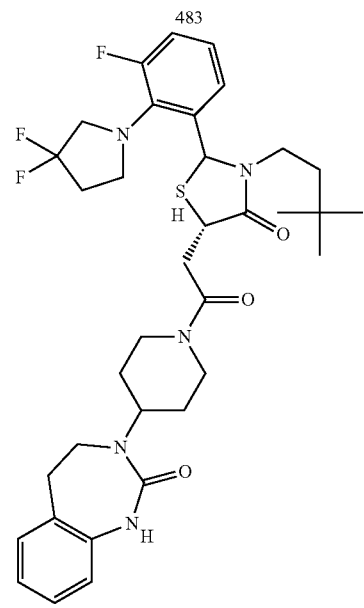
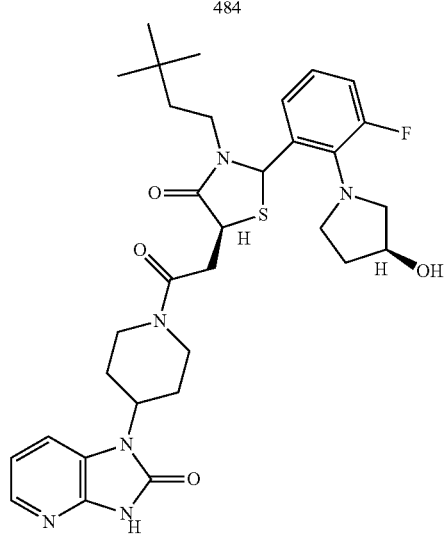
482
-continued
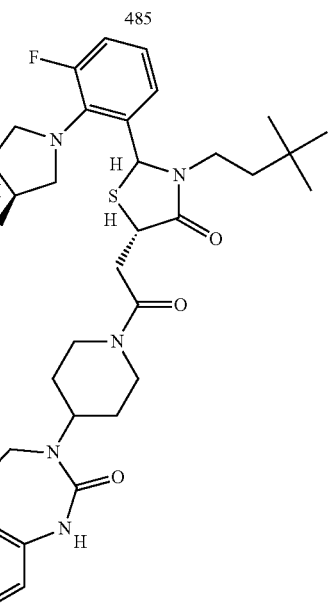
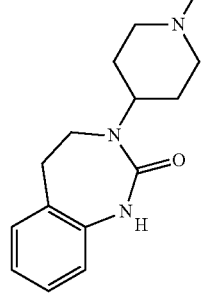

| 483 -continued | 484 -continued |
|---|---|
| 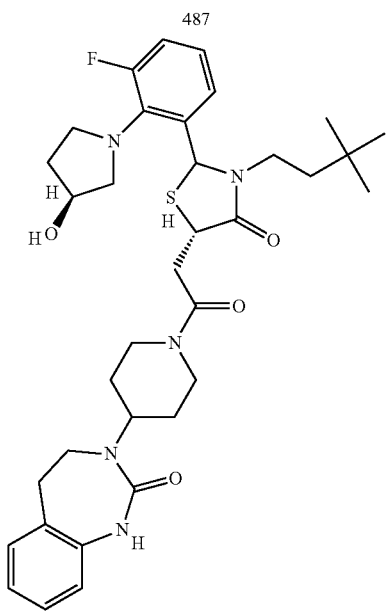<br>487 | 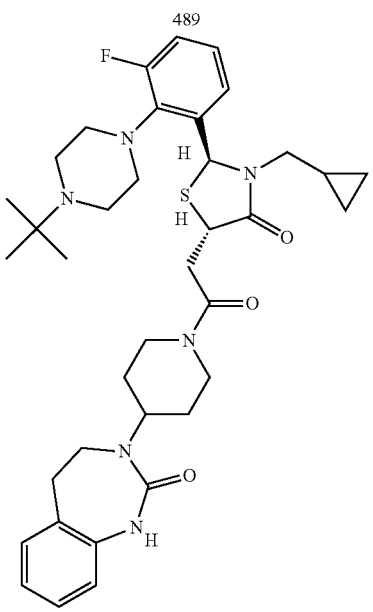<br>489 |
| 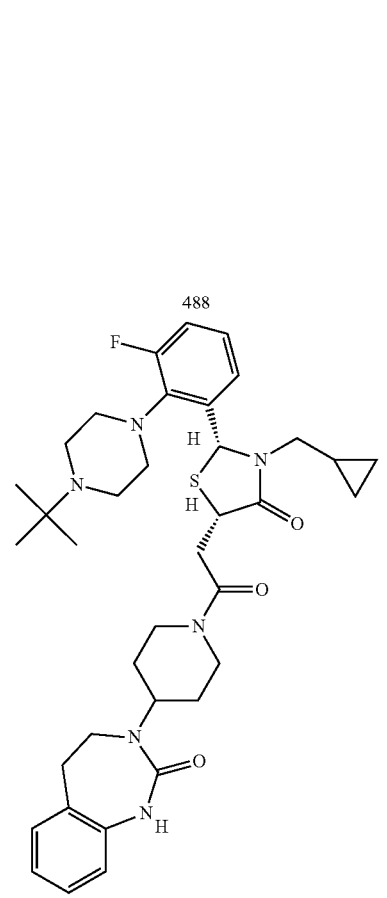<br>488 | 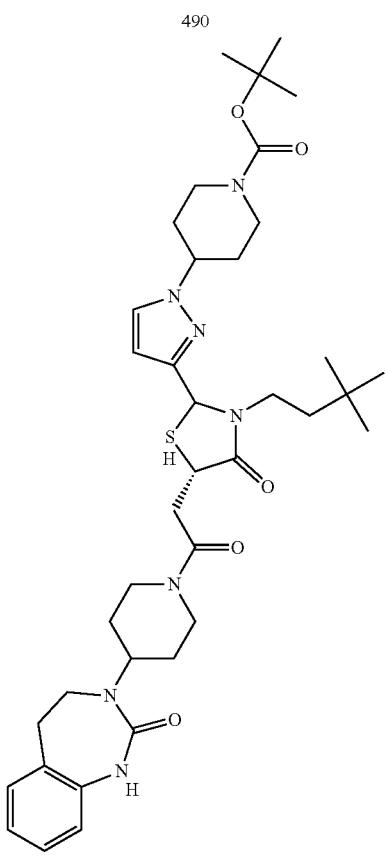<br>490 |

485
-continued
491
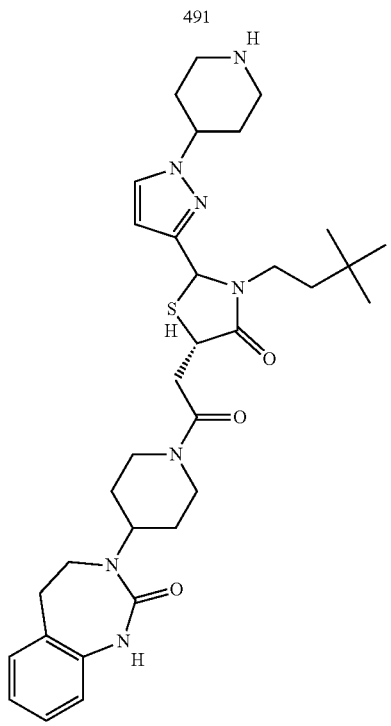
492
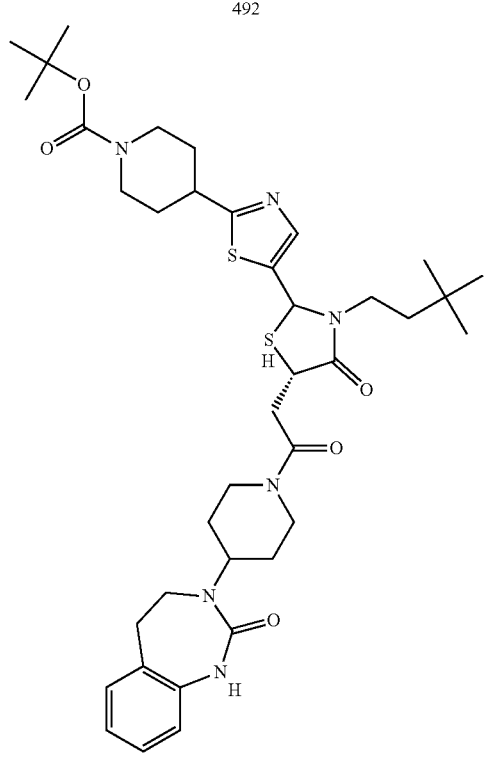
486
-continued
493
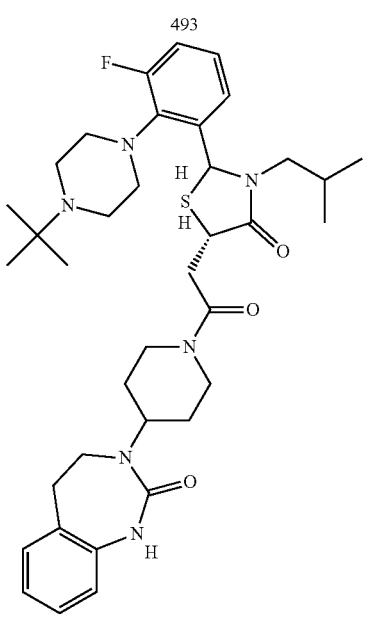
494
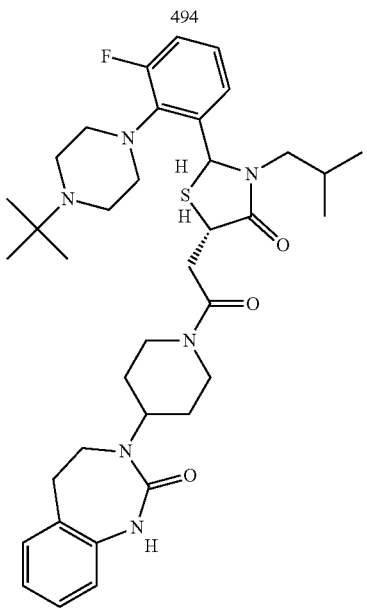

487
-continued
495
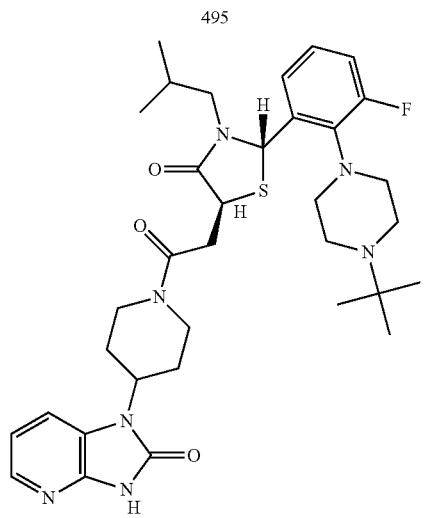
496
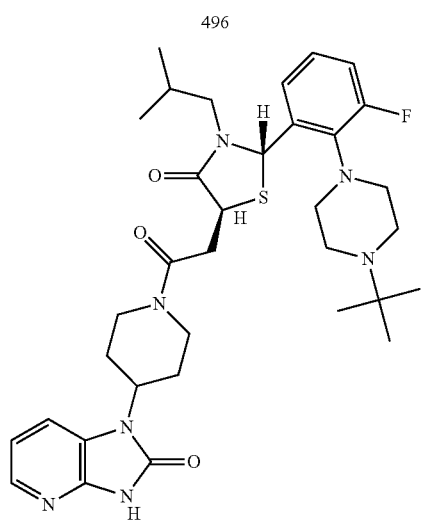
488
-continued
497
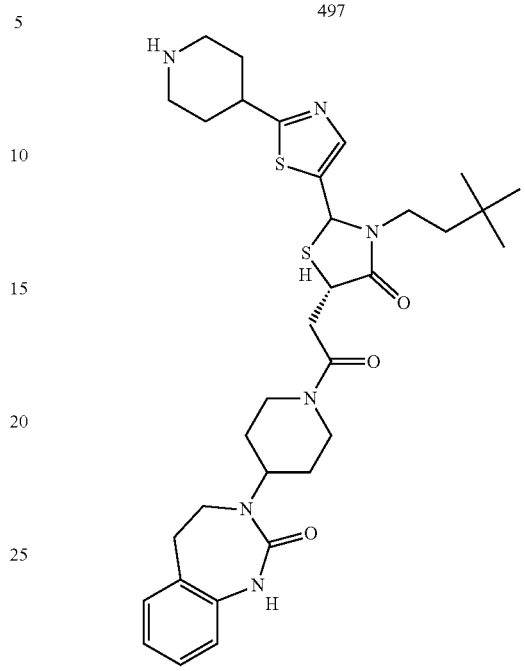
498
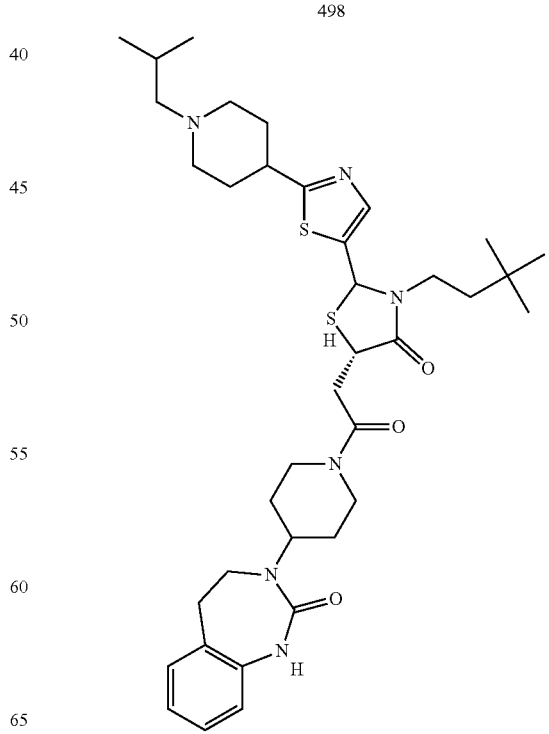

| 489 -continued | 490 -continued |
|---|---|
| 499<br>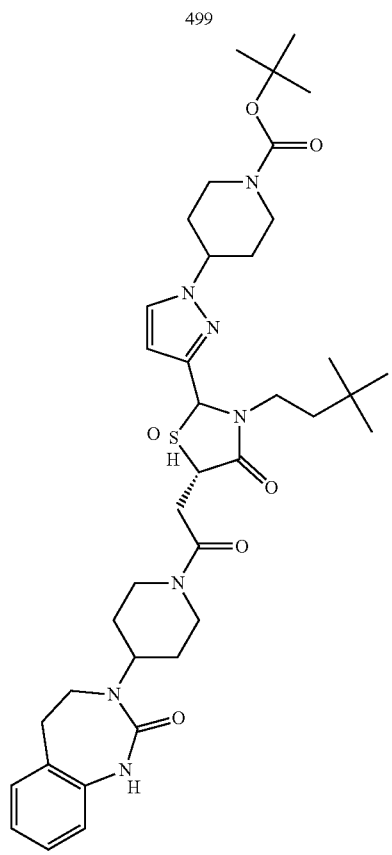 | 501<br>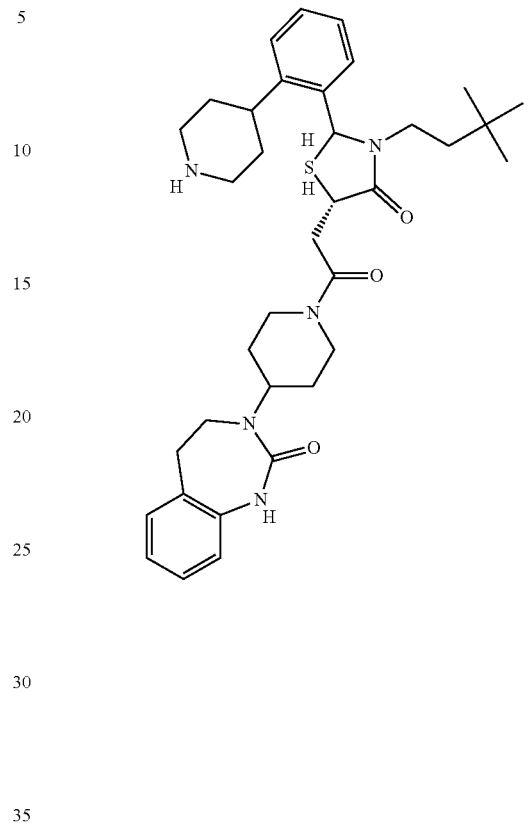 |
| 500<br>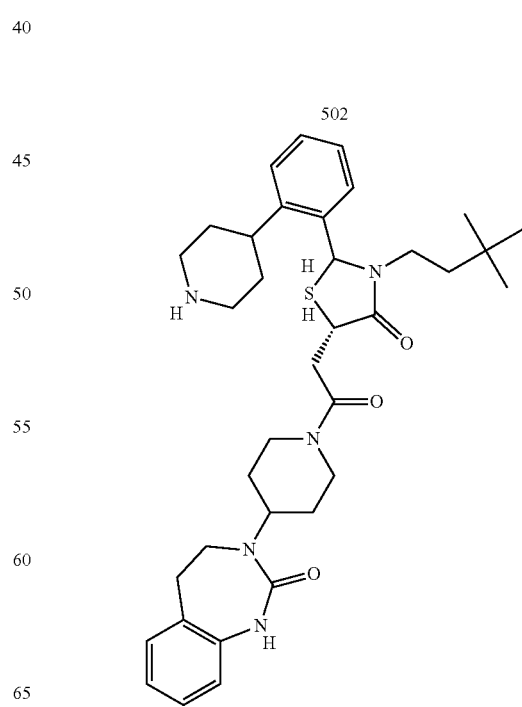 | 502<br>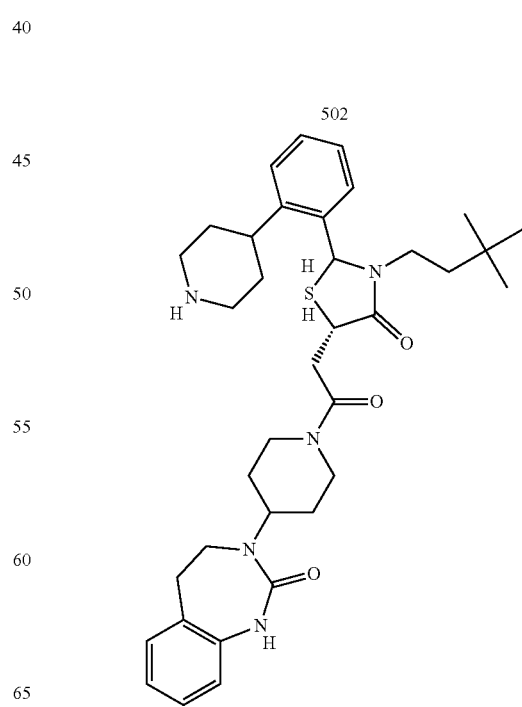 |

| 491 -continued | 492 -continued |
|---|---|
| 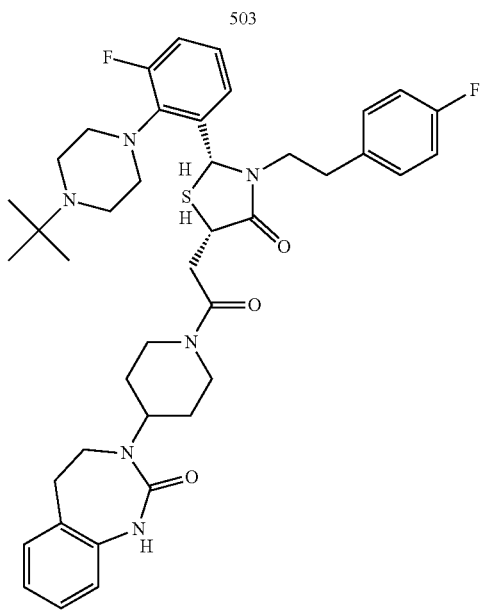
503 | 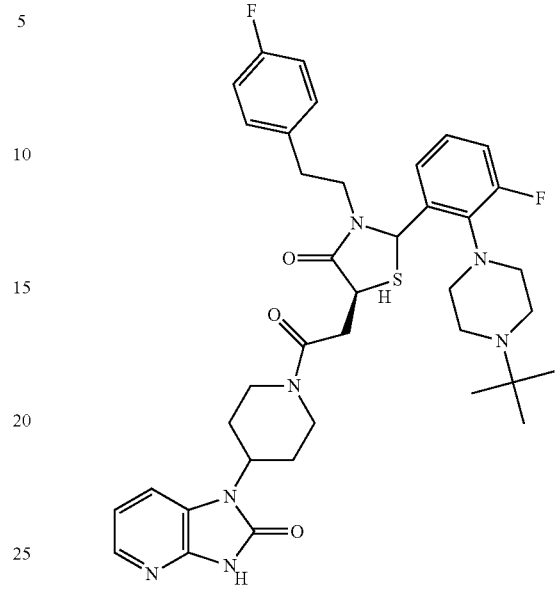
505 |
| 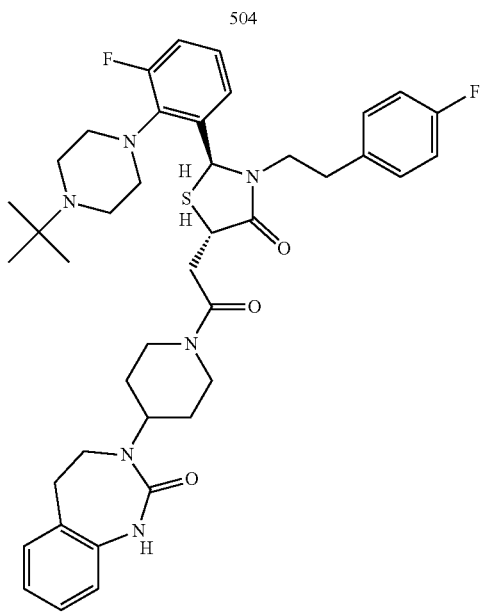
504 | 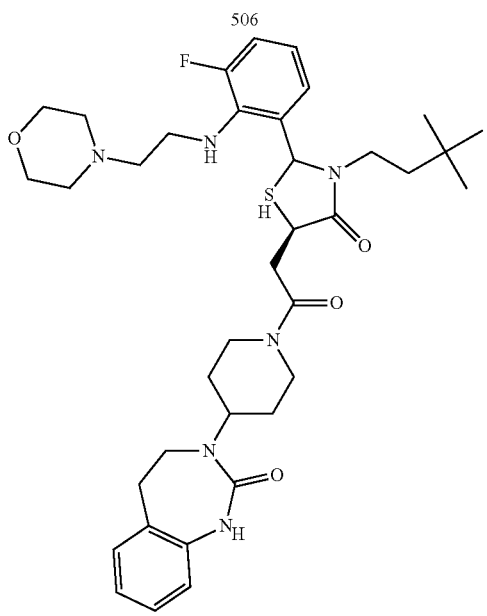
506 |

| 493 -continued | 494 -continued |
|---|---|
| 507 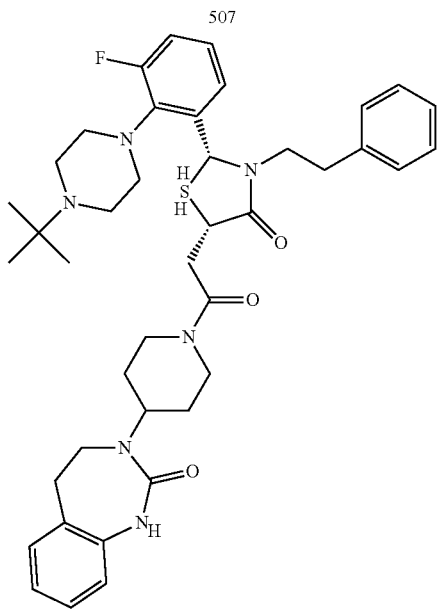 | 509 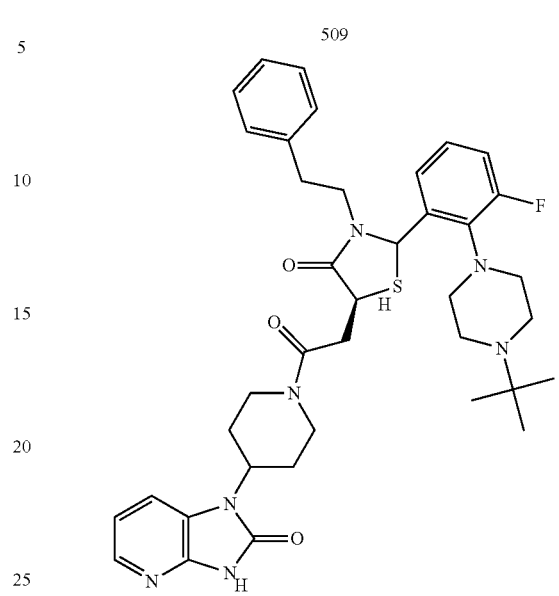 |
| 508 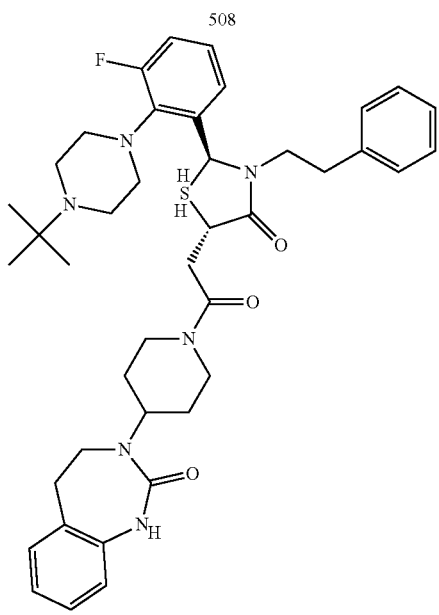 | 510 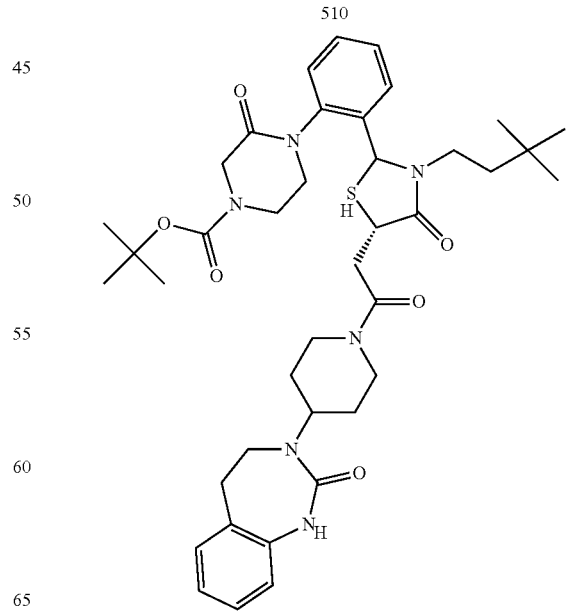 |

495
-continued
511
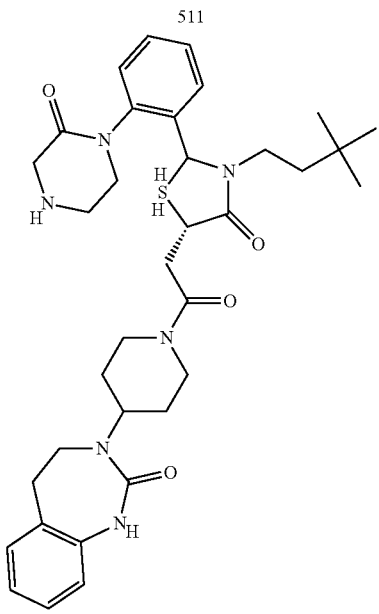
512
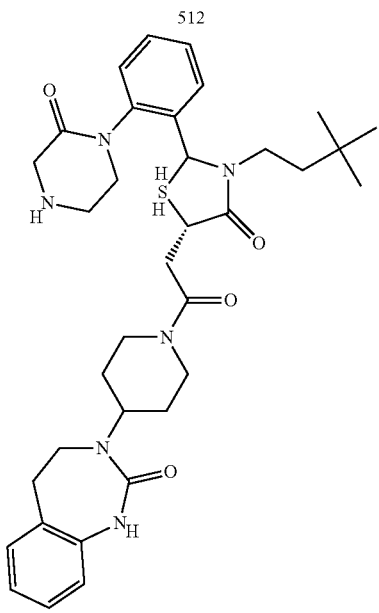
496
-continued
513
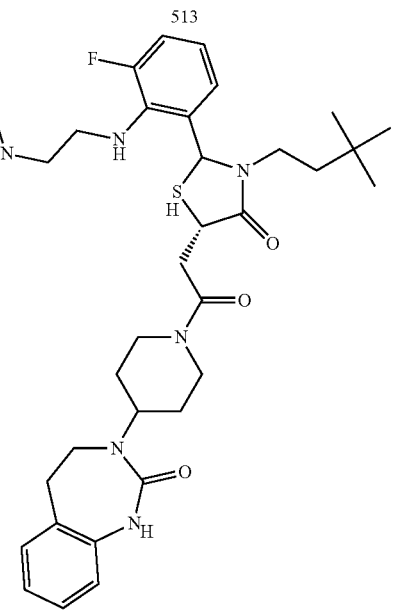
514
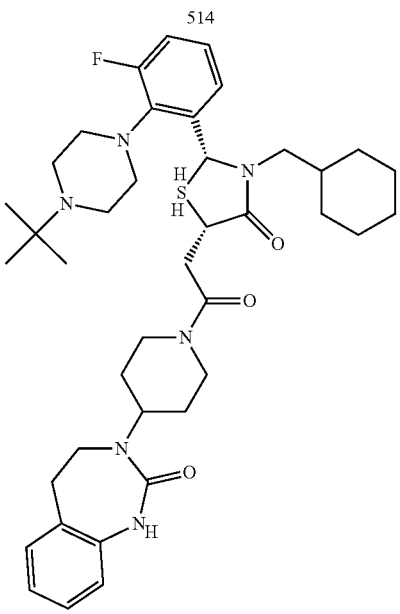

| 497 -continued | 498 -continued |
|---|---|
| 515 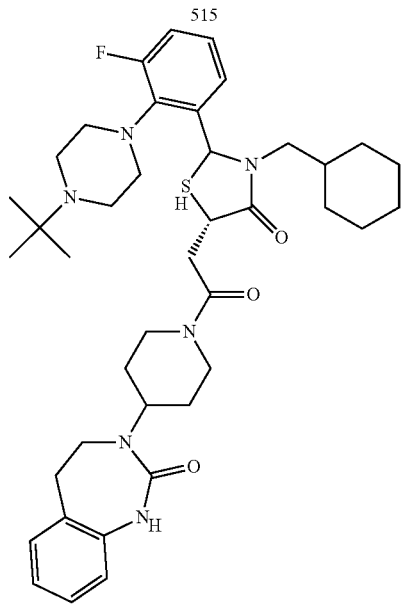 | 518 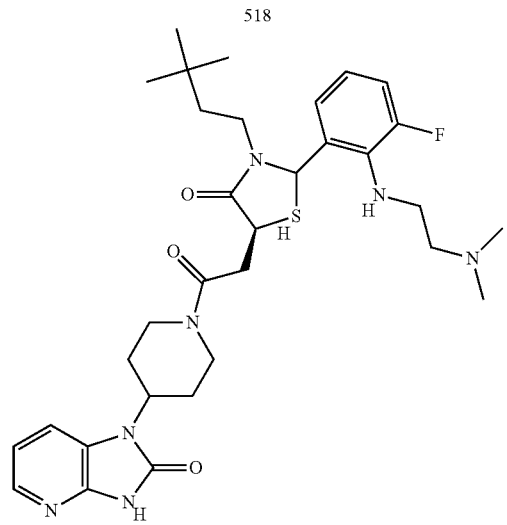 |
| 516 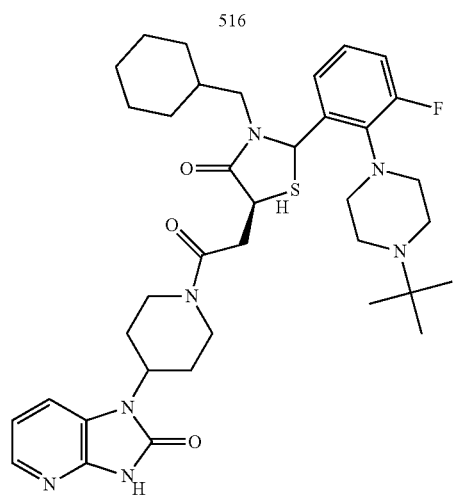 | |
| 517 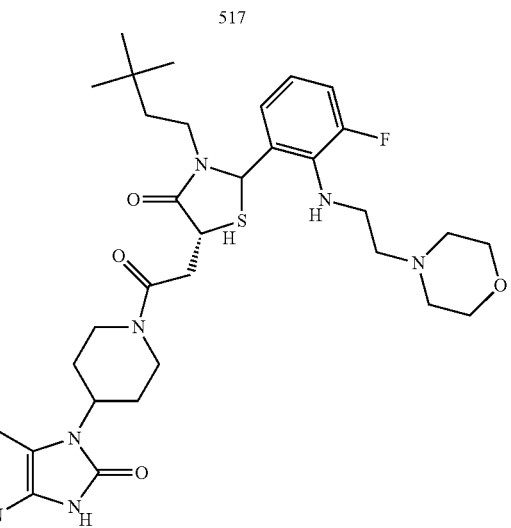 | 519 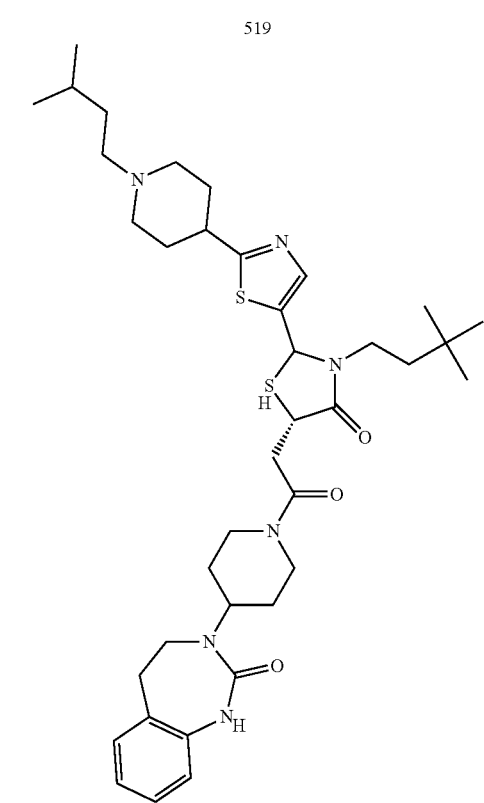 |

| 499 -continued | 500 -continued |
|---|---|
| 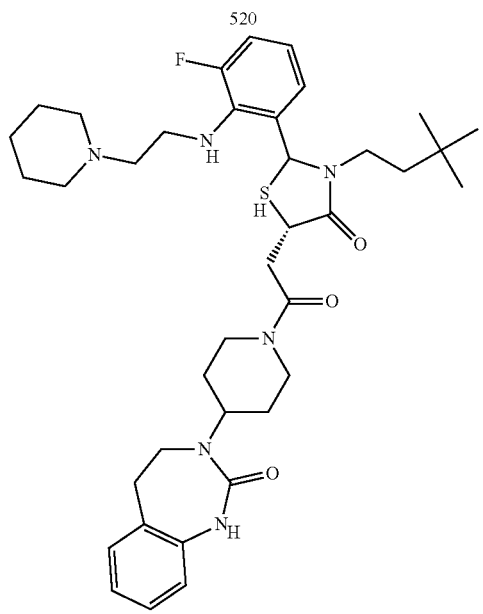 | 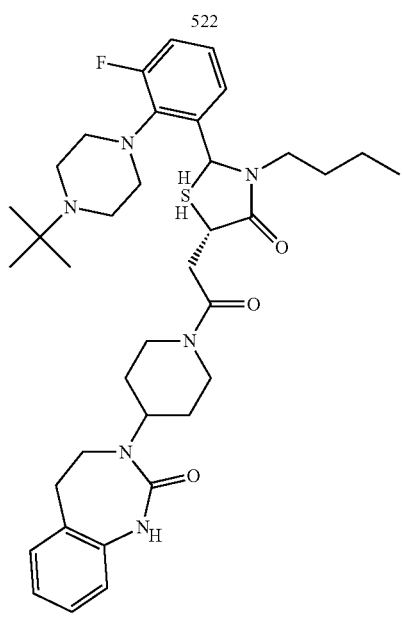 |

524
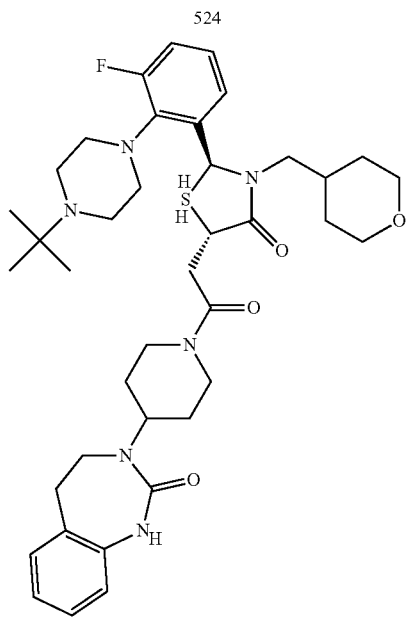
525
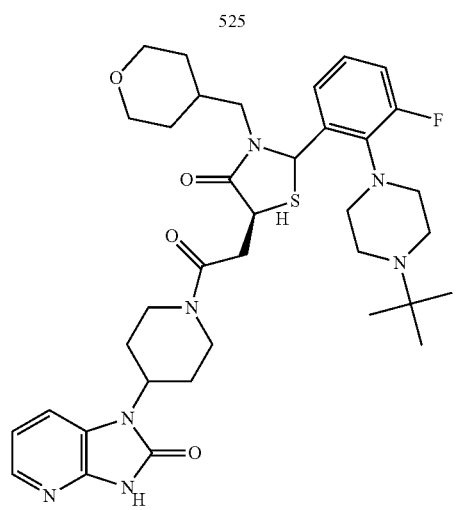
526
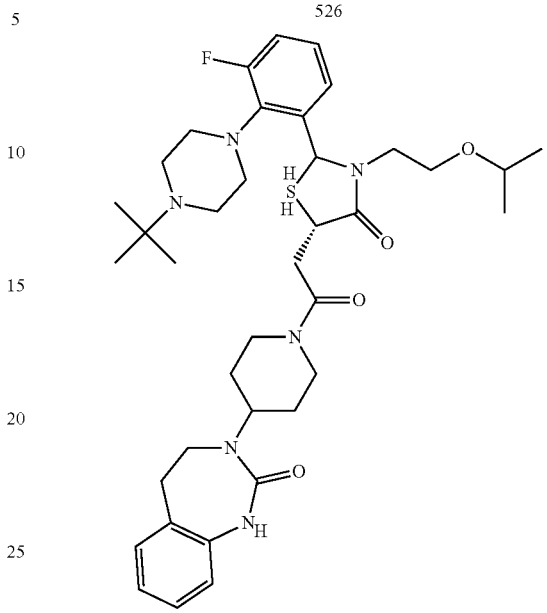
527
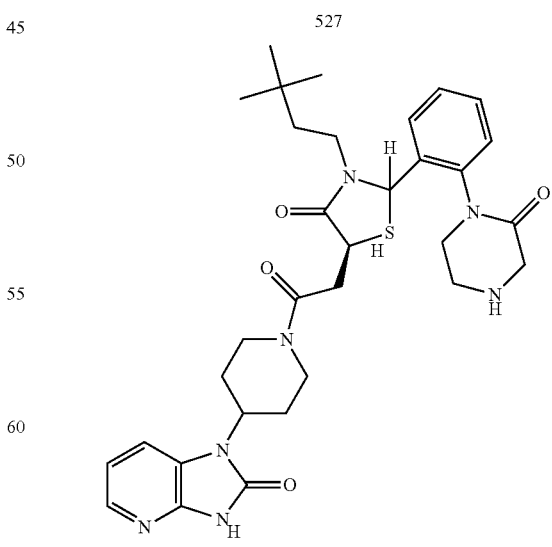

528
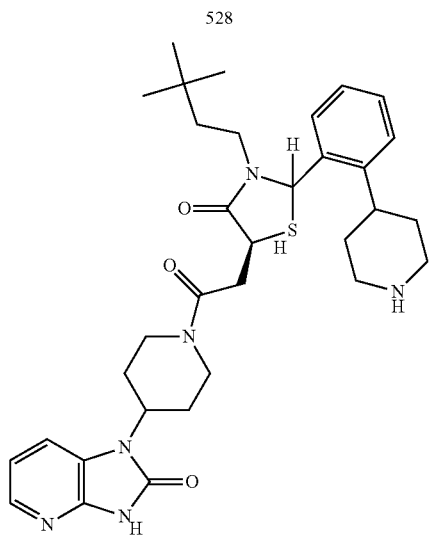
529
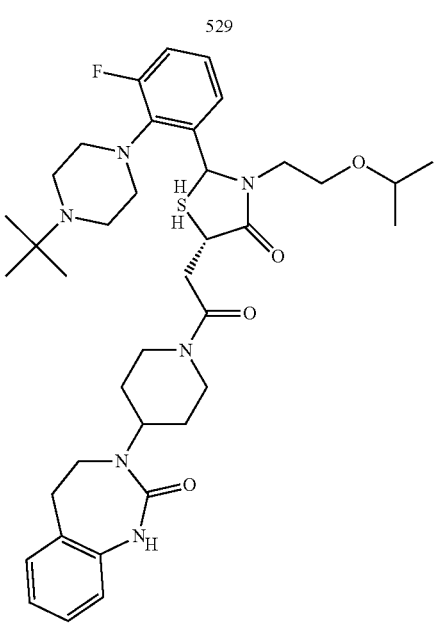
530
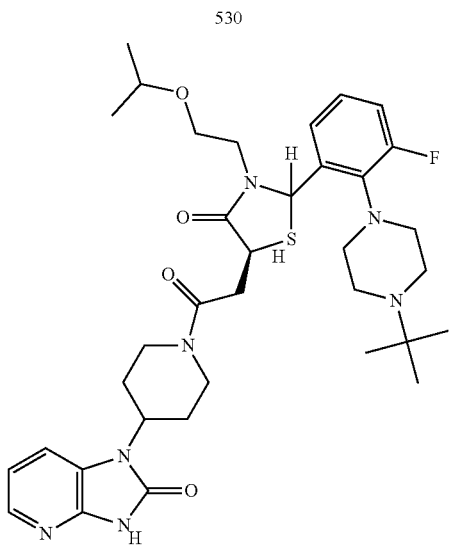
531
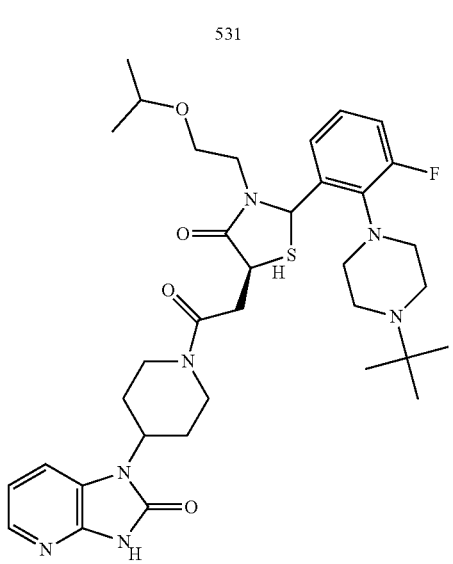

505
-continued
532
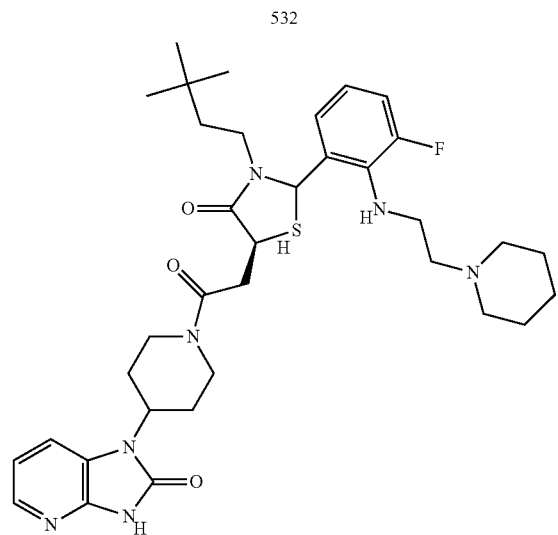
533
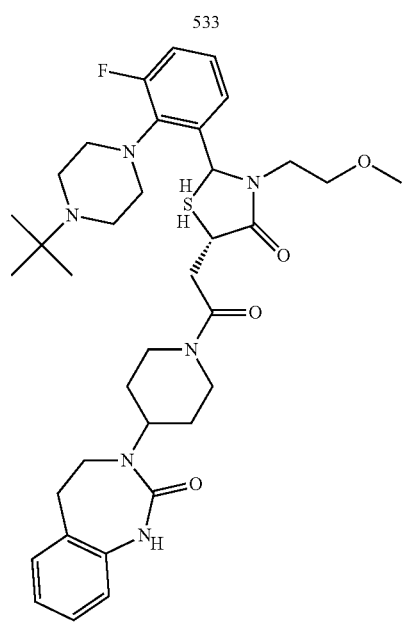
506
-continued
534
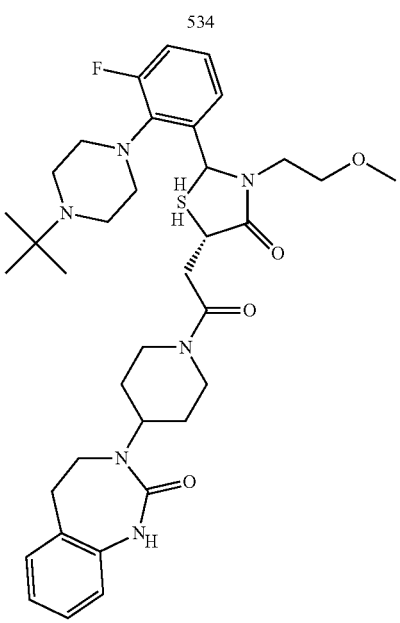
535
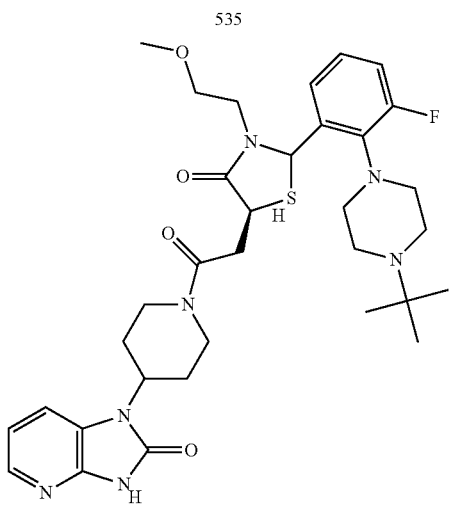

| 507 -continued | 508 -continued |
|---|---|
| 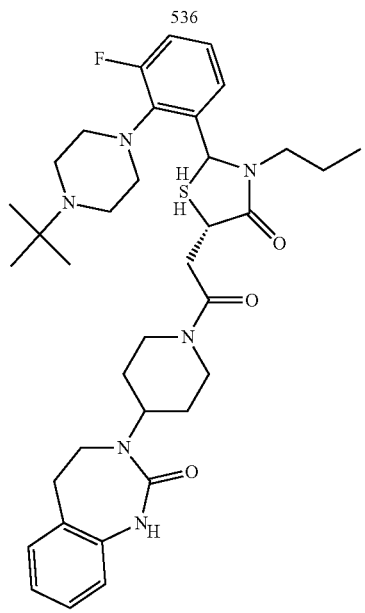 536 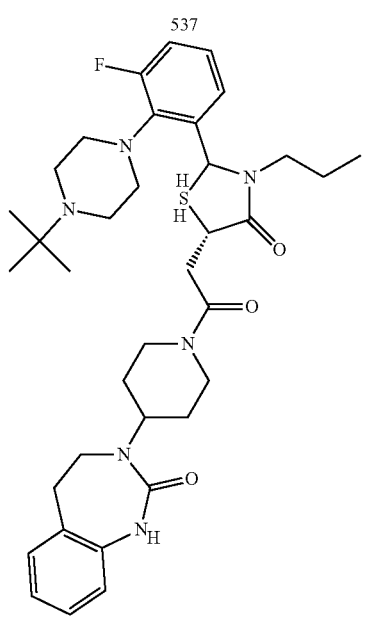 537 | 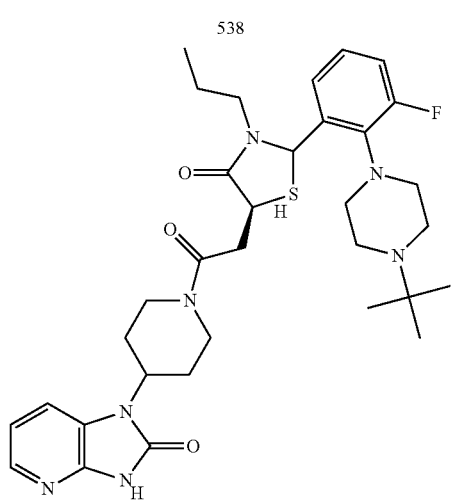 538 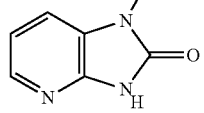 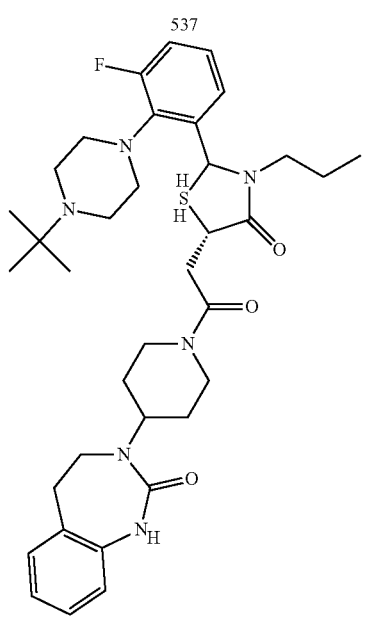 539 |

540
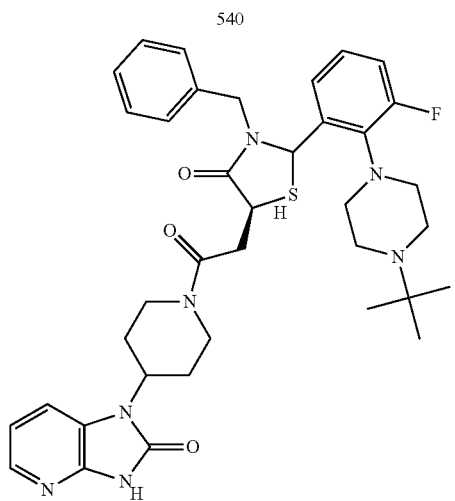
542
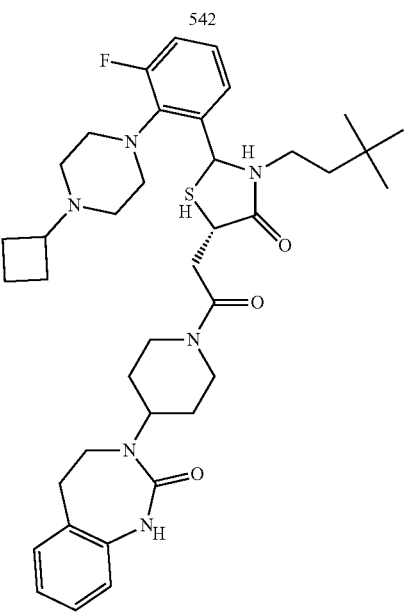
541
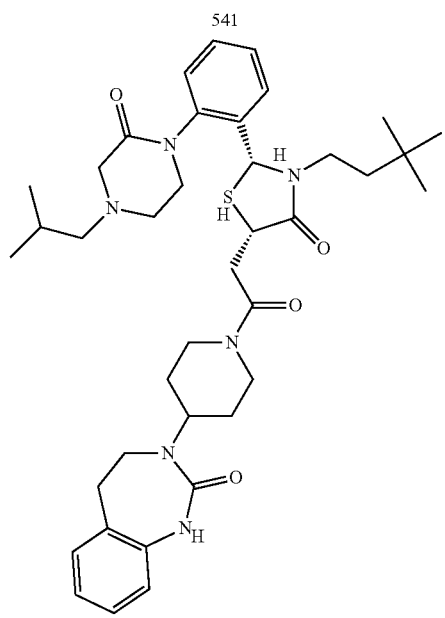
543
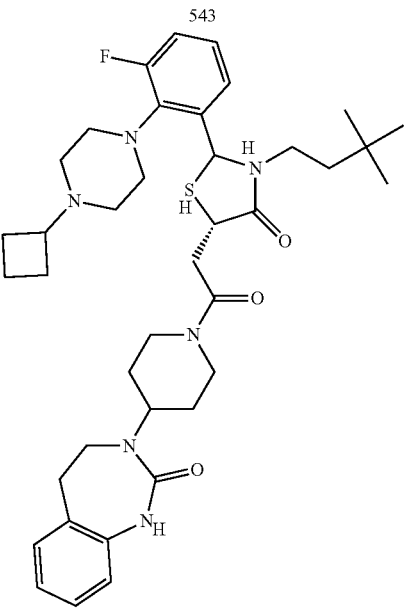

511
-continued
544
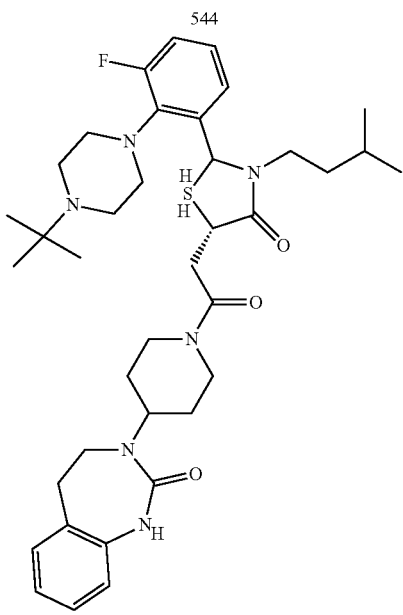
545
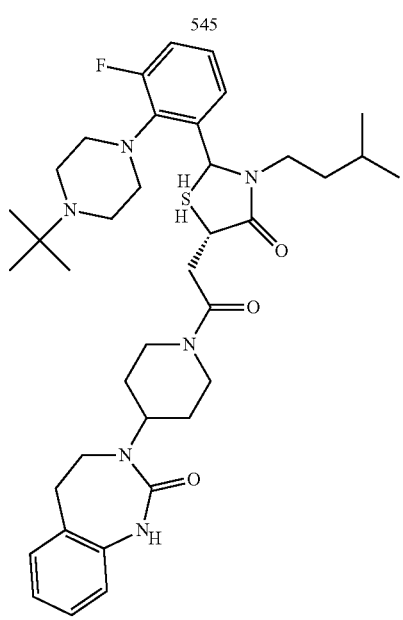
512
-continued
546
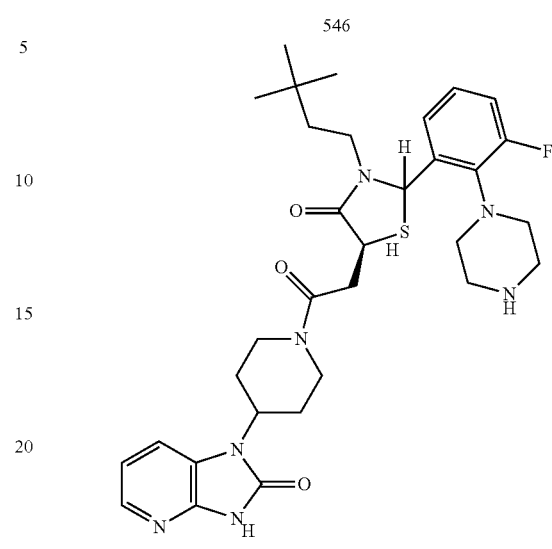
547
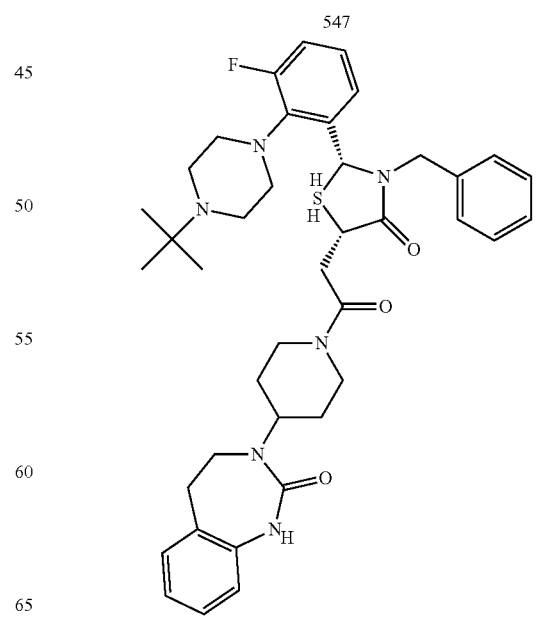

513
-continued
548
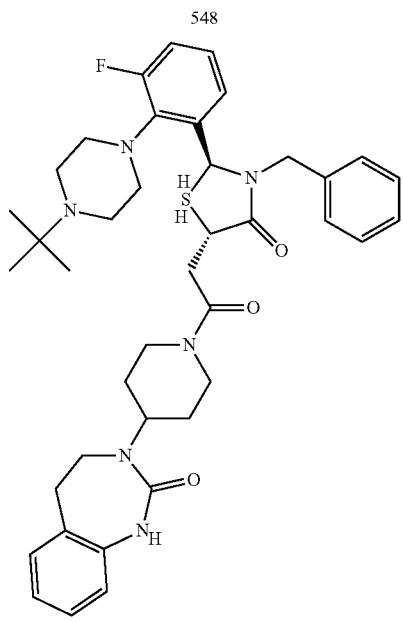
549
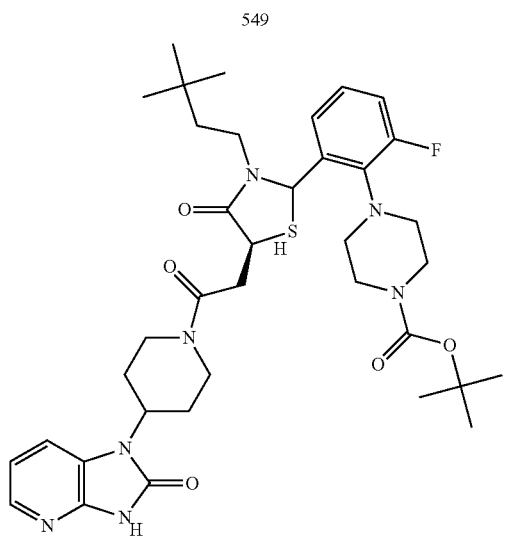
514
-continued
550
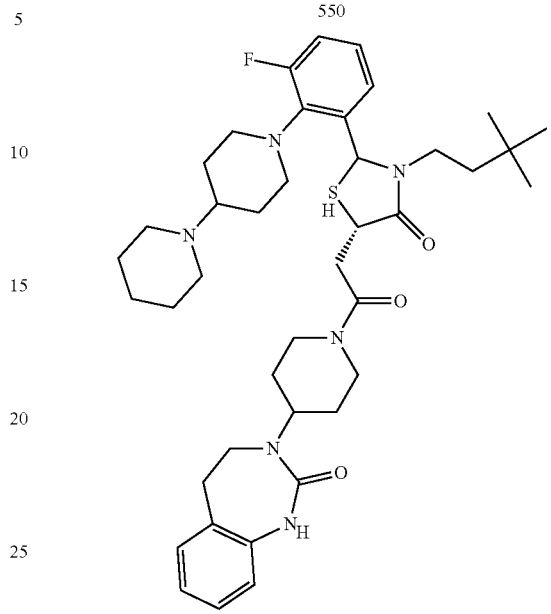
551
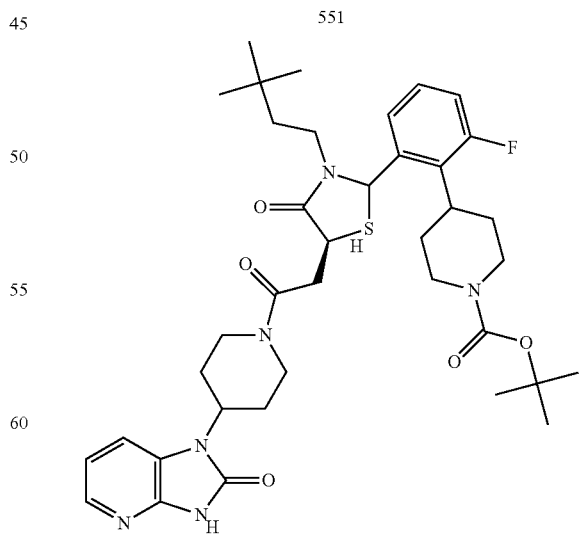

| 515 -continued | 516 -continued |
|---|---|
| 552 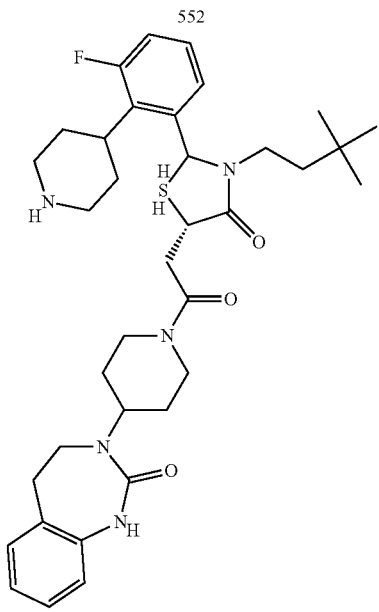 | 554 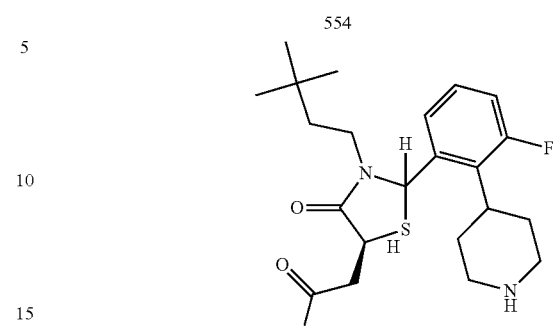 |
| 553 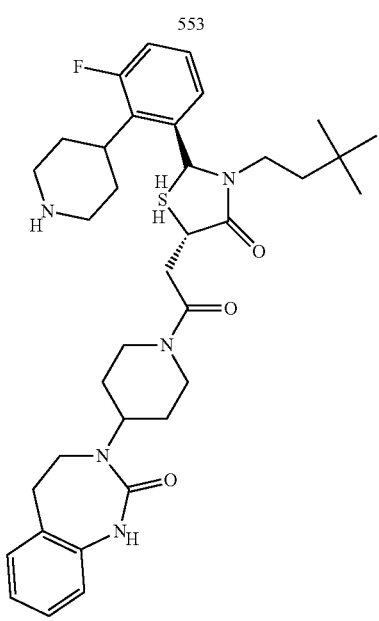 | 555 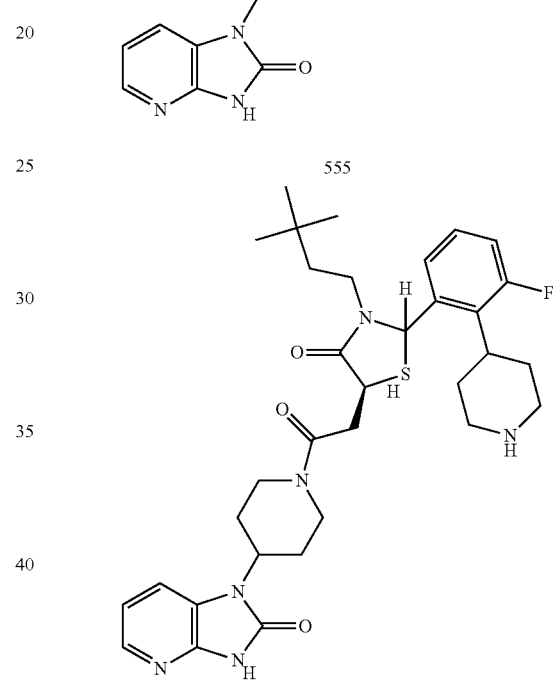 |
|  | 556 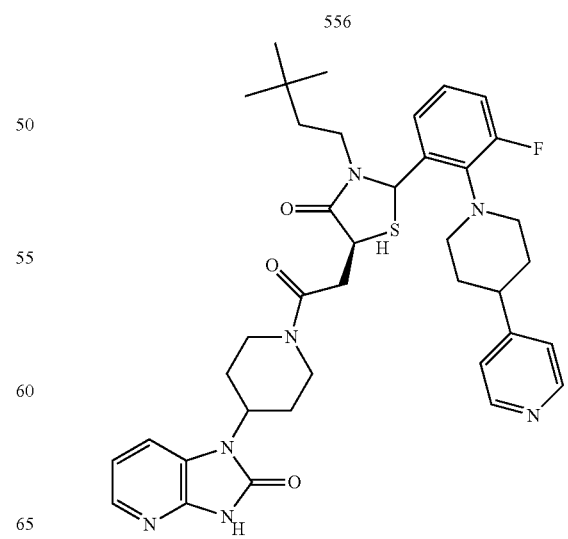 |

517
-continued
557
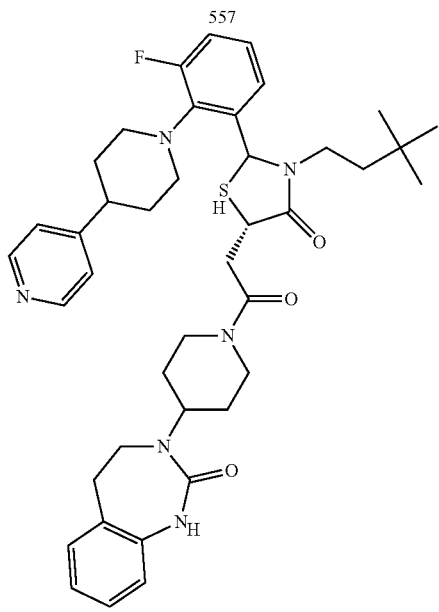
558
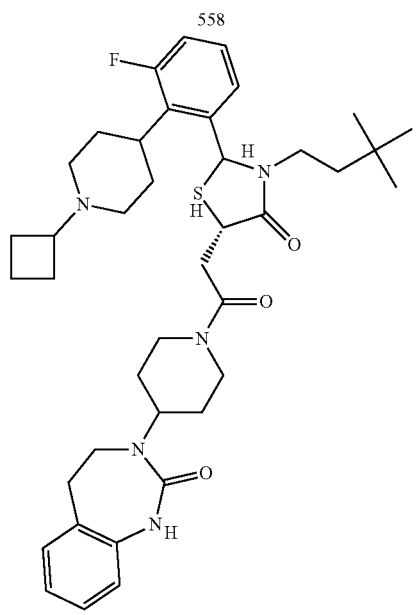
518
-continued
559
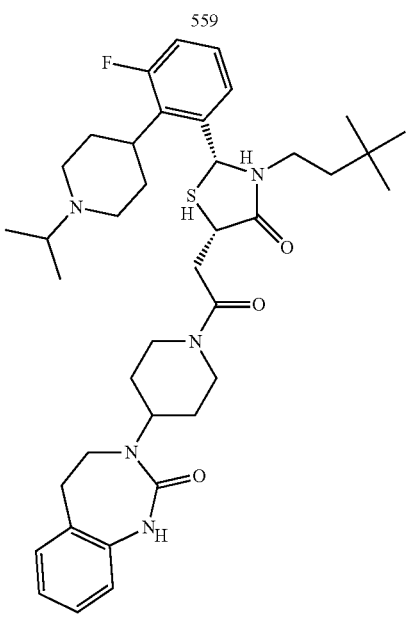
560
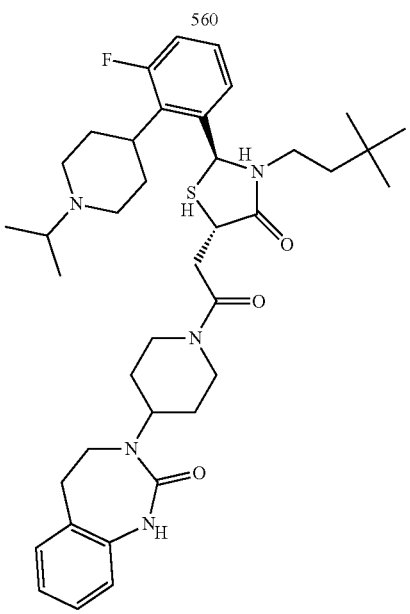

519
-continued

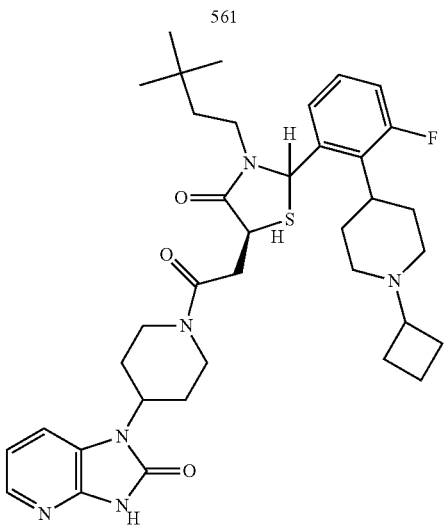
561

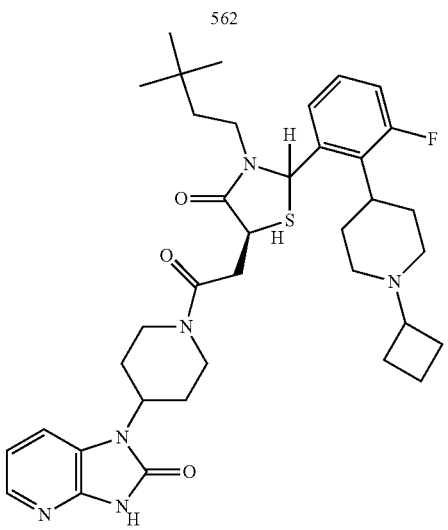
562

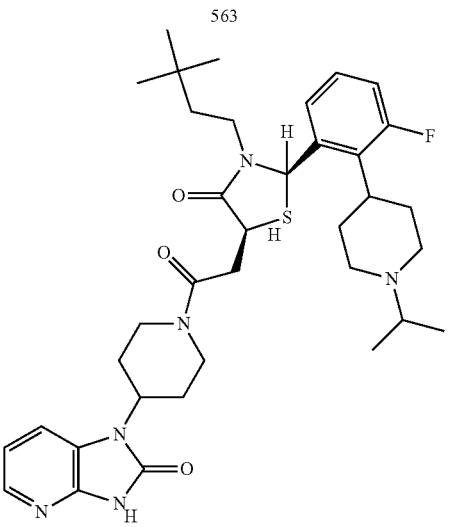
563

564

520
-continued

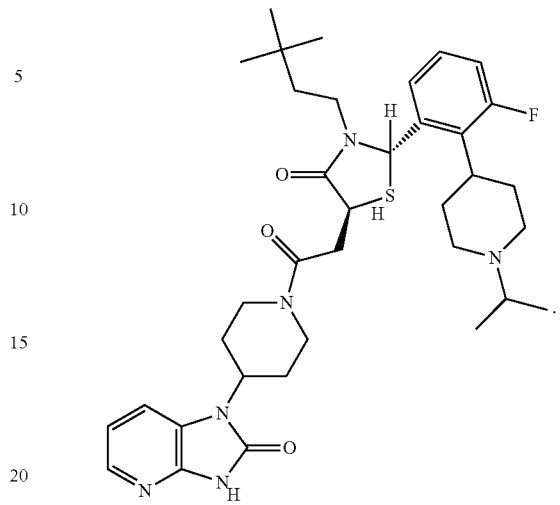

2. A pharmaceutical composition comprising a compound according to claim 1, and a pharmaceutically acceptable carrier, adjuvant, or vehicle.

3. The pharmaceutical composition according to claim 2, further comprising an additional therapeutic agent.

4. A method of reducing the risk of or ameliorating one or more of the following conditions or diseases in a subject: migraine or pain, comprising administering a therapeutically effective amount of a composition according to claim 2 to said subject in need thereof.

5. The method according to claim 4, wherein said method is used to reduce the risk or ameliorate migraine.

6. The method according to claim 4 or claim 5, further comprising an additional therapeutic agent.

7. The method according to claim 6, wherein said additional agent is selected from an anti-inflammatory agent, an analgesic agent, or an anti-migraine agent.

8. The method according to claim 7, wherein said additional agent is selected from an interleukin inhibitor, an NK-1 receptor antagonist an NMDA antagonist, an NR2B antagonist; a bradykinin-1 receptor antagonist; an adenosine A1 receptor agonist; a sodium channel blocker, an opiate against, a lipoxygenase inhibitor, an alpha receptor antagonist, an alpha receptor agonist, a vanilloid receptor antagonist, an mGluR5 agonist, antagonist or potentiator, a GABA A receptor modulator, nicotinic antagonists or agonists, muscarinic agonists or antagonists, a selective serotonin reuptake inhibitor, a tricyclic antidepressant, a leukotriene antagonist, an inhibitor of nitric oxide or an inhibitor of the synthesis of nitric oxide.

9. The method according to claim 6, wherein said additional agent is selected from an ergot alkaloid.

10. The method according to claim 6, wherein said additional agent is selected from a beta-adrenergic antagonist, a MAO inhibitor, a calcium channel blocker, an anticonvulsant, an angiotensin II antagonist, an angiotensin converting enzyme inhibitor, or botulinum toxin type A.

11. The method according to claim 6, wherein said additional agent is selected from a potentiator such as caffeine, an H2-antagonist, a decongestant, an antitussive, a diuretic, a prokinetic agent, or a sedating or non-sedating antihistamine.

12. The method according to claim 4, wherein said disease is selected from pain and said method is useful for ameliorating or reducing the risk of chronic pain; neurogenic inflammatory pain; neuropathic pain; eye pain and tooth pain.

* * * * *